US008716529B2

(12) United States Patent
Scott et al.

(10) Patent No.: US 8,716,529 B2
(45) Date of Patent: May 6, 2014

(54) AMINE DERIVATIVE COMPOUNDS FOR TREATING OPHTHALMIC DISEASES AND DISORDERS

(75) Inventors: Ian L. Scott, Monroe, WA (US); Vladimir A. Kuksa, Kenmore, WA (US); Mark W. Orme, Seattle, WA (US); Feng Hong, Bellevue, WA (US); Thomas L. Little, Redmond, WA (US); Ryo Kubota, Seattle, WA (US)

(73) Assignee: Acucela Inc., Seattle, WA (US)

( * ) Notice: Subject to any disclaimer, the term of this patent is extended or adjusted under 35 U.S.C. 154(b) by 0 days.

(21) Appl. No.: 13/278,925

(22) Filed: Oct. 21, 2011

(65) Prior Publication Data

US 2012/0041039 A1    Feb. 16, 2012

Related U.S. Application Data

(63) Continuation of application No. 12/256,415, filed on Oct. 22, 2008, now Pat. No. 8,076,516.

(60) Provisional application No. 60/984,667, filed on Nov. 1, 2007.

(51) Int. Cl.
    *C07C 213/00*    (2006.01)
(52) U.S. Cl.
    USPC .......................................................... 564/354
(58) Field of Classification Search
    USPC .......................................................... 564/354
    See application file for complete search history.

(56) References Cited

U.S. PATENT DOCUMENTS

| | | | |
|---|---|---|---|
| 3,911,151 A | 10/1975 | Yokoyama et al. | |
| 4,013,633 A * | 3/1977 | Haase et al. | 534/648 |
| 4,214,001 A | 7/1980 | Engelherdt et al. | |
| 4,412,856 A | 11/1983 | Brunner et al. | |
| 4,873,254 A | 10/1989 | Hargreaves | |
| 5,049,587 A | 9/1991 | Okamoto et al. | |
| 5,227,372 A | 7/1993 | Folkman | |
| 5,446,065 A * | 8/1995 | Witte et al. | 514/604 |
| 5,523,302 A * | 6/1996 | Cain et al. | 514/254.1 |
| 5,879,871 A * | 3/1999 | Ikesu et al. | 430/552 |
| 5,929,117 A | 7/1999 | Muller et al. | |
| 6,051,605 A | 4/2000 | Capiris et al. | |
| 6,162,943 A | 12/2000 | Lui et al. | |
| 6,664,286 B1 * | 12/2003 | May et al. | 514/415 |
| 6,713,458 B1 | 3/2004 | Yerxa et al. | |
| RE38,761 E | 7/2005 | Levitzki et al. | |
| 7,396,844 B1 | 7/2008 | Takayanagi | |
| 8,076,516 B2 | 12/2011 | Scott et al. | |
| 2002/0042116 A1 | 4/2002 | Simon et al. | |
| 2002/0058685 A1 | 5/2002 | Hamilton | |
| 2003/0032078 A1 | 2/2003 | Travis | |
| 2003/0186961 A1 | 10/2003 | Hamilton et al. | |
| 2003/0203912 A1 | 10/2003 | May | |
| 2004/0058964 A1 | 3/2004 | Devadas | |
| 2004/0186061 A1 | 9/2004 | Meese et al. | |
| 2006/0069078 A1 | 3/2006 | Rando | |
| 2006/0069110 A1 | 3/2006 | Andersen et al. | |
| 2006/0116373 A1 | 6/2006 | Dollinger et al. | |
| 2006/0128662 A1 | 6/2006 | Tagmore et al. | |
| 2006/0211694 A1 | 9/2006 | Devadas et al. | |
| 2006/0252107 A1 | 11/2006 | Kubota et al. | |
| 2006/0281812 A1 | 12/2006 | Slatter et al. | |
| 2006/0281821 A1 | 12/2006 | Palczewski et al. | |
| 2007/0072920 A1 | 3/2007 | Hellberg et al. | |
| 2007/0149480 A1 | 6/2007 | Ghosh et al. | |
| 2009/0016483 A1 | 1/2009 | Scott et al. | |
| 2009/0062353 A1 | 3/2009 | Scott et al. | |
| 2009/0281149 A1 | 11/2009 | Scott et al. | |
| 2012/0041038 A1 | 2/2012 | Scott et al. | |
| 2012/0041039 A1 | 2/2012 | Scott et al. | |

FOREIGN PATENT DOCUMENTS

| | | | |
|---|---|---|---|
| CA | 2199771 | 9/1997 | |
| CH | 396941 | 8/1965 | |
| DE | 2821410 | 11/1978 | |
| DE | 4041780 | 6/1992 | |
| EP | 0181163 | * 10/1985 | ........... C07D 295/08 |
| EP | 0181163 | 5/1986 | |
| EP | 0525360 | 2/1993 | |
| GB | 884663 | 11/1959 | |
| GB | 2455176 | 6/2009 | |
| JP | H05-222073 | 8/1993 | |
| JP | H7-247274 A | 9/1995 | |
| JP | 2006176443 | * 12/2004 | ........... C07D 133/89 |
| JP | 2009-542628 | 12/2009 | |
| KR | 2001-0073153 | 7/2001 | |
| WO | WO-95-19952 | 7/1995 | |
| WO | WO 97/32879 | * 2/1997 | ........... C07D 487/04 |
| WO | WO 97/11069 | 3/1997 | |
| WO | WO 9732879 | * 12/1997 | ........... C07D 487/04 |
| WO | WO-99-16783 | 4/1999 | |
| WO | WO 0017133 | * 3/2000 | |

(Continued)

OTHER PUBLICATIONS

Keenan et al. Bioorganic & Medicinal Chemistry (1998), 6(8),1309-1335.*
Koshinaka et al. Chemical & Pharmaceutical Bulletin (1988), 36(8),2955-67.*
Dorwald F. A. Side Reactions in Organic Synthesis, 2005, Wiley: VCH, Weinheim p. IX of Preface p. 1-15.*
Venkatesh et al., J. Pharm. Sci. 89, 145-54 (2000) (p. 146, left column).*
Beauchamp et al. Journal of Applied Physiology, 2001, 90, 2279-2288.*

(Continued)

*Primary Examiner* — Nizal Chandrakumar
(74) *Attorney, Agent, or Firm* — Wilson Sonsini Goodrich & Rosati

(57) ABSTRACT

Provided are amine derivative compounds, pharmaceutical compositions thereof, and methods of treating ophthalmic diseases and disorders, such as age-related macular degeneration and Stargardt's Disease, using said compounds and compositions.

12 Claims, 2 Drawing Sheets

(56) References Cited

FOREIGN PATENT DOCUMENTS

| | | | |
|---|---|---|---|
| WO | WO 01/34573 | 5/2001 | |
| WO | WO 0164631 * | 9/2001 | |
| WO | WO-03-059872 | 7/2003 | |
| WO | WO-2004-013082 | 2/2004 | |
| WO | WO-2004-030671 | 4/2004 | |
| WO | WO-2005-105760 | 11/2005 | |
| WO | WO 2006044497 * | 4/2006 | ....... A61K 31/47447 |
| WO | WO 2006/063128 | 6/2006 | |
| WO | WO 2006/120544 | 11/2006 | |
| WO | WO 2007/042321 | 4/2007 | |
| WO | WO-2007-079593 | 7/2007 | |
| WO | WO-2008-011560 | 1/2008 | |
| WO | WO-2008-021388 | 2/2008 | |
| WO | WO-2008-077057 | 6/2008 | |
| WO | WO-2008-131368 | 10/2008 | |
| WO | WO-2009-005794 | 1/2009 | |
| WO | WO-2009-058216 | 5/2009 | |

OTHER PUBLICATIONS

Radu et al. Proceedings of the National Academy of Sciences, 2003, 110 (8), 4742-4767, Fig 1A, on p. 4743.*
CA2704199 Examination Report dated Jan. 8, 2013.
CN2008801123780.0 Office action dated Feb. 17, 2013 (English translation only).
Kier L "Structural information from molecular connectivity," *J. Pharm. Sci.* 9:1034-1039 (1980).
Kuliev et al., "Synthesis of b-aminoethyl aryl sulfides," Doklady Akademiya Nauk Azerbaidzhanskoi SSR 31(5):13-16 (1975) (with English translation).
MX/a/2010/004718 Office action dated Feb. 15, 2013 (English translation only).
Park et al., "N-Aralkylated 4-(2-Aminoethoxy_phenylacetamide Derivatives as Potent Analgesic and Antiinflammatory Agents," Korean J. of Med. Chem, vol. 1, No. 1 (1991).
PK 1243/2008 Search Report dated Feb. 2, 2010 (English translation only).
Sieving et al. "Inhibition of the visual cycle in vivo by 13-*cis* retinoic acid protects from light damage and provides a mechanism for night blindness in isotretinoin therapy." *PNAS* 98(4):1835-1840 (Feb. 13, 2001).
U.S. Appl. No. 12/256,415 Office Action mailed Jun. 21, 2010.
U.S. Appl. No. 12/256,415 Office Action mailed Nov. 30, 2010.
U.S. Appl. No. 13/278,909 Final Office Action mailed Sep. 21, 2012.
U.S. Appl. No. 13/278,909 Office Action mailed May 15, 2012.
CA2704199 Examination Report dated Sep. 30, 2013.
EP08832783.8 Office Action dated Apr. 24, 2013.
JP 2010-532020 Office Action dated Oct. 8, 2013 with English translation.
MX/a/2010/004718 Office action dated Oct. 10, 2013.
NZ601573 Examination Report dated Aug. 7, 2012.
PH1-2010-500891 Office Action dated Jun. 20, 2013.
RU2010122261 Office Action dated Mar. 15, 2013.
GB0819399.7 Search Report dated Apr. 1, 2009.
CAPLUS Database Accession No. 1981:120698 from KIER,. "Structural information from molecualr connectivity." J Pharm Sci, 1980, 9:1034-1039.
Golczak et al., "Positively charged retinoids are potent and selective inhibitors of the trans-cis isomerization in the retinoid (visual) cycle," *PNAS* 102(23):8162-8167 (2005).
Maeda et al., "Evaluation of the role of the retinol G protein-coupled receptor (RGR) in the vertebrate retina in vivo," *Journal of Neurochem.* 85(4):944-956 (2003).
Mata et al., "Isomerization and Oxidation of Vitamin A in Cone-Dominant Retinas: A Novel Pathway for Visual-Pigment Regeneration in Daylight," *Neuron* 36:69-80 (2002).
Minami et al. "Enzymatic Approach to Unnatural Glycosides with Diverse Aglycon Scaffolds Using Glycosyltransferase VinC." *Journal of American Chemical Society*, 2005, 127:6148-6149.
Rangisetty et al., "1-[2-Methocy-5-(3-phenylpropyl)]-2-aminopropane unexpectedly shows 5-HT2A Serotonin Receptor Affinity and Antagonist Character." *J. Med. Chem.*, 2001, 44:3283-3291.
Tavora De Albuquerque Silva et al., "Advances in Prodrug Design." *Mini Reviews in Medicinal Chemistry*, 2005, 5:893-914.
Zanon-Moreno et al., "Serotonin Levels in Aqueous Humor of Patients with Primary Open-Angle Glaucoma." *Molecular Vision*, 2008, 14:2143-47.
PCT/US2008/12060 International Search Report and Written Opinion dated Feb. 2, 2009.
EP08832783.8 Extended Search Report dated Jul. 18, 2012.
GB0819399.7 Examination Report dated Mar. 9, 2012.
KR2010-7012034 Examination Report dated Feb. 23, 2012.
CA2704199 Examination Report dated Jul. 11, 2012.

* cited by examiner

AMINE DERIVATIVE COMPOUNDS FOR TREATING OPHTHALMIC DISEASES AND DISORDERS

CROSS-REFERENCE

This application claims the benefit of U.S. Provisional Application No. 60/984,667, filed Nov. 1, 2007, which is incorporated herein by reference in its entirety.

BACKGROUND OF THE INVENTION

Neurodegenerative diseases, such as glaucoma, macular degeneration, and Alzheimer's disease, affect millions of patients throughout the world. Because the loss of quality of life associated with these diseases is considerable, drug research and development in this area is of great importance.

Age-related macular degeneration (AMD) affects between ten and fifteen million patients in the United States, and it is the leading cause of blindness in aging populations worldwide. AMD affects central vision and causes the loss of photoreceptor cells in the central part of retina called the macula. Macular degeneration can be classified into two types: dry-form and wet-form. The dry-form is more common than the wet; about 90% of age-related macular degeneration patients are diagnosed with the dry-form. The wet-form of the disease and geographic atrophy, which is the end-stage phenotype of dry-form AMD, causes the most serious vision loss. All patients who develop wet-form AMD are believed to previously have developed dry-form AMD for a prolonged period of time. The exact causes of AMD are still unknown. The dry-form of AMD may result from the senescence and thinning of macular tissues associated with the deposition of pigment in the macular retinal pigment epithelium. In wet-form AMD, new blood vessels grow beneath the retina, form scar tissue, bleed, and leak fluid. The overlying retina can be severely damaged, creating "blind" areas in the central vision.

For the vast majority of patients who have the dry-form of AMD, no effective treatment is yet available. Because the dry-form of AMD precedes development of the wet-form of AMD, therapeutic intervention to prevent or delay disease progression in the dry-form of AMD would benefit patients with dry-form AMD and might reduce the incidence of the wet-form of AMD.

Decline of vision noticed by the patient or characteristic features detected by an ophthalmologist during a routine eye exam may be the first indicator of AMD. The formation of "drusen," or membranous debris beneath the retinal pigment epithelium of the macula is often the first physical sign that AMD is developing. Late symptoms include the perceived distortion of straight lines and, in advanced cases, a dark, blurry area or area with absent vision appears in the center of vision; and/or there may be color perception changes.

Different forms of genetically-linked macular degenerations may also occur in younger patients. In other maculopathies, factors in the disease are heredity, nutritional, traumatic, infection, or other ecologic factors.

Glaucoma is a broad term used to describe a group of diseases that causes a slowly progressive visual field loss, usually asymptomatically. The lack of symptoms may lead to a delayed diagnosis of glaucoma until the terminal stages of the disease. The prevalence of glaucoma is estimated to be 2.2 million in the United States, with about 120,000 cases of blindness attributable to the condition. The disease is particularly prevalent in Japan, which has four million reported cases. In many parts of the world, treatment is less accessible than in the United States and Japan, thus glaucoma ranks as a leading cause of blindness worldwide. Even if subjects afflicted with glaucoma do not become blind, their vision is often severely impaired.

The progressive loss of peripheral visual field in glaucoma is caused by the death of ganglion cells in the retina. Ganglion cells are a specific type of projection neuron that connects the eye to the brain. Glaucoma is usually accompanied by an increase in intraocular pressure. Current treatment includes use of drugs that lower the intraocular pressure; however, contemporary methods to lower the intraocular pressure are often insufficient to completely stop disease progression. Ganglion cells are believed to be susceptible to pressure and may suffer permanent degeneration prior to the lowering of intraocular pressure. An increasing number of cases of normal-tension glaucoma are observed in which ganglion cells degenerate without an observed increase in the intraocular pressure. Current glaucoma drugs only treat intraocular pressure and are ineffective in preventing or reversing the degeneration of ganglion cells.

Recent reports suggest that glaucoma is a neurodegenerative disease, similar to Alzheimer's disease and Parkinson's disease in the brain, except that it specifically affects retinal neurons. The retinal neurons of the eye originate from diencephalon neurons of the brain. Though retinal neurons are often mistakenly thought not to be part of the brain, retinal cells are key components of the central nervous system, interpreting the signals from the light-sensing cells.

Alzheimer's disease (AD) is the most common form of dementia among the elderly. Dementia is a brain disorder that seriously affects a person's ability to carry out daily activities Alzheimer's is a disease that affects four million people in the United States alone. It is characterized by a loss of nerve cells in areas of the brain that are vital to memory and other mental functions. Currently available drugs can ameliorate AD symptoms for a relatively finite period of time, but no drugs are available that treat the disease or completely stop the progressive decline in mental function. Recent research suggests that glial cells that support the neurons or nerve cells may have defects in AD sufferers, but the cause of AD remains unknown. Individuals with AD seem to have a higher incidence of glaucoma and age-related macular degeneration, indicating that similar pathogenesis may underlie these neurodegenerative diseases of the eye and brain. (See Giasson et al., *Free Radic. Biol. Med.* 32:1264-75 (2002); Johnson et al., *Proc. Natl. Acad. Sci. USA* 99:11830-35 (2002); Dentchev et al., *Mol. Vis.* 9:184-90 (2003).

Neuronal cell death underlies the pathology of these diseases. Unfortunately, very few compositions and methods that enhance retinal neuronal cell survival, particularly photoreceptor cell survival, have been discovered. A need therefore exists to identify and develop compositions that can be used for treatment and prophylaxis of a number of retinal diseases and disorders that have neuronal cell death as a primary, or associated, element in their pathogenesis.

In vertebrate photoreceptor cells, the irradiance of a photon causes isomerization of 11-cis-retinylidene chromophore to all-trans-retinylidene and uncoupling from the visual opsin receptors. This photoisomerization triggers conformational changes of opsins, which, in turn, initiate the biochemical chain of reactions termed phototransduction (Filipek et al., *Annu. Rev. Physiol.* 65:851-79 (2003)). Regeneration of the visual pigments requires that the chromophore be converted back to the 11-cis-configuration in the processes collectively called the retinoid (visual) cycle (see, e.g., McBee et al., *Prog. Retin. Eye Res.* 20:469-52 (2001)). First, the chromophore is released from the opsin and reduced in the photoreceptor by retinol dehydrogenases. The product, all-trans-retinol, is trapped in the adjacent retinal pigment epithelium (RPE) in the form of insoluble fatty acid esters in subcellular structures known as retinosomes (Imanishi et al., *J. Cell Biol.* 164:373-87 (2004)).

In Stargardt's disease (Allikmets et al., *Nat. Genet.* 15:236-46 (1997)), a disease associated with mutations in the ABCR transporter that acts as a flippase, the accumulation of all-trans-retinal may be responsible for the formation of a lipofuscin pigment, A2E, which is toxic towards retinal pigment epithelial cells and causes progressive retinal degeneration and, consequently, loss of vision (Mata et al., *Proc. Natl. Acad. Sci. USA* 97:7154-59 (2000); Weng et al., *Cell* 98:13-23 (1999)). Treating patients with an inhibitor of retinol dehydrogenases, 13-cis-RA (Isotretinoin, Accutane®, Roche), has been considered as a therapy that might prevent or slow the formation of A2E and might have protective properties to maintain normal vision (Radu et al., *Proc. Natl. Acad. Sci. USA* 100:4742-47 (2003)). 13-cis-RA has been used to slow the synthesis of 11-cis-retinal by inhibiting 11-cis-RDH (Law et al., *Biochem. Biophys. Res. Commun.* 161:825-9 (1989)), but its use can also be associated with significant night blindness. Others have proposed that 13-cis-RA works to prevent chromophore regeneration by binding RPE65, a protein essential for the isomerization process in the eye (Gollapalli et al., *Proc. Natl. Acad. Sci. USA* 101:10030-35 (2004)). Gollapalli et al. reported that 13-cis-RA blocked the formation of A2E and suggested that this treatment may inhibit lipofuscin accumulation and, thus, delay either the onset of visual loss in Stargardt's disease or age-related macular degeneration, which are both associated with retinal pigment-associated lipofuscin accumulation. However, blocking the retinoid cycle and forming unliganded opsin may result in more severe consequences and worsening of the patient's prognosis (see, e.g., Van Hooser et al., *J. Biol. Chem.* 277: 19173-82 (2002); Woodruff et al., *Nat. Genet.* 35:158-164 (2003)). Failure of the chromophore to form may lead to progressive retinal degeneration and may produce a phenotype similar to Leber Congenital Amaurosis (LCA), which is a very rare genetic condition affecting children shortly after birth.

SUMMARY OF THE INVENTION

A need exists in the art for an effective treatment for treating ophthalmic diseases or disorders resulting in ophthalmic dysfunction including those described above. In particular, there existis a pressing need for compositions and methods for treating Stargardt's disease and age-related macular degeneration (AMD) without causing further unwanted side effects such as progressive retinal degeneration, LCA-like conditions, night blindness, or systemic vitamin A deficiency. A need also exists in the art for effective treatments for other ophthalmic diseases and disorders that adversely affect the retina.

The present invention relates to amine derivative compounds, which are inhibitors of an isomerization step of the retinoid cycle and are useful for treating ophthalmic diseases and disorders. Also provided are pharmaceutical compositions comprising the amine derivative compounds and methods for treating various ophthalmic diseases, using these compounds.

Accordingly, in one embodiment, is a compound of Formula (A) or tautomer, stereoisomer, geometric isomer or a pharmaceutically acceptable solvate, hydrate, salt, N-oxide or prodrug thereof:

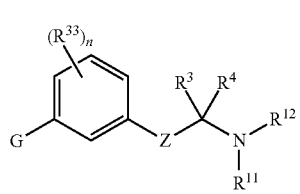

Formula (A)

wherein,

Z is a bond, $-C(R^1)(R^2)-$, $-C(R^9)(R^{10})-C(R^1)(R^2)-$, $-X-C(R^{31})(R^{32})-$, $-C(R^9)(R^{10})-C(R^1)(R^2)-C(R^{36})(R^{37})-$ or $-X-C(R^{31})(R^{32})-C(R^1)(R^2)-$;

X is $-O-$, $-S-$, $-S(=O)-$, $-S(=O)_2-$, $-N(R^{30})-$, $-C(=O)-$, $-C(=CH_2)-$, $-C(=N-NR^{35})-$, or $-C(=N-OR^{35})-$;

G is selected from $-C(R^{41})_2-C(R^{41})_2-R^{40}$, $-C(R^{42})_2-S-R^{40}$, $-C(R^{42})_2-SO-R^{40}$, $-C(R^{42})_2-SO_2-R^{40}$, $-C(R^{42})_2-O-R^{40}$, $-C(R^{42})_2-N(R^{42})-R^{40}$, $-C(=O)-N(R^{42})-R^{40}$;

$R^{40}$ is selected from $-C(R^{16})(R^{17})(R^{18})$, aryl, or heteroaryl;

each $R^{41}$ is independently selected from hydrogen, hydroxy, $OR^6$, alkyl, or two $R^{41}$ groups together may form an oxo;

each $R^{42}$ is independently selected from hydrogen or alkyl;

$R^1$ and $R^2$ are each independently selected from hydrogen, halogen, $C_1$-$C_5$ alkyl, fluoroalkyl, $-OR^6$ or $-NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, $-OR^6$ or $-NR^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^7$ and $R^8$ are each independently selected from hydrogen, alkyl, carbocyclyl, heterocyclyl, $-C(=O)R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, $-OR^{19}$, $-NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, $-C(=O)R^{23}$, $-C(NH)NH_2$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, $-C(=O)R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroarylkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, $OR^{34}$, alkyl, or fluoroalkyl; and n is 0, 1, 2, 3, or 4; with the provision that G is not an unsubstituted normal alkyl and the provision that the compound of Formula A is not:

C-attached heterocyclyl; or $R^3$ and $R^4$ together with the carbon atom to which they are attached, form a carbocyclyl or heterocyclyl; or $R^3$ and $R^4$ together form an imino;

$R^7$ and $R^8$ are each independently selected from hydrogen, alkyl, carbocyclyl, heterocyclyl, —C(=O)$R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ form an oxo;

$R^{11}$ and $R^{12}$ are each independently selected from hydrogen, alkyl, carbocyclyl, —C(=O)$R^{23}$, $SO_2R^{23}$, $CO_2R^{23}$ or

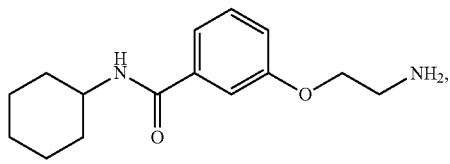

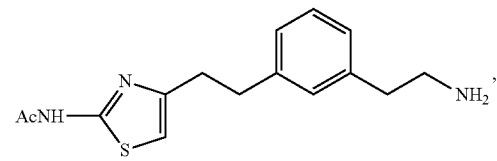

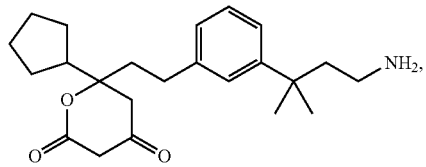

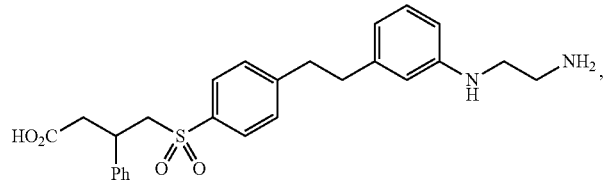

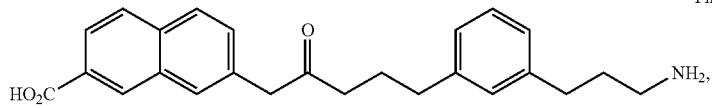

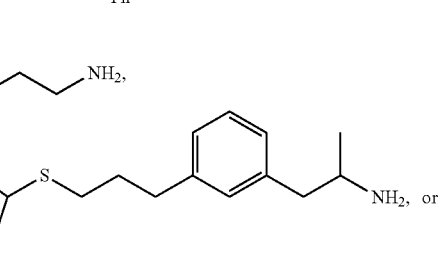

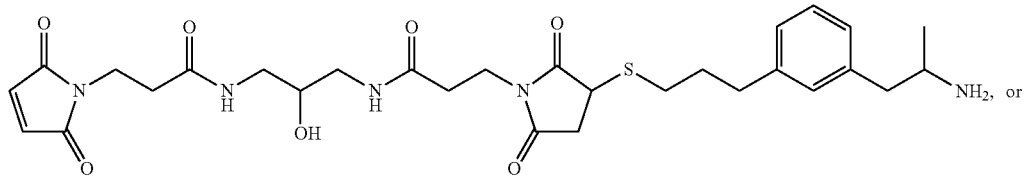

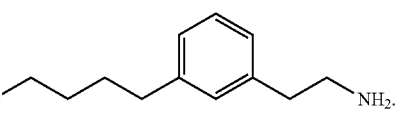

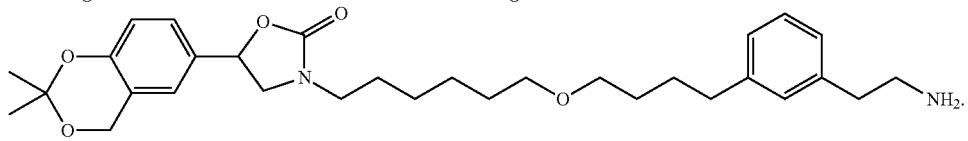

In another embodiment is the compound of Formula (A) wherein,

Z is a bond, —C($R^1$)($R^2$)—, —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)— or —X—C($R^{31}$)($R^{32}$)—C($R^1$)($R^2$)—;

X is —O—, —S—, —S(=O)—, —S(=O)$_2$—, —N($R^{30}$)—, —C(=O)—, —C(=CH$_2$)—, —C(=N—NR$^{35}$)—, or —C(=N—OR$^{35}$)—;

$R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —$OR^6$ or —$NR^7R^8$; or $R^{36}$ and $R^{37}$ together form an oxo;

$R^3$ and $R^4$ are each independently selected from hydrogen, alkyl, alkenyl, fluoroalkyl, aryl, heteroaryl, carbocyclyl or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, and $R^{29}$ is independently selected from hydrogen, alkyl, alkenyl, fluoroalkyl, aryl, heteroaryl, carbocyclyl or heterocyclyl;

each $R^{33}$ is independently selected from halogen, $OR^{34}$, alkyl, or fluoroalkyl; and n is 0, 1, 2, 3, or 4.

In another embodiment is the compound of Formula (A) having the structure of Formula (B)

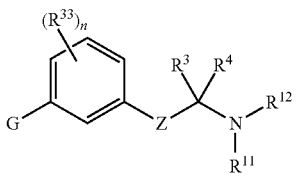

Formula (B)

wherein,
Z is —C(R$^9$)(R$^{10}$)—C(R$^1$)(R$^2$)— or —O—C(R$^{31}$)(R$^{32}$)—;
R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;
R$^{31}$ and R$^{32}$ are each independently selected from hydrogen, C$_1$-C$_5$ alkyl, or fluoroalkyl;
R$^3$ and R$^4$ are each independently selected from hydrogen or alkyl; or R$^3$ and R$^4$ together form an imino;
R$^7$ and R$^8$ are each independently selected from hydrogen, alkyl, carbocyclyl or —C(=O)R$^{13}$; or R$^7$ and R$^8$, together with the nitrogen atom to which they are attached, form an N-heterocyclyl;
R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ together form an oxo; or optionally, R$^9$ and R$^1$ together form a direct bond to provide a double bond; or optionally, R$^9$ and R$^1$ together form a direct bond, and R$^{10}$ and R$^2$ together form a direct bond to provide a triple bond;
R$^{11}$ and R$^{12}$ are each independently selected from hydrogen, alkyl, carbocyclyl or —C(=O)R$^{23}$; or R$^{11}$ and R$^{12}$, together with the nitrogen atom to which they are attached, form an N-heterocyclyl; and
each R$^{13}$, R$^{22}$ and R$^{23}$ is independently selected from alkyl, alkenyl, aryl, aralkyl, carbocyclyl, heteroaryl or heterocyclyl;
R$^6$, R$^{19}$, and R$^{34}$ are each independently hydrogen or alkyl;
each R$^{33}$ is independently selected from halogen, OR$^{34}$, alkyl, or fluoroalkyl; and n is 0, 1, 2, 3, or 4;
R$^{20}$ and R$^{21}$ are each independently selected from hydrogen, alkyl, carbocyclyl, —C(=O)R$^{22}$; or R$^{20}$ and R$^{21}$, together with the nitrogen atom to which they are attached, form an N-heterocyclyl; and
each R$^{24}$, R$^{25}$, R$^{26}$, R$^{27}$, R$^{28}$ and R$^{29}$ is independently selected from hydrogen, alkyl, alkenyl, fluoroalkyl, aryl, heteroaryl, carbocyclyl or heterocyclyl.

In another embodiment is the compound of Formula (B) wherein,
Z is —C(R$^9$)(R$^{10}$)—C(R$^1$)(R$^2$)— or —O—C(R$^{31}$)(R$^{32}$)—;
R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;
R$^{31}$ and R$^{32}$ are each independently selected from hydrogen, C$_1$-C$_5$ alkyl, or fluoroalkyl;
R$^3$ and R$^4$ are each independently selected from hydrogen or alkyl; or R$^3$ and R$^4$ together form an imino;
R$^7$ and R$^8$ are each independently selected from hydrogen, alkyl, carbocyclyl or —C(=O)R$^{13}$; or R$^7$ and R$^8$, together with the nitrogen atom to which they are attached, form an N-heterocyclyl;
R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ together form an oxo;
R$^{11}$ and R$^{12}$ are each independently selected from hydrogen, alkyl, carbocyclyl or —C(=O)R$^{23}$; or R$^{11}$ and R$^{12}$, together with the nitrogen atom to which they are attached, form an N-heterocyclyl; and
each R$^{13}$, R$^{22}$ and R$^{23}$ is independently selected from alkyl, alkenyl, aryl, aralkyl, carbocyclyl, heteroaryl or heterocyclyl;
R$^6$, R$^{19}$, and R$^{34}$ are each independently hydrogen or alkyl;
each R$^{33}$ is independently selected from halogen, OR$^{34}$, alkyl, or fluoroalkyl; and n is 0, 1, 2, 3, or 4;
R$^{20}$ and R$^{21}$ are each independently selected from hydrogen, alkyl, carbocyclyl, —C(=O)R$^{22}$; or R$^{20}$ and R$^{21}$, together with the nitrogen atom to which they are attached, form an N-heterocyclyl; and
each R$^{24}$, R$^{25}$, R$^{26}$, R$^{27}$, R$^{28}$ and R$^{29}$ is independently selected from hydrogen, alkyl, alkenyl, fluoroalkyl, aryl, heteroaryl, carbocyclyl or heterocyclyl.

In another embodiment is the compound of Formula (B) wherein,
G is selected from —C(R$^{41}$)$_2$—C(R$^{41}$)$_2$—R$^{40}$;
R$^{40}$ is selected from —C(R$^{16}$)(R$^{17}$)(R$^{18}$), aryl, or heteroaryl;
each R$^{41}$ is independently selected from hydrogen, hydroxy, OR$^6$, alkyl, or two R$^{41}$ groups together may form an oxo.

In another embodiment is the compound of Formula (B) wherein,
G is selected from —C(R$^{41}$)$_2$—C(R$^{41}$)$_2$—R$^{40}$;
R$^{40}$ is selected from —C(R$^{16}$)(R$^{17}$)(R$^{18}$), aryl, or heteroaryl;
each R$^{41}$ is independently selected from hydrogen, hydroxy, OR$^6$, alkyl, or two R$^{41}$ groups together may form an oxo.

In another embodiment is the compound of Formula (B) having the structure of Formula (C)

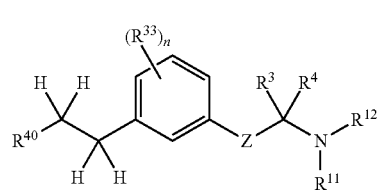

Formula (C)

wherein,
Z is —C(R$^9$)(R$^{10}$)—C(R$^1$)(R$^2$)— or —O—C(R$^{31}$)(R$^{32}$)—;
R$^{40}$ is selected from —C(R$^{16}$)(R$^{17}$)(R$^{18}$), aryl, or heteroaryl;
R$^{16}$ and R$^{17}$ are each independently selected from hydrogen, alkyl, halo, aryl, heteroaryl, aralkyl, heteroarylalkyl or fluoroalkyl; or R$^{16}$ and R$^{17}$, together with the carbon to which they are attached form a carbocyclyl or heterocycle;
R$^{18}$ is selected from hydrogen, alkyl, alkoxy, hydroxy, halo or fluoroalkyl;
R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;
R$^{31}$ and R$^{32}$ are each independently selected from hydrogen, C$_1$-C$_5$ alkyl, or fluoroalkyl;
R$^3$ and R$^4$ are each independently selected from hydrogen or alkyl; or R$^3$ and R$^4$ together form an imino;
R$^7$ and R$^8$ are each independently selected from hydrogen, alkyl, carbocyclyl or —C(=O)R$^{13}$; or R$^7$ and R$^8$, together with the nitrogen atom to which they are attached, form an N-heterocyclyl;
R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ together form an oxo; or optionally, R$^9$ and R$^1$ together form a direct bond to provide a double bond; or optionally, R$^9$ and R$^1$ together form a direct bond, and R$^{10}$ and R$^2$ together form a direct bond to provide a triple bond;

$R^{11}$ and $R^{12}$ are each independently selected from hydrogen, alkyl, carbocyclyl or —C(=O)$R^{23}$; or $R^{11}$ and $R^{12}$, together with the nitrogen atom to which they are attached, form an N-heterocyclyl; and each $R^{13}$, $R^{22}$ and $R^{23}$ is independently selected from alkyl, alkenyl, aryl, aralkyl, carbocyclyl, heteroaryl or heterocyclyl;

$R^6$, $R^{19}$, and $R^{34}$ are each independently hydrogen or alkyl;

each $R^{33}$ is independently selected from halogen, $OR^{34}$, alkyl, or fluoroalkyl; and n is 0, 1, 2, 3, or 4;

$R^{20}$ and $R^{21}$ are each independently selected from hydrogen, alkyl, carbocyclyl, —C(=O)$R^{22}$; or $R^{20}$ and $R^{21}$, together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl.

In another embodiment is the compound of Formula (C) wherein, $R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ together form an oxo.

In another embodiment is the compound of Formula (C) having the structure of Formula (D):

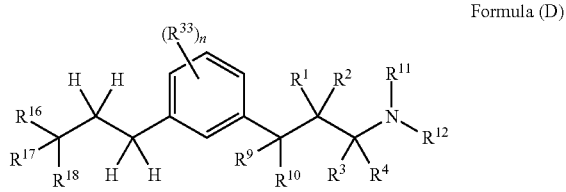

Formula (D)

wherein, $R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^3$ and $R^4$ are each independently selected from hydrogen or alkyl; or $R^3$ and $R^4$ together form an imino;

$R^7$ and $R^8$ are each independently selected from hydrogen, alkyl, carbocyclyl or —C(=O)$R^{13}$; or $R^7$ and $R^8$, together with the nitrogen atom to which they are attached, form an N-heterocyclyl;

$R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ together form an oxo;

$R^{11}$ and $R^{12}$ are each independently selected from hydrogen, alkyl, carbocyclyl or —C(=O)$R^{23}$; or $R^{11}$ and $R^{12}$, together with the nitrogen atom to which they are attached, form an N-heterocyclyl;

each $R^{13}$, $R^{22}$ and $R^{23}$ is independently selected from alkyl, alkenyl, aryl, aralkyl, carbocyclyl, heteroaryl or heterocyclyl;

$R^6$, $R^{19}$ and $R^{34}$ are each independently hydrogen or alkyl;

$R^{20}$ and $R^{21}$ are each independently selected from hydrogen, alkyl, carbocyclyl, —C(=O)$R^{22}$; or $R^{20}$ and $R^{21}$, together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocycle;

each $R^{33}$ is independently selected from halogen, $OR^{34}$, alkyl, or fluoroalkyl; and n is 0, 1, 2, 3, or 4; and $R^{18}$ is selected from a hydrogen, alkyl, alkoxy, hydroxy, halo or fluoroalkyl.

In another embodiment is the compound of Formula (D) wherein n is 0 and each of $R^{11}$ and $R^{12}$ is hydrogen. in a further embodiment is the compound wherein each of $R^3$, $R^4$, $R^{14}$ and $R^{15}$ is hydrogen. In a further embodiment is the compound wherein, $R^1$ and $R^2$ are each independently selected from hydrogen, halogen, $C_1$-$C_5$ alkyl, or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently hydrogen or alkyl;

$R^{16}$ and $R^{17}$, together with the carbon to which they are attached form a carbocyclyl or heterocycle; and $R^{18}$ is selected from a hydrogen, alkoxy or hydroxy.

In a further embodiment is the compound wherein $R^{16}$ and $R^{17}$, together with the carbon to which they are attached, form a cyclopropyl, cyclobutyl, cyclopentyl, cyclohexyl, cycloheptyl, or cyclooctyl, and $R^{18}$ is hydrogen or hydroxy.

In another embodiment is the compound of Formula (D), wherein $R^{11}$ is hydrogen and $R^{12}$ is —C(=O)$R^{23}$, wherein $R^{23}$ is alkyl.

In a further embodiment is the compound of Formula (D), wherein $R^1$ and $R^2$ are each independently selected from hydrogen, halogen, $C_1$-$C_5$ alkyl, or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently selected from hydrogen or alkyl;

$R^{16}$ and $R^{17}$, together with the carbon atom to which they are attached, form a carbocyclyl; and $R^{18}$ is hydrogen, hydroxy or alkoxy.

In a further embodiment is the compound of Formula (D) wherein, n is 0;

$R^{16}$ and $R^{17}$, together with the carbon atom to which they are attached, form a cyclopentyl, cyclohexyl or cyclohexyl; and $R^{18}$ is hydrogen or hydroxy.

In a further embodiment is the compound of Formula (D) wherein, $R^1$ and $R^2$ are each independently selected from hydrogen, halogen, $C_1$-$C_5$ alkyl or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently hydrogen or alkyl;

$R^{16}$ and $R^{17}$ is independently selected from $C_1$-$C_{13}$ alkyl; and $R^{18}$ is hydrogen, hydroxy or alkoxy.

In another embodiment is the compound of Formula (C) having the structure of Formula (E):

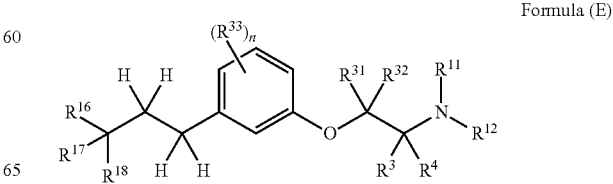

Formula (E)

wherein, $R^{31}$ and $R^{32}$ are each independently selected from hydrogen, $C_1$-$C_5$ alkyl, or fluoroalkyl;

$R^3$ and $R^4$ are each independently selected from hydrogen or alkyl; or $R^3$ and $R^4$ together form an imino;

$R^{11}$ and $R^{12}$ are each independently selected from hydrogen, alkyl, carbocyclyl, or —C(=O)$R^{23}$; or $R^{11}$ and $R^{12}$, together with the nitrogen atom to which they are attached, form an N-heterocyclyl;

$R^{23}$ is selected from alkyl, alkenyl, aryl, carbocyclyl, heteroaryl or heterocyclyl;

$R^{14}$ and $R^{15}$ are each independently selected from hydrogen or alkyl;

$R^{16}$ and $R^{17}$ are each independently selected from hydrogen, $C_1$-$C_{13}$ alkyl, halo or fluoroalkyl; or $R^{16}$ and $R^{17}$, together with the carbon atom to which they are attached, form a carbocyclyl or heterocycle;

$R^{18}$ is selected from a hydrogen, alkyl, alkoxy, hydroxy, halo or fluoroalkyl;

$R^{34}$ is hydrogen or alkyl; and each $R^{33}$ is independently selected from halogen, OR$^{34}$, alkyl, or fluoroalkyl; and n is 0, 1, 2, 3, or 4.

In another embodiment is the compound of Formula (E) wherein n is 0 and each of $R^{11}$ and $R^{12}$ is hydrogen.

In a further embodiment is the compound of Formula (E) wherein each $R^3$, $R^4$, $R^{14}$ and $R^{15}$ is hydrogen.

In a further embodiment is the compound of Formula (E) wherein, $R^{31}$ and $R^{32}$ are each independently hydrogen, or $C_1$-$C_5$ alkyl;

$R^{16}$ and $R^{17}$, together with the carbon atom to which they are attached, form a carbocyclyl; and $R^{18}$ is hydrogen, hydroxy, or alkoxy.

In a further embodiment is the compound of Formula (E) wherein $R^{16}$ and $R^{17}$, together with the carbon atom to which they are attached form a cyclopropyl, cyclobutyl, cyclopentyl, cyclohexyl, cycloheptyl or cyclooctyl and $R^{18}$ is hydrogen or hydroxy.

In a further embodiment is the compound of Formula (E) wherein, $R^{31}$ and $R^{32}$ are each independently selected from hydrogen, or $C_1$-$C_5$ alkyl; and $R^{18}$ is hydrogen, hydroxy or alkoxy.

In a further embodiment is the compound of Formula (E) wherein, $R^{31}$ and $R^{32}$ are each independently hydrogen, or $C_1$-$C_5$ alkyl;

$R^6$ and $R^{19}$ are each independently hydrogen or alkyl;

$R^{16}$ and $R^{17}$ is independently selected from $C_1$-$C_{13}$ alkyl; and $R^{18}$ is hydrogen, hydroxy or alkoxy.

In another embodiment is the compound of Formula (A) wherein,

Z is a bond, —X—C($R^{31}$)($R^{32}$)—, or —X—C($R^{31}$)($R^{32}$)—C($R^1$)($R^2$)—; and X is —S—, —S(=O)—, —S(=O)$_2$—, —N($R^{30}$)—, —C(=O)—, —C(=CH$_2$)—, —C(=N—N$R^{35}$)—, or —C(=N—OR$^{35}$)—.

In a further embodiment is the compound of Formula (A) wherein,

G is selected from —C($R^{41}$)$_2$—C($R^{41}$)$_2$—$R^{40}$;

$R^{40}$ is selected from —C($R^{16}$)($R^{17}$)($R^{18}$), aryl, or heteroaryl;

each $R^{41}$ is independently selected from hydrogen, hydroxy, OR$^6$, alkyl, or two $R^{41}$ groups together may form an oxo.

In another embodiment is the compound of Formula (A) having the structure of Formula (F):

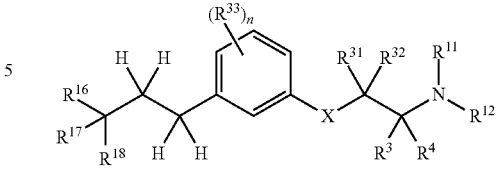

Formula (F)

wherein,

X is —S—, —S(=O)—, —S(=O)$_2$—, —N($R^{30}$)—, —C(=O)—, —C(=CH$_2$)—, —C(=N—N$R^{35}$)—, or —C(=N—OR$^{35}$)—;

$R^{31}$ and $R^{32}$ are each independently selected from hydrogen, $C_1$-$C_5$ alkyl, or fluoroalkyl;

$R^3$ and $R^4$ are each independently selected from hydrogen or alkyl; or $R^3$ and $R^4$ together form an imino;

$R^{11}$ and $R^{12}$ are each independently selected from hydrogen, alkyl, carbocyclyl, or —C(=O)$R^{23}$; or $R^{11}$ and $R^{12}$, together with the nitrogen atom to which they are attached, form an N-heterocyclyl;

$R^{23}$ is selected from alkyl, alkenyl, aryl, carbocyclyl, heteroaryl or heterocyclyl;

$R^{16}$ and $R^{17}$ are each independently selected from hydrogen, $C_1$-$C_{13}$ alkyl, halo or fluoroalkyl; or $R^{16}$ and $R^{17}$, together with the carbon atom to which they are attached, form a carbocyclyl or heterocycle;

$R^{30}$, $R^{34}$ and $R^{35}$ are each independently hydrogen or alkyl;

$R^{18}$ is selected from a hydrogen, alkyl, alkoxy, hydroxy, halo or fluoroalkyl;

each $R^{33}$ is independently selected from halogen, OR$^{34}$, alkyl, or fluoroalkyl; and n is 0, 1, 2, 3, or 4.

In a further embodiment is the compound of Formula (F) wherein n is 0 and each $R^{11}$ and $R^{12}$ is hydrogen.

In a further embodiment is the compound of Formula (F) wherein each $R^3$, $R^4$, $R^{14}$ and $R^{15}$ is hydrogen.

In a further embodiment is the compound of Formula (F) wherein, $R^{31}$ and $R^{32}$ are each independently hydrogen, or $C_1$-$C_5$ alkyl;

$R^{16}$ and $R^{17}$, together with the carbon atom to which they are attached, form a carbocyclyl or heterocycle; and $R^{18}$ is hydrogen, hydroxy, or alkoxy.

In a further embodiment is the compound of Formula (F) wherein $R^{16}$ and $R^{17}$, together with the carbon atom to which they are attached form a cyclopropyl, cyclobutyl, cyclopentyl, cyclohexyl, cycloheptyl or cyclooctyl and $R^{18}$ is hydrogen or hydroxy.

In a further embodiment is the compound of Formula (F) wherein, $R^{31}$ and $R^{32}$ are each independently selected from hydrogen, or $C_1$-$C_5$ alkyl; $R^{16}$ and $R^{17}$ is independently selected from $C_1$-$C_{13}$ alkyl; and $R^{18}$ is hydrogen, hydroxy or alkoxy.

In one embodiment is a compound having a structure of Formula (I):

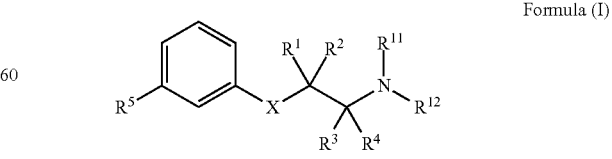

Formula (I)

as a tautomer or a mixture of tautomers, or as a pharmaceutically acceptable salt, hydrate, solvate, N-oxide or prodrug thereof, wherein:

R¹ and R² are each the same or different and independently hydrogen, halogen, $C_1$-$C_5$ alkyl, fluoroalkyl, —OR⁶, or —NR⁷R⁸; or R¹ and R² form an oxo;

R³ and R⁴ are each the same or different and independently hydrogen or alkyl;

R⁵ is $C_5$-$C_{15}$ alkyl, aralkyl, heterocyclylalkyl, heteroarylalkyl or carbocyclylalkyl;

R⁶ is hydrogen or alkyl;

R⁷ and R⁸ are each the same or different and independently hydrogen, alkyl, carbocyclyl, or —C(=O)R¹³; or R⁷ and R⁸, together with the nitrogen atom to which they are attached, form an N-heterocyclyl;

X is —C(R⁹)(R¹⁰)— or —O—;

R⁹ and R¹⁰ are each the same or different and independently hydrogen, halogen, alkyl, fluoroalkyl, —OR⁶, —NR⁷R⁸ or carbocyclyl; or R⁹ and R¹⁰ form an oxo;

R¹¹ and R¹² are each the same or different and independently hydrogen, alkyl, or —C(=O)R¹³; or R¹¹ and R¹², together with the nitrogen atom to which they are attached, form an N-heterocyclyl; and R¹³ is alkyl, alkenyl, aryl, carbocyclyl, heteroaryl or heterocyclyl.

In another embodiment is the compound of Formula (I) having a structure of Formula (Ia):

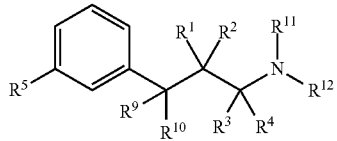

Formula (Ia)

as a tautomer or a mixture of tautomers, or as a pharmaceutically acceptable salt, hydrate, solvate, N-oxide or prodrug thereof, wherein:

R¹ and R² are each the same or different and independently hydrogen, halogen, $C_1$-$C_5$ alkyl, fluoroalkyl, —OR⁶, or —NR⁷R⁸; or R¹ and R² form an oxo;

R³ and R⁴ are each the same or different and independently hydrogen or alkyl;

R⁵ is $C_5$-$C_{15}$ alkyl, aralkyl, heterocyclylalkyl, heteroarylalkyl or carbocyclylalkyl;

R⁶ is hydrogen or alkyl;

R⁷ and R⁸ are each the same or different and independently hydrogen, alkyl, carbocyclyl, or —C(=O)R¹³; or R⁷ and R⁸, together with the nitrogen atom to which they are attached, form an N-heterocyclyl;

R⁹ and R¹⁰ are each the same or different and independently hydrogen, halogen, alkyl, fluoroalkyl, —OR⁶, —NR⁷R⁸ or carbocyclyl; or R⁹ and R¹⁰ form an oxo;

R¹¹ and R¹² are each the same or different and independently hydrogen, alkyl, or —C(=O)R¹³; or R¹¹ and R¹², together with the nitrogen atom to which they are attached, form an N-heterocyclyl; and R¹³ is alkyl, alkenyl, aryl, carbocyclyl, heteroaryl or heterocyclyl.

In a further embodiment is the compound of Formula (Ia) wherein each of R¹¹ and R¹² is hydrogen.

In a further embodiment is the compound of Formula (Ia) wherein each of R⁹ and R¹⁰ is independently hydrogen, halogen, alkyl or —OR⁶, wherein R⁶ is hydrogen or alkyl.

In a further embodiment is the compound of Formula (Ia) wherein R⁵ is $C_5$-$C_9$ alkyl, aralkyl, or carbocyclylalkyl.

In a further embodiment is the compound of Formula (Ia) wherein each of $R_1$, $R_2$, $R_3$ and $R_4$ is hydrogen;
each of $R_9$ and $R_{10}$ is independently hydrogen or —$OR_6$, wherein $R_6$ is hydrogen or alkyl; and
$R_5$ is $C_5$-$C_9$ alkyl.

In a further embodiment is the compound of Formula (Ia) wherein R⁵ is $C_5$-$C_9$ alkyl substituted with —OR⁶, wherein R⁶ is hydrogen or alkyl.

In a further embodiment is the compound of Formula (Ia) wherein
each of R¹, R², R³ and R⁴ is hydrogen;
each of R⁹ and R¹⁰ is independently hydrogen or —OR⁶, wherein R⁶ is hydrogen or alkyl; and
R⁵ is aralkyl.

In a further embodiment is the compound of Formula (Ia) wherein
each of R¹, R², R³ and R⁴ is hydrogen;
each of R⁹ and R¹⁰ is independently hydrogen or —OR⁶, wherein R⁶ is hydrogen or alkyl; and
R⁵ is carbocyclylalkyl.

In another embodiment is the compound of Formula (I) having a structure of Formula (Ib):

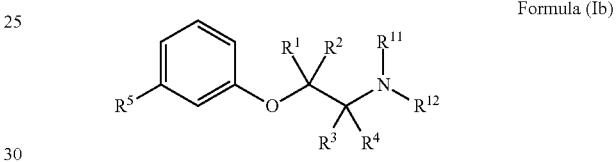

Formula (Ib)

as a tautomer or a mixture of tautomers, or as a pharmaceutically acceptable salt, hydrate, solvate, N-oxide or prodrug thereof, wherein:

R¹ and R² are each the same or different and independently hydrogen, $C_1$-$C_5$ alkyl, or fluoroalkyl;

R³ and R⁴ are each the same or different and independently hydrogen or alkyl;

R⁵ is $C_5$-$C_{15}$ alkyl, aralkyl, heterocyclylalkyl, heteroarylalkyl or carbocyclylalkyl;

R¹¹ and R¹² are each the same or different and independently hydrogen, alkyl, or —C(=O)R¹³; or R¹¹ and R¹², together with the nitrogen atom to which they are attached, form an N-heterocyclyl; and R¹³ is alkyl, alkenyl, aryl, carbocyclyl, heteroaryl or heterocyclyl.

In another embodiment is the compound of Formula (Ib) wherein R¹¹ and R¹² is hydrogen.

In another embodiment is the compound of Formula (Ib) wherein each of R³ and R⁴ is hydrogen.

In another embodiment is the compound of Formula (Ib) wherein
each of R¹, R², R³ and R⁴ is hydrogen, and
R⁵ is $C_5$-$C_9$ alkyl, carbocyclylalkyl, heteroarylalkyl, or heterocyclylalkyl.

In a further embodiment is the compound of Formula (I) selected from the group consisting of:
3-(3-pentylphenyl)propan-1-amine;
3-(3-hexylphenyl)propan-1-amine;
3-(3-(3,3-dimethylbutyl)phenyl)propan-1-amine;
3-(3-(octan-4-yl)phenyl)propan-1-amine;
4-(3-(3-aminopropyl)phenyl)butan-1-ol;
6-(3-(3-aminopropyl)phenyl)hexan-1-ol;
3-(3-(6-methoxyhexyl)phenyl)propan-1-amine;
4-(3-(3-aminopropyl)phenethyl)heptan-4-ol;
1-(3-(3-aminopropyl)phenyl)-3-ethylpentan-3-ol;
4-(3-(3-aminopropyl)phenyl)-2-methylbutan-2-ol;
3-(3-(3-aminopropyl)phenyl)propan-1-ol;

3-(3-(3-methoxypropyl)phenyl)propan-1-amine;
1-(3-(3-aminopropyl)phenyl)hexan-3-ol;
4-(3-(3-amino-1-hydroxypropyl)phenethyl)heptan-4-ol;
3-(3-(2,6-dimethylphenethyl)phenyl)propan-1-amine;
3-(3-phenethylphenyl)propan-1-amine;
3-(3-(3-phenylpropyl)phenyl)propan-1-amine;
3-amino-1-(3-(3-phenylpropyl)phenyl)propan-1-ol;
3-(3-(2-methylphenethyl)phenyl)propan-1-amine;
3-(3-(2-(biphenyl-3-yl)ethyl)phenyl)propan-1-amine;
3-(3-(4-phenylbutyl)phenyl)propan-1-amine;
3-(3-(2-(naphthalen-2-yl)ethyl)phenyl)propan-1-amine;
3-(3-(2-cyclohexylethyl)phenyl)propan-1-amine;
3-(3-(2-cyclopentylethyl)phenyl)propan-1-amine;
3-amino-1-(3-(2-cyclopentylethyl)phenyl)propan-1-ol;
1-(3-(3-aminopropyl)phenethyl)cyclohexanol;
1-(3-(3-amino-1-hydroxypropyl)phenethyl)cyclohexanol;
1-(3-(3-aminopropyl)phenethyl)cycloheptanol;
1-(3-(3-amino-1-hydroxypropyl)phenethyl)cycloheptanol;
4-(3-(2-aminoethoxy)phenethyl)heptan-4-ol;
1-(3-(2-aminoethoxy)phenethyl)cyclohexanol;
1-(3-(2-aminoethoxy)phenethyl)cycloheptanol;
4-(3-(2-aminoethoxy)phenethyl)tetrahydro-2H-thiopyran-4-ol;
6-(3-(2-aminoethoxy)phenyl)hexan-1-ol;
2-(3-(3-cyclopentylpropyl)phenoxy)ethanamine;
2-(3-(2-(pyridin-3-yl)ethyl)phenoxy)ethanamine;
2-(3-(2-(pyridin-2-yl)ethyl)phenoxy)ethanamine; and
2-(3-(2-(thiophen-2-yl)ethyl)phenoxy)ethanamine.

In another embodiment is the compound of Formula (B) wherein,
G is selected from —C(R$^{42}$)$_2$—S—R$^{40}$, —C(R$^{42}$)$_2$—SO—R$^{40}$, —C(R$^{42}$)$_2$—SO$_2$—R$^{40}$, —C(R$^{42}$)$_2$—O—R$^{40}$, —C(R$^{42}$)$_2$—N(R$^{42}$)—R$^{40}$, —C(=O)—N(R$^{42}$)—R$^{40}$;
R$^{40}$ is selected from —C(R$^{16}$)(R$^{17}$)(R$^{18}$), aryl, or heteroaryl;
R$^{42}$ is selected from hydrogen or alkyl.

In another embodiment is the compound of Formula (B) wherein,
G is selected from from —C(R$^{42}$)$_2$—S—R$^{40}$, —C(R$^{42}$)$_2$—SO—R$^{40}$, —C(R$^{42}$)$_2$—SO$_2$—R$^{40}$, —C(R$^{42}$)$_2$—O—R$^{40}$, —C(R$^{42}$)$_2$—N(R$^{42}$)—R$^{40}$, —C(=O)—N(R$^{42}$)—R$^{40}$;
R$^{40}$ is selected from —C(R$^{16}$)(R$^{17}$)(R$^{18}$), aryl, or heteroaryl;
R$^{42}$ is selected from hydrogen or alkyl.

In another embodiment is the compound of Formula (B) wherein,
G is selected from from —C(R$^{42}$)$_2$—S—R$^{40}$, —C(R$^{42}$)$_2$—SO—R$^{40}$, —C(R$^{42}$)$_2$—SO$_2$—R$^{40}$, —C(R$^{42}$)$_2$—O—R$^{40}$.

In another embodiment is the compound of Formula (B) wherein,
G is selected from —C(R$^{42}$)$_2$—N(R$^{42}$)—R$^{40}$, —C(=O)—N(R$^{42}$)—R$^{40}$.

In another embodiment is the compound of Formula (B) wherein,
G is selected from —C(R$^{42}$)$_2$—N(R$^{42}$)—R$^{40}$, —C(=O)—N(R$^{42}$)—R$^{40}$.

In another embodiment is the compound of Formula (B) wherein,
R$^{42}$ is a hydrogen or C$_1$-C$_3$ alkyl; and
R$^{40}$ is aryl or heteroaryl.

In another embodiment is the compound of Formula (B) wherein,
R$^{40}$ is selected from —C(R$^{16}$)(R$^{17}$)(R$^{18}$);
R$^{16}$ and R$^{17}$ are each independently selected from hydrogen, alkyl, halo, aryl, heteroaryl, aralkyl, heteroaryalkyl or fluoroalkyl; and
R$^{18}$ is selected from hydrogen, alkyl, alkoxy, hydroxy, halo or fluoroalkyl.

In another embodiment is the compound of Formula (B) wherein,
R$^{40}$ is selected from —C(R$^{16}$)(R$^{17}$)(R$^{18}$);
R$^{16}$ and R$^{17}$ are each independently selected from hydrogen, alkyl, halo, aryl, heteroaryl, aralkyl, heteroaryalkyl or fluoroalkyl; or R$^{16}$ and R$^{17}$, together with the carbon to which they are attached form a carbocyclyl or heterocycle;
R$^{18}$ is selected from hydrogen, alkyl, alkoxy, hydroxy, halo or fluoroalkyl.

In an additional embodiment is the compound of Formula (A) wherein one, more than one, or all of the non-exchangeable $^1$H atoms have been substituted with $^2$H atoms.

In a further embodiment is the compound of Formula (A) selected from the group consisting of:

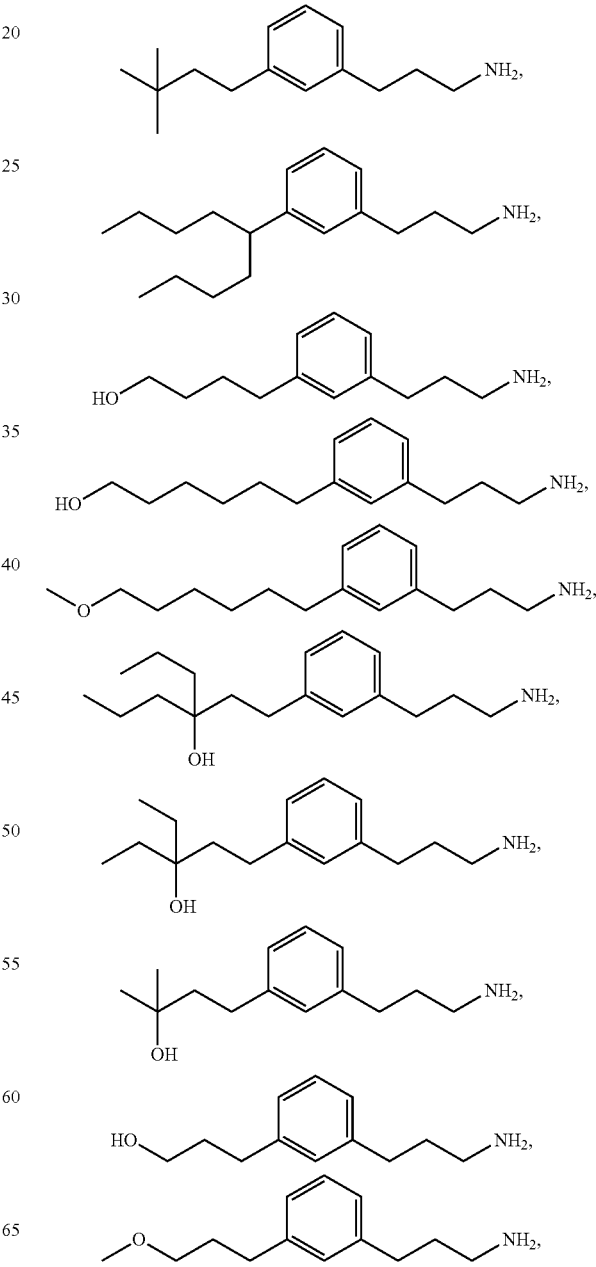

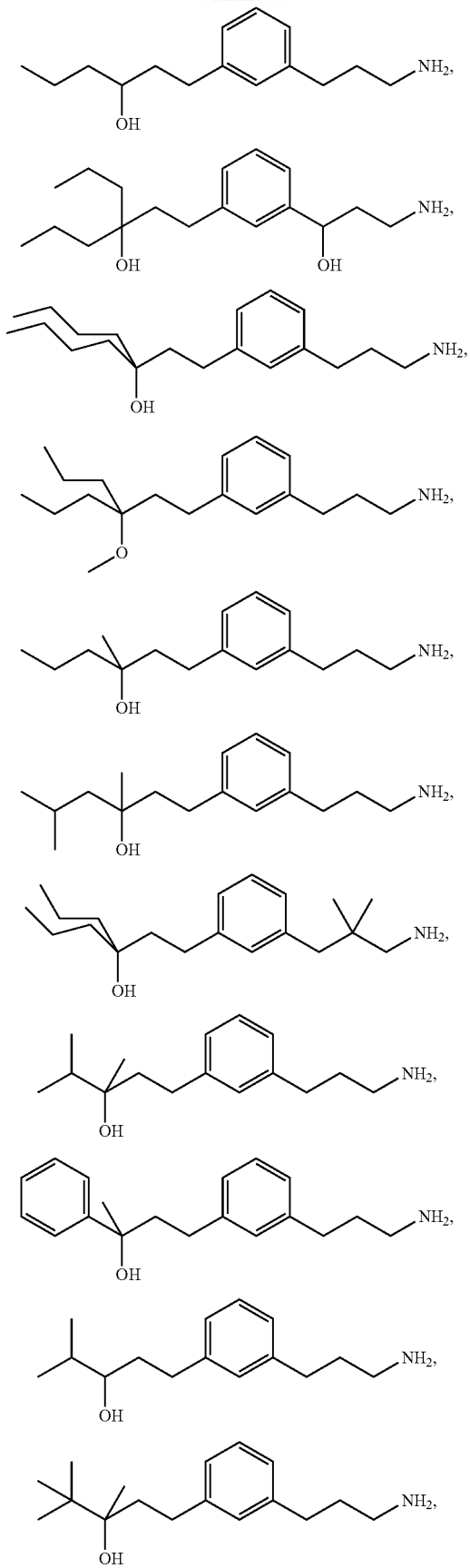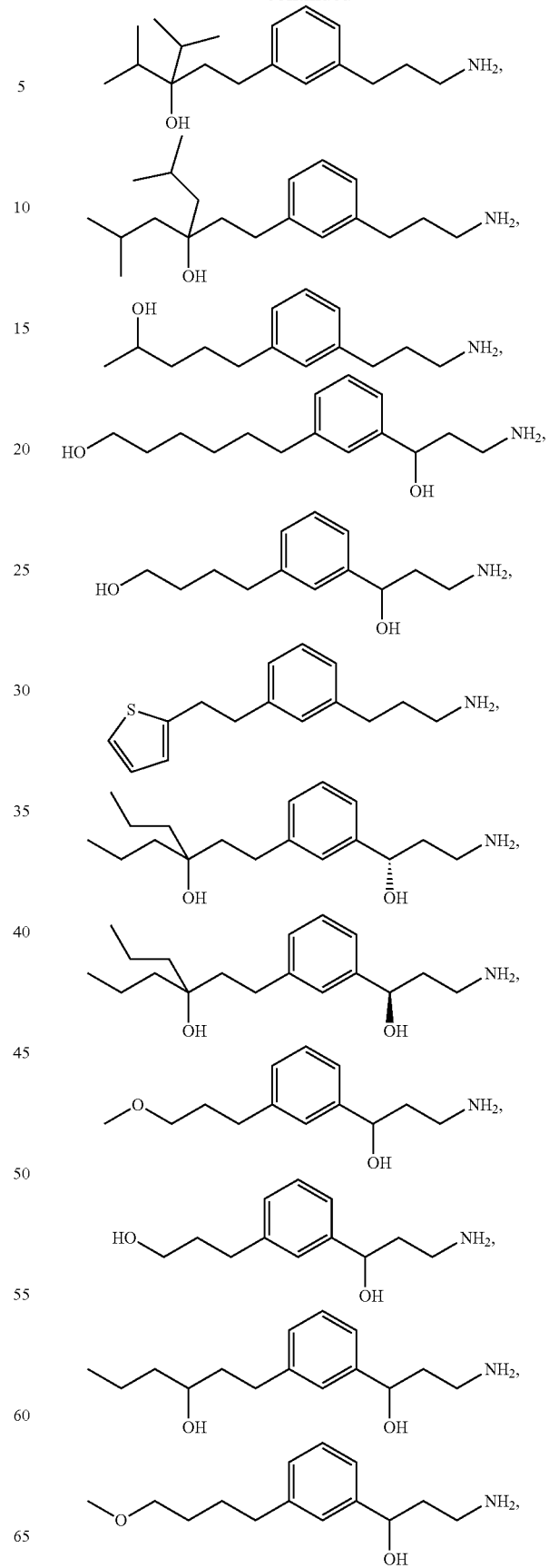

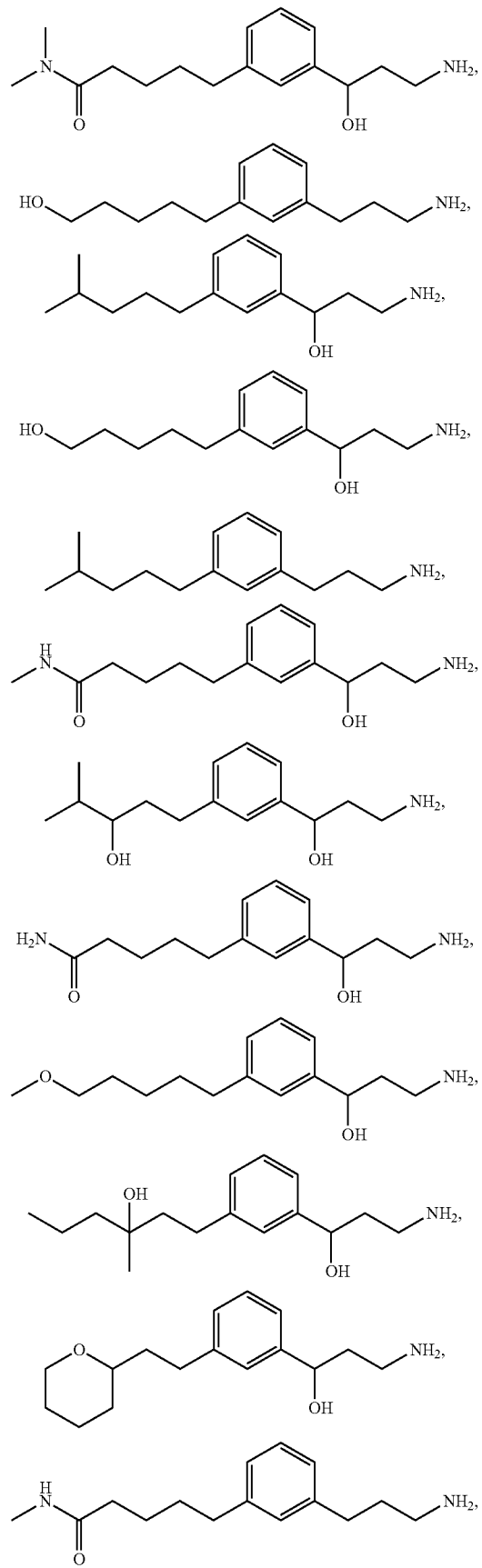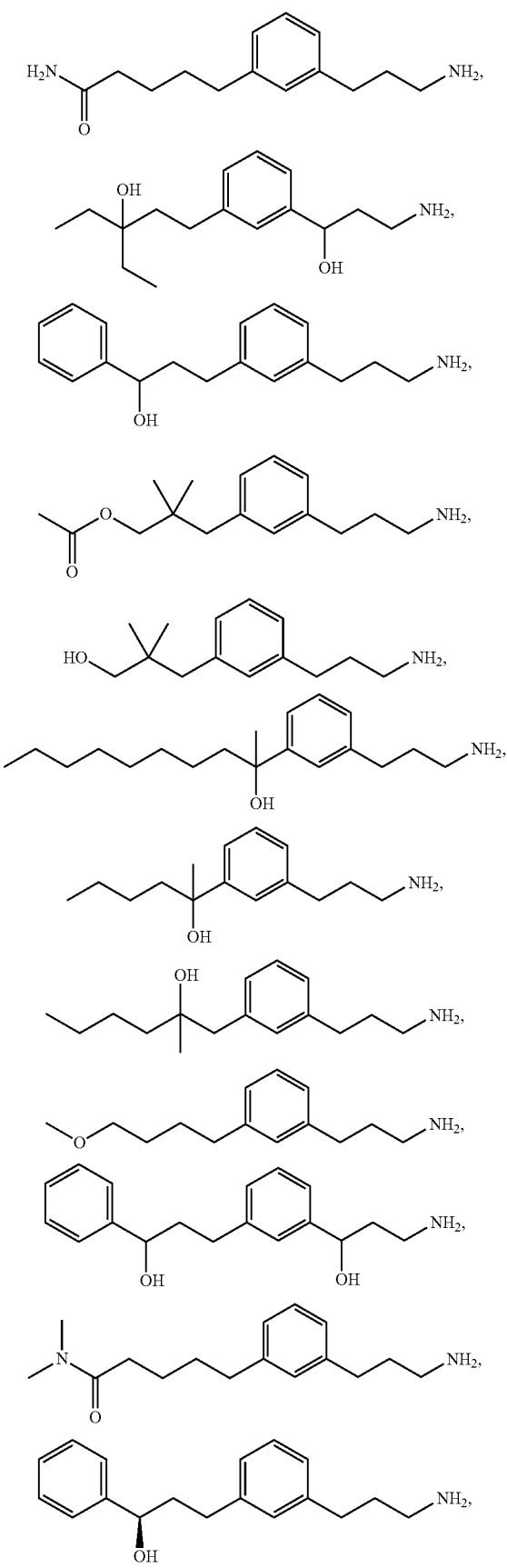

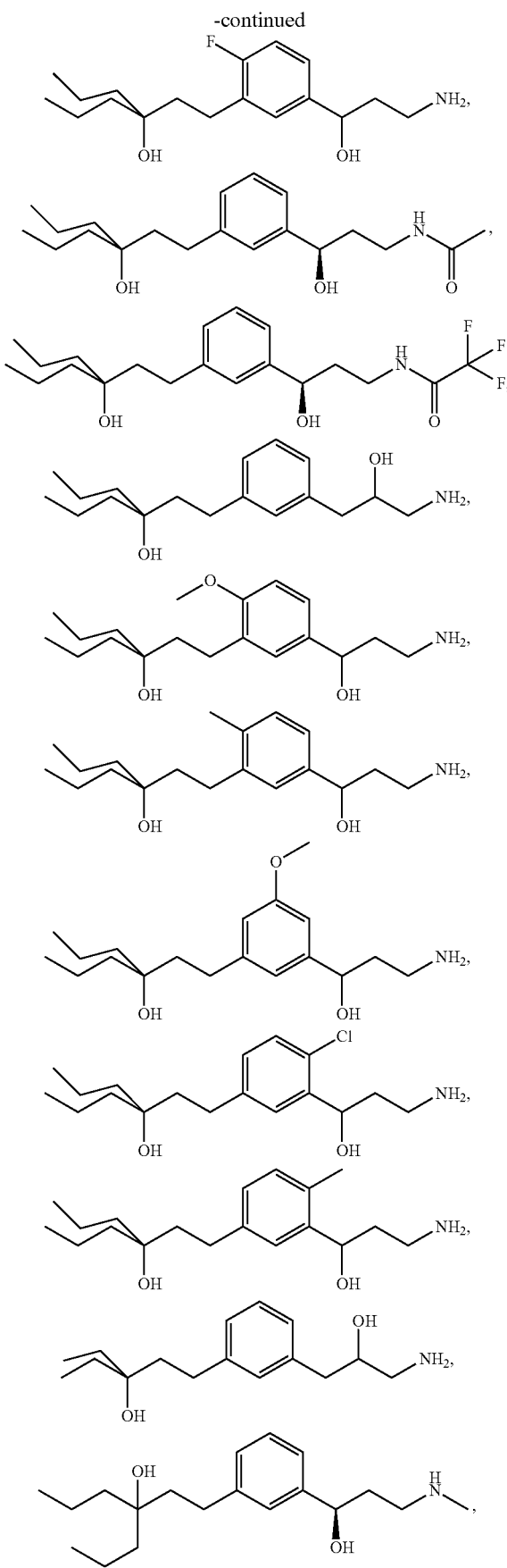
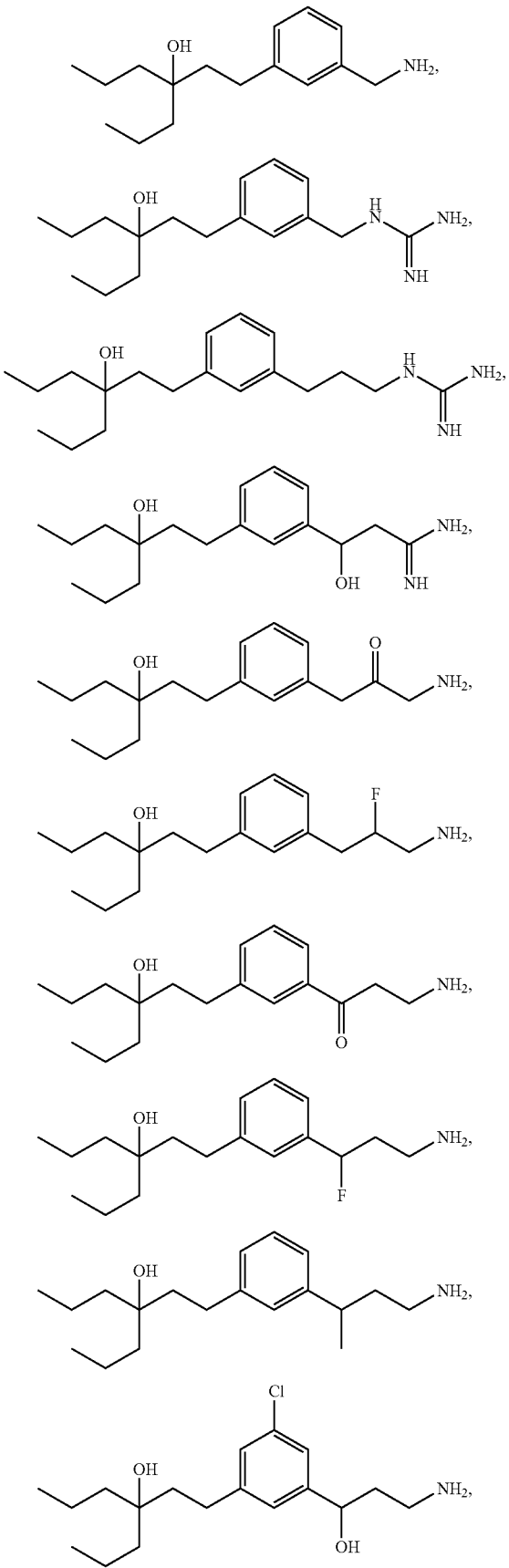

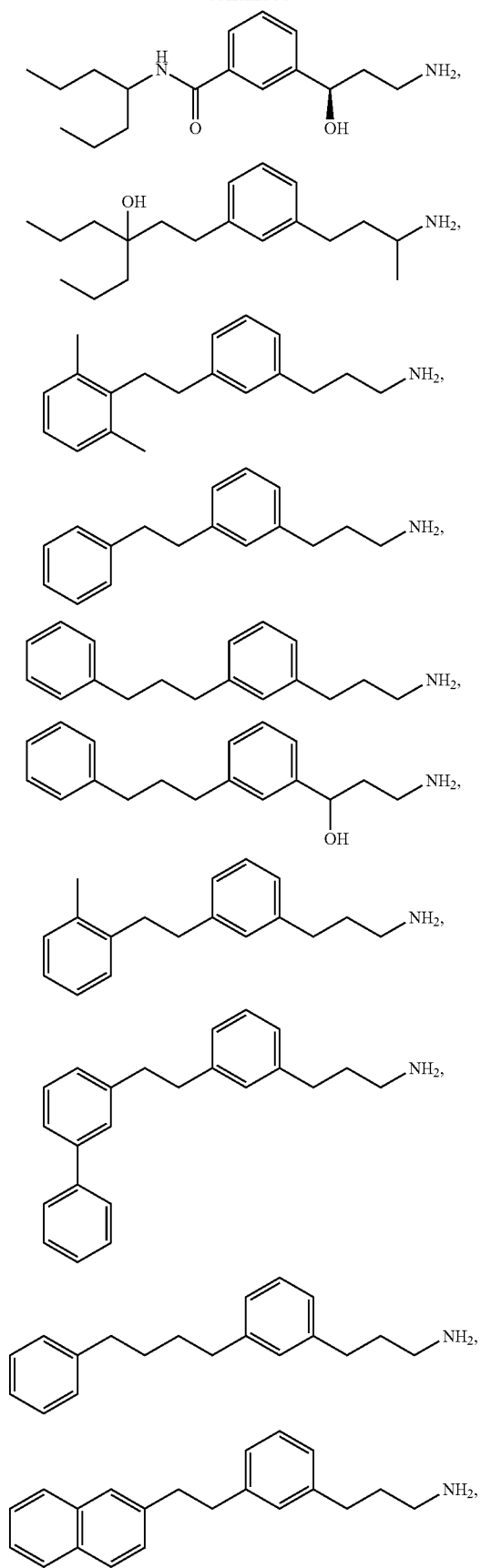
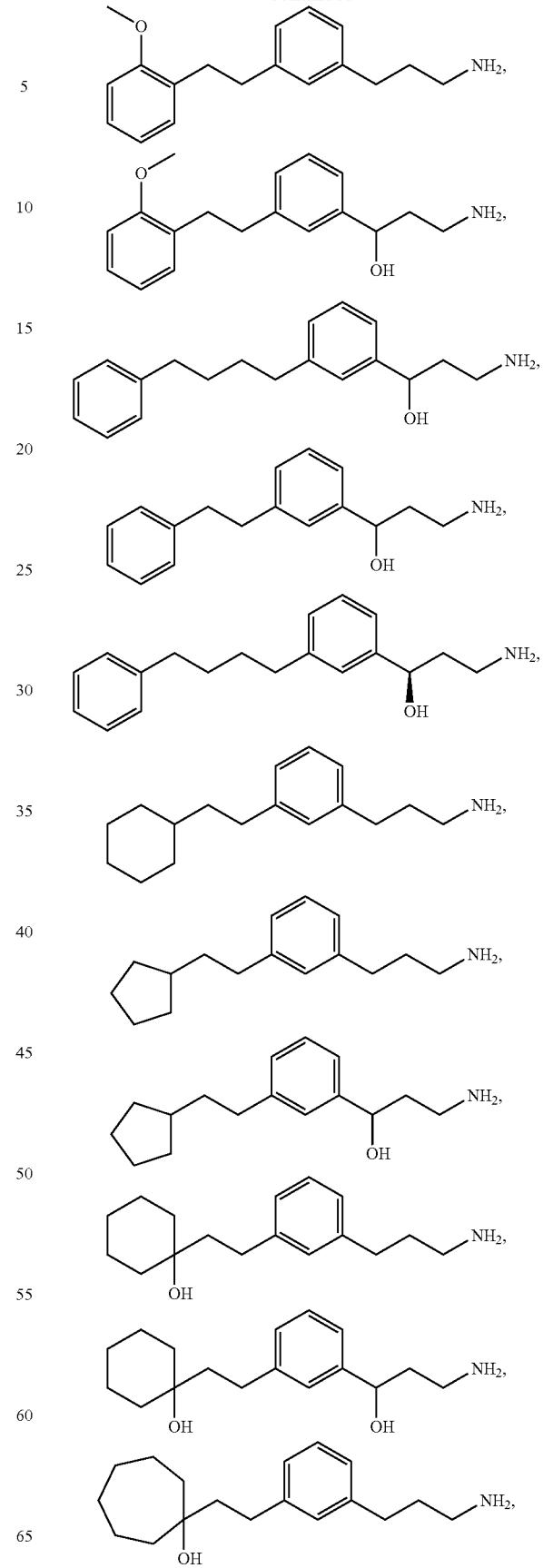

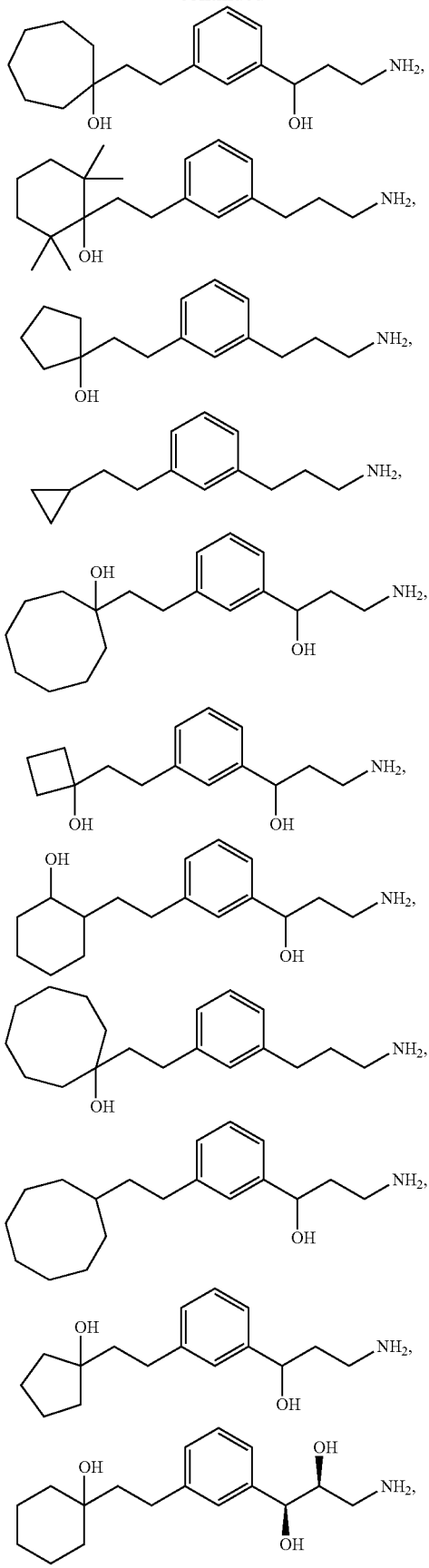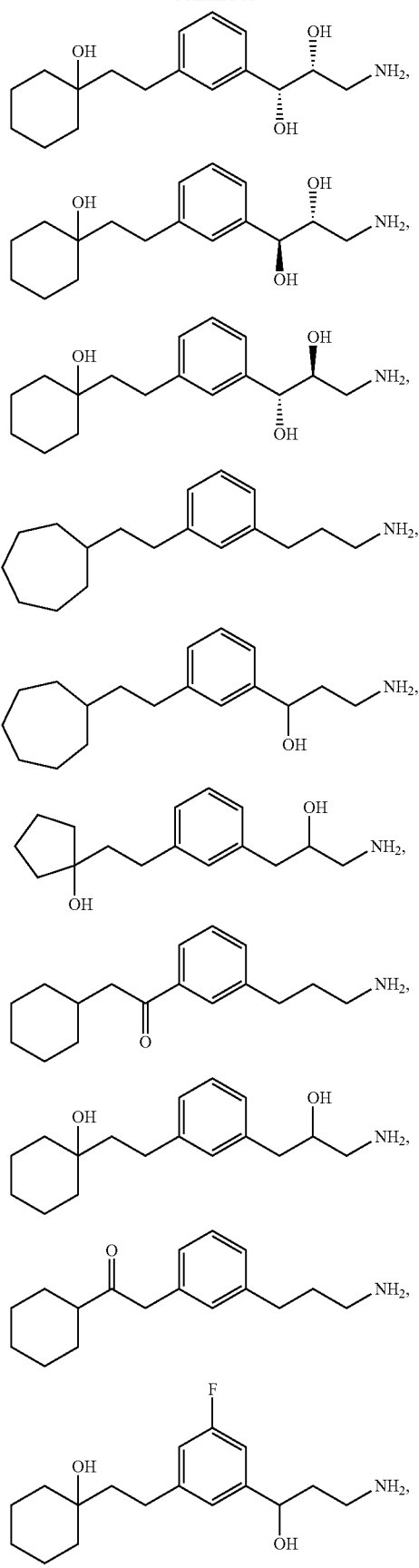

27
-continued
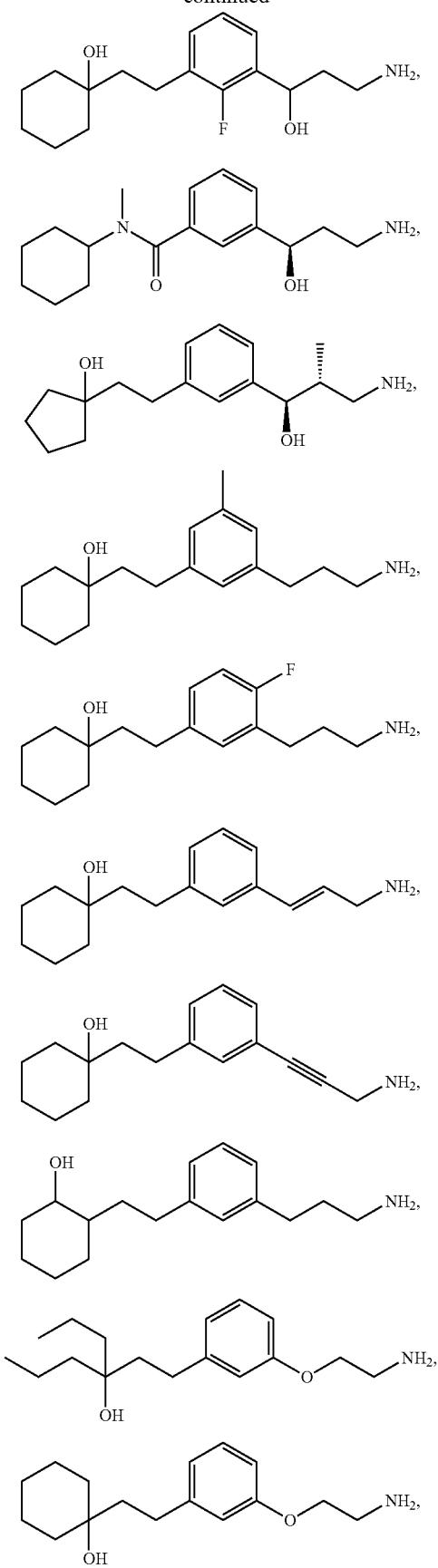
28
-continued
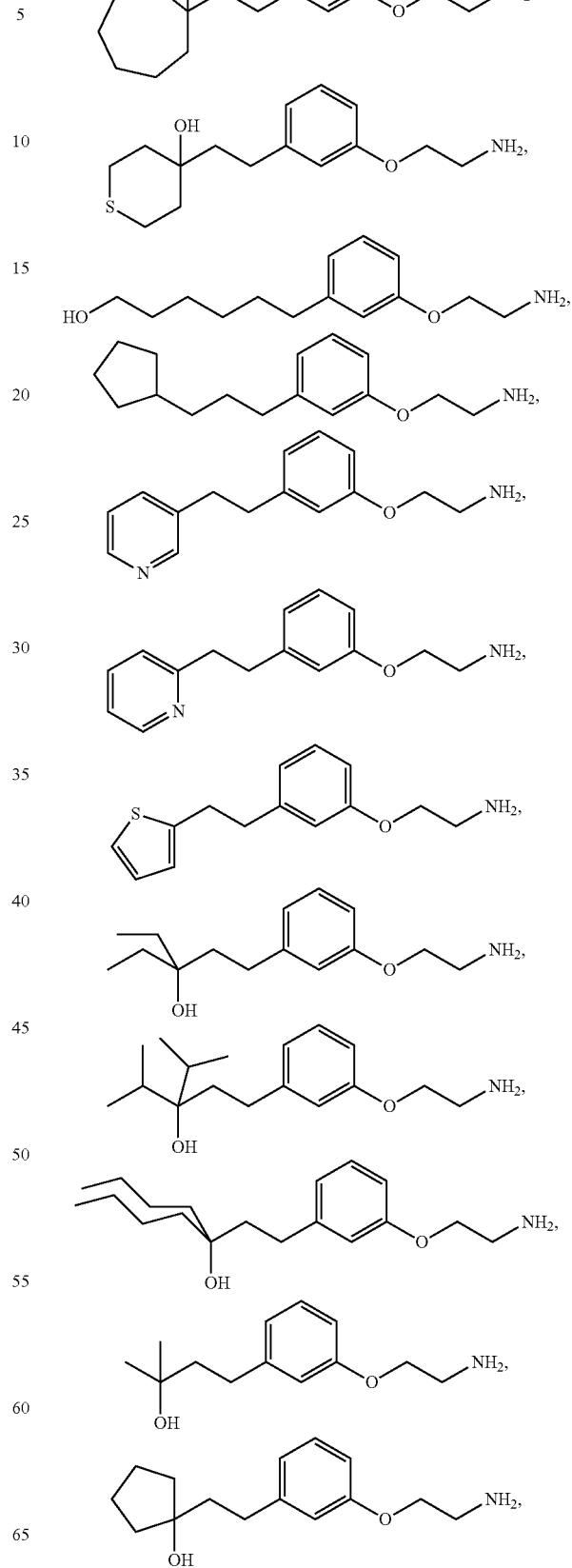

-continued
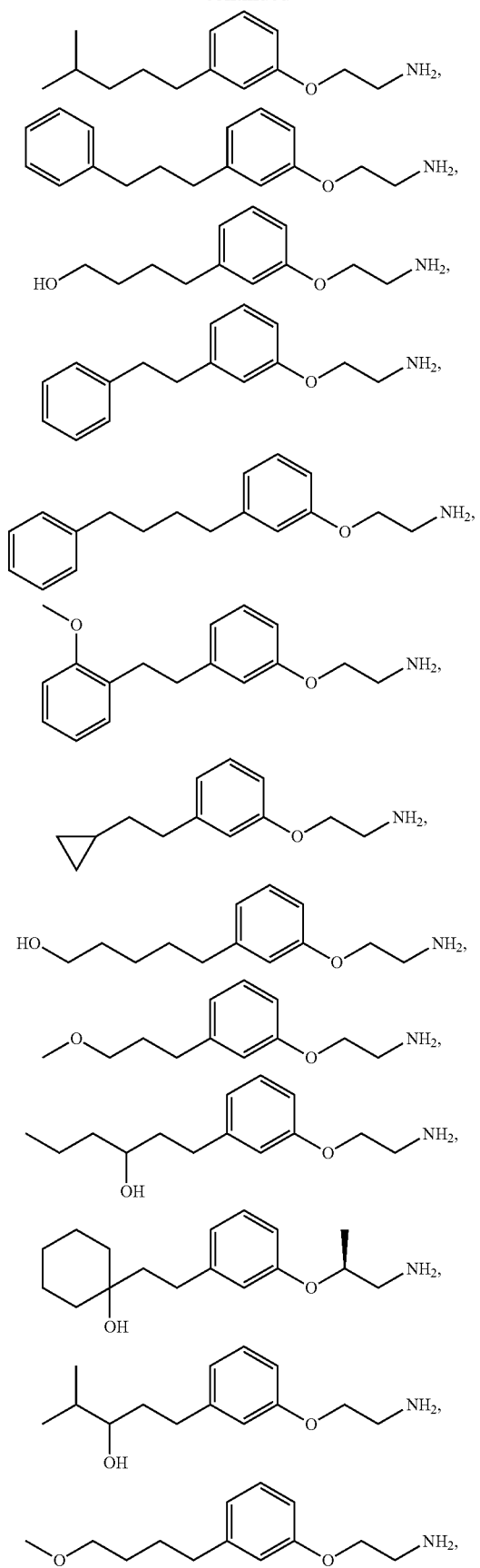
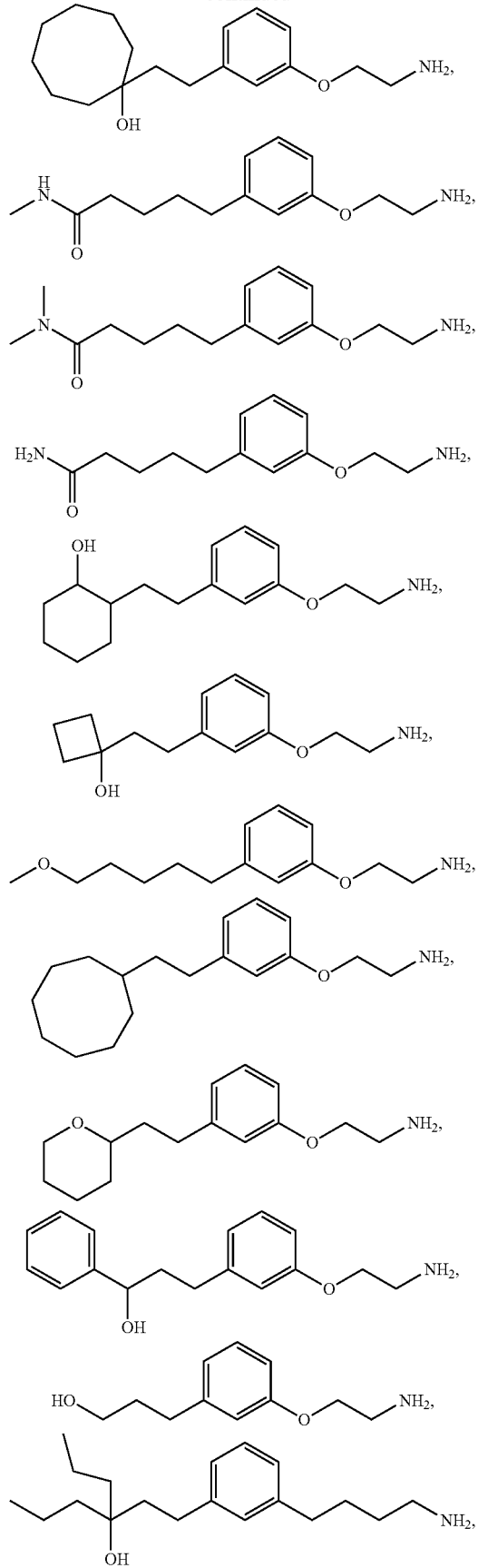

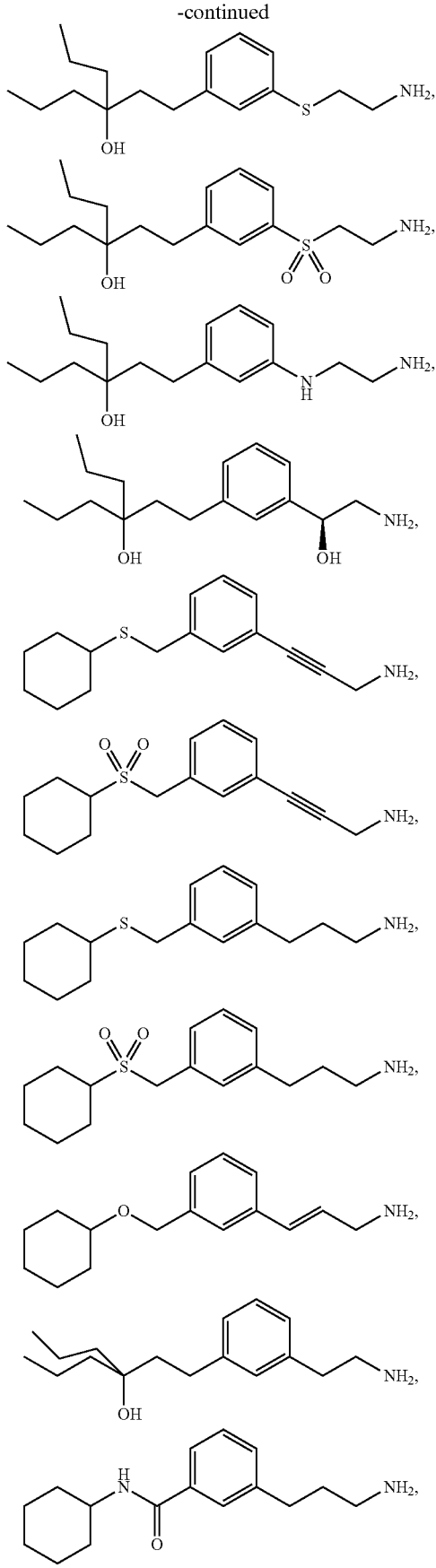

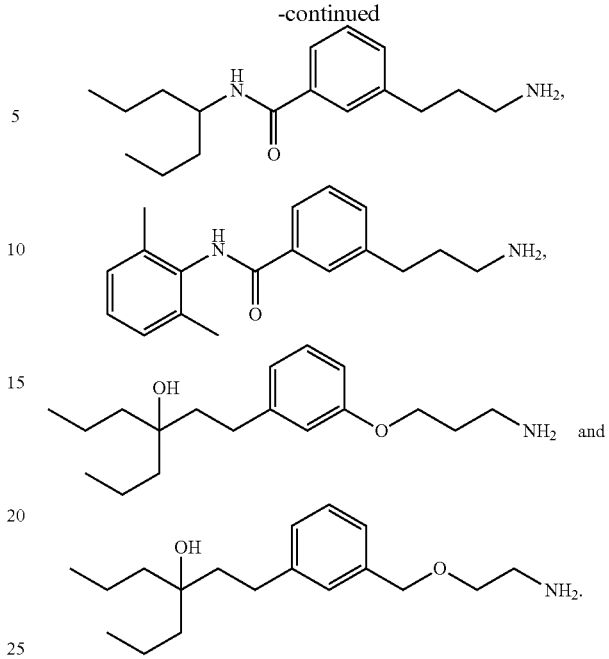

In one embodiment is a pharmaceutical composition comprising a pharmaceutically acceptable carrier and a compound of Formula (A) or tautomer, stereoisomer, geometric isomer, or pharmaceutically acceptable solvate, hydrate, salt, N-oxide or prodrug thereof:

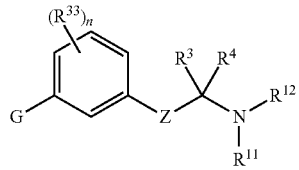

Formula (A)

wherein,

Z is a bond, —C(R$^1$)(R$^2$)—, —C(R$^9$)(R$^{10}$)—C(R$^1$)(R$^2$)—, —X—C(R$^{31}$)(R$^{32}$)—, —C(R$^9$)(R$^{10}$)—C(R$^1$)(R$^2$)—C(R$^{36}$)(R$^{37}$)— or —X—C(R$^{31}$)(R$^{32}$)—C(R$^1$)(R$^2$)—;

X is —O—, —S—, —S(=O)—, —S(=O)$_2$—, —N(R$^{30}$)—, —C(=O)—, —C(=CH$_2$)—, —C(=N—NR$^{35}$)—, or —C(=N—OR$^{35}$)—;

G is selected from —C(R$^{41}$)$_2$—C(R$^{41}$)$_2$—R$^{40}$, —C(R$^{42}$)$_2$—S—R$^{40}$, —C(R$^{42}$)$_2$—SO—R$^{40}$, —C(R$^{42}$)$_2$—SO$_2$—R$^{40}$, —C(R$^{42}$)$_2$—O—R$^{40}$, —C(R$^{42}$)$_2$—N(R$^{42}$)—R$^{40}$, —C(=O)—N(R$^{42}$)—R$^{40}$;

R$^{40}$ is selected from —C(R$^{16}$)(R$^{17}$)(R$^{18}$), aryl, or heteroaryl;

each R$^{41}$ is independently selected from hydrogen, hydroxy, OR$^6$, alkyl, or two R$^{41}$ groups together may form an oxo;

each R$^{42}$ is independently selected from hydrogen or alkyl;

R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;

R$^{31}$ and R$^{32}$ are each independently selected from hydrogen, C$_1$-C$_5$ alkyl, or fluoroalkyl;

R$^{36}$ and R$^{37}$ are each independently selected from hydrogen, halogen, C$_1$-C$_5$ alkyl, fluoroalkyl, —OR$^6$ or —NR$^7$R$^8$; or R$^{36}$ and R$^{37}$ together form an oxo; or optionally, R$^{36}$ and R$^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^7$ and $R^8$ are each independently selected from hydrogen, alkyl, carbocyclyl, heterocyclyl, —C(=O)$R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroaryalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, $OR^{34}$, alkyl, or fluoroalkyl; and n is 0, 1, 2, 3, or 4; with the provision that G is not an unsubstituted normal alkyl and the provision that the compound of Formula A is not:

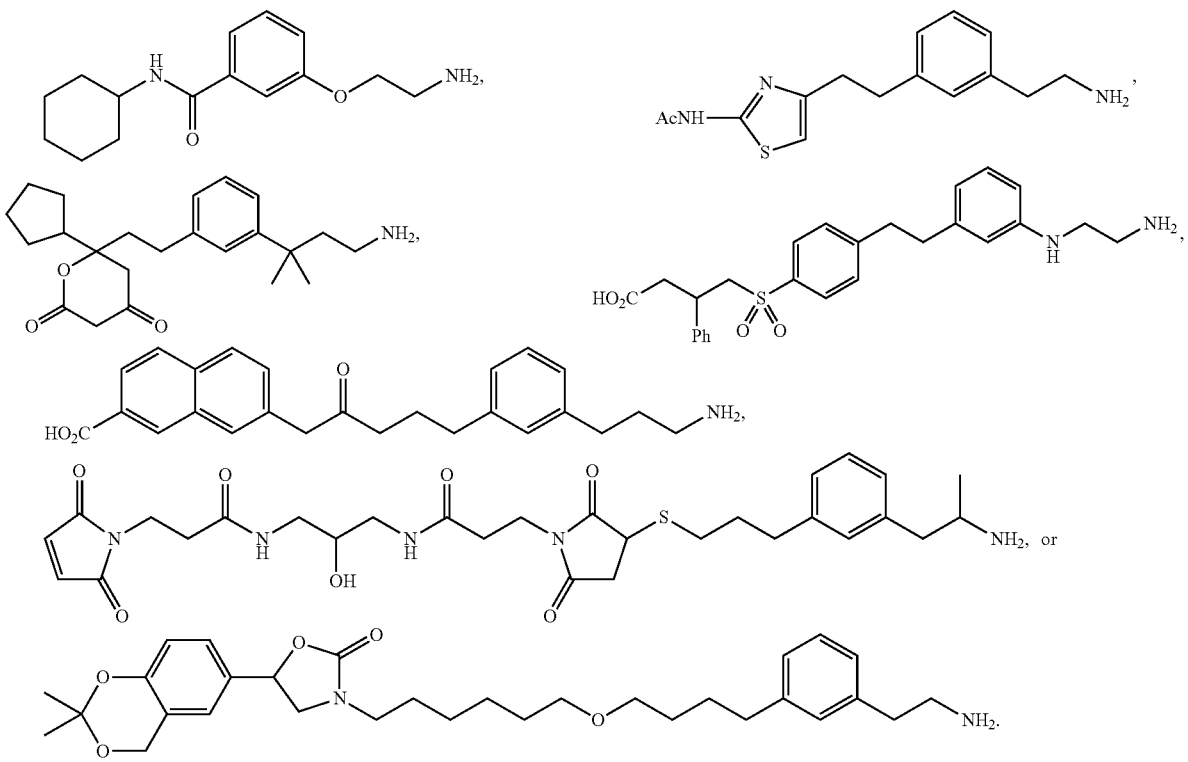

$R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)$R^{23}$, —C(NH)$NH_2$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl; and In an additional embodiment is a non-retinoid compound that inhibits an isomerase reaction resulting in production of 11-cis retinol, wherein said isomerase reaction occurs in RPE, and wherein said compound has an $ED_{50}$ value of 1 mg/kg or less when administered to a subject. In a further embodiment is the non-retinoid compound wherein the $ED_{50}$ value is measured after administering a single dose of the compound to said subject for about 2 hours or longer. In a further embodiment is the non-retinoid compound, wherein the non-retinoid compound is an alkoxyl compound. In an additional embodiment is a pharmaceutical composition comprising a pharmaceutically acceptable carrier and a non-retinoid compound as described herein. In an additional embodiment is a method for treating an ophthalmic disease or disorder in a subject, comprising administering to the subject a pharmaceutical composition comprising a pharmaceutically acceptable carrier and a non-retinoid compound as described herein.

In an additional embodiment is a compound that inhibits 11-cis-retinol production with an $IC_{50}$ of about 1 μM or less when assayed in vitro, utilizing extract of cells that express RPE65 and LRAT, wherein the extract further comprises CRALBP, wherein the compound is stable in solution for at least about 1 week at room temperature. In a further embodiment, the compound inhibits 11-cis-retinol production with an $IC_{50}$ of about 0.1 µM or less. In a further embodiment, the compound inhibits 11-cis-retinol production with an $IC_{50}$ of about 0.01 µM or less. In a further embodiment, the compound that inhibits 11-cis-retinol production is a non-retinoid compound. In an additional embodiment is a pharmaceutical composition comprising a pharmaceutically acceptable carrier and a compound that inhibits 11-cis-retinol production as described herein. In an additional embodiment is a method for treating an ophthalmic disease or disorder in a subject, comprising administering to the subject a pharmaceutical composition comprising a pharmaceutically acceptable carrier and a compound that inhibits 11-cis-retinol production as described herein. In an additional embodiment is a method of modulating chromophore flux in a retinoid cycle comprising introducing into a subject a compound that inhibits 11-cis-retinol production as described herein.

In an additional embodiment is a method for treating an ophthalmic disease or disorder in a subject, comprising administering to the subject a compound of Formula (G) or tautomer, stereoisomer, geometric isomer or a pharmaceutically acceptable solvate, hydrate, salt, N-oxide or prodrug thereof:

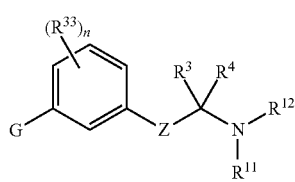

Formula (G)

wherein,
Z is a bond, —C($R^1$)($R^2$)—, —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)— or —X—C($R^{31}$)($R^{32}$)—C($R^1$)($R^2$)—;

X is —O—, —S—, —S(=O)—, —S(=O)$_2$—, —N($R^{30}$)—, —C(=O)—, —C(=CH$_2$)—, —C(=N—N$R^{35}$)—, or —C(=N—O$R^{35}$)—;

G is selected from —C($R^{41}$)$_2$—C($R^{41}$)$_2$—$R^{40}$, —C($R^{42}$)$_2$—S—$R^{40}$, —C($R^{42}$)$_2$—SO—$R^{40}$, —C($R^{42}$)$_2$—SO$_2$—$R^{40}$, —C($R^{42}$)$_2$—O—$R^{40}$, —C($R^{42}$)$_2$—N($R^{42}$)—$R^{40}$, —C(=O)—N($R^{42}$)—$R^{40}$;

$R^{40}$ is selected from —C($R^{16}$)($R^{17}$)($R^{18}$), aryl, or heteroaryl;
each $R^{41}$ is independently selected from hydrogen, hydroxy, $OR^6$, alkyl, or two $R^{41}$ groups together may form an oxo;
each $R^{42}$ is independently selected from hydrogen or alkyl;
$R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;
$R^{31}$ and $R^{32}$ are each independently selected from hydrogen, $C_1$-$C_5$ alkyl, or fluoroalkyl;
$R^{36}$ and $R^{37}$ are each independently selected from hydrogen, halogen, $C_1$-$C_5$ alkyl, fluoroalkyl, —$OR^6$ or —$NR^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;
$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^5$ is $C_5$-$C_{15}$ alkyl or carbocyclyalkyl;
$R^7$ and $R^8$ are each independently selected from hydrogen, alkyl, carbocyclyl, heterocyclyl, —C(=O)$R^{13}$, SO$_2R^{13}$, CO$_2R^{13}$ or SO$_2NR^{24}R^{25}$; or $R^7$ and $R^8$ together with the nitrogen atom to which they are attached, form an N-heterocyclyl;
$R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;
$R^{11}$ and $R^{12}$ are each independently selected from hydrogen, alkyl, carbocyclyl, —C(=O)$R^{23}$, —C(NH)NH$_2$, SO$_2R^{23}$, CO$_2R^{23}$ or SO$_2NR^{28}R^{29}$; or $R^{11}$ and $R^{12}$, together with the nitrogen atom to which they are attached, form an N-heterocyclyl;
each $R^{13}$, $R^{22}$ and $R^{23}$ is independently selected from alkyl, heteroalkyl, alkenyl, aryl, aralkyl, carbocyclyl, heteroaryl or heterocyclyl;
$R^6$, $R^{19}$, $R^{30}$, $R^{34}$ and $R^{35}$ are each independently hydrogen or alkyl;
$R^{20}$ and $R^{21}$ are each independently selected from hydrogen, alkyl, carbocyclyl, heterocyclyl, —C(=O)$R^{22}$, SO$_2R^{22}$, CO$_2R^{22}$ or SO$_2NR^{26}R^{27}$; or $R^{20}$ and $R^{21}$ together with the nitrogen atom to which they are attached, form an N-heterocyclyl; and
each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;
$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;
$R^{18}$ is selected from hydrogen, alkyl, alkoxy, hydroxy, halo or fluoroalkyl;
each $R^{33}$ is independently selected from halogen, $OR^{34}$, alkyl, or fluoroalkyl; and n is 0, 1, 2, 3, or 4.

In an additional embodiment is a method of modulating chromophore flux in a retinoid cycle comprising introducing into a subject a compound of Formula (G). In a further embodiment is the method resulting in a reduction of lipofuscin pigment accumulated in an eye of the subject. In a further embodiment is the method resulting in a reduction of lipofuscin pigment accumulated in an eye of the subject, wherein the lipofuscin pigment is N-retinylidene-N-retinyl-ethanolamine (A2E).

In a further embodiment is the method of treating an ophthalmic disease or disorder in a subject as described herein resulting in a reduction of lipofuscin pigment accumulated in an eye of the subject. In a further embodiment is the method of treating an ophthalmic disease or disorder in a subject as described herein resulting in a reduction of lipofuscin pigment accumulated in an eye of the subject, wherein the lipofuscin pigment is N-retinylidene-N-retinyl-ethanolamine (A2E).

In a further embodiment is the method of treating an ophthalmic disease or disorder in a subject as described herein, wherein the ophthalmic disease or disorder is age-related macular degeneration or Stargardt's macular dystrophy. In a further embodiment is the method of treating an ophthalmic disease or disorder in a subject as described herein, wherein the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS. In a further embodiment is the method of treating an ophthalmic disease or disorder in a subject as described herein resulting in a reduction of lipofuscin pigment accumulated in an eye of the subject. In a further embodiment is the method of treating an ophthalmic disease or disorder in a subject as described herein resulting in a reduction of lipofuscin pigment accumulated in an eye of the subject, wherein the lipofuscin pigment is N-retinylidene-N-retinyl-ethanolamine (A2E).

In another embodiment is a method of inhibiting dark adaptation of a rod photoreceptor cell of the retina comprising contacting the retina with a compound of Formula (G). In another embodiment is a method of inhibiting dark adaptation of a rod photoreceptor cell of the retina comprising contacting the retina with a non-retinoid compound as described herein. In another embodiment is a method of inhibiting dark adaptation of a rod photoreceptor cell of the retina comprising contacting the retina with a compound that inhibits 11-cis-retinol production as described herein.

In another embodiment is a method of inhibiting regeneration of rhodopsin in a rod photoreceptor cell of the retina comprising contacting the retina with a compound of Formula (G). In another embodiment is a method of inhibiting regeneration of rhodopsin in a rod photoreceptor cell of the retina comprising contacting the retina with a non-retinoid compound as described herein. In another embodiment is a method of inhibiting regeneration of rhodopsin in a rod photoreceptor cell of the retina comprising contacting the retina with a compound that inhibits 11-cis-retinol production as described herein.

In another embodiment is a method of reducing ischemia in an eye of a subject comprising administering to the subject a pharmaceutical composition comprising a pharmaceutically acceptable carrier and a compound of Formula (G). In an additional embodiment is a method of reducing ischemia in an eye of a subject comprising administering to the subject a pharmaceutical composition comprising a pharmaceutically acceptable carrier and a non-retinoid compound as described herein. In an additional embodiment is a method of reducing ischemia in an eye of a subject comprising administering to the subject a pharmaceutical composition comprising a pharmaceutically acceptable carrier and a compound that inhibits 11-cis-retinol production as described herein. In a further embodiment is the method of reducing ischemia in an eye of a subject, wherein the pharmaceutical composition is administered under conditions and at a time sufficient to inhibit dark adaptation of a rod photoreceptor cell, thereby reducing ischemia in the eye.

In an additional embodiment is a method of inhibiting neovascularization in the retina of an eye of a subject comprising administering to the subject a pharmaceutical composition comprising a pharmaceutically acceptable carrier and a non-retinoid compound as described herein. In an additional embodiment is a method of inhibiting neovascularization in the retina of an eye of a subject comprising administering to the subject a pharmaceutical composition comprising a pharmaceutically acceptable carrier and a compound that inhibits 11-cis-retinol production as described herein. In a further embodiment is the method of inhibiting neovascularization in the retina of an eye of a subject, wherein the pharmaceutical composition is administered under conditions and at a time sufficient to inhibit dark adaptation of a rod photoreceptor cell, thereby inhibiting neovascularization in the retina.

In an additional embodiment is a method of inhibiting degeneration of a retinal cell in a retina comprising contacting the retina with a compound of Formula (G). In an additional embodiment is a method of inhibiting degeneration of a retinal cell in a retina comprising contacting the retina with a non-retinoid compound as described herein. In an additional embodiment is a method of inhibiting degeneration of a retinal cell in a retina comprising contacting the retina with a compound that inhibits 11-cis-retinol production as described herein.

In a further embodiment is the method of inhibiting degeneration of a retinal cell in a retina wherein the retinal cell is a retinal neuronal cell. In a further embodiment is the method of inhibiting degeneration of a retinal cell in a retina wherein the retinal neuronal cell is a photoreceptor cell.

In another embodiment is a method of reducing lipofuscin pigment accumulated in a subject's retina comprising administering to the subject a pharmaceutical composition comprising a pharmaceutically acceptable carrier and a compound of Formula (G). In an additional embodiment is a method of reducing lipofuscin pigment accumulated in a subject's retina wherein the lipofuscin is N-retinylidene-N-retinyl-ethanolamine (A2E).

In an additional embodiment is a method of inhibiting reducing lipofuscin pigment accumulated in a subject's retina comprising administering to the subject a pharmaceutical composition comprising a pharmaceutically acceptable carrier and a non-retinoid compound as described herein. In an additional embodiment is a method of reducing lipofuscin pigment accumulated in a subject's retina comprising administering to the subject a pharmaceutical composition comprising a pharmaceutically acceptable carrier and a compound that inhibits 11-cis-retinol production as described herein. In an additional embodiment is a method of reducing lipofuscin pigment accumulated in a subject's retina wherein the lipofuscin is N-retinylidene-N-retinyl-ethanolamine (A2E).

In an additional embodiment is a method of modulating chromophore flux in a retinoid cycle comprising introducing into a subject a compound of Formula (G) or tautomer, stereoisomer, geometric isomer or a pharmaceutically acceptable solvate, hydrate, salt, N-oxide or prodrug thereof:

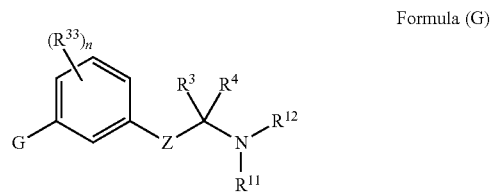

Formula (G)

wherein,
Z is a bond, —C($R^1$)($R^2$)—, —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)— or —X—C($R^{31}$)($R^{32}$)—C($R^1$)($R^2$)—;
X is —O—, —S—, —S(=O)—, —S(=O)$_2$—, —N($R^{30}$)—, —C(=O)—, —C(=CH$_2$)—, —C(=N—N$R^{35}$)—, or —C(=N—O$R^{35}$)—;
G is selected from —C($R^{41}$)$_2$—C($R^{41}$)$_2$—$R^{40}$, —C($R^{42}$)$_2$—S—$R^{40}$, —C($R^{42}$)$_2$—SO—$R^{40}$, —C($R^{42}$)$_2$—SO$_2$—$R^{40}$, —C($R^{42}$)$_2$—O—$R^{40}$, —C($R^{42}$)$_2$—N($R^{42}$)—$R^{40}$, —C(=O)—N($R^{42}$)—$R^{40}$;

$R^{40}$ is selected from —C($R^{16}$)($R^{17}$)($R^{18}$), aryl, or heteroaryl;

each $R^{41}$ is independently selected from hydrogen, hydroxy, $OR^6$, alkyl, or two $R^{41}$ groups together may form an oxo;

each $R^{42}$ is independently selected from hydrogen or alkyl;

$R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —$OR^6$ or —$NR^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^5$ is $C_5$-$C_{15}$ alkyl or carbocyclyalkyl;

$R^7$ and $R^8$ are each independently selected from hydrogen, alkyl, carbocyclyl, heterocyclyl, —C(=O)$R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)$R^{23}$, —C(NH)$NH_2$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, $OR^{34}$, alkyl, or fluoroalkyl; and n is 0, 1, 2, 3, or 4.

In a further embodiment is the method for treating an ophthalmic disease or disorder in a subject, comprising administering to the subject a compound of Formula (G), wherein the compound of Formula (G) is selected from the group consisting of:

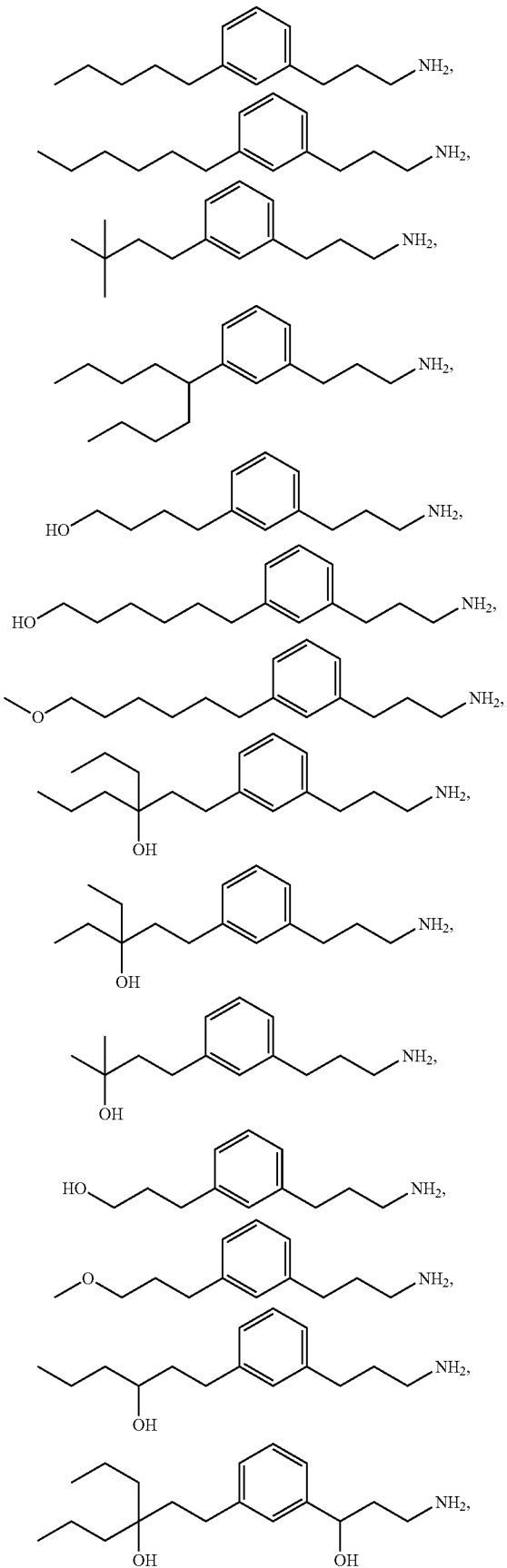

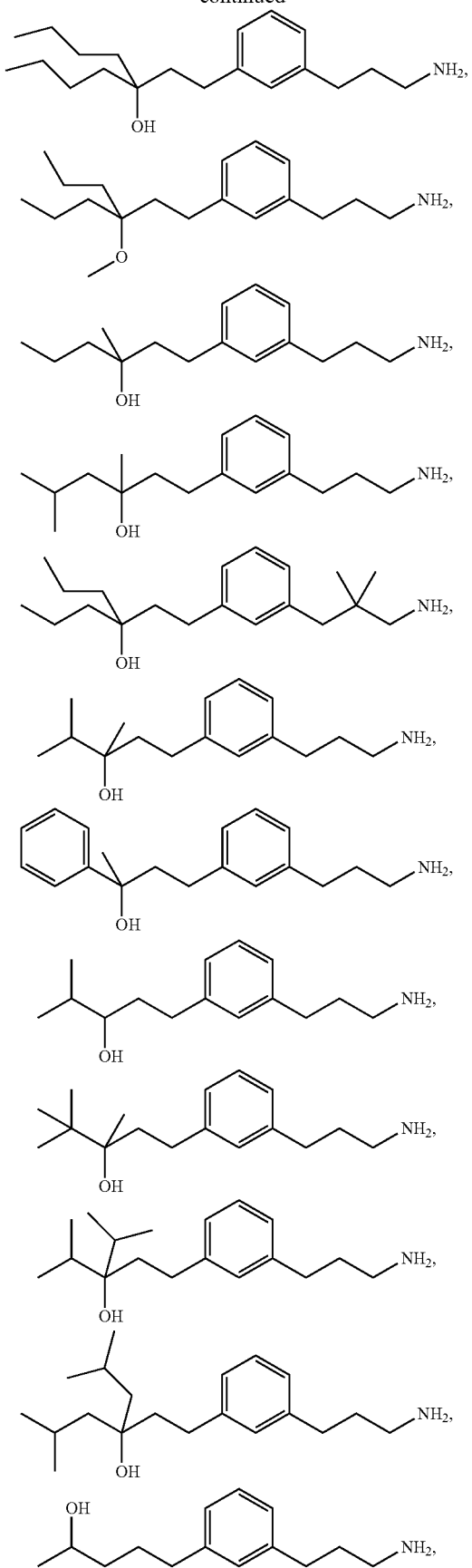
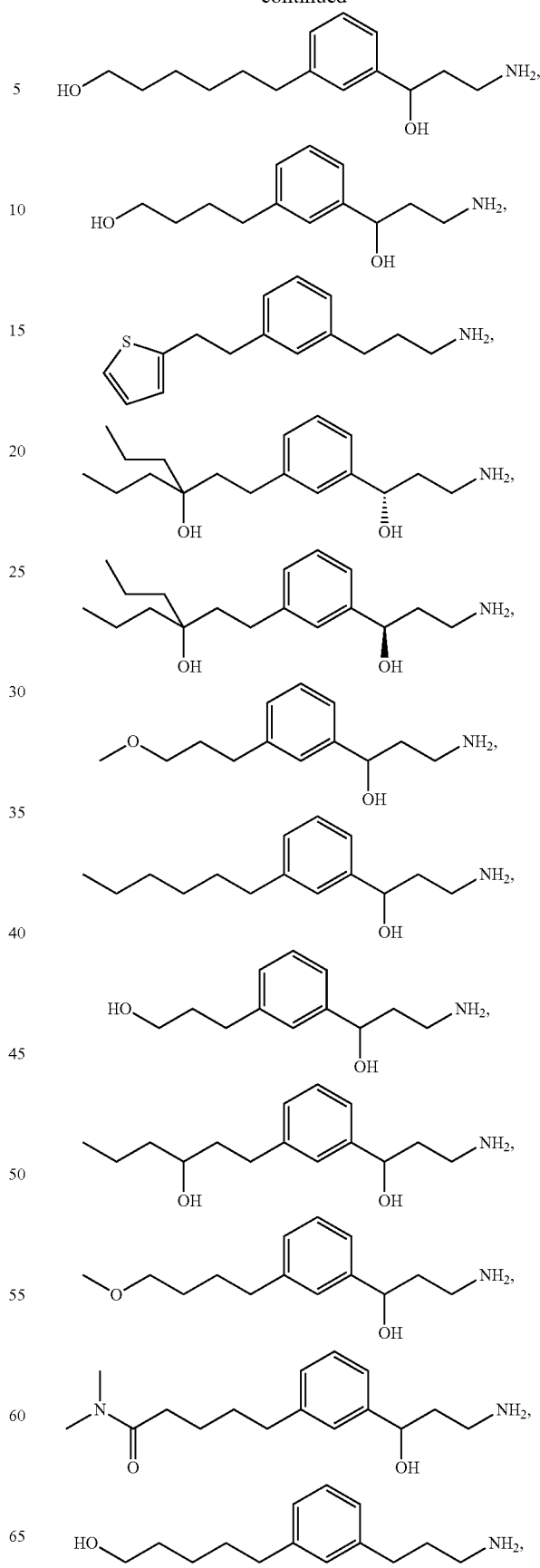

43
-continued
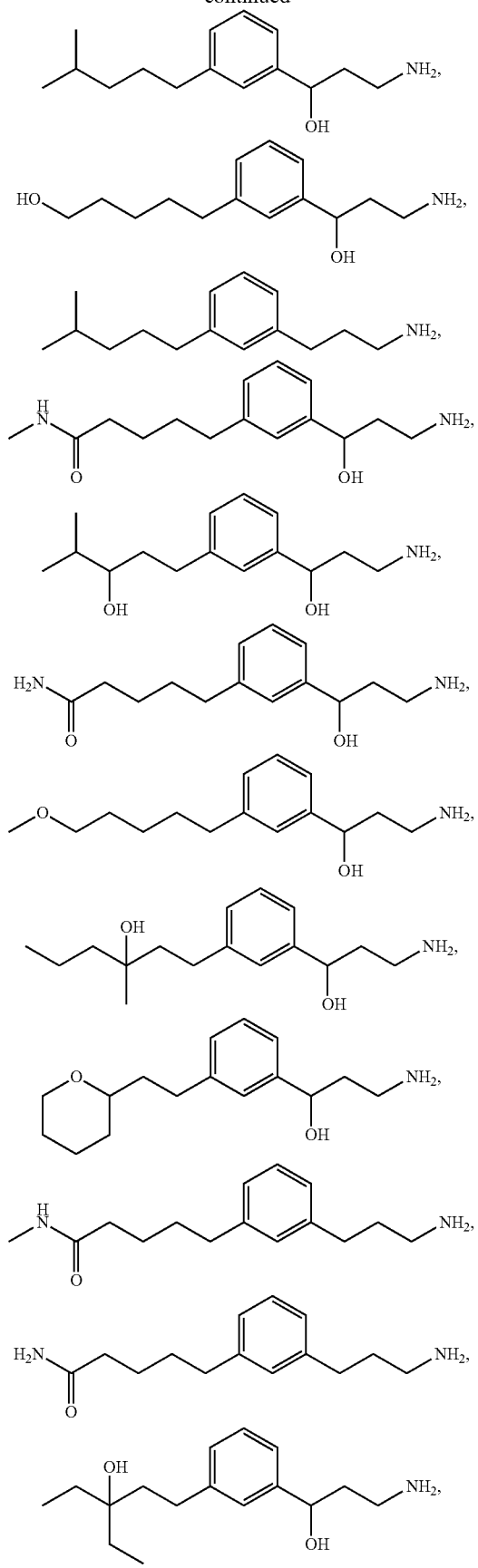
44
-continued
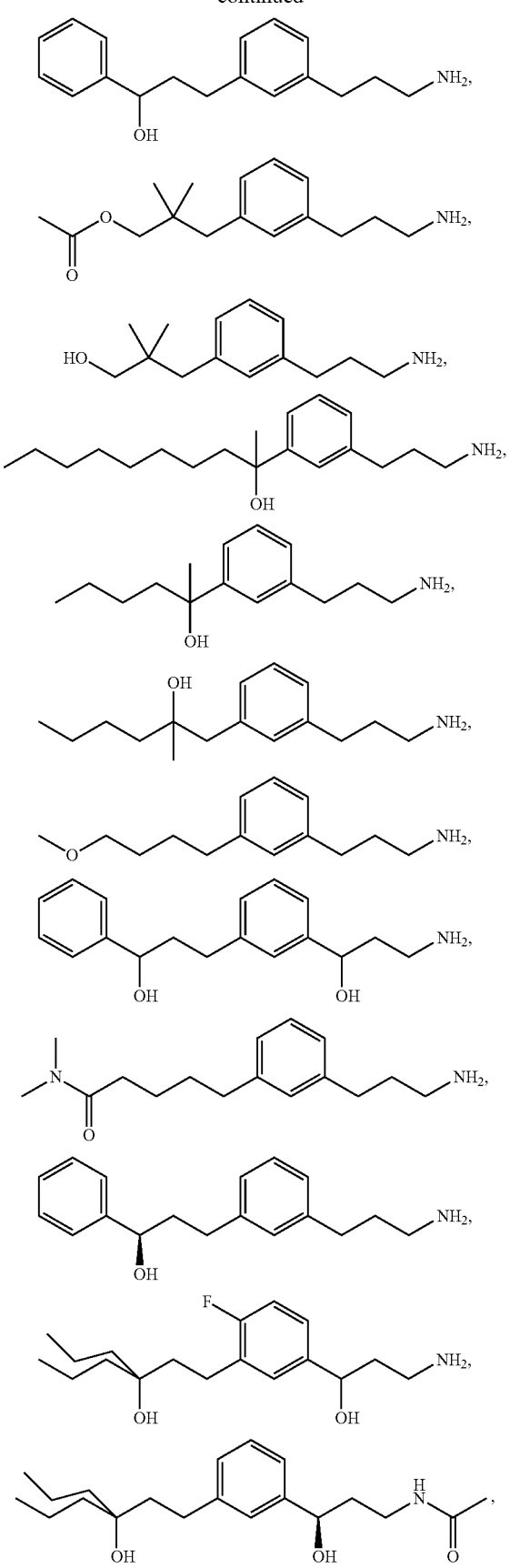

-continued
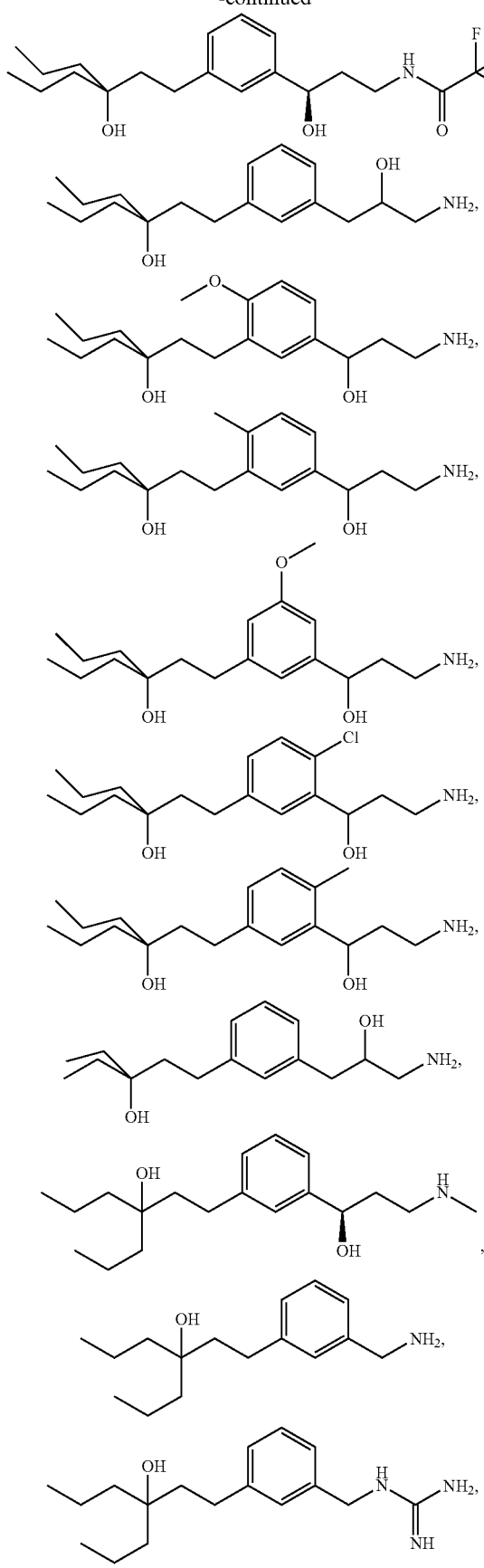
-continued
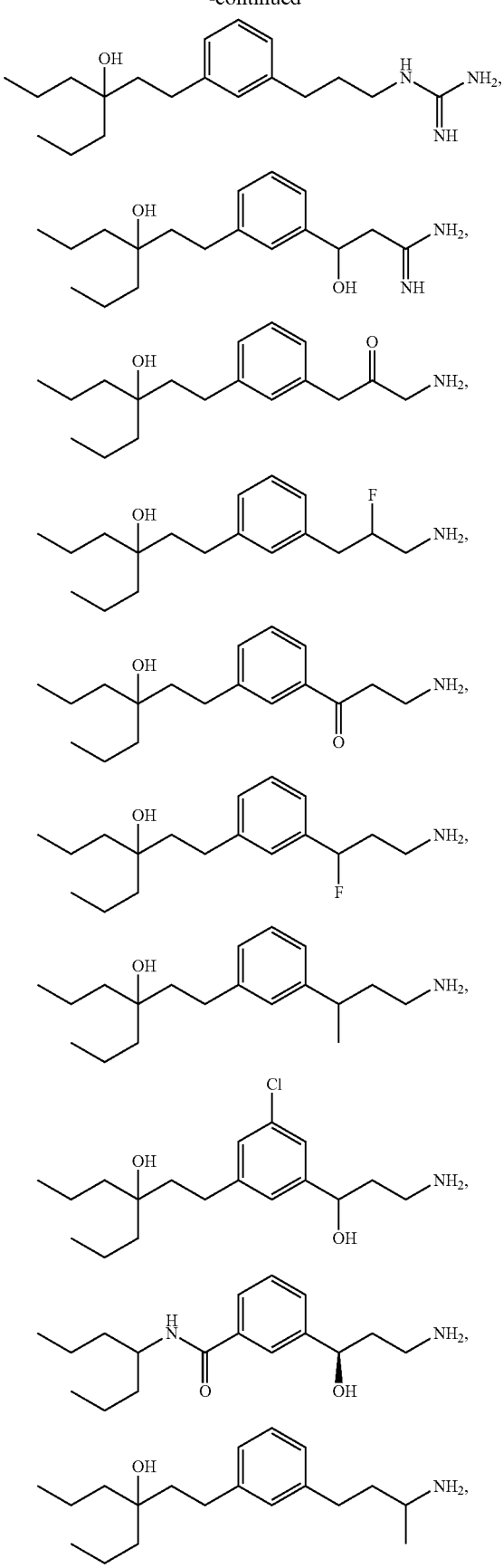

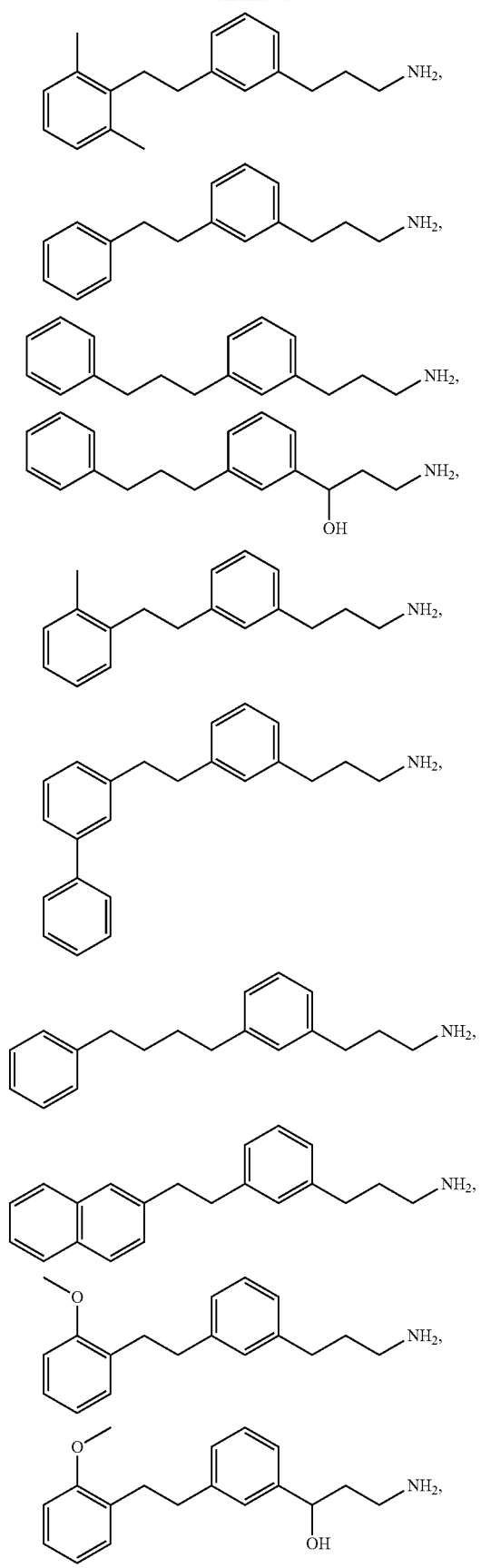

49
-continued
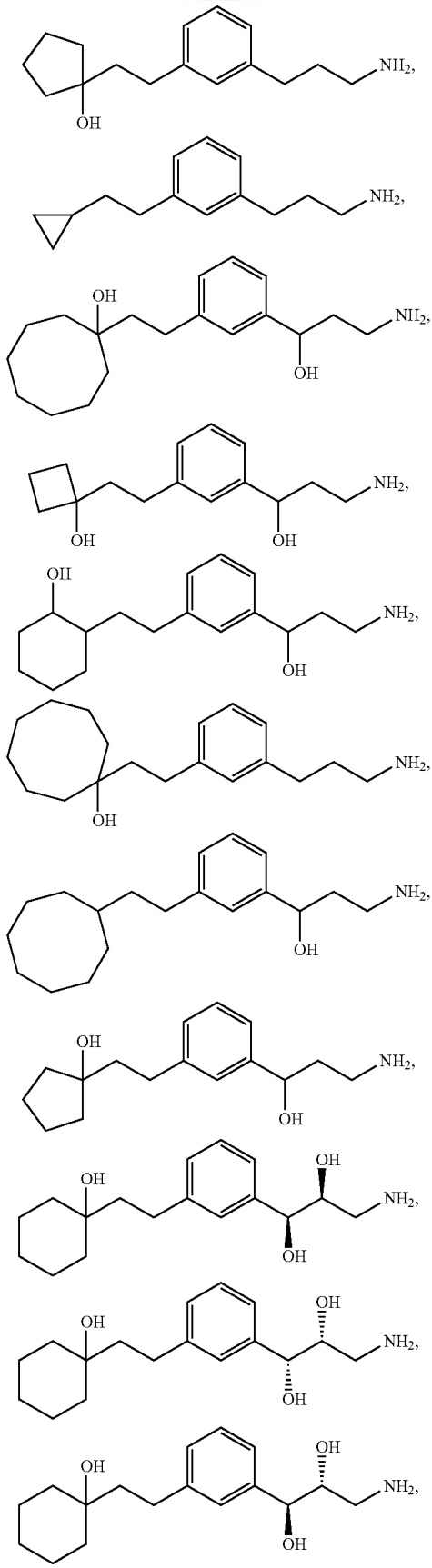
50
-continued
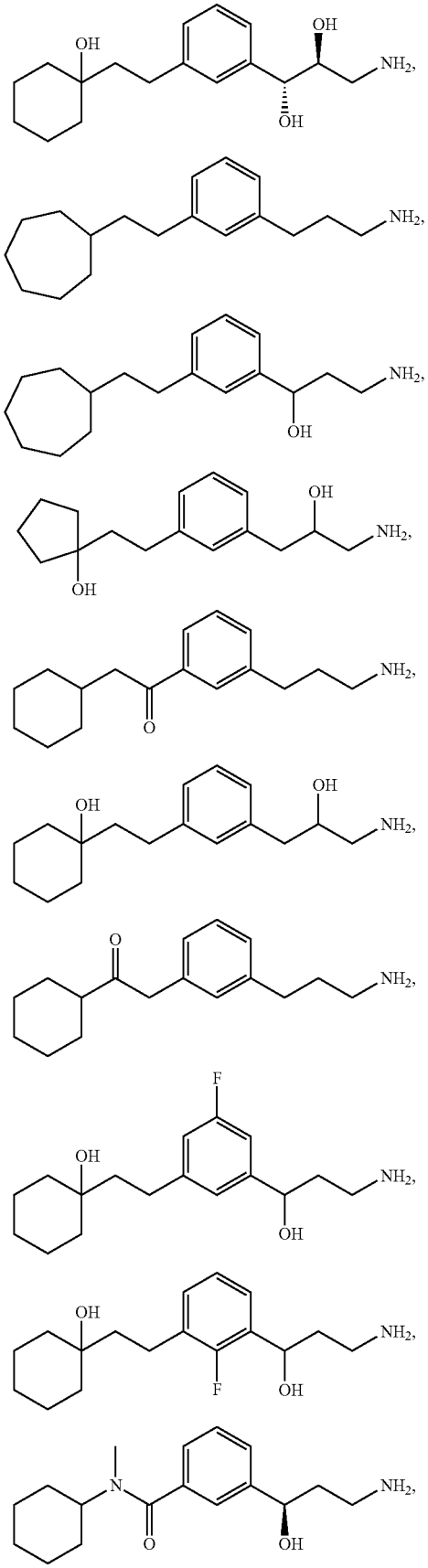

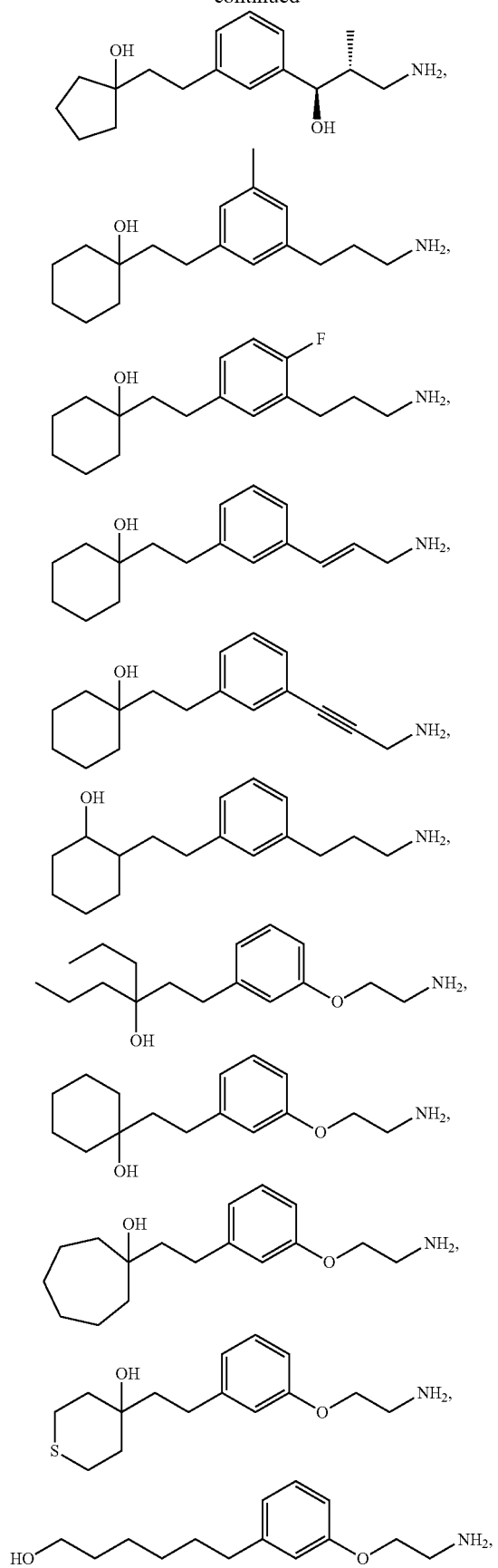
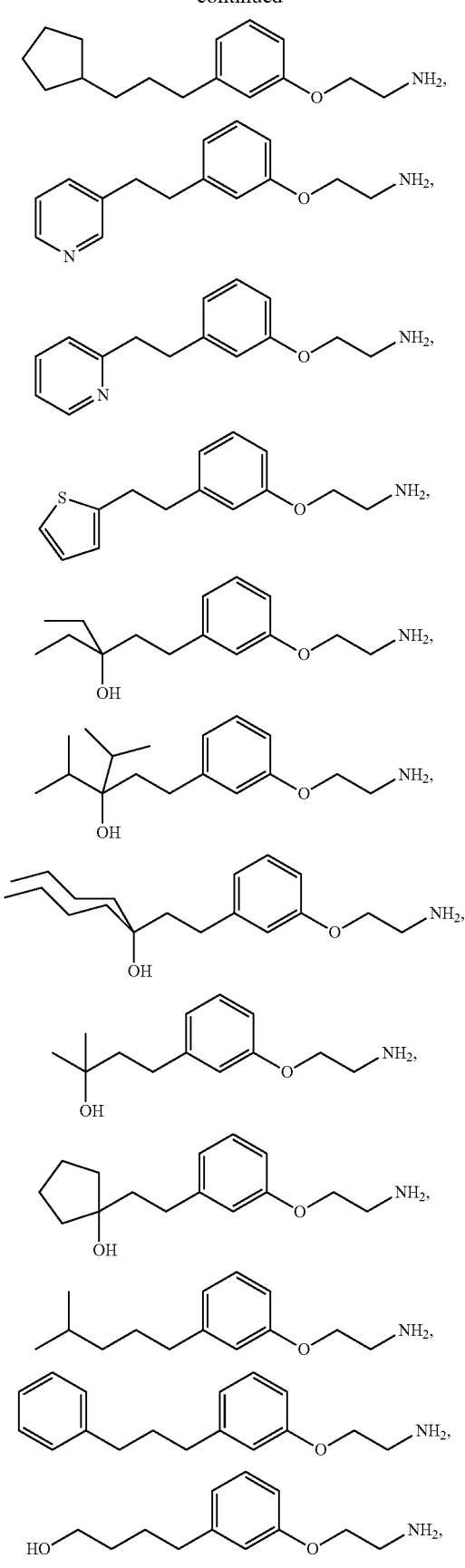

-continued
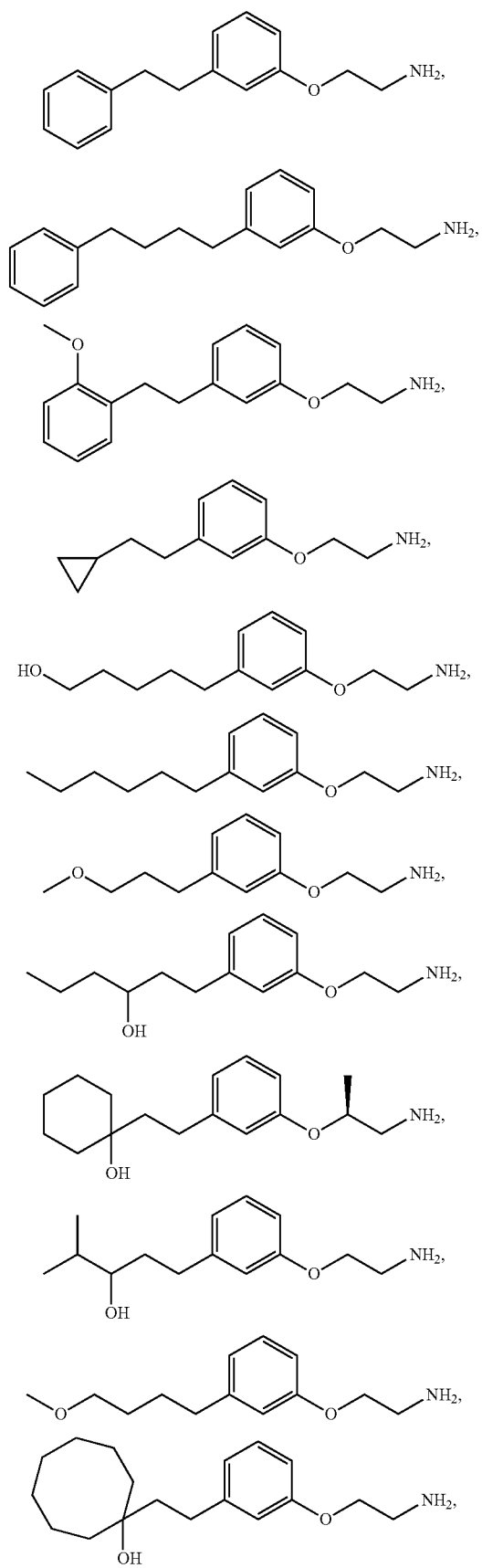
-continued
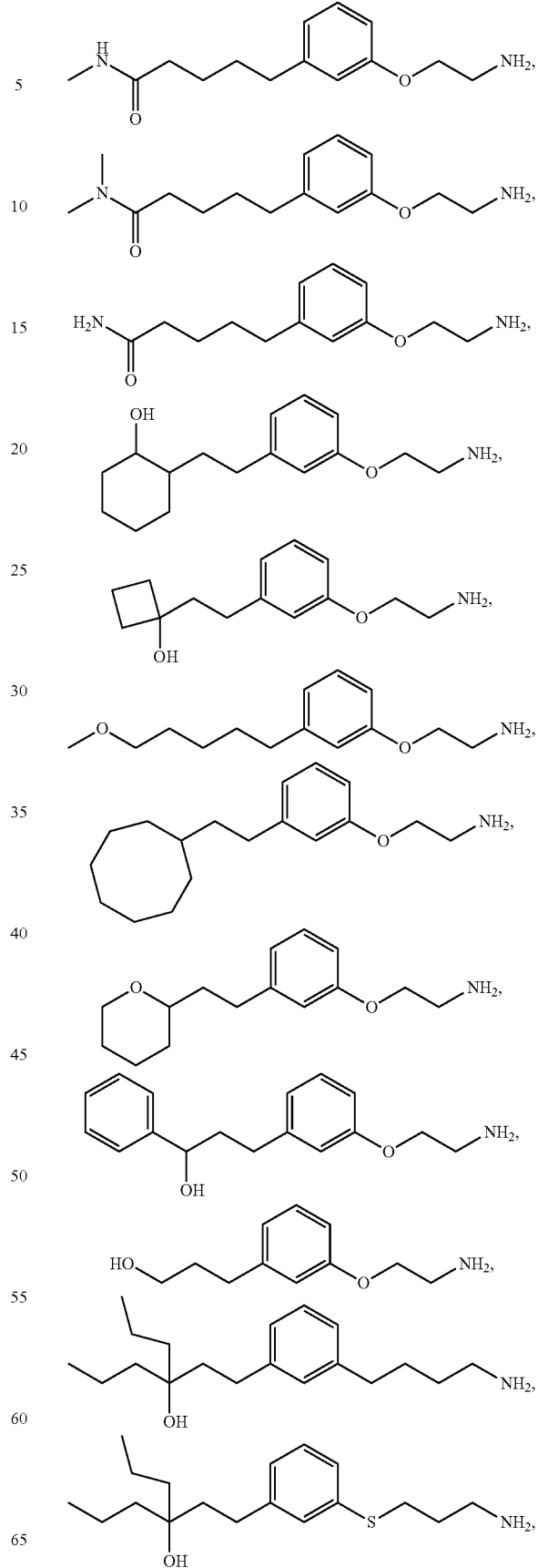

-continued

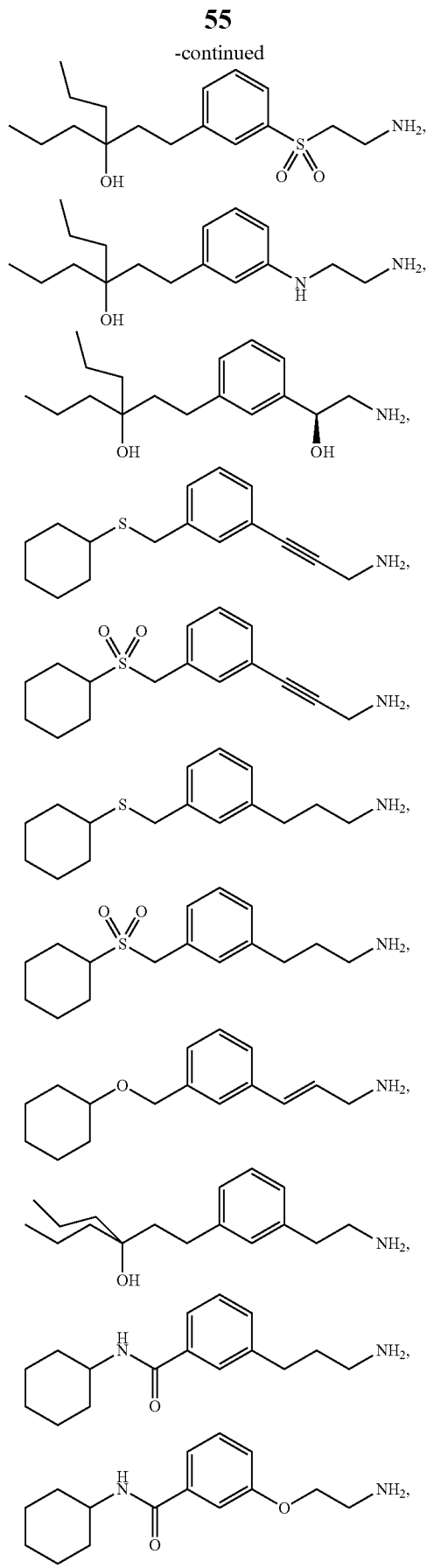

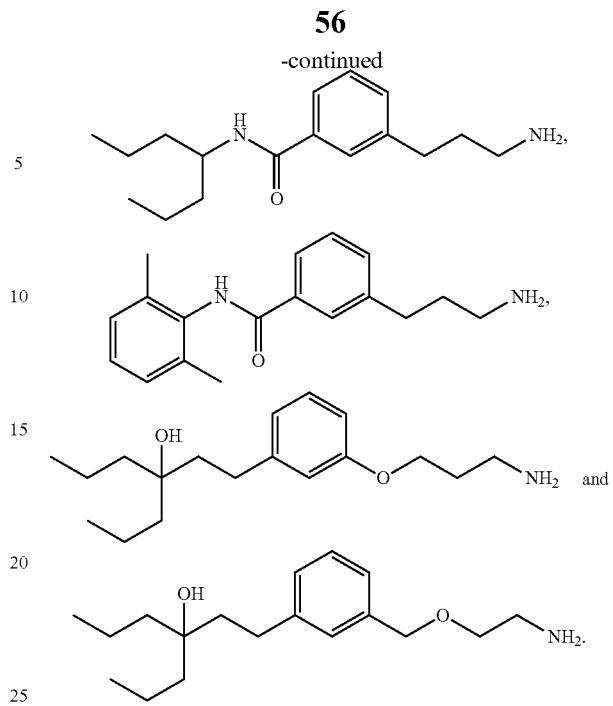

Incorporation by Reference

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 illustrates concentration-dependent inhibition of isomerase activity by the compound of Example 19 (Compound 19).

DETAILED DESCRIPTION OF THE INVENTION

Figure 1:
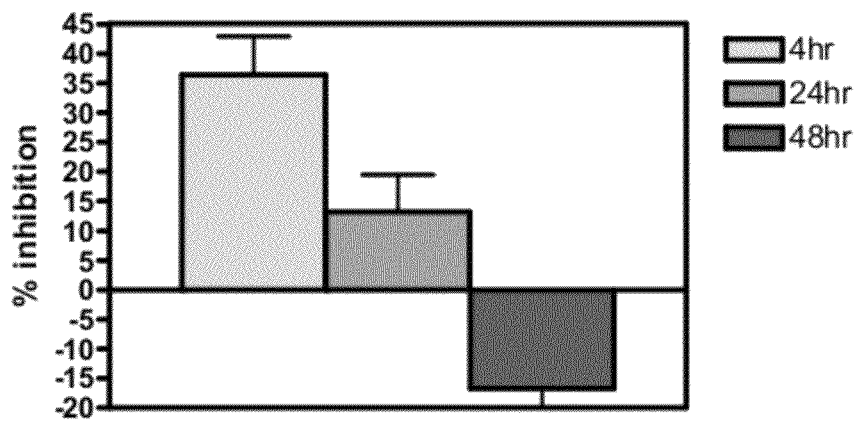
FIG. 1 illustrates isomerase inhibitory activity of the compound of Example 3 (Compound 3). The animals were orally gavaged with 1 mg/kg compound, then "photo-bleached" (5000 Lux white light for 10 minutes) at 4, 24 and 48 hours after dosing, and returned to darkness to allow recovery of the 11-cis-retinal content of the eyes. Mice were sacrificed 2 hours after bleaching, eyes were enucleated, and retinoid content was analyzed by HPLC.

Amine derivative compounds are described herein that inhibit an isomerization step of the retinoid cycle. These compounds and compositions comprising these compounds are useful for inhibiting degeneration of retinal cells or for enhancing retinal cell survival. The compounds described herein are, therefore, useful for treating ophthalmic diseases and disorders, including retinal diseases or disorders, such as age related macular degeneration and Stargardt's disease.

I. Amine derivative Compounds

In certain embodiments, amine derivative compounds comprising a meta-substituted linkage terminating in a nitrogen-containing moiety are provided. The nitrogen-containing moiety can be, for example, an amine, an amide or an N-heterocyclyl. The linkage comprises three linking atoms, including at least two carbon atoms and up to one heteroatom, such as sulfur, oxygen and nitrogen. These linking atoms form a combination of linearly constructed stable chemical bonds, including single, double or triple carbon-carbon bonds, carbon-nitrogen bonds, nitrogen-nitrogen bonds, carbon-oxygen bonds, carbon-sulfur bonds, and the like.

Accordingly, in one embodiment, is a compound of Formula (A) or tautomer, stereoisomer, geometric isomer or a pharmaceutically acceptable solvate, hydrate, salt, N-oxide or prodrug thereof:

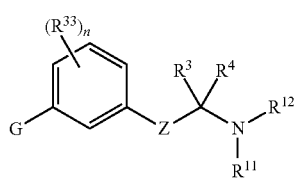

Formula (A)

wherein,

Z is a bond, —C($R^1$)($R^2$)—, —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)— or —X—C($R^{31}$)($R^{32}$)—C($R^1$)($R^2$)—;

X is —O—, —S—, —S(=O)—, —S(=O)$_2$—, —N($R^{30}$)—, —C(=O)—, —C(=CH$_2$)—, —C(=N—N$R^{35}$)—, or —C(=N—O$R^{35}$)—;

G is selected from —C($R^{41}$)$_2$—C($R^{41}$)$_2$—$R^{40}$, —C($R^{42}$)$_2$—S—$R^{40}$, —C($R^{42}$)$_2$—SO—$R^{40}$, —C($R^{42}$)$_2$—SO$_2$—$R^{40}$, —C($R^{42}$)$_2$—O—$R^{40}$, —C($R^{42}$)$_2$—N($R^{42}$)—$R^{40}$, —C(=O)—N($R^{42}$)—$R^{40}$;

$R^{40}$ is selected from —C($R^{16}$)($R^{17}$)($R^{18}$), aryl, or heteroaryl;

each $R^{41}$ is independently selected from hydrogen, hydroxy, OR$^6$, alkyl, or two $R^{41}$ groups together may form an oxo;

each $R^{42}$ is independently selected from hydrogen or alkyl;

$R^1$ and $R^2$ are each independently selected from hydrogen, halogen, $C_1$-$C_5$ alkyl, fluoroalkyl, —OR$^6$ or —NR$^7$R$^8$; or $R^1$ and $R^2$ together form an oxo;

$R^{31}$ and $R^{32}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —OR$^6$ or —NR$^7$R$^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^7$ and $R^8$ are each independently selected from hydrogen, alkyl, carbocyclyl, heterocyclyl, —C(=O)R$^{13}$, SO$_2$R$^{13}$, CO$_2$R$^{13}$ or SO$_2$NR$^{24}$R$^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, —OR$^{19}$, —NR$^{20}$R$^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)R$^{23}$, —C(NH)NH$_2$, SO$_2$R$^{23}$, CO$_2$R$^{23}$ or SO$_2$NR$^{28}$R$^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)R$^{22}$, SO$_2$R$^{22}$, CO$_2$R$^{22}$ or SO$_2$NR$^{26}$R$^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroaryalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, OR$^{34}$, alkyl, or fluoroalkyl; and n is 0, 1, 2, 3, or 4; with the provision that G is not an unsubstituted normal alkyl and the provision that the compound of Formula A is not:

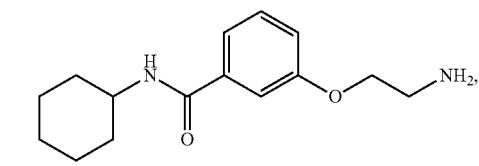

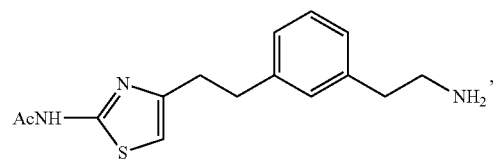

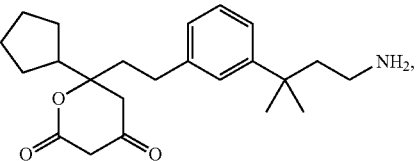

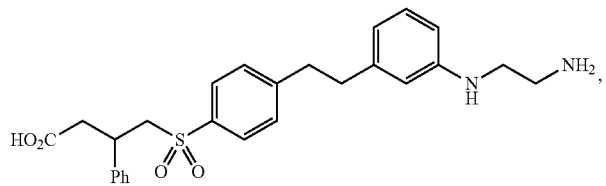

-continued

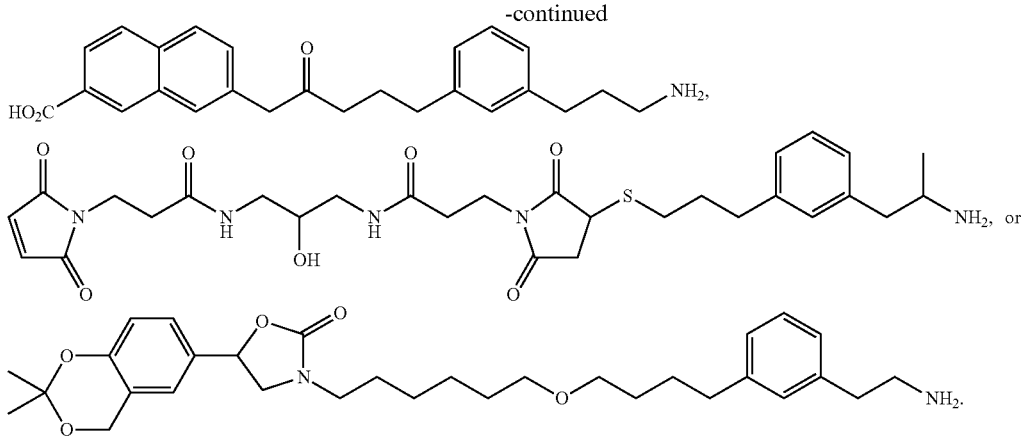

In another embodiment is the compound of Formula (A) wherein,

Z is a bond, —C(R¹)(R²)—, —C(R⁹)(R¹⁰)—C(R¹)(R²)—, —X—C(R³¹)(R³²)—, —C(R⁹)(R¹⁰)—C(R¹)(R²)—C(R³⁶)(R³⁷)— or —X—C(R³¹)(R³²)—C(R¹)(R²)—;

X is —O—, —S—, —S(=O)—, —S(=O)₂—, —N(R³⁰)—, —C(=O)—, —C(=CH₂)—, —C(=N—NR³⁵)—, or —C(=N—OR³⁵)—;

R¹ and R² are each independently selected from hydrogen, halogen, C₁-C₅ alkyl, fluoroalkyl, —OR⁶ or —NR⁷R⁸; or R¹ and R² together form an oxo;

R³¹ and R³² are each independently selected from hydrogen, C₁-C₅ alkyl, or fluoroalkyl;

R³⁶ and R³⁷ are each independently selected from hydrogen, halogen, C₁-C₅ alkyl, fluoroalkyl, —OR⁶ or —NR⁷R⁸; or R³⁶ and R³⁷ together form an oxo;

R³ and R⁴ are each independently selected from hydrogen, alkyl, alkenyl, fluoroalkyl, aryl, heteroaryl, carbocyclyl or C-attached heterocyclyl; or R³ and R⁴ together with the carbon atom to which they are attached, form a carbocyclyl or heterocyclyl; or R³ and R⁴ together form an imino;

R⁷ and R⁸ are each independently selected from hydrogen, alkyl, carbocyclyl, heterocyclyl, —C(=O)R¹³, SO₂R¹³, CO₂R¹³ or SO₂NR²⁴R²⁵; or R⁷ and R⁸ together with the nitrogen atom to which they are attached, form an N-heterocyclyl;

R⁹ and R¹⁰ are each independently selected from hydrogen, halogen, alkyl, fluoroalkyl, —OR¹⁹, —NR²⁰R²¹ or carbocyclyl; or R⁹ and R¹⁰ form an oxo;

R¹¹ and R¹² are each independently selected from hydrogen, alkyl, carbocyclyl, —C(=O)R²³, SO₂R²³, CO₂R²³ or SO₂NR²⁸R²⁹; or R¹¹ and R¹², together with the nitrogen atom to which they are attached, form an N-heterocyclyl;

each R¹³, R²² and R²³ is independently selected from alkyl, heteroalkyl, alkenyl, aryl, aralkyl, carbocyclyl, heteroaryl or heterocyclyl;

R⁶, R¹⁹, R³⁰, R³⁴ and R³⁵ are each independently hydrogen or alkyl;

R²⁰ and R²¹ are each independently selected from hydrogen, alkyl, carbocyclyl, heterocyclyl, —C(=O)R²², SO₂R²², CO₂R²² or SO₂NR²⁶R²⁷; or R²⁰ and R²¹ together with the nitrogen atom to which they are attached, form an N-heterocyclyl; and R²⁴, R²⁵, R²⁶, R²⁷, R²⁸ and R²⁹ is independently selected from hydrogen, alkyl, alkenyl, fluoroalkyl, aryl, heteroaryl, carbocyclyl or heterocyclyl;

each R³³ is independently selected from halogen, OR³⁴, alkyl, or fluoroalkyl; and n is 0, 1, 2, 3, or 4.

In another embodiment is the compound of Formula (A) having the structure of Formula (B)

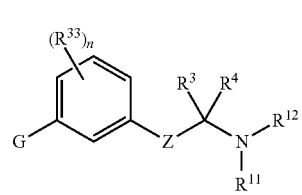

Formula (B)

wherein,

Z is —C(R⁹)(R¹⁰)—C(R¹)(R²)— or —O—C(R³¹)(R³²)—;

R¹ and R² are each independently selected from hydrogen, halogen, C₁-C₅ alkyl, fluoroalkyl, —OR⁶ or —NR⁷R⁸; or R¹ and R² together form an oxo;

R³¹ and R³² are each independently selected from hydrogen, C₁-C₅ alkyl, or fluoroalkyl;

R³ and R⁴ are each independently selected from hydrogen or alkyl; or R³ and R⁴ together form an imino;

R⁷ and R⁸ are each independently selected from hydrogen, alkyl, carbocyclyl or —C(=O)R¹³; or R⁷ and R⁸, together with the nitrogen atom to which they are attached, form an N-heterocyclyl;

R⁹ and R¹⁰ are each independently selected from hydrogen, halogen, alkyl, fluoroalkyl, —OR¹⁹, —NR²⁰R²¹ or carbocyclyl; or R⁹ and R¹⁰ together form an oxo; or optionally, R⁹ and R¹ together form a direct bond to provide a double bond; or optionally, R⁹ and R¹ together form a direct bond, and R¹⁰ and R² together form a direct bond to provide a triple bond;

R¹¹ and R¹² are each independently selected from hydrogen, alkyl, carbocyclyl or —C(=O)R²³; or R¹¹ and R¹², together with the nitrogen atom to which they are attached, form an N-heterocyclyl; and each R¹³, R²² and R²³ is independently selected from alkyl, alkenyl, aryl, aralkyl, carbocyclyl, heteroaryl or heterocyclyl;

R⁶, R¹⁹, and R³⁴ are each independently hydrogen or alkyl;

each R³³ is independently selected from halogen, OR³⁴, alkyl, or fluoroalkyl; and n is 0, 1, 2, 3, or 4;

R²⁰ and R²¹ are each independently selected from hydrogen, alkyl, carbocyclyl, —C(=O)R²²; or R²⁰ and R²¹, together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl.

In another embodiment is the compound of Formula (B) wherein,

Z is $-C(R^9)(R^{10})-C(R^1)(R^2)-$ or $-O-C(R^{31})(R^{32})-$;

$R^1$ and $R^2$ are each independently selected from hydrogen, halogen, $C_1$-$C_5$ alkyl, fluoroalkyl, $-OR^6$ or $-NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^3$ and $R^4$ are each independently selected from hydrogen or alkyl; or $R^3$ and $R^4$ together form an imino;

$R^7$ and $R^8$ are each independently selected from hydrogen, alkyl, carbocyclyl or $-C(=O)R^{13}$; or $R^7$ and $R^8$, together with the nitrogen atom to which they are attached, form an N-heterocyclyl;

$R^9$ and $R^{10}$ are each independently selected from hydrogen, halogen, alkyl, fluoroalkyl, $-OR^{19}$, $-NR^{20}R^{21}$ or carbocyclyl; or $R^9$ and $R^{10}$ together form an oxo;

$R^{11}$ and $R^{12}$ are each independently selected from hydrogen, alkyl, carbocyclyl or $-C(=O)R^{23}$; or $R^{11}$ and $R^{12}$, together with the nitrogen atom to which they are attached, form an N-heterocyclyl; and each $R^{13}$, $R^{22}$ and $R^{23}$ is independently selected from alkyl, alkenyl, aryl, aralkyl, carbocyclyl, heteroaryl or heterocyclyl;

$R^6$, $R^{19}$, and $R^{34}$ are each independently hydrogen or alkyl;

each $R^{33}$ is independently selected from halogen, $OR^{34}$, alkyl, or fluoroalkyl; and n is 0, 1, 2, 3, or 4;

$R^{20}$ and $R^{21}$ are each independently selected from hydrogen, alkyl, carbocyclyl, $-C(=O)R^{22}$; or $R^{20}$ and $R^{21}$, together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl.

In another embodiment is the compound of Formula (B) wherein,

G is selected from $-C(R^{41})_2-C(R^{41})_2-R^{40}$;

$R^{40}$ is selected from $-C(R^{16})(R^{17})(R^{18})$, aryl, or heteroaryl;

each $R^{41}$ is independently selected from hydrogen, hydroxy, $OR^6$, alkyl, or two $R^{41}$ groups together may form an oxo.

In another embodiment is the compound of Formula (B) wherein,

G is selected from $-C(R^{41})_2-C(R^{41})_2-R^{4o}$;

$R^{40}$ is selected from $-C(R^{16})(R^{17})(R^{18})$, aryl, or heteroaryl;

each $R^{41}$ is independently selected from hydrogen, hydroxy, $OR^6$, alkyl, or two $R^{41}$ groups together may form an oxo.

In another embodiment is the compound of Formula (B) having the structure of Formula (C)

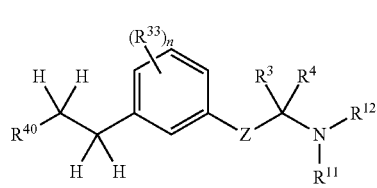

Formula (C)

wherein,

Z is $-C(R^9)(R^{10})-C(R^1)(R^2)-$ or $-O-C(R^{31})(R^{32})-$;

$R^{40}$ is selected from $-C(R^{16})(R^{17})(R^{18})$, aryl, or heteroaryl;

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

$R^1$ and $R^2$ are each independently selected from hydrogen, halogen, $C_1$-$C_5$ alkyl, fluoroalkyl, $-OR^6$ or $-NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^3$ and $R^4$ are each independently selected from hydrogen or alkyl; or $R^3$ and $R^4$ together form an imino;

$R^7$ and $R^8$ are each independently selected from hydrogen, alkyl, carbocyclyl or $-C(=O)R^{13}$; or $R^7$ and $R^8$, together with the nitrogen atom to which they are attached, form an N-heterocyclyl;

$R^9$ and $R^{10}$ are each independently selected from hydrogen, halogen, alkyl, fluoroalkyl, $-OR^{19}$, $-NR^{20}R^{21}$ or carbocyclyl; or $R^9$ and $R^{10}$ together form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl or $-C(=O)R^{23}$; or $R^{11}$ and $R^{12}$, together with the nitrogen atom to which they are attached, form an N-heterocyclyl; and each $R^{13}$, $R^{22}$ and $R^{23}$ is independently selected from alkyl, alkenyl, aryl, aralkyl, carbocyclyl, heteroaryl or heterocyclyl;

$R^6$, $R^{19}$, and $R^{34}$ are each independently hydrogen or alkyl;

each $R^{33}$ is independently selected from halogen, $OR^{34}$, alkyl, or fluoroalkyl; and n is 0, 1, 2, 3, or 4;

$R^{20}$ and $R^{21}$ are each independently selected from hydrogen, alkyl, carbocyclyl, $-C(=O)R^{22}$; or $R^{20}$ and $R^{21}$, together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl.

In another embodiment is the compound of Formula (C) wherein, $R^9$ and $R^{10}$ are each independently selected from hydrogen, halogen, alkyl, fluoroalkyl, $-OR^{19}$, $-NR^{20}R^{21}$ or carbocyclyl; or $R^9$ and $R^{10}$ together form an oxo.

In another embodiment is the compound of Formula (C) having the structure of Formula (D):

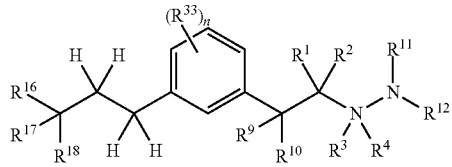

Formula (D)

wherein, $R^1$ and $R^2$ are each independently selected from hydrogen, halogen, $C_1$-$C_5$ alkyl, fluoroalkyl, $-OR^6$ or $-NR^7R^8$; or $R^1$ and $R^2$ together form an oxo;

$R^3$ and $R^4$ are each independently selected from hydrogen or alkyl; or $R^3$ and $R^4$ together form an imino;

$R^7$ and $R^8$ are each independently selected from hydrogen, alkyl, carbocyclyl or $-C(=O)R^{13}$; or $R^7$ and $R^8$, together with the nitrogen atom to which they are attached, form an N-heterocyclyl;

$R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ together form an oxo;

$R^{11}$ and $R^{12}$ are each independently selected from hydrogen, alkyl, carbocyclyl or —$C(=O)R^{23}$; or $R^{11}$ and $R^{12}$, together with the nitrogen atom to which they are attached, form an N-heterocyclyl;

each $R^{13}$, $R^{22}$ and $R^{23}$ is independently selected from alkyl, alkenyl, aryl, aralkyl, carbocyclyl, heteroaryl or heterocyclyl;

$R^6$, $R^{19}$ and $R^{34}$ are each independently hydrogen or alkyl;

$R^{20}$ and $R^{21}$ are each independently selected from hydrogen, alkyl, carbocyclyl, —$C(=O)R^{22}$; or $R^{20}$ and $R^{21}$, together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocycle;

each $R^{33}$ is independently selected from halogen, $OR^{34}$, alkyl, or fluoroalkyl; and n is 0, 1, 2, 3, or 4; and $R^{18}$ is selected from a hydrogen, alkyl, alkoxy, hydroxy, halo or fluoroalkyl.

In another embodiment is the compound of Formula (D) wherein n is 0 and each of $R^{11}$ and $R^{12}$ is hydrogen. In a further embodiment is the compound wherein each of $R^3$, $R^4$, $R^{14}$ and $R^{15}$ is hydrogen. In a further embodiment is the compound wherein, $R^1$ and $R^2$ are each independently selected from hydrogen, halogen, $C_1$-$C_5$ alkyl, or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently hydrogen or alkyl;

$R^{16}$ and $R^{17}$, together with the carbon to which they are attached form a carbocyclyl or heterocycle; and $R^{18}$ is selected from a hydrogen, alkoxy or hydroxy.

In a further embodiment is the compound wherein $R^{16}$ and $R^{17}$, together with the carbon to which they are attached, form a cyclopropyl, cyclobutyl, cyclopentyl, cyclohexyl, cycloheptyl, or cyclooctyl, and $R^{18}$ is hydrogen or hydroxy.

In another embodiment is the compound of Formula (D), wherein $R^{11}$ is hydrogen and $R^{12}$ is —$C(=O)R^{23}$, wherein $R^{23}$ is alkyl.

In a further embodiment is the compound of Formula (D), wherein $R^1$ and $R^2$ are each independently selected from hydrogen, halogen, $C_1$-$C_5$ alkyl, or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently selected from hydrogen or alkyl;

$R^{16}$ and $R^{17}$, together with the carbon atom to which they are attached, form a carbocyclyl; and $R^{18}$ is hydrogen, hydroxy or alkoxy.

In a further embodiment is the compound of Formula (D) wherein, n is 0;

$R^{16}$ and $R^{17}$, together with the carbon atom to which they are attached, form, a cyclopentyl, cyclohexyl or cyclohexyl; and $R^{18}$ is hydrogen or hydroxy.

In a further embodiment is the compound of Formula (D) wherein, $R^1$ and $R^2$ are each independently selected from hydrogen, halogen, $C_1$-$C_5$ alkyl or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently hydrogen or alkyl;

$R^{16}$ and $R^{17}$ is independently selected from $C_1$-$C_{13}$ alkyl; and $R^{18}$ is hydrogen, hydroxy or alkoxy.

In another embodiment is the compound of Formula (C) having the structure of Formula (E):

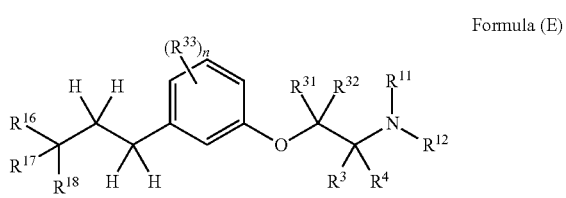

Formula (E)

wherein, $R^{31}$ and $R^{32}$ are each independently selected from hydrogen, $C_1$-$C_5$ alkyl, or fluoroalkyl;

$R^3$ and $R^4$ are each independently selected from hydrogen or alkyl; or $R^3$ and $R^4$ together form an imino;

$R^{11}$ and $R^{12}$ are each independently selected from hydrogen, alkyl, carbocyclyl, or —$C(=O)R^{23}$; or $R^{11}$ and $R^{12}$, together with the nitrogen atom to which they are attached, form an N-heterocyclyl;

$R^{23}$ is selected from alkyl, alkenyl, aryl, carbocyclyl, heteroaryl or heterocyclyl;

$R^{14}$ and $R^{15}$ are each independently selected from hydrogen or alkyl;

$R^{16}$ and $R^{17}$ are each independently selected from hydrogen, $C_1$-$C_{13}$ alkyl, halo or fluoroalkyl; or $R^{16}$ and $R^{17}$, together with the carbon atom to which they are attached, form a carbocyclyl or heterocycle;

$R^{18}$ is selected from a hydrogen, alkyl, alkoxy, hydroxy, halo or fluoroalkyl;

$R^{34}$ is hydrogen or alkyl; and each $R^{33}$ is independently selected from halogen, $OR^{34}$, alkyl, or fluoroalkyl; and n is 0, 1, 2, 3, or 4.

In another embodiment is the compound of Formula (E) wherein n is 0 and each of $R^{11}$ and $R^{12}$ is hydrogen.

In a further embodiment is the compound of Formula (E) wherein each $R^3$, $R^4$, $R^{14}$ and $R^{15}$ is hydrogen.

In a further embodiment is the compound of Formula (E) wherein, $R^{31}$ and $R^{32}$ are each independently hydrogen, or $C_1$-$C_5$ alkyl;

$R^{16}$ and $R^{17}$, together with the carbon atom to which they are attached, form a carbocyclyl; and $R^{18}$ is hydrogen, hydroxy, or alkoxy.

In a further embodiment is the compound of Formula (E) wherein $R^{16}$ and $R^{17}$, together with the carbon atom to which they are attached form a cyclopropyl, cyclobutyl, cyclopentyl, cyclohexyl, cycloheptyl or cyclooctyl and $R^{18}$ is hydrogen or hydroxy.

In a further embodiment is the compound of Formula (E) wherein, $R^{31}$ and $R^{32}$ are each independently selected from hydrogen, or $C_1$-$C_5$ alkyl; and $R^{18}$ is hydrogen, hydroxy or alkoxy.

In a further embodiment is the compound of Formula (E) wherein, $R^{31}$ and $R^{32}$ are each independently hydrogen, or $C_1$-$C_5$ alkyl;

$R^6$ and $R^{19}$ are each independently hydrogen or alkyl;
$R^{16}$ and $R^{17}$ is independently selected from $C_1$-$C_{13}$ alkyl; and
$R^{18}$ is hydrogen, hydroxy or alkoxy.

In another embodiment is the compound of Formula (A) wherein,
Z is a bond, —X—C($R^{31}$)($R^{32}$)—, or —X—C($R^{31}$)($R^{32}$)—C($R^1$)($R^2$)—; and
X is —S—, —S(=O)—, —S(=O)$_2$—, —N($R^{30}$)—, —C(=O)—, —C(=CH$_2$)—, —C(=N—N$R^{35}$)—, or —C(=N—O$R^{35}$)—.

In a further embodiment is the compound of Formula (A) wherein,
G is selected from —C($R^{41}$)$_2$—C($R^{41}$)$_2$—$R^{40}$;
$R^{40}$ is selected from —C($R^{16}$)($R^{17}$)($R^{18}$), aryl, or heteroaryl;
each $R^{41}$ is independently selected from hydrogen, hydroxy, O$R^6$, alkyl, or two $R^{41}$ groups together may form an oxo.

In another embodiment is the compound of Formula (A) having the structure of Formula (F):

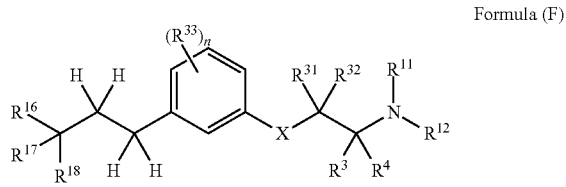

Formula (F)

wherein,
X is —S—, —S(=O)—, —S(=O)$_2$—, —N($R^{30}$)—, —C(=O)—, —C(=CH$_2$)—, —C(=N—N$R^{35}$)—, or —C(=N—O$R^{35}$)—;
$R^{31}$ and $R^{32}$ are each independently selected from hydrogen, $C_1$-$C_5$ alkyl, or fluoroalkyl;
$R^3$ and $R^4$ are each independently selected from hydrogen or alkyl; or $R^3$ and $R^4$ together form an imino;
$R^{11}$ and $R^{12}$ are each independently selected from hydrogen, alkyl, carbocyclyl, or —C(=O)$R^{23}$; or $R^{11}$ and $R^{12}$, together with the nitrogen atom to which they are attached, form an N-heterocyclyl;
$R^{23}$ is selected from alkyl, alkenyl, aryl, carbocyclyl, heteroaryl or heterocyclyl;
$R^{16}$ and $R^{17}$ are each independently selected from hydrogen, $C_1$-$C_{13}$ alkyl, halo or fluoroalkyl; or $R^{16}$ and $R^{17}$, together with the carbon atom to which they are attached, form a carbocyclyl or heterocycle;
$R^{30}$, $R^{34}$ and $R^{35}$ are each independently hydrogen or alkyl;
$R^{18}$ is selected from a hydrogen, alkyl, alkoxy, hydroxy, halo or fluoroalkyl;
each $R^{33}$ is independently selected from halogen, O$R^{34}$, alkyl, or fluoroalkyl; and n is 0, 1, 2, 3, or 4.

In a further embodiment is the compound of Formula (F) wherein n is 0 and each $R^{11}$ and $R^{12}$ is hydrogen.

In a further embodiment is the compound of Formula (F) wherein each $R^3$, $R^4$, $R^{14}$ and $R^{15}$ is hydrogen.

In a further embodiment is the compound of Formula (F) wherein,
$R^{31}$ and $R^{32}$ are each independently hydrogen, or $C_1$-$C_5$ alkyl;
$R^{16}$ and $R^{17}$, together with the carbon atom to which they are attached, form a carbocyclyl or heterocycle; and
$R^{18}$ is hydrogen, hydroxy, or alkoxy.

In a further embodiment is the compound of Formula (F) wherein $R^{16}$ and $R^{17}$, together with the carbon atom to which they are attached form a cyclopropyl, cyclobutyl, cyclopentyl, cyclohexyl, cycloheptyl or cyclooctyl and $R^{18}$ is hydrogen or hydroxy.

In a further embodiment is the compound of Formula (F) wherein, $R^{31}$ and $R^{32}$ are each independently selected from hydrogen, or $C_1$-$C_5$ alkyl; $R^{16}$ and $R^{17}$ is independently selected from $C_1$-$C_{13}$ alkyl; and $R^{18}$ is hydrogen, hydroxy or alkoxy.

In one embodiment is a compound having a structure of Formula (I):

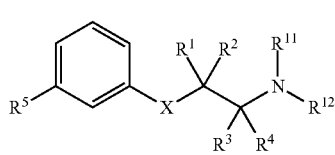

Formula (I)

as a tautomer or a mixture of tautomers, or as a pharmaceutically acceptable salt, hydrate, solvate, N-oxide or prodrug thereof, wherein:
$R^1$ and $R^2$ are each the same or different and independently hydrogen, halogen, $C_1$-$C_5$ alkyl, fluoroalkyl, —O$R^6$, or —N$R^7R^8$; or $R^1$ and $R^2$ form an oxo;
$R^3$ and $R^4$ are each the same or different and independently hydrogen or alkyl;
$R^5$ is $C_5$-$C_{15}$ alkyl, aralkyl, heterocyclylalkyl, heteroarylalkyl or carbocyclylalkyl;
$R^6$ is hydrogen or alkyl;
$R^7$ and $R^8$ are each the same or different and independently hydrogen, alkyl, carbocyclyl, or —C(=O)$R^{13}$; or
$R^7$ and $R^8$, together with the nitrogen atom to which they are attached, form an N-heterocyclyl;
X is —C($R^9$)($R^{10}$)— or —O—;
$R^9$ and $R^{10}$ are each the same or different and independently hydrogen, halogen, alkyl, fluoroalkyl, —O$R^6$, —N$R^7R^8$ or carbocyclyl; or $R^9$ and $R^{10}$ form an oxo;
$R^{11}$ and $R^{12}$ are each the same or different and independently hydrogen, alkyl, or —C(=O)$R^{13}$; or
$R^{11}$ and $R^{12}$, together with the nitrogen atom to which they are attached, form an N-heterocyclyl; and
$R^{13}$ is alkyl, alkenyl, aryl, carbocyclyl, heteroaryl or heterocyclyl.

In another embodiment is the compound of Formula (I) having a structure of Formula (Ia):

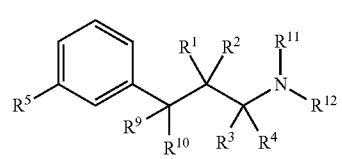

Formula (Ia)

as a tautomer or a mixture of tautomers, or as a pharmaceutically acceptable salt, hydrate, solvate, N-oxide or prodrug thereof, wherein:
$R^1$ and $R^2$ are each the same or different and independently hydrogen, halogen, $C_1$-$C_5$ alkyl, fluoroalkyl, —O$R^6$, or —N$R^7R^8$; or $R^1$ and $R^2$ form an oxo;
$R^3$ and $R^4$ are each the same or different and independently hydrogen or alkyl;
$R^5$ is $C_5$-$C_{15}$ alkyl, aralkyl, heterocyclylalkyl, heteroarylalkyl or carbocyclylalkyl;
$R^6$ is hydrogen or alkyl;
$R^7$ and $R^8$ are each the same or different and independently hydrogen, alkyl, carbocyclyl, or —C(=O)$R^{13}$; or R$^7$ and R$^8$, together with the nitrogen atom to which they are attached, form an N-heterocyclyl;

R$^9$ and R$^{10}$ are each the same or different and independently hydrogen, halogen, alkyl, fluoroalkyl, —OR$^6$, —NR$^7$R$^8$ or carbocyclyl; or R$^9$ and R$^{10}$ form an oxo;

R$^{11}$ and R$^{12}$ are each the same or different and independently hydrogen, alkyl, or —C(=O)R$^{13}$; or R$^{11}$ and R$^{12}$, together with the nitrogen atom to which they are attached, form an N-heterocyclyl; and R$^{13}$ is alkyl, alkenyl, aryl, carbocyclyl, heteroaryl or heterocyclyl.

In a further embodiment is the compound of Formula (Ia) wherein each of R$^{11}$ and R$^{12}$ is hydrogen.

In a further embodiment is the compound of Formula (Ia) wherein each of R$^9$ and R$^{10}$ is independently hydrogen, halogen, alkyl or —OR$^6$, wherein R$^6$ is hydrogen or alkyl.

In a further embodiment is the compound of Formula (Ia) wherein R$^5$ is C$_5$-C$_9$ alkyl, aralkyl, or carbocyclylalkyl.

In a further embodiment is the compound of Formula (Ia) wherein each of R$_1$, R$_2$, R$_3$ and R$_4$ is hydrogen;
each of R$_9$ and R$_{10}$ is independently hydrogen or —OR$_6$, wherein R$_6$ is hydrogen or alkyl; and
R$_5$ is C$_5$-C$_9$ alkyl.

In a further embodiment is the compound of Formula (Ia) wherein R$^5$ is C$_5$-C$_9$ alkyl substituted with —OR$^6$, wherein R$^6$ is hydrogen or alkyl.

In a further embodiment is the compound of Formula (Ia) wherein each of R$^1$, R$^2$, R$^3$ and R$^4$ is hydrogen;
each of R$^9$ and R$^{10}$ is independently hydrogen or —OR$^6$, wherein R$^6$ is hydrogen or alkyl; and
R$^5$ is aralkyl.

In a further embodiment is the compound of Formula (Ia) wherein each of R$^1$, R$^2$, R$^3$ and R$^4$ is hydrogen;
each of R$^9$ and R$^{10}$ is independently hydrogen or —OR$^6$, wherein R$^6$ is hydrogen or alkyl; and
R$^5$ is carbocyclylalkyl.

In another embodiment is the compound of Formula (I) having a structure of Formula (Ib):

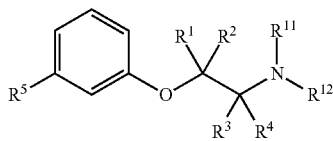

Formula (Ib)

as a tautomer or a mixture of tautomers, or as a pharmaceutically acceptable salt, hydrate, solvate, N-oxide or prodrug thereof, wherein:

R$^1$ and R$^2$ are each the same or different and independently hydrogen, C$_1$-C$_5$ alkyl, or fluoroalkyl;

R$^3$ and R$^4$ are each the same or different and independently hydrogen or alkyl;

R$^5$ is C$_5$-C$_{15}$ alkyl, aralkyl, heterocyclylalkyl, heteroarylalkyl or carbocyclylalkyl;

R$^{11}$ and R$^{12}$ are each the same or different and independently hydrogen, alkyl, or —C(=O)R$^{13}$; or R$^{11}$ and R$^{12}$, together with the nitrogen atom to which they are attached, form an N-heterocyclyl; and R$^{13}$ is alkyl, alkenyl, aryl, carbocyclyl, heteroaryl or heterocyclyl.

In another embodiment is the compound of Formula (Ib) wherein R$^{11}$ and R$^{12}$ is hydrogen.

In another embodiment is the compound of Formula (Ib) wherein each of R$^3$ and R$^4$ is hydrogen.

In another embodiment is the compound of Formula (Ib) wherein
each of R$^1$, R$^2$, R$^3$ and R$^4$ is hydrogen, and
R$^5$ is C$_5$-C$_9$ alkyl, carbocyclylalkyl, heteroarylalkyl, or heterocyclylalkyl.

In a further embodiment is the compound of Formula (I) selected from the group consisting of:
3-(3-pentylphenyl)propan-1-amine;
3-(3-hexylphenyl)propan-1-amine;
3-(3-(3,3-dimethylbutyl)phenyl)propan-1-amine;
3-(3-(octan-4-yl)phenyl)propan-1-amine;
4-(3-(3-aminopropyl)phenyl)butan-1-ol;
6-(3-(3-aminopropyl)phenyl)hexan-1-ol;
3-(3-(6-methoxyhexyl)phenyl)propan-1-amine;
4-(3-(3-aminopropyl)phenethyl)heptan-4-ol;
1-(3-(3-aminopropyl)phenyl)-3-ethylpentan-3-ol;
4-(3-(3-aminopropyl)phenyl)-2-methylbutan-2-ol;
3-(3-(3-aminopropyl)phenyl)propan-1-ol;
3-(3-(3-methoxypropyl)phenyl)propan-1-amine;
1-(3-(3-aminopropyl)phenyl)hexan-3-ol;
4-(3-(3-amino-1-hydroxypropyl)phenethyl)heptan-4-ol;
3-(3-(2,6-dimethylphenethyl)phenyl)propan-1-amine;
3-(3-phenethylphenyl)propan-1-amine;
3-(3-(3-phenylpropyl)phenyl)propan-1-amine;
3-amino-1-(3-(3-phenylpropyl)phenyl)propan-1-ol;
3-(3-(2-methylphenethyl)phenyl)propan-1-amine;
3-(3-(2-(biphenyl-3-yl)ethyl)phenyl)propan-1-amine;
3-(3-(4-phenylbutyl)phenyl)propan-1-amine;
3-(3-(2-(naphthalen-2-yl)ethyl)phenyl)propan-1-amine;
3-(3-(2-cyclohexylethyl)phenyl)propan-1-amine;
3-(3-(2-cyclopentylethyl)phenyl)propan-1-amine;
3-amino-1-(3-(2-cyclopentylethyl)phenyl)propan-1-ol;
1-(3-(3-aminopropyl)phenethyl)cyclohexanol;
1-(3-(3-amino-1-hydroxypropyl)phenethyl)cyclohexanol;
1-(3-(3-aminopropyl)phenethyl)cycloheptanol;
1-(3-(3-amino-1-hydroxypropyl)phenethyl)cycloheptanol;
4-(3-(2-aminoethoxy)phenethyl)heptan-4-ol;
1-(3-(2-aminoethoxy)phenethyl)cyclohexanol;
1-(3-(2-aminoethoxy)phenethyl)cycloheptanol;
4-(3-(2-aminoethoxy)phenethyl)tetrahydro-2H-thiopyran-4-ol;
6-(3-(2-aminoethoxy)phenyl)hexan-1-ol;
2-(3-(3-cyclopentylpropyl)phenoxy)ethanamine;
2-(3-(2-(pyridin-3-yl)ethyl)phenoxy)ethanamine;
2-(3-(2-(pyridin-2-yl)ethyl)phenoxy)ethanamine; and
2-(3-(2-(thiophen-2-yl)ethyl)phenoxy)ethanamine.

In another embodiment is the compound of Formula (B) wherein,

G is selected from from —C(R$^{42}$)$_2$—S—R$^{40}$, —C(R$^{42}$)$_2$—SO—R$^{40}$, —C(R$^{42}$)$_2$—SO$_2$—R$^{40}$, —C(R$^{42}$)$_2$—O—R$^{40}$, —C(R$^{42}$)$_2$—N(R$^{42}$)—R$^{40}$, —C(=O)—N(R$^{42}$)—R$^{40}$;
R$^{40}$ is selected from —C(R$^{16}$)(R$^{17}$)(R$^{18}$), aryl, or heteroaryl;
R$^{42}$ is selected from hydrogen or alkyl.

In another embodiment is the compound of Formula (B) wherein,

G is selected from from —C(R$^{42}$)$_2$—S—R$^{40}$, —C(R$^{42}$)$_2$—SO—R$^{40}$, —C(R$^{42}$)$_2$—SO$_2$—R$^{40}$, —C(R$^{42}$)$_2$—O—R$^{40}$, —C(R$^{42}$)$_2$—N(R$^{42}$)—R$^{40}$, —C(=O)—N(R$^{42}$)—R$^{40}$;
R$^{40}$ is selected from —C(R$^{16}$)(R$^{17}$)(R$^{18}$), aryl, or heteroaryl;
R$^{42}$ is selected from hydrogen or alkyl.

In another embodiment is the compound of Formula (B) wherein,

G is selected from from —C(R$^{42}$)$_2$—S—R$^{40}$, —C(R$^{42}$)$_2$—SO—R$^{40}$, —C(R$^{42}$)$_2$—SO$_2$—R$^{40}$, —C(R$^{42}$)$_2$—O—R$^{40}$.

In another embodiment is the compound of Formula (B) wherein,

G is selected from —C(R$^{42}$)$_2$—N(R$^{42}$)—R$^{40}$, —C(=O)—N(R$^{42}$)—R$^{40}$.

In another embodiment is the compound of Formula (B) wherein,

G is selected from —C(R$^{42}$)$_2$—N(R$^{42}$)—R$^{40}$, —C(=O)—N(R$^{42}$)—R$^{40}$.

In another embodiment is the compound of Formula (B) wherein,

R$^{42}$ is a hydrogen or C$_1$-C$_3$ alkyl; and

R$^{40}$ is aryl or heteroaryl.

In another embodiment is the compound of Formula (B) wherein,

R$^{40}$ is selected from —C(R$^{16}$)(R$^{17}$)(R$^{18}$);

R$^{16}$ and R$^{17}$ are each independently selected from hydrogen, alkyl, halo, aryl, heteroaryl, aralkyl, heteroarylalkyl or fluoroalkyl; and R$^{18}$ is selected from hydrogen, alkyl, alkoxy, hydroxy, halo or fluoroalkyl.

In another embodiment is the compound of Formula (B) wherein,

R$^{40}$ is selected from —C(R$^{16}$)(R$^{17}$)(R$^{18}$);

R$^{16}$ and R$^{17}$ are each independently selected from hydrogen, alkyl, halo, aryl, heteroaryl, aralkyl, heteroarylalkyl or fluoroalkyl; or R$^{16}$ and R$^{17}$, together with the carbon to which they are attached form a carbocyclyl or heterocycle;

R$^{18}$ is selected from hydrogen, alkyl, alkoxy, hydroxy, halo or fluoroalkyl.

In an additional embodiment is the compound of Formula (A) wherein one, more than one, or all of the non-exchangeable $^1$H atoms have been substituted with $^2$H atoms.

In a further embodiment is the compound of Formula (A) selected from the group consisting of:

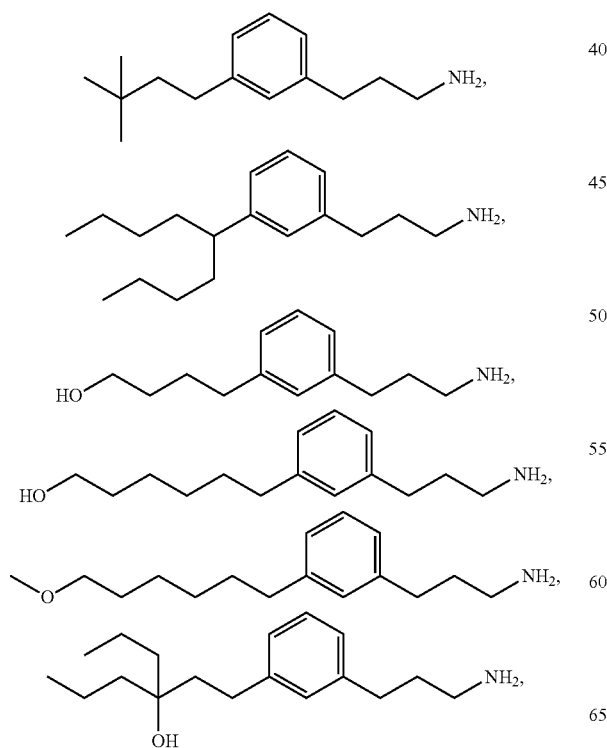

-continued

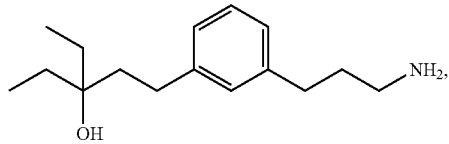

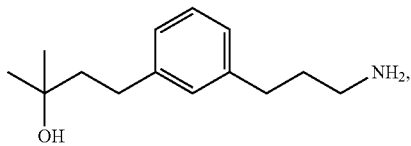

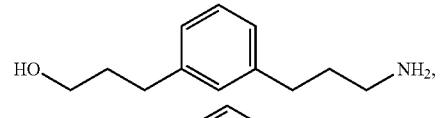

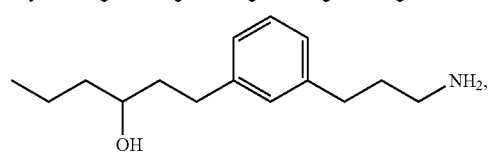

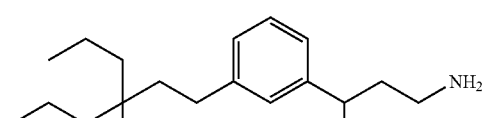

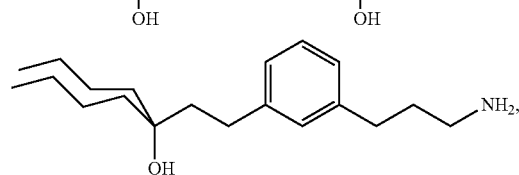

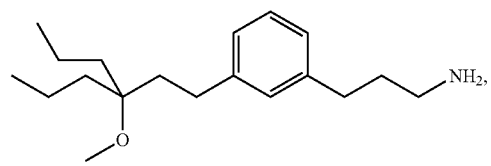

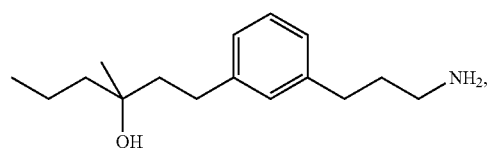

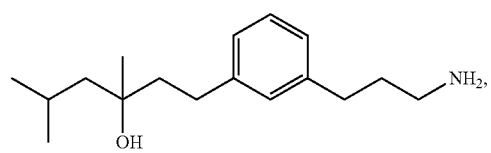

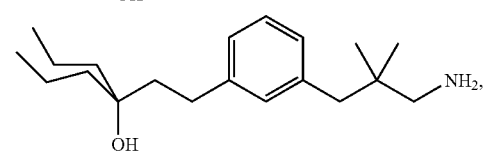

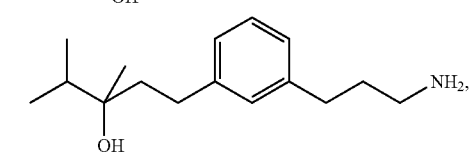

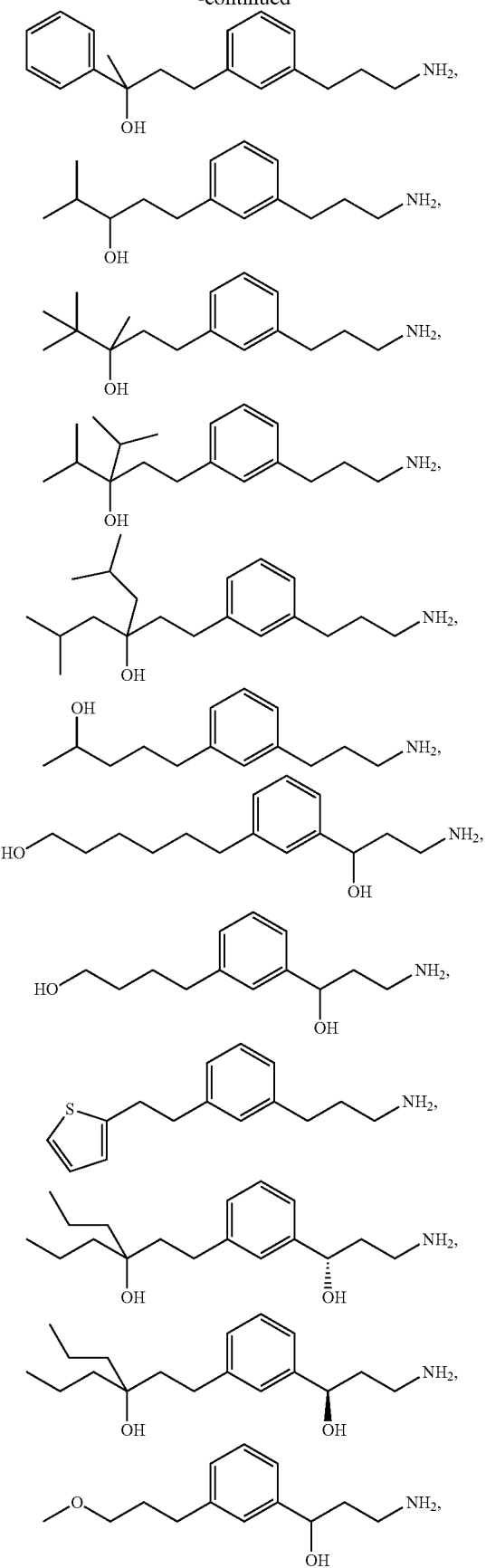
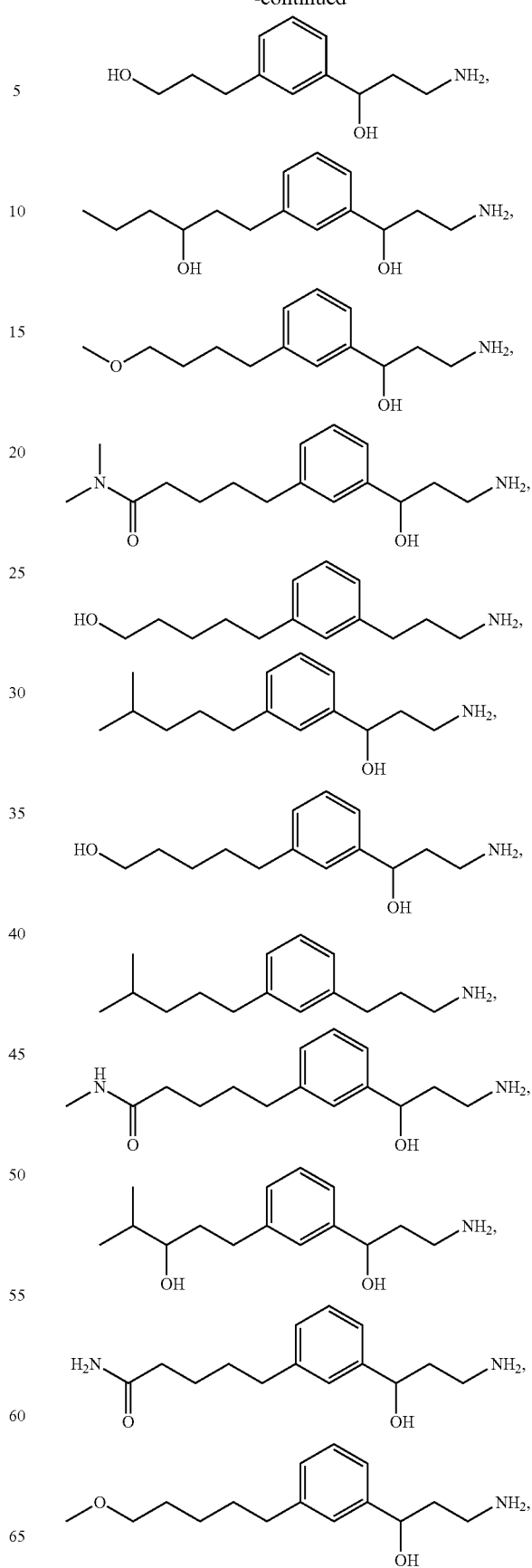

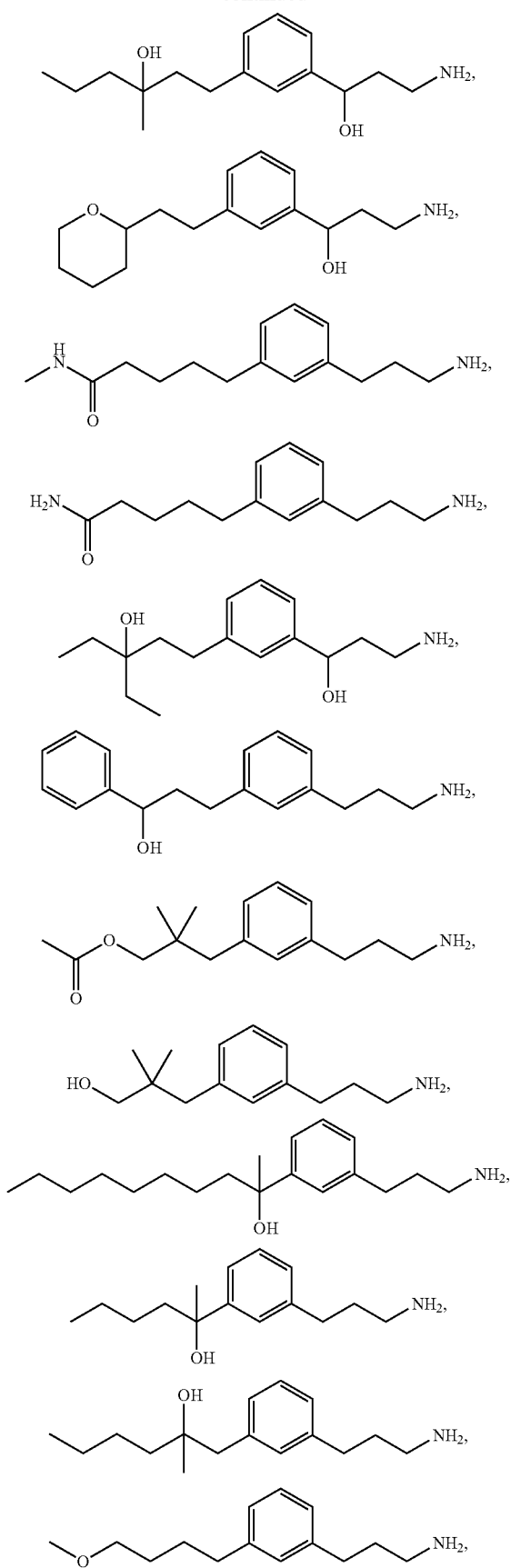

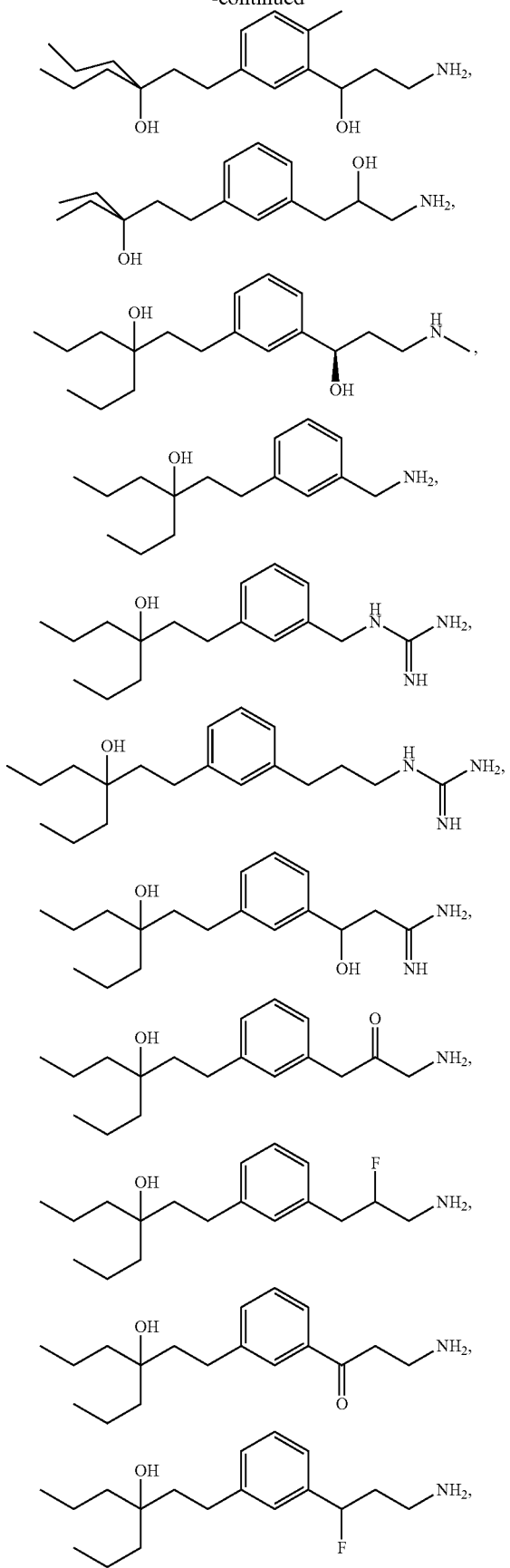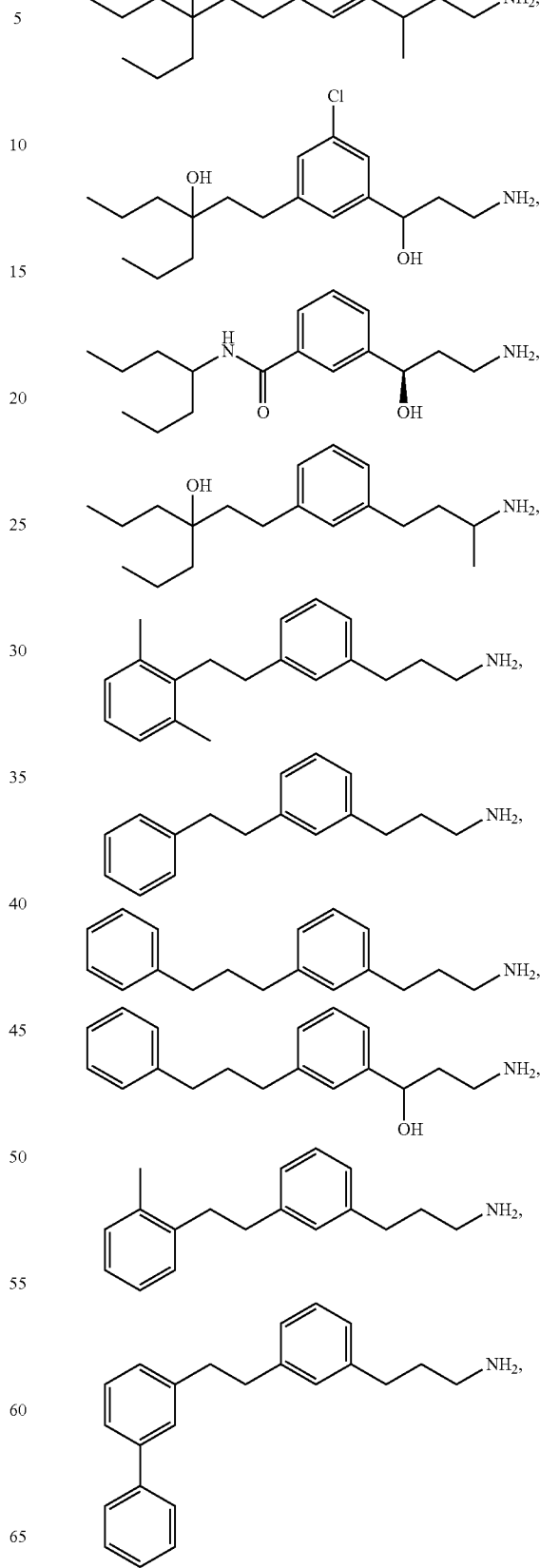

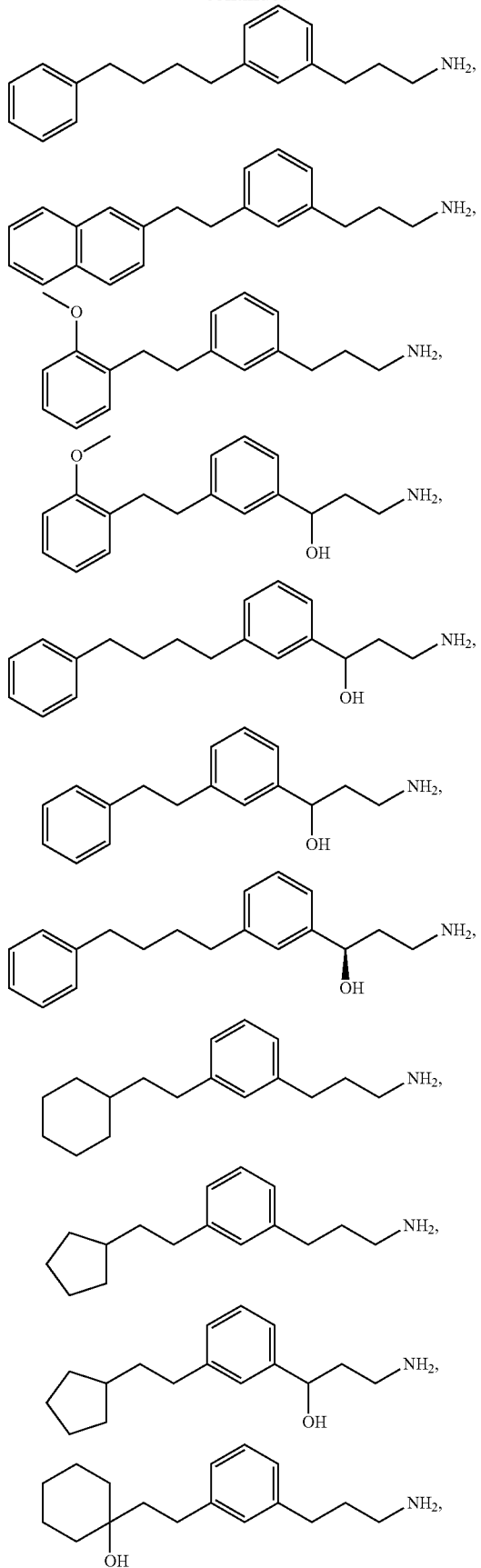
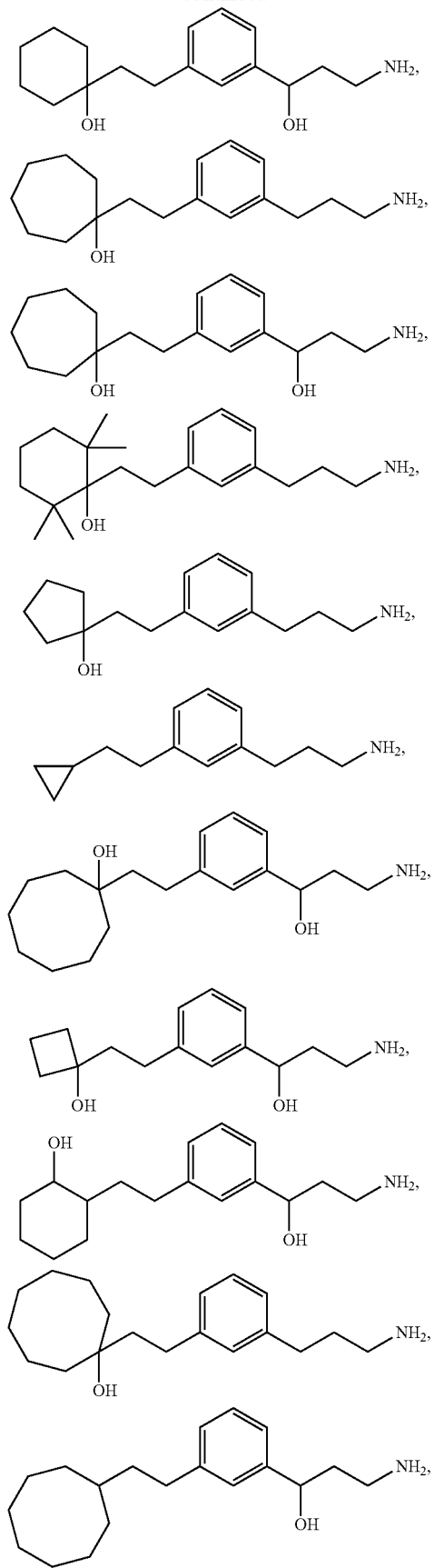

79
-continued
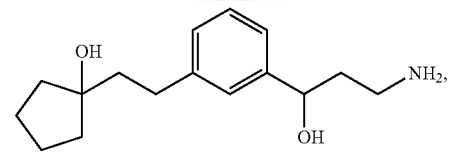
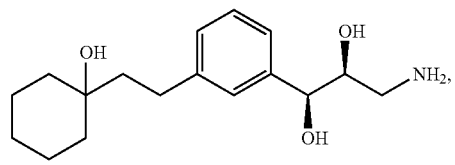
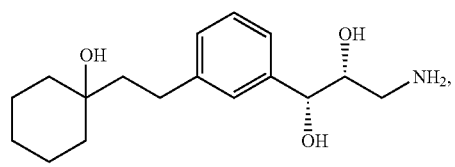
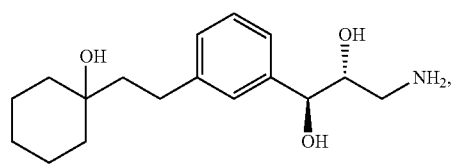
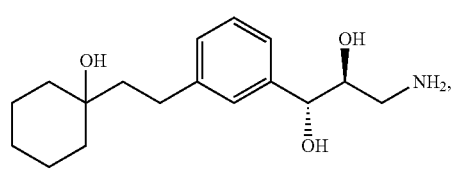
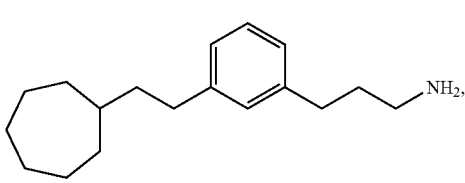
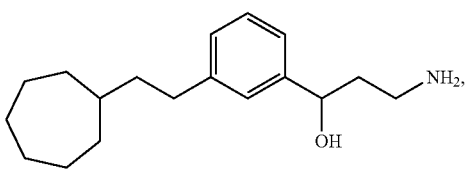
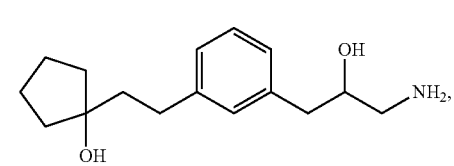
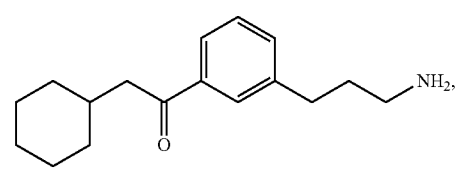
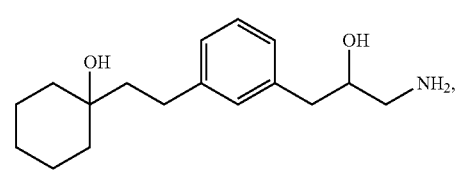
80
-continued
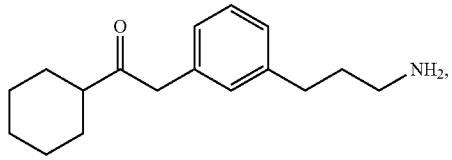
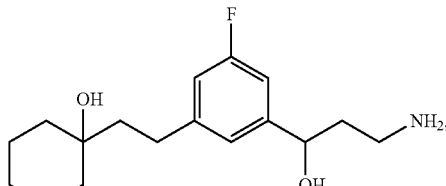
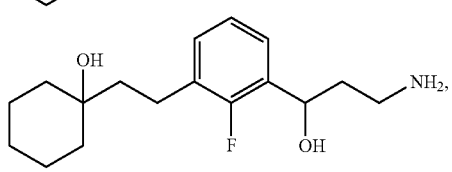
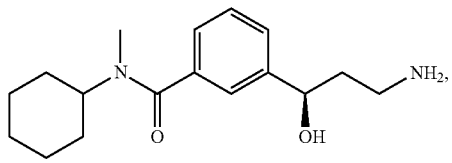
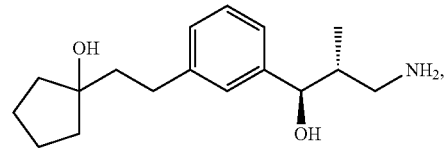
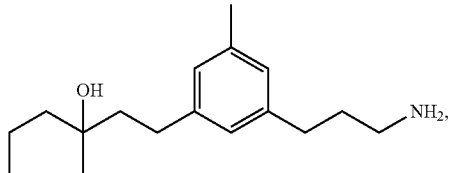
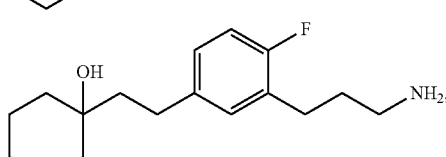
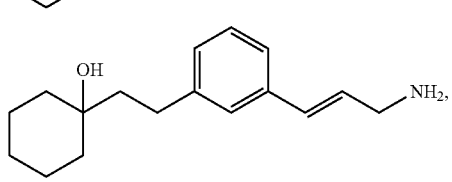
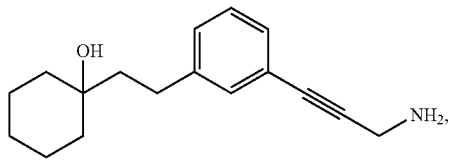
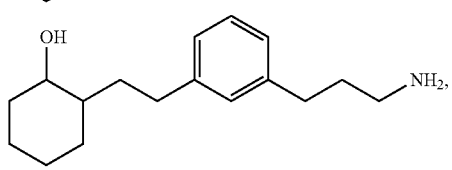

81
-continued
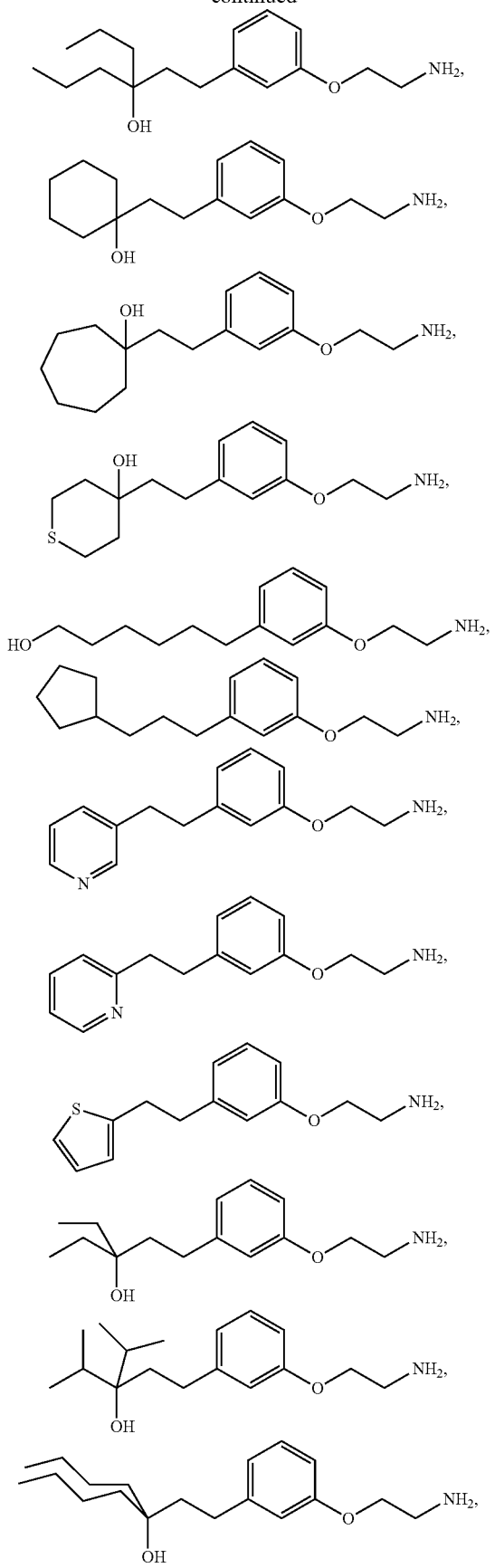
82
-continued
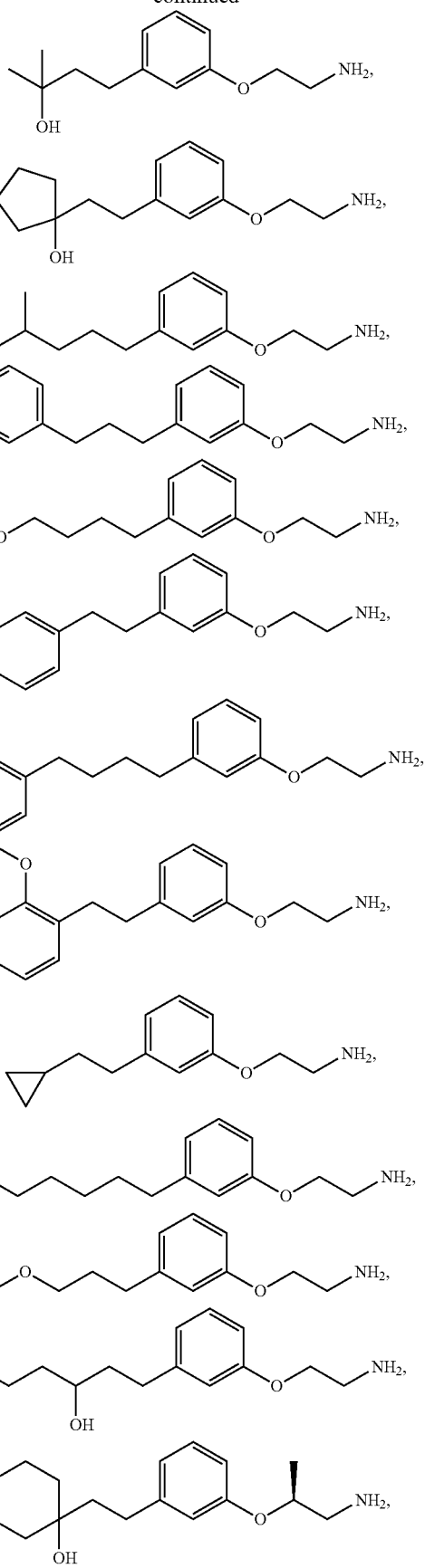

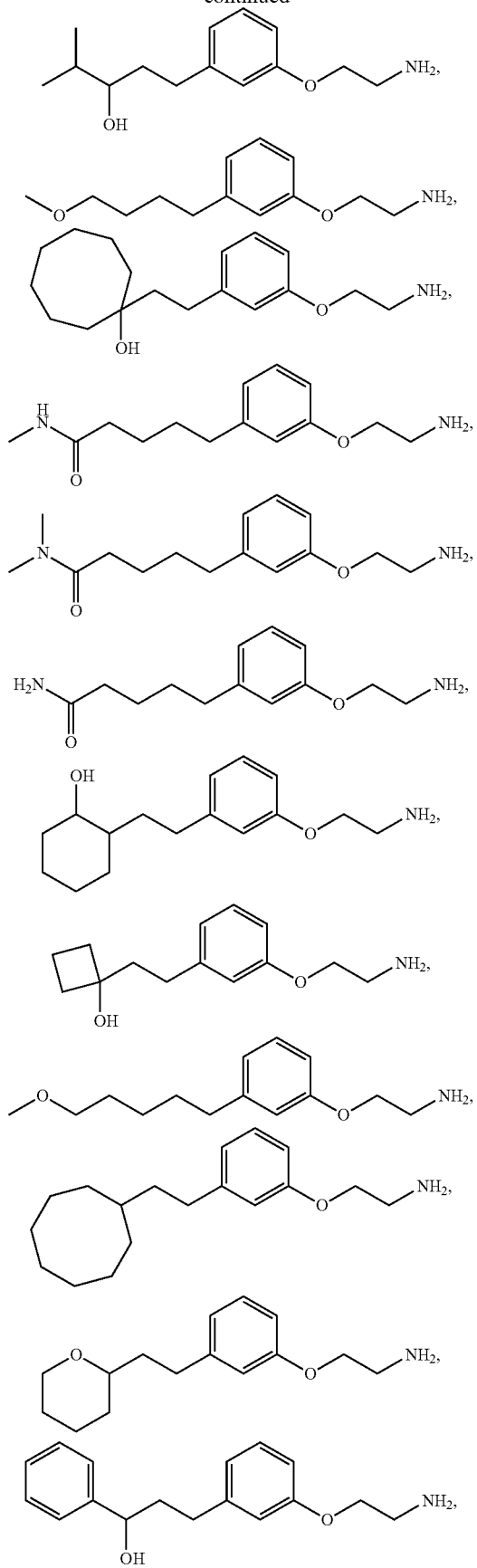
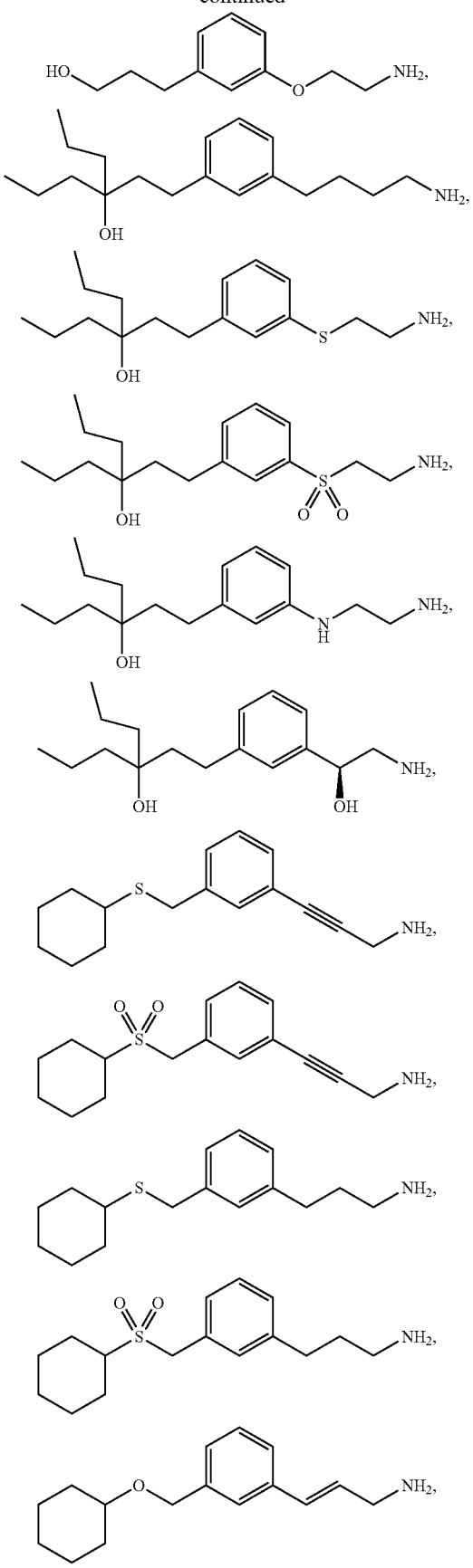

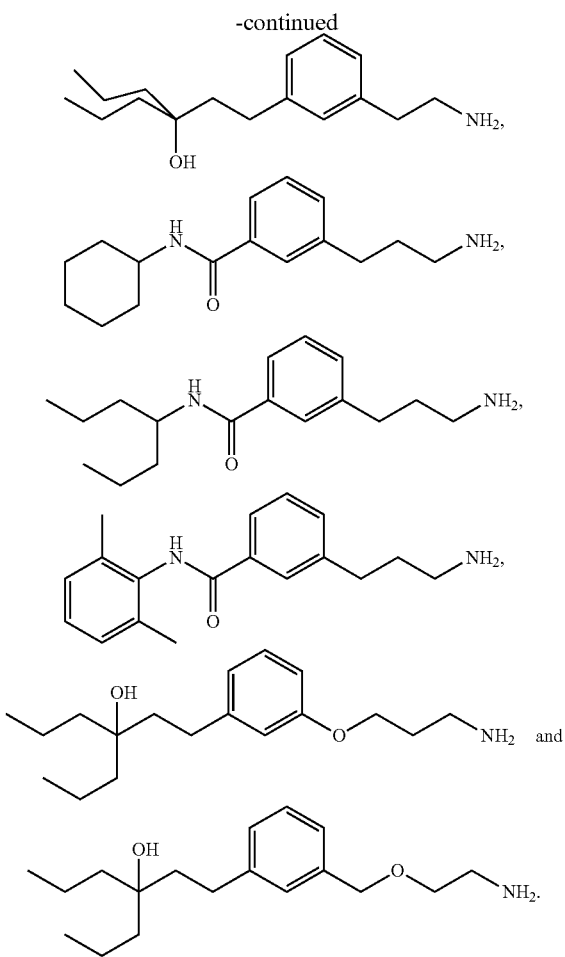

In one embodiment is a pharmaceutical composition comprising a pharmaceutically acceptable carrier and a compound of Formula (A) or tautomer, stereoisomer, geometric isomer, or pharmaceutically acceptable solvate, hydrate, salt, N-oxide or prodrug thereof:

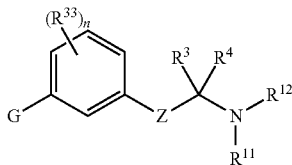

Formula (A)

wherein,

Z is a bond, —C($R^1$)($R^2$)—, —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)— or —X—C($R^{31}$)($R^{32}$)—C($R^1$)($R^2$)—;

X is —O—, —S—, —S(=O)—, —S(=O)$_2$—, —N($R^{30}$)—, —C(=O)—, —C(=CH$_2$)—, —C(=N—N$R^{35}$)—, or —C(=N—O$R^{35}$)—;

G is selected from —C($R^{41}$)$_2$—C($R^{41}$)$_2$—$R^{40}$, —C($R^{42}$)$_2$—S—$R^{40}$, —C($R^{42}$)$_2$—SO—$R^{40}$, —C($R^{42}$)$_2$—SO$_2$—$R^{40}$, —C($R^{42}$)$_2$—O—$R^{40}$, —C($R^{42}$)$_2$—N($R^{42}$)—$R^{40}$, —C(=O)—N($R^{42}$)—$R^{40}$;

$R^{40}$ is selected from —C($R^{16}$)($R^{17}$)($R^{18}$), aryl, or heteroaryl;

each $R^{41}$ is independently selected from hydrogen, hydroxy, O$R^6$, alkyl, or two $R^{41}$ groups together may form an oxo;

each $R^{42}$ is independently selected from hydrogen or alkyl;

$R^1$ and $R^2$ are each independently selected from hydrogen, halogen, $C_1$-$C_5$ alkyl, fluoroalkyl, —O$R^6$ or —N$R^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —O$R^6$ or —N$R^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^7$ and $R^8$ are each independently selected from hydrogen, alkyl, carbocyclyl, heterocyclyl, —C(=O)$R^{13}$, SO$_2R^{13}$, CO$_2R^{13}$ or SO$_2$N$R^{24}R^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, —O$R^{19}$, —N$R^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)$R^{23}$, —C(NH)NH$_2$, SO$_2R^{23}$, CO$_2R^{23}$ or SO$_2$N$R^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, SO$_2R^{22}$, CO$_2R^{22}$ or SO$_2$N$R^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, O$R^{34}$, alkyl, or fluoroalkyl; and n is 0, 1, 2, 3, or 4; with the provision that G is not an unsubstituted normal alkyl and the provision that the compound of Formula A is not:

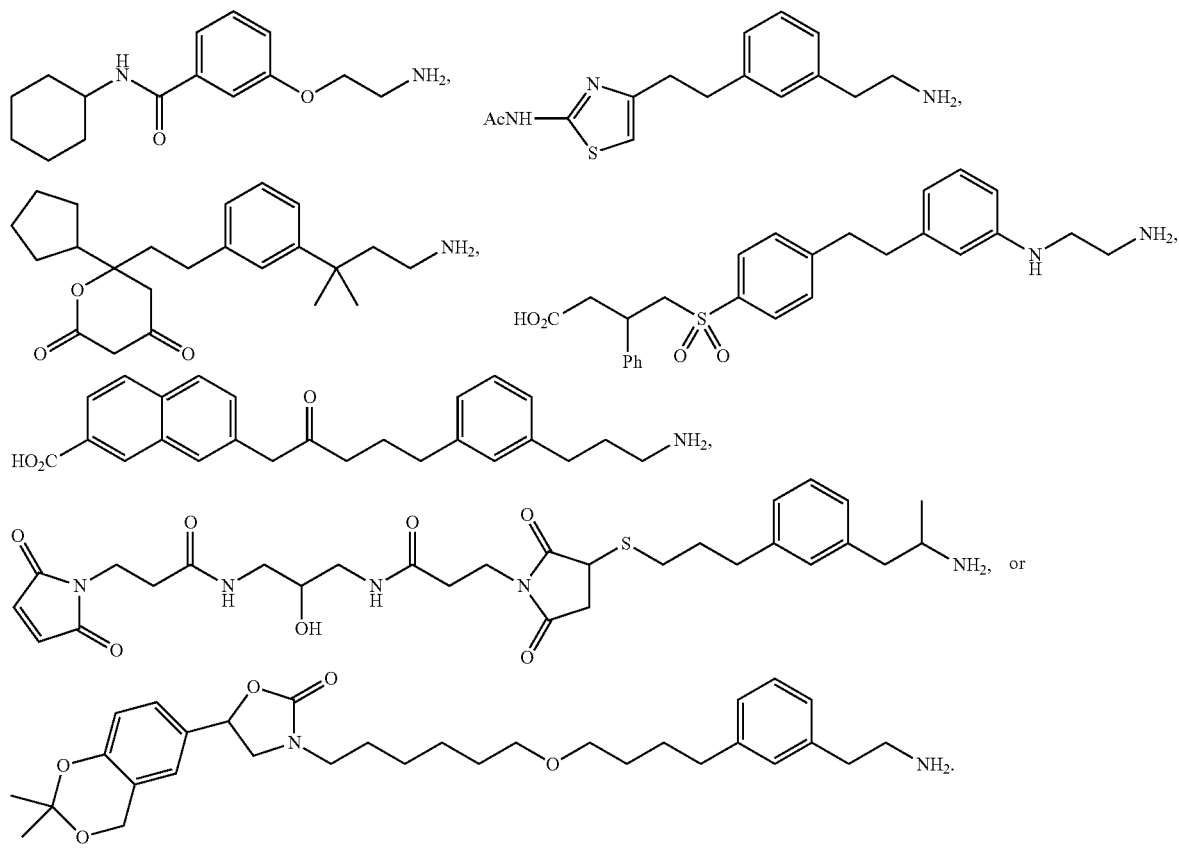

In an additional embodiment is a non-retinoid compound that inhibits an isomerase reaction resulting in production of 11-cis retinol, wherein said isomerase reaction occurs in RPE, and wherein said compound has an $ED_{50}$ value of 1 mg/kg or less when administered to a subject. In a further embodiment is the non-retinoid compound wherein the $ED_{50}$ value is measured after administering a single dose of the compound to said subject for about 2 hours or longer. In a further embodiment is the non-retinoid compound, wherein the non-retinoid compound is an alkoxyl compound. In an additional embodiment is a pharmaceutical composition comprising a pharmaceutically acceptable carrier and a non-retinoid compound as described herein. In an additional embodiment is a method for treating an ophthalmic disease or disorder in a subject, comprising administering to the subject a pharmaceutical composition comprising a pharmaceutically acceptable carrier and a non-retinoid compound as described herein.

In an additional embodiment is a compound that inhibits 11-cis-retinol production with an $IC_{50}$ of about 1 μM or less when assayed in vitro, utilizing extract of cells that express RPE65 and LRAT, wherein the extract further comprises CRALBP, wherein the compound is stable in solution for at least about 1 week at room temperature. In a further embodiment, the compound inhibits 11-cis-retinol production with an $IC_{50}$ of about 0.1 μM or less. In a further embodiment, the compound inhibits 11-cis-retinol production with an $IC_{50}$ of about 0.01 μM or less. In a further embodiment, the compound that inhibits 11-cis-retinol production is a non-retinoid compound. In an additional embodiment is a pharmaceutical composition comprising a pharmaceutically acceptable carrier and a compound that inhibits 11-cis-retinol production as described herein. In an additional embodiment is a method for treating an ophthalmic disease or disorder in a subject, comprising administering to the subject a pharmaceutical composition comprising a pharmaceutically acceptable carrier and a compound that inhibits 11-cis-retinol production as described herein. In an additional embodiment is a method of modulating chromophore flux in a retinoid cycle comprising introducing into a subject a compound that inhibits 11-cis-retinol production as described herein.

In an additional embodiment is a method for treating an ophthalmic disease or disorder in a subject, comprising administering to the subject a compound of Formula (G) or tautomer, stereoisomer, geometric isomer or a pharmaceutically acceptable solvate, hydrate, salt, N-oxide or prodrug thereof:

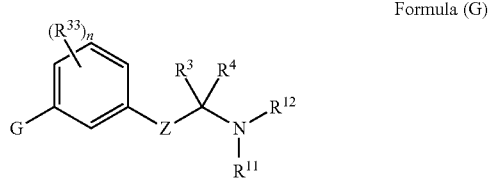

Formula (G)

wherein,
Z is a bond, —C($R^1$)($R^2$)—, —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)— or —X—C($R^{31}$)($R^{32}$)—C($R^1$)($R^2$)—;
X is —O—, —S—, —S(=O)—, —S(=O)$_2$—, —N($R^{30}$)—, —C(=O)—, —C(=CH$_2$)—, —C(=N—N$R^{35}$)—, or —C(=N—O$R^{35}$)—;

G is selected from —C(R$^{41}$)$_2$—C(R$^{41}$)$_2$—R$^{40}$, —C(R$^{42}$)$_2$—S—R$^{40}$, —C(R$^{42}$)$_2$—SO—R$^{40}$, —C(R$^{42}$)$_2$—SO$_2$—R$^{40}$, —C(R$^{42}$)$_2$—O—R$^{40}$, —C(R$^{42}$)$_2$—N(R$^{42}$)—R$^{40}$, —C(=O)—N(R$^{42}$)—R$^{40}$;

R$^{40}$ is selected from —C(R$^{16}$)(R$^{17}$)(R$^{18}$), aryl, or heteroaryl;

each R$^{41}$ is independently selected from hydrogen, hydroxy, OR$^6$, alkyl, or two R$^{41}$ groups together may form an oxo;

each R$^{42}$ is independently selected from hydrogen or alkyl;

R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;

R$^{31}$ and R$^{32}$ are each independently selected from hydrogen, C$_1$-C$_5$ alkyl, or fluoroalkyl;

R$^{36}$ and R$^{37}$ are each independently selected from hydrogen, halogen, C$_1$-C$_5$ alkyl, fluoroalkyl, —OR$^6$ or —NR$^7$R$^8$; or R$^{36}$ and R$^{37}$ together form an oxo; or optionally, R$^{36}$ and R$^1$ together form a direct bond to provide a double bond; or optionally, R$^{36}$ and R$^1$ together form a direct bond, and R$^{37}$ and R$^2$ together form a direct bond to provide a triple bond;

R$^3$ and R$^4$ are each independently selected from hydrogen, alkyl, alkenyl, fluoroalkyl, aryl, heteroaryl, carbocyclyl or C-attached heterocyclyl; or R$^3$ and R$^4$ together with the carbon atom to which they are attached, form a carbocyclyl or heterocyclyl; or R$^3$ and R$^4$ together form an imino;

R$^5$ is C$_5$-C$_{15}$ alkyl or carbocyclyalkyl;

R$^7$ and R$^8$ are each independently selected from hydrogen, alkyl, carbocyclyl, heterocyclyl, —C(=O)R$^{13}$, SO$_2$R$^{13}$, CO$_2$R$^{13}$ or SO$_2$NR$^{24}$R$^{25}$; or R$^7$ and R$^8$ together with the nitrogen atom to which they are attached, form an N-heterocyclyl;

R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ form an oxo; or optionally, R$^9$ and R$^1$ together form a direct bond to provide a double bond; or optionally, R$^9$ and R$^1$ together form a direct bond, and R$^{10}$ and R$^2$ together form a direct bond to provide a triple bond;

R$^{11}$ and R$^{12}$ are each independently selected from hydrogen, alkyl, carbocyclyl, —C(=O)R$^{23}$, —C(NH)NH$_2$, SO$_2$R$^{23}$, CO$_2$R$^{23}$ or SO$_2$NR$^{28}$R$^{29}$; or R$^{11}$ and R$^{12}$, together with the nitrogen atom to which they are attached, form an N-heterocyclyl;

each R$^{13}$, R$^{22}$ and R$^{23}$ is independently selected from alkyl, heteroalkyl, alkenyl, aryl, aralkyl, carbocyclyl, heteroaryl or heterocyclyl;

R$^6$, R$^{19}$, R$^{30}$, R$^{34}$ and R$^{35}$ are each independently hydrogen or alkyl;

R$^{20}$ and R$^{21}$ are each independently selected from hydrogen, alkyl, carbocyclyl, heterocyclyl, —C(=O)R$^{22}$, SO$_2$R$^{22}$, CO$_2$R$^{22}$ or SO$_2$NR$^{26}$R$^{27}$; or R$^{20}$ and R$^{21}$ together with the nitrogen atom to which they are attached, form an N-heterocyclyl; and each R$^{24}$, R$^{25}$, R$^{26}$, R$^{27}$, R$^{28}$ and R$^{29}$ is independently selected from hydrogen, alkyl, alkenyl, fluoroalkyl, aryl, heteroaryl, carbocyclyl or heterocyclyl;

R$^{16}$ and R$^{17}$ are each independently selected from hydrogen, alkyl, halo, aryl, heteroaryl, aralkyl, heteroarylalkyl or fluoroalkyl; or R$^{16}$ and R$^{17}$, together with the carbon to which they are attached form a carbocyclyl or heterocycle;

R$^{18}$ is selected from hydrogen, alkyl, alkoxy, hydroxy, halo or fluoroalkyl;

each R$^{33}$ is independently selected from halogen, OR$^{34}$, alkyl, or fluoroalkyl; and n is 0, 1, 2, 3, or 4.

In an additional embodiment is a method of modulating chromophore flux in a retinoid cycle comprising introducing into a subject a compound of Formula (G). In a further embodiment is the method resulting in a reduction of lipofuscin pigment accumulated in an eye of the subject. In a further embodiment is the method resulting in a reduction of lipofuscin pigment accumulated in an eye of the subject, wherein the lipofuscin pigment is N-retinylidene-N-retinyl-ethanolamine (A2E).

In a further embodiment is the method of treating an ophthalmic disease or disorder in a subject as described herein resulting in a reduction of lipofuscin pigment accumulated in an eye of the subject. In a further embodiment is the method of treating an ophthalmic disease or disorder in a subject as described herein resulting in a reduction of lipofuscin pigment accumulated in an eye of the subject, wherein the lipofuscin pigment is N-retinylidene-N-retinyl-ethanolamine (A2E).

In a further embodiment is the method of treating an ophthalmic disease or disorder in a subject as described herein, wherein the ophthalmic disease or disorder is age-related macular degeneration or Stargardt's macular dystrophy. In a further embodiment is the method of treating an ophthalmic disease or disorder in a subject as described herein, wherein the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS. In a further embodiment is the method of treating an ophthalmic disease or disorder in a subject as described herein resulting in a reduction of lipofuscin pigment accumulated in an eye of the subject. In a further embodiment is the method of treating an ophthalmic disease or disorder in a subject as described herein resulting in a reduction of lipofuscin pigment accumulated in an eye of the subject, wherein the lipofuscin pigment is N-retinylidene-N-retinyl-ethanolamine (A2E).

In another embodiment is a method of inhibiting dark adaptation of a rod photoreceptor cell of the retina comprising contacting the retina with a compound of Formula (G). In another embodiment is a method of inhibiting dark adaptation of a rod photoreceptor cell of the retina comprising contacting the retina with a non-retinoid compound as described herein. In another embodiment is a method of inhibiting dark adaptation of a rod photoreceptor cell of the retina comprising contacting the retina with a compound that inhibits 11-cis-retinol production as described herein.

In another embodiment is a method of inhibiting regeneration of rhodopsin in a rod photoreceptor cell of the retina comprising contacting the retina with a compound of Formula (G). In another embodiment is a method of inhibiting regeneration of rhodopsin in a rod photoreceptor cell of the retina comprising contacting the retina with a non-retinoid compound as described herein. In another embodiment is a method of inhibiting regeneration of rhodopsin in a rod photoreceptor cell of the retina comprising contacting the retina with a compound that inhibits 11-cis-retinol production as described herein.

In another embodiment is a method of reducing ischemia in an eye of a subject comprising administering to the subject a pharmaceutical composition comprising a pharmaceutically acceptable carrier and a compound of Formula (G).

In an additional embodiment is a method of reducing ischemia in an eye of a subject comprising administering to the subject a pharmaceutical composition comprising a pharmaceutically acceptable carrier and a non-retinoid compound as described herein. In an additional embodiment is a method of reducing ischemia in an eye of a subject comprising administering to the subject a pharmaceutical composition comprising a pharmaceutically acceptable carrier and a compound that inhibits 11-cis-retinol production as described herein. In a further embodiment is the method of reducing ischemia in an eye of a subject, wherein the pharmaceutical composition is administered under conditions and at a time sufficient to inhibit dark adaptation of a rod photoreceptor cell, thereby reducing ischemia in the eye.

In an additional embodiment is a method of inhibiting neovascularization in the retina of an eye of a subject comprising administering to the subject a pharmaceutical composition comprising a pharmaceutically acceptable carrier and a non-retinoid compound as described herein. In an additional embodiment is a method of inhibiting neovascularization in the retina of an eye of a subject comprising administering to the subject a pharmaceutical composition comprising a pharmaceutically acceptable carrier and a compound that inhibits 11-cis-retinol production as described herein. In a further embodiment is the method of inhibiting neovascularization in the retina of an eye of a subject, wherein the pharmaceutical composition is administered under conditions and at a time sufficient to inhibit dark adaptation of a rod photoreceptor cell, thereby inhibiting neovascularization in the retina.

In an additional embodiment is a method of inhibiting degeneration of a retinal cell in a retina comprising contacting the retina with a compound of Formula (G). In an additional embodiment is a method of inhibiting degeneration of a retinal cell in a retina comprising contacting the retina with a non-retinoid compound as described herein. In an additional embodiment is a method of inhibiting degeneration of a retinal cell in a retina comprising contacting the retina with a compound that inhibits 11-cis-retinol production as described herein.

In a further embodiment is the method of inhibiting degeneration of a retinal cell in a retina wherein the retinal cell is a retinal neuronal cell. In a further embodiment is the method of inhibiting degeneration of a retinal cell in a retina wherein the retinal neuronal cell is a photoreceptor cell.

In another embodiment is a method of reducing lipofuscin pigment accumulated in a subject's retina comprising administering to the subject a pharmaceutical composition comprising a pharmaceutically acceptable carrier and a compound of Formula (G). In an additional embodiment is a method of reducing lipofuscin pigment accumulated in a subject's retina wherein the lipofuscin is N-retinylidene-N-retinyl-ethanolamine (A2E).

In an additional embodiment is a method of inhibiting reducing lipofuscin pigment accumulated in a subject's retina comprising administering to the subject a pharmaceutical composition comprising a pharmaceutically acceptable carrier and a non-retinoid compound as described herein. In an additional embodiment is a method of reducing lipofuscin pigment accumulated in a subject's retina comprising administering to the subject a pharmaceutical composition comprising a pharmaceutically acceptable carrier and a compound that inhibits 11-cis-retinol production as described herein. In an additional embodiment is a method of reducing lipofuscin pigment accumulated in a subject's retina wherein the lipofuscin is N-retinylidene-N-retinyl-ethanolamine (A2E).

In an additional embodiment is a method of modulating chromophore flux in a retinoid cycle comprising introducing into a subject a compound of Formula (G) or tautomer, stereoisomer, geometric isomer or a pharmaceutically acceptable solvate, hydrate, salt, N-oxide or prodrug thereof:

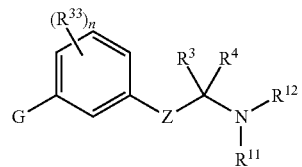

Formula (G)

wherein,

Z is a bond, —C(R$^1$)(R$^2$)—, —C(R$^9$)(R$^{10}$)—C(R$^1$)(R$^2$)—, —X—C(R$^{31}$)(R$^{32}$)—, —C(R$^9$)(R$^{10}$)—C(R$^1$)(R$^2$)—C(R$^{36}$)(R$^{37}$)— or —X—C(R$^{31}$)(R$^{32}$)—C(R$^1$)(R$^2$)—;

X is —O—, —S—, —S(=O)—, —S(=O)$_2$—, —N(R$^{30}$)—, —C(=O)—, —C(=CH$_2$)—, —C(=N—NR$^{35}$)—, or —C(=N—OR$^{35}$)—;

G is selected from —C(R$^{41}$)$_2$—C(R$^{41}$)$_2$—R$^{40}$, —C(R$^{42}$)$_2$—S—R$^{40}$, —C(R$^{42}$)$_2$—SO—R$^{40}$, —C(R$^{42}$)$_2$—SO$_2$—R$^{40}$, —C(R$^{42}$)$_2$—O—R$^{40}$, —C(R$^{42}$)$_2$—N(R$^{42}$)—R$^{40}$, —C(=O)—N(R$^{42}$)—R$^{40}$;

R$^{40}$ is selected from —C(R$^{16}$)(R$^{17}$)(R$^{18}$), aryl, or heteroaryl;

each R$^{41}$ is independently selected from hydrogen, hydroxy, OR$^6$, alkyl, or two R$^{41}$ groups together may form an oxo;

each R$^{42}$ is independently selected from hydrogen or alkyl;

R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;

R$^{31}$ and R$^{32}$ are each independently selected from hydrogen, C$_1$-C$_5$ alkyl, or fluoroalkyl;

R$^{36}$ and R$^{37}$ are each independently selected from hydrogen, halogen, C$_1$-C$_5$ alkyl, fluoroalkyl, —OR$^6$ or —NR$^7$R$^8$; or R$^{36}$ and R$^{37}$ together form an oxo; or optionally, R$^{36}$ and R$^1$ together form a direct bond to provide a double bond; or optionally, R$^{36}$ and R$^1$ together form a direct bond, and R$^{37}$ and R$^2$ together form a direct bond to provide a triple bond;

R$^3$ and R$^4$ are each independently selected from hydrogen, alkyl, alkenyl, fluoroalkyl, aryl, heteroaryl, carbocyclyl or C-attached heterocyclyl; or R$^3$ and R$^4$ together with the carbon atom to which they are attached, form a carbocyclyl or heterocyclyl; or R$^3$ and R$^4$ together form an imino;

R$^5$ is C$_5$-C$_{15}$ alkyl or carbocyclylalkyl;

R$^7$ and R$^8$ are each independently selected from hydrogen, alkyl, carbocyclyl, heterocyclyl, —C(=O)R$^{13}$, SO$_2$R$^{13}$, CO$_2$R$^{13}$ or SO$_2$NR$^{24}$R$^{25}$; or R$^7$ and R$^8$ together with the nitrogen atom to which they are attached, form an N-heterocyclyl;

R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ form an oxo; or optionally, R$^9$ and R$^1$ together form a direct bond to provide a double bond; or optionally, R$^9$ and R$^1$ together form a direct bond, and R$^{10}$ and R$^2$ together form a direct bond to provide a triple bond;

R$^{11}$ and R$^{12}$ are each independently selected from hydrogen, alkyl, carbocyclyl, —C(=O)R$^{23}$, —C(NH)NH$_2$, SO$_2$R$^{23}$, CO$_2$R$^{23}$ or SO$_2$NR$^{28}$R$^{29}$; or R$^{11}$ and R$^{12}$, together with the nitrogen atom to which they are attached, form an N-heterocyclyl;

each R$^{13}$, R$^{22}$ and R$^{23}$ is independently selected from alkyl, heteroalkyl, alkenyl, aryl, aralkyl, carbocyclyl, heteroaryl or heterocyclyl;

R$^6$, R$^{19}$, R$^{30}$, R$^{34}$ and R$^{35}$ are each independently hydrogen or alkyl;

$R^{20}$ and $R^{21}$ are each independently selected from hydrogen, alkyl, carbocyclyl, heterocyclyl, —C(=O)$R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, $OR^{34}$, alkyl, or fluoroalkyl; and n is 0, 1, 2, 3, or 4.

In a further embodiment is the method for treating an ophthalmic disease or disorder in a subject, comprising administering to the subject a compound of Formula (G), wherein the compound of Formula (G) is selected from the group consisting of:

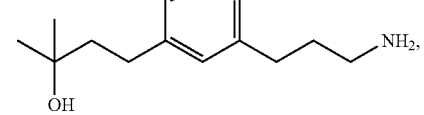

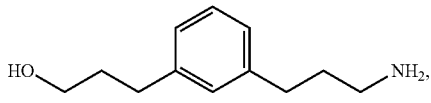

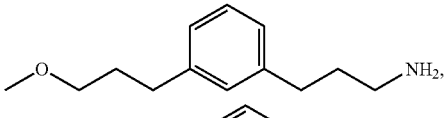

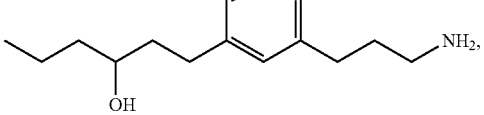

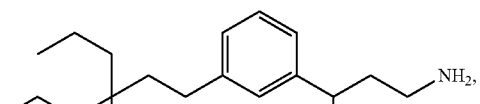

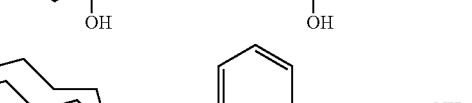

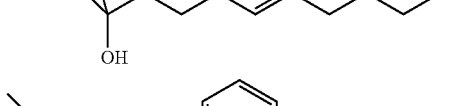


-continued

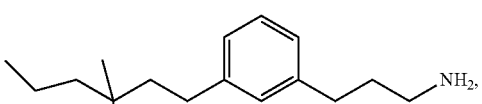

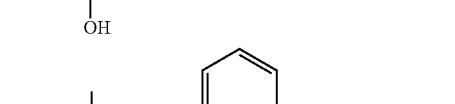

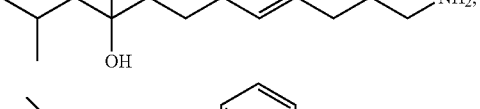

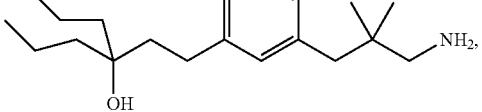

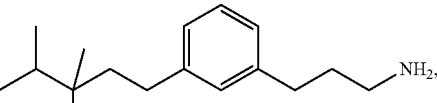

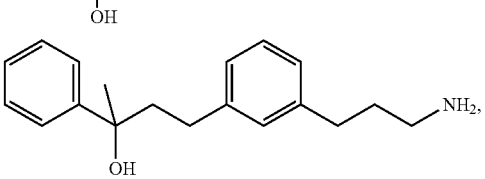

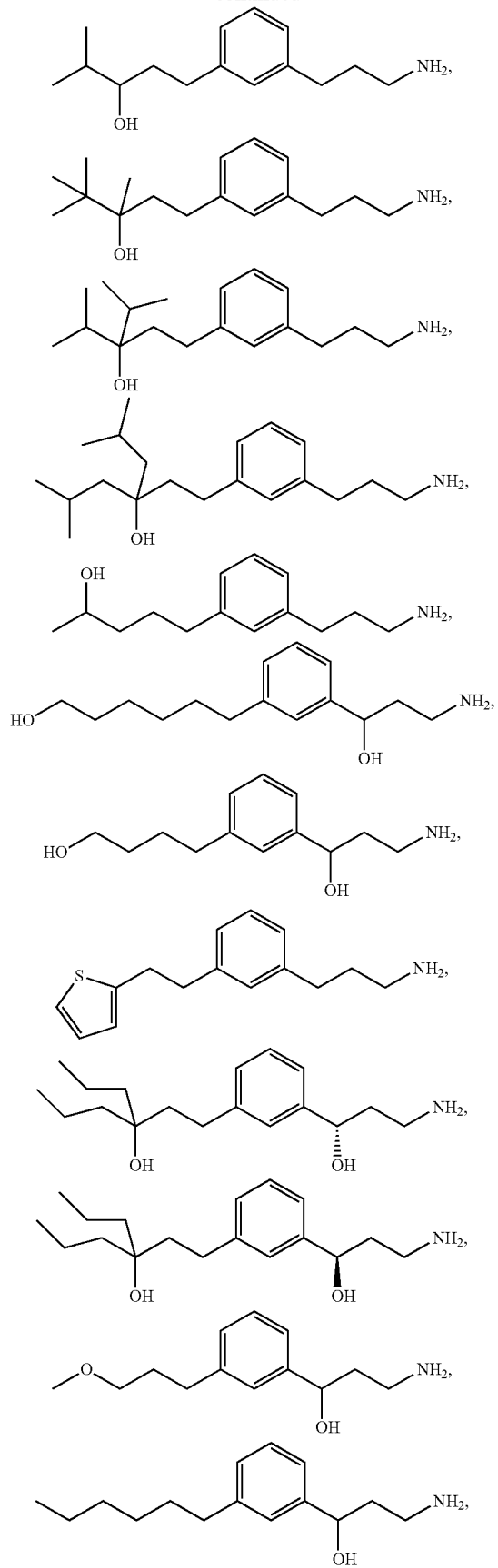
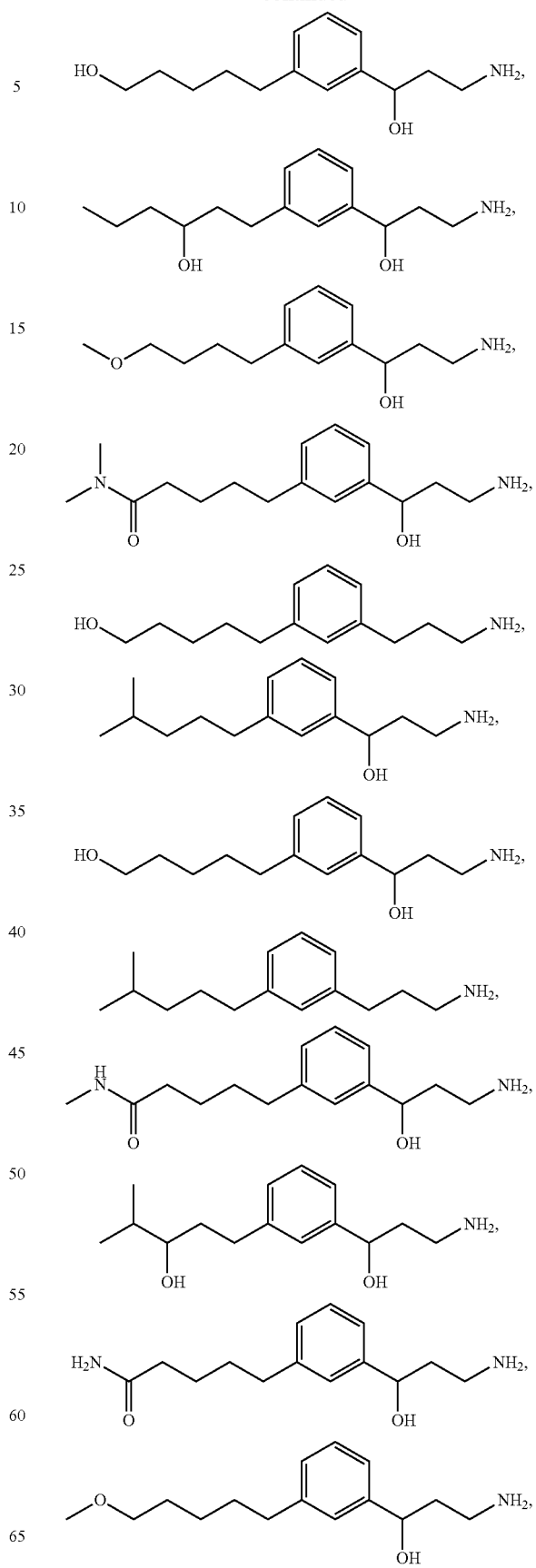

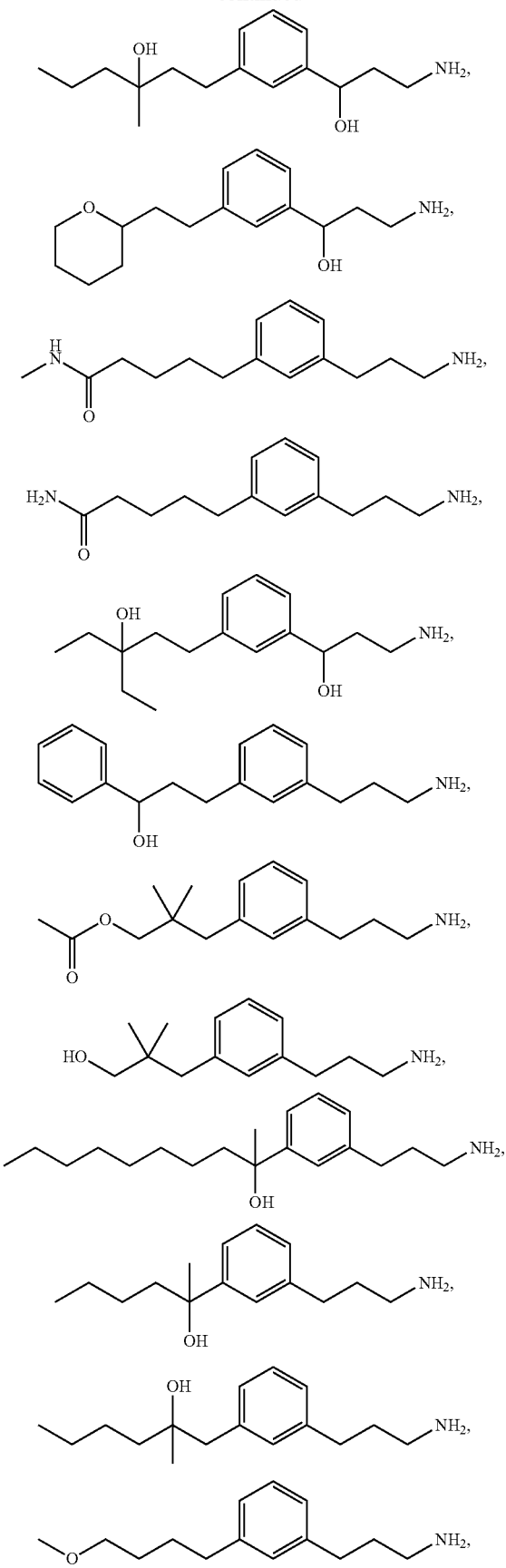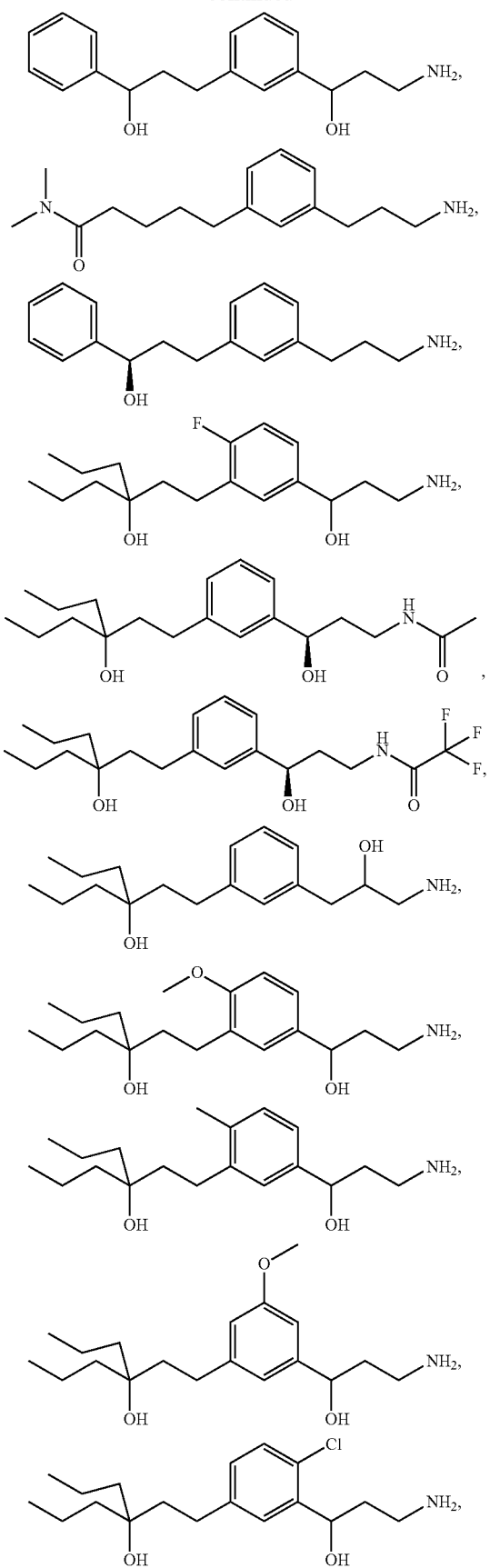

99
-continued
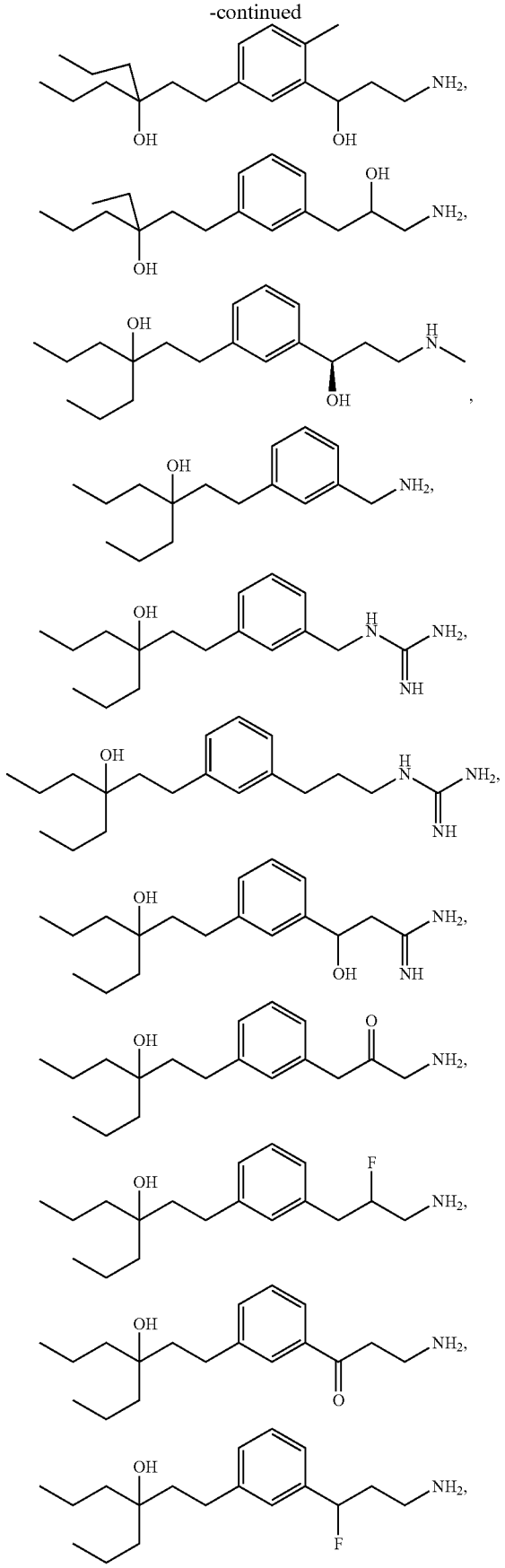
100
-continued
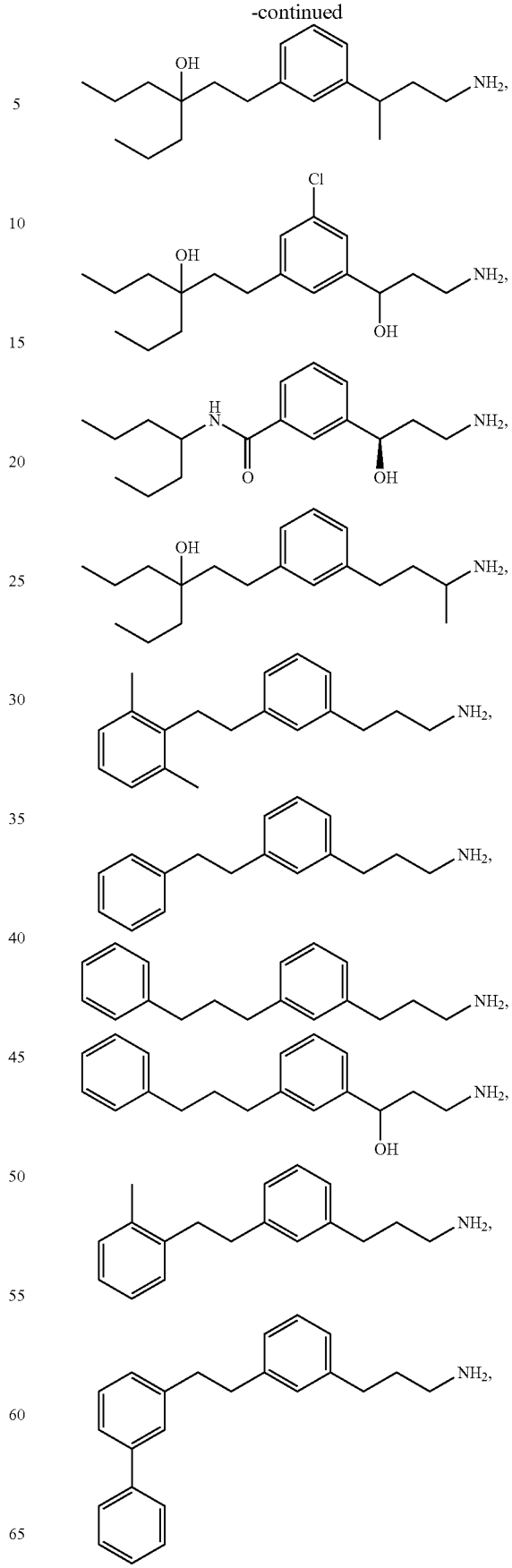

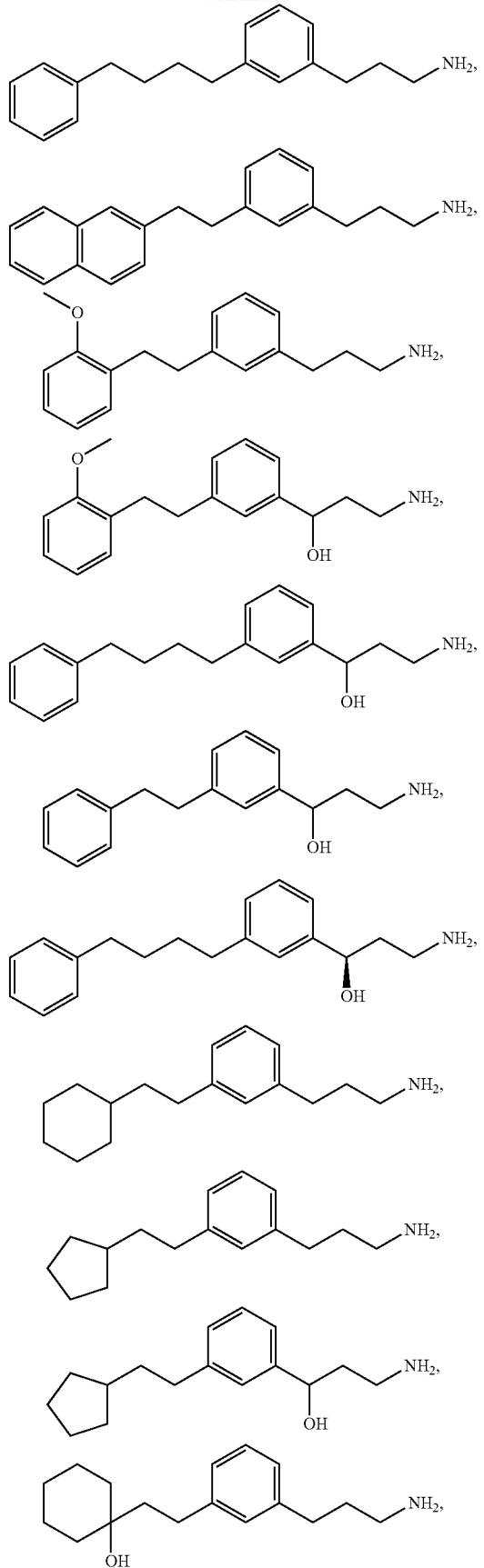
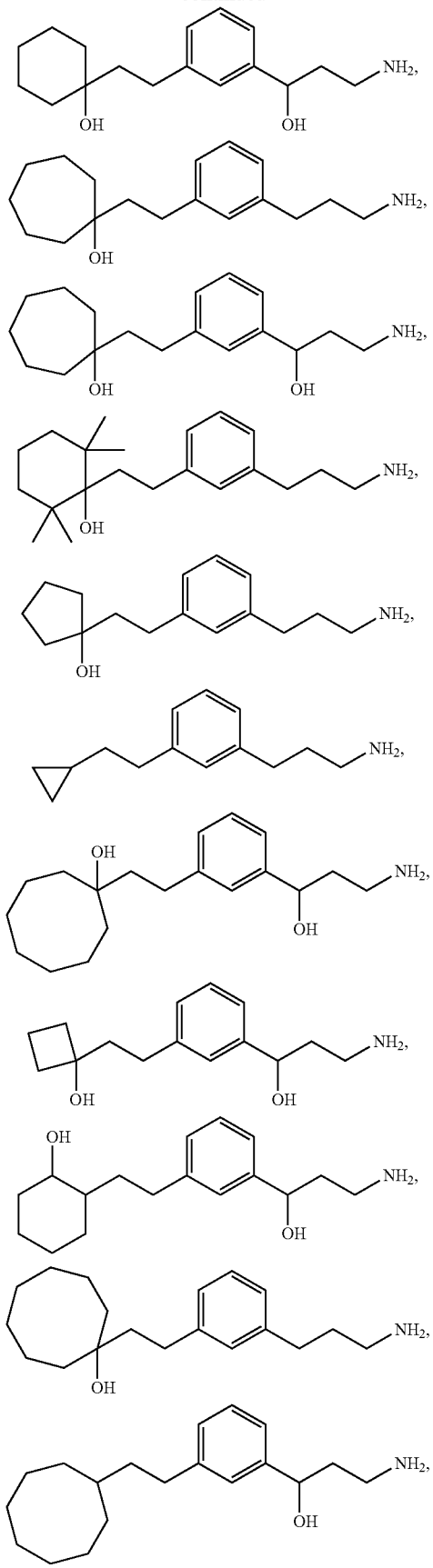

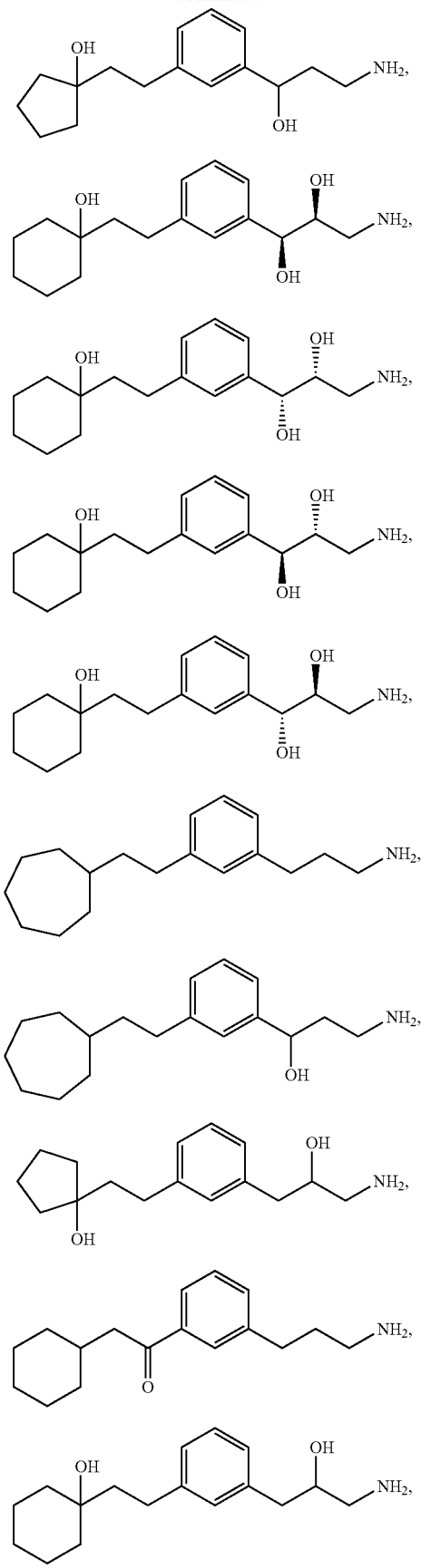
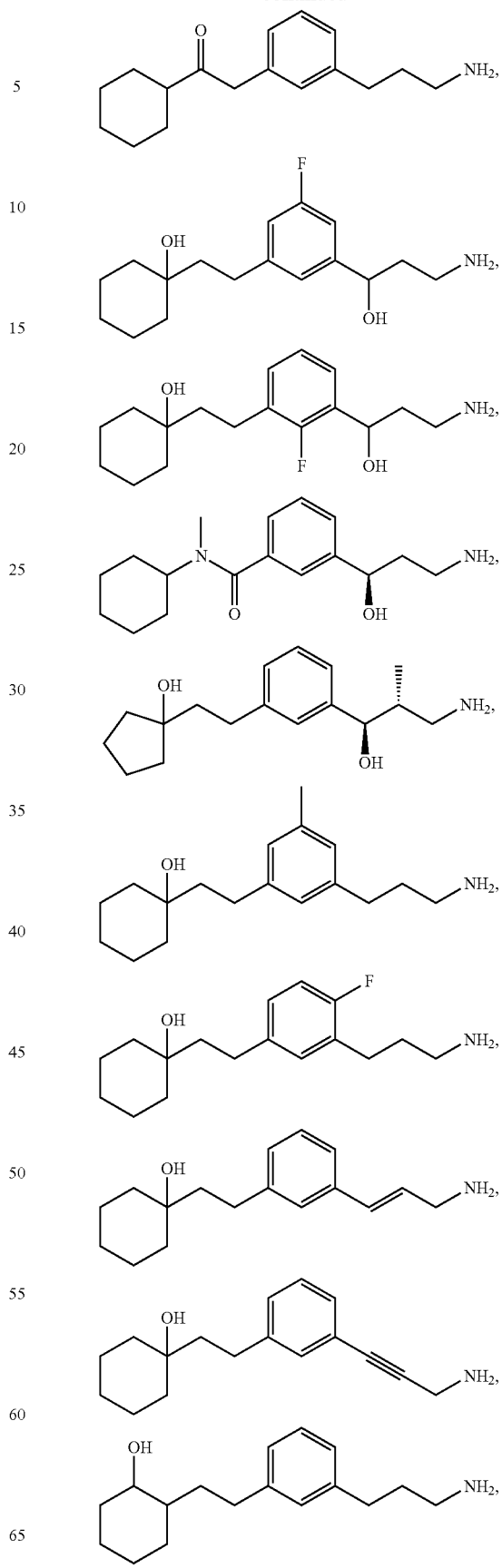

105
-continued
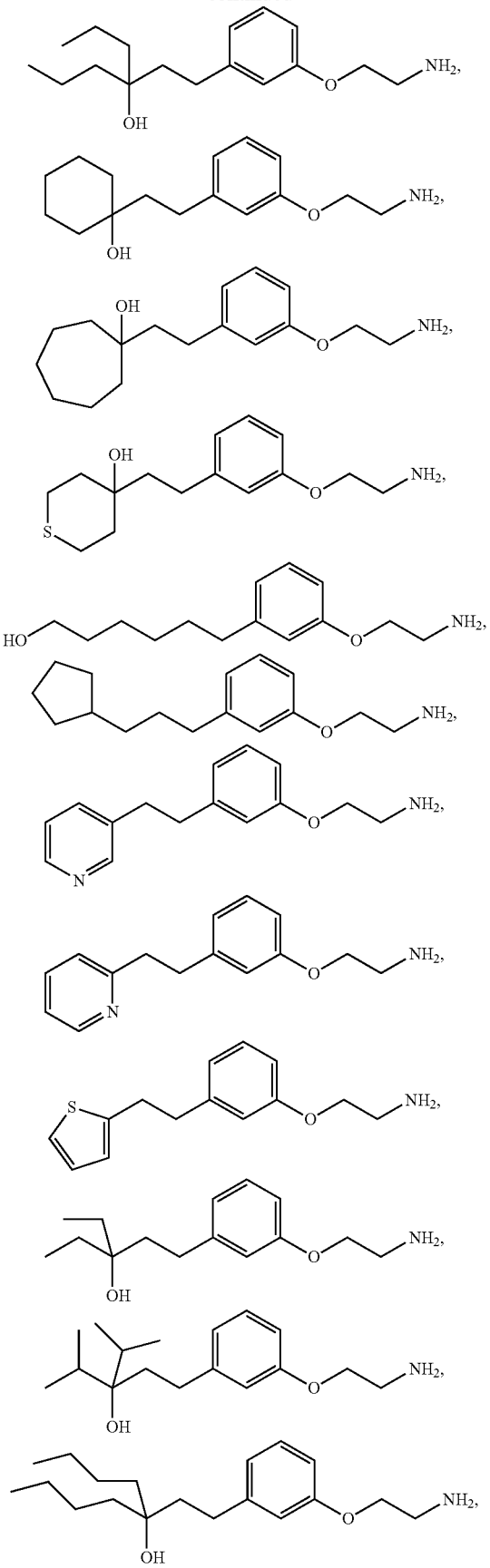
106
-continued
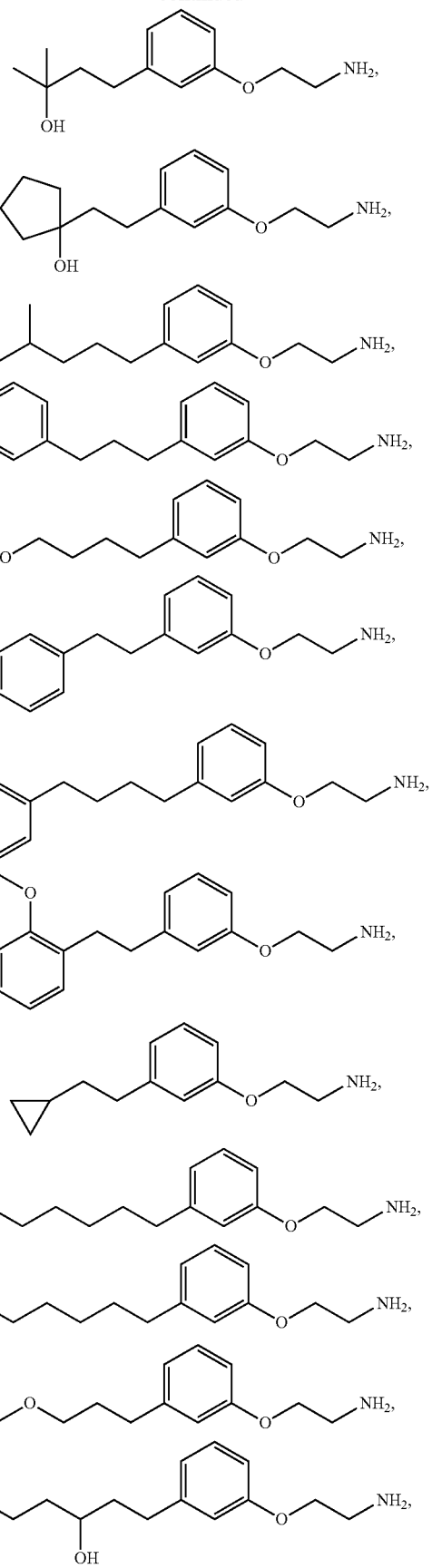

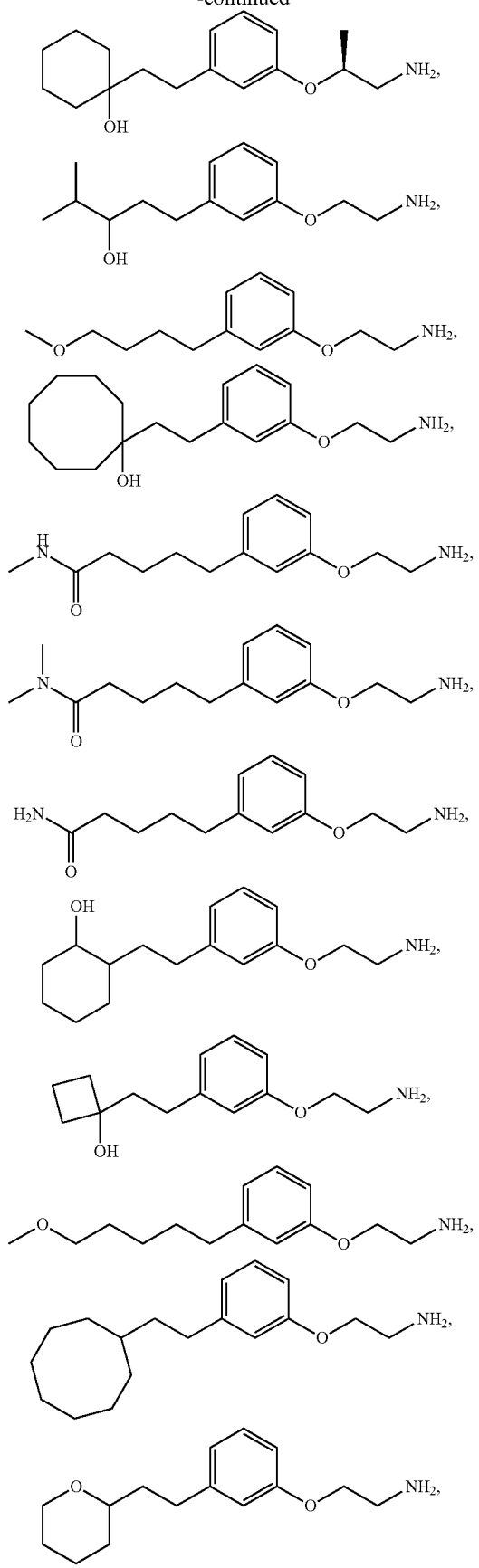
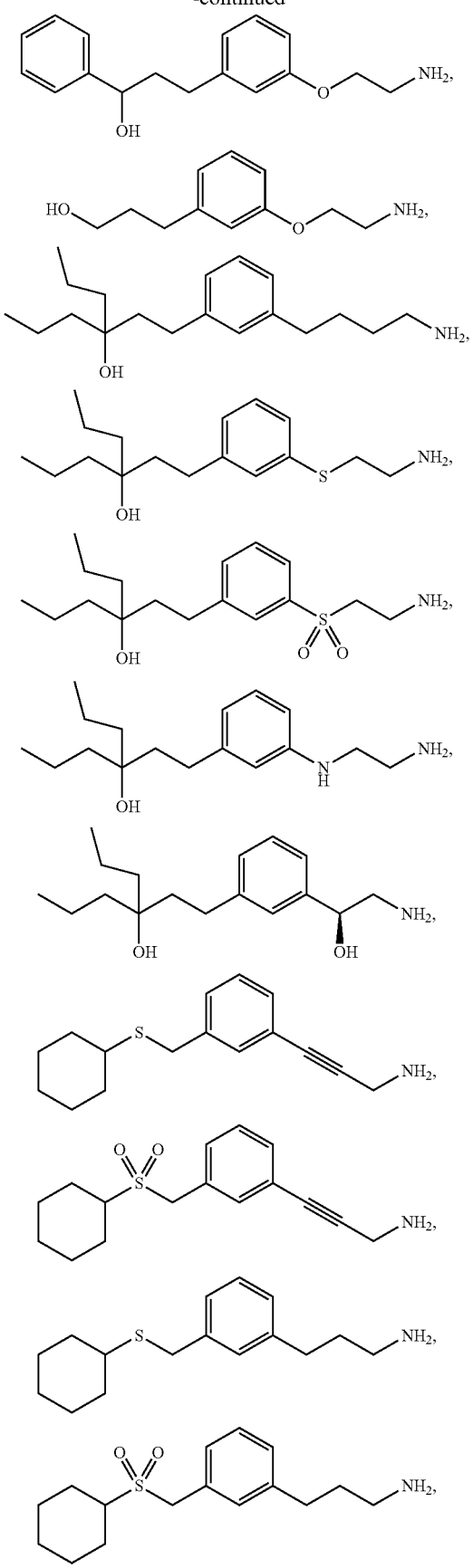

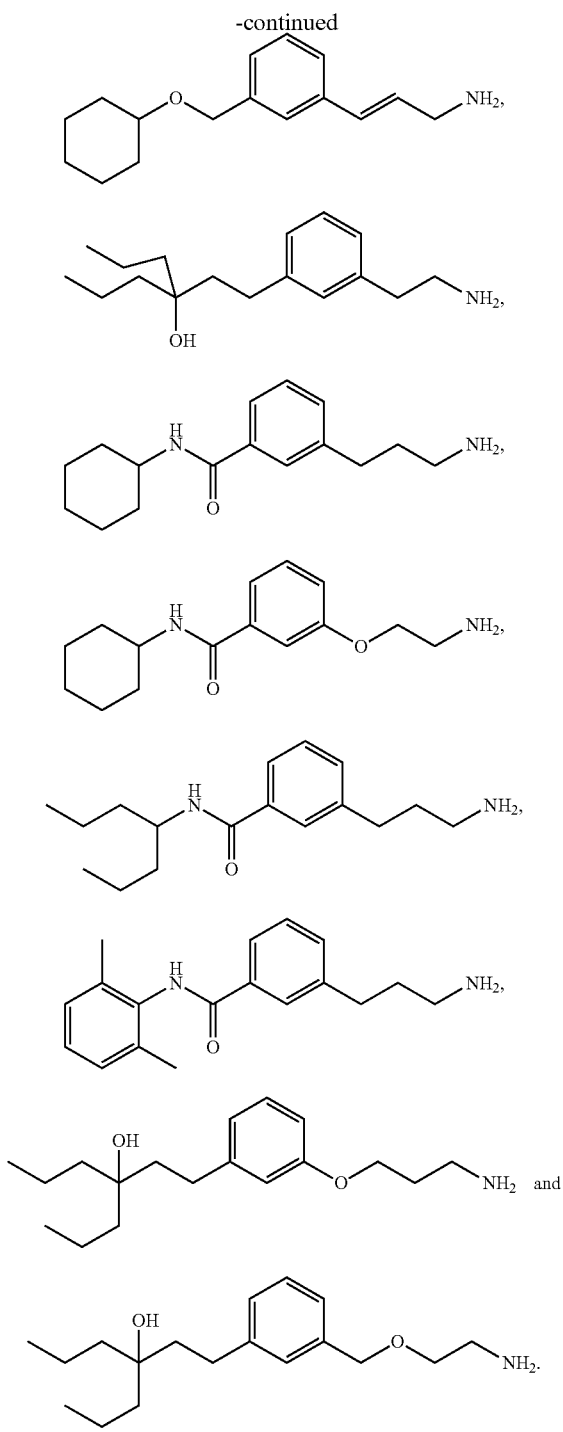

In certain embodiments, amine derivative compounds comprising a meta-substituted linkage terminating in a nitrogen-containing moiety are provided. The nitrogen-containing moiety can be, for example, an amine, an amide or an N-heterocyclyl. The linkage comprises three linking atoms, including at least two carbon atoms and up to one heteroatom, such as sulfur, oxygen and nitrogen. These linking atoms form a combination of linearly constructed stable chemical bonds, including single, double or triple carbon-carbon bonds, carbon-nitrogen bonds, nitrogen-nitrogen bonds, carbon-oxygen bonds, carbon-sulfur bonds, and the like.

Thus, the compounds can be represented by Formula (I)

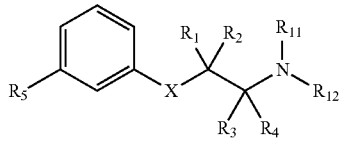

Formula (I)

as a tautomer or a mixture of tautomers, or as a pharmaceutically acceptable salt, hydrate, solvate, N-oxide or prodrug thereof, wherein:

$R_1$ and $R_2$ are each the same or different and independently hydrogen, halogen, $C_1$-$C_5$ alkyl, fluoroalkyl, —$OR_6$ or —$NR_7R_8$; or $R_1$ and $R_2$ form an oxo;

$R_3$ and $R_4$ are each the same or different and independently hydrogen or alkyl;

$R_5$ is $C_5$-$C_{15}$ alkyl, aralkyl, heterocyclylalkyl, heteroarylalkyl or carbocyclylalkyl;

$R_6$ is hydrogen or alkyl;

$R_7$ and $R_8$ are each the same or different and independently hydrogen, alkyl, carbocyclyl, or —C(=O)$R_{13}$; or $R_7$ and $R_8$, together with the nitrogen atom to which they are attached, form an N-heterocyclyl;

X is —C($R_9$)($R_{10}$)— or —O—;

$R_9$ and $R_{10}$ are each the same or different and independently hydrogen, halogen, alkyl, fluoroalkyl, —$OR_6$, —$NR_7R_8$ or carbocyclyl; or $R_9$ and $R_{10}$ form an oxo;

$R_{11}$ and $R_{12}$ are each the same or different and independently hydrogen, alkyl, or —C(=O)$R_{13}$; or $R_{11}$ and $R_{12}$, together with the nitrogen atom to which they are attached, form an N-heterocyclyl; and $R_{13}$ is alkyl, alkenyl, aryl, aralkyl, carbocyclyl, heteroaryl or heterocyclyl.

In certain embodiments, each of $R_{11}$ and $R_{12}$ is hydrogen.

In other embodiments, $R_{11}$ is hydrogen and $R_{12}$ is —C(=O)$R_{13}$, wherein $R_{13}$ is alkyl.

In certain embodiments, each of $R_3$ and $R_4$ is hydrogen.

In other certain embodiments, $R_1$ and $R_2$ are each independently hydrogen, halogen, $C_1$-$C_5$ alkyl or —$OR_6$, wherein $R_6$ is hydrogen or alkyl.

In other embodiments, $R_9$ and $R_{10}$ are each independently hydrogen, halogen, alkyl or —$OR_6$, wherein $R_6$ is hydrogen or alkyl.

In another specific embodiment, each of $R_1$, $R_2$, $R_9$ and $R_{10}$ is independently hydrogen or —$OR_6$, wherein $R_6$ is hydrogen or alkyl.

In a specific embodiment, $R_9$ and $R_{10}$ together form oxo.

In certain other embodiments, $R_5$ is $C_5$-$C_9$ alkyl.

In yet other embodiments, $R_5$ is aralkyl.

In other embodiments, $R_5$ is heteroarylalkyl.

In still other embodiments, $R_5$ is heterocyclylalkyl.

In certain other embodiments, $R_5$ is carbocyclylalkyl.

In one embodiment, X is —C($R_9$)($R_{10}$)—, and the compound of Formula (I) can be represented by a structure of Formula (Ia):

Formula (Ia)

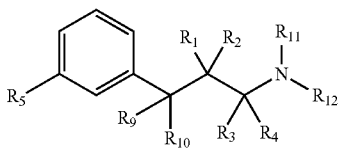

as a tautomer or a mixture of tautomers, or as a pharmaceutically acceptable salt, hydrate, solvate, N-oxide or prodrug thereof, wherein:

$R_1$ and $R_2$ are each the same or different and independently hydrogen, halogen, $C_1$-$C_5$ alkyl, fluoroalkyl, —$OR_6$, or —$NR_7R_8$; or $R_1$ and $R_2$ form an oxo;

$R_3$ and $R_4$ are each the same or different and independently hydrogen or alkyl;

$R_5$ is $C_5$-$C_{15}$ alkyl, aralkyl, heterocyclylalkyl, heteroarylalkyl, or carbocyclylalkyl;

$R_6$ is hydrogen or alkyl;

$R_7$ and $R_8$ are each the same or different and independently hydrogen, alkyl, carbocyclyl, or —C(=O)$R_{13}$; or $R_7$ and $R_8$, together with the nitrogen atom to which they are attached, form an N-heterocyclyl;

$R_9$ and $R_{10}$ are each the same or different and independently hydrogen, halogen, alkyl, fluoroalkyl, —$OR_6$, —$NR_7R_8$ or carbocyclyl; or $R_9$ and $R_{10}$ form an oxo;

$R_{11}$ and $R_{12}$ are each the same or different and independently hydrogen, alkyl, or —C(=O)$R_{13}$; or $R_{11}$ and $R_{12}$, together with the nitrogen atom to which they are attached, form an N-heterocyclyl; and $R_{13}$ is alkyl, alkenyl, aryl, carbocyclyl, heteroaryl, or heterocyclyl.

In certain embodiments of the compound having a structure represented by Formula (Ia), each of $R_{11}$ and $R_{12}$ is hydrogen.

In other embodiments, $R_{11}$ is hydrogen and $R_{12}$ is —C(=O)$R_{13}$, wherein $R_{13}$ is alkyl.

In other embodiments, each of $R_3$ and $R_4$ is hydrogen.

In a specific embodiment, each of $R_9$ and $R_{10}$ is independently hydrogen, halogen, alkyl or —$OR_6$, wherein $R_6$ is hydrogen or alkyl.

In certain embodiments, $R_5$ is $C_5$-$C_9$ alkyl.

In other certain embodiments, $R_5$ is aralkyl.

In still other certain embodiments, $R_5$ is carbocyclylalkyl.

In further embodiments, each of $R_{11}$ and $R_{12}$ is hydrogen, each of $R_1$, $R_2$, $R_3$ and $R_4$ is hydrogen, each of $R_9$ and $R_{10}$ is independently hydrogen or —$OR_6$, wherein $R_6$ is hydrogen or alkyl, and $R_5$ is $C_5$-$C_9$ alkyl.

In certain specific embodiments, $R_5$ is $C_5$-$C_9$ alkyl substituted with —$OR_6$, wherein $R_6$ is hydrogen or alkyl.

Certain compounds disclosed herein have the structures shown in Table 1. The example number refers to a specific Example herein that describes the preparation of the compound having the structure/name shown.

TABLE 1

| Example Number | Structure | Name |
|---|---|---|
| 27 | 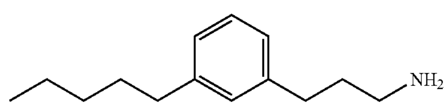 | 3-(3-pentylphenyl)propan-1-amine |
| 28 | 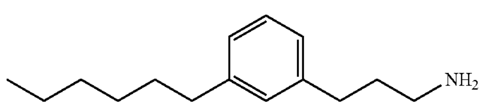 [SMILES: CCCCCCc1cccc(CCCN)c1] | 3-(3-hexylphenyl)propan-1-amine |
| 29 | 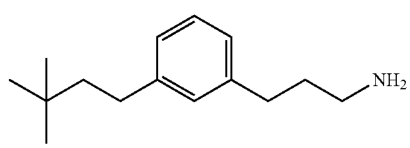 [SMILES: CC(C)(C)CCc1cccc(CCCN)c1] | 3-(3-(3,3-dimethylbutyl)phenyl)propan-1-amine |
| 34 | 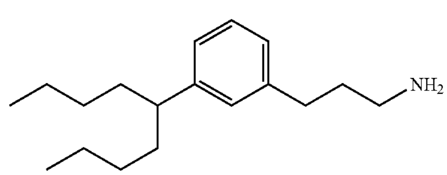 [SMILES: CCCCC(CCCC)c1cccc(CCCN)c1] | 3-(3-(octan-4-yl)phenyl)propan-1-amine |
| 23 | 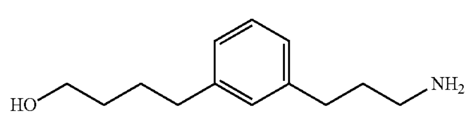 [SMILES: NCCCc1cccc(CCCCO)c1] | 4-(3-(3-aminopropyl)phenyl)butan-1-ol |
| 30 | 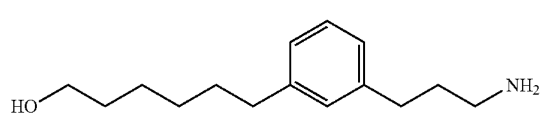 [SMILES: NCCCc1cccc(CCCCCCO)c1] | 6-(3-(3-aminopropyl)phenyl)hexan-1-ol |

TABLE 1-continued

| Example Number | Structure | Name |
|---|---|---|
| 33 | 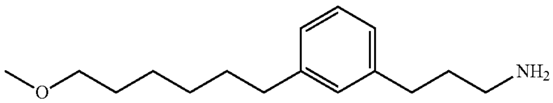 [SMILES: COCCCCCCc1cccc(CCCN)c1] | 3-(3-(6-methoxyhexyl)phenyl)propan-1-amine |
| 3 | 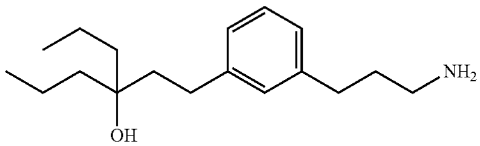 [SMILES: CCCC(O)(CCC)CCc1cccc(CCCN)c1] | 4-(3-(3-aminopropyl)phenethyl)heptan-4-ol |
| 2 | 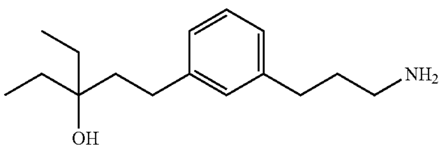 [SMILES: CCC(O)(CC)CCc1cccc(CCCN)c1] | 1-(3-(3-aminopropyl)phenyl)-3-ethylpentan-3-ol |
| 4 | 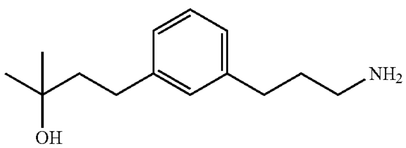 [SMILES: CC(C)(O)CCc1cccc(CCCN)c1] | 4-(3-(3-aminopropyl)phenyl)-2-methylbutan-2-ol |
| 6 | 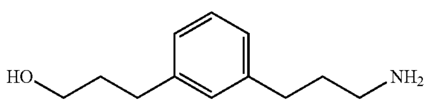 [SMILES: NCCCc1cccc(CCCO)c1] | 3-(3-(3-aminopropyl)phenyl)propan-1-ol |
| 5 | 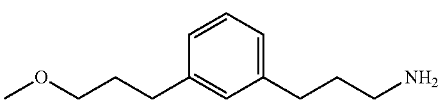 | 3-(3-(3-methoxypropyl)phenyl)propan-1-amine |
| 8 | 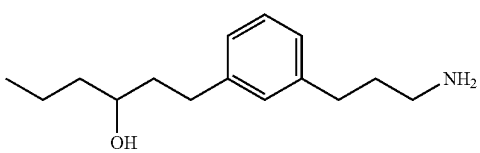 [SMILES: CCCC(O)CCc1cccc(CCCN)c1] | 1-(3-(3-aminopropyl)phenyl)hexan-3-ol |
| 19 | 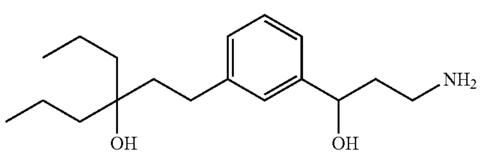 [SMILES: CCCC(O)(CCC)CCc1cccc(C(O)CCN)c1] | 4-(3-(3-amino-1-hydroxypropyl)phenethyl)heptan-4-ol |
| 39 | 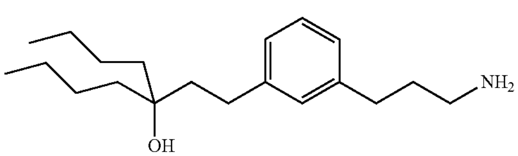 [SMILES: CCCCC(O)(CCCC)CCc1cccc(CCCN)c1] | 5-(3-(3-aminopropyl)phenethyl)nonan-5-ol |
| 40 | 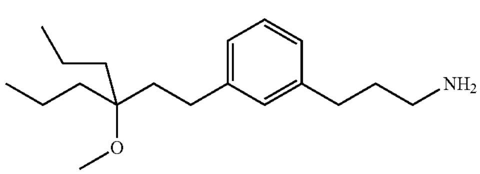 [SMILES: CCCC(CCC)(CCc1cccc(CCCN)c1)OC] | 3-(3-(3-methoxy-3-propylhexyl)phenyl)propan-1-amine |

TABLE 1-continued

| Example Number | Structure | Name |
|---|---|---|
| 41 | 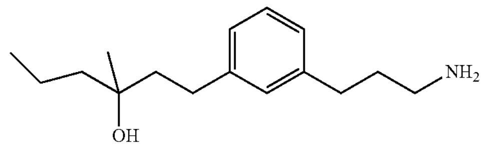 [SMILES: CCCC(C)(O)CCc1cccc(CCCN)c1] | 1-(3-(3-aminopropyl)phenyl)-3-methylhexan-3-ol |
| 42 | 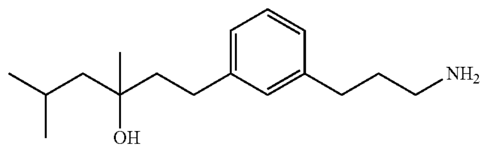 [SMILES: CC(C)CC(C)(O)CCc1cccc(CCCN)c1] | 1-(3-(3-aminopropyl)phenyl)-3,5-dimethylhexan-3-ol |
| 44 | 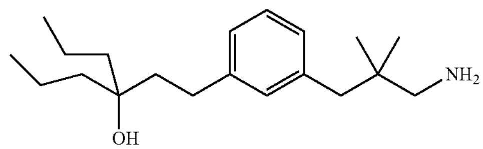 [SMILES: CCCC(O)(CCC)CCc1cccc(CC(C)(C)CN)c1] | 4-(3-(3-amino-2,2-dimethylpropyl)phenethyl)heptan-4-ol |
| 45 | 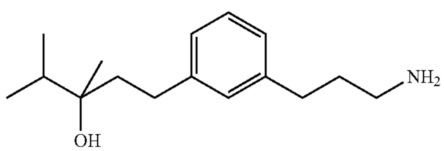 [SMILES: CC(C)C(C)(O)CCc1cccc(CCCN)c1] | 1-(3-(3-aminopropyl)phenyl)-3,4-dimethylpentan-3-ol |
| 46 | 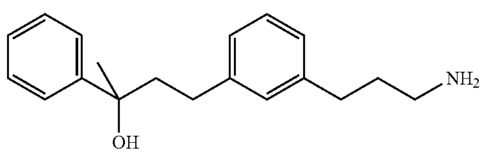 [SMILES: CC(O)(CCc1cccc(CCCN)c1)c1ccccc1] | 4-(3-(3-aminopropyl)phenyl)-2-phenylbutan-2-ol |
| 47 | 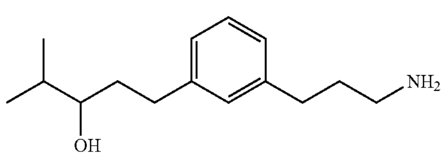 | 1-(3-(3-aminopropyl)phenyl)-4-methylpentan-3-ol |
| 49 | 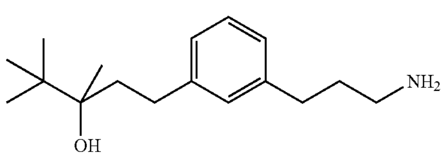 [SMILES: CC(C)(C)C(C)(O)CCc1cccc(CCCN)c1] | 1-(3-(3-aminopropyl)phenyl)-3,4,4-trimethylpentan-3-ol |
| 55 | 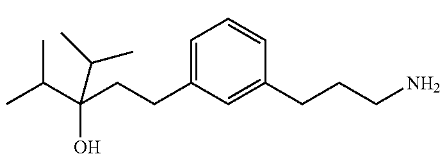 | 1-(3-(3-aminopropyl)phenyl)-3-isopropyl-4-methylpentan-3-ol |
| 56 | 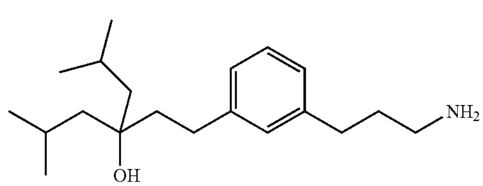 [SMILES: CC(C)CC(O)(CCc1cccc(CCCN)c1)CC(C)C] | 4-(3-(3-aminopropyl)phenethyl)-2,6-dimethylheptan-4-ol |
| 57 | 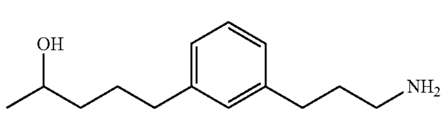 | 5-(3-(3-aminopropyl)phenyl)pentan-2-ol |

TABLE 1-continued

| Example Number | Structure | Name |
|---|---|---|
| 59 | 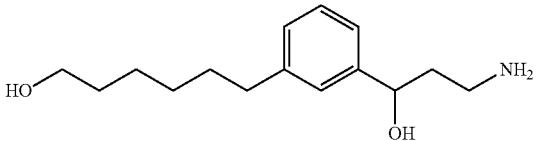 [SMILES: NCCC(O)c1cccc(CCCCCCO)c1] | 6-(3-(3-amino-1-hydroxypropyl)phenyl)hexan-1-ol |
| 60 | 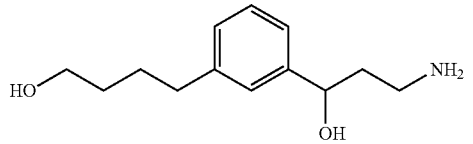 [SMILES: NCCC(O)c1cccc(CCCCO)c1] | 4-(3-(3-amino-1-hydroxypropyl)phenyl)butan-1-ol |
| 62 | 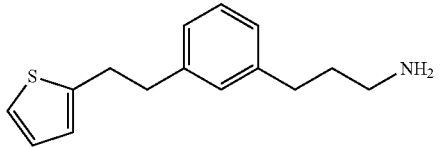 [SMILES: NCCCc1cccc(CCc2cccs2)c1] | 3-(3-(2-(thiophen-2-yl)ethyl)phenyl)propan-1-amine |
| 70 | 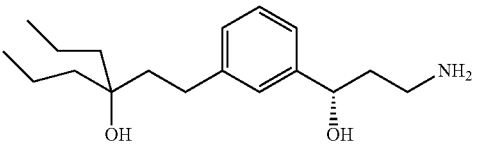 [SMILES: CCCC(O)(CCC)CCc1cccc([C@@H](O)CCN)c1] | (S)-4-(3-(3-amino-1-hydroxypropyl)phenethyl)heptan-4-ol |
| 71 | 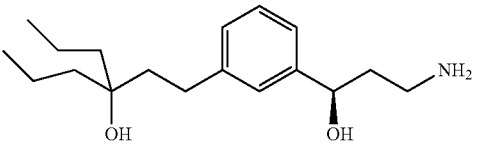 [SMILES: CCCC(O)(CCC)CCc1cccc([C@H](O)CCN)c1] | (R)-4-(3-(3-amino-1-hydroxypropyl)phenethyl)heptan-4-ol |
| 72 | 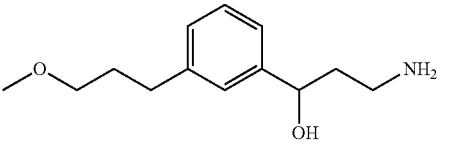 | 3-amino-1-(3-(3-methoxypropyl)phenyl)propan-1-ol |
| 73 | 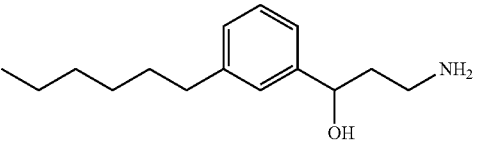 [SMILES: CCCCCCc1cccc(C(O)CCN)c1] | 3-amino-1-(3-hexylphenyl)propan-1-ol |
| 79 | 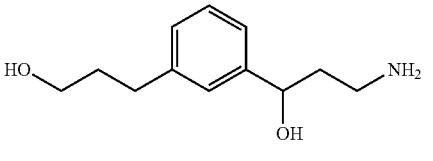 [SMILES: NCCC(O)c1cccc(CCCO)c1] | 3-amino-1-(3-(3-hydroxypropyl)phenyl)propan-1-ol |
| 80 | 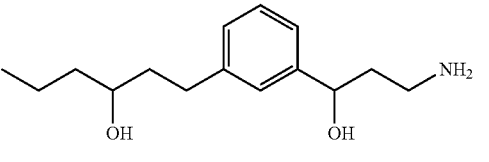 [SMILES: CCCC(O)CCc1cccc(C(O)CCN)c1] | 1-(3-(3-amino-1-hydroxypropyl)phenyl)hexan-3-ol |
| 82 | 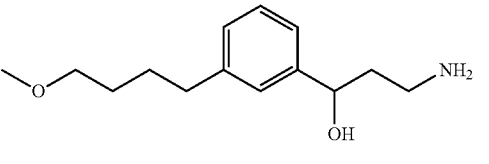 | 3-amino-1-(3-(4-methoxybutyl)phenyl)propan-1-ol |

TABLE 1-continued

| Example Number | Structure | Name |
|---|---|---|
| 86 | 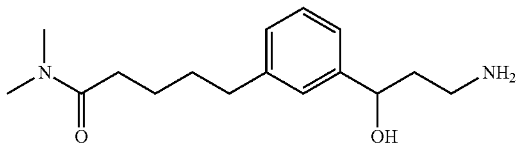 [SMILES: CN(C)C(=O)CCCCc1cccc(C(O)CCN)c1] | 5-(3-(3-amino-1-hydroxypropyl)phenyl)-N,N-dimethylpentanamide |
| 87 | 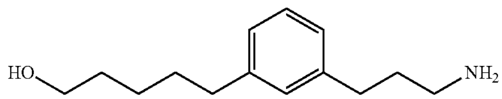 [SMILES: NCCCc1cccc(CCCCCO)c1] | 5-(3-(3-aminopropyl)phenyl)pentan-1-ol |
| 90 | 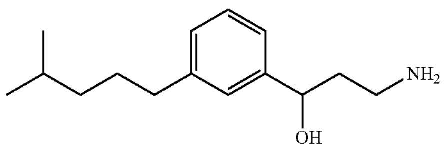 [SMILES: CC(C)CCCc1cccc(C(O)CCN)c1] | 3-amino-1-(3-(4-methylpentyl)phenyl)propan-1-ol |
| 91 | 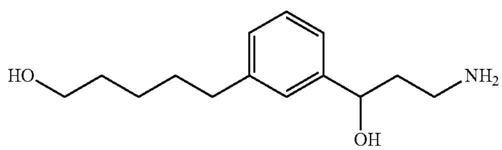 [SMILES: NCCC(O)c1cccc(CCCCCO)c1] | 5-(3-(3-amino-1-hydroxypropyl)phenyl)pentan-1-ol |
| 92 | 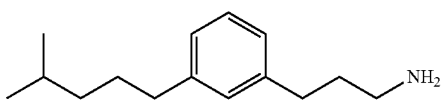 [SMILES: CC(C)CCCc1cccc(CCCN)c1] | 3-(3-(4-methylpentyl)phenyl-propan-1-amine |
| 97 | 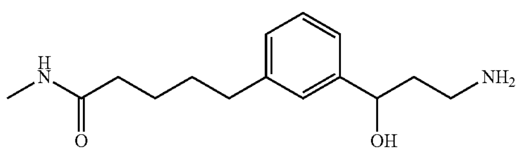 [SMILES: CNC(=O)CCCCc1cccc(C(O)CCN)c1] | 5-(3-(3-aminopropyl)phenyl)-N,N-dimethylpentanamide |
| 102 | 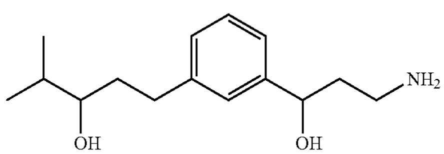 [SMILES: CC(C)C(O)CCc1cccc(C(O)CCN)c1] | 1-(3-(3-amino-1-hydroxypropyl)phenyl)-4-methylpentan-3-ol |
| 104 | 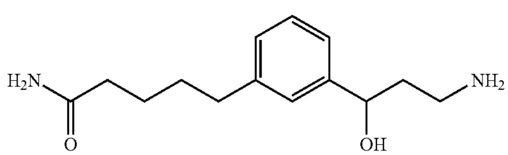 [SMILES: NCCC(O)c1cccc(CCCCC(N)=O)c1] | 5-(3-(3-amino-1-hydroxypropyl)phenyl)pentanamide |
| 106 | 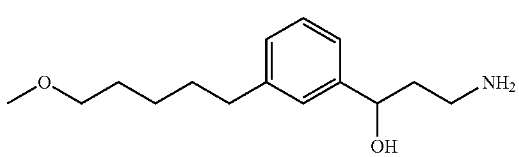 [SMILES: COCCCCCc1cccc(C(O)CCN)c1] | 3-amino-1-(3-(5-methoxypentyl)phenyl)propan-1-ol |
| 109 | 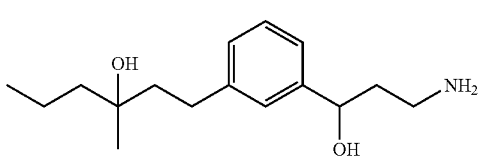 [SMILES: CCCC(C)(O)CCc1cccc(C(O)CCN)c1] | 1-(3-(3-amino-1-hydroxypropyl)phenyl)-3-methylhexan-3-ol |

TABLE 1-continued

| Example Number | Structure | Name |
|---|---|---|
| 110 | 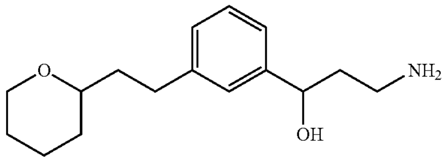 [SMILES: NCCC(O)c1cccc(CCC2CCCCO2)c1] | 3-amino-1-(3-(2-(tetrahydro-2H-pyran-2-yl)ethyl)phenyl)propan-1-ol |
| 111 | 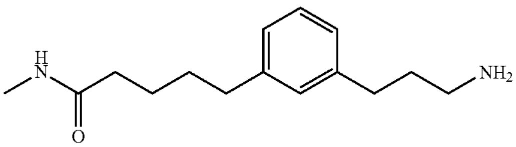 [SMILES: CNC(=O)CCCCc1cccc(CCCN)c1] | 5-(3-(3-aminopropyl)phenyl)-N-methylpentanamide |
| 112 | 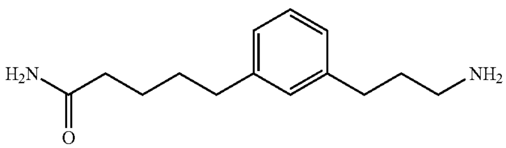 [SMILES: NCCCc1cccc(CCCCC(N)=O)c1] | 5-(3-(3-aminopropyl)phenyl)pentanamide |
| 113 | 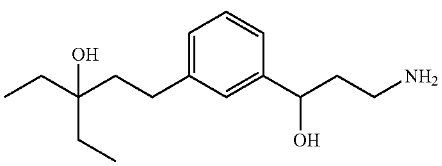 [SMILES: CCC(O)(CC)CCc1cccc(C(O)CCN)c1] | 1-(3-(3-amino-1-hydroxypropyl)phenyl)-3-ethylpentan-3-ol |
| 116 | 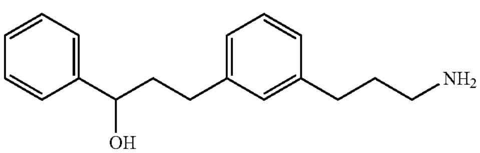 [SMILES: NCCCc1cccc(CCC(O)c2ccccc2)c1] | 3-(3-(3-aminopropyl)phenyl)-1-phenylpropan-1-ol |
| 117 | 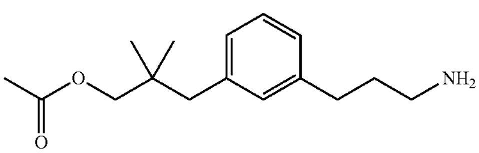 [SMILES: CC(=O)OCC(C)(C)Cc1cccc(CCCN)c1] | 3-(3-(3-aminopropyl)phenyl)-2,2-dimethylpropyl acetate |
| 118 | 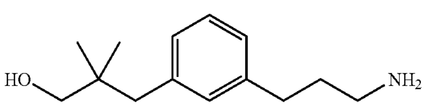 [SMILES: CC(C)(CO)Cc1cccc(CCCN)c1] | 3-(3-(3-aminopropyl)phenyl)-2,2-dimethylpropan-1-ol |
| 119 | 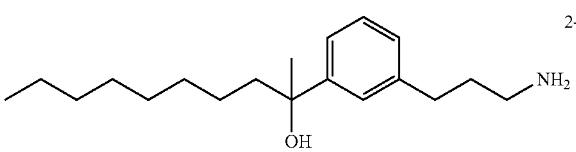 | 2-(3-(3-aminopropyl)phenyl)decan-2-ol |
| 120 | 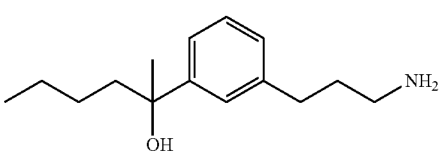 [SMILES: CCCCC(C)(O)c1cccc(CCCN)c1] | 2-(3-(3-aminopropyl)phenyl)hexan-2-ol |
| 121 | 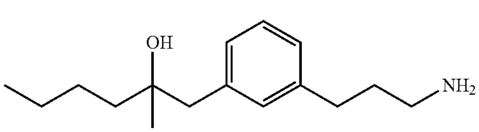 [SMILES: CCCCC(C)(O)Cc1cccc(CCCN)c1] | 1-(3-(3-aminopropyl)phenyl)-2-methylhexan-2-ol |

TABLE 1-continued

| Example Number | Structure | Name |
|---|---|---|
| 122 | 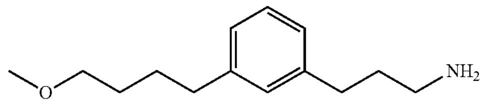 | 3-(3-(4-methoxybutyl)phenyl)propan-1-amine |
| 124 | 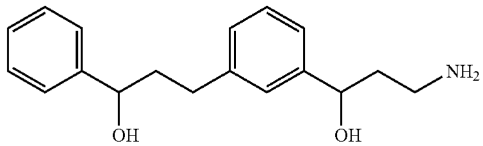 [SMILES: NCCC(O)c1cccc(CCC(O)c2ccccc2)c1] | 3-amino-1-(3-(3-hydroxy-3-phenylpropyl)phenyl)propan-1-ol |
| 126 | 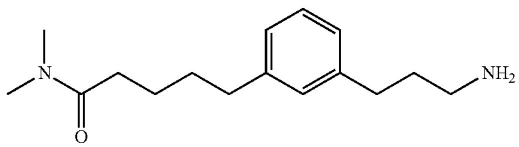 [SMILES: CN(C)C(=O)CCCCc1cccc(CCCN)c1] | 5-(3-(3-aminopropyl)phenyl)-N,N-dimethylpentanamide |
| 132 | 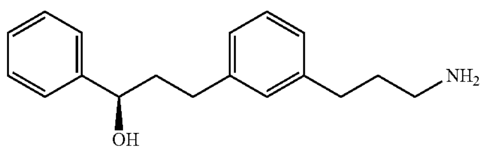 [SMILES: NCCCc1cccc(CC[C@@H](O)c2ccccc2)c1] | (R)-3-(3-(3-aminopropyl)phenyl)-1-phenylpropan-1-ol |
| 140 | 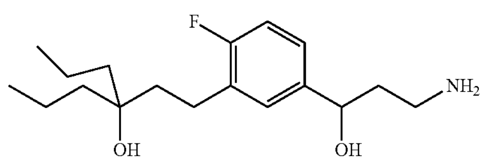 [SMILES: CCCC(O)(CCC)CCc1cc(C(O)CCN)ccc1F] | 4-(5-(3-amino-1-hydroxypropyl)-2-fluorophenethyl)heptan-4-ol |
| 141 | 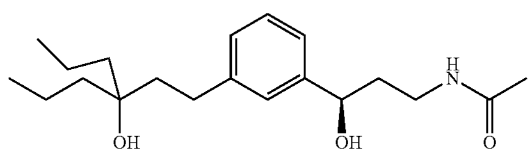 [SMILES: CCCC(O)(CCC)CCc1cccc([C@H](O)CCNC(C)=O)c1] | (R)-N-(3-hydroxy-3-(3-(3-hydroxy-3-propylhexyl)phenyl)propyl)acetamide |
| 142 | 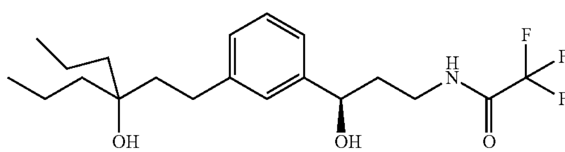 [SMILES: CCCC(O)(CCC)CCc1cccc([C@H](O)CCNC(=O)C(F)(F)F)c1] | (R)-2,2,2-trifluoro-N-(3-hydroxy-3-(3-(3-hydroxy-3-propylhexyl)phenyl)propyl)acetamide |
| 143 | 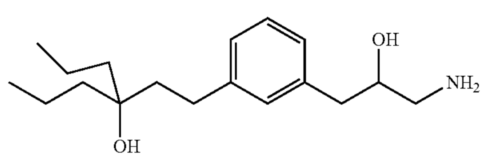 [SMILES: CCCC(O)(CCC)CCc1cccc(CC(O)CN)c1] | 4-(3-(3-amino-2-hydroxypropyl)phenethyl)heptan-4-ol |
| 144 | 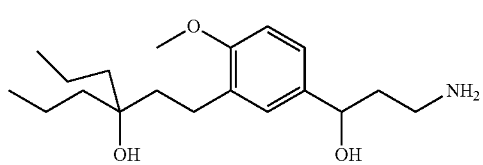 [SMILES: CCCC(O)(CCC)CCc1cc(C(O)CCN)ccc1OC] | 4-(5-(3-amino-1-hydroxypropyl)-2-methoxyphenethyl)heptan-4-ol |
| 145 | 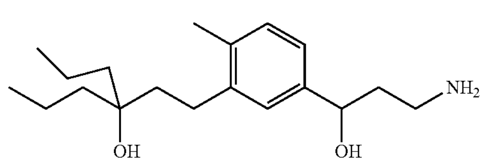 [SMILES: CCCC(O)(CCC)CCc1cc(C(O)CCN)ccc1C] | 4-(5-(3-amino-1-hydroxypropyl)-2-methylphenethyl)heptan-4-ol |

TABLE 1-continued

| Example Number | Structure | Name |
|---|---|---|
| 146 | 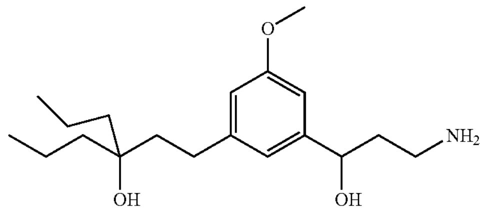 [SMILES: CCCC(O)(CCC)CCc1cc(OC)cc(C(O)CCN)c1] | 4-(3-(3-amino-1-hydroxypropyl)-5-methoxyphenethyl)heptan-4-ol |
| 147 | 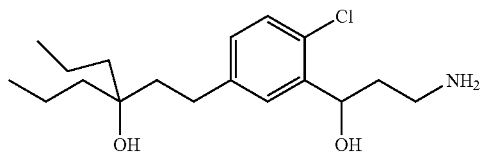 [SMILES: CCCC(O)(CCC)CCc1ccc(Cl)c(C(O)CCN)c1] | 4-(3-(3-amino-1-hydroxypropyl)-4-chlorophenethyl)heptan-4-ol |
| 148 | 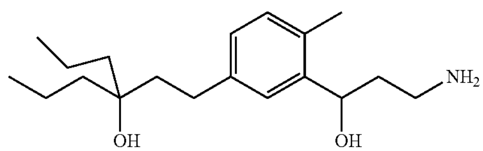 [SMILES: CCCC(O)(CCC)CCc1ccc(C)c(C(O)CCN)c1] | 4-(3-(3-amino-1-hydroxypropyl)-4-methylphenethyl)heptan-4-ol |
| 149 | 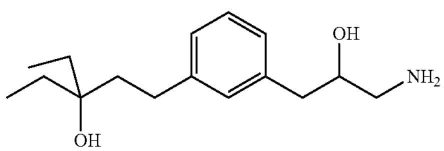 [SMILES: CCC(O)(CC)CCc1cccc(CC(O)CN)c1] | 1-(3-(3-amino-2-hydroxypropyl)phenyl)-3-ethylpentan-3-ol |
| 167 | 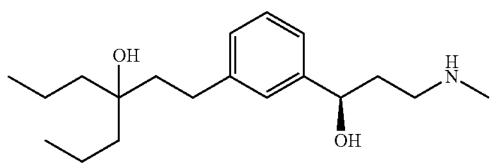 [SMILES: CCCC(O)(CCC)CCc1cccc([C@H](O)CCNC)c1] | (R)-4-(3-(1-hydroxy-3-(methylamino)propyl)phenethyl)heptan-4-ol |
| 161 | 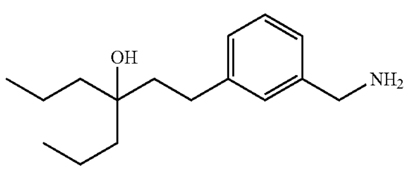 [SMILES: CCCC(O)(CCC)CCc1cccc(CN)c1] | 4-(3-(aminomethyl)phenethyl)heptan-4-ol |
| 168 | 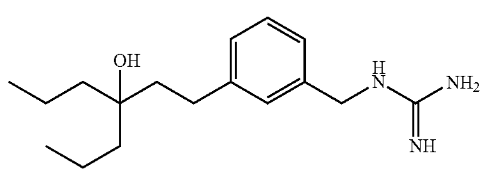 [SMILES: CCCC(O)(CCC)CCc1cccc(CNC(=N)N)c1] | 1-(3-(3-hydroxy-3-propylhexyl)benzyl)guanidine |
| 169 | 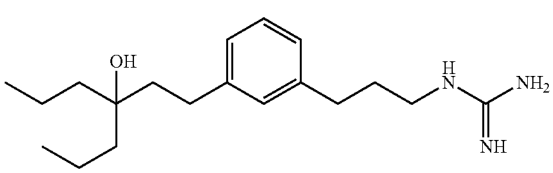 [SMILES: CCCC(O)(CCC)CCc1cccc(CCCNC(=N)N)c1] | 1-(3-(3-(3-hydroxy-3-propylhexyl)phenyl)propyl)guanidine |
| 170 | 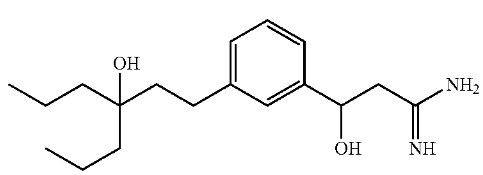 [SMILES: CCCC(O)(CCC)CCc1cccc(C(O)CC(=N)N)c1] | 3-hydroxy-3-(3-(3-hydroxy-3-propylhexyl)phenyl)propanimidamide |

TABLE 1-continued

| Example Number | Structure | Name |
| --- | --- | --- |
| 171 | 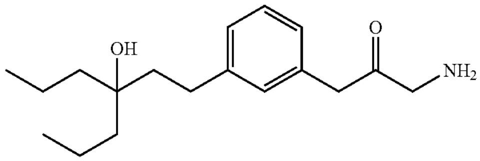 [SMILES: CCCC(O)(CCC)CCc1cccc(CC(=O)CN)c1] | 1-amino-3-(3-(3-hydroxy-3-propylhexyl)phenyl)propan-2-one |
| 172 | 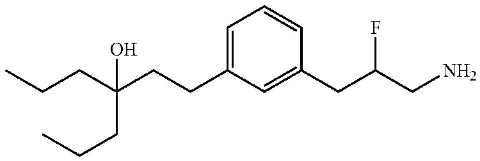 [SMILES: CCCC(O)(CCC)CCc1cccc(CC(F)CN)c1] | 4-(3-(3-amino-2-fluoropropyl)phenethyl)heptan-4-ol |
| 173 | 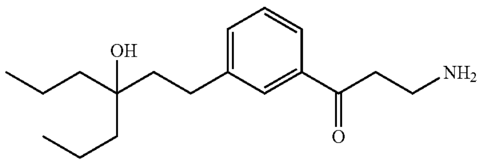 [SMILES: CCCC(O)(CCC)CCc1cccc(C(=O)CCN)c1] | 3-amino-1-(3-(3-hydroxy-3-propylhexyl)phenyl)propan-1-one |
| 174 | 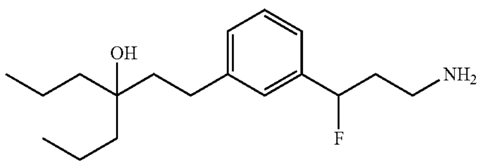 | 4-(3-(3-amino-1-fluoropropyl)phenethyl)heptan-4-ol |
| 175 | 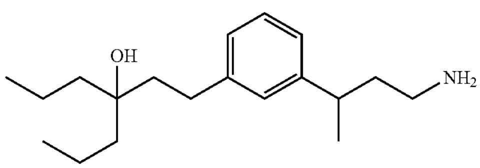 [SMILES: CCCC(O)(CCC)CCc1cccc(C(C)CCN)c1] | 4-(3-(4-aminobutan-2-yl)phenethyl)heptan-4-ol |
| 176 | 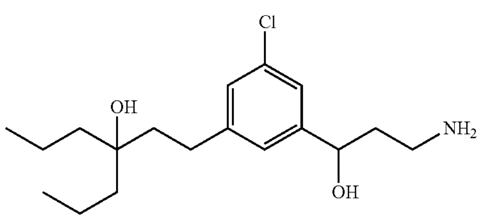 [SMILES: CCCC(O)(CCC)CCc1cc(Cl)cc(C(O)CCN)c1] | 4-(3-(3-amino-1-hydroxypropyl)-5-chlorophenethyl)heptan-4-ol |
| 177 | 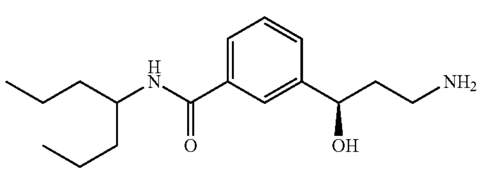 [SMILES: CCCC(CCC)NC(=O)c1cccc([C@H](O)CCN)c1] | (R)-3-(3-amino-1-hydroxypropyl)-N-(heptan-4-yl)benzamide |
| 178 | 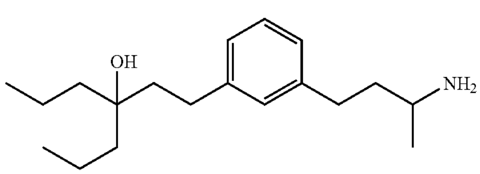 [SMILES: CCCC(O)(CCC)CCc1cccc(CCC(C)N)c1] | 4-(3-(3-aminobutyl)phenethyl)heptan-4-ol |

In further embodiments, each of $R_{11}$ and $R_{12}$ is hydrogen, each of $R_1$, $R_2$, $R_3$ and $R_4$ is hydrogen, and each of $R_9$ and $R_{10}$ is independently hydrogen or —$OR_6$, wherein $R_6$ is hydrogen or alkyl, and $R_5$ is aralkyl.

In certain specific embodiments, the alkylene portion of $R_5$ is ethylene, propylene, or butylene.

In certain embodiments, the aryl portion of $R_5$ is phenyl, tolyl, xylenyl, biphenyl, or naphthyl.

Certain compounds disclosed herein have the structures shown in Table 2. The example number refers to a specific Example herein that describes the preparation of the compound having the structure/name shown.

TABLE 2

| Example Number | Structure | Name |
|---|---|---|
| 1 | 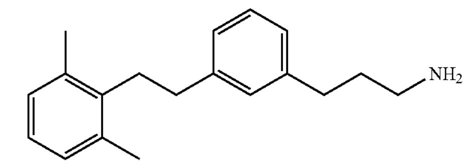 [SMILES: Cc1cccc(C)c1CCc1cccc(CCCN)c1] | 3-(3-(2,6-dimethylphenethyl)phenyl)propan-1-amine |
| 22 | 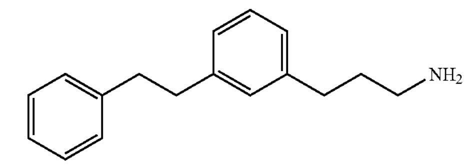 [SMILES: NCCCc1cccc(CCc2ccccc2)c1] | 3-(3-phenethylphenyl)propan-1-amine |
| 26 | 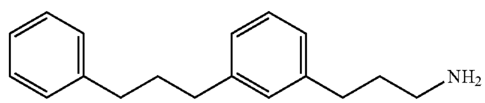 [SMILES: NCCCc1cccc(CCCc2ccccc2)c1] | 3-(3-(3-phenylpropyl)phenyl)propan-1-amine |
| 18 | 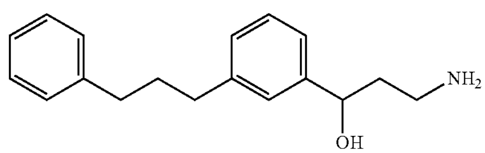 [SMILES: NCCC(O)c1cccc(CCCc2ccccc2)c1] | 3-amino-1-(3-(3-phenylpropyl)phenyl)propan-1-ol |
| 31 | 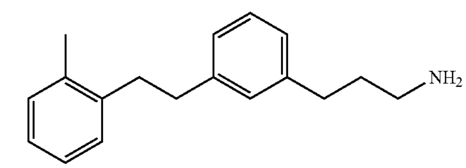 [SMILES: Cc1ccccc1CCc1cccc(CCCN)c1] | 3-(3-(2-methylphenethyl)phenyl)propan-1-amine |
| 32 | 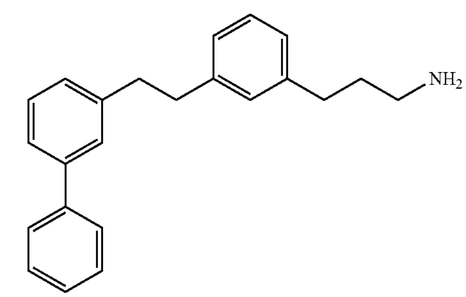 [SMILES: NCCCc1cccc(CCc2cccc(-c3ccccc3)c2)c1] | 3-(3-(2-(biphenyl-3-yl)ethyl)phenyl)propan-1-amine |
| 35 | 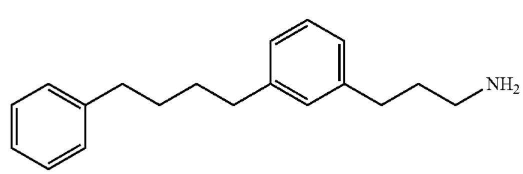 [SMILES: NCCCc1cccc(CCCCc2ccccc2)c1] | 3-(3-(4-phenylbutyl)phenyl)propan-1-amine |
| 21 | 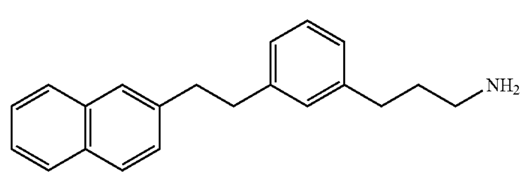 [SMILES: NCCCc1cccc(CCc2ccc3ccccc3c2)c1] | 3-(3-(2-(naphthalen-2-yl)ethyl)phenyl)propan-1-amine |

TABLE 2-continued

| Example Number | Structure | Name |
|---|---|---|
| 58 | 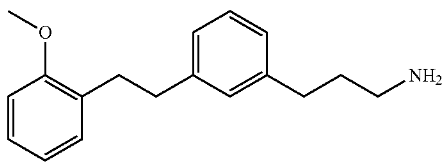 [SMILES: COc1ccccc1CCc1cccc(CCCN)c1] | 3-(3-(2-methoxyphenethyl)phenyl)propan-1-amine |
| 61 | 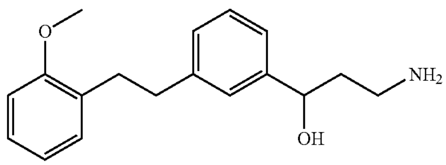 [SMILES: COc1ccccc1CCc1cccc(C(O)CCN)c1] | 3-amino-1-(3-(2-methoxyphenethyl)phenyl)propan-1-ol |
| 63 | 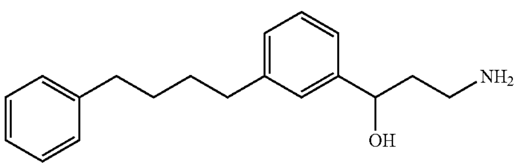 [SMILES: NCCC(O)c1cccc(CCCCc2ccccc2)c1] | 3-amino-1-(3-(4-phenylbutyl)phenyl)propan-1-ol |
| 85 | 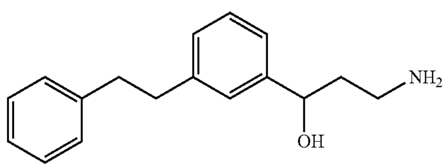 [SMILES: NCCC(O)c1cccc(CCc2ccccc2)c1] | 3-amino-1-(3-phenethylphenyl)propan-1-ol |
| 138 | 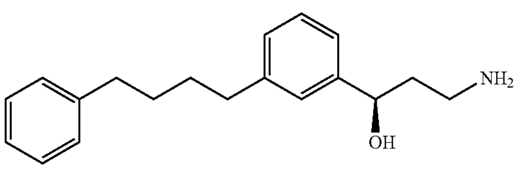 [SMILES: NCC[C@@H](O)c1cccc(CCCCc2ccccc2)c1] | (R)-3-amino-1-(3-(4-phenylbutyl)phenyl)propan-1-ol |

In further embodiments, each of $R_{11}$ and $R_{12}$ is hydrogen, each of $R_1$, $R_2$, $R_3$ and $R_4$ is hydrogen, each of $R_9$ and $R_{10}$ is independently hydrogen or —$OR_6$, wherein $R_6$ is hydrogen or alkyl, and $R_5$ is carbocyclylalkyl. In certain embodiments, the carbocyclylalkyl can be further substituted with —$OR_6$, wherein $R_6$ is hydrogen or alkyl.

In certain specific embodiments, the alkylene portion of $R_5$ is ethylene, propylene. or butylene.

In certain embodiments, the carbocyclyl portion of $R_5$ is cyclohexyl, cyclopentyl or cycloheptyl.

Certain compounds disclosed herein have the structures shown in Table 3. The example number refers to a specific Example herein that describes the preparation of the compound having the structure/name shown.

TABLE 3

| Example Number | Structure | Name |
|---|---|---|
| 25 | 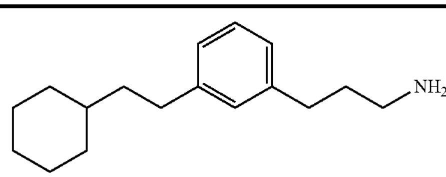 | 3-(3-(2-cyclohexylethyl)phenyl)propan-1-amine |
| 24 | 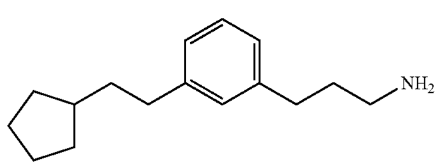 [SMILES: NCCCc1cccc(CCC2CCCC2)c1] | 3-(3-(2-cyclopentylethyl)phenyl)propan-1-amine |

TABLE 3-continued

| Example Number | Structure | Name |
|---|---|---|
| 17 | 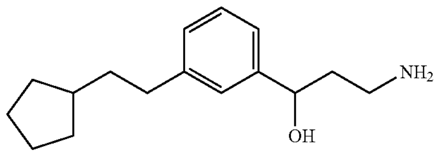 [SMILES: NCCC(O)c1cccc(CCC2CCCC2)c1] | 3-amino-1-(3-(2-cyclopentylethyl)phenyl)propan-1-ol |
| 7 | 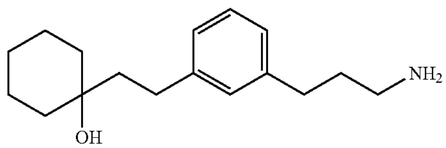 [SMILES: NCCCc1cccc(CCC2(O)CCCCC2)c1] | 1-(3-(3-aminopropyl)phenethyl)cyclohexanol |
| 15 | 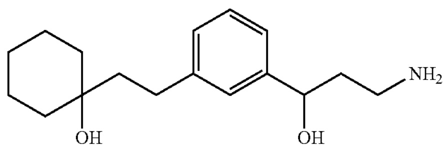 [SMILES: NCCC(O)c1cccc(CCC2(O)CCCCC2)c1] | 1-(3-(3-amino-1-hydroxypropyl)phenethyl)cyclohexanol |
| 20 | 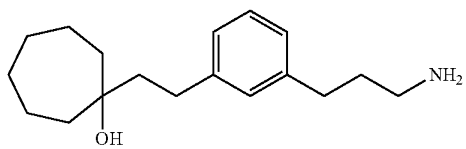 [SMILES: NCCCc1cccc(CCC2(O)CCCCCC2)c1] | 1-(3-(3-aminopropyl)phenethyl)cycloheptanol |
| 16 | 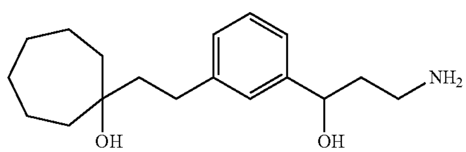 [SMILES: NCCC(O)c1cccc(CCC2(O)CCCCCC2)c1] | 1-(3-(3-amino-1-hydroxypropyl)phenethyl)cycloheptanol |
| 43 | 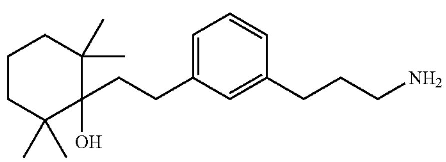 [SMILES: CC1(C)CCCC(C)(C)C1(O)CCc1cccc(CCCN)c1] | 1-(3-(3-aminopropyl)phenethyl)-2,2,6,6-tetramethylcyclohexanol |
| 48 | 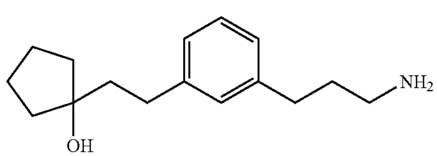 | 1-(3-(3-aminopropyl)phenethyl)cyclopentanol |
| 76 | 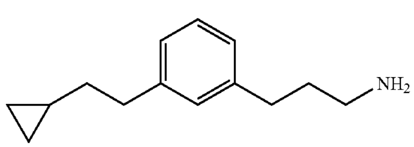 [SMILES: NCCCc1cccc(CCC2CC2)c1] | 3-(3-(2-cyclopropylethyl)phenyl-propan-1-amine |
| 95 | 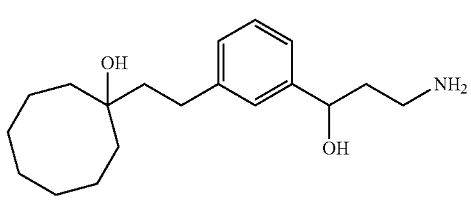 [SMILES: NCCC(O)c1cccc(CCC2(O)CCCCCCC2)c1] | 1-(3-(3-amino-1-hydroxypropyl)phenethyl)cyclooctanol |

TABLE 3-continued

| Example Number | Structure | Name |
|---|---|---|
| 98 | 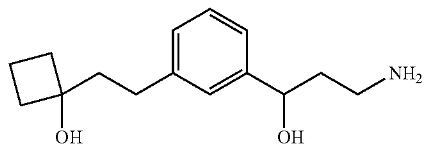 [SMILES: NCCC(O)c1cccc(CCC2(O)CCC2)c1] | 1-(3-(3-amino-1-hydroxypropyl)phenethyl)cyclobutanol |
| 100 | 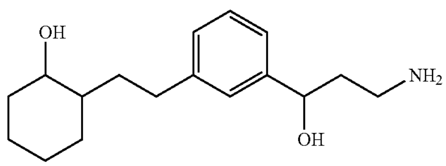 [SMILES: NCCC(O)c1cccc(CCC2CCCCC2O)c1] | 2-(3-(3-amino-1-hydroxypropyl)phenethyl)cyclohexanol |
| 103 | 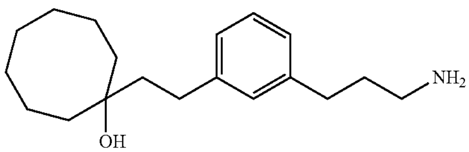 [SMILES: NCCCc1cccc(CCC2(O)CCCCCCC2)c1] | 1-(3-(3-aminopropyl)phenethyl)cyclooctanol |
| 105 | 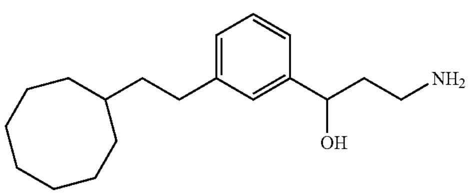 [SMILES: NCCC(O)c1cccc(CCC2CCCCCCC2)c1] | 3-amino-1-(3-(2-cyclooctylethyl)phenyl)propan-1-ol |
| 115 | 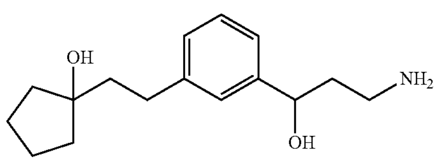 [SMILES: NCCC(O)c1cccc(CCC2(O)CCCC2)c1] | 1-(3-(3-amino-1-hydroxypropyl)phenethyl)cyclopentanol |
| 128 | 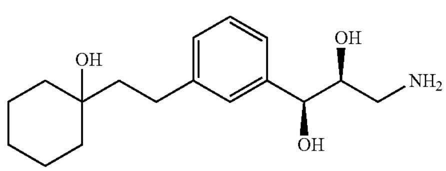 [SMILES: NC[C@H](O)[C@@H](O)c1cccc(CCC2(O)CCCCC2)c1] | (1S,2S)-3-amino-1-(3-(2-(1-hydroxycyclohexyl)ethyl)phenyl)propane-1,2-diol |
| 129 | 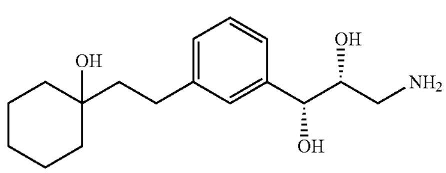 [SMILES: NC[C@@H](O)[C@H](O)c1cccc(CCC2(O)CCCCC2)c1] | (1R,2R)-3-amino-1-(3-(2-(1-hydroxycyclohexyl)ethyl)phenyl)propane-1,2-diol |
| 130 | 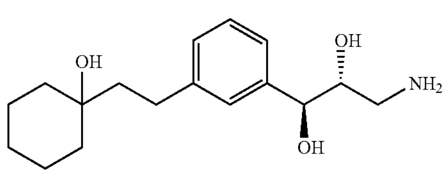 [SMILES: NC[C@@H](O)[C@@H](O)c1cccc(CCC2(O)CCCCC2)c1] | (1S,2R)-3-amino-1-(3-(2-(1-hydroxycyclohexyl)ethyl)phenyl)propane-1,2-diol |
| 131 | 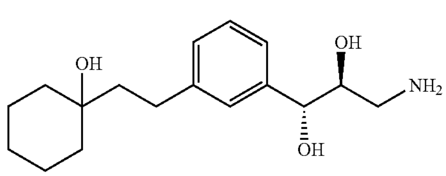 [SMILES: NC[C@H](O)[C@H](O)c1cccc(CCC2(O)CCCCC2)c1] | (1R,2S)-3-amino-1-(3-(2-(1-hydroxycyclohexyl)ethyl)phenyl)propane-1,2-diol |

TABLE 3-continued

| Example Number | Structure | Name |
|---|---|---|
| 133 | 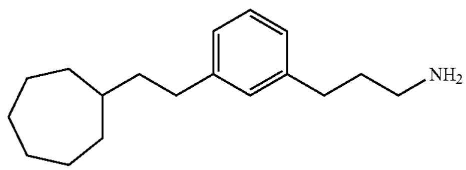 [SMILES: NCCCc1cccc(CCC2CCCCCC2)c1] | 3-(3-(2-cycloheptylethyl)phenyl)propan-1-amine |
| 137 | 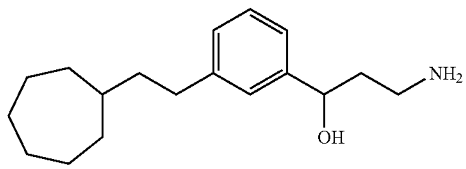 [SMILES: NCCC(O)c1cccc(CCC2CCCCCC2)c1] | 3-amino-1-(3-(2-cycloheptylethyl)phenyl)propan-1-ol |
| 150 | 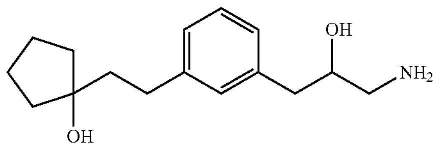 [SMILES: NCC(O)Cc1cccc(CCC2(O)CCCC2)c1] | 1-(3-(3-amino-2-hydroxypropyl)phenethyl)cyclopentanol |
| 151 | 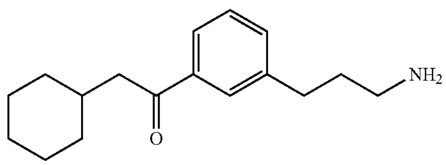 [SMILES: NCCCc1cccc(C(=O)CC2CCCCC2)c1] | 1-(3-(3-aminopropyl)phenyl)-2-cyclohexylethanone |
| 152 | 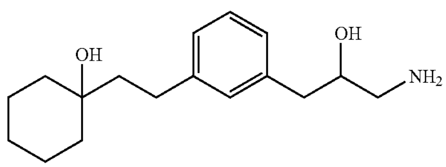 [SMILES: NCC(O)Cc1cccc(CCC2(O)CCCCC2)c1] | 1-(3-(3-amino-2-hydroxypropyl)phenethyl)cyclohexanol |
| 153 | 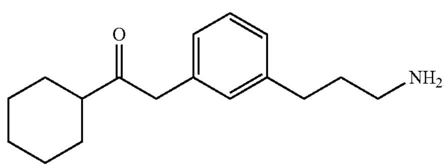 [SMILES: NCCCc1cccc(CC(=O)C2CCCCC2)c1] | 2-(3-(3-aminopropyl)phenyl)-1-cyclohexylethanone |
| 154 | 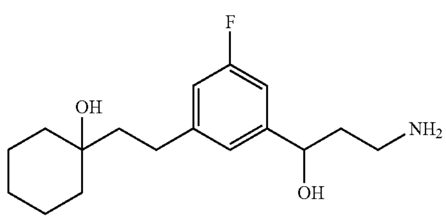 [SMILES: NCCC(O)c1cc(F)cc(CCC2(O)CCCCC2)c1] | 1-(3-(3-amino-1-hydroxypropyl)-5-fluorophenethyl)cyclohexanol |
| 155 | 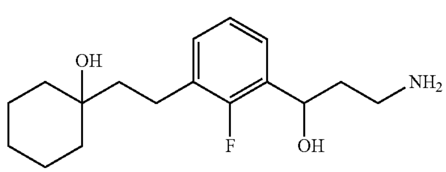 [SMILES: NCCC(O)c1cccc(CCC2(O)CCCCC2)c1F] | 1-(3-(3-amino-1-hydroxypropyl)-2-fluorophenethyl)cyclohexanol |
| 179 | 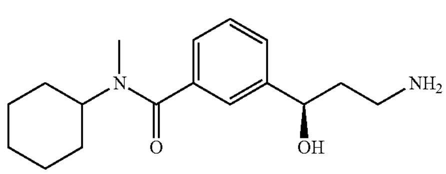 [SMILES: CN(C(=O)c1cccc([C@H](O)CCN)c1)C1CCCCC1] | (R)-3-(3-amino-1-hydroxypropyl)-N-cyclohexyl-N-methylbenzamide |

TABLE 3-continued

| Example Number | Structure | Name |
|---|---|---|
| 180 | 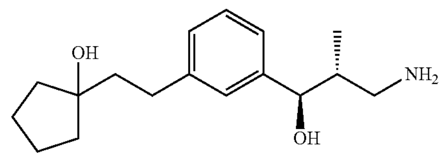 [SMILES: C[C@H](CN)[C@@H](O)c1cccc(CCC2(O)CCCC2)c1] | 1-(3-((1R,2R)-3-amino-1-hydroxy-2-methylpropyl)phenethyl)cyclopentanol |
| 181 | 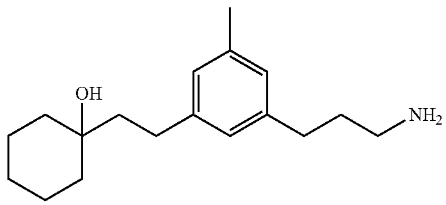 [SMILES: Cc1cc(CCCN)cc(CCC2(O)CCCCC2)c1] | 1-(3-(3-aminopropyl)-5-methylphenethyl)cyclohexanol |
| 182 | 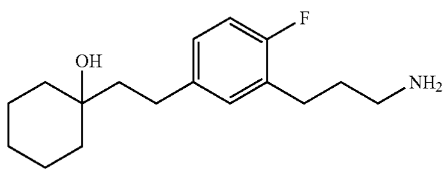 [SMILES: NCCCc1cc(CCC2(O)CCCCC2)ccc1F] | 1-(3-(3-aminopropyl)-4-fluorophenethyl)cyclohexanol |
| 183 | 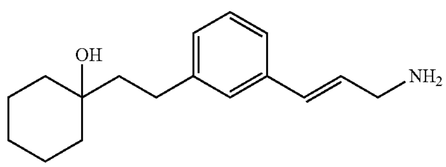 [SMILES: NC/C=C/c1cccc(CCC2(O)CCCCC2)c1] | (E)-1-(3-(3-aminoprop-1-enyl)phenethyl)cyclohexanol |
| 184 | 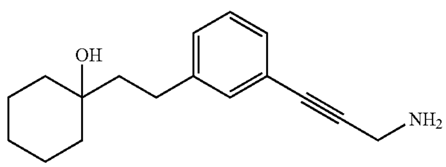 [SMILES: NCC#Cc1cccc(CCC2(O)CCCCC2)c1] | 1-(3-(3-aminoprop-1-ynyl)phenethyl)cyclohexanol |
| 187 | 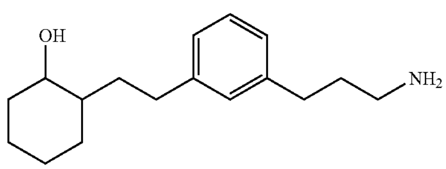 [SMILES: NCCCc1cccc(CCC2CCCCC2O)c1] | 2-(3-(3-aminopropyl)phenethyl)cyclohexanol |

In another embodiment, X is —O—, and the compound of Formula (I) can be represented by a structure of Formula (Ib):

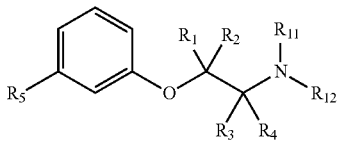

Formula (Ib)

as a tautomer or a mixture of tautomers, or as a pharmaceutically acceptable salt, hydrate, solvate, N-oxide or prodrug thereof, wherein:

$R_1$ and $R_2$ are each the same or different and independently hydrogen, $C_1$-$C_5$ alkyl, or fluoroalkyl;

$R_3$ and $R_4$ are each the same or different and independently hydrogen or alkyl;

$R_5$ is $C_5$-$C_{15}$ alkyl, aralkyl, heterocyclylalkyl, heteroarylalkyl, or carbocyclylalkyl;

$R_{11}$ and $R_{12}$ are each the same or different and independently hydrogen, alkyl, or —C(=O)$R_{13}$; or $R_{11}$ and $R_{12}$, together with the nitrogen atom to which they are attached, form an N-heterocyclyl; and $R_{13}$ is alkyl, alkenyl, aryl, carbocyclyl, heteroaryl, or heterocyclyl.

In certain embodiments of the compound having a structure represented by Formula (Ib), each of $R_{11}$ and $R_{12}$ is hydrogen.

In other embodiments, $R_{11}$ is hydrogen and $R_{12}$ is —C(=O)$R_{13}$, wherein $R_{13}$ is alkyl.

In other embodiments, each of $R_3$ and $R_4$ is hydrogen.

In certain embodiments, $R_5$ is $C_5$-$C_9$ alkyl.

In other certain embodiments, $R_5$ is carbocyclylalkyl.

In certain other embodiments, $R_5$ is heteroarylalkyl.

In yet other certain embodiments, $R_5$ is heterocyclylalkyl.

In further embodiments, each of $R_{11}$ and $R_{12}$ is hydrogen, each of $R_1$, $R_2$, $R_3$ and $R_4$ is hydrogen, and $R_5$ is $C_5$-$C_9$ alkyl. In certain specific embodiments, $R_5$ is $C_5$-$C_9$ alkyl substituted with —$OR_6$, wherein $R_6$ is hydrogen or alkyl.

In other embodiments, each of $R_{11}$ and $R_{12}$ is hydrogen, each of $R_1$, $R_2$, $R_3$ and $R_4$ is hydrogen, and $R_5$ is heteroarylalkyl, wherein the alkylene portion of $R_5$ is ethylene, propylene, or butylene.

In other embodiments, each of $R_{11}$ and $R_{12}$ is hydrogen, each of $R_1$, $R_2$, $R_3$ and $R_4$ is hydrogen, and $R_5$ is heterocyclylalkyl, wherein the alkylene portion of $R_5$ is ethylene, propylene, or butylene.

In other embodiments, each of $R_{11}$ and $R_{12}$ is hydrogen, each of $R_1$, $R_2$, $R_3$ and $R_4$ is hydrogen, and $R_5$ is carbocyclylalkyl, wherein the alkylene portion of $R_5$ is ethylene, propylene, or butylene.

Certain compounds disclosed herein have the structures shown in Table 4. The example number refers to a specific Example herein that describes the preparation of the compound having the structure/name shown.

TABLE 4

| Example Number | Structure | Name |
| --- | --- | --- |
| 9 | 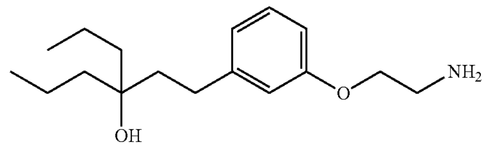 [SMILES: CCCC(O)(CCC)CCc1cccc(OCCN)c1] | 4-(3-(2-aminoethoxy) phenethyl) heptan-4-ol |
| 12 | 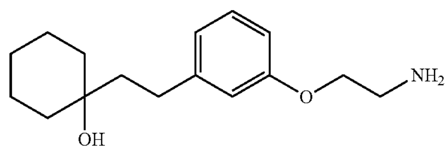 [SMILES: NCCOc1cccc(CCC2(O)CCCCC2)c1] | 1-(3-(2-aminoethoxy) phenethyl)cyclohexanol |
| 10 | 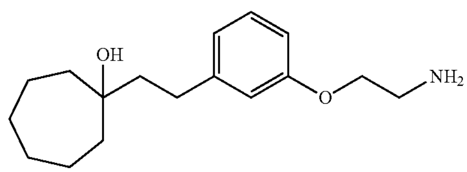 [SMILES: NCCOc1cccc(CCC2(O)CCCCCC2)c1] | 1-(3-(2-aminoethoxy) phenethyl)cycloheptanol |
| 11 | 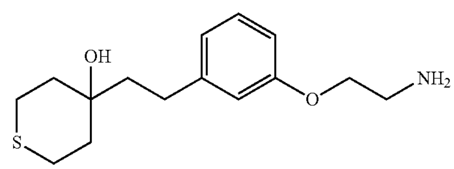 [SMILES: NCCOc1cccc(CCC2(O)CCSCC2)c1] | 4-(3-(2-aminoethoxy)phenethyl)tetrahydro-2H-thiopyran-4-ol |
| 13 | 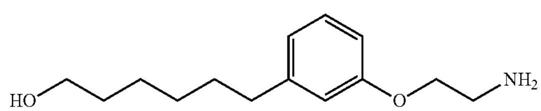 [SMILES: NCCOc1cccc(CCCCCCO)c1] | 6-(3-(2-aminoethoxy) phenyl)hexan-1-ol |
| 14 | 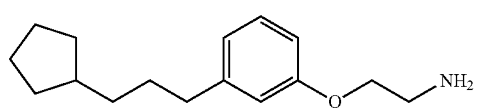 [SMILES: NCCOc1cccc(CCCC2CCCC2)c1] | 2-(3-(3-cyclopentylpropyl) phenoxy)ethanamine |
| 36 | 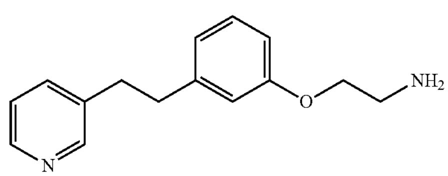 [SMILES: NCCOc1cccc(CCc2cccnc2)c1] | 2-(3-(2-(pyridin-3-yl)ethyl) phenoxy)ethanamine |
| 37 | 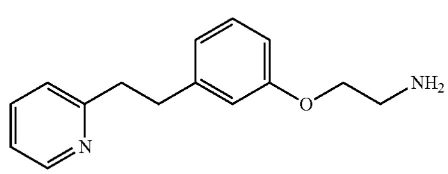 [SMILES: NCCOc1cccc(CCc2ccccn2)c1] | 2-(3-(2-(pyridin-2-yl)ethyl) phenoxy)ethanamine |

TABLE 4-continued

| Example Number | Structure | Name |
|---|---|---|
| 38 | 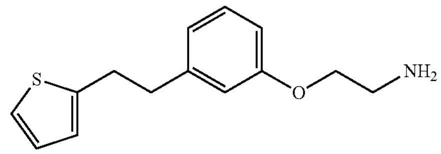 [SMILES: NCCOc1cccc(CCc2cccs2)c1] | 2-(3-(2-(thiophen-2-yl)ethyl)phenoxy)ethanamine |
| 50 | 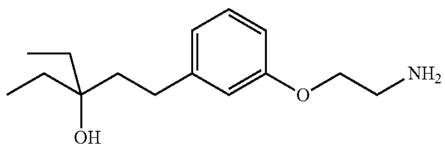 [SMILES: CCC(O)(CC)CCc1cccc(OCCN)c1] | 1-(3-(2-aminoethoxy)phenyl)-3-ethylpentan-3-ol |
| 51 | 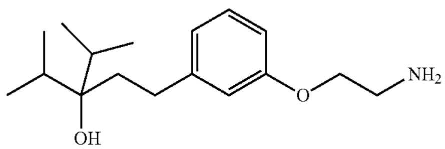 | 1-(3-(2-aminoethoxy)phenyl)-3-isopropyl-4-methylpentan-3-ol |
| 52 | 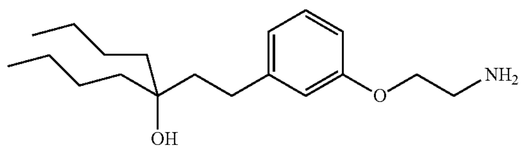 [SMILES: CCCCC(O)(CCCC)CCc1cccc(OCCN)c1] | 5-(3-(2-aminoethoxy)phenethyl)nonan-5-ol |
| 53 | 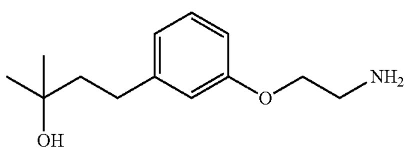 [SMILES: CC(C)(O)CCc1cccc(OCCN)c1] | 4-(3-(2-aminoethoxy)phenyl)-2-methylbutan-2-ol |
| 54 | 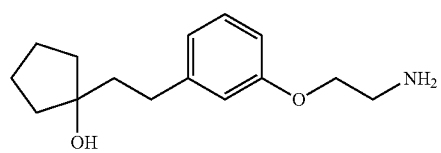 | 1-(3-(2-aminoethoxy)phenethyl)cyclopentanol |
| 64 | 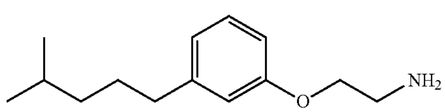 [SMILES: CC(C)CCCc1cccc(OCCN)c1] | 2-(3-(4-methylpentyl)phenoxy)ethanamine |
| 65 | 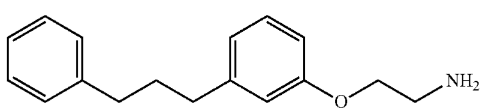 [SMILES: NCCOc1cccc(CCCc2ccccc2)c1] | 2-(3-(3-phenylpropyl)phenoxy)ethanamine |
| 66 | 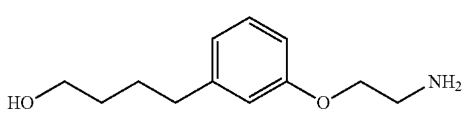 [SMILES: NCCOc1cccc(CCCCO)c1] | 4-(3-(2-aminoethoxy)phenyl)butan-1-ol |
| 67 | 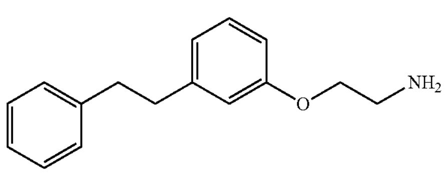 [SMILES: NCCOc1cccc(CCc2ccccc2)c1] | 2-(3-phenethylphenoxy)ethanamine |

TABLE 4-continued

| Example Number | Structure | Name |
|---|---|---|
| 68 | 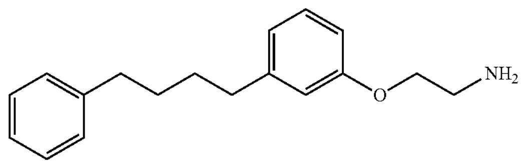 [SMILES: NCCOc1cccc(CCCCc2ccccc2)c1] | 2-(3-(4-phenylbutyl)phenoxy)ethanamine |
| 69 | 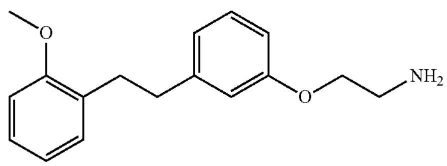 [SMILES: COc1ccccc1CCc1cccc(OCCN)c1] | 2-(3-(2-methoxyphenethyl)phenoxy)ethanamine |
| 74 | 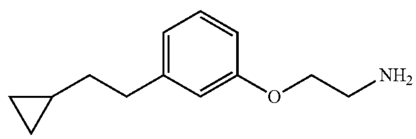 [SMILES: NCCOc1cccc(CCC2CC2)c1] | 2-(3-(2-cyclopropylethyl)phenoxy)ethanamine |
| 75 | 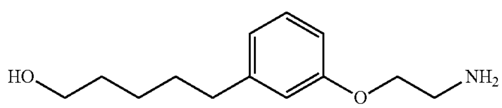 [SMILES: NCCOc1cccc(CCCCCO)c1] | 5-(3-(2-aminoethoxy)phenyl)pentan-1-ol |
| 77 | 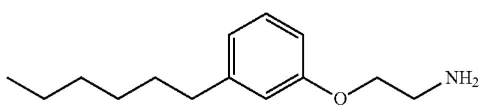 [SMILES: CCCCCCc1cccc(OCCN)c1] | 2-(3-hexylphenoxy)ethanamine |
| 78 | 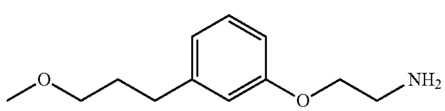 | 2-(3-(3-methoxypropyl)phenoxy)ethanamine |
| 81 | 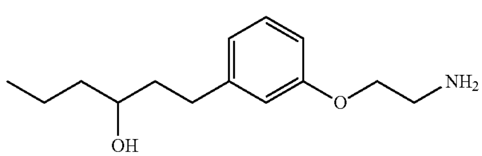 [SMILES: CCCC(O)CCc1cccc(OCCN)c1] | 1-(3-(2-aminoethoxy)phenyl)hexan-3-ol |
| 83 | 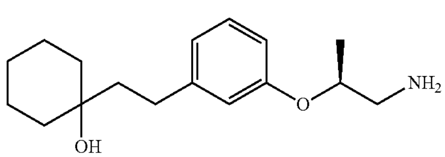 [SMILES: C[C@@H](CN)Oc1cccc(CCC2(O)CCCCC2)c1] | (S)-1-(3-(1-aminopropan-2-yloxy)phenethyl)cyclohexanol |
| 84 | 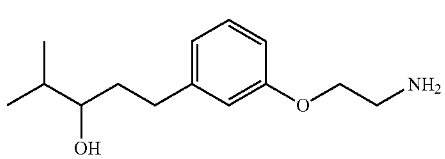 [SMILES: CC(C)C(O)CCc1cccc(OCCN)c1] | 1-(3-(2-aminoethoxy)phenyl)-4-methylpentan-3-ol |
| 88 | 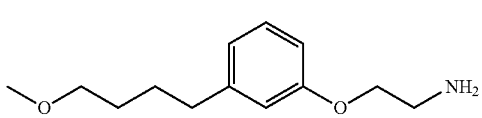 [SMILES: COCCCCc1cccc(OCCN)c1] | 2-(3-(4-methoxybutyl)phenoxy)ethanamine |

TABLE 4-continued

| Example Number | Structure | Name |
|---|---|---|
| 89 | 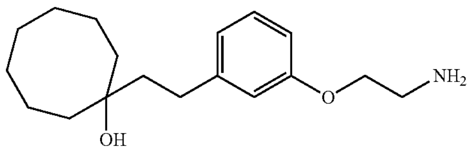 [SMILES: NCCOc1cccc(CCC2(O)CCCCCCC2)c1] | 1-(3-(2-aminoethoxy)phenethyl)cyclooctanol |
| 93 | 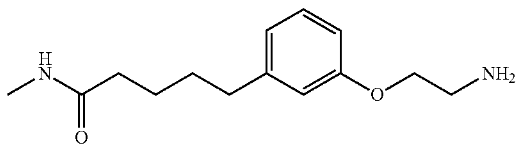 | 5-(3-(2-aminoethoxy)phenyl)-N-methylpentanamide |
| 94 | 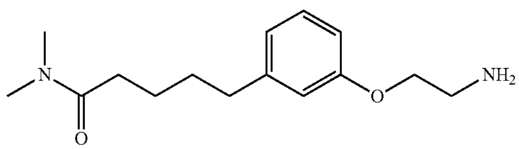 | 5-(3-(2-aminoethoxy)phenyl)-N,N-dimethylpentanamide |
| 96 | 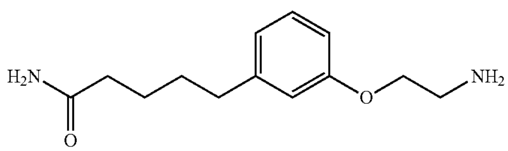 [SMILES: NCCOc1cccc(CCCCC(N)=O)c1] | 5-(3-(2-aminoethoxy)phenyl)pentanamide |
| 99 | 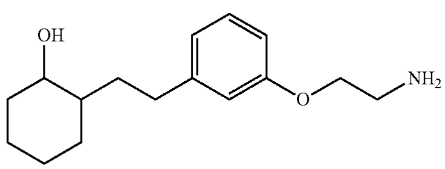 [SMILES: NCCOc1cccc(CCC2CCCCC2O)c1] | 2-(3-(2-aminoethoxy)phenethyl)cyclohexanol |
| 101 | 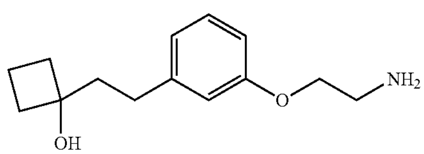 [SMILES: NCCOc1cccc(CCC2(O)CCC2)c1] | 1-(3-(2-aminoethoxy)phenethyl)cyclobutanol |
| 107 | 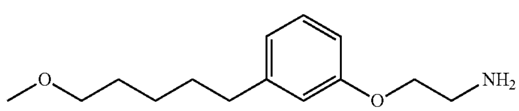 [SMILES: COCCCCCc1cccc(OCCN)c1] | 2-(3-(5-methoxypentyl)phenoxy)ethanamine |
| 108 | 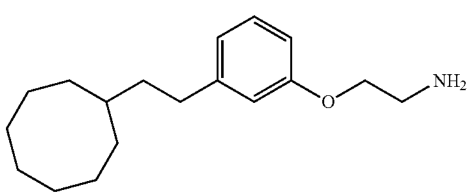 [SMILES: NCCOc1cccc(CCC2CCCCCCC2)c1] | 2-(3-(2-cyclooctylethyl)phenoxy)ethanamine |
| 114 | 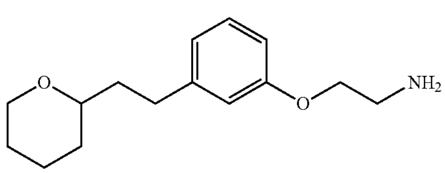 [SMILES: NCCOc1cccc(CCC2CCCCO2)c1] | 2-(3-(2-(tetrahydro-2H-pyran-2-yl)ethyl)phenoxy)ethanamine |

TABLE 4-continued

| Example Number | Structure | Name |
|---|---|---|
| 123 | 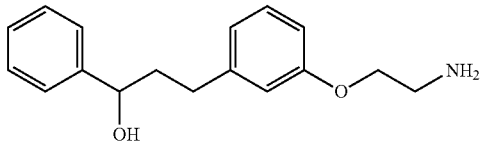 [SMILES: NCCOc1cccc(CCC(O)c2ccccc2)c1] | 3-(3-(2-aminoethoxy)phenyl)-1-phenylpropan-1-ol |
| 125 | 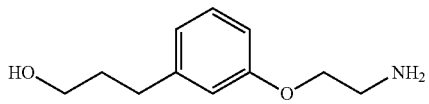 [SMILES: NCCOc1cccc(CCCO)c1] | 3-(3-(2-aminoethoxy)phenyl)propan-1-ol |

Certain compounds disclosed herein have the structures shown in Table 5. The example number refers to a specific Example herein that describes the preparation of the compound having the structure/name shown.

TABLE 5

| Example Number | Structure | Name |
|---|---|---|
| 127 | 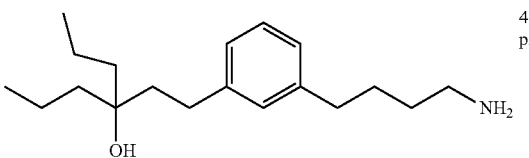 | 4-(3-(4-aminobutyl)phenethyl)heptan-4-ol |
| 134 | 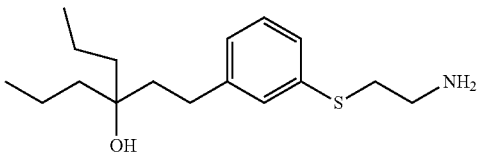 [SMILES: CCCC(O)(CCC)CCc1cccc(SCCN)c1] | 4-(3-(2-aminoethylthio)phenethyl)heptan-4-ol |
| 135 | 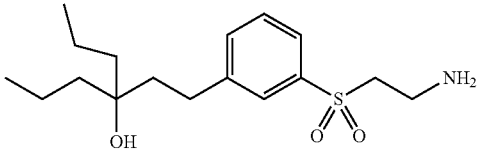 [SMILES: CCCC(O)(CCC)CCc1cccc(S(=O)(=O)CCN)c1] | 4-(3-(2-aminoethylsulfonyl)phenethyl)heptan-4-ol |
| 136 | 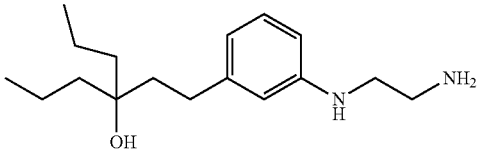 [SMILES: CCCC(O)(CCC)CCc1cccc(NCCN)c1] | 4-(3-(2-aminoethylamino)phenethyl)heptan-4-ol |
| 139 | 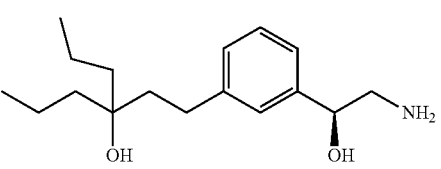 [SMILES: CCCC(O)(CCC)CCc1cccc([C@H](O)CN)c1] | (S)-4-(3-(2-amino-1-hydroxyethyl)phenethyl)heptan-4-ol |
| 156 | 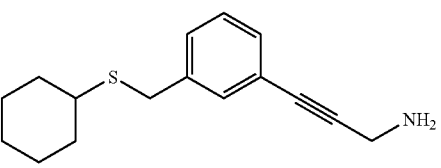 [SMILES: NCC#Cc1cccc(CSC2CCCCC2)c1] | 3-(3-(cyclohexylthiomethyl)phenyl)prop-2-yn-1-amine |

TABLE 5-continued

| Example Number | Structure | Name |
|---|---|---|
| 157 | 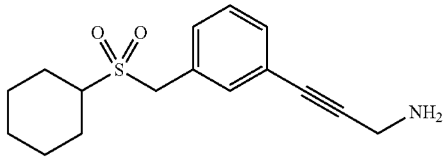 [SMILES: NCC#Cc1cccc(CS(=O)(=O)C2CCCCC2)c1] | 3-(3-(cyclohexylsulfonylmethyl)phenyl)prop-2-yn-1-amine |
| 158 | 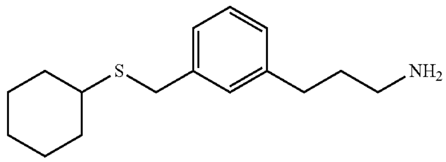 [SMILES: NCCCc1cccc(CSC2CCCCC2)c1] | 3-(3-(cyclohexylthiomethyl)phenyl)propan-1-amine |
| 159 | 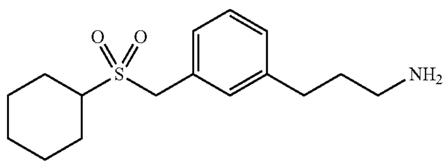 [SMILES: NCCCc1cccc(CS(=O)(=O)C2CCCCC2)c1] | 3-(3-(cyclohexylsulfonylmethyl)phenyl)propan-1-amine |
| 160 | 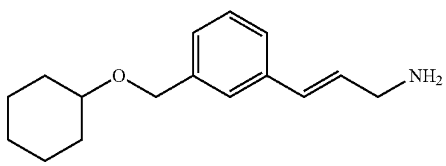 [SMILES: NC/C=C/c1cccc(COC2CCCCC2)c1] | (E)-3-(3-(cyclohexyloxymethyl)phenyl)prop-2-en-1-amine |
| 162 | 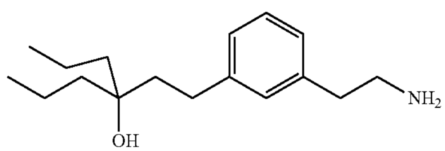 [SMILES: CCCC(O)(CCC)CCc1cccc(CCN)c1] | 4-(3-(2-aminoethyl)phenethyl)heptan-4-ol |
| 163 | 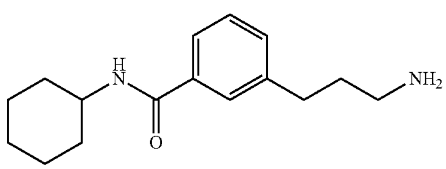 [SMILES: NCCCc1cccc(C(=O)NC2CCCCC2)c1] | 3-(3-aminopropyl)-o-cyclohexylbenzamide |
| 164 | 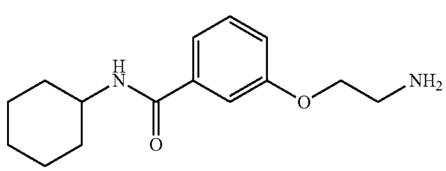 [SMILES: NCCOc1cccc(C(=O)NC2CCCCC2)c1] | 3-(2-aminoethoxy)-N-cyclohexylbenzamide |
| 165 | 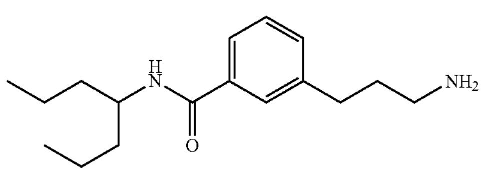 [SMILES: CCCC(CCC)NC(=O)c1cccc(CCCN)c1] | 3-(3-aminopropyl)-N-(heptan-4-yl)benzamide |
| 166 | 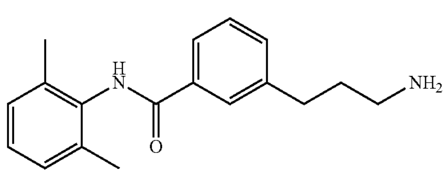 [SMILES: Cc1cccc(C)c1NC(=O)c1cccc(CCCN)c1] | 3-(3-aminopropyl)-N-(2,6-dimethylphenyl)benzamide |

| Example Number | Structure | Name |
|---|---|---|
| 185 | 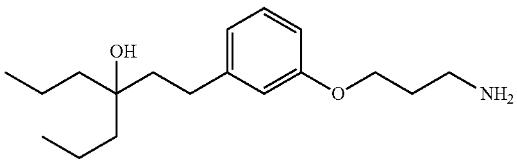 [SMILES: CCCC(O)(CCC)CCc1cccc(OCCCN)c1] | 4-(3-(3-aminopropoxy)phenethyl)heptan-4-ol |
| 186 | 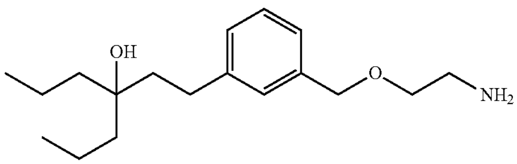 [SMILES: CCCC(O)(CCC)CCc1cccc(COCCN)c1] | 4-(3-((2-aminoethoxy)methyl)phenethyl)heptan-4-ol |

II. Definitions

As used herein and in the appended claims, the singular forms "a," "and," and "the" include plural referents unless the context clearly dictates otherwise. Thus, for example, reference to "a compound" includes a plurality of such compounds, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

"Sulfanyl" refers to the —S— radical.
"Sulfinyl" refers to the —S(=O)— radical.
"Sulfonyl" refers to the —S(=O)$_2$— radical.
"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Imino" refers to the =NH radical.
"Thioxo" refers to the =S radical.

"Alkyl" refers to a straight or branched hydrocarbon chain radical consisting solely of carbon and hydrogen atoms, containing no unsaturation, having from one to fifteen carbon atoms (e.g., C$_1$-C$_{15}$ alkyl). In certain embodiments, an alkyl comprises one to thirteen carbon atoms (e.g., C$_1$-C$_{13}$ alkyl). In certain embodiments, an alkyl comprises one to eight carbon atoms (e.g., C$_1$-C$_8$ alkyl). In other embodiments, an alkyl comprises five to fifteen carbon atoms (e.g., C$_5$-C$_{15}$ alkyl). In other embodiments, an alkyl comprises five to eight carbon atoms (e.g., C$_5$-C$_8$ alkyl). The alkyl is attached to the rest of the molecule by a single bond, for example, methyl (Me), ethyl (Et), n-propyl, 1-methylethyl(iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain is optionally substituted by one or more of the following substituents: halo, cyano, nitro, aryl, cycloalkyl, heterocyclyl, heteroaryl, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t R^a$ (where t is 1 or 2), —S(O)$_t$O$R^a$ (where t is 1 or 2) and —S(O)$_t$N($R^a$)$_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted by one or more of the following substituents: halo, cyano, nitro, aryl, cycloalkyl, heterocyclyl, heteroaryl, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t R^a$ (where t is 1 or 2), —S(O)$_t$O$R^a$ (where t is 1 or 2) and —S(O)$_t$N($R^a$)$_2$ (where t is 1 or 2) where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl, fluorenyl, and naphthyl. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—$N(R^a)_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and Re is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is optionally saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—$N(R^a)_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, and includes fused or bridged ring systems. The heteroatom(s) in the heterocyclyl radical is optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—$OC(O)$—$R^a$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl,isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]

thieno[2,3-d]pyrimidinyl, 5,6,7,8-tetrahydropyrido[4,5-c] pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—$N(R^a)_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2) and —$R^b$—S(O)$_t N(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The compounds, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. When the compounds described herein contain olefinic double bonds or other centers of geometric asymmetry, and unless specified otherwise, it is intended that the compounds include both E and Z geometric isomers (e.g., cis or trans.) Likewise, all possible isomers, as well as their racemic and optically pure forms, and all tautomeric forms are also intended to be included.

"Stereoisomers" are compounds that have the same sequence of covalent bonds and differ in the relative disposition of their atoms in space. "Enantiomers" refers to two stereoisomers that are nonsuperimposeable mirror images of one another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$— or $^{14}C$-enriched carbon are within the scope of this invention.

The compounds of the present invention may also contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. All isotopic variations of the compounds of the present invention, whether radioactive or not, are encompassed within the scope of the present invention.

In certain embodiments, the amine derivative compounds disclosed herein have some or all of the $^1H$ atoms replaced with $^2H$ atoms. The methods of synthesis for deuterium-containing amine derivative compounds are known in the art and include, by way of non-limiting example only, the following synthetic methods.

Deuterated starting materials, such as acid i and acid ii, are readily available and are subjected to the synthetic methods described herein for the synthesis of amine derivative compounds.

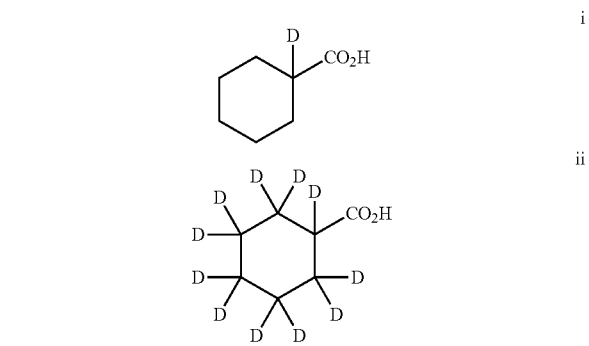

Other deuterated starting materials are also employed in the synthesis of deuterium-containing amine derivative compounds as shown, in a non-limiting example, in the scheme below. Large numbers of deuterium-containing reagents and building blocks are available commercially from chemical vendors, such as Aldrich Chemical Co.

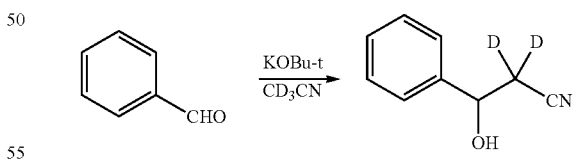

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

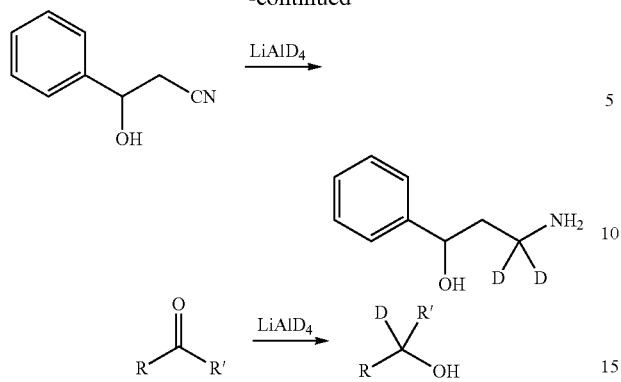

Deuterium gas and palladium catalyst are employed to reduce unsaturated carbon-carbon linkages and to perform a reductive substitution of aryl carbon-halogen bonds as illustrated, by way of example only, in the reaction schemes below.

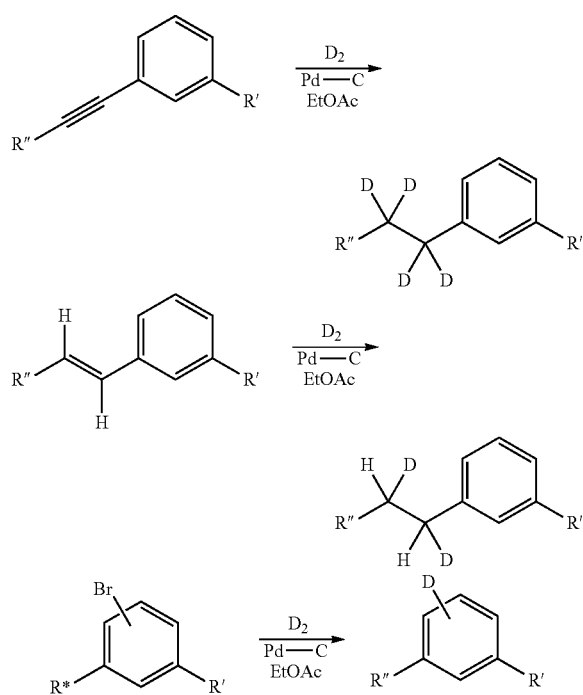

In one embodiments, the amine derivative compound contains one deuterium atom. In another embodiment, the amine derivative compound contains two deuterium atoms. In another embodiment, the amine derivative compound contains three deuterium atoms. In another embodiment, the amine derivative compound contains four deuterium atoms. In another embodiment, the amine derivative compound contains five deuterium atoms. In another embodiment, the amine derivative compound contains six deuterium atoms. In another embodiment, the amine derivative compound is fully substituted with deuterium atoms and contains no non-exchangeable $^1$H hydrogen atoms.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

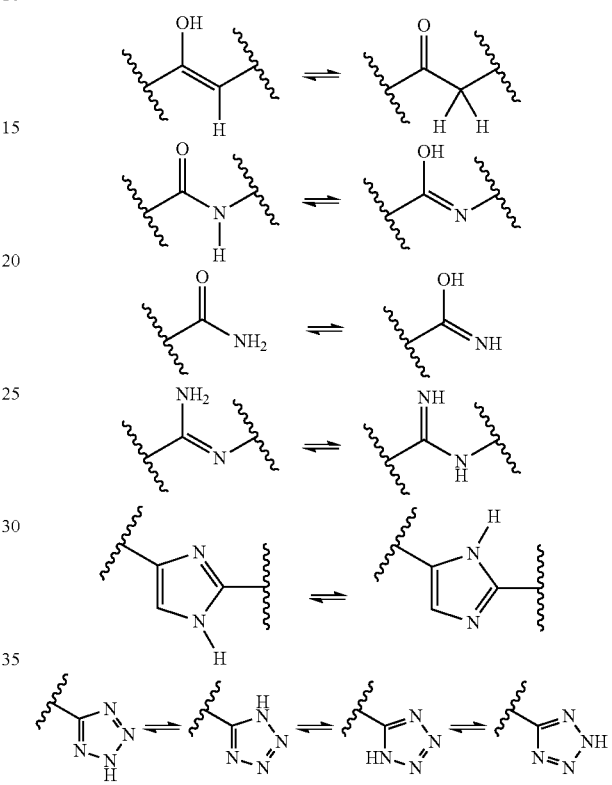

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the amine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorus acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$— or $^{14}C$-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

"Non-retinoid compound" refers to any compound that is not a retinoid. A retinoid is a compound that has a diterpene skeleton possessing a trimethylcyclohexenyl ring and a polyene chain that terminates in a polar end group. Examples of retinoids include retinaldehyde and derived imine/hydrazide/oxime, retinol and any derived ester, retinol amine and any derived amide, retinoic acid and any derived ester or amide. A non-retinoid compound can comprise though not require an internal cyclic group (e.g., aromatic group). A non-retinoid compound can contain though not require an amine derivative group.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-chugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

The compounds of the invention are synthesized by an appropriate combination of generally well known synthetic methods. Techniques useful in synthesizing the compounds of the invention are both readily apparent and accessible to those of skill in the relevant art.

The discussion below is offered to illustrate how, in principle, to gain access to the compounds claimed under this invention and to give details on certain of the diverse methods available for use in assembling the compounds of the invention. However, the discussion is not intended to define or limit the scope of reactions or reaction sequences that are useful in preparing the compounds of the present invention. The compounds of this invention may be made by the procedures and techniques disclosed in the Examples section below, as well as by known organic synthesis techniques.

III. Preparation of the Amine Derivative Compounds

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the amine derivative compounds described herein is P. H. Stahl & C. G. Wermuth "Handbook of Pharmaceutical Salts", Verlag Helvetica Chimica Acta, Zurich, 2002.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to the following moieties:

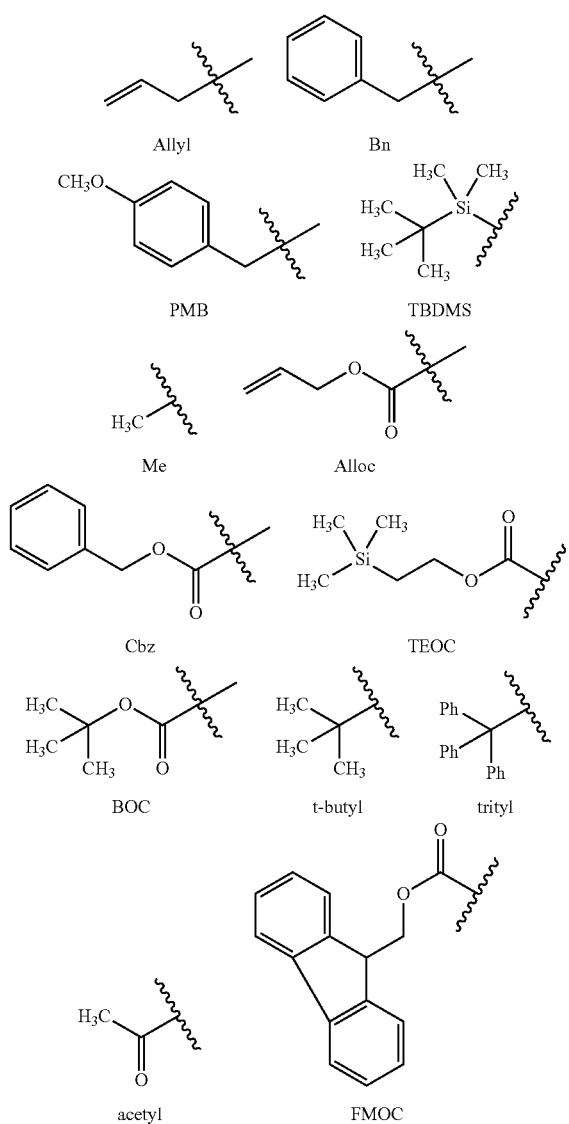

Generally speaking, compounds of Formula (I) can be prepared in a stepwise manner involving initial acetylene, or olefin formation followed by hydrogenation to provide the alkanyl substituent on the phenyl. The nitrogen-containing moiety can be linked to the phenyl via the formation and modification of a side chain at the meta-position of the alkanyl.

1. Alkanyl Formation

Methods A-C below describe various approaches to alkanyl formation on the phenyl ring.

More specifically, Method A illustrates the formation of an alkane through hydrogenation of an alkyne. Method B shows the construction of an alkane intermediate through the hydrogenation of a cis or trans olefin.

Catalysts suitable for hydrogenation reactions are known to those skilled in the art. Exemplary catalysts include, for example, palladium on charcoal, palladium hydroxide, platinum, platinum oxide, Raney nickel, rhodium, Wilkinson's catalyst (chloro tris(triphenylphosphine)rhodium), and Lindlar's catalyst (Pd—CaCO$_3$—PbO).

Hydrogen sources suitable for reducing alkynes to alkanes via hydrogenation are known to those skilled in the art. Exemplary hydrogen sources include, for example, hydrogen gas, ammonium formate, sodium borohydride, cyclohexene, cyclohexadiene and hydrazine.

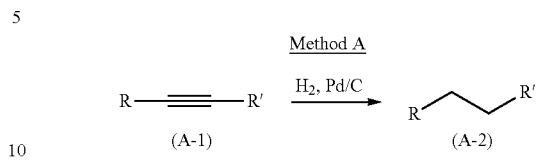

Method B shows the construction of an alkane intermediate through the hydrogenation of a cis or trans olefin.

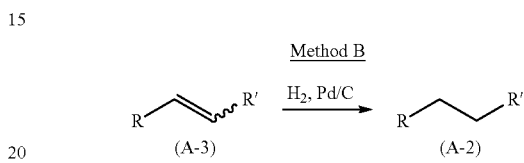

The alkyne (A-1) and olefin (A-3) can be prepared according to known methods in the art (see, e.g., Methods C-G).

Methods C-G illustrate the formation of an alkyne or olefin side chain on a phenyl (indicated by Ar). More specifically, Method C shows the coupling of a triple bond with a phenyl based on a Sonogashira reaction. Typically, palladium(0) catalyst is used in combination with a base to couple an aryl halide with an acetylene derivative. R' can be, for example, alkyl, aryl, heterocyclyl, heteroaryl, carbocyclyl, or derivatives thereof, which can be further modified, as described herein.

2. Alkanyl Formation

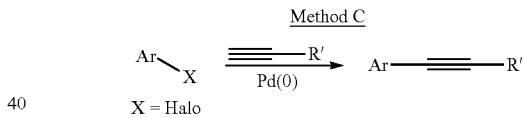

Method D shows the formation of a terminal alkyne. Typically, the Sonogashira reaction is used to link an aryl halide to an acetylene derivative such as 2-methyl-3-butyn-2-ol. In a subsequent step, base is used to reveal the terminal alkyne. This alkyne can be further modified in subsequent Sonogashira type reactions.

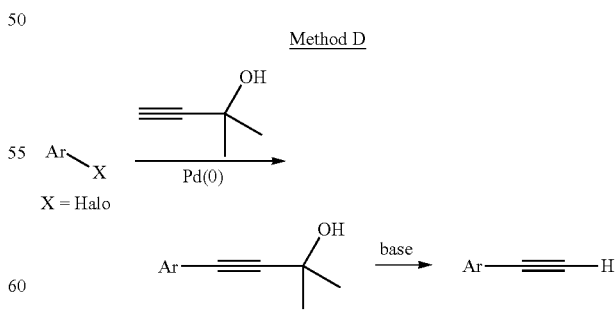

Method E shows the coupling of an olefin with a phenyl based on a Heck reaction. Typically, palladium(0) catalyst is used in combination with a base to couple an aryl halide with a vinyl derivative. R' can be further modified, as described herein.

Method E

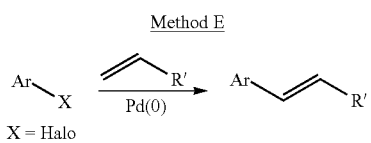

X = Halo

Method F shows the formation of an olefinic bond based on a Wittig reaction. Typically, a phosphonium salt is coupled to an aldehyde in the presence of a suitable base during which a molecule of triarylphosphine oxide is eliminated.

Method F

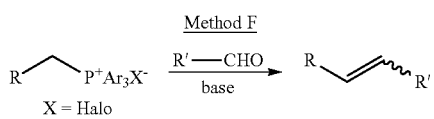

X = Halo

Method G shows the formation of an olefinic bond via the elimination of $H_2O$ in the presence of acid.

Method G

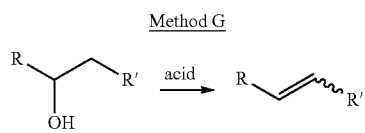

In addition, direct alkylation of a phenyl group can be carried out by, for example, coupling an alkyl boronate with a phenyl halide in the presence of a Pd-based catalyst. Other methods for direct alkylation of a phenyl ring include, for example, coupling an aralkyl or alkyl Grignards reagent with the phenyl ring.

Nitrogen-Containing Side Chain Formation and Modification

Methods H-T below describe various approaches to side chain formation and modifications.

Generally speaking, a suitably substituted phenyl derivative can be coupled to a diverse range of side chains, which may be further modified to provide the final linkages and the nitrogen-containing moieties of compounds of Formula (I).

Method H illustrates an aryl halide coupled with an allyl alcohol in the presence of a palladium(0) catalyst. The terminal alcohol group of allyl alcohol has been simultaneously oxidized to an aldehyde group, which can be further modified via reductive amination to an amine ($-NR_{11}R_{12}$).

Method H

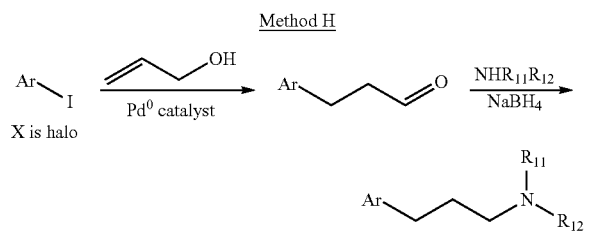

X is halo

Method I illustrates an aldol condensation between an aryl aldehyde or aryl ketone with a nitrile reagent comprising at least one α-hydrogen. The resulting condensation intermediate can be further reduced to an amine ($-NR_{11}R_{12}$).

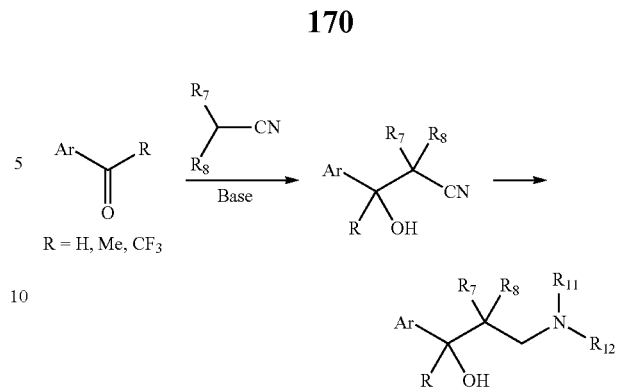

R = H, Me, $CF_3$

Method J shows an acylation reaction to form a ketone-based linkage. One skilled in the art will recognize that the R' group may comprise functional groups that can be further modified.

Method J

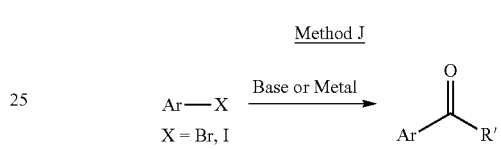

X = Br, I

Method K shows a side chain precursor (R'OH) attached to an aryl derivative via an oxygen atom in a condensation reaction in which a molecule of $H_2O$ is eliminated. R' may comprise functional groups that can be further modified to prepare linkages and nitrogen-containing moieties of compounds of Formula (I).

Method K

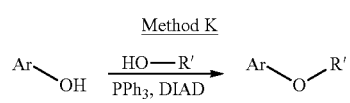

In addition, side chains based on alkyne or olefin derivatives can be first prepared according to Methods C-G, as previously described. The alkyne or olefin derivatives can be further hydrogenated and modified to provide the terminal nitrogen-containing moiety.

The following methods illustrate a variety of synthetic pathways to manipulate or modify the side chain moiety by reduction, oxidation, nucleophilic or electrophilic substitution, acylation and the like. As a result, a diverse group of linkages can be synthesized.

Method L illustrates an amination process in which a carboxylic acid is converted to an amine. Typically, the carboxylic acid (or ester) can be first reduced to a primary alcohol, which can then be converted to an amine via a mesylate, halide, azide, phthalimide, or Mitsunobu reaction and the like. Suitable reducing agents include, for example, sodium borohydride ($NaBH_4$), sodium cyanoborohydride ($NaBH_3CN$), sodium triacetoxyborohydride ($NaBH(OCOCH_3)_3$), lithium aluminum hydride ($LiAlH_4$) and the like. As shown, the resulting amine can be further functionalized, by methods known to those skilled in the art.

An amination process in which a carboxylic acid is first converted to an acid chloride and the halide is displaced by a suitable amine synthon is illustrated in Method M. The resulting amide can be reduced and/or further functionalized, by methods known to those skilled in the art.

Additional or alternative modifications can be carried out according to the methods illustrated below.

Scheme I illustrates a complete synthetic sequence for preparing a compound of Formula (I).

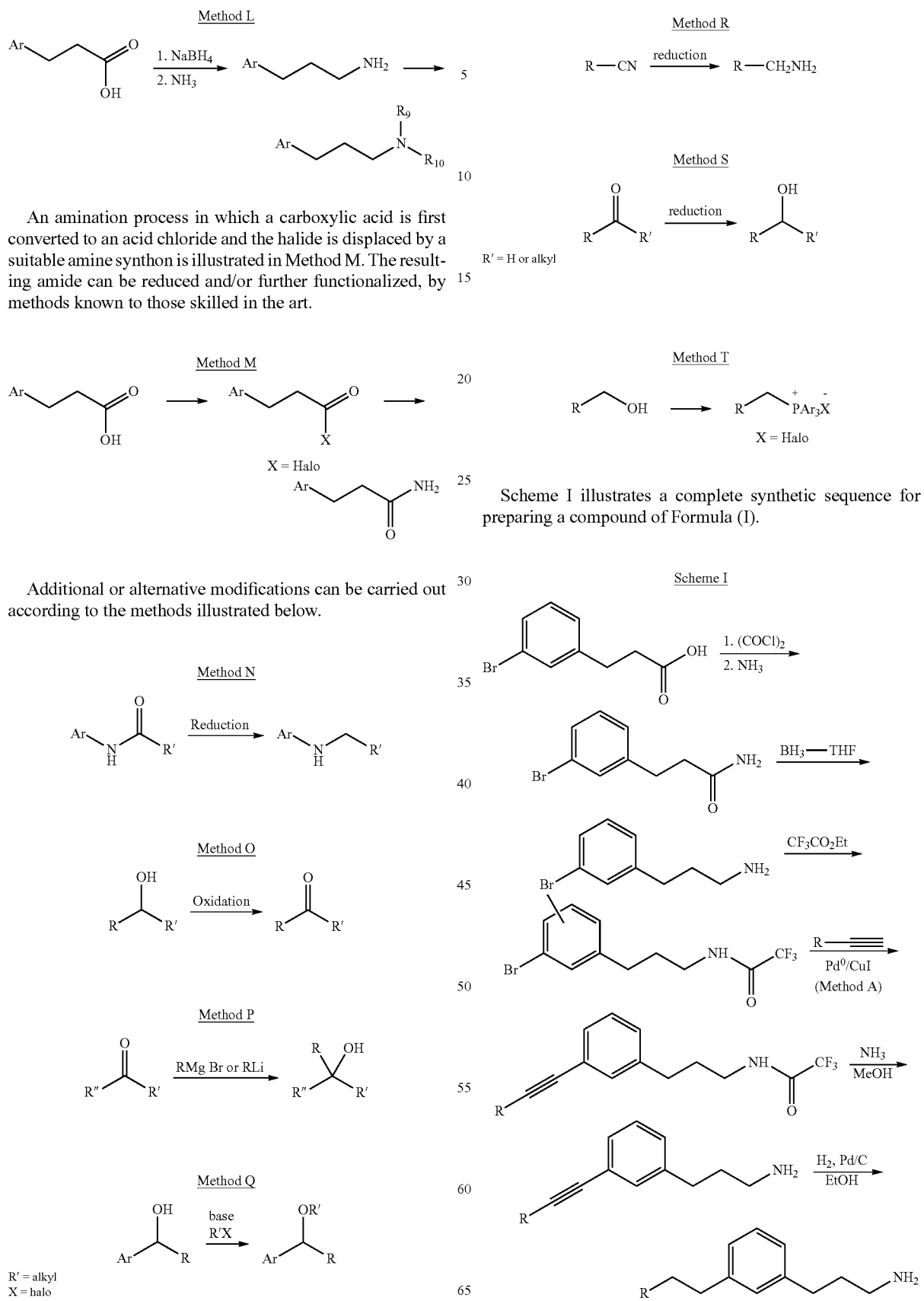

In Scheme I, the side chain moiety is first constructed and the amine protected. The acetylene moiety is then formed through coupling with a terminal acetylene according to Method C. The coupling product is then deprotected to give rise to an alkyne. The alkanyl linkage is formed through hydrogenation of the alkyne (see, e.g., Method A). Other nitrogen-containing moieties can be further derived from the terminal amine, according to known methods in the art.

In addition to the generic reaction schemes and methods discussed above, other exemplary reaction schemes are also provided to illustrate methods for preparing any compound having a structure of Formula (I) or any of its subgenus structures, including Formulae (Ia) and (Ib).

IV. Treatment of Ophthalmic Diseases and Disorders

Amine derivative compounds as described herein, including compounds having the structure as set forth in Formula (I) and substructures thereof, are useful for treating an ophthalmic disease or disorder by inhibiting one or more steps in the visual cycle.

In an additional embodiment is a non-retinoid compound that inhibits an isomerase reaction resulting in production of 11-cis retinol, wherein said isomerase reaction occurs in RPE, and wherein said compound has an $ED_{50}$ value of 1 mg/kg or less when administered to a subject. In a further embodiment is the non-retinoid compound wherein the $ED_{50}$ value is measured after administering a single dose of the compound to said subject for about 2 hours or longer. In a further embodiment is the non-retinoid compound, wherein the non-retinoid compound is an alkoxyl compound. In an additional embodiment is a pharmaceutical composition comprising a pharmaceutically acceptable carrier and a non-retinoid compound as described herein. In an additional embodiment is a method for treating an ophthalmic disease or disorder in a subject, comprising administering to the subject a pharmaceutical composition comprising a pharmaceutically acceptable carrier and a non-retinoid compound as described herein.

In an additional embodiment is a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature. In a further embodiment, the compound inhibits 11-cis-retinol production with an $IC_{50}$ of about 0.1 µM or less. In a further embodiment, the compound inhibits 11-cis-retinol production with an $IC_{50}$ of about 0.01 µM or less. In a further embodiment, the compound that inhibits 11-cis-retinol production is a non-retinoid compound. In an additional embodiment is a pharmaceutical composition comprising a pharmaceutically acceptable carrier and a compound that inhibits 11-cis-retinol production as described herein. In an additional embodiment is a method for treating an ophthalmic disease or disorder in a subject, comprising administering to the subject a pharmaceutical composition comprising a pharmaceutically acceptable carrier and a compound that inhibits 11-cis-retinol production as described herein. In an additional embodiment is a method of modulating chromophore flux in a retinoid cycle comprising introducing into a subject a compound that inhibits 11-cis-retinol production as described herein.

In an additional embodiment is a method for treating an ophthalmic disease or disorder in a subject, comprising administering to the subject a compound of Formula (G) or tautomer, stereoisomer, geometric isomer or a pharmaceutically acceptable solvate, hydrate, salt, N-oxide or prodrug thereof:

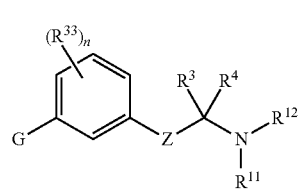

Formula (G)

wherein,

Z is a bond, —C($R^1$)($R^2$)—, —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)— or —X—C($R^{31}$)($R^{32}$)—C($R^1$)($R^2$)—;

X is —O—, —S—, —S(=O)—, —S(=O)$_2$—, —N($R^{30}$)—, —C(=O)—, —C(=CH$_2$)—, —C(=N—N$R^{35}$)—, or —C(=N—O$R^{35}$)—;

G is selected from —C(each)$_2$-C($R^{41}$)$_2$—$R^{40}$, —C($R^{42}$)$_2$—S—$R^{40}$, —C($R^{42}$)$_2$—SO—$R^{40}$, —C($R^{42}$)$_2$—SO$_2$—$R^{40}$, —C($R^{42}$)$_2$—O—$R^{40}$, —C($R^{42}$)$_2$—N($R^{42}$)—$R^{40}$, —C(=O)—N($R^{42}$)—$R^{40}$;

$R^{40}$ is selected from —C($R^{16}$)($R^{17}$)($R^{18}$), aryl, or heteroaryl;

each $R^{41}$ is independently selected from hydrogen, hydroxy, O$R^6$, alkyl, or two $R^{41}$ groups together may form an oxo;

each $R^{42}$ is independently selected from hydrogen or alkyl;

$R^1$ and $R^2$ are each independently selected from hydrogen, halogen, $C_1$-$C_5$ alkyl, fluoroalkyl, —O$R^6$ or —N$R^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —O$R^6$ or —N$R^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^5$ is $C_5$-$C_{15}$ alkyl or carbocyclyalkyl;

$R^7$ and $R^8$ are each independently selected from hydrogen, alkyl, carbocyclyl, heterocyclyl, —C(=O)$R^{13}$, SO$_2R^{13}$, CO$_2R^{13}$ or SO$_2$N$R^{24}R^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, —O$R^{19}$, —N$R^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)$R^{23}$, —C(NH)NH$_2$, SO$_2R^{23}$, CO$_2R^{23}$ or SO$_2$N$R^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, SO$_2R^{22}$, $CO_2R^{22}$ or $SO_2NR^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, $OR^{34}$, alkyl, or fluoroalkyl; and n is 0, 1, 2, 3, or 4.

In an additional embodiment is a method of modulating chromophore flux in a retinoid cycle comprising introducing into a subject a compound of Formula (G). In a further embodiment is the method resulting in a reduction of lipofuscin pigment accumulated in an eye of the subject. In a further embodiment is the method resulting in a reduction of lipofuscin pigment accumulated in an eye of the subject, wherein the lipofuscin pigment is N-retinylidene-N-retinyl-ethanolamine (A2E).

In a further embodiment is the method of treating an ophthalmic disease or disorder in a subject as described herein resulting in a reduction of lipofuscin pigment accumulated in an eye of the subject. In a further embodiment is the method of treating an ophthalmic disease or disorder in a subject as described herein resulting in a reduction of lipofuscin pigment accumulated in an eye of the subject, wherein the lipofuscin pigment is N-retinylidene-N-retinyl-ethanolamine (A2E).

In a further embodiment is the method of treating an ophthalmic disease or disorder in a subject as described herein, wherein the ophthalmic disease or disorder is age-related macular degeneration or Stargardt's macular dystrophy. In a further embodiment is the method of treating an ophthalmic disease or disorder in a subject as described herein, wherein the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS. In a further embodiment is the method of treating an ophthalmic disease or disorder in a subject as described herein resulting in a reduction of lipofuscin pigment accumulated in an eye of the subject. In a further embodiment is the method of treating an ophthalmic disease or disorder in a subject as described herein resulting in a reduction of lipofuscin pigment accumulated in an eye of the subject, wherein the lipofuscin pigment is N-retinylidene-N-retinyl-ethanolamine (A2E).

In another embodiment is a method of inhibiting dark adaptation of a rod photoreceptor cell of the retina comprising contacting the retina with a compound of Formula (G). In another embodiment is a method of inhibiting dark adaptation of a rod photoreceptor cell of the retina comprising contacting the retina with a non-retinoid compound as described herein. In another embodiment is a method of inhibiting dark adaptation of a rod photoreceptor cell of the retina comprising contacting the retina with a compound that inhibits 11-cis-retinol production as described herein.

In another embodiment is a method of inhibiting regeneration of rhodopsin in a rod photoreceptor cell of the retina comprising contacting the retina with a compound of Formula (G). In another embodiment is a method of inhibiting regeneration of rhodopsin in a rod photoreceptor cell of the retina comprising contacting the retina with a non-retinoid compound as described herein. In another embodiment is a method of inhibiting regeneration of rhodopsin in a rod photoreceptor cell of the retina comprising contacting the retina with a compound that inhibits 11-cis-retinol production as described herein.

In another embodiment is a method of reducing ischemia in an eye of a subject comprising administering to the subject a pharmaceutical composition comprising a pharmaceutically acceptable carrier and a compound of Formula (G).

In an additional embodiment is a method of reducing ischemia in an eye of a subject comprising administering to the subject a pharmaceutical composition comprising a pharmaceutically acceptable carrier and a non-retinoid compound as described herein. In an additional embodiment is a method of reducing ischemia in an eye of a subject comprising administering to the subject a pharmaceutical composition comprising a pharmaceutically acceptable carrier and a compound that inhibits 11-cis-retinol production as described herein. In a further embodiment is the method of reducing ischemia in an eye of a subject, wherein the pharmaceutical composition is administered under conditions and at a time sufficient to inhibit dark adaptation of a rod photoreceptor cell, thereby reducing ischemia in the eye.

In an additional embodiment is a method of inhibiting neovascularization in the retina of an eye of a subject comprising administering to the subject a pharmaceutical composition comprising a pharmaceutically acceptable carrier and a non-retinoid compound as described herein. In an additional embodiment is a method of inhibiting neovascularization in the retina of an eye of a subject comprising administering to the subject a pharmaceutical composition comprising a pharmaceutically acceptable carrier and a compound that inhibits 11-cis-retinol production as described herein. In a further embodiment is the method of inhibiting neovascularization in the retina of an eye of a subject, wherein the pharmaceutical composition is administered under conditions and at a time sufficient to inhibit dark adaptation of a rod photoreceptor cell, thereby inhibiting neovascularization in the retina.

In an additional embodiment is a method of inhibiting degeneration of a retinal cell in a retina comprising contacting the retina with a compound of Formula (G). In an additional embodiment is a method of inhibiting degeneration of a retinal cell in a retina comprising contacting the retina with a non-retinoid compound as described herein. In an additional embodiment is a method of inhibiting degeneration of a retinal cell in a retina comprising contacting the retina with a compound that inhibits 11-cis-retinol production as described herein.

In a further embodiment is the method of inhibiting degeneration of a retinal cell in a retina wherein the retinal cell is a retinal neuronal cell. In a further embodiment is the method of inhibiting degeneration of a retinal cell in a retina wherein the retinal neuronal cell is a photoreceptor cell.

In another embodiment is a method of reducing lipofuscin pigment accumulated in a subject's retina comprising administering to the subject a pharmaceutical composition comprising a pharmaceutically acceptable carrier and a compound of Formula (G). In an additional embodiment is a method of reducing lipofuscin pigment accumulated in a subject's retina wherein the lipofuscin is N-retinylidene-N-retinyl-ethanolamine (A2E).

In an additional embodiment is a method of inhibiting reducing lipofuscin pigment accumulated in a subject's retina comprising administering to the subject a pharmaceutical composition comprising a pharmaceutically acceptable carrier and a non-retinoid compound as described herein. In an additional embodiment is a method of reducing lipofuscin pigment accumulated in a subject's retina comprising administering to the subject a pharmaceutical composition comprising a pharmaceutically acceptable carrier and a compound that inhibits 11-cis-retinol production as described herein. In an additional embodiment is a method of reducing lipofuscin pigment accumulated in a subject's retina wherein the lipofuscin is N-retinylidene-N-retinyl-ethanolamine (A2E).

In an additional embodiment is a method of modulating chromophore flux in a retinoid cycle comprising introducing into a subject a compound of Formula (G) or tautomer, stereoisomer, geometric isomer or a pharmaceutically acceptable solvate, hydrate, salt, N-oxide or prodrug thereof:

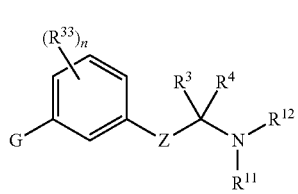

Formula (G)

wherein,

Z is a bond, —C($R^1$)($R^2$)—, —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)— or —X—C($R^{31}$)($R^{32}$)—C($R^1$)($R^2$)—;

X is —O—, —S—, —S(=O)—, —S(=O)$_2$—, —N($R^{30}$)—, —C(=O)—, —C(=CH$_2$)—, —C(=N—NR$^{35}$)—, or —C(=N—OR$^{35}$)—;

G is selected from —C($R^{41}$)$_2$—C($R^{41}$)$_2$—$R^{40}$, —C($R^{42}$)$_2$—S—$R^{40}$, —C($R^{42}$)$_2$—SO—$R^{40}$, —C($R^{42}$)$_2$—SO$_2$—$R^{40}$, —C($R^{42}$)$_2$—O—$R^{40}$, —C($R^{42}$)$_2$—N($R^{42}$)—$R^{40}$, —C(=O)—N($R^{42}$)—$R^{40}$;

$R^{40}$ is selected from —C($R^{16}$)($R^{17}$)($R^{18}$), aryl, or heteroaryl;

each $R^{41}$ is independently selected from hydrogen, hydroxy, O$R^6$, alkyl, or two $R^{41}$ groups together may form an oxo;

each $R^{42}$ is independently selected from hydrogen or alkyl;

$R^1$ and $R^2$ are each independently selected from hydrogen, halogen, $C_1$-$C_5$ alkyl, fluoroalkyl, —OR$^6$ or —NR$^7$R$^8$; or $R^1$ and $R^2$ together form an oxo;

$R^{31}$ and $R^{32}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —OR$^6$ or —NR$^7$R$^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^5$ is $C_5$-$C_{15}$ alkyl or carbocyclyalkyl;

$R^7$ and $R^8$ are each independently selected from hydrogen, alkyl, carbocyclyl, heterocyclyl, —C(=O)R$^{13}$, SO$_2$R$^{13}$, CO$_2$R$^{13}$ or SO$_2$NR$^{24}$R$^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, —OR$^{19}$, —NR$^{20}$R$^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)R$^{23}$, —C(NH)NH$_2$, SO$_2$R$^{23}$, CO$_2$R$^{23}$ or SO$_2$NR$^{28}$R$^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)R$^{22}$, SO$_2$R$^{22}$, CO$_2$R$^{22}$ or SO$_2$NR$^{26}$R$^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, OR$^{34}$, alkyl, or fluoroalkyl; and n is 0, 1, 2, 3, or 4.

In a further embodiment is the method for treating an ophthalmic disease or disorder in a subject, comprising administering to the subject a compound of Formula (G), wherein the compound of Formula (G) is selected from the group consisting of:

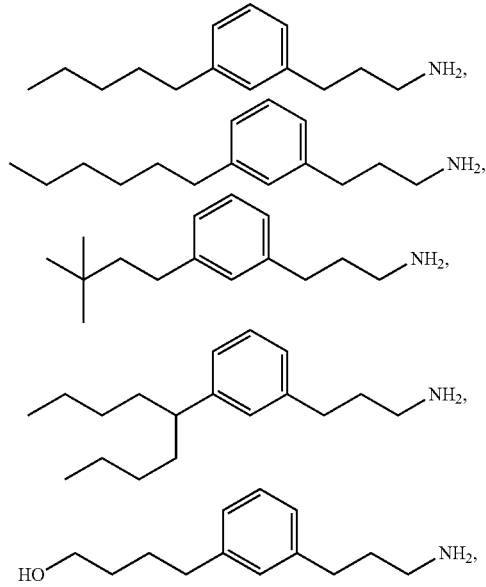

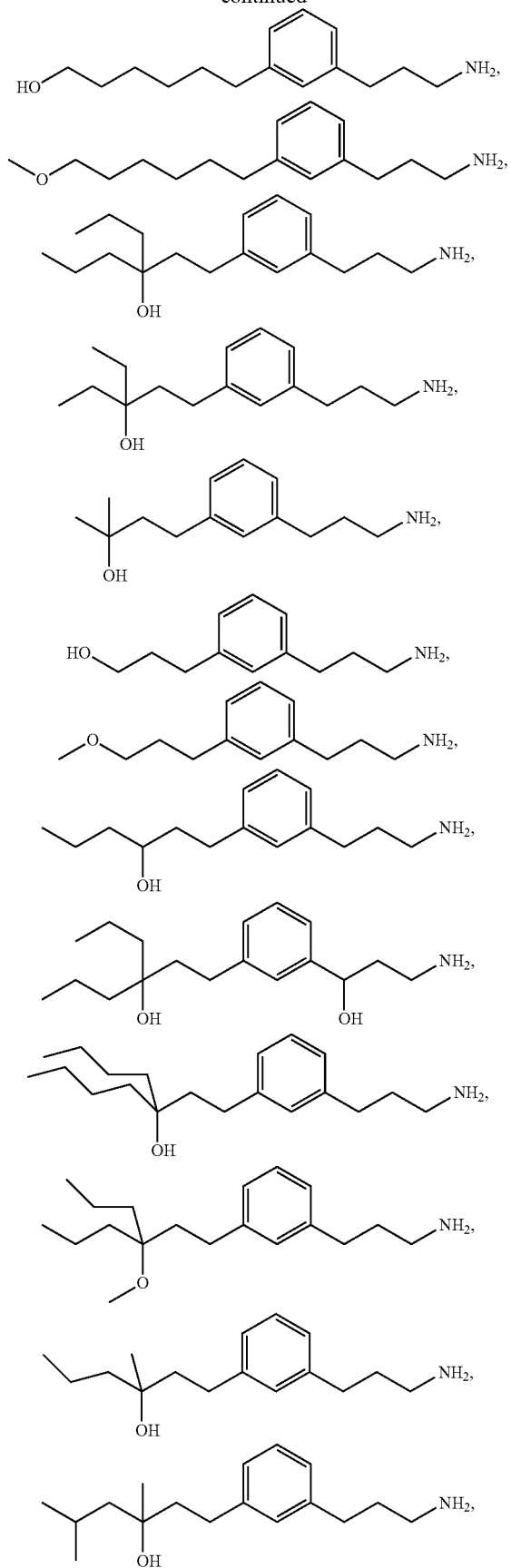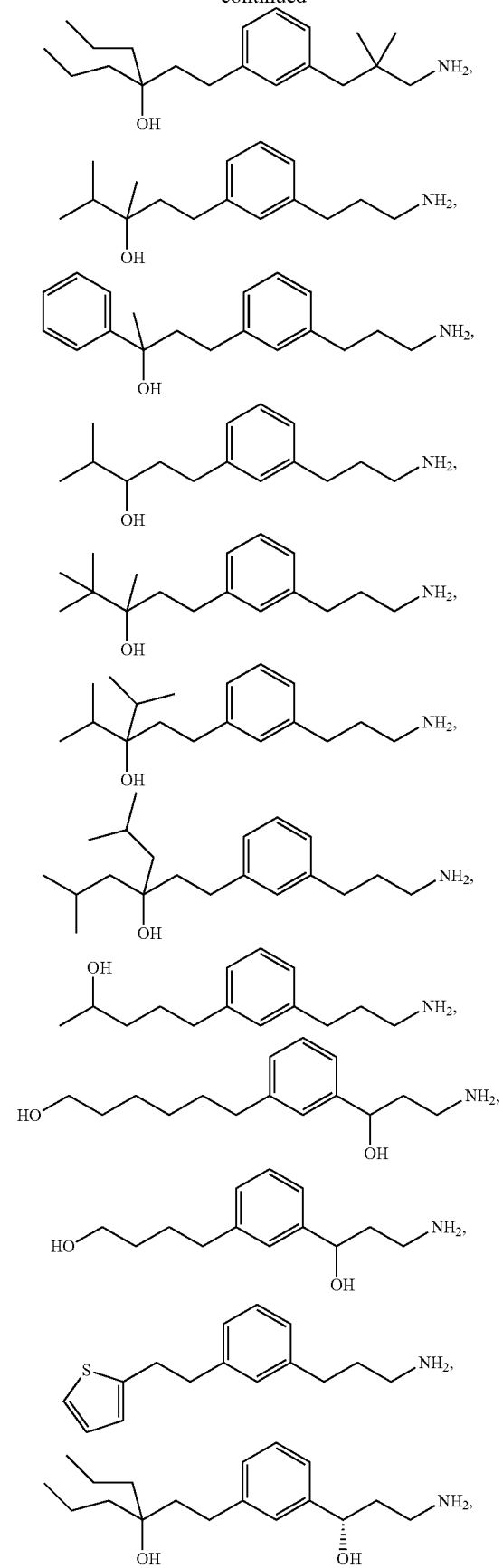

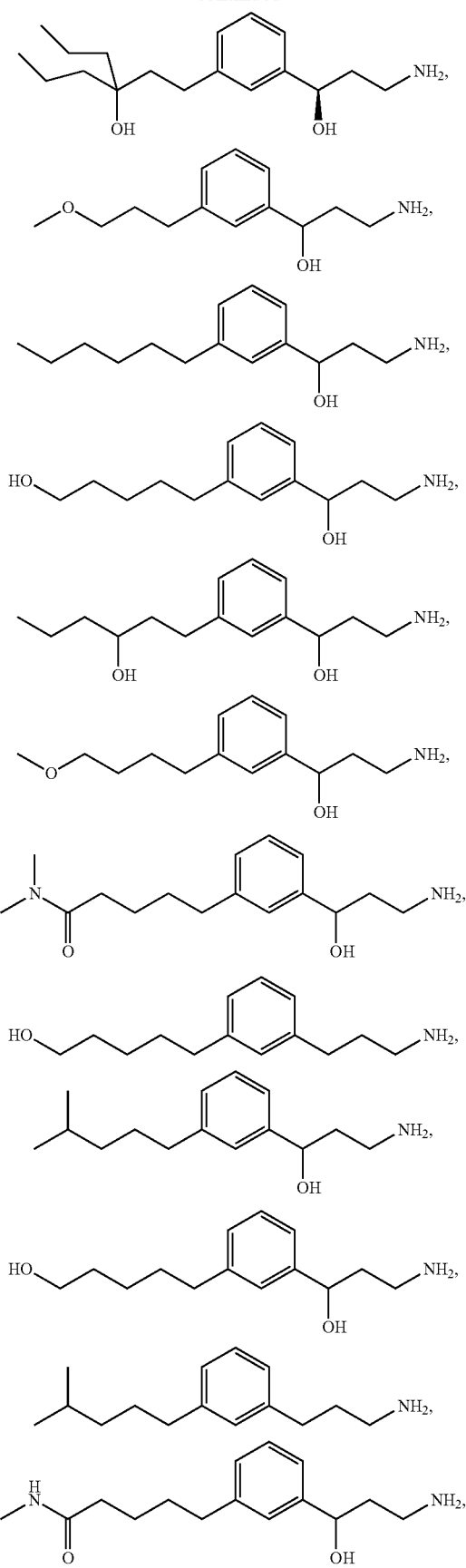
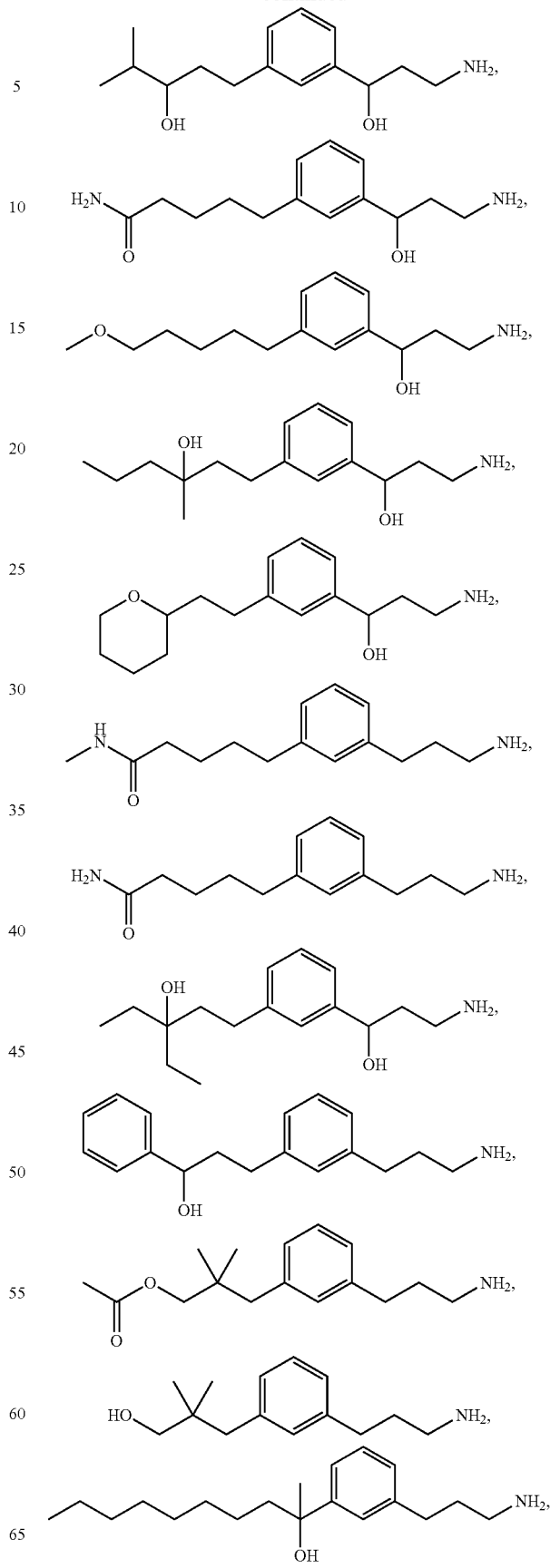

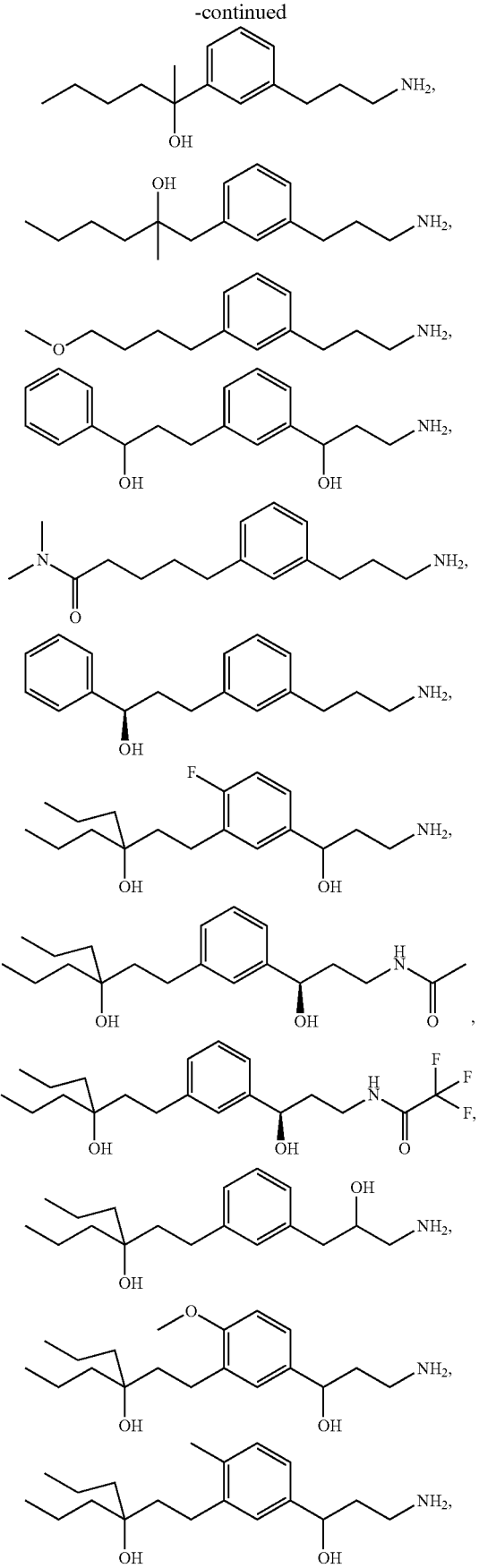
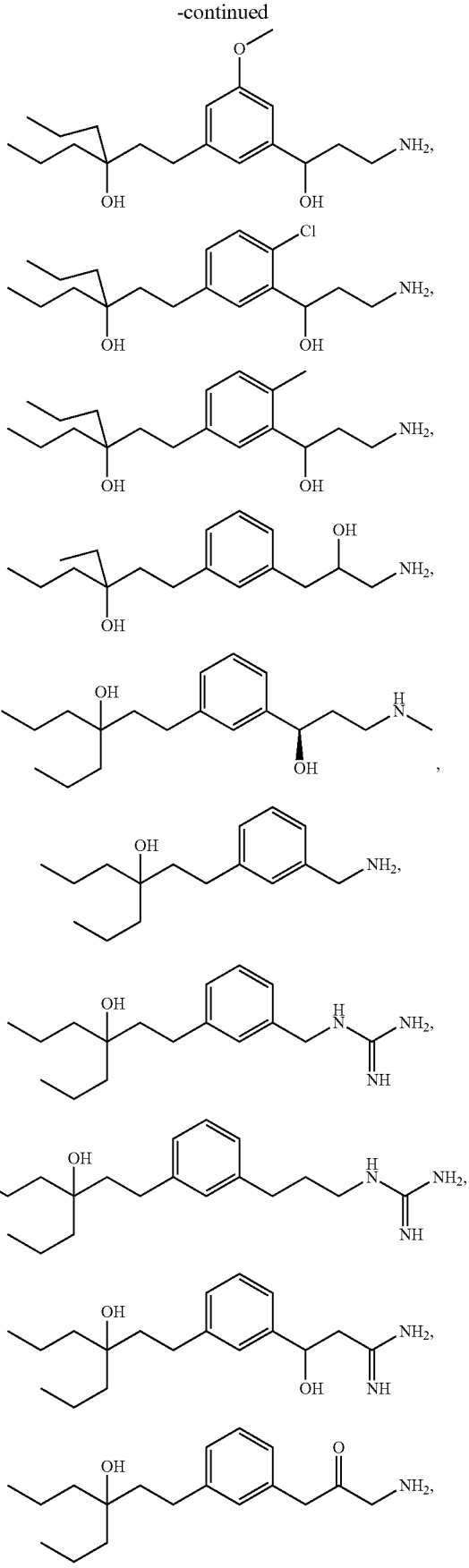

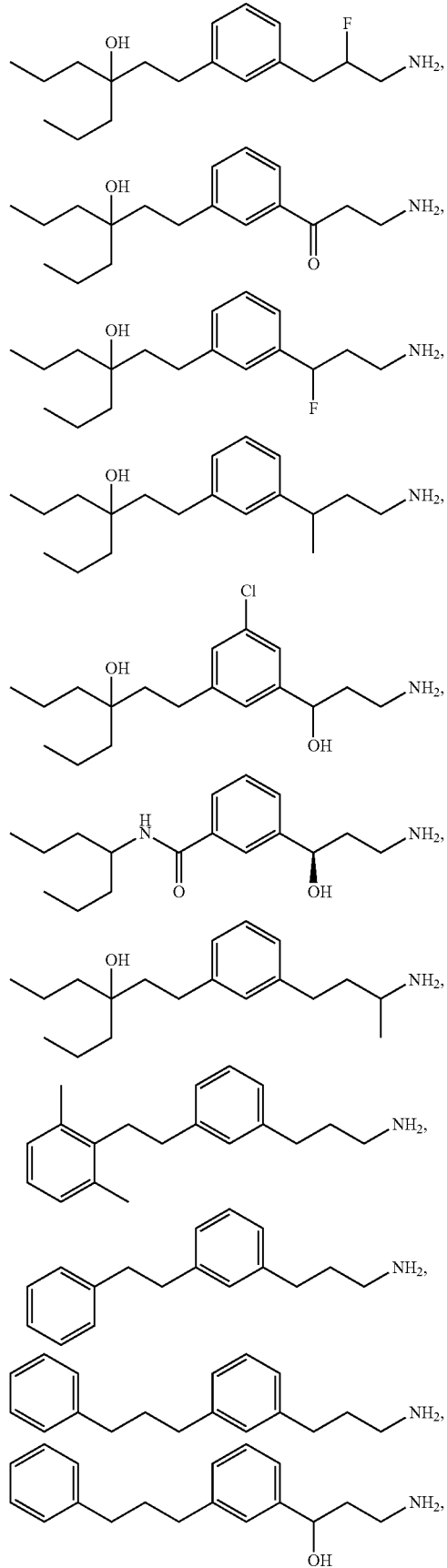

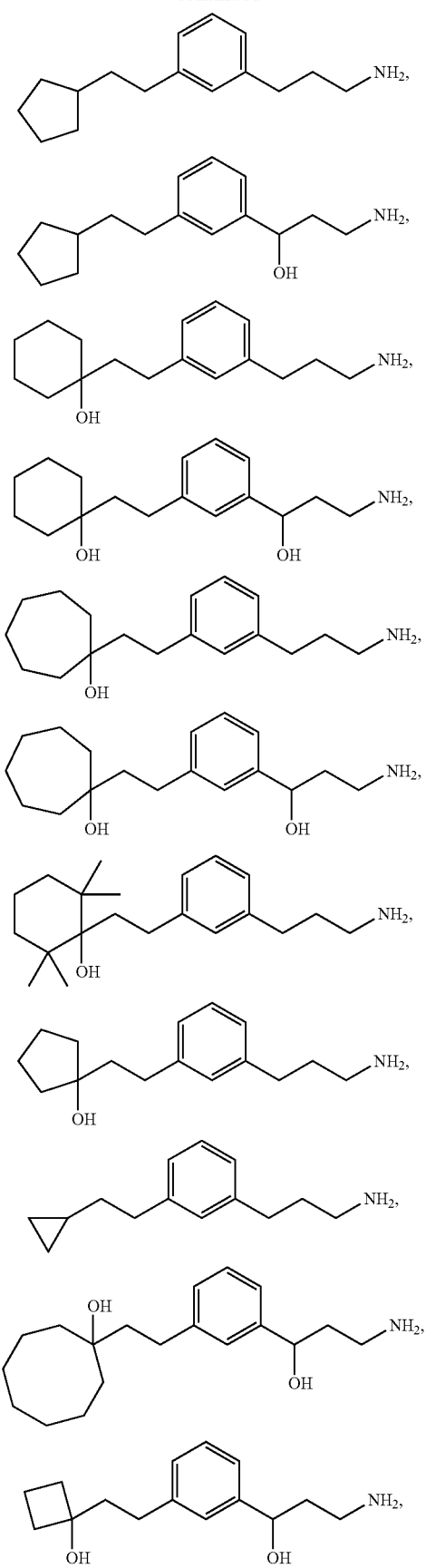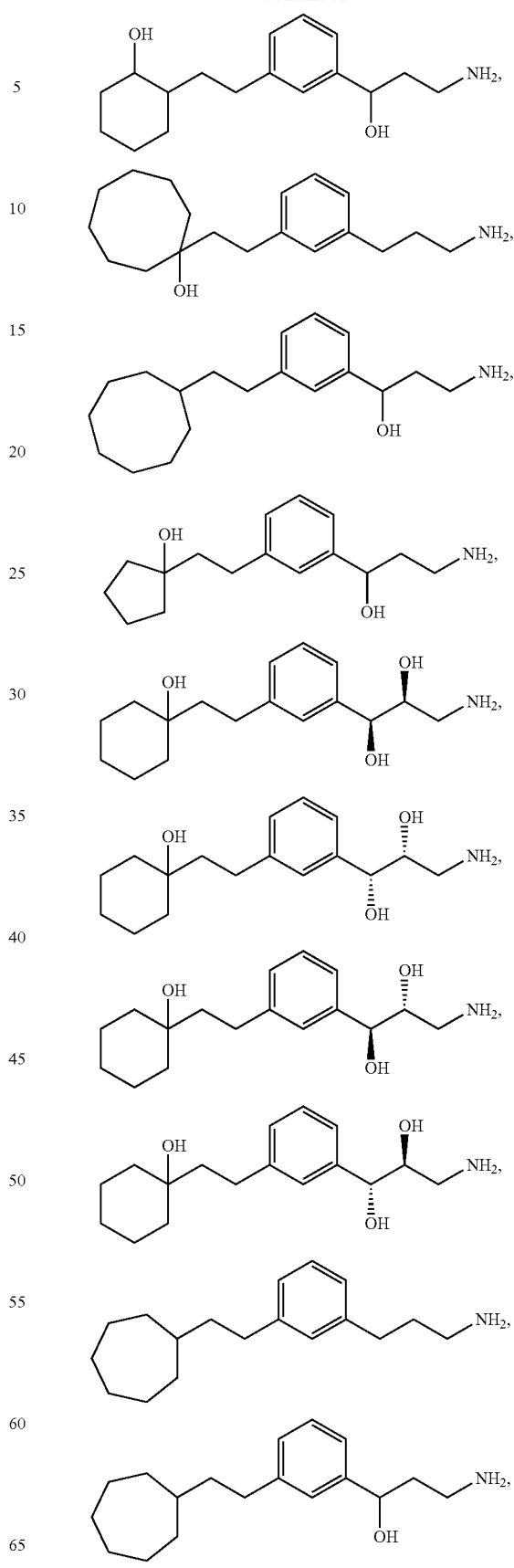

189
-continued
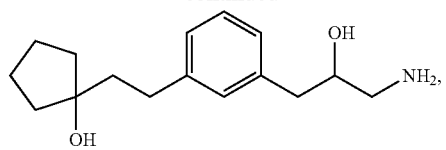
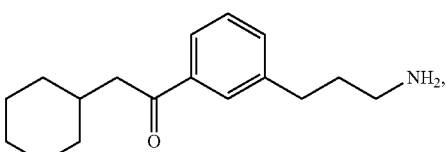
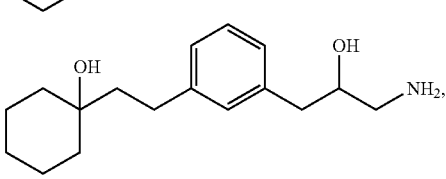
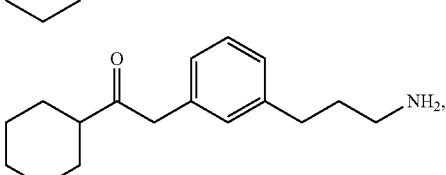
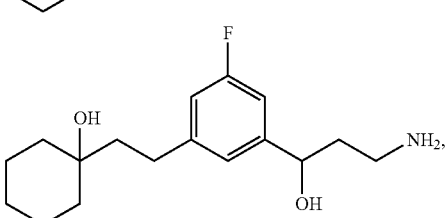
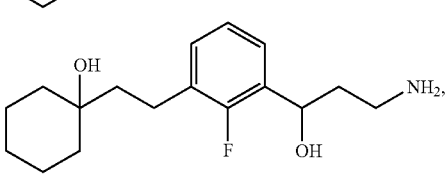
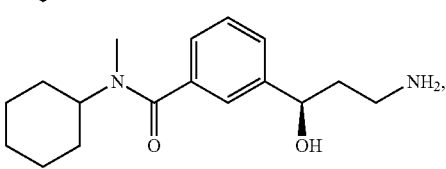
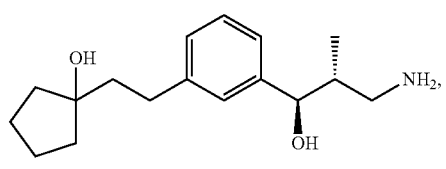
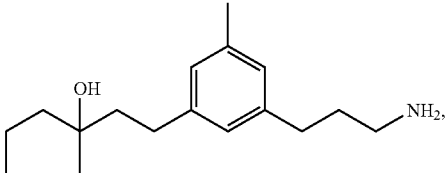
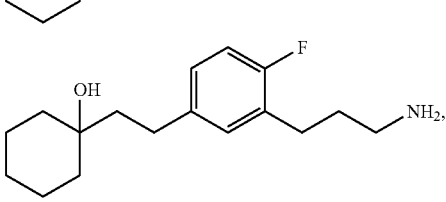
190
-continued
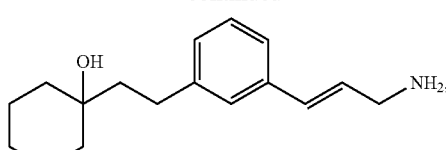
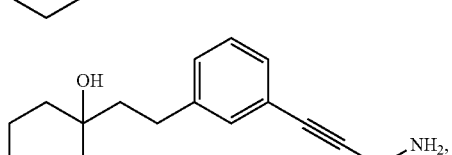
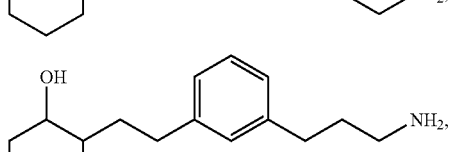
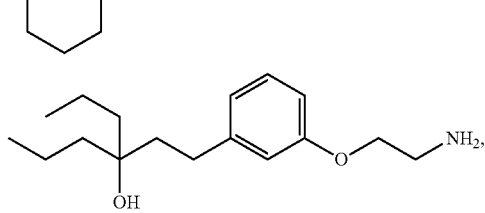
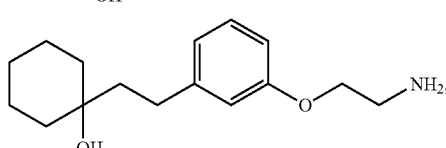
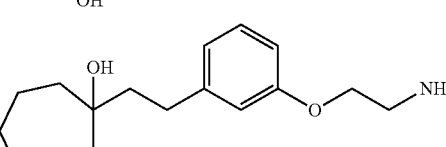
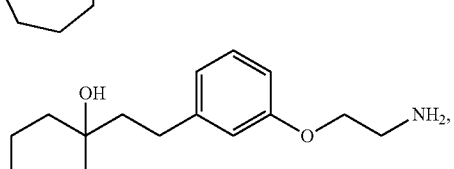
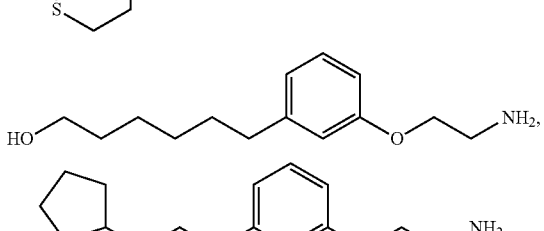
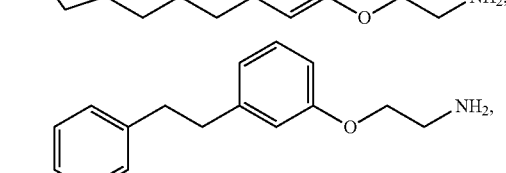
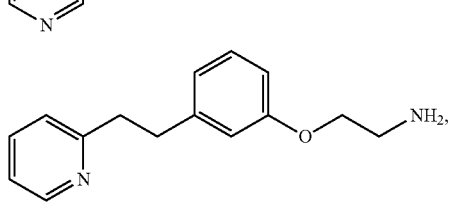

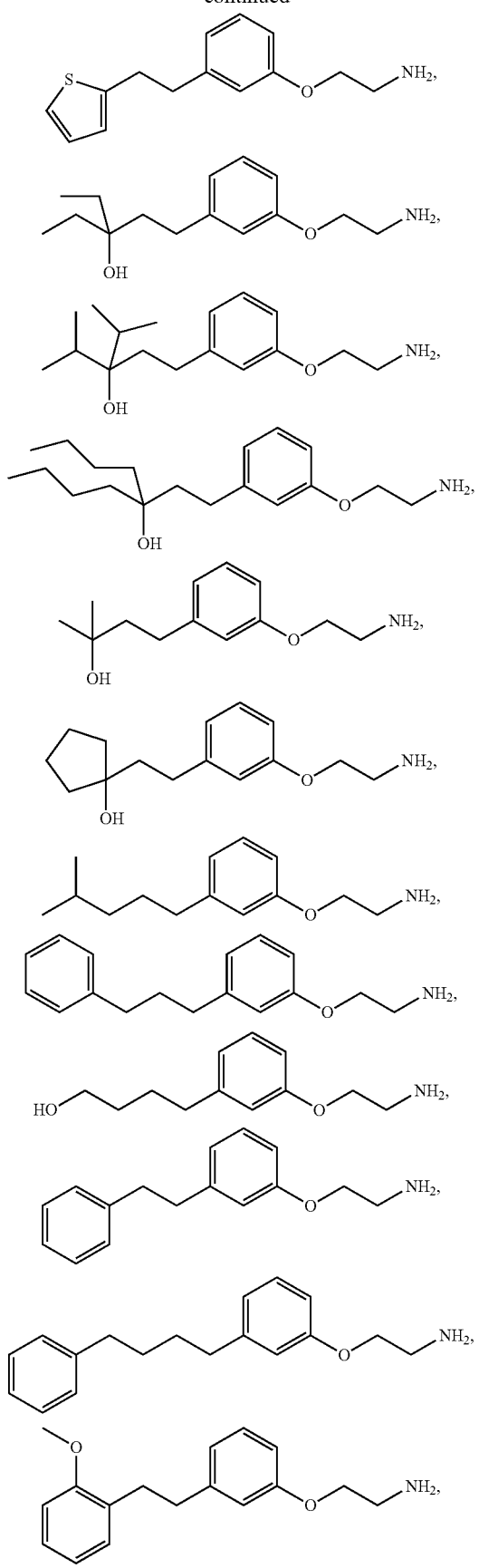
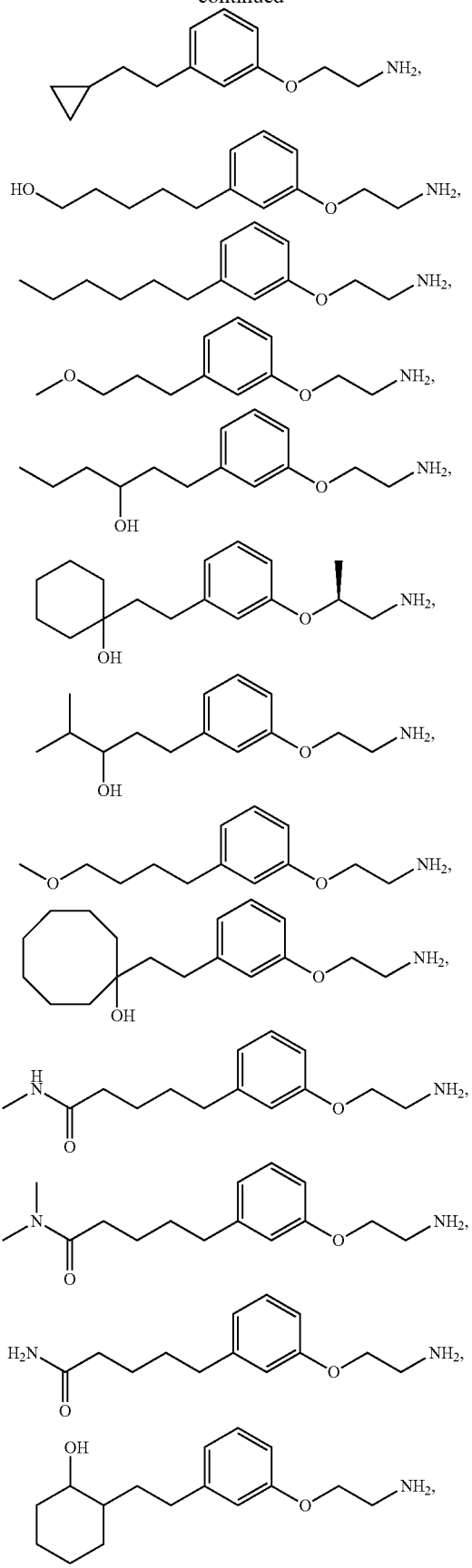

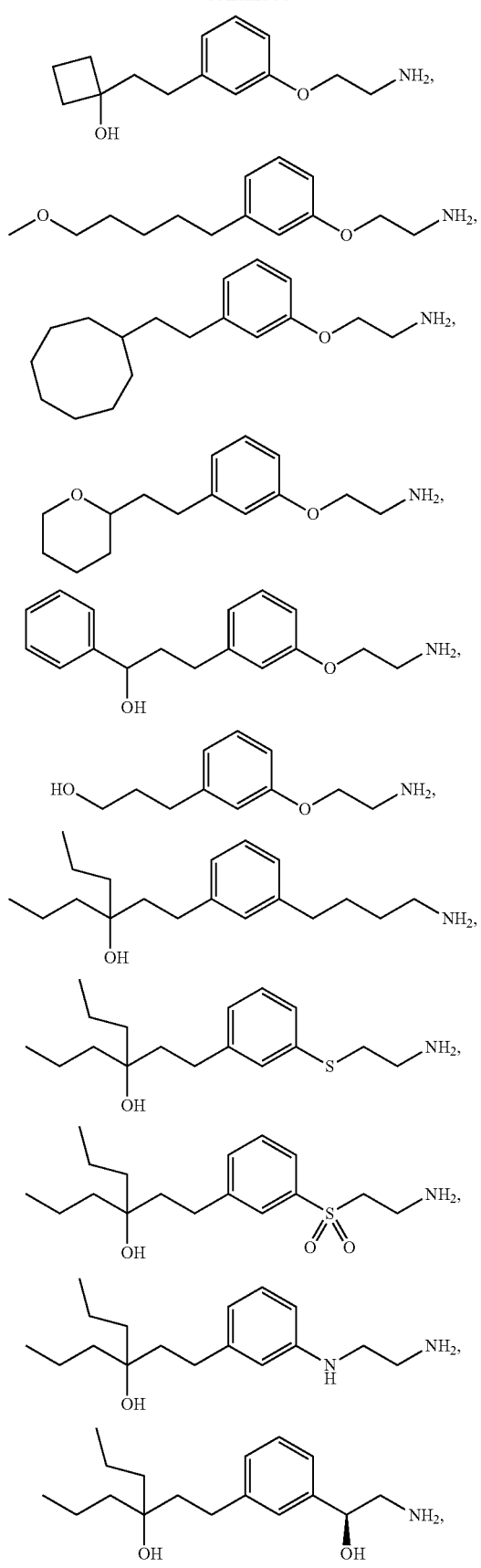
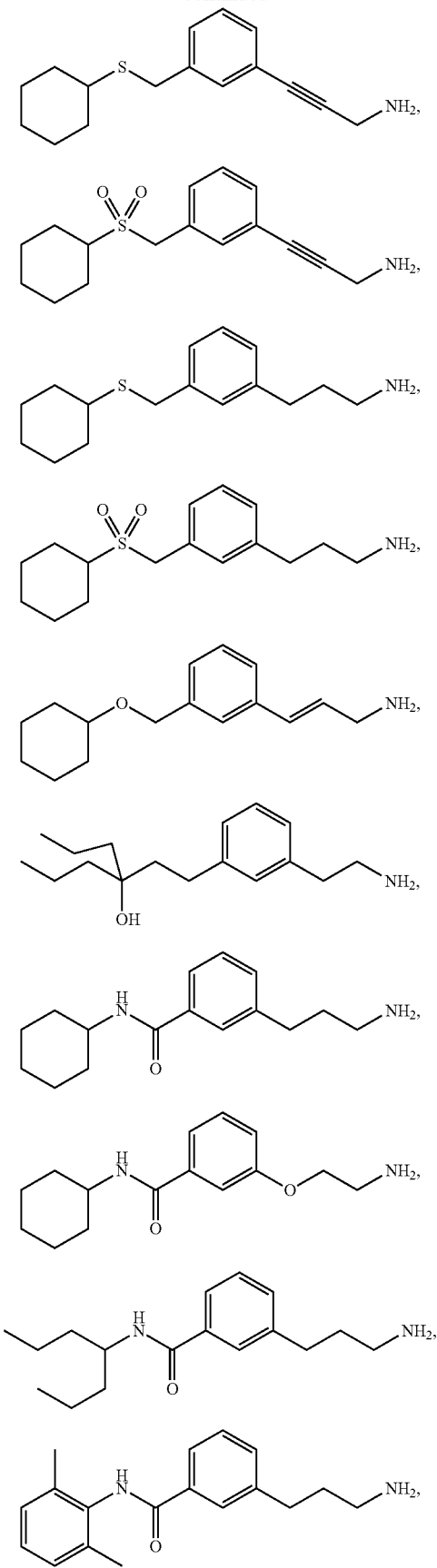

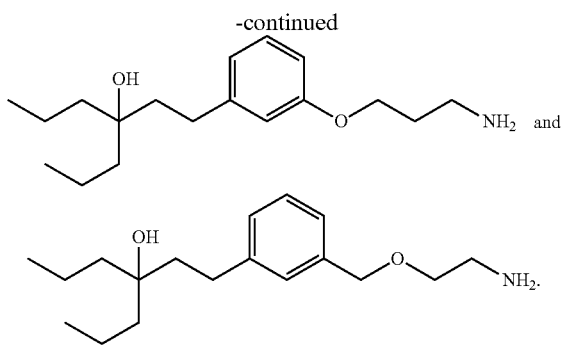

In some embodiments, the compounds disclosed herein function by inhibiting or blocking the activity of a visual cycle trans-cis isomerase. The compounds described herein, may inhibit, block, or in some manner interfere with the isomerization step in the visual cycle. In a particular embodiment, the compound inhibits isomerization of an all-trans-retinol ester; in certain embodiments, the all-trans-retinyl ester is a fatty acid ester of all-trans-retinol, and the compound inhibits isomerization of all-trans-retinol to 11-cis-retinol. The compound may bind to, or in some manner interact with, and inhibit the isomerase activity of at least one visual cycle isomerase, which may also be referred to herein and in the art as a retinal isomerase or an isomerohydrolase. The compound may block or inhibit binding of an all-trans-retinol ester substrate to an isomerase. Alternatively, or in addition, the compound may bind to the catalytic site or region of the isomerase, thereby inhibiting the capability of the enzyme to catalyze isomerization of an all-trans-retinol ester substrate. On the basis of scientific data to date, at least one isomerase that catalyzes the isomerization of all-trans-retinol esters is believed to be located in the cytoplasm of RPE cells. As discussed herein, each step, enzyme, substrate, intermediate, and product of the visual cycle is not yet elucidated (see, e.g., Moiseyev et al., *Proc. Natl. Acad. Sci. USA* 102: 12413-18 (2004); Chen et al., *Invest. Ophthalmol. Vis. Sci.* 47:1177-84 (2006); Lamb et al. supra).

A method for determining the effect of a compound on isomerase activity may be performed in vitro as described herein and in the art (Stecher et al., *J Biol Chem* 274:8577-85 (1999); see also Golczak et al., *Proc. Natl. Acad. Sci. USA* 102:8162-67 (2005)). Retinal pigment epithelium (RPE) microsome membranes isolated from an animal (such as bovine, porcine, human, for example) may serve as the source of the isomerase. The capability of the amine derivative compounds to inhibit isomerase may also be determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo (see, e.g., Maeda et al., *J. Neurochem* 85:944-956 (2003); Van Hooser et al., *J Biol Chem* 277: 19173-82, 2002). Electroretinographic (ERG) recording may be performed as previously described (Haeseleer et al., *Nat. Neurosci.* 7:1079-87 (2004); Sugitomo et al., *J. Toxicol. Sci.* 22 Suppl 2:315-25 (1997); Keating et al., *Documenta Ophthalmologica* 100:77-92 (2000)). See also Deigner et al., *Science*, 244: 968-971 (1989); Gollapalli et al., *Biochim Biophys Acta.* 1651: 93-101 (2003); Parish, et al., *Proc. Natl. Acad. Sci. USA* 95:14609-13 (1998); Radu, et al., *Proc Natl Acad Sci USA* 101: 5928-33 (2004)). In certain embodiments, compounds that are useful for treating a subject who has or who is at risk of developing any one of the ophthalmic and retinal diseases or disorders described herein have $IC_{50}$ levels (compound concentration at which 50% of isomerase activity is inhibited) as measured in the isomerase assays described herein or known in the art that is less than about 1 µM; in other embodiments, the determined $IC_{50}$ level is less than about 10 nM; in other embodiments, the determined $IC_{50}$ level is less than about 50 nM; in certain other embodiments, the determined $IC_{50}$ level is less than about 100 nM; in other certain embodiments, the determined $IC_{50}$ level is less than about 10 µM; in other embodiments, the determined $IC_{50}$ level is less than about 50 µM; in other certain embodiments, the determined $IC_{50}$ level is less than about 100 µM or about 500 µM; in other embodiments, the determined $IC_{50}$ level is between about 1 µM and 10 µM; in other embodiments, the determined $IC_{50}$ level is between about 1 nM and 10 nM. When administered into a subject, one or more compounds of the present invention exhibits an $ED_{50}$ value of about 5 mg/kg, 5 mg/kg or less as ascertained by inhibition of an isomerase reaction that results in production of 11-cis retinol. In some embodiments, the compounds of the present invention have $ED_{50}$ values of about 1 mg/kg when administered into a subject. In other embodiments, the compounds of the present invention have $ED_{50}$ values of about 0.1 mg/kg when administered into a subject. The $ED_{50}$ values can be measured after about 2 hours, 4 hours, 6 hours, 8 hours or longer upon administering a subject compound or a pharmaceutical composition thereof.

The compounds described herein may be useful for treating a subject who has an ophthalmic disease or disorder, particularly a retinal disease or disorder such as age-related macular degeneration or Stargardt's macular dystrophy. In one embodiment, the compounds described herein may inhibit (i.e., prevent, reduce, slow, abrogate, or minimize) accumulation of lipofuscin pigments and lipofuscin-related and/or associated molecules in the eye. In another embodiment, the compounds may inhibit (i.e., prevent, reduce, slow, abrogate, or minimize) N-retinylidene-N-retinylethanolamine (A2E) accumulation in the eye. The ophthalmic disease may result, at least in part, from lipofuscin pigments accumulation and/or from accumulation of A2E in the eye. Accordingly, in certain embodiments, methods are provided for inhibiting or preventing accumulation of lipofuscin pigments and/or A2E in the eye of a subject. These methods comprise administering to the subject a composition comprising a pharmaceutically acceptable or suitable excipient (i.e., pharmaceutically acceptable or suitable carrier) and an amine derivative compound as described in detail herein, including a compound having the structure as set forth in Formula (I) and substructures thereof, and the specific amine derivative compounds described herein.

Accumulation of lipofuscin pigments in retinal pigment epithelium (RPE) cells has been linked to progression of retinal diseases that result in blindness, including age-related macular degeneration (De Laey et al., *Retina* 15:399-406 (1995)). Lipofuscin granules are autofluorescent lysosomal residual bodies (also called age pigments). The major fluorescent species of lipofuscin is A2E (an orange-emitting fluorophore), which is a positively charged Schiff-base condensation-product formed by all-trans retinaldehyde with phosphatidylethanolamine (2:1 ratio) (see, e.g., Eldred et al., *Nature* 361:724-6 (1993); see also, Sparrow, *Proc. Natl. Acad. Sci. USA* 100:4353-54 (2003)). Much of the indigestible lipofuscin pigment is believed to originate in photoreceptor cells; deposition in the RPE occurs because the RPE internalize membranous debris that is discarded daily by the photoreceptor cells. Formation of this compound is not believed to occur by catalysis by any enzyme, but rather A2E forms by a spontaneous cyclization reaction. In addition, A2E has a pyridinium bisretinoid structure that once formed may not be enzymatically degraded. Lipofuscin, and thus A2E, accumulate with aging of the human eye and also accumulate in a juvenile form of macular degeneration called Stargardt's disease, and in several other congenital retinal dystrophies.

A2E may induce damage to the retina via several different mechanisms. At low concentrations, A2E inhibits normal proteolysis in lysosomes (Holz et al., *Invest. Ophthalmol. Vis. Sci.* 40:737-43 (1999)). At higher, sufficient concentrations, A2E may act as a positively charged lysosomotropic detergent, dissolving cellular membranes, and may alter lysosomal function, release proapoptotic proteins from mitochondria, and ultimately kill the RPE cell (see, e.g., Eldred et al., supra; Sparrow et al., *Invest. Ophthalmol. Vis. Sci.* 40:2988-95 (1999); Holz et al., supra; Finneman et al., *Proc. Natl. Acad. Sci. USA* 99:3842-347 (2002); Suter et al., *J. Biol. Chem.* 275:39625-30 (2000)). A2E is phototoxic and initiates blue light-induced apoptosis in RPE cells (see, e.g., Sparrow et al., *Invest. Ophthalmol. Vis. Sci.* 43:1222-27 (2002)). Upon exposure to blue light, photooxidative products of A2E are formed (e.g., epoxides) that damage cellular macromolecules, including DNA (Sparrow et al., *J. Biol. Chem.* 278(20):18207-13 (2003)). A2E self-generates singlet oxygen that reacts with A2E to generate epoxides at carbon-carbon double bonds (Sparrow et al., supra). Generation of oxygen reactive species upon photoexcitation of A2E causes oxidative damage to the cell, often resulting in cell death. An indirect method of blocking formation of A2E by inhibiting biosynthesis of the direct precursor of A2E, all-trans-retinal, has been described (see U.S. Patent Application Publication No. 2003/0032078). However, the usefulness of the method described therein is limited because generation of all-trans retinal is an important component of the visual cycle. Other therapies described include neutralizing damage caused by oxidative radical species by using superoxide-dismutase mimetics (see, e.g., U.S. Patent Application Publication No. 2004/0116403) and inhibiting A2E-induced cytochrome C oxidase in retinal cells with negatively charged phospholipids (see, e.g., U.S. Patent Application Publication No. 2003/0050283).

The amine derivative compounds described herein may be useful for preventing, reducing, inhibiting, or decreasing accumulation (i.e., deposition) of A2E and A2E-related and/or derived molecules in the RPE. Without wishing to be bound by theory, because the RPE is critical for the maintenance of the integrity of photoreceptor cells, preventing, reducing, or inhibiting damage to the RPE may inhibit degeneration (i.e., enhance the survival or increase or prolong cell viability) of retinal neuronal cells, particularly, photoreceptor cells. Compounds that bind specifically to or interact with A2E A2E-related and/or derived molecules or that affect A2E formation or accumulation may also reduce, inhibit, prevent, or decrease one or more toxic effects of A2E or of A2E-related and/or derived molecules that result in retinal neuronal cell (including a photoreceptor cell) damage, loss, or neurodegeneration, or in some manner decrease retinal neuronal cell viability. Such toxic effects include induction of apoptosis, self-generation of singlet oxygen and generation of oxygen reactive species; self-generation of singlet oxygen to form A2E-epoxides that induce DNA lesions, thus damaging cellular DNA and inducing cellular damage; dissolving cellular membranes; altering lysosomal function; and effecting release of proapoptotic proteins from mitochondria.

In other embodiments, the compounds described herein may be used for treating other ophthalmic diseases or disorders, for example, glaucoma, cone-rod dystrophy, retinal detachment, hemorrhagic or hypertensive retinopathy, retinitis pigmentosa, optic neuropathy, inflammatory retinal disease, proliferative vitreoretinopathy, genetic retinal dystrophies, traumatic injury to the optic nerve (such as by physical injury, excessive light exposure, or laser light), hereditary optic neuropathy, neuropathy due to a toxic agent or caused by adverse drug reactions or vitamin deficiency, Sorsby's fundus dystrophy, uveitis, a retinal disorder associated with Alzheimer's disease, a retinal disorder associated with multiple sclerosis; a retinal disorder associated with viral infection (cytomegalovirus or herpes simplex virus), a retinal disorder associated with Parkinson's disease, a retinal disorder associated with AIDS, or other forms of progressive retinal atrophy or degeneration. In another specific embodiment, the disease or disorder results from mechanical injury, chemical or drug-induced injury, thermal injury, radiation injury, light injury, laser injury. The subject compounds are useful for treating both hereditary and non-hereditary retinal dystrophy. These methods are also useful for preventing ophthalmic injury from environmental factors such as light-induced oxidative retinal damage, laser-induced retinal damage, "flash bomb injury," or "light dazzle", refractive errors including but not limited to myopia (see, e.g., Quinn G E et al. Nature 1999; 399:113-114; Zadnik K et al. Nature 2000; 404:143-144; Gwiazda J et al. Nature 2000; 404: 144), etc.

In other embodiments, methods are provided herein for inhibiting neovascularization (including but not limited to neovascular glycoma) in the retina using any one or more of the amine derivative compound as described in detail herein, including a compound having the structure as set forth in Formula (I) and substructures thereof, and the specific amine derivative compounds described herein. In certain other embodiments, methods are provided for reducing hypoxia in the retina using the compounds described herein. These methods comprise administering to a subject, in need thereof, a composition comprising a pharmaceutically acceptable or suitable excipient (i.e., pharmaceutically acceptable or suitable carrier) and an amine derivative compound as described in detail herein, including a compound having the structure as set forth in Formula (I) and substructures thereof, and the specific amine derivative compounds described herein.

Merely by way of explanation and without being bound by any theory, and as discussed in further detail herein, dark-adapted rod photoreceptors engender a very high metabolic demand (i.e., expenditure of energy (ATP consumption) and consumption of oxygen). The resultant hypoxia may cause and/or exacerbate retinal degeneration, which is likely exaggerated under conditions in which the retinal vasculature is already compromised, including, but not limited to, such conditions as diabetic retinopathy, macular edema, diabetic maculopathy, retinal blood vessel occlusion (which includes retinal venous occlusion and retinal arterial occlusion), retinopathy of prematurity, ischemia reperfusion related retinal injury, as well as in the wet form of age-related macular degeneration (AMD). Furthermore, retinal degeneration and hypoxia may lead to neovascularization, which in turn may worsen the extent of retinal degeneration. The amine derivative compounds described herein that modulate the visual cycle can be administered to prevent, inhibit, and/or delay dark adaptation of rod photoreceptor cells, and may therefore reduce metabolic demand, thereby reducing hypoxia and inhibiting neovascularization.

By way of background, oxygen is a critical molecule for preservation of retinal function in mammals, and retinal hypoxia may be a factor in many retinal diseases and disorders that have ischemia as a component. In most mammals (including humans) with dual vascular supply to the retina, oxygenation of the inner retina is achieved through the intraretinal microvasculature, which is sparse compared to the choriocapillaris that supplies oxygen to the RPE and photoreceptors. The different vascular supply networks create an uneven oxygen tension across the thickness of the retina (Cringle et al., *Invest. Ophthalmol. Vis. Sci.* 43:1922-27 (2002)). Oxygen fluctuation across the retinal layers is related to both the differing capillary densities and disparity in oxygen consumption by various retinal neurons and glia.

Local oxygen tension can significantly affect the retina and its microvasculature by regulation of an array of vasoactive agents, including, for example, vascular endothelial growth factor (VEGF). (See, e.g., Werdich et al., *Exp. Eye Res.* 79:623 (2004); Arden et al., *Br. J. Ophthalmol.* 89:764 (2005)). Rod photoreceptors are believed to have the highest metabolic rate of any cell in the body (see, e.g., Arden et al., supra). During dark adaptation, the rod photoreceptors recover their high cytoplasmic calcium levels via cGMP-gated calcium channels with concomitant extrusion of sodium ions and water. The efflux of sodium from the cell is an ATP-dependent process, such that the retinal neurons consume up to an estimated five times more oxygen under scotopic (i.e., dark adapted), compared with photopic (i.e., light adapted) conditions. Thus, during characteristic dark adaptation of photoreceptors, the high metabolic demand leads to significant local reduction of oxygen levels in the dark-adapted retina (Ahmed et al, *Invest. Ophthalmol. Vis. Sci.* 34:516 (1993)).

Without being bound by any one theory, retinal hypoxia may be further increased in the retina of subjects who have diseases or conditions such as, for example, central retinal vein occlusion in which the retinal vasculature is already compromised. Increasing hypoxia may increase susceptibility to sight-threatening, retinal neovascularization. Neovascularization is the formation of new, functional microvascular networks with red blood cell perfusion, and is a characteristic of retinal degenerative disorders, including, but not limited to, diabetic retinopathy, retinopathy of prematurity, wet AMD and central retinal vein occlusions. Preventing or inhibiting dark adaptation of rod photoreceptor cells, thereby decreasing expenditure of energy and consumption of oxygen (i.e., reducing metabolic demand), may inhibit or slow retinal degeneration, and/or may promote regeneration of retinal cells, including rod photoreceptor cells and retinal pigment epithelial (RPE) cells, and may reduce hypoxia and may inhibit neovascularization.

Methods are described herein for inhibiting (i.e., reducing, preventing, slowing or retarding, in a biologically or statistically significant manner) degeneration of retinal cells (including retinal neuronal cells as described herein and RPE cells) and/or for reducing (i.e., preventing or slowing, inhibiting, abrogating in a biologically or statistically significant manner) retinal ischemia. Methods are also provided for inhibiting (i.e., reducing, preventing, slowing or retarding, in a biologically or statistically significant manner) neovascularization in the eye, particularly in the retina. Such methods comprise contacting the retina, and thus, contacting retinal cells (including retinal neuronal cells such as rod photoreceptor cells, and RPE cells) with at least one of the amine derivative compounds described herein that inhibits at least one visual cycle trans-cis isomerase (which may include inhibition of isomerization of an all-trans-retinal ester), under conditions and at a time that may prevent, inhibit, or delay dark adaptation of a rod photoreceptor cell in the retina. As described in further detail herein, in particular embodiments, the compound that contacts the retina interacts with an isomerase enzyme or enzymatic complex in a RPE cell in the retina and inhibits, blocks, or in some manner interferes with the catalytic activity of the isomerase. Thus, isomerization of an all-trans-retinal ester is inhibited or reduced. The amine derivative compounds described herein or compositions comprising said compounds may be administered to a subject who has developed and manifested an ophthalmic disease or disorder or who is at risk of developing an ophthalmic disease or disorder, or to a subject who presents or who is at risk of presenting a condition such as retinal neovascularization or retinal ischemia.

By way of background, the visual cycle (also called retinoid cycle) refers to the series of enzyme and light-mediated conversions between the 11-cis and all-trans forms of retinal-retinal that occur in the photoreceptor and retinal pigment epithelial (RPE) cells of the eye. In vertebrate photoreceptor cells, a photon causes isomerization of the 11-cis-retinylidene chromophore to all-trans-retinylidene coupled to the visual opsin receptors. This photoisomerization triggers conformational changes of opsins, which, in turn, initiate the biochemical chain of reactions termed phototransduction (Filipek et al., *Annu. Rev. Physiol.* 65 851-79 (2003)). After absorption of light and photoisomerization of 11-cis-retinal to all-trans retinal, regeneration of the visual chromophore is a critical step in restoring photoreceptors to their dark-adapted state. Regeneration of the visual pigment requires that the chromophore be converted back to the 11-cis-configuration (reviewed in McBee et al., *Prog. Retin. Eye Res.* 20:469-52 (2001)). The chromophore is released from the opsin and reduced in the photoreceptor by retinol dehydrogenases. The product, all-trans-retinol, is trapped in the adjacent retinal pigment epithelium (RPE) in the form of insoluble fatty acid esters in subcellular structures known as retinosomes (Imanishi et al., *J. Cell Biol.* 164:373-78 (2004)).

During the visual cycle in rod receptor cells, the 11-cis retinal chromophore within the visual pigment molecule, which is called rhodopsin, absorbs a photon of light and is isomerized to the all-trans configuration, thereby activating the phototransduction cascade. Rhodopsin is a G-protein coupled receptor (GPCR) that consists of seven membrane-spanning helices that are interconnected by extracellular and cytoplasmic loops. When the all-trans form of the retinoid is still covalently bound to the pigment molecule, the pigment is referred to as metarhodopsin, which exists in different forms (e.g., metarhodopsin I and metarhodopsin II). The all-trans retinoid is then hydrolyzed and the visual pigment is in the form of the apoprotein, opsin, which is also called apo-rhodopsin in the art and herein. This all-trans retinoid is transported or chaperoned out of the photoreceptor cell and across the extracellular space to the RPE cells, where the retinoid is converted to the 11-cis isomer. The movement of the retinoids between the RPE and photoreceptors cells is believed to be accomplished by different chaperone polypeptides in each of the cell types. See Lamb et al., *Progress in Retinal and Eye Research* 23:307-80 (2004).

Under light conditions, rhodopsin continually transitions through the three forms, rhodopsin, metarhodopsin, and apo-rhodopsin. When most of the visual pigment is in the rhodopsin form (i.e., bound with 11-cis retinal), the rod photoreceptor cell is in a "dark-adapted" state. When the visual pigment is predominantly in the metarhodopsin form (i.e., bound with all-trans-retinal), the state of the photoreceptor cell is referred to as a "light-adapted," and when the visual pigment is apo-rhodopsin (or opsin) and no longer has bound chromophore, the state of the photoreceptor cell is referred to as "rhodopsin-depleted." Each of the three states of the photoreceptor cell has different energy requirements, and differing levels of ATP and oxygen are consumed. In the dark-adapted state, rhodopsin has no regulatory effect on cation channels, which are open, resulting in an influx of cations ($Na^+/K^+$ and $Ca^{2+}$). To maintain the proper level of these cations in the cell during the dark state, the photoreceptor cells actively transport the cations out of the cell via ATP-dependent pumps. Thus maintenance of this "dark current" requires a large amount of energy, resulting in high metabolic demand. In the light-adapted state, metarhodopsin triggers an enzymatic cascade process that results in hydrolysis of GMP, which in turn, closes cation-specific channels in the photoreceptor cell membrane. In the rhodopsin-depleted state, the chromophore is hydrolyzed from metarhodopsin to form the apoprotein, opsin (apo-rhodopsin), which partially regulates the cation channels such that the rod photoreceptor cells exhibit an attenuated current compared with the photoreceptor in the dark-adapted state, resulting in a moderate metabolic demand.

Under normal light conditions, the incidence of rod photoreceptors in the dark adapted state is small, in general, 2% or less, and the cells are primarily in the light-adapted or rhodopsin-depleted states, which overall results in a relatively low metabolic demand compared with cells in the dark-adapted state. At night, however, the relative incidence of the dark-adapted photoreceptor state increases profoundly, due to the absence of light adaptation and to the continued operation of the "dark" visual cycle in RPE cells, which replenishes the rod photoreceptor cells with 11-cis-retinal. This shift to dark adaptation of the rod photoreceptor causes an increase in metabolic demand (that is, increased ATP and oxygen consumption), leading ultimately to retinal hypoxia and subsequent initiation of angiogenesis. Most ischaemic insults to the retina therefore occur in the dark, for example, at night during sleep.

Without being bound by any theory, therapeutic intervention during the "dark" visual cycle may prevent retinal hypoxia and neovascularization that are caused by high metabolic activity in the dark-adapted rod photoreceptor cell. Merely by way of one example, altering the "dark" visual cycle by administering any one of the compounds described herein, which is an isomerase inhibitor, rhodopsin (i.e., 11-cis retinal bound) may be reduced or depleted, preventing or inhibiting dark adaptation of rod photoreceptors. This in turn may reduce retinal metabolic demand, attenuating the night-time risk of retinal ischemia and neovascularization, and thereby inhibiting or slowing retinal degeneration.

In one embodiment, at least one of the compounds described herein (i.e., a compound having the structure as set forth in Formula (I) and substructures thereof described herein) that, for example, blocks, reduces, inhibits, or in some manner attenuates the catalytic activity of a visual cycle isomerase in a statistically or biologically significant manner, may prevent, inhibit, or delay dark adaptation of a rod photoreceptor cell, thereby inhibiting (i.e., reducing, abrogating, preventing, slowing the progression of, or decreasing in a statistically or biologically significant manner) degeneration of retinal cells (or enhancing survival of retinal cells) of the retina of an eye. In another embodiment, the amine derivative compounds may prevent or inhibit dark adaptation of a rod photoreceptor cell, thereby reducing ischemia (i.e., decreasing, preventing, inhibiting, slowing the progression of ischemia in a statistically or biologically significant manner). In yet another embodiment, any one of the amine derivative compounds described herein may prevent dark adaptation of a rod photoreceptor cell, thereby inhibiting neovascularization in the retina of an eye. Accordingly, methods are provided herein for inhibiting retinal cell degeneration, for inhibiting neovascularization in the retina of an eye of a subject, and for reducing ischemia in an eye of a subject wherein the methods comprise administering at least one amine derivative compound described herein, under conditions and at a time sufficient to prevent, inhibit, or delay dark adaptation of a rod photoreceptor cell. These methods and compositions are therefore useful for treating an ophthalmic disease or disorder including, but not limited to, diabetic retinopathy, diabetic maculopathy, retinal blood vessel occlusion, retinopathy of prematurity, or ischemia reperfusion related retinal injury.

The amine derivative compounds described herein (i.e., an amine derivative compound as described in detail herein, including a compound having the structure as set forth in Formula (I), and substructures thereof, and the specific amine derivative compounds described herein) may prevent (i.e., delay, slow, inhibit, or decrease) recovery of the visual pigment chromophore, which may prevent or inhibit or retard the formation of retinals and may increase the level of retinal esters, which perturbs the visual cycle, inhibiting regeneration of rhodopsin, and which prevents, slows, delays or inhibits dark adaptation of a rod photoreceptor cell. In certain embodiments, when dark adaptation of rod photoreceptor cells is prevented in the presence of the compound, dark adaptation is substantially prevented, and the number or percent of rod photoreceptor cells that are rhodopsin-depleted or light adapted is increased compared with the number or percent of cells that are rhodopsin-depleted or light-adapted in the absence of the agent. Thus, in certain embodiments when dark adaptation of rod photoreceptor cells is prevented (i.e., substantially prevented), only at least 2% of rod photoreceptor cells are dark-adapted, similar to the percent or number of cells that are in a dark-adapted state during normal, light conditions. In other embodiments, at least 5-10%, 10-20%, 20-30%, 30-40%, 40-50%, 50-60%, or 60-70% of rod photoreceptor cells are dark-adapted after administration of an agent. In other embodiments, the compound acts to delay dark adaptation, and in the presence of the compound dark adaptation of rod photoreceptor cells may be delayed 30 minutes, one hour, two hours, three hours, or four hours compared to dark adaptation of rod photoreceptors in the absence of the compound. By contrast, when an amine derivative compound is administered such that the compound effectively inhibits isomerization of substrate during light-adapted conditions, the compound is administered in such a manner to minimize the percent of rod photoreceptor cells that are dark-adapted, for example, only 2%, 5%, 10%, 20%, or 25% of rod photoreceptors are dark-adapted (see e.g., U.S. Patent Application Publication No. 2006/0069078; Patent Application No. PCT/US2007/002330).

In the retina in the presence of at least one amine derivative compound, regeneration of rhodopsin in a rod photoreceptor cell may be inhibited or the rate of regeneration may be reduced (i e., inhibited, reduced, or decreased in a statistically or biologically significant manner), at least in part, by preventing the formation of retinals, reducing the level of retinals, and/or increasing the level of retinyl esters. To determine the level of regeneration of rhodopsin in a rod photoreceptor cell, the level of regeneration of rhodopsin (which may be called a first level) may be determined prior to permitting contact between the compound and the retina (i.e., prior to administration of the agent). After a time sufficient for the compound and the retina and cells of the retina to interact, (i.e., after administration of the compound), the level of regeneration of rhodopsin (which may be called a second level) may be determined. A decrease in the second level compared with the first level indicates that the compound inhibits regeneration of rhodopsin. The level of rhodopsin generation may be determined after each dose, or after any number of doses, and ongoing throughout the therapeutic regimen to characterize the effect of the agent on regeneration of rhodopsin.

In certain embodiments, the subject in need of the treatments described herein, may have a disease or disorder that results in or causes impairment of the capability of rod photoreceptors to regenerate rhodopsin in the retina. By way of example, inhibition of rhodopsin regeneration (or reduction of the rate of rhodopsin regeneration) may be symptomatic in patients with diabetes. In addition to determining the level of regeneration of rhodopsin in the subject who has diabetes before and after administration of an amine derivative compound described herein, the effect of the compound may also be characterized by comparing inhibition of rhodopsin regeneration in a first subject (or a first group or plurality of subjects) to whom the compound is administered, to a second subject (or second group or plurality of subjects) who has diabetes but who does not receive the agent.

In another embodiment, a method is provided for preventing or inhibiting dark adaptation of a rod photoreceptor cell (or a plurality of rod photoreceptor cells) in a retina comprising contacting the retina and at least one of the amine derivative compounds described herein (i.e., a compound as described in detail herein, including a compound having the structure as set forth in Formula (I), and substructures thereof, and the specific amine derivative compounds described herein), under conditions and at a time sufficient to permit interaction between the agent and an isomerase present in a retinal cell (such as an RPE cell). A first level of 11-cis-retinal in a rod photoreceptor cell in the presence of the compound may be determined and compared to a second level of 11-cis-retinal in a rod photoreceptor cell in the absence of the compound. Prevention or inhibition of dark adaptation of the rod photoreceptor cell is indicated when the first level of 11-cis-retinal is less than the second level of 11-cis-retinal.

Inhibiting regeneration of rhodopsin may also include increasing the level of 11-cis-retinyl esters present in the RPE cell in the presence of the compound compared with the level of 11-cis-retinyl esters present in the RPE cell in the absence of the compound (i.e., prior to administration of the agent). A two-photon imaging technique may be used to view and analyze retinosome structures in the RPE, which structures are believed to store retinyl esters (see, e.g., Imanishi et al., *J. Cell Biol.* 164:373-83 (2004), Epub 2004 Jan. 26.). A first level of retinyl esters may be determined prior to administration of the compound, and a second level of retinyl esters may be determined after administration of a first dose or any subsequent dose, wherein an increase in the second level compared to the first level indicates that the compound inhibits regeneration of rhodopsin.

Retinyl esters may be analyzed by gradient HPLC according to methods practiced in the art (see, for example, Mata et al., *Neuron* 36:69-80 (2002); Trevino et al. *J. Exp. Biol.* 208: 4151-57 (2005)). To measure 11-cis and all-trans retinals, retinoids may be extracted by a formaldehyde method (see, e.g., Suzuki et al., *Vis. Res.* 28:1061-70 (1988); Okajima and Pepperberg, *Exp. Eye Res.* 65:331-40 (1997)) or by a hydroxylamine method (see, e.g., Groenendijk et al., *Biochim. Biophys. Acta.* 617:430-38 (1980)) before being analyzed on isocratic HPLC (see, e.g., Trevino et al., supra). The retinoids may be monitored spectrophotometrically (see, e.g., Maeda et al., *J. Neurochem.* 85:944-956 (2003); Van Hooser et al., *J. Biol. Chem.* 277:19173-82 (2002)).

In another embodiment of the methods described herein for treating an ophthalmic disease or disorder, for inhibiting retinal cell degeneration (or enhancing retinal cell survival), for inhibiting neovascularization, and for reducing ischemia in the retina, preventing or inhibiting dark adaptation of a rod photoreceptor cell in the retina comprises increasing the level of apo-rhodopsin (also called opsin) in the photoreceptor cell. The total level of the visual pigment approximates the sum of rhodopsin and apo-rhodopsin and the total level remains constant. Therefore, preventing, delaying, or inhibiting dark adaptation of the rod photoreceptor cell may alter the ratio of apo-rhodopsin to rhodopsin. In particular embodiments, preventing, delaying, or inhibiting dark adaptation by administering an amine derivative compound described herein may increase the ratio of the level of apo-rhodopsin to the level of rhodopsin compared to the ratio in the absence of the agent (for example, prior to administration of the agent). An increase in the ratio (i.e., a statistically or biologically significant increase) of apo-rhodopsin to rhodopsin indicates that the percent or number of rod photoreceptor cells that are rhodopsin-depleted is increased and that the percent or number of rod photoreceptor cells that are dark-adapted is decreased. The ratio of apo-rhodopsin to rhodopsin may be determined throughout the course of therapy to monitor the effect of the agent.

Determining or characterizing the capability of compound to prevent, delay, or inhibit dark adaptation of a rod photoreceptor cell may be determined in animal model studies. The level of rhodopsin and the ratio of apo-rhodopsin to rhodopsin may be determined prior to administration (which may be called a first level or first ratio, respectively) of the agent and then after administration of a first or any subsequent dose of the agent (which may be called a second level or second ratio, respectively) to determine and to demonstrate that the level of apo-rhodopsin is greater than the level of apo-rhodopsin in the retina of animals that did not receive the agent. The level of rhodopsin in rod photoreceptor cells may be performed according to methods practiced in the art and provided herein (see, e.g., Yan et al. *J. Biol. Chem.* 279:48189-96 (2004)).

A subject in need of such treatment may be a human or may be a non-human primate or other animal (i.e., veterinary use) who has developed symptoms of an ophthalmic disease or disorder or who is at risk for developing an ophthalmic disease or disorder. Examples of non-human primates and other animals include but are not limited to farm animals, pets, and zoo animals (e.g., horses, cows, buffalo, llamas, goats, rabbits, cats, dogs, chimpanzees, orangutans, gorillas, monkeys, elephants, bears, large cats, etc.).

Also provided herein are methods for inhibiting (reducing, slowing, preventing) degeneration and enhancing retinal neuronal cell survival (or prolonging cell viability) comprising administering to a subject a composition comprising a pharmaceutically acceptable carrier and an amine derivative compound described in detail herein, including a compound having any one of the structures set forth in Formula (I) and substructures thereof, and specific amine derivative compounds recited herein. Retinal neuronal cells include photoreceptor cells, bipolar cells, horizontal cells, ganglion cells, and amacrine cells. In another embodiment, methods are provided for enhancing survival or inhibiting degeneration of a mature retinal cell such as a RPE cell or a Müller glial cell. In other embodiments, a method for preventing or inhibiting photoreceptor degeneration in an eye of a subject are provided. A method that prevents or inhibits photoreceptor degeneration may include a method for restoring photoreceptor function in an eye of a subject. Such methods comprise administering to the subject a composition comprising an amine derivative compound as described herein and a pharmaceutically or acceptable carrier (i.e., excipient or vehicle). More specifically, these methods comprise administering to a subject a pharmaceutically acceptable excipient and an amine derivative compound described herein, including a compound having any one of the structures set forth in Formula (I) or substructures thereof described herein. Without wishing to be bound by theory, the compounds described herein may inhibit an isomerization step of the retinoid cycle (i.e., visual cycle) and/or may slow chromophore flux in a retinoid cycle in the eye.

The ophthalmic disease may result, at least in part, from lipofuscin pigment(s) accumulation and/or from accumulation of N-retinylidene-N-retinylethanolamine (A2E) in the eye. Accordingly, in certain embodiments, methods are provided for inhibiting or preventing accumulation of lipofuscin pigment(s) and/or A2E in the eye of a subject. These methods comprise administering to the subject a composition comprising a pharmaceutically acceptable carrier and an amine derivative compound as described in detail herein, including a compound having the structure as set forth in Formula (I) or substructures thereof.

An amine derivative compound can be administered to a subject who has an excess of a retinoid in an eye (e.g., an excess of 11-cis-retinol or 11-cis-retinal), an excess of retinoid waste products or intermediates in the recycling of all-trans-retinal, or the like. Methods described herein and practiced in the art may be used to determine whether the level of one or more endogenous retinoids in a subject are altered (increased or decreased in a statistically significant or biologically significant manner) during or after administration of any one of the compounds described herein. Rhodopsin, which is composed of the protein opsin and retinal (a vitamin A form), is located in the membrane of the photoreceptor cell in the retina of the eye and catalyzes the only light-sensitive step in vision. The 11-cis-retinal chromophore lies in a pocket of the protein and is isomerized to all-trans retinal when light is absorbed. The isomerization of retinal leads to a change of the shape of rhodopsin, which triggers a cascade of reactions that lead to a nerve impulse that is transmitted to the brain by the optic nerve.

Methods of determining endogenous retinoid levels in a vertebrate eye, and an excess or deficiency of such retinoids, are disclosed in, for example, U.S. Patent Application Publication No: 2005/0159662 (the disclosure of which is incorporated by reference herein in its entirety). Other methods of determining endogenous retinoid levels in a subject, which is useful for determining whether levels of such retinoids are above the normal range, and include for example, analysis by high pressure liquid chromatography (HPLC) of retinoids in a biological sample from a subject. For example, retinoid levels can be determined in a biological sample that is a blood sample (which includes serum or plasma) from a subject. A biological sample may also include vitreous fluid, aqueous humor, intraocular fluid, subretinal fluid, or tears.

For example, a blood sample can be obtained from a subject, and different retinoid compounds and levels of one or more of the retinoid compounds in the sample can be separated and analyzed by normal phase high pressure liquid chromatography (HPLC) (e.g., with a HP1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. An excess in retinoids can be determined, for example, by comparison of the profile of retinoids (i.e., qualitative, e.g., identity of specific compounds, and quantitative, e.g., the level of each specific compound) in the sample with a sample from a normal subject. Persons skilled in the art who are familiar with such assays and techniques and will readily understand that appropriate controls are included.

As used herein, increased or excessive levels of endogenous retinoid, such as 11-cis-retinol or 11-cis-retinal, refer to levels of endogenous retinoid higher than those found in a healthy eye of a young vertebrate of the same species. Administration of an amine derivative compound can reduce or eliminate the requirement for endogenous retinoid. In certain embodiments, the level of endogenous retinoid may be compared before and after any one or more doses of an amine derivative compound is administered to a subject to determine the effect of the compound on the level of endogenous retinoids in the subject.

In another embodiment, the methods described herein for treating an ophthalmic disease or disorder, for inhibiting neovascularization, and for reducing ischemia in the retina comprise administering at least one of the amine derivative compounds described herein, thereby effecting a decrease in metabolic demand, which includes effecting a reduction in ATP consumption and in oxygen consumption in rod photoreceptor cells. As described herein, consumption of ATP and oxygen in a dark-adapted rod photoreceptor cell is greater than in rod photoreceptor cells that are light-adapted or rhodopsin-depleted; thus, use of the compounds in the methods described herein may reduce the consumption of ATP in the rod photoreceptor cells that are prevented, inhibited, or delayed from dark adaptation compared with rod photoreceptor cells that are dark-adapted (such as the cells prior to administration or contact with the compound or cells that are never exposed to the compound).

The methods described herein that may prevent or inhibit dark adaptation of a rod photoreceptor cell may therefore reduce hypoxia (i.e., reduce in a statistically or biologically significant manner) in the retina. For example, the level of hypoxia (a first level) may be determined prior to initiation of the treatment regimen, that is, prior to the first dosing of the compound (or a composition, as described herein, comprising the compound). The level of hypoxia (for example, a second level) may be determined after the first dosing, and/or after any second or subsequent dosing to monitor and characterize hypoxia throughout the treatment regimen. A decrease (reduction) in the second (or any subsequent) level of hypoxia compared to the level of hypoxia prior to initial administration indicates that the compound and the treatment regiment prevent dark adaptation of the rod photoreceptor cells and may be used for treating ophthalmic diseases and disorders. Consumption of oxygen, oxygenation of the retina, and/or hypoxia in the retina may be determined using methods practiced in the art. For example, oxygenation of the retina may be determined by measuring the fluorescence of flavoproteins in the retina (see, e.g., U.S. Pat. No. 4,569,354). Another exemplary method is retinal oximetry that measures blood oxygen saturation in the large vessels of the retina near the optic disc. Such methods may be used to identify and determine the extent of retinal hypoxia before changes in retinal vessel architecture can be detected.

A biological sample may be a blood sample (from which serum or plasma may be prepared), biopsy specimen, body fluids (e.g., vitreous fluid, aqueous humor, intraocular fluid, subretinal fluid, or tears), tissue explant, organ culture, or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject or biological source may be a human or non-human animal, a primary cell culture (e.g., a retinal cell culture), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiable cell lines, transformed cell lines, and the like. Mature retinal cells, including retinal neuronal cells, RPE cells, and Müller glial cells, may be present in or isolated from a biological sample as described herein. For example, the mature retinal cell may be obtained from a primary or long-term cell culture or may be present in or isolated from a biological sample obtained from a subject (human or non-human animal).

3. Retinal Cells

The retina is a thin layer of nervous tissue located between the vitreous body and choroid in the eye. Major landmarks in the retina are the fovea, the macula, and the optic disc. The retina is thickest near the posterior sections and becomes thinner near the periphery. The macula is located in the posterior retina and contains the fovea and foveola. The foveola contains the area of maximal cone density and, thus, imparts the highest visual acuity in the retina. The foveola is contained within the fovea, which is contained within the macula.

The peripheral portion of the retina increases the field of vision. The peripheral retina extends anterior to the ciliary body and is divided into four regions: the near periphery (most posterior), the mid-periphery, the far periphery, and the ora serrata (most anterior). The ora serrata denotes the termination of the retina.

The term neuron (or nerve cell) as understood in the art and used herein denotes a cell that arises from neuroepithelial cell precursors. Mature neurons (i.e. fully differentiated cells) display several specific antigenic markers. Neurons may be classified functionally into four groups: (1) afferent neurons (or sensory neurons) that transmit information into the brain for conscious perception and motor coordination; (2) motor neurons that transmit commands to muscles and glands; (3) interneurons that are responsible for local circuitry; and (4) projection interneurons that relay information from one region of the brain to another region and therefore have long axons. Interneurons process information within specific subregions of the brain and have relatively shorter axons. A neuron typically has four defined regions: the cell body (or soma); an axon; dendrites; and presynaptic terminals. The dendrites serve as the primary input of information from other neural cells. The axon carries the electrical signals that are initiated in the cell body to other neurons or to effector organs. At the presynaptic terminals, the neuron transmits information to another cell (the postsynaptic cell), which may be another neuron, a muscle cell, or a secretory cell.

The retina is composed of several types of neuronal cells. As described herein, the types of retinal neuronal cells that may be cultured in vitro by this method include photoreceptor cells, ganglion cells, and interneurons such as bipolar cells, horizontal cells, and amacrine cells. Photoreceptors are specialized light-reactive neural cells and comprise two major classes, rods and cones. Rods are involved in scotopic or dim light vision, whereas photopic or bright light vision originates in the cones. Many neurodegenerative diseases, such as AMD, that result in blindness affect photoreceptors.

Extending from their cell bodies, the photoreceptors have two morphologically distinct regions, the inner and outer segments. The outer segment lies furthermost from the photoreceptor cell body and contains disks that convert incoming light energy into electrical impulses (phototransduction). The outer segment is attached to the inner segment with a very small and fragile cilium. The size and shape of the outer segments vary between rods and cones and are dependent upon position within the retina. See Hogan, "Retina" in *Histology of the Human Eye: an Atlas and Text Book* (Hogan et al. (eds). W B Saunders; Philadelphia, Pa. (1971)); *Eye and Orbit*, $8^{th}$ Ed., Bron et al., (Chapman and Hall, 1997).

Ganglion cells are output neurons that convey information from the retinal interneurons (including horizontal cells, bipolar cells, amacrine cells) to the brain. Bipolar cells are named according to their morphology, and receive input from the photoreceptors, connect with amacrine cells, and send output radially to the ganglion cells. Amacrine cells have processes parallel to the plane of the retina and have typically inhibitory output to ganglion cells. Amacrine cells are often subclassified by neurotransmitter or neuromodulator or peptide (such as calretinin or calbindin) and interact with each other, with bipolar cells, and with photoreceptors. Bipolar cells are retinal interneurons that are named according to their morphology; bipolar cells receive input from the photoreceptors and sent the input to the ganglion cells. Horizontal cells modulate and transform visual information from large numbers of photoreceptors and have horizontal integration (whereas bipolar cells relay information radially through the retina).

Other retinal cells that may be present in the retinal cell cultures described herein include glial cells, such as Müller glial cells, and retinal pigment epithelial cells (RPE). Glial cells surround nerve cell bodies and axons. The glial cells do not carry electrical impulses but contribute to maintenance of normal brain function. Müller glia, the predominant type of glial cell within the retina, provide structural support of the retina and are involved in the metabolism of the retina (e.g., contribute to regulation of ionic concentrations, degradation of neurotransmitters, and remove certain metabolites (see, e.g., Kljavin et al., *J. Neurosci.* 11:2985 (1991))). Müller's fibers (also known as sustentacular fibers of retina) are sustentacular neuroglial cells of the retina that run through the thickness of the retina from the internal limiting membrane to the bases of the rods and cones where they form a row of junctional complexes.

Retinal pigment epithelial (RPE) cells form the outermost layer of the retina, separated from the blood vessel-enriched choroids by Bruch's membrane. RPE cells are a type of phagocytic epithelial cell, with some functions that are macrophage-like, which lies immediately below the retinal photoreceptors. The dorsal surface of the RPE cell is closely apposed to the ends of the rods, and as discs are shed from the rod outer segment they are internalized and digested by RPE cells. Similar process occurs with the disc of the cones. RPE cells also produce, store, and transport a variety of factors that contribute to the normal function and survival of photoreceptors. Another function of RPE cells is to recycle vitamin A as it moves between photoreceptors and the RPE during light and dark adaptation in the process known as the visual cycle.

Described herein is an exemplary long-term in vitro cell culture system permits and promotes the survival in culture of mature retinal cells, including retinal neurons, for at least 2-4 weeks, over 2 months, or for as long as 6 months. The cell culture system may be used for identifying and characterizing the amine derivative compounds that are useful in the methods described herein for treating and/or preventing an ophthalmic disease or disorder or for preventing or inhibiting accumulation in the eye of lipofuscin(s) and/or A2E. Retinal cells are isolated from non-embryonic, non-tumorigenic tissue and have not been immortalized by any method such as, for example, transformation or infection with an oncogenic virus. The cell culture system comprises all the major retinal neuronal cell types (photoreceptors, bipolar cells, horizontal cells, amacrine cells, and ganglion cells), and also may include other mature retinal cells such as retinal pigment epithelial cells and Müller glial cells.

For example, a blood sample can be obtained from a subject, and different retinoid compounds and levels of one or more of the retinoid compounds in the sample can be separated and analyzed by normal phase high pressure liquid chromatography (HPLC) (e.g., with a HP1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. An excess in retinoids can be determined, for example, by comparison of the profile of retinoids (i.e., qualitative, e.g., identity of specific compounds, and quantitative, e.g., the level of each specific compound) in the sample with a sample from a normal subject. Persons skilled in the art who are familiar with such assays and techniques and will readily understand that appropriate controls are included.

As used herein, increased or excessive levels of endogenous retinoid, such as 11-cis-retinol or 11-cis-retinal, refer to levels of endogenous retinoid higher than those found in a healthy eye of a young vertebrate of the same species. Administration of an amine derivative compound and reduce or eliminate the requirement for endogenous retinoid.

4. In Vivo and in Vitro Methods for Determining Therapeutic Effectiveness of Compounds In one embodiment, methods are provided for using the compounds described herein for enhancing or prolonging retinal cell survival, including retinal neuronal cell survival and RPE cell survival. Also provided herein are methods for inhibiting or preventing degeneration of a retinal cell, including a retinal neuronal cell (e.g., a photoreceptor cell, an amacrine cell, a horizontal cell, a bipolar cell, and a ganglion cell) and other mature retinal cells such as retinal pigment epithelial cells and Müller glial cells using the compounds described herein. Such methods comprise, in certain embodiments, administration of an amine derivative compound as described herein. Such a compound is useful for enhancing retinal cell survival, including photoreceptor cell survival and retinal pigment epithelia survival, inhibiting or slowing degeneration of a retinal cell, and thus increasing retinal cell viability, which can result in slowing or halting the progression of an ophthalmic disease or disorder or retinal injury, which are described herein.

The effect of an amine derivative compound on retinal cell survival (and/or retinal cell degeneration) may be determined by using cell culture models, animal models, and other methods that are described herein and practiced by persons skilled in the art. By way of example, and not limitation, such methods and assays include those described in Oglivie et al., *Exp. Neurol.* 161:675-856 (2000); U.S. Pat. No. 6,406,840; WO 01/81551; WO 98/12303; U.S. Patent Application No. 2002/0009713; WO 00/40699; U.S. Pat. Nos. 6,117,675; 5,736,516; WO 99/29279; WO 01/83714; WO 01/42784; U.S. Pat. Nos. 6,183,735; 6,090,624; WO 01/09327; U.S. Pat. No. 5,641,750; U.S. Patent Application Publication No. 2004/0147019; and U.S. Patent Application Publication No. 2005/0059148.

Compounds described herein that may be useful for treating an ophthalmic disease or disorder (including a retinal disease or disorder) may inhibit, block, impair, or in some manner interfere with one or more steps in the visual cycle (also called the retinoid cycle herein and in the art). Without wishing to be bound by a particular theory, an amine derivative compound may inhibit or block an isomerization step in the visual cycle, for example, by inhibiting or blocking a functional activity of a visual cycle trans-cis isomerase. The compounds described herein may inhibit, directly or indirectly, isomerization of all-trans-retinol to 11-cis-retinol. The compounds may bind to, or in some manner interact with, and inhibit the isomerase activity of at least one isomerase in a retinal cell. Any one of the compounds described herein may also directly or indirectly inhibit or reduce the activity of an isomerase that is involved in the visual cycle. The compound may block or inhibit the capability of the isomerase to bind to one or more substrates, including but not limited to, an all-trans-retinal ester substrate or all-trans-retinol. Alternatively, or in addition, the compound may bind to the catalytic site or region of the isomerase, thereby inhibiting the capability of the enzyme to catalyze isomerization of at least one substrate. On the basis of scientific data to date, an at least one isomerase that catalyzes the isomerization of a substrate during the visual cycle is believed to be located in the cytoplasm of RPE cells. As discussed herein, each step, enzyme, substrate, intermediate, and product of the visual cycle is not yet elucidated. While a polypeptide called RPE65, which has been found in the cytoplasm and membrane bound in RPE cells, is hypothesized to have isomerase activity (and has also been referred to in the art as having isomerohydrolase activity) (see, e.g., Moiseyev et al., *Proc. Natl. Acad. Sci. USA* 102:12413-18 (2004); Chen et al., *Invest. Ophthalmol. Vis. Sci.* 47:1177-84 (2006)), other persons skilled in the art believe that the RPE65 acts primarily as a chaperone for all-trans-retinal esters (see, e.g., Lamb et al. supra).

Exemplary methods are described herein and practiced by persons skilled in the art for determining the level of enzymatic activity of a visual cycle isomerase in the presence of any one of the compounds described herein. A compound that decreases isomerase activity may be useful for treating an ophthalmic disease or disorder. Thus, methods are provided herein for detecting inhibition of isomerase activity comprising contacting (i.e., mixing, combining, or in some manner permitting the compound and isomerase to interact) a biological sample comprising the isomerase and an amine derivative compound described herein and then determining the level of enzymatic activity of the isomerase. A person having skill in the art will appreciate that as a control, the level of activity of the isomerase in the absence of a compound or in the presence of a compound known not to alter the enzymatic activity of the isomerase can be determined and compared to the level of activity in the presence of the compound. A decrease in the level of isomerase activity in the presence of the compound compared to the level of isomerase activity in the absence of the compound indicates that the compound may be useful for treating an ophthalmic disease or disorder, such as age-related macular degeneration or Stargardt's disease. A decrease in the level of isomerase activity in the presence of the compound compared to the level of isomerase activity in the absence of the compound indicates that the compound may also be useful in the methods described herein for inhibiting or preventing dark adaptation, inhibiting neovascularization and reducing hypoxia and thus useful for treating an ophthalmic disease or disorder, for example, diabetic retinopathy, diabetic maculopathy, retinal blood vessel occlusion, retinopathy of prematurity, or ischemia reperfusion related retinal injury.

The capability of an amine derivative compound described herein to inhibit or to prevent dark adaptation of a rod photoreceptor cell by inhibiting regeneration of rhodopsin may be determined by in vitro assays and/or in vivo animal models. By way of example, inhibition of regeneration may be determined in a mouse model in which a diabetes-like condition is induced chemically or in a diabetic mouse model (see, e.g., Phipps et al., *Invest. Ophthalmol. Vis. Sci.* 47:3187-94 (2006); Ramsey et al., *Invest. Ophthalmol. Vis. Sci.* 47:5116-24 (2006)). The level of rhodopsin (a first level) may be determined (for example, spectrophotometrically) in the retina of animals prior to administration of the agent and compared with the level (a second level) of rhodopsin measured in the retina of animals after administration of the agent. A decrease in the second level of rhodopsin compared with the first level of rhodopsin indicates that the agent inhibits regeneration of rhodopsin. The appropriate controls and study design to determine whether regeneration of rhodopsin is inhibited in a statistically significant or biologically significant manner can be readily determined and implemented by persons skilled in the art.

Methods and techniques for determining or characterizing the effect of any one of the compounds described herein on dark adaptation and rhodopsin regeneration in rod photoreceptor cells in a mammal, including a human, may be performed according to procedures described herein and practiced in the art. For example, detection of a visual stimulus after exposure to light (i.e., photobleaching) versus time in darkness may be determined before administration of the first dose of the compound and at a time after the first dose and/or any subsequent dose. A second method for determining prevention or inhibition of dark adaptation by the rod photoreceptor cells includes measurement of the amplitude of at least one, at least two, at least three, or more electroretinogram components, which include, for example, the a-wave and the b-wave. See, for example, Lamb et al., supra; Asi et al., *Documenta Ophthalmologica* 79:125-39 (1992).

Inhibiting regeneration of rhodopsin by an amine derivative compound described herein comprises reducing the level of the chromophore, 11-cis-retinal, that is produced and present in the RPE cell, and consequently reducing the level of 11-cis-retinal that is present in the photoreceptor cell. Thus, the compound, when permitted to contact the retina under suitable conditions and at a time sufficient to prevent dark adaptation of a rod photoreceptor cell and to inhibit regeneration of rhodopsin in the rod photoreceptor cell, effects a reduction in the level of 11-cis-retinal in a rod photoreceptor cell (i.e., a statistically significant or biologically significant reduction). That is, the level of 11-cis retinal in a rod photoreceptor cell is greater prior to administration of the compound when compared with the level of 11-cis-retinal in the photoreceptor cell after the first and/or any subsequent administration of the compound. A first level of 11-cis-retinal may be determined prior to administration of the compound, and a second level of 11-cis-retinal may be determined after administration of a first dose or any subsequent dose to monitor the effect of the compound. A decrease in the second level compared to the first level indicates that the compound inhibits regeneration of rhodopsin and thus inhibits or prevents dark adaptation of the rod photoreceptor cells.

An exemplary method for determining or characterizing the capability of an amine derivative compound to reduce retinal hypoxia includes measuring the level of retinal oxygenation, for example, by Magnetic Resonance Imaging (MRI) to measure changes in oxygen pressure (see, e.g., Luan et al., *Invest. Ophthalmol. Vis. Sci.* 47:320-28 (2006)). Methods are also available and routinely practiced in the art to determine or characterize the capability of compounds described herein to inhibit degeneration of a retinal cell (see, e.g., Wenzel et al., *Prog. Retin. Eye Res.* 24:275-306 (2005)).

Animal models may be used to characterize and identify compounds that may be used to treat retinal diseases and disorders. A recently developed animal model may be useful for evaluating treatments for macular degeneration has been described by Ambati et al. (*Nat. Med.* 9:1390-97 (2003); Epub 2003 Oct. 19). This animal model is one of only a few exemplary animal models presently available for evaluating a compound or any molecule for use in treating (including preventing) progression or development of a retinal disease or disorder. Animal models in which the ABCR gene, which encodes an ATP-binding cassette transporter located in the rims of photoreceptor outer segment discs, may be used to evaluate the effect of a compound. Mutations in the ABCR gene are associated with Stargardt's disease, and heterozygous mutations in ABCR have been associated with AMD. Accordingly, animals have been generated with partial or total loss of ABCR function and may used to characterize the amine derivative compounds described herein. (See, e.g., Mata et al., *Invest. Ophthalmol. Sci.* 42:1685-90 (2001); Weng et al., *Cell* 98:13-23 (1999); Mata et al., *Proc. Natl. Acad. Sci. USA* 97:7154-49 (2000); US 2003/0032078; U.S. Pat. No. 6,713,300). Other animal models include the use of mutant ELOVL4 transgenic mice to determine lipofuscin accumulation, electrophysiology, and photoreceptor degeneration, or prevention or inhibition thereof (see, e.g., Karan et al., *Proc. Natl. Acad. Sci. USA* 102:4164-69 (2005)).

The effect of any one of the compounds described herein may be determined in a diabetic retinopathy animal model, such as described in Luan et al. or may be determined in a normal animal model, in which the animals have been light or dark adapted in the presence and absence of any one of the compounds described herein. Another exemplary method for determining the capability of the agent to reduce retinal hypoxia measures retinal hypoxia by deposition of a hydroxyprobe (see, e.g., de Gooyer et al. (*Invest. Ophthalmol. Vis. Sci.* 47:5553-60 (2006)). Such a technique may be performed in an animal model using $Rho^-/Rho^-$ knockout mice (see de Gooyer et al., supra) in which at least one compound described herein is administered to group(s) of animals in the presence and absence of the at least one compound, or may be performed in normal, wildtype animals in which at least one compound described herein is administered to group(s) of animals in the presence and absence of the at least one compound. Other animal models include models for determining photoreceptor function, such as rat models that measure elctroretinographic (ERG) oscillatory potentials (see, e.g., Liu et al., *Invest. Ophthalmol. Vis. Sci.* 47:5447-52 (2006); Akula et al., *Invest. Ophthalmol. Vis. Sci.* 48:4351-59 (2007); Liu et al., *Invest. Ophthalmol. Vis. Sci.* 47:2639-47 (2006); Dembinska et al., *Invest. Ophthalmol. Vis. Sci.* 43:2481-90 (2002); Penn et al., *Invest. Ophthalmol. Vis. Sci.* 35:3429-35 (1994); Hancock et al., *Invest. Ophthalmol. Vis. Sci.* 45:1002-1008 (2004)).

A method for determining the effect of a compound on isomerase activity may be performed in vitro as described herein and in the art (Stecher et al., *J. Biol. Chem.* 274:8577-85 (1999); see also Golczak et al., *Proc. Natl. Acad. Sci. USA* 102:8162-67 (2005)). Retinal pigment epithelium (RPE) microsome membranes isolated from an animal (such as bovine, porcine, human, for example) may serve as the source of the isomerase. The capability of the amine derivative compounds to inhibit isomerase may also be determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo (see, e.g., Maeda et al., *J. Neurochem.* 85:944-956 (2003); Van Hooser et al., *J. Biol. Chem.* 277: 19173-82, 2002). Electroretinographic (ERG) recording may be performed as previously described (Haeseleer et al., *Nat. Neurosci.* 7:1079-87 (2004); Sugitomo et al., *J. Toxicol. Sci.* 22 Suppl 2:315-25 (1997); Keating et al., *Documenta Ophthalmologica* 100:77-92 (2000)). See also Deigner et al., *Science,* 244: 968-971 (1989); Gollapalli et al., *Biochim. Biophys. Acta* 1651: 93-101 (2003); Parish, et al., *Proc. Natl. Acad. Sci. USA* 95:14609-13 (1998); Radu et al., *Proc Natl Acad Sci USA* 101: 5928-33 (2004).

Cell culture methods, such as the method described herein, are also useful for determining the effect of a compound described herein on retinal neuronal cell survival. Exemplary cell culture models are described herein and described in detail in U.S. Patent Application Publication No. US 2005-0059148 and U.S. Patent Application Publication No. US2004-0147019 (which are incorporated by reference in their entirety), which are useful for determining the capability of an amine derivative compound as described herein to enhance or prolong survival of neuronal cells, particularly retinal neuronal cells, and of retinal pigment epithelial cells, and inhibit, prevent, slow, or retard degeneration of an eye, or the retina or retinal cells thereof, or the RPE, and which compounds are useful for treating ophthalmic diseases and disorders.

The cell culture model comprises a long-term or extended culture of mature retinal cells, including retinal neuronal cells (e.g., photoreceptor cells, amacrine cells, ganglion cells, horizontal cells, and bipolar cells). The cell culture system and methods for producing the cell culture system provide extended culture of photoreceptor cells. The cell culture system may also comprise retinal pigment epithelial (RPE) cells and Müller glial cells.

The retinal cell culture system may also comprise a cell stressor. The application or the presence of the stressor affects the mature retinal cells, including the retinal neuronal cells, in vitro, in a manner that is useful for studying disease pathology that is observed in a retinal disease or disorder. The cell culture model provides an in vitro neuronal cell culture system that will be useful in the identification and biological testing of an amine derivative compound that is suitable for treatment of neurological diseases or disorders in general, and for treatment of degenerative diseases of the eye and brain in particular. The ability to maintain primary, in vitro-cultured cells from mature retinal tissue, including retinal neurons over an extended period of time in the presence of a stressor enables examination of cell-to-cell interactions, selection and analysis of neuroactive compounds and materials, use of a controlled cell culture system for in vitro CNS and ophthalmic tests, and analysis of the effects on single cells from a consistent retinal cell population.

The cell culture system and the retinal cell stress model comprise cultured mature retinal cells, retinal neurons, and a retinal cell stressor, which may be used for screening and characterizing an amine derivative compound that are capable of inducing or stimulating the regeneration of CNS tissue that has been damaged by disease. The cell culture system provides a mature retinal cell culture that is a mixture of mature retinal neuronal cells and non-neuronal retinal cells. The cell culture system comprises all the major retinal neuronal cell types (photoreceptors, bipolar cells, horizontal cells, amacrine cells, and ganglion cells), and may also include other mature retinal cells such as RPE and Müller glial cells. By incorporating these different types of cells into the in vitro culture system, the system essentially resembles an "artificial organ" that is more akin to the natural in vivo state of the retina.

Viability of one or more of the mature retinal cell types that are isolated (harvested) from retinal tissue and plated for tissue culture may be maintained for an extended period of time, for example, from two weeks up to six months. Viability of the retinal cells may be determined according to methods described herein and known in the art. Retinal neuronal cells, similar to neuronal cells in general, are not actively dividing cells in vivo and thus cell division of retinal neuronal cells would not necessarily be indicative of viability. An advantage of the cell culture system is the ability to culture amacrine cells, photoreceptors, and associated ganglion projection neurons and other mature retinal cells for extended periods of time, thereby providing an opportunity to determine the effectiveness of an amine derivative compound described herein for treatment of retinal disease.

The biological source of the retinal cells or retinal tissue may be mammalian (e.g., human, non-human primate, ungulate, rodent, canine, porcine, bovine, or other mammalian source), avian, or from other genera. Retinal cells including retinal neurons from post-natal non-human primates, post-natal pigs, or post-natal chickens may be used, but any adult or post-natal retinal tissue may be suitable for use in this retinal cell culture system.

In certain instances, the cell culture system may provide for robust long-term survival of retinal cells without inclusion of cells derived from or isolated or purified from non-retinal tissue. Such a cell culture system comprises cells isolated solely from the retina of the eye and thus is substantially free of types of cells from other parts or regions of the eye that are separate from the retina, such as the ciliary body, iris, choroid, and vitreous. Other cell culture methods include the addition of non-retinal cells, such as ciliary body cell and/or stem cells (which may or may not be retinal stem cells) and/or additional purified glial cells.

The in vitro retinal cell culture systems described herein may serve as physiological retinal models that can be used to characterize aspects of the physiology of the retina. This physiological retinal model may also be used as a broader general neurobiology model. A cell stressor may be included in the model cell culture system. A cell stressor, which as described herein is a retinal cell stressor, adversely affects the viability or reduces the viability of one or more of the different retinal cell types, including types of retinal neuronal cells, in the cell culture system. A person skilled in the art would readily appreciate and understand that as described herein a retinal cell that exhibits reduced viability means that the length of time that a retinal cell survives in the cell culture system is reduced or decreased (decreased lifespan) and/or that the retinal cell exhibits a decrease, inhibition, or adverse effect of a biological or biochemical function (e.g., decreased or abnormal metabolism; initiation of apoptosis; etc.) compared with a retinal cell cultured in an appropriate control cell system (e.g., the cell culture system described herein in the absence of the cell stressor). Reduced viability of a retinal cell may be indicated by cell death; an alteration or change in cell structure or morphology; induction and/or progression of apoptosis; initiation, enhancement, and/or acceleration of retinal neuronal cell neurodegeneration (or neuronal cell injury).

Methods and techniques for determining cell viability are described in detail herein and are those with which skilled artisans are familiar. These methods and techniques for determining cell viability may be used for monitoring the health and status of retinal cells in the cell culture system and for determining the capability of the amine derivative compounds described herein to alter (preferably increase, prolong, enhance, improve) retinal cell or retinal pigment epithelial cell viability or retinal cell survival.

The addition of a cell stressor to the cell culture system is useful for determining the capability of an amine derivative compound to abrogate, inhibit, eliminate, or lessen the effect of the stressor. The retinal cell culture system may include a cell stressor that is chemical (e.g., A2E, cigarette smoke concentrate); biological (for example, toxin exposure; beta-amyloid; lipopolysaccharides); or non-chemical, such as a physical stressor, environmental stressor, or a mechanical force (e.g., increased pressure or light exposure) (see, e.g., US 2005-0059148).

The retinal cell stressor model system may also include a cell stressor such as, but not limited to, a stressor that may be a risk factor in a disease or disorder or that may contribute to the development or progression of a disease or disorder, including but not limited to, light of varying wavelengths and intensities; A2E; cigarette smoke condensate exposure; oxidative stress (e.g., stress related to the presence of or exposure to hydrogen peroxide, nitroprusside, $Zn^{++}$, or $Fe^{++}$); increased pressure (e.g., atmospheric pressure or hydrostatic pressure), glutamate or glutamate agonist (e.g., N-methyl-D-aspartate (NMDA); alpha-amino-3-hydroxy-5-methylisoxazole-4-proprionate (AMPA); kainic acid; quisqualic acid; ibotenic acid; quinolinic acid; aspartate; trans-1-aminocyclopentyl-1,3-dicarboxylate (ACPD)); amino acids (e.g., aspartate, L-cysteine; beta-N-methylamine-L-alanine); heavy metals (such as lead); various toxins (for example, mitochondrial toxins (e.g., malonate, 3-nitroproprionic acid; rotenone, cyanide); MPTP (1-methyl-4-phenyl-1,2,3,6,-tetrahydropyridine), which metabolizes to its active, toxic metabolite MPP+ (1-methyl-4-phenylpyridine)); 6-hydroxydopamine; alpha-synuclein; protein kinase C activators (e.g., phorbol myristate acetate); biogenic amino stimulants (for example, methamphetamine, MDMA (3-4 methylenedioxymethamphetamine)); or a combination of one or more stressors. Useful retinal cell stressors include those that mimic a neurodegenerative disease that affects any one or more of the mature retinal cells described herein. A chronic disease model is of particular importance because most neurodegenerative diseases are chronic. Through use of this in vitro cell culture system, the earliest events in long-term disease development processes may be identified because an extended period of time is available for cellular analysis.

A retinal cell stressor may alter (i.e., increase or decrease in a statistically significant manner) viability of retinal cells such as by altering survival of retinal cells, including retinal neuronal cells and RPE cells, or by altering neurodegeneration of retinal neuronal cells and/or RPE cells. Preferably, a retinal cell stressor adversely affects a retinal neuronal cell or RPE cell such that survival of a retinal neuronal cell or RPE cell is decreased or adversely affected (i.e., the length of time during which the cells are viable is decreased in the presence of the stressor) or neurodegeneration (or neuron cell injury) of the cell is increased or enhanced. The stressor may affect only a single retinal cell type in the retinal cell culture or the stressor may affect two, three, four, or more of the different cell types. For example, a stressor may alter viability and survival of photoreceptor cells but not affect all the other major cell types (e.g., ganglion cells, amacrine cells, horizontal cells, bipolar cells, RPE, and Müller glia). Stressors may shorten the survival time of a retinal cell (in vivo or in vitro), increase the rapidity or extent of neurodegeneration of a retinal cell, or in some other manner adversely affect the viability, morphology, maturity, or lifespan of the retinal cell.

The effect of a cell stressor (in the presence and absence of an amine derivative compound) on the viability of retinal cells in the cell culture system may be determined for one or more of the different retinal cell types. Determination of cell viability may include evaluating structure and/or a function of a retinal cell continually at intervals over a length of time or at a particular time point after the retinal cell culture is prepared. Viability or long term survival of one or more different retinal cell types or one or more different retinal neuronal cell types may be examined according to one or more biochemical or biological parameters that are indicative of reduced viability, such as apoptosis or a decrease in a metabolic function, prior to observation of a morphological or structural alteration.

A chemical, biological, or physical cell stressor may reduce viability of one or more of the retinal cell types present in the cell culture system when the stressor is added to the cell culture under conditions described herein for maintaining the long-term cell culture. Alternatively, one or more culture conditions may be adjusted so that the effect of the stressor on the retinal cells can be more readily observed. For example, the concentration or percent of fetal bovine serum may be reduced or eliminated from the cell culture when cells are exposed to a particular cell stressor (see, e.g., US 2005-0059148). Alternatively, retinal cells cultured in media containing serum at a particular concentration for maintenance of the cells may be abruptly exposed to media that does not contain any level of serum.

The retinal cell culture may be exposed to a cell stressor for a period of time that is determined to reduce the viability of one or more retinal cell types in the retinal cell culture system. The cells may be exposed to a cell stressor immediately upon plating of the retinal cells after isolation from retinal tissue. Alternatively, the retinal cell culture may be exposed to a stressor after the culture is established, or any time thereafter. When two or more cell stressors are included in the retinal cell culture system, each stressor may be added to the cell culture system concurrently and for the same length of time or may be added separately at different time points for the same length of time or for differing lengths of time during the culturing of the retinal cell system. An amine derivative compound may be added before the retinal cell culture is exposed to a cell stressor, may be added concurrently with the cell stressor, or may be added after exposure of the retinal cell culture to the stressor.

Photoreceptors may be identified using antibodies that specifically bind to photoreceptor-specific proteins such as opsins, peripherins, and the like. Photoreceptors in cell culture may also be identified as a morphologic subset of immunocytochemically labeled cells by using a pan-neuronal marker or may be identified morphologically in enhanced contrast images of live cultures. Outer segments can be detected morphologically as attachments to photoreceptors.

Retinal cells including photoreceptors can also be detected by functional analysis. For example, electrophysiology methods and techniques may be used for measuring the response of photoreceptors to light. Photoreceptors exhibit specific kinetics in a graded response to light. Calcium-sensitive dyes may also be used to detect graded responses to light within cultures containing active photoreceptors. For analyzing stress-inducing compounds or potential neurotherapeutics, retinal cell cultures can be processed for immunocytochemistry, and photoreceptors and/or other retinal cells can be counted manually or by computer software using photomicroscopy and imaging techniques. Other immunoassays known in the art (e.g., ELISA, immunoblotting, flow cytometry) may also be useful for identifying and characterizing the retinal cells and retinal neuronal cells of the cell culture model system described herein.

The retinal cell culture stress models may also be useful for identification of both direct and indirect pharmacologic agent effects by the bioactive agent of interest, such as an amine derivative compound as described herein. For example, a bioactive agent added to the cell culture system in the presence of one or more retinal cell stressors may stimulate one cell type in a manner that enhances or decreases the survival of other cell types. Cell/cell interactions and cell/extracellular component interactions may be important in understanding mechanisms of disease and drug function. For example, one neuronal cell type may secrete trophic factors that affect growth or survival of another neuronal cell type (see, e.g., WO 99/29279).

In another embodiment, an amine derivative compound is incorporated into screening assays comprising the retinal cell culture stress model system described herein to determine whether and/or to what level or degree the compound increases or prolongs viability (i.e., increases in a statistically significant or biologically significant manner) of a plurality of retinal cells. A person skilled in the art would readily appreciate and understand that as described herein a retinal cell that exhibits increased viability means that the length of time that a retinal cell survives in the cell culture system is increased (increased lifespan) and/or that the retinal cell maintains a biological or biochemical function (normal metabolism and organelle function; lack of apoptosis; etc.) compared with a retinal cell cultured in an appropriate control cell system (e.g., the cell culture system described herein in the absence of the compound). Increased viability of a retinal cell may be indicated by delayed cell death or a reduced number of dead or dying cells; maintenance of structure and/or morphology; lack of or delayed initiation of apoptosis; delay, inhibition, slowed progression, and/or abrogation of retinal neuronal cell neurodegeneration or delaying or abrogating or preventing the effects of neuronal cell injury. Methods and techniques for determining viability of a retinal cell and thus whether a retinal cell exhibits increased viability are described in greater detail herein and are known to persons skilled in the art.

In certain embodiments, a method is provided for determining whether an amine derivative compound, enhances survival of photoreceptor cells. One method comprises contacting a retinal cell culture system as described herein with an amine derivative compound under conditions and for a time sufficient to permit interaction between the retinal neuronal cells and the compound. Enhanced survival (prolonged survival) may be measured according to methods described herein and known in the art, including detecting expression of rhodopsin.

The capability of an amine derivative compound to increase retinal cell viability and/or to enhance, promote, or prolong cell survival (that is, to extend the time period in which retinal cells, including retinal neuronal cells, are viable), and/or impair, inhibit, or impede degeneration as a direct or indirect result of the herein described stress may be determined by any one of several methods known to those skilled in the art. For example, changes in cell morphology in the absence and presence of the compound may be determined by visual inspection such as by light microscopy, confocal microscopy, or other microscopy methods known in the art. Survival of cells can also be determined by counting viable and/or nonviable cells, for instance. Immunochemical or immunohistological techniques (such as fixed cell staining or flow cytometry) may be used to identify and evaluate cytoskeletal structure (e.g., by using antibodies specific for cytoskeletal proteins such as glial fibrillary acidic protein, fibronectin, actin, vimentin, tubulin, or the like) or to evaluate expression of cell markers as described herein. The effect of an amine derivative compound on cell integrity, morphology, and/or survival may also be determined by measuring the phosphorylation state of neuronal cell polypeptides, for example, cytoskeletal polypeptides (see, e.g., Sharma et al., *J. Biol. Chem.* 274:9600-06 (1999); Li et al., *J. Neurosci.* 20:6055-62 (2000)). Cell survival or, alternatively cell death, may also be determined according to methods described herein and known in the art for measuring apoptosis (for example, annexin V binding, DNA fragmentation assays, caspase activation, marker analysis, e.g., poly(ADP-ribose) polymerase (PARP), etc.).

In the vertebrate eye, for example, a mammalian eye, the formation of A2E is a light-dependent process and its accumulation leads to a number of negative effects in the eye. These include destabilization of retinal pigment epithelium (RPE) membranes, sensitization of cells to blue-light damage, and impaired degradation of phospholipids. Products of the oxidation of A2E (and A2E related molecules) by molecular oxygen (oxiranes) were shown to induce DNA damage in cultured RPE cells. All these factors lead to a gradual decrease in visual acuity and eventually to vision loss. If reducing the formation of retinals during vision processes were possible, this reduction would lead to decreased amounts of A2E in the eye. Without wishing to be bound by theory, decreased accumulation of A2E may reduce or delay degenerative processes in the RPE and retina and thus may slow down or prevent vision loss in dry AMD and Stargardt's Disease.

In another embodiment, methods are provided for treating and/or preventing degenerative diseases and disorders, including neurodegenerative retinal diseases and ophthalmic diseases, and retinal diseases and disorders as described herein. A subject in need of such treatment may be a human or non-human primate or other animal who has developed symptoms of a degenerative retinal disease or who is at risk for developing a degenerative retinal disease. As described herein a method is provided for treating (which includes preventing or prophylaxis) an ophthalmic disease or disorder by administrating to a subject a composition comprising a pharmaceutically acceptable carrier and an amine derivative compound (e.g., a compound having the structure of Formula (I), and substructures thereof) As described herein, a method is provided for enhancing survival of neuronal cells such as retinal neuronal cells, including photoreceptor cells, and/or inhibiting degeneration of retinal neuronal cells by administering the pharmaceutical compositions described herein comprising an amine derivative compound.

Enhanced survival (or prolonged or extended survival) of one or more retinal cell types in the presence of an amine derivative compound indicates that the compound may be an effective agent for treatment of a degenerative disease, particularly a retinal disease or disorder, and including a neurodegenerative retinal disease or disorder. Cell survival and enhanced cell survival may be determined according to methods described herein and known to a skilled artisan including viability assays and assays for detecting expression of retinal cell marker proteins. For determining enhanced survival of photoreceptor cells, opsins may be detected, for instance, including the protein rhodopsin that is expressed by rods.

In another embodiment, the subject is being treated for Stargardt's disease or Stargardt's macular degeneration. In Stargardt's disease, which is associated with mutations in the ABCA4 (also called ABCR) transporter, the accumulation of all-trans-retinal has been proposed to be responsible for the formation of a lipofuscin pigment, A2E, which is toxic towards retinal cells and causes retinal degeneration and consequently loss of vision.

In yet another embodiment, the subject is being treated for age-related macular degeneration (AMD). In various embodiments, AMD can be wet- or dry-form. In AMD, vision loss primarily occurs when complications late in the disease either cause new blood vessels to grow under the macula or the macula atrophies. Without intending to be bound by any particular theory, the accumulation of all-trans-retinal has been proposed to be responsible for the formation of a lipofuscin pigment, N-retinylidene-N-retinylethanolamine (A2E) and A2E related molecules, which are toxic towards RPE and retinal cells and cause retinal degeneration and consequently loss of vision.

A neurodegenerative retinal disease or disorder for which the compounds and methods described herein may be used for treating, curing, preventing, ameliorating the symptoms of, or slowing, inhibiting, or stopping the progression of, is a disease or disorder that leads to or is characterized by retinal neuronal cell loss, which is the cause of visual impairment. Such a disease or disorder includes but is not limited to age-related macular degeneration (including dry-form and wet-form of macular degeneration) and Stargardt's macular dystrophy.

Age-related macular degeneration as described herein is a disorder that affects the macula (central region of the retina) and results in the decline and loss of central vision. Age-related macular degeneration occurs typically in individuals over the age of 55 years. The etiology of age-related macular degeneration may include both environmental influences and genetic components (see, e.g., Lyengar et al., *Am. J. Hum. Genet.* 74:20-39 (2004) (Epub 2003 Dec. 19); Kenealy et al., *Mol. Vis.* 10:57-61 (2004); Gorin et al., *Mol. Vis.* 5:29 (1999)). More rarely, macular degeneration occurs in younger individuals, including children and infants, and generally, these disorders results from a genetic mutation. Types of juvenile macular degeneration include Stargardt's disease (see, e.g., Glazer et al., *Ophthalmol. Clin. North Am.* 15:93-100, viii (2002); Weng et al., *Cell* 98:13-23 (1999)); Doyne's honeycomb retinal dystrophy (see, e.g., Kermani et al., *Hum. Genet.* 104:77-82 (1999)); Sorsby's fundus dystrophy, Malattia Levintinese, fundus flavimaculatus, and autosomal dominant hemorrhagic macular dystrophy (see also Seddon et al., *Ophthalmology* 108:2060-67 (2001); Yates et al., *J. Med. Genet.* 37:83-7 (2000); Jaakson et al., *Hum. Mutat.* 22:395-403 (2003)). Geographic atrophy of the RPE is an advanced form of non-neovascular dry-type age-related macular degeneration, and is associated with atrophy of the choriocapillaris, RPE, and retina.

Stargardt's macular degeneration, a recessive inherited disease, is an inherited blinding disease of children. The primary pathologic defect in Stargardt's disease is also an accumulation of toxic lipofuscin pigments such as A2E in cells of the retinal pigment epithelium (RPE). This accumulation appears to be responsible for the photoreceptor death and severe visual loss found in Stargardt's patients. The compounds described herein may slow the synthesis of 11-cis-retinaldehyde (11cRAL or retinal) and regeneration of rhodopsin by inhibiting isomerase in the visual cycle. Light activation of rhodopsin results in its release of all-trans-retinal, which constitutes the first reactant in A2E biosynthesis. Treatment with amine derivative compounds may inhibit lipofuscin accumulation and thus delay the onset of visual loss in Stargardt's and AMD patients without toxic effects that would preclude treatment with an amine derivative compound. The compounds described herein may be used for effective treatment of other forms of retinal or macular degeneration associated with lipofuscin accumulation.

Administration of an amine derivative compound to a subject can prevent formation of the lipofuscin pigment, A2E (and A2E related molecules), that is toxic towards retinal cells and causes retinal degeneration. In certain embodiments, administration of an amine derivative compound can lessen the production of waste products, e.g., lipofuscin pigment, A2E (and A2E related molecules), ameliorate the development of AMD (e.g., dry-form) and Stargardt's disease, and reduce or slow vision loss (e.g., choroidal neovascularization and/or chorioretinal atrophy). In previous studies, with 13-cis-retinoic acid (Accutane® or Isotretinoin), a drug commonly used for the treatment of acne and an inhibitor of 11-cis-retinol dehydrogenase, has been administered to patients to prevent A2E accumulation in the RPE. However, a major drawback in this proposed treatment is that 13-cis-retinoic acid can easily isomerize to all-trans-retinoic acid. All-trans-retinoic acid is a very potent teratogenic compound that adversely affects cell proliferation and development. Retinoic acid also accumulates in the liver and may be a contributing factor in liver diseases.

In yet other embodiments, an amine derivative compound is administered to a subject such as a human with a mutation in the ABCA4 transporter in the eye. The amine derivative compound can also be administered to an aging subject. As used herein, an aging human subject is typically at least 45, or at least 50, or at least 60, or at least 65 years old. In Stargardt's disease, which is associated with mutations in the ABCA4 transporter, the accumulation of all-trans-retinal has been proposed to be responsible for the formation of a lipofuscin pigment, A2E (and A2E related molecules), that is toxic towards retinal cells and causes retinal degeneration and consequently loss of vision. Without wishing to be bound by theory, an amine derivative compound described herein may be a strong inhibitor of an isomerase involved in the visual cycle. Treating patients with an amine derivative compound as described herein may prevent or slow the formation of A2E (and A2E related molecules) and can have protective properties for normal vision.

In other certain embodiments, one or more of the compounds described herein may be used for treating other ophthalmic diseases or disorders, for example, glaucoma, retinal detachment, hemorrhagic retinopathy, retinitis pigmentosa, an inflammatory retinal disease, proliferative vitreoretinopathy, retinal dystrophy, hereditary optic neuropathy, Sorsby's fundus dystrophy, uveitis, a retinal injury, optical neuropathy, and retinal disorders associated with other neurodegenerative diseases such as Alzheimer's disease, multiple sclerosis, Parkinson's disease or other neurodegenerative diseases that affect brain cells, a retinal disorder associated with viral infection, or other conditions such as AIDS. A retinal disorder also includes light damage to the retina that is related to increased light exposure (i.e., overexposure to light), for example, accidental strong or intense light exposure during surgery; strong, intense, or prolonged sunlight exposure, such as at a desert or snow covered terrain; during combat, for example, when observing a flare or explosion or from a laser device, and the like. Retinal diseases can be of degenerative or non-degenerative nature. Non-limiting examples of degenerative retinal diseases include age-related macular degeneration, and Stargardt's macular dystrophy. Examples of non-degenerative retinal diseases include but are not limited hemorrhagic retinopathy, retinitis pigmentosa, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, and a retinal disorder associated with AIDS.

In other certain embodiments, at least one of the compounds described herein may be used for treating, curing, preventing, ameliorating the symptoms of, or slowing, inhibiting, or stopping the progression of, certain ophthalmic diseases and disorders including but not limited to diabetic retinopathy, diabetic maculopathy, diabetic macular edema, retinal ischemia, ischemia-reperfusion related retinal injury, and retinal blood vessel occlusion (including venous occlusion and arterial occlusion).

Diabetic retinopathy is a leading cause of blindness in humans and is a complication of diabetes. Diabetic retinopathy occurs when diabetes damages blood vessels inside the retina. Non-proliferative retinopathy is a common, usually mild form that generally does not interfere with vision. Abnormalities are limited to the retina, and vision is impaired only if the macula is involved. If left untreated retinopathy can progress to proliferative retinopathy, the more serious form of diabetic retinopathy. Proliferative retinopathy occurs when new blood vessels proliferate in and around the retina. Consequently, bleeding into the vitreous, swelling of the retina, and/or retinal detachment may occur, leading to blindness.

Other ophthalmic diseases and disorders that may be treated using the methods and compositions described herein include diseases, disorders, and conditions that are associated with, exacerbated by, or caused by ischemia in the retina. Retinal ischemia includes ischemia of the inner retina and the outer retina. Retinal ischemia can occur from either choroidal or retinal vascular diseases, such as central or branch retinal vision occlusion, collagen vascular diseases and thrombocytopenic purpura. Retinal vasculitis and occlusion is seen with Eales disease and systemic lupus erythematosus.

Retinal ischemia may be associated with retinal blood vessel occlusion. In the United States, both branch and central retinal vein occlusions are the second most common retinal vascular diseases after diabetic retinopathy. About 7% to 10% of patients who have retinal venous occlusive disease in one eye eventually have bilateral disease. Visual field loss commonly occurs from macular edema, ischemia, or vitreous hemorrhage secondary to disc or retinal neovascularization induced by the release of vascular endothelial growth factor.

Arteriolosclerosis at sites of retinal arteriovenous crossings (areas in which arteries and veins share a common adventitial sheath) causes constriction of the wall of a retinal vein by a crossing artery. The constriction results in thrombus formation and subsequent occlusion of the vein. The blocked vein may lead to macular edema and hemorrhage secondary to breakdown in the blood-retina barrier in the area drained by the vein, disruption of circulation with turbulence in venous flow, endothelial damage, and ischemia. Clinically, areas of ischemic retina appear as feathery white patches called cotton-wool spots.

Branch retinal vein occlusions with abundant ischemia cause acute central and paracentral visual field loss corresponding to the location of the involved retinal quadrants. Retinal neovascularization due to ischemia may lead to vitreous hemorrhage and subacute or acute vision loss.

Two types of central retinal vein occlusion, ischemic and nonischemic, may occur depending on whether widespread retinal ischemia is present. Even in the nonischemic type, the macula may still be ischemic. Approximately 25% central retinal vein occlusion is ischemic. Diagnosis of central retinal vein occlusion can usually be made on the basis of characteristic ophthalmoscopic findings, including retinal hemorrhage in all quadrants, dilated and tortuous veins, and cotton-wool spots. Macular edema and foveal ischemia can lead to vision loss. Extracellular fluid increases interstitial pressure, which may result in areas of retinal capillary closure (i.e., patchy ischemic retinal whitening) or occlusion of a cilioretinal artery.

Patients with ischemic central retinal vein occlusion are more likely to present with a sudden onset of vision loss and have visual acuity of less than 20/200, a relative afferent pupillary defect, abundant intraretinal hemorrhages, and extensive nonperfusion on fluorescein angiography. The natural history of ischemic central retinal vein occlusion is associated with poor outcomes: eventually, approximately two-thirds of patients who have ischemic central retinal vein occlusion will have ocular neovascularization and one-third will have neovascular glaucoma. The latter condition is a severe type of glaucoma that may lead to rapid visual field and vision loss, epithelial edema of the cornea with secondary epithelial erosion and predisposition to bacterial keratitis, severe pain, nausea and vomiting, and, eventually, phthisis bulbi (atrophy of the globe with no light perception).

As used herein, a patient (or subject) may be any mammal, including a human, that may have or be afflicted with a neurodegenerative disease or condition, including an ophthalmic disease or disorder, or that may be free of detectable disease. Accordingly, the treatment may be administered to a subject who has an existing disease, or the treatment may be prophylactic, administered to a subject who is at risk for developing the disease or condition. Treating or treatment refers to any indicia of success in the treatment or amelioration of an injury, pathology or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being.

The treatment or amelioration of symptoms can be based on objective or subjective parameters; including the results of a physical examination. Accordingly, the term "treating" includes the administration of the compounds or agents described herein to treat pain, hyperalgesia, allodynia, or nociceptive events and to prevent or delay, to alleviate, or to arrest or inhibit development of the symptoms or conditions associated with pain, hyperalgesia, allodynia, nociceptive events, or other disorders. The term "therapeutic effect" refers to the reduction, elimination, or prevention of the disease, symptoms of the disease, or sequelae of the disease in the subject. Treatment also includes restoring or improving retinal neuronal cell functions (including photoreceptor function) in a vertebrate visual system, for example, such as visual acuity and visual field testing etc., as measured over time (e.g., as measured in weeks or months). Treatment also includes stabilizing disease progression (i.e., slowing, minimizing, or halting the progression of an ophthalmic disease and associated symptoms) and minimizing additional degeneration of a vertebrate visual system. Treatment also includes prophylaxis and refers to the administration of an amine derivative compound to a subject to prevent degeneration or further degeneration or deterioration or further deterioration of the vertebrate visual system of the subject and to prevent or inhibit development of the disease and/or related symptoms and sequelae.

Various methods and techniques practiced by a person skilled in the medical and ophthalmological arts to determine and evaluate a disease state and/or to monitor and assess a therapeutic regimen include, for example, fluorescein angiogram, fundus photography, indocyanine green dye tracking of the choroidal circulatory system, opthalmoscopy, optical coherence tomography (OCT), and visual acuity testing.

A fluorescein angiogram involves injecting a fluorescein dye intravenously and then observing any leakage of the dye as it circulates through the eye. Intravenous injection of indocyanine green dye may also be used to determine if vessels in the eye are compromised, particularly in the choroidal circulatory system that is just behind the retina. Fundus photography may be used for examining the optic nerve, macula, blood vessels, retina, and the vitreous. Microaneurysms are visible lesions in diabetic retinopathy that may be detected in digital fundus images early in the disease (see, e.g., U.S. Patent Application Publication No. 2007/0002275). An ophthalmoscope may be used to examine the retina and vitreous. Opthalmoscopy is usually performed with dilated pupils, to allow the best view inside the eye. Two types of ophthalmoscopes may be used: direct and indirect. The direct ophthalmoscope is generally used to view the optic nerve and the central retina. The periphery, or entire retina, may be viewed by using an indirect ophthalmoscope. Optical coherence tomography (OCT) produces high resolution, high speed, non-invasive, cross-sectional images of body tissue. OCT is noninvasive and provides detection of microscopic early signs of disruption in tissues.

A subject or patient refers to any vertebrate or mammalian patient or subject to whom the compositions described herein can be administered. The term "vertebrate" or "mammal" includes humans and non-human primates, as well as experimental animals such as rabbits, rats, and mice, and other animals, such as domestic pets (such as cats, dogs, horses), farm animals, and zoo animals. Subjects in need of treatment using the methods described herein may be identified according to accepted screening methods in the medical art that are employed to determine risk factors or symptoms associated with an ophthalmic disease or condition described herein or to determine the status of an existing ophthalmic disease or condition in a subject. These and other routine methods allow the clinician to select patients in need of therapy using the methods and formulations described herein.

V. Pharmaceutical Compositions

In certain embodiments, an amine derivative compound may be administered as a pure chemical. In other embodiments, the amine derivative compound can be combined with a pharmaceutical carrier (also referred to herein as a pharmaceutically acceptable excipient (i.e., a pharmaceutically suitable and acceptable carrier, diluent, etc., which is a non-toxic, inert material that does not interfere with the activity of the active ingredient)) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)), the disclosure of which is hereby incorporated herein by reference, in its entirety.

Accordingly, provided herein is a pharmaceutical composition comprising one or more amine derivative compounds, or a stereoisomer, tautomer, prodrug, pharmaceutically acceptable salt, hydrate, solvate, acid salt hydrate, N-oxide or isomorphic crystalline form thereof, of a compound described herein, together with one or more pharmaceutically acceptable carriers and, optionally, other therapeutic and/or prophylactic ingredients. The carrier(s) (or excipient(s)) is acceptable or suitable if the carrier is compatible with the other ingredients of the composition and not deleterious to the recipient (i.e., the subject) of the composition. A pharmaceutically acceptable or suitable composition includes an ophthalmologically suitable or acceptable composition.

In one embodiment is a pharmaceutical composition comprising a pharmaceutically acceptable carrier and a compound of Formula (A) or tautomer, stereoisomer, geometric isomer, or pharmaceutically acceptable solvate, hydrate, salt, N-oxide or prodrug thereof:

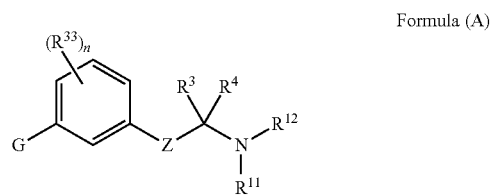

Formula (A)

wherein,

Z is a bond, —C(R$^1$)(R$^2$)—, —C(R$^9$)(R$^{10}$)—C(R$^1$)(R$^2$)—, —X—C(R$^{31}$)(R$^{32}$)—, —C(R$^9$)(R$^{10}$)—C(R$^1$)(R$^2$)—C(R$^{36}$)(R$^{37}$)— or —X—C(R$^{31}$)(R$^{32}$)—C(R$^1$)(R$^2$)—;

X is —O—, —S—, —S(=O)—, —S(=O)$_2$—, —N(R$^{30}$)—, —C(=O)—, —C(=CH$_2$)—, —C(=N—NR$^{35}$)—, or —C(=N—OR$^{35}$)—;

G is selected from —C(R$^{41}$)$_2$—C(R$^{41}$)$_2$—R$^{40}$, —C(R$^{42}$)$_2$—S—R$^{40}$, —C(R$^{42}$)$_2$—SO—R$^{40}$, —C(R$^{42}$)$_2$—SO$_2$—R$^{40}$, —C(R$^{42}$)$_2$—O—R$^{40}$, —C(R$^{42}$)$_2$—N(R$^{42}$)—R$^{40}$, —C(=O)—N(R$^{42}$)—R$^{40}$;

R$^{40}$ is selected from —C(R$^{16}$)(R$^{17}$)(R$^{18}$), aryl, or heteroaryl;

each R$^{41}$ is independently selected from hydrogen, hydroxy, OR$^6$, alkyl, or two R$^{41}$ groups together may form an oxo;

each R$^{42}$ is independently selected from hydrogen or alkyl;

R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;

R$^{31}$ and R$^{32}$ are each independently selected from hydrogen, C$_1$-C$_5$ alkyl, or fluoroalkyl;

R$^{36}$ and R$^{37}$ are each independently selected from hydrogen, halogen, C$_1$-C$_5$ alkyl, fluoroalkyl, —OR$^6$ or —NR$^7$R$^8$; or R$^{36}$ and R$^{37}$ together form an oxo; or optionally, R$^{36}$ and R$^1$ together form a direct bond to provide a double bond; or optionally, R$^{36}$ and R$^1$ together form a direct bond, and R$^{37}$ and R$^2$ together form a direct bond to provide a triple bond;

R$^3$ and R$^4$ are each independently selected from hydrogen, alkyl, alkenyl, fluoroalkyl, aryl, heteroaryl, carbocyclyl or C-attached heterocyclyl; or R$^3$ and R$^4$ together with the carbon atom to which they are attached, form a carbocyclyl or heterocyclyl; or R$^3$ and R$^4$ together form an imino;

R$^7$ and R$^8$ are each independently selected from hydrogen, alkyl, carbocyclyl, heterocyclyl, —C(=O)R$^{13}$, SO$_2$R$^{13}$, CO$_2$R$^{13}$ or SO$_2$NR$^{24}$R$^{25}$; or R$^7$ and R$^8$ together with the nitrogen atom to which they are attached, form an N-heterocyclyl;

R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ form an oxo; or optionally, R$^9$ and R$^1$ together form a direct bond to provide a double bond; or optionally, R$^9$ and R$^1$ together form a direct bond, and R$^{10}$ and R$^2$ together form a direct bond to provide a triple bond;

R$^{11}$ and R$^{12}$ are each independently selected from hydrogen, alkyl, carbocyclyl, —C(=O)R$^{23}$, —C(NH)NH$_2$, SO$_2$R$^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, $OR^{34}$, alkyl, or fluoroalkyl; and n is 0, 1, 2, 3, or 4; with the provision that G is not an unsubstituted normal alkyl and the provision that the compound of Formula A is not:

Various embodiments further provide pharmaceutical compositions comprising a pharmaceutically acceptable excipient and a compound of Formula (I):

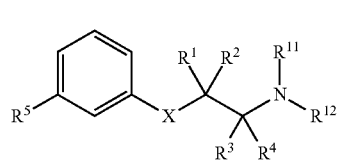

Formula (I)

as a tautomer or a mixture of tautomers, or as a pharmaceutically acceptable salt, hydrate, solvate, N-oxide or prodrug thereof, wherein:

$R^1$ and $R^2$ are each the same or different and independently hydrogen, halogen, $C_1$-$C_5$ alkyl, fluoroalkyl, —$OR^6$, or —$NR^7R^8$; or $R^1$ and $R^2$ form an oxo;

$R^3$ and $R^4$ are each the same or different and independently hydrogen or alkyl;

$R^5$ is $C_5$-$C_{15}$ alkyl, aralkyl, heterocyclylalkyl, heteroarylalkyl or carbocyclylalkyl;

$R^6$ is hydrogen or alkyl;

$R^7$ and $R^8$ are each the same or different and independently hydrogen, alkyl, carbocyclyl, or —C(=O)$R^{13}$; or

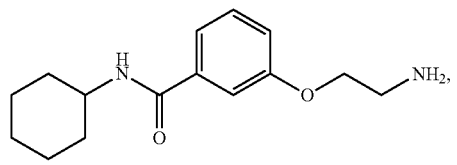
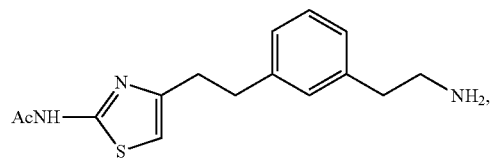
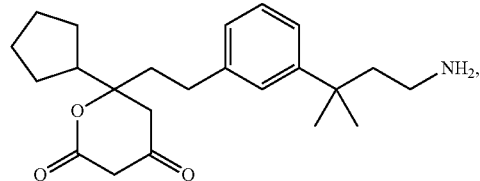
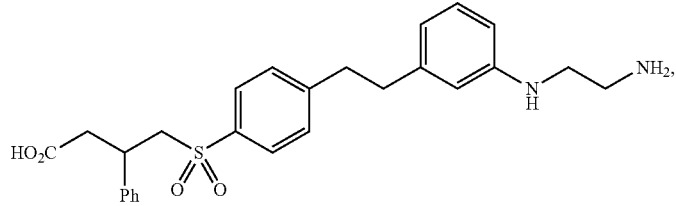
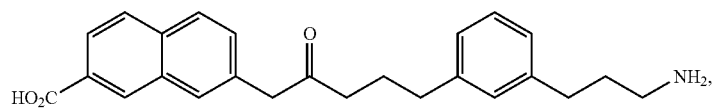
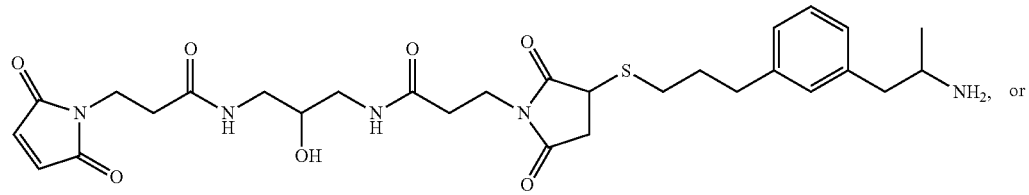, or
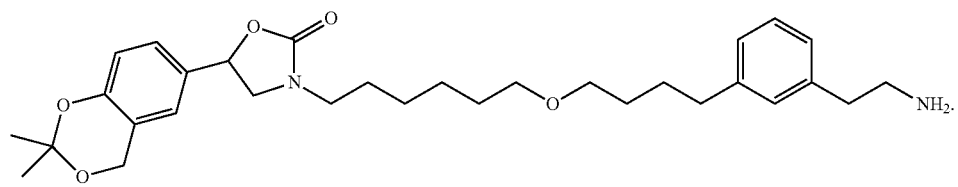.

R$^7$ and R$^8$, together with the nitrogen atom to which they are attached, form an N-heterocyclyl;

X is —C(R$^9$)(R$^{10}$)— or —O—;

R$^9$ and R$^{10}$ are each the same or different and independently hydrogen, halogen, alkyl, fluoroalkyl, —OR$^6$, —NR$^7$R$^8$ or carbocyclyl; or R$^9$ and R$^{10}$ form an oxo;

R$^{11}$ and R$^{12}$ are each the same or different and independently hydrogen, alkyl, or —C(=O)R$^{13}$; or R$^{11}$ and R$^{12}$, together with the nitrogen atom to which they are attached, form an N-heterocyclyl; and R$^{13}$ is alkyl, alkenyl, aryl, carbocyclyl, heteroaryl or heterocyclyl.

A pharmaceutical composition (e.g., for oral administration or delivery by injection, or combined devices, or for application as an eye drop) may be in the form of a liquid or solid. A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampules, disposable syringes or multiple dose vials made of glass or plastic. Physiological saline is commonly used as an excipient, and an injectable pharmaceutical composition or a composition that is delivered ocularly is preferably sterile.

At least one amine derivative compound can be administered to human or other nonhuman vertebrates. In certain embodiments, the compound is substantially pure, in that it contains less than about 5% or less than about 1%, or less than about 0.1%, of other organic small molecules, such as contaminating intermediates or by-products that are created, for example, in one or more of the steps of a synthesis method. In other embodiments, a combination of one or more amine derivative compounds can be administered.

An amine derivative compound can be delivered to a subject by any suitable means, including, for example, orally, parenterally, intraocularly, intravenously, intraperitoneally, intranasally (or other delivery methods to the mucous membranes, for example, of the nose, throat, and bronchial tubes), or by local administration to the eye, or by an intraocular or periocular device. Modes of local administration can include, for example, eye drops, intraocular injection or periocular injection. Periocular injection typically involves injection of the synthetic isomerization inhibitor, i.e., amine derivative compound as described herein, under the conjunctiva or into the Tennon's space (beneath the fibrous tissue overlying the eye). Intraocular injection typically involves injection of the amine derivative compound into the vitreous. In certain embodiments, the administration is non-invasive, such as by eye drops or oral dosage form, or as a combined device.

An amine derivative compound can be formulated for administration using pharmaceutically acceptable (suitable) carriers or vehicles as well as techniques routinely used in the art. A pharmaceutically acceptable or suitable carrier includes an ophthalmologically suitable or acceptable carrier. A carrier is selected according to the solubility of the amine derivative compound. Suitable ophthalmological compositions include those that are administrable locally to the eye, such as by eye drops, injection or the like. In the case of eye drops, the formulation can also optionally include, for example, ophthalmologically compatible agents such as isotonizing agents such as sodium chloride, concentrated glycerin, and the like; buffering agents such as sodium phosphate, sodium acetate, and the like; surfactants such as polyoxyethylene sorbitan mono-oleate (also referred to as Polysorbate 80), polyoxyl stearate 40, polyoxyethylene hydrogenated castor oil, and the like; stabilization agents such as sodium citrate, sodium edentate, and the like; preservatives such as benzalkonium chloride, parabens, and the like; and other ingredients. Preservatives can be employed, for example, at a level of from about 0.001 to about 1.0% weight/volume. The pH of the formulation is usually within the range acceptable to ophthalmologic formulations, such as within the range of about pH 4 to 8, or pH 5 to 7, or pH 6 to 7, or pH 4 to 7, or pH 5 to 8, or pH 6 to 8, or pH 4 to 6, or pH 5 to 6, or pH 7 to 8.

In additional embodiments, the compositions described herein further comprise cyclodextrins. Cyclodextrins are cyclic oligosaccharides containing 6, 7, or 8 glucopyranose units, referred to as α-cyclodextrin, β-cyclodextrin, or γ-cyclodextrin respectively. Cyclodextrins have been found to be particularly useful in pharmaceutical formulations. Cyclodextrins have a hydrophilic exterior, which enhances water-soluble, and a hydrophobic interior which forms a cavity. In an aqueous environment, hydrophobic portions of other molecules often enter the hydrophobic cavity of cyclodextrin to form inclusion compounds. Additionally, cyclodextrins are also capable of other types of nonbonding interactions with molecules that are not inside the hydrophobic cavity. Cyclodextrins have three free hydroxyl groups for each glucopyranose unit, or 18 hydroxyl groups on α-cyclodextrin, 21 hydroxyl groups on β-cyclodextrin, and 24 hydroxyl groups on γ-cyclodextrin. One or more of these hydroxyl groups can be reacted with any of a number of reagents to form a large variety of cyclodextrin derivatives. Some of the more common derivatives of cyclodextrin are hydroxypropyl ethers, sulfonates, and sulfoalkylethers. Shown below is the structure of β-cyclodextrin and the hydroxypropyl-β-cyclodextrin (HPβCD).

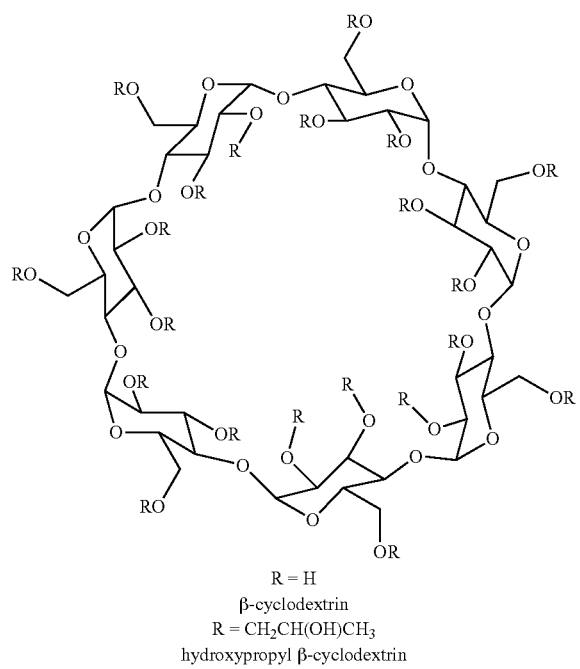

R = H
β-cyclodextrin
R = CH$_2$CH(OH)CH$_3$
hydroxypropyl β-cyclodextrin

The use of cyclodextrins in pharmaceutical compositions is well known in the art as cyclodextrins and cyclodextrin derivatives are often used to improve the solubility of a drug.

Inclusion compounds are involved in many cases of enhanced solubility; however other interactions between cyclodextrins and insoluble compounds can also improve solubility. Hydroxypropyl-β-cyclodextrin (HPβCD) is commercially available as a pyrogen free product. It is a nonhygroscopic white powder that readily dissolves in water. HPβCD is thermally stable and does not degrade at neutral pH.

Ophthalmic formulations utilizing cyclodextrins have been disclosed. For example, U.S. Pat. No. 5,227,372 discloses methods related to retaining ophthalmological agents in ocular tissues. US Patent Application Publication 2007/0149480 teaches the use of cyclodextrins to prepare ophthalmic formulations of a small molecule kinase inhibitor with poor water solubility.

The concentration of the cyclodextrin used in the compositions and methods disclosed herein can vary according to the physiochemical properties, pharmacokinetic properties, side effect or adverse events, formulation considerations, or other factors associated with the therapeutically active agent, or a salt or prodrug thereof. The properties of other excipients in a composition may also be important. Thus, the concentration or amount of cyclodextrin used in accordance with the compositions and methods disclosed herein can vary. In certain compositions, the concentration of the cyclodextrin is from 10% to 25%.

For injection, the amine derivative compound can be provided in an injection grade saline solution, in the form of an injectable liposome solution, slow-release polymer system or the like. Intraocular and periocular injections are known to those skilled in the art and are described in numerous publications including, for example, Spaeth, Ed., *Ophthalmic Surgery: Principles of Practice*, W. B. Sanders Co., Philadelphia, Pa., 85-87, 1990.

For delivery of a composition comprising at least one of the compounds described herein via a mucosal route, which includes delivery to the nasal passages, throat, and airways, the composition may be delivered in the form of an aerosol. The compound may be in a liquid or powder form for intramucosal delivery. For example, the composition may be delivered via a pressurized aerosol container with a suitable propellant, such as a hydrocarbon propellant (e.g., propane, butane, isobutene). The composition may be delivered via a non-pressurized delivery system such as a nebulizer or atomizer.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The amine derivative compounds described herein may be formulated for sustained or slow-release. Such compositions may generally be prepared using well known technology and administered by, for example, oral, periocular, intraocular, rectal or subcutaneous implantation, or by implantation at the desired target site. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained-release formulation depends upon the site of implantation, the rate and expected duration of release, and the nature of the condition to be treated or prevented.

Systemic drug absorption of a drug or composition administered via an ocular route is known to those skilled in the art (see, e.g., Lee et al., *Int. J. Pharm.* 233:1-18 (2002)). In one embodiment, an amine derivative compound is delivered by a topical ocular delivery method (see, e.g., *Curr. Drug Metab.* 4:213-22 (2003)). The composition may be in the form of an eye drop, salve, or ointment or the like, such as, aqueous eye drops, aqueous ophthalmic suspensions, non-aqueous eye drops, and non-aqueous ophthalmic suspensions, gels, ophthalmic ointments, etc. For preparing a gel, for example, carboxyvinyl polymer, methyl cellulose, sodium alginate, hydroxypropyl cellulose, ethylene maleic anhydride polymer and the like can be used.

The dose of the composition comprising at least one of the amine derivative compounds described herein may differ, depending upon the patient's (e.g., human) condition, that is, stage of the disease, general health status, age, and other factors that a person skilled in the medical art will use to determine dose. When the composition is used as eye drops, for example, one to several drops per unit dose, preferably 1 or 2 drops (about 50 µl per 1 drop), may be applied about 1 to about 6 times daily.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with neurodegeneration of retinal neuronal cells and/or degeneration of other mature retinal cells such as RPE cells. Optimal doses may generally be determined using experimental models and/or clinical trials. The optimal dose may depend upon the body mass, weight, or blood volume of the patient.

The doses of the amine derivative compounds can be suitably selected depending on the clinical status, condition and age of the subject, dosage form and the like. In the case of eye drops, an amine derivative compound can be administered, for example, from about 0.01 mg, about 0.1 mg, or about 1 mg, to about 25 mg, to about 50 mg, to about 90 mg per single dose. Eye drops can be administered one or more times per day, as needed. In the case of injections, suitable doses can be, for example, about 0.0001 mg, about 0.001 mg, about 0.01 mg, or about 0.1 mg to about 10 mg, to about 25 mg, to about 50 mg, or to about 90 mg of the amine derivative compound, one to seven times per week. In other embodiments, about 1.0 to about 30 mg of the amine derivative compound can be administered one to seven times per week.

Oral doses can typically range from 1.0 to 1000 mg, one to four times, or more, per day. An exemplary dosing range for oral administration is from 10 to 250 mg one to three times per day. If the composition is a liquid formulation, the composition comprises at least 0.1% active compound at particular mass or weight (e.g., from 1.0 to 1000 mg) per unit volume of carrier, for example, from about 2% to about 60%.

In certain embodiments, at least one amine derivative compound described herein may be administered under conditions and at a time that inhibits or prevents dark adaptation of rod photoreceptor cells. In certain embodiments, the compound is administered to a subject at least 30 minutes (half hour), 60 minutes (one hour), 90 minutes (1.5 hour), or 120 minutes (2 hours) prior to sleeping. In certain embodiments, the compound may be administered at night before the subject sleeps. In other embodiments, a light stimulus may be blocked or removed during the day or under normal light conditions by placing the subject in an environment in which light is removed, such as placing the subject in a darkened room or by applying an eye mask over the eyes of the subject. When the light stimulus is removed in such a manner or by other means contemplated in the art, the agent may be administered prior to sleeping.

The doses of the compounds that may be administered to prevent or inhibit dark adaptation of a rod photoreceptor cell can be suitably selected depending on the clinical status, condition and age of the subject, dosage form and the like. In the case of eye drops, the compound (or the composition comprising the compound) can be administered, for example, from about 0.01 mg, about 0.1 mg, or about 1 mg, to about 25 mg, to about 50 mg, to about 90 mg per single dose. In the case of injections, suitable doses can be, for example, about 0.0001 mg, about 0.001 mg, about 0.01 mg, or about 0.1 mg to about 10 mg, to about 25 mg, to about 50 mg, or to about 90 mg of the compound, administered any number of days between one to seven days per week prior to sleeping or prior to removing the subject from all light sources. In certain other embodiments, for administration of the compound by eye drops or injection, the dose is between 1-10 mg (compound)/kg (body weight of subject) (i.e., for example, 80-800 mg total per dose for a subject weighing 80 kg). In other embodiments, about 1.0 to about 30 mg of compound can be administered one to seven times per week. Oral doses can typically range from about 1.0 to about 1000 mg, administered any number of days between one to seven days per week. An exemplary dosing range for oral administration is from about 10 to about 800 mg once per day prior to sleeping. In other embodiments, the composition may be delivered by intravitreal administration.

Also provided are methods of manufacturing the compounds and pharmaceutical compositions described herein. A composition comprising a pharmaceutically acceptable excipient or carrier and at least one of the amine derivative compounds described herein may be prepared by synthesizing the compound according to any one of the methods described herein or practiced in the art and then formulating the compound with a pharmaceutically acceptable carrier. Formulation of the composition will be appropriate and dependent on several factors, including but not limited to, the delivery route, dose, and stability of the compound.

Other embodiments and uses will be apparent to one skilled in the art in light of the present disclosures. The following examples are provided merely as illustrative of various embodiments and shall not be construed to limit the invention in any way.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Unless otherwise noted, reagents and solvents were used as received from commercial suppliers. Anhydrous solvents and oven-dried glassware were used for synthetic transformations sensitive to moisture and/or oxygen. Flash column chromatography and thin layer chromatography (TLC) were performed on silica gel unless otherwise noted. Proton and carbon nuclear magnetic resonance spectra were obtained with a Varian VnmrS 400 at 400 MHz for proton and 100 MHz for carbon, or with a Bruker AMX 500 or 300 spectrometers at 500 or 300 MHz for proton and 125 or 75 MHz for carbon, as noted. Spectra are given in ppm ($\delta$) and coupling constants, J, are reported in Hertz. For proton spectra either tetramethylsilane was used as an internal standard or the solvent peak was used as the reference peak. For carbon spectra the solvent peak was used as the reference. Chiral HPLC analysis was performed using a Chiralpak IA column (4.6 mm×250 mm, 5µ) with diode array detection. The flow rate was 1 mL/min.

Analytical HPLC Methods

HPLC analyses were obtained using a Hypersil BDS C18 column (250×4.6 mm, Phenomenex) with detection at 254 nm using a standard solvent gradient program (Method 1).

Analytical HPLC Method 1

| Time (min) | Flow (mL/min) | % A | % B |
| --- | --- | --- | --- |
| 0.0 | 1.0 | 70.0 | 30.0 |
| 15.0 | 1.0 | 0.0 | 100.0 |
| 20.0 | 1.0 | 0.0 | 100.0 |

A = Water with 0.05% Trifluoroacetic Acid
B = Acetonitrile with 0.05% Trifluoroacetic Acid Analytical HPLC Method 2

| Time (min) | Flow (mL/min) | % A | % B |
| --- | --- | --- | --- |
| 0.0 | 1.0 | 90.0 | 10.0 |
| 10.0 | 1.0 | 5.0 | 95.0 |

A = Water with 0.05% Trifluoroacetic Acid
B = Acetonitrile with 0.05% Trifluoroacetic Acid
Column = Gemini C18, 4.6 × 150 mm, 5µ

Preparative HPLC Methods

Preparative HPLC was performed using a YMC ODA-A column (500 mm×30 mm×10µ) at ambient temperature with detection at 220 nm using an injection volume of 5 mL and a standard solvent gradient program (Method 1P or 2P).

Preparative HPLC Method 1P

| Time (min) | Flow (mL/min) | % A | % B |
|---|---|---|---|
| 0.0 | 30 | 90 | 10 |
| 5.0 | 30 | 90 | 10 |
| 25 | 30 | 20 | 80 |
| 35 | 30 | 20 | 80 |

A = Water with 0.05% Trifluoroacetic Acid
B = Acetonitrile with 0.05% Trifluoroacetic Acid

*Preparative HPLC Method 2P

| Time (min) | Flow | % A | % B |
|---|---|---|---|
| 0.0 | 30 | 90 | 10 |
| 5.0 | 30 | 90 | 10 |
| 25 | 30 | 20 | 80 |
| 35 | 30 | 20 | 80 |

A = Water
B = Acetonitrile

Preparative HPLC Method 3P

| Time (min) | Flow (mL/min) | % A | % B |
|---|---|---|---|
| 0.0 | 30 | 50 | 50 |
| 5.0 | 30 | 50 | 50 |
| 25 | 30 | 0 | 100 |
| 35 | 30 | 0 | 100 |

A = Water with 0.05% Trifluoroacetic Acid
B = Acetonitrile with 0.05% Trifluoroacetic Acid Solvents for sample preparation: Methanol, Acetonitrile, Acetonitrile:Methanol(1:1)

Preparative HPLC Method 3P

| Time (min) | Flow (mL/min) | % A | % B |
|---|---|---|---|
| 0.0 | 30 | 90 | 10 |
| 5.0 | 30 | 90 | 10 |
| 25 | 30 | 20 | 80 |
| 35 | 30 | 20 | 80 |

A = Water
B = Acetonitrile

Solvents for sample preparation: Methanol, Acetonitrile, Acetonitrile:Methanol(1:1)

Example 1

Preparation of 3-(3-(2,6-Dimethylphenethyl)Phenyl)Propan-1-Amine

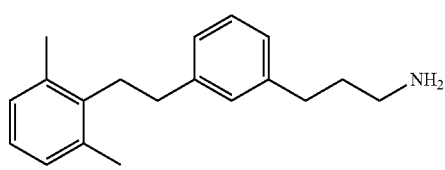 [SMILES: Cc1cccc(C)c1CCc1cccc(CCCN)c1]

3-(3-(2,6-Dimethylphenethyl)phenyl)propan-1-amine was prepared following the method shown in Scheme 1.

SCHEME 1

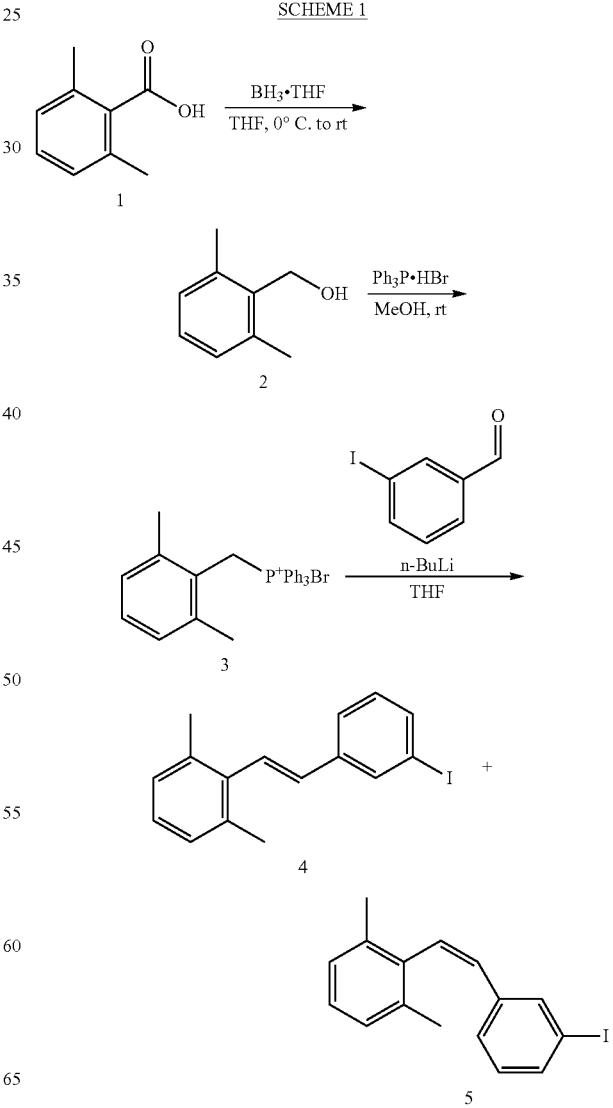

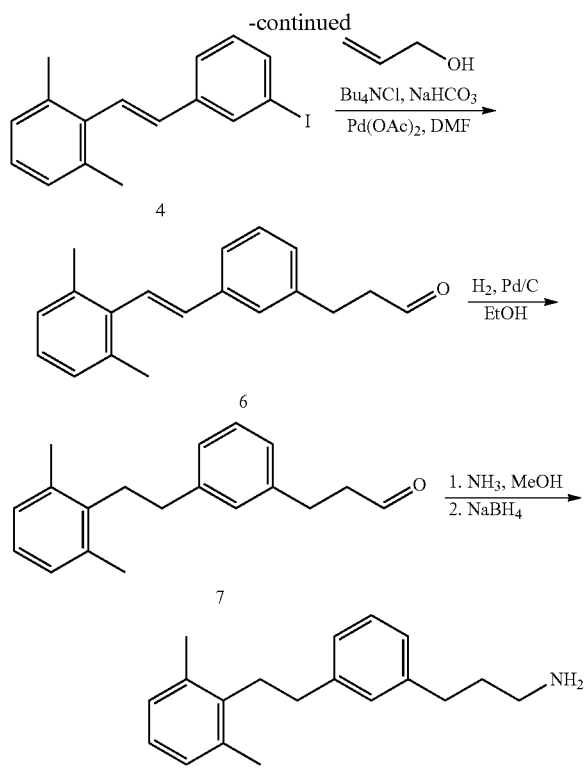

Step 1: To a stirred solution of 2,6-dimethylbenzoic acid (1) (10.0 g, 66.6 mmol) in THF (100 mL) at 0° C. was added borane-THF complex (80 mL of a 1M solution in THF, 80.0 mmol) dropwise over 20 min and then the reaction mixture was warmed to room temperature. After 64 h the reaction mixture was quenched by slow addition of MeOH (70 mL) and the resulting solution was concentrated under reduced pressure. The residue was suspended in EtOAc (300 mL) and washed with water and brine. The organic layer was dried over $Na_2SO_4$ and concentrated under reduced pressure to give alcohol 2 as a white solid. Yield (9.10 g, >99%): $^1$H NMR (500 MHz, CDCl$_3$) δ 7.03-7.13 (m, 3H), 4.74 (d, J=5.1 Hz, 2H), 2.43 (s, 6H), 1.28 (t, J=5.2 Hz, 1H); ESI MS m/z 119 [M+H−H$_2$O]$^+$.

Step 2: To a stirred solution of triphenylphosphine hydrobromide (22.0 g, 64.0 mmol) in MeOH (80 mL) was added a solution of alcohol 2 (8.72 g, 64.0 mmol) in MeOH (70 mL) and the reaction mixture was stirred at room temperature for 48 h. The reaction solution was concentrated under reduced pressure and the residue was triturated with a mixture of acetone (20 mL) and diethyl ether (50 mL). The precipitate was collected by vacuum filtration, washed with diethyl ether (30 mL) and hexanes (30 mL), and concentrated under reduced pressure to provide triphenylphosphine salt 3 as a white solid. Yield (23.0 g, 78%): mp 240-246° C. $^1$H NMR (300 MHz, DMSO-d$_6$) δ 7.51-7.95 (m, 15H), 7.15 (dt, J=7.7, 2.6 Hz, 1H), 6.96 (d, J=7.7 Hz, 2H), 4.94 (d, J=14.6 Hz, 2H), 1.76 (s, 6H); ESI MS m/z 381 [M−Br]$^+$; HPLC (Method 1) 97.0% (AUC), t$_R$=13.78 min.

Step 3: To a stirred suspension of triphenylphosphine salt 3 (8.76 g, 19.0 mmol) in THF (60 mL) at −78° C. was added n-butyl lithium (7.8 mL, 2.5M solution in hexanes, 19.5 mmol) and the reaction mixture was warmed to room temperature. After 30 min the reaction mixture was again cooled to −78° C., a solution of 3-iodobenzaldehyde (4.41 g, 19.0 mmol) in THF (15 mL) was added, and the reaction mixture was warmed to room temperature. After 1 h, the reaction was quenched with saturated aqueous NH$_4$Cl (50 mL) and extracted with EtOAc. The combined organic layers were concentrated under reduced pressure and the resulting residue was dissolved in MeOH (70 mL). The MeOH solution was partitioned between hexanes and water. The combined organics were washed with 70% MeOH-water (100 mL), dried over Na$_2$SO$_4$ and concentrated under reduced pressure. The residue was purified by flash chromatography (100% hexanes) to give trans-alkene 4 (2.12 g, 33%) as a white solid and cis-alkene 5 (1.15 g, 18%) as a colorless oil. 4: $^1$H NMR (500 MHz, CDCl$_3$) δ 7.84 (s, 1H), 7.59 (d, J=7.7 Hz, 1H), 7.44 (d, J=7.7 Hz, 1H), 7.06-7.10 (m, 5H), 6.49 (d, J=16.6 Hz, 1H), 2.35 (s, 6H). 5: $^1$H NMR (500 MHz, CDCl$_3$) δ 7.44 (d, J=7.8 Hz, 1H), 7.37 (s, 1H), 7.13 (t, J=7.5 Hz, 1H), 7.04 (d, J=7.6 Hz, 2H), 6.88 (d, J=7.9 Hz, 1H), 6.81 (t, J=7.8 Hz, 1H), 6.59 (d, J=12.2 Hz, 1H), 6.53 (d, J=12.2 Hz, 1H), 2.14 (s, 6H).

Step 4: To a stirred solution of trans-alkene 4 (1.86 g, 5.60 mmol) in DMF (5 mL) was added NaHCO$_3$ (1.49 g, 17.7 mmol), tetrabutylammonium chloride (1.58 g, 5.70 mmol), and allyl alcohol (0.683 g, 11.8 mmol). The reaction flask was purged with nitrogen for 10 min then Pd(OAc)$_2$ (0.029 g, 0.130 mmol) was added. After purging with nitrogen for an additional 10 min the solution was stirred under nitrogen at room temperature. After 18 h the solution was diluted with EtOAc (50 mL) and the resulting mixture was washed with water, 5% aqueous LiCl solution, and brine. The organics were dried over MgSO$_4$ and concentrated under reduced pressure to afford a dark oil. Purification by flash chromatography (0 to 20% EtOAc-hexanes gradient) provided aldehyde 6 as a colorless oil. Yield 1.05 g (71%): $^1$H NMR (500 MHz, CDCl$_3$) δ 9.85 (t, J=1.1 Hz, 1H), 7.39 (d, J=7.8 Hz, 1H), 7.29-7.32 (m, 2H), 7.07-7.12 (m, 5H), 6.57 (d, J=16.6 Hz, 1H), 2.99 (t, J=7.6 Hz, 2H), 2.38-2.84 (m, 2H), 2.37 (s, 6H).

Step 5: To a solution of aldehyde 6 (0.200 g, 0.76 mmol) in EtOH (15 mL) under nitrogen in a Parr flask was added 10% Pd/C (50% wet, 0.020 g). The flask was pressurized with hydrogen gas to 30 PSI and the mixture was shaken for 1.5 h. The reaction mixture was filtered over diatomaceous earth, the filter cake washed with EtOH (50 mL), and the filtrate concentrated under reduced pressure to a yellow residue. Purification by flash chromatography (0 to 20% EtOAc-hexanes) afforded aldehyde 7 as a yellow oil. Yield (0.100 g, 50%): $^1$H NMR (500 MHz, CDCl$_3$) δ 9.82 (t, J=1.4 Hz, 1H), 7.23 (d, J=7.5 Hz, 1H), 7.09 (d, J=7.6 Hz, 1H), 7.00-7.06 (m, 5H), 2.88-2.95 (m, 4H), 2.71-2.78 (m, 4H), 2.32 (s, 6H).

Step 6: To a stirred solution of aldehyde 7 (0.100 g, 0.38 mmol) in MeOH (5 mL) was added 7M NH$_3$ in MeOH (1 mL) and a small scoop of powdered molecular sieves. The flask was stoppered and stirred for 1.5 h, at which time NaBH$_4$ (0.022 g, 0.58 mmol) was added. The solution was stirred for an additional 3 h, filtered over diatomaceous earth, the filter cake rinsed with MeOH (50 mL) and the filtrate concentrated under reduced pressure. Purification of the resulting residue by flash chromatography (5% 7 M NH$_3$ in MeOH—CH$_2$Cl$_2$) gave 3-(3-(2,6-dimethylphenethyl)phenyl)propan-1-amine as a free base. Yield (0.050 g, 50%). The free base was converted to the HCl salt by the following procedure: To a stirred solution of 3-(3-(2,6-dimethylphenethyl)phenyl)propan-1-amine (0.050 g, 0.17 mmol) in diethyl ether (2 mL) was added 1N HCl in ether (0.2 mL, 0.2 mmol). After stirring for 1 h, the solid was collected by filtration and dried under vacuum to give Example 1 hydrochloride as a white solid. Yield (0.022 g, 42%): mp 106-108° C.; $^1$H NMR (500 MHz, CD$_3$OD) δ 7.22 (d, J=7.5 Hz, 1H), 7.06 (d, J=7.4 Hz, 2H), 6.99-6.96 (m, 4H), 2.89-2.92 (m, 4H), 2.72-2.75 (m, 2H), 2.67 (t, J=7.5 Hz, 2H), 2.26 (s, 6H), 1.93 (t, J=7.7 Hz, 2H);

$^{13}$C NMR (75 MHz, CD$_3$OD) δ 143.8, 141.7, 139.3, 127.1, 129.7, 129.6, 129.1, 127.6, 127.0, 126.9; ESI MS m/z 268 [M+H]$^+$; HPLC (Method 1) 98.9% (AUC), t$_R$=11.77 min. HRMS calcd for C$_{19}$H$_{25}$N [M+H]: 268.2065, Found: 268.2064.

Example 2

Preparation of 1-(3-(3-Aminopropyl)Phenyl)-3-Ethylpentan-3-ol

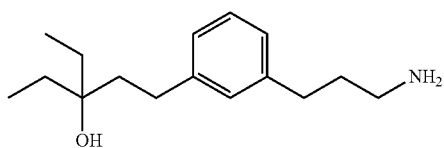 [SMILES: CCC(O)(CC)CCc1cccc(CCCN)c1]

1-(3-(3-Aminopropyl)phenyl)-3-ethylpentan-3-ol was prepared following the method shown in scheme 2:

SCHEME 2

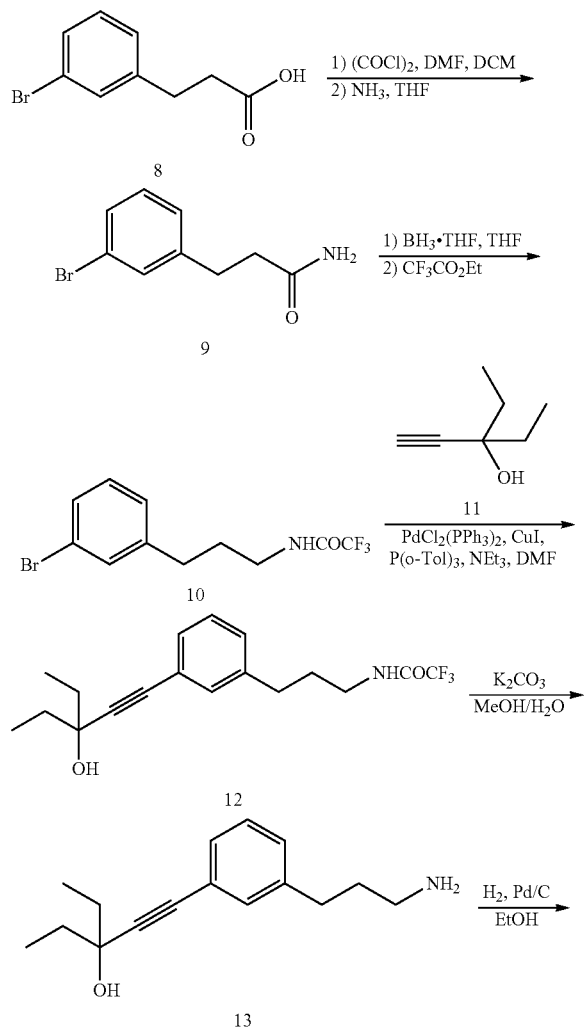

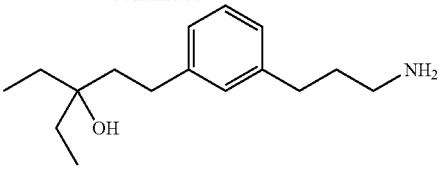

Step 1: To a stirred solution of 3-(3-bromophenyl)propanoic acid (8) (25.0 g, 109.1 mmole) in CH$_2$Cl$_2$ (150 ml) was added oxalyl chloride (27.7 g, 218.3 mmol) followed by DMF (2 drops). The solution was stirred at room temperature overnight. The mixture was concentrated under reduced pressure to give the crude acid chloride which was used immediately in the next reaction.

Step 2: The crude acid chloride was dissolved in anhydrous THF (150 ml) and cooled in an ice bath. Ammonia gas was bubbled into the solution for 3-4 minutes and the mixture was warmed to room temperature and stirred overnight. The mixture was concentrated under reduced pressure and the residue was partitioned between saturated aqueous NaHCO$_3$ and EtOAc. The combined organics were dried over Na$_2$SO$_4$ and concentrated under reduced pressure to give amide 9 as a white solid. Yield (23.9 g, 96%): $^1$H NMR (400 MHz, DMSO-d$_6$) δ 7.40 (s, 1H), 7.35 (dt, J=6.4, 2.4 Hz, 1H), 7.26 (br s, 1H), 7.18-7.24 (m, 2H), 6.75 (br s, 1H), 2.78 (t, J=7.6 Hz, 2H), 2.34 (t, J=7.6 Hz, 2H).

Step 3: To an ice-cold, stirred solution of amide 9 (23.85 g, 104.6 mmole) in THF (250 ml) was added BH$_3$-THF (209 ml of a 1.0 M solution in THF, 209 mmol). The solution was warmed to room temperature and stirred for 18 h. The reaction was quenched by the slow addition of 6N HCl until pH 1 was achieved. The solution was stirred at room temperature for 4 h then the pH was adjusted to >10 with the addition of 50% aqueous NaOH. The solution was extracted with EtOAc and the combined organic layers were washed with brine, dried over Na$_2$SO$_4$ and concentrated under reduced pressure to give crude 3-(3-bromophenyl)propan-1-amine which was used immediately in the next reaction.

Step 4: Crude 3-(3-bromophenyl)propan-1-amine (ca. 104.6 mmol) was stirred with ethyl trifluoroacetate (30 ml) overnight. The mixture was concentrated under reduced pressure. Purification by flash chromatography (20% EtOAc-hexanes) gave trifluoroacetamide 10. Yield (21.1 g, 62%): $^1$H NMR (400 MHz, DMSO-d$_6$) δ 9.40 (br s, 1H), 7.43 (s, 1H), 7.36 (dt, J=7.2, 2.0 Hz, 1H), 7.19-7.25 (m, 2H), 3.16 (q, J=6.8 Hz, 2H), 2.57 (t, J=7.6 Hz, 2H), 1.77 (quint, J=7.2 Hz, 2H).

Step 5: To a degassed solution of N-(3-(3-bromophenyl)propyl)-2,2,2-trifluoroacetamide (10) (0.930 g, 3 mmol) and 3-ethylpent-1-yn-3-ol (11) (0.670 g, 6 mmol) in triethylamine (4 mL) and DMF (12 mL) was added PdCl$_2$(PPh$_3$)$_2$ (0.053 g, 0.075 mmol), P(o-Tol)$_3$ (0.046 g, 0.15 mmol), and CuI (0.014 g, 0.075 mmol). The resulting mixture was degassed and stirred under argon at 90° C. for 6 h. The mixture was cooled to room temperature then concentrated under reduced pressure and diluted with EtOAc (100 mL) and water (70 mL). After vigorous shaking, the layers were separated. The organic layer was treated with charcoal, dried over MgSO$_4$, filtered, and evaporated under reduced pressure. Purification by flash chromatography (7 to 60% EtOAc-hexanes gradient) gave N-(3-(3-(3-ethyl-3-hydroxypentyl)phenyl)propyl)-2,2,2-trifluoroacetamide (12) as a yellow oil. Yield (0.663 g, 65%): $^1$H NMR (400 MHz, DMSO-d$_6$) δ 9.40 (s, 1H), 7.17-7.28 (m, 4H), 3.16 (q, J=7.2 Hz, 2H), 2.56 (t, J=7.2 Hz, 2H), 1.76 (quint, J=7.2 Hz, 2H), 1.53-1.67 (m, 4H), 0.97 (t, J=7.2 Hz, 6H).

Step 6: N-(3-(3-(3-ethyl-3-hydroxypentyl)phenyl)propyl)-2,2,2-trifluoroacetamide (12) (0.660 g, 1.93 mmol) was dissolved in MeOH (15 mL), and an aqueous solution of K$_2$CO$_3$ (0.42 g/3 mL) was added. The resulting mixture was stirred at 45° C. for 4 h. After cooling to room temperature, the reaction mixture was concentrated under reduced pressure then partitioned between EtOAc (50 mL) and water (50 mL). The combined organics were dried over Na$_2$SO$_4$, and concentrated under reduced pressure. Purification by flash chromatography (80 to 100% (9:1 EtOAc: 7M NH$_3$ in MeOH): hexanes gradient) gave 1-(3-(3-aminopropyl)phenyl)-3-ethylpent-1-yn-3-ol (13) as a light yellow oil. Yield (0.421 g, 89%): $^1$H NMR (400 MHz, DMSO-d$_6$) δ 7.15-7.26 (m, 4H), 5.11 (s, 1H), 2.56 (t, J=7.6 Hz, 2H), 2.47 (t, J=5.2 Hz, 2H), 1.55-1.65 (m, 6H), 1.39 (br s, 2H), 0.97 (t, J=7.6 Hz, 6H).

Step 7: A degassed solution of 1-(3-(3-aminopropyl)phenyl)-3-ethylpent-1-yn-3-ol (13, 0.130 g, 0.53 mmol) in EtOH was stirred with a catalytic amount of 10% Pd/C under hydrogen atmosphere (atmospheric pressure) for 16 h. Filtration through a 0.45 μm membrane filter and concentration under reduced pressure gave Example 2 as a clear oil. Yield (0.120 g, 91%): $^1$H NMR (400 MHz, DMSO-d$_6$) δ 7.13 (t, J=7.6 Hz, 1H), 6.93-6.99 (m, 3H), 3.91 (br s, 1H), 2.45-2.56 (m, 6H), 1.50-1.62 (m, 4H), 1.40 (br s, 2H), 1.38 (q, J=7.6 Hz, 4H), 0.79 (t, J=7.6 Hz, 6H).

Example 3

Preparation of 4-(3-(3-Aminopropyl)Phenethyl)Heptan-4-ol

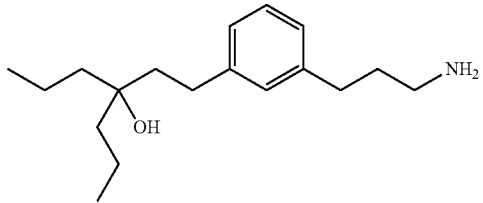 [SMILES: CCCC(O)(CCC)CCc1cccc(CCCN)c1]

4-(3-(3-Aminopropyl)phenethyl)heptan-4-ol was prepared following the method used in Example 2.

Step 1: To a degassed solution of N-(3-(3-bromophenyl)propyl)-2,2,2-trifluoroacetamide (10) (2.29 g, 7.4 mmol) and 4-ethynylheptan-4-ol (2.4 g, 18.5 mmol) in triethylamine (2 mL) and DMF (18 mL) was added PdCl$_2$(PPh$_3$)$_2$ (0.130 g, 0.185 mmol), P(o-Tol)$_3$ (0.113 g, 0.37 mmol), and CuI (0.070 g, 0.37 mmol). The resulting mixture was degassed and stirred under argon at 90° C. overnight. The mixture was cooled to room temperature and the solids were removed by filtration through Celite. The filtrate was partitioned between diethyl ether and water and the combined organics were washed with brine, dried over Na$_2$SO$_4$ and concentrated under reduced pressure. Purification by flash chromatography (6 to 50% EtOAc-hexanes gradient) gave N-(3-(3-(3-ethyl-3-hydroxypentyl)phenyl)propyl)-2,2,2-trifluoroacetamide (12) as an amber oil. Yield (2.6 g, 95%): $^1$H NMR (400 MHz, DMSO-d$_6$) δ 9.40 (s, 1H), 7.18-7.29 (m, 4H), 3.16 (q, J=7.2 Hz, 2H), 2.56 (t, J=7.2 Hz, 2H), 1.76 (quint, J=7.2 Hz, 2H), 1.53-1.67 (m, 8H), 0.97 (t, J=7.2 Hz, 6H).

Step 2: To a solution of 2,2,2-trifluoro-N-(3-(3-(3-hydroxy-3-propylhex-1-ynyl)phenyl)propyl)acetamide (2.6 g, 7.0 mmol) in MeOH (50 mL) was added concentrated aqueous NH$_4$OH (ca. 25 mL) and the solution was stirred at room temperature overnight. More concentrated aqueous NH$_4$OH (5 mL) was added and the mixture was stirred overnight. The volatiles were removed by concentration under reduced pressure and the residue was extracted twice with EtOAc. The organic solution was washed with water and brine, dried over Na$_2$SO$_4$ and concentrated under reduced pressure. Purification by flash chromatography (0 to 20% (20% 7M NH$_3$ in MeOH-EtOAc)-EtOAc gradient) gave 4-((3-(3-aminopropyl)phenyl)ethynyl)heptan-4-ol as a clear oil. Yield (1.58 g, 83%): $^1$H NMR (400 MHz, DMSO-d$_6$) δ 7.14-7.26 (m, 4H), 5.12 (s, 1H), 2.56 (t, J=7.2 Hz, 2H), 2.47 (t obs, J=7.2 Hz, 2H), 1.42-1.63 (m, 12H), 0.90 (t, J=7.2 Hz, 6H).

Step 3: Hydrogenation of 4-(3-(3-aminopropyl)styryl)heptan-4-ol following the method used in Example 2, except that the reaction was run over 2 h, gave Example 3 as a clear oil. Yield (0.2516 g, 50%): $^1$H NMR (400 MHz, CD$_3$OD) δ 7.15 (t, J=7.2 Hz, 1H), 6.98-7.02 (m, 3H), 2.55-2.67 (m, 6H), 1.77 (quint, J=7.6 Hz, 2H), 1.67 (dt, J=8.0, 4.4 Hz, 2H), 1.43-1.49 (m, 4H), 1.31-1.42 (m, 4H), 0.93 (t, J=7.2, 6H).

Example 4

Preparation of 4-(3-(3-Aminopropyl)Phenyl)-2-Methylbutan-2-ol

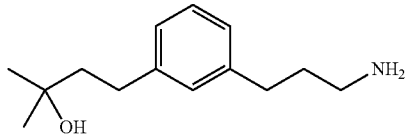 [SMILES: CC(C)(O)CCc1cccc(CCCN)c1]

4-(3-(3-Aminopropyl)phenyl)-2-methylbutan-2-ol was prepared following the method used in Example 2.

Step 1: Coupling of 2-methylbut-3-yn-2-ol with bromide 10 in THF at 70° C. without the use of tri-o-tolylphosphine gave 2,2,2-trifluoro-N-(3-(3-(3-hydroxy-3-methylbut-1-ynyl)phenyl)propyl)acetamide. Yield (0.5 g, 81%): $^1$H NMR (400 MHz, DMSO-d$_6$) δ 9.40 (br s, 1H), 7.17-7.28 (m, 4H), 3.16 (q, J=7.2 Hz, 2H), 2.56 (t, J=7.2 Hz, 2H), 1.76 (quint, J=7.6 Hz, 2H), 1.44 (s, 3H), 1.35 (s, 3H).

Step 2: Deprotection of 2,2,2-trifluoro-N-(3-(3-(3-hydroxy-3-methylbut-1-ynyl)phenyl)propyl)acetamide gave 4-(3-(3-aminopropyl)phenyl)-2-methylbut-3-yn-2-ol. The product was purified by flash chromatography (80% to 100% (10% 7 N NH$_3$-MeOH in EtOAc)-hexanes gradient) to give a light yellow oil. Yield (0.212 g, 62%): $^1$H NMR (400 MHz, DMSO-d$_6$) δ 7.14-7.26 (m, 4H), 5.41 (br s, 1H), 2.56 (t, J=7.2 Hz, 2H), 2.47-2.50 (m, 2H), 1.55-1.63 (m, 2H), 1.44 (s, 6H), 1.36 (br s, 2H).

Step 3: Hydrogenation of 4-(3-(3-aminopropyl)phenyl)-2-methylbut-3-yn-2-ol following the method used Example 2, except that the reaction was run for 3.5 h, gave Example 4. Yield (0.0488 g, 80%): $^1$H NMR (400 MHz, DMSO-d$_6$) δ 7.13 (t, J=7.6 Hz, 1H), 6.96-6.99 (m, 3H), 4.19 (br s, 1H), 2.45-2.57 (m, 6H), 1.55-1.62 (m, 4H), 1.48 (br s, 2H), 1.12 (s, 6H).

Example 5

Preparation of 3-(3-(3-Methoxypropyl)Phenyl)Propan-1-Amine

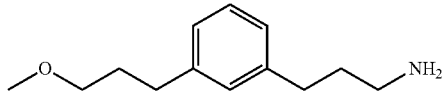

3-(3-(3-Methoxypropyl)phenyl)propan-1-amine was prepared following the method used in Example 4.

Step 1: Coupling of 3-methoxyprop-1-yne with bromide 10 gave 2,2,2-trifluoro-N-(3-(3-(3-methoxyprop-1-ynyl)phenyl)-propyl)acetamide as a light yellow oil. Yield (0.193 g, 32%): $^1$H NMR (400 MHz, DMSO-$d_6$) δ 9.40 (br s, 1H), 7.21-7.31 (m, 4H), 4.30 (s, 2H), 3.31 (s, 3H), 3.16 (q, J=7.2 Hz, 2H), 2.56 (t, J=7.6 Hz, 2H), 1.77 (quint, J=7.2 Hz, 2H).

Step 2: Deprotection of 2,2,2-trifluoro-N-(3-(3-(3-methoxyprop-1-ynyl)phenyl)propyl)acetamide gave 3-(3-(3-methoxyprop-1-ynyl)phenyl)propan-1-amine as a clear oil. Yield (0.069 g, 54%): $^1$H NMR (400 MHz, DMSO-$d_6$) δ 7.19-7.28 (m, 4H), 4.29 (s, 2H), 3.31 (s, 3H), 2.57 (t, J=7.6 Hz, 2H), 2.48-2.51 (m, 2H), 1.56-1.63 (m, 2H), 1.36 (br s, 2H).

Step 3: Hydrogenation of 3-(3-(4-methoxybut-1-ynyl)phenyl)propan-1-amine following the method used to prepare Example 4 gave Example 5. Yield (0.018 g): $^1$H NMR (400 MHz, DMSO-$d_6$) δ 7.15 (t, J=7.6 Hz, 1H), 6.94-6.99 (m, 3H), 3.28 (t, J=6.4 Hz, 2H), 3.21 (s, 3H), 2.45-2.57 (m, 6H), 1.71-1.78 (m, 2H), 1.59 (quint, J=7.2 Hz, 2H), 1.50 (br s, 2H).

Example 6

Preparation of 3-(3-(3-Aminopropyl)Phenyl)Propan-1-ol

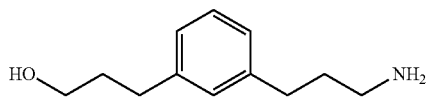 [SMILES: NCCCc1cccc(CCCO)c1]

3-(3-(3-Aminopropyl)phenyl)propan-1-ol was prepared following the method used in Example 4.

Step 1: Coupling of prop-2-yn-1-ol with bromide 10 gave 2,2,2-trifluoro-N-(3-(3-(3-hydroxyprop-1-ynyl)phenyl)propyl)acetamide as a light yellow oil. Yield (0.148 g, 26%): $^1$H NMR (400 MHz, DMSO-$d_6$) δ 9.41 (br s, 1H), 7.19-7.29 (m, 4H), 5.28 (t, J=5.6 Hz, 1H), 4.27 (d, J=6.4 Hz, 2H), 3.16 (t, J=7.2 Hz, 2H), 2.56 (t, J=7.6 Hz, 2H), 1.76 (q, J=7.6 Hz, 2H).

Step 2: Deprotection of 2,2,2-trifluoro-N-(3-(3-(3-hydroxyprop-1-ynyl)phenyl)propyl)acetamide gave 3-(3-(3-aminopropyl)phenyl)prop-2-yn-1-ol as a clear oil. Yield (0.073 g, 76%): $^1$H NMR (400 MHz, DMSO-$d_6$) δ 7.17-7.27 (m, 4H), 5.28 (br s, 1H), 4.27 (d, J=3.6 Hz, 2H), 2.59 (t, J=7.6 Hz, 2H), 2.47-2.49 (m, 2H), 1.52-1.63 (m, 4H).

Step 3: Hydrogenation of 3-(3-(3-aminopropyl)phenyl)prop-2-yn-1-ol following the method used to prepare Example 4 gave Example 6 as a clear oil. Yield (0.018 g): $^1$H NMR (400 MHz, DMSO-$d_6$) δ 7.14 (t, J=7.6 Hz, 1H), 6.94-6.99 (m, 3H), 4.41 (br s, 1H), 3.38 (t, J=6.4 Hz, 2H), 2.45-2.56 (m, 6H), 1.55-1.70 (m, 6H).

Example 7

Preparation of 1-(3-(3-Aminopropyl)Phenethyl)Cyclohexanol

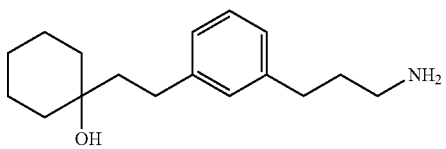 [SMILES: NCCCc1cccc(CCC2(O)CCCCC2)c1]

1-(3-(3-Aminopropyl)phenethyl)cyclohexanol was prepared following the method used in Example 4 except that hydrogenation was conducted before deprotection of the amine.

Step 1: To a solution of bromide 10 (2.0 g, 6.45 mmol) and 1-ethynylcyclohexanol (1.2 g, 9.67 mmol) in triethylamine (40 mL) was added CuI (0.0246 g, 0.129 mmol). The mixture was degassed with argon for 2-3 min, then PdCl$_2$(PPh$_3$)$_2$ (0.0905 g, 0.129 mmol) was added. The reaction mixture was degassed with argon again then stirred at 70° C. overnight under argon. After cooling to room temperature, the mixture was concentrated under reduced pressure and suspended in EtOAc-hexanes (50%, 50 mL). Solids were removed by filtration and the filtrate was concentrated under reduced pressure. Purification by flash chromatography gave 2,2,2-trifluoro-N-(3-(3-((1-hydroxycyclohexyl)ethynyl)phenyl)propyl)acetamide as a clear oil. Yield (1.74 g, 76%): $^1$H NMR (400 MHz, DMSO-$d_6$) δ 9.40 (br s, 1H), 7.26 (t, J=7.6 Hz, 1H), 7.17-7.24 (m, 3H), 5.37 (s, 1H), 3.16 (q, J=6.8 Hz, 2H), 2.56 (t, J=7.2 Hz, 2H), 1.15-1.83 (m, 12H).

Step 2: A solution of 2,2,2-trifluoro-N-(3-(3-((1-hydroxycyclohexyl)ethynyl)phenyl)propyl)acetamide (0.51 g, 1.44 mmol) in MeOH (15 mL) was degassed with argon for 2 min. To this solution was added 10% Pd/C (0.075 g) and the mixture was placed under H$_2$ at 40 PSI on a Parr shaker overnight. Solids were removed by filtration and the filtrate was concentrated under reduced pressure to give the crude product as a clear oil. This compound was used in the next synthetic step without purification. Yield (0.509 g, 99%): $^1$H NMR (400 MHz, DMSO-$d_6$) δ 9.40 (br s, 1H), 7.14 (t, J=7.6 Hz, 1H), 6.95-7.00 (m, 3H), 3.96 (s, 1H), 3.18 (q, J=6.8 Hz, 2H), 2.51-2.57 (m, 4H), 1.72-1.79 (m, 2H), 1.15-1.59 (m, 12H).

Step 3: 2,2,2-Trifluoro-N-(3-(3-((1-hydroxycyclohexyl)ethynyl)phenyl)propyl)acetamide was deprotected following the method used in Example 2 except that 5 equivalents of K$_2$CO$_3$ were used and the reaction mixture was heated at 55° C. for 3 h. Purification by flash chromatography (10% 7M NH$_3$ in MeOH—CH$_2$Cl$_2$) gave Example 7 as a white solid. Yield (0.840 g, 96%): $^1$H NMR (400 MHz, DMSO-$d_6$) δ 7.13 (t, J=7.2 Hz, 1H), 6.93-6.99 (m, 3H), 3.96 (br s, 1H), 2.49-2.57 (m, 4H), 1.16-1.63 (m, 18H).

Example 8

Preparation of 1-(3-(3-Aminopropyl)Phenyl)Hexan-3-ol

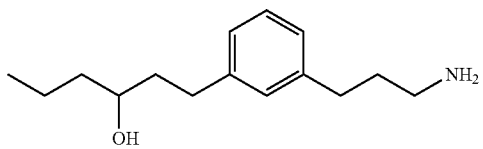 [SMILES: CCCC(O)CCc1cccc(CCCN)c1]

1-(3-(3-Aminopropyl)phenyl)hexan-3-ol was prepared following the method used in Example 4.

Step 1: Coupling of hex-1-yn-3-ol with bromide 10 gave 2,2,2-trifluoro-N-(3-(3-(3-hydroxyhex-1-ynyl)phenyl)propyl)acetamide as a brown oil. Yield (0.271 g, 41%).

Step 2: Deprotection of 2,2,2-trifluoro-N-(3-(3-(3-hydroxyhex-1-ynyl)phenyl)propyl)acetamide gave 1-(3-(3-aminopropyl)phenyl)hex-1-yn-3-ol. Yield (0.086 g, 45%): $^1$H NMR (400 MHz, DMSO-$d_6$) δ 7.16-7.26 (m, 4H), 5.36 (t, J=5.2 Hz, 1H), 4.41 (dt, J=6.4, 5.2 Hz, 1H), 2.56 (t, J=7.2 Hz, 2H), 2.47-2.49 (m, 2H), 1.38-1.64 (m, 8H), 0.90 (t, J=7.2 Hz, 3H).

Step 3: Hydrogenation of 1-(3-(3-aminopropyl)phenyl)hex-1-yn-3-ol following the method used to prepare Example 4 gave Example 8. Yield (0.0296 g): $^1$H NMR (400 MHz, DMSO-$d_6$) δ 7.13 (t, J=7.6 Hz, 1H), 6.92-6.99 (m, 3H), 4.33 (d, J=5.2 Hz, 1H), 3.89 (m, 1H), 2.45-2.67 (m, 6H), 1.23-1.62 (m, 10H), 0.83 (t, J=7.2 Hz, 3H).

Example 9

Preparation of 4-(3-(2-Aminoethoxy)Phenethyl)Heptan-4-ol

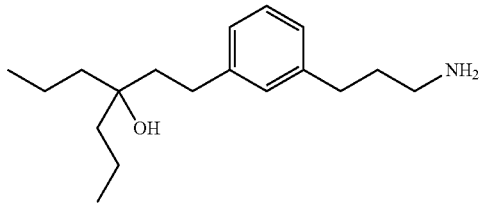 [SMILES: CCCC(O)(CCC)CCc1cccc(CCCN)c1]

4-(3-(2-Aminoethoxy)phenethyl)heptan-4-ol was prepared following the method shown in scheme 3:

SCHEME 3

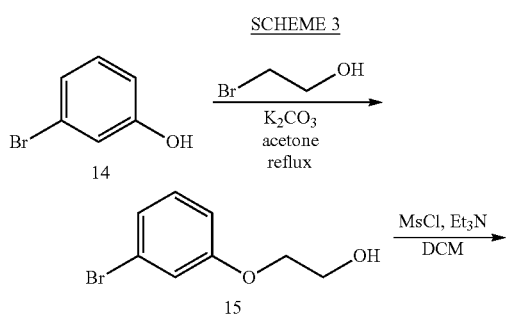

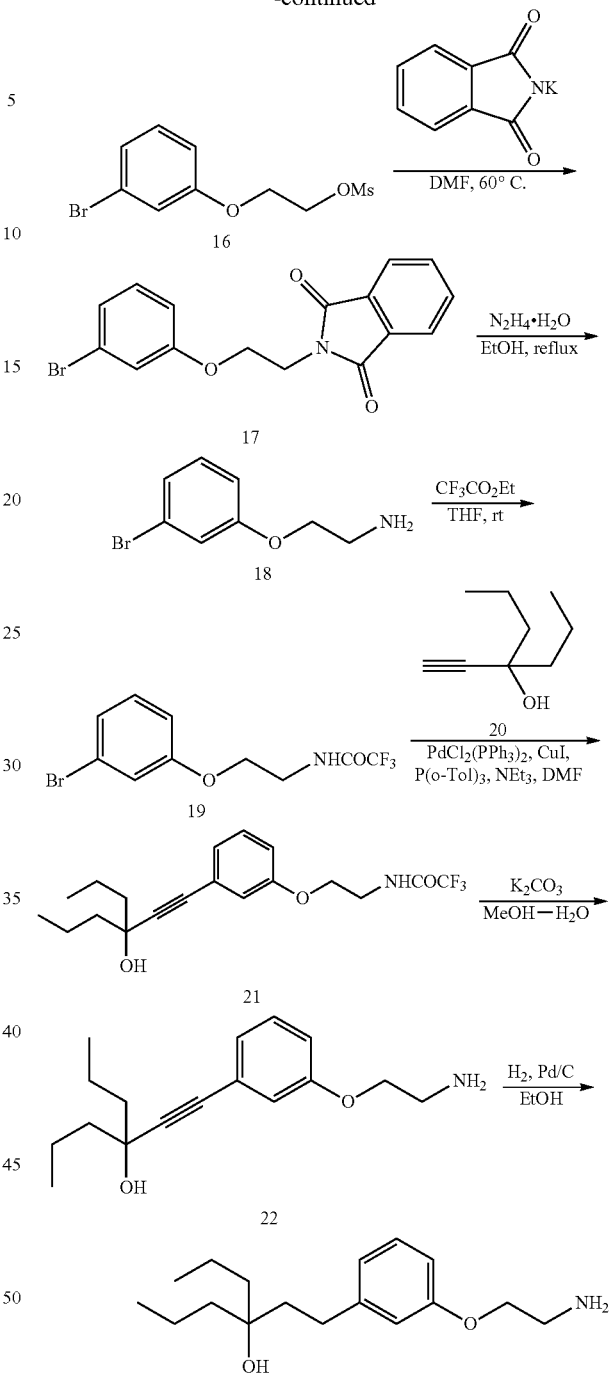

Step 1: To a solution of 3-bromophenol (14) (36.38 g, 210.3 mmol) in acetone (175 ml) was added $K_2CO_3$ (0.033 g, 237 mmol) and 2-bromoethanol (20 ml, 283.3 mmol). The reaction mixture was heated at reflux under argon for 4 days. After cooling to room temperature, the mixture was filtered and the filtrate was concentrated under reduced pressure. The residue was dissolved in diethyl ether (150 ml) and the solution was washed successively with water, 10% aqueous NaOH, 5% aqueous NaOH, water, and brine. The solution was dried over $MgSO_4$ and concentrated under reduced pressure to give 2-(3-bromophenoxy)ethanol (15) as a light brown oil. Yield (21.07 g, 46%): $^1$H NMR (400 MHz, CDCl$_3$) δ 7.14 (t, J=7.8

Hz, 1H), 7.07-7.12 (m, 2H), 6.85 (ddd, J=7.8, 2.4, 1.3 Hz, 1H), 4.06 (m, 2H), 3.95 (m, 2H), 2.11 (t, J=12.3 Hz, 1H).

Step 2: To an ice cold mixture of 2-(3-bromophenoxy)ethanol (15) (16.06 g, 74.0 mmol) and triethylamine (9.12 g, 90.13 ml) in anhydrous CH$_2$Cl$_2$ (120 ml) under argon was slowly added neat methanesulfonyl chloride (6 ml, 77.2 mmol). The reaction mixture was stirred at 0° C. for 15 min. The mixture was concentrated under reduced pressure and the residue was partitioned between EtOAc and water. The combined organics were washed with water and brine, dried over MgSO$_4$, and concentrated under reduced pressure to give 2-(3-bromophenoxy)ethyl methanesulfonate (16) as a brownish oil. This product was used without further purification in the next reaction. Yield (21.32 g, 98%): $^1$H NMR (400 MHz, CDCl$_3$) δ 7.16 (t, J=7.8 Hz, 1H), 7.11-7.14 (m, 1H), 7.07 (m, 1H), 6.39 (ddd, J=7.6, 2.5, 1.8 Hz, 1H), 4.56 (m, 2H), 4.22 (m, 2H), 3.08 (s, 3H).

Step 3: To a solution of mesylate 16 (24.05 g, 81.5 mmol) in anhydrous DMF (160 ml) was added potassium phthalimide (15.53 g, 83.8 mmol) and the reaction mixture was stirred at 60° C. for 14 h. The mixture was concentrated under reduced pressure and the residue was partitioned between hexane-EtOAc (7:1) and water. A precipitate formed which was collected by filtration, washed excessively with water and hexane, then dried in vacuum to give N-(2-(3-Bromophenoxy)ethyl)phthalimide (17) as white fluffy crystals (22.05 g). To collect a second batch of crystals, the organic layer of the filtrate was concentrated under reduced pressure. The residue was suspended in 10% EtOAc-hexanes. The solution was washed with water and the precipitate collected by filtration, washed excessively with water, then hexane and dried in vacuum to give phthalimide 17 (5.65 g). Combined yield (21.18 g, 98%). $^1$H NMR (400 MHz, CDCl$_3$) δ 7.86 (m, 2H), 7.73 (m, 2H), 7.03-7.12 (m, 3H), 6.80 (ddd, J=8.0, 2.5, 1.4 Hz, 1H), 4.21 (t, J=6.9 Hz, 2H), 4.10 (t, J=6.0 Hz, 2H).

Step 4: To a suspension of phthalimide 17 (22.82 g, 65.9 mmol) in absolute EtOH (200 ml) was added hydrazine hydrate (6 ml, 123.7 mmol) and reaction mixture was heated at reflux under argon for 1.5 h. After cooling to room temperature, the mixture was filtered and the filtrate was concentrated under reduced pressure. The residue was re-suspended in hexane (100 ml) and solids were removed by filtration. The filtrate was concentrated under reduced pressure. The residue was then taken up in EtOH and concentrated under reduced pressure. This procedure was repeated with toluene to give amine 18 as a thick yellow oil. Yield (10.63 g, 75%): $^1$H NMR (400 MHz, CDCl$_3$) δ 7.06-7.15 (m, 3H), 6.84 (ddd, J=8.0, 2.5, 1.2 Hz, 1H), 3.96 (t, J=5.3 Hz, 2H), 3.07 (t, J=5.09 Hz, 2H), 1.43 (s, 2H).

Step 5: To a solution of amine 18 (10.63 g, 49.2 mmol) in anhydrous THF (80 ml) was added ethyl trifluoroacetate (12 ml, 100.6 mmol) and the reaction mixture was stirred at room temperature overnight. The solution was concentrated under reduced pressure and the residue was dissolved in 50% EtOAc-hexanes. The solution was filtered through a layer of a silica gel and eluted with 50% EtOAc-hexanes. Concentration under reduced pressure gave bromide 19 as pale yellow oil which crystallized upon standing to a pale yellow solid. Yield (13.69 g, 89%): $^1$H NMR (400 MHz, CDCl$_3$) δ 7.16 (t, J=8.0 Hz, 1H), 7.12-7.14 (m, 1H), 7.05-7.07 (m, 1H), 6.83 (ddd, J=7.6, 2.5, 1.8 Hz, 1H), 6.75 (br s, 1H), 4.09 (t, J=4.9 Hz, 2H), 3.78 (dt, J=5.5 Hz, 2H).

Step 6: Bromide 19 was coupled with alkynol 20 following the procedure described in Example 2 except that the reaction was run for 20 h, to give alkyne 21 as a yellow oil. Yield (0.89 g, 73%): $^1$H NMR (400 MHz, CDCl$_3$) δ 7.22 (t, J=8.0 Hz, 1H), 7.06 (dt, J=7.6, 1.0 Hz, 1H), 6.93 (dd, J=2.5, 1.4 Hz, 1H), 6.85 (ddd, J=8.4, 2.7, 1.0 Hz, 1H), 6.77 (br s, 1H), 4.09 (t, J=5.1 Hz, 2H), 3.78 (dt, J=5.5 Hz, 2H), 2.00 (s, 1H), 1.67-1.73 (m, 4H), 1.57-1.61 (m, 4H), 0.98 (t, J=7.4 Hz, 6H).

Step 7: Alkyne 21 was deprotected according to the procedure described in Example 2 except that the reaction was run with 5 equivalents of K$_2$CO$_3$ at room temperature for 7 h, followed by purification by flash chromatography (eluent 90% EtOAc: (7M NH$_3$ in MeOH) to give amine 22 trifluoroacetate as a cream-colored solid. Yield (5 g, 76%). $^1$H NMR (400 MHz, DMSO-d$_6$) δ 7.23 (t, J=7.8 Hz, 1H), 6.92-6.93 (m, 1H), 6.90-6.91 (m, 1H), 6.85-6.86 (m, 1H), 5.13 (br s, 1H), 3.89 (t, J=5.9 Hz, 2H), 2.83 (t, J=5.7 Hz, 2H), 1.42-1.60 (m, 10H), 0.89 (t, J=7.2 Hz, 6H); $^{13}$C NMR (100 MHz, DMSO-d6) δ 159.28, 130.47, 124.49, 124.26, 117,34, 115.80, 94.78, 83,15, 71.03, 70.26, 44.86, 41.60, 17.96, 15.01. ESI MS m/z 276.39 [M+H]$^1$, 258.38 [M+H−H$_2$O].$^1$.

Step 8: Hydrogenation of amine 22 was conducted following the method used to prepare Example 2. A solution of the crude product in 10% MeOH—CH$_2$Cl$_2$ (5 mL) was filtered through Celite/silica/sand. The solids in the funnel were rinsed with more 10% MeOH—CH$_2$Cl$_2$, then the filtrate was concentrated under reduced pressure to give Example 9 as a colorless oil. Yield (0.201 g, 80%): $^1$H NMR (400 MHz, CDCl$_3$) δ 7.18 (t, J=8.0 Hz, 1H), 6.72-6.80 (m, 3H), 3.98 (t, J=5.2 Hz, 2H), 3.07 (t, J=5.2 Hz, 2H), 2.58-2.62 (m, 2H), 1.70-1.75 (m, 2H), 1.45-1.50 (m, 7H), 1.32-1.37 (m, 4H), 0.94 (t, J=6.8 Hz, 6H).

Example 10

Preparation of 1-(3-(2-Aminoethoxy)Phenethyl)Cycloheptanol

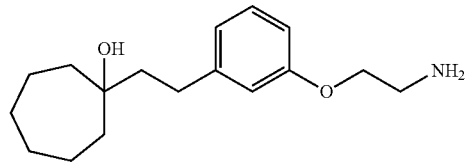 [SMILES: NCCOc1cccc(CCC2(O)CCCCCC2)c1]

1-(3-(2-Aminoethoxy)phenethyl)cycloheptanol was prepared following the method used in Example 9:

Step 1: Bromide 19 was coupled with 1-ethynylcycloheptanol following the procedure described in Example 2 except that 1.5 equivalents of alkyne and triethylamine were used and the reaction was heated for 2 h. After the reaction mixture was cooled to room temperature, it was partitioned between EtOAc and water then the combined organics were filtered through Celite. The filtrate was dried over Na$_2$SO$_4$ and treated with activated charcoal. Following filtration, the solution was concentrated under reduced pressure. Purification by flash chromatography (10 to 50% EtOAc-hexanes gradient) gave 2,2,2-trifluoro-N-(2-(3-((1-hydroxycycloheptyl)ethynyl)phenoxy)ethyl)acetamide as an orange oil. Yield (1.078 g, 60%): $^1$H NMR (400 MHz, CDCl$_3$) δ 7.2 (br s, 1H), 7.18 (t, J=8.0 Hz, 1H), 7.02 (dt, J=7.2, 0.8 Hz, 1H), 6.90 (dd, J=2.4, 1.6 Hz, 1H), 6.81 (ddd, J=8.4, 2.4, 0.8 Hz, 1H), 4.05 (t, J=5.2 Hz, 2H), 3.72 (q, J=5.3 Hz, 2H), 2.43 (br s, 1H), 2.05-2.11 (m, 2H), 1.84-1.91 (m, 2H), 1.53-1.70 (m, 8H).

Step 2: To a solution of 2,2,2-trifluoro-N-(2-(3-((1-hydroxycycloheptyl)ethynyl)phenoxy)ethyl)acetamide (1.07 g, 2.9 mmol) in MeOH (20 mL) was added saturated aqueous K$_2$CO$_3$ (ca. 10 mL). The reaction mixture was stirred vigorously and heated at 50° C. for 2 h. After removal of the volatiles by concentration under reduced pressure, the mixture was partitioned into EtOAc and water. The organic layer was dried over Na$_2$SO$_4$ and concentrated under reduced pressure. Purification by flash chromatography (10% 7M NH$_3$ in MeOH-EtOAc) gave 1-((3-(2-aminoethoxy)phenyl)ethynyl)cycloheptanol as a pale yellow solid. (Yield 0.70 g, 88%): $^1$H NMR (400 MHz, CDCl$_3$) δ 7.19 (t, J=8.0 Hz, 1H), 7.01 (dt, J=8.0, 0.8 Hz, 1H), 6.95 (dd, J=2.8, 1.6 Hz, 1H), 6.85 (ddd, J=8.4, 2.4, 1.2 Hz, 1H), 3.97 (t, J=4.8 Hz, 2H), 3.07 (br s, 2H), 2.08-2.13 (m, 2H), 1.87-1.94 (m, 2H), 1.59-1.74 (m, 11H).

Step 3: Hydrogenation of 1-((3-(2-aminoethoxy)phenyl)ethynyl)cycloheptanol following the method used to prepare example 2 gave Example 10 as a colorless oil. Yield (0.186 g, 52%): $^1$H NMR (400 MHz, CDCl$_3$) δ 7.16 (t, J=8.0 Hz, 1H), 6.75-6.79 (m, 2H), 6.70 (dd, J=8.0, 2.0 Hz, 1H), 3.96 (t, J=5.2 Hz, 2H), 3.04 (t, J=4.8 Hz, 2H), 2.63-2.67 (m, 2H), 2.10 (br s, 2H), 1.72-1.76 (m, 2H), 1.67-1.69 (m, 4H), 1.36-1.65 (m, 8H).

Example 11

Preparation of 4-(3-(2-Aminoethoxy)Phenethyl)Tetrahydro-2H-Thiopyran-4-ol

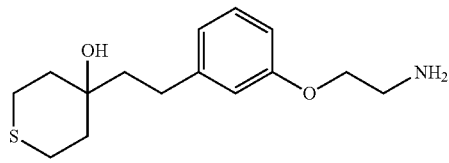 [SMILES: NCCOc1cccc(CCC2(O)CCSCC2)c1]

4-(3-(2-Aminoethoxy)phenethyl)tetrahydro-2H-thiopyran-4-ol was prepared following the method used in Examples 2 and 9.

Step 1: Coupling of 4-ethynyltetrahydro-2H-thiopyran-4-ol with bromide 19 was conducted following the method used in Example 2 except that the reaction was run in THF at 60° C. overnight. Purification by flash chromatography (1:2 EtOAc:heptane) gave 2,2,2-trifluoro-N-(3-(3-((4-hydroxytetrahydro-2H-thiopyran-4-yl)ethynyl)phenyl)propyl)acetamide as a pale yellow oil. Yield (0.822 g, 72%): $^1$H NMR (400 MHz, CDCl$_3$) δ 7.26 (t, J=4.5 Hz, 1H), 7.07 (dt, J=7.6, 1.2 Hz, 1H), 6.95 (dd, J=2.5, 1.4 Hz, 1H), 6.87 (ddd, J=8.2, 2.5, 0.8 Hz, 1H), 4.10 (m, 2H), 3.79 (q, J=5.5 Hz, 2H), 2.73-2.92 (m, 4H), 2.26-2.31 (m, 2H), 2.01-2.04 (m, 2H).

Step 2: Deprotection of 2,2,2-trifluoro-N-(3-(3-((4-hydroxytetrahydro-2H-thiopyran-4-yl)ethynyl)phenyl)propyl)acetamide was conducted following the method used for the preparation of Example 9 except that 2 equivalents of K$_2$CO$_3$ were used and the reaction was heated at 50° C. for 2 h. After cooling to room temperature, the reaction mixture was partitioned between EtOAc and water. The combined organics were washed with water and brine, dried over Na$_2$SO$_4$ and concentrated under reduced pressure. Purification by flash chromatography (CH$_2$Cl$_2$/EtOH/NH$_4$OH 85:14:1) gave 4-((3-(2-aminoethoxy)phenyl)ethynyl)tetrahydro-2H-thiopyran-4-ol as a white amorphous solid. Yield (0.41 g, 68%): $^1$H NMR (400 MHz, DMSO-d$_6$) δ 7.23-7.28 (m, 1H), 6.93-6.98 (m, 3H), 5.69 (br s, 1H), 3.90 (t, J=5.8 Hz, 2H), 2.83 (t, J=5.8 Hz, 2H), 2.69 (t, J=5.6 Hz, 4H), 2.09 (dt, J=13.0, 4.6 Hz, 2H), 1.80 (quint, J=6.6 Hz, 2H), 1.60 (br s, 2H).

Step 3: Hydrogenation of 4-((3-(2-aminoethoxy)phenyl)ethynyl)tetrahydro-2H-thiopyran-4-ol was conducted following the method used to prepare Example 2 except that EtOAc-MeOH (90%) was used as the reaction solvent. Example 11 was isolated as a colorless oil. Yield (0.179 g, 98%): $^1$H NMR (400 MHz, DMSO-d$_6$) δ 7.13 (t, J=8 Hz, 1H), 6.34-6.88 (m, 3H), 4.26 (br s, 1H), 3.86 (t, J=6.0 Hz, 2H), 2.57-2.88 (m, 4H), 2.53-2.56 (m, 2H), 2.32-2.37 (m, 2H), 1.73-1.78 (m, 2H), 1.42-1.62 (m, 6H).

Example 12

Preparation of 1-(3-(2-Aminoethoxy)Phenethyl)Cyclohexanol

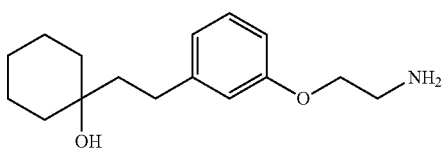 [SMILES: NCCOc1cccc(CCC2(O)CCCCC2)c1]

1-(3-(2-Aminoethoxy)phenethyl)cyclohexanol was prepared following the method shown in Scheme 4:

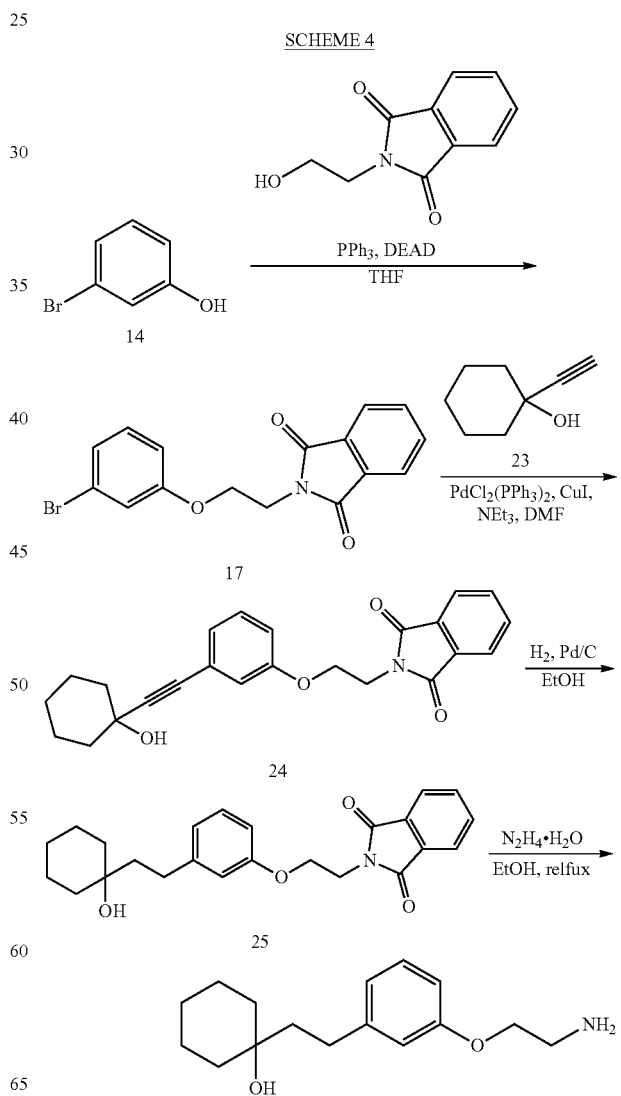

SCHEME 4

Step 1: To an ice cold solution of 3-bromophenol (14) (2.0 g, 11.56 mmol), N-(2-hydroxyethyl)phthalimide (2.21 g, 11.6 mmol) and triphenyl phosphine (3.03 g, 11.6 mmol) in anhydrous THF (25 mL) was added diethyl azodicarboxylate (2.57 g, 12.7 mmol) slowly. The reaction mixture was allowed to warm to room temperature and stirred overnight. After concentration under reduced pressure, 50% EtOAc-hexanes (100 mL) was added and the mixture was warmed to 60° C. After cooling to room temperature, the solids were removed by filtration and the filtrate was concentrated under reduced pressure. Purification by flash chromatography (10% EtOAc-hexanes) gave bromide 17 as a white solid. Yield (1.92 g, 48%): $^1$H NMR (400 MHz, DMSO-$d_6$) δ 7.82-7.88 (m, 4H), 7.19 (t, J=8.4 Hz, 1H), 7.06-7.09 (m, 2H), 6.87-6.90 (m, 1H), 4.22 (t, J=5.6 Hz, 2H), 3.93 (t, J=5.6 Hz, 2H).

Step 2: Coupling of bromide 17 with 1-ethynylcyclohexanol following the method used in Example 7 followed by purification by flash chromatography (20% EtOAc-hexanes) gave compound 24 as a pale yellow oil. Yield (1.22 g, 57%): $^1$H NMR (400 MHz, DMSO-$d_6$) δ 7.82-7.88 (m, 4H), 7.21 (t, J=8.0 Hz, 1H), 6.92 (dt, J=8.0, 0.8 Hz, 1H), 6.84-6.88 (m, 2H), 5.38 (br s, 1H), 4.20 (t, J=5.6 Hz, 2H), 3.95 (t, J=5.6 Hz, 2H), 1.78-1.82 (m, 2H), 1.59-1.62 (m, 2H), 1.41-1.53 (m, 4H), 1.22-1.94 (m, 1H).

Step 3: Hydrogenation of compound 24 following the method used in Example 7 gave alcohol 25. Yield (0.512 g, quant.): $^1$H NMR (400 MHz, DMSO-$d_6$) δ 7.81-7.88 (m, 4H), 7.10 (t, J=7.6 Hz, 1H), 6.64-6.71 (m, 3H), 4.16 (t, J=5.6 Hz, 2H), 3.93 (t, J=6.8 Hz, 2H), 3.30 (s, 1H), 2.47-2.53 (m, 4H), 1.15-1.56 (m, 10H).

Step 4: Deprotection of alcohol 25 was conducted following the method used in Example 9 except that 5 equivalents of hydrazine hydrate were used and the reaction was heated at 70° C. for 4 h. After cooling to room temperature, solids were removed by filtration and the filtrate was concentrated under reduced pressure. Purification by flash chromatography (10% 7M NH$_3$ in MeOH—CH$_2$Cl$_2$) gave Example 12. Yield (0.341, 68%): $^1$H NMR (400 MHz, DMSO-$d_6$) δ 7.13 (t, J=8.0 Hz, 1H), 6.73-6.75 (m, 3H), 3.96 (br s, 1H), 3.86 (t, J=5.6 Hz, 2H), 2.83 (t, J=6.0 Hz, 2H), 2.52-2.56 (m, 2H), 1.16-1.60 (m, 12H).

Example 13

Preparation of 6-(3-(2-Aminoethoxy)Phenyl)Hexan-1-ol

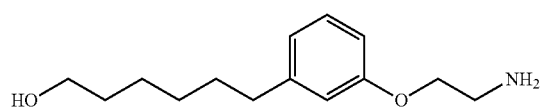 [SMILES: NCCOc1cccc(CCCCCCO)c1]

6-(3-(2-Aminoethoxy)phenyl)hexan-1-ol was prepared following the method shown in scheme 5:

SCHEME 5

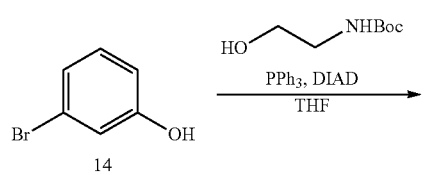

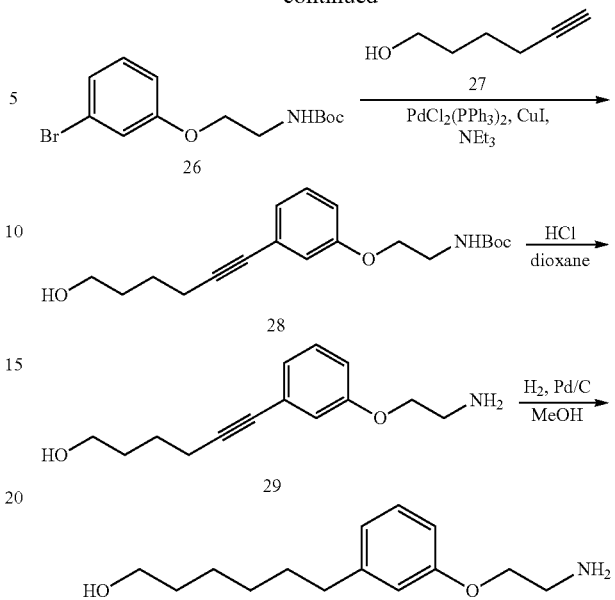

Step 1: To a solution of 3-bromophenol (14) (5.0 g, 28.9 mmol) in THF (100 mL) was added tert-butyl 2-hydroxyethylcarbamate (9.3 g, 161 mmol) and PPh$_3$ (30 g, 115 mmol). A solution of diisopropyl azodicarboxylate (22.6 mL, 115.6 mmol) in THF (40 mL) was added dropwise at room temperature. The reaction was stirred overnight at 50° C. After cooling to room temperature, the mixture was concentrated under reduced pressure. The residue was dissolved in EtOAc, washed with brine, dried over Na$_2$SO$_4$ and concentrated under reduced pressure. Purification by column chromatography (6% EtOAc-hexanes) provided bromide 26 as a colorless oil. Yield (8.34 g, 91%): $^1$H NMR (400 MHz, CDCl$_3$) δ 7.14 (t, J=8.0 Hz, 1H), 7.05-7.11 (m, 2H), 6.81-6.84 (m, 1H), 4.96 (br s, 1H), 4.00 (t, J=5.2 Hz, 2H), 3.52 (q, J=4.8 Hz, 2H), 1.45 (s, 9H).

Step 2: To a degassed solution (bubbled with N$_2$) of bromide 26 (0.600 g, 1.89 mmol) and alcohol 27 (0.241 mL, 2.27 mmol) in Et$_3$N (20 mL) was added PdCl$_2$(PPh$_3$)$_2$ (0.040 g, 0.056 mmol) and CuI (0.011 g, 0.056 mmol). The mixture was heated overnight at 70° C. After cooling to room temperature, the mixture was concentrated under reduced pressure, dissolved in EtOAc and filtered. The filtrate was washed with water and brine, dried over Na$_2$SO$_4$ and concentrated under reduced pressure. Purification by flash chromatography (20% EtOAc-hexanes) provided alkyne 28 as a brown oil. Yield (0.500 g, 79%): $^1$H NMR (400 MHz, CDCl$_3$) δ 7.17 (t, J=7.6 Hz, 1H), 6.99 (d, J=7.6 Hz, 1H), 6.91 (s, 1H), 6.81 (d, J=8.4 Hz, 1H), 4.72 (br s, 1H), 4.00 (t, J=4.8 Hz, 2H), 3.72 (m, 2H), 3.48-3.55 (m, 2H), 2.46 (d, J=6.8 Hz, 2H), 1.66-1.79 (m, 4H), 1.58 (s, 1H), 1.45 (s, 9H).

Step 3: Alkyne 28 (500 mg, 1.52 mmol) was dissolved in HCl-dioxane (12 mL of a saturated solution) and stirred overnight at room temperature. The mixture was concentrated under reduced pressure then purified by Prep HPLC using Method 2P to give amine 29 hydrochloride as a brown solid. Yield (0.161 g, 40%): $^1$H NMR (400 MHz, DMSO-$d_6$) δ 8.15 (br s, 3H), 7.22-7.27 (m, 1H), 6.92-6.97 (m, 3H), 4.14 (t, J=5.0 Hz, 2H), 3.40 (t, J=5.8 Hz, 2H), 3.14-3.15 (m, 2H), 2.39 (t, J=6.6 Hz, 2H), 1.51-1.53 (m, 4H).

Step 4: To a stirred solution of amine 29 hydrochloride (0.100 g, 0.42 mmol) in MeOH was added 5% Pd/C (30% w/w, 0.023 g) under nitrogen. The mixture was bubbled with hydrogen then stirred at 50° C. for 2 h under hydrogen. After cooling to room temperature, the solids were removed by filtration through Celite. The filter cake was rinsed with additional MeOH and the filtrate concentrated under reduced pressure. Example 13 hydrochloride was isolated as a cream-colored solid. Yield (0.048 g, 47%): $^1$H NMR (400 MHz, CD$_3$OD) δ 7.18 (t, J=8.0 Hz, 1H), 6.78-6.83 (m, 3H), 4.19 (t, J=5.2 Hz, 2H), 3.52 (t, J=6.6 Hz, 2H), 3.34 (t, J=5.2 Hz, 2H), 2.59 (t, J=7.6 Hz, 2H), 1.58-1.63 (m, 2H), 1.43-1.52 (m, 2H), 1.24-1.42 (m, 4H).

Example 14

Preparation of 2-(3-(3-Cyclopentylpropyl)Phenoxy)Ethanamine

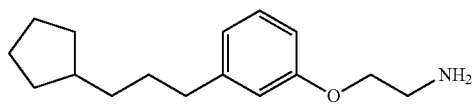 [SMILES: NCCOc1cccc(CCCC2CCCC2)c1]

2-(3-(3-Cyclopentylpropyl)phenoxy)ethanamine was prepared following the method used in Example 13.

Step 1: Coupling of prop-2-ynylcyclopentane with bromide 26 and purification by flash chromatography (15% EtOAc-hexanes) gave tert-butyl 2-(3-(3-cyclopentylprop-1-ynyl)phenoxy)ethylcarbamate as a white solid. Yield (0.500 g, 77%): $^1$H NMR (400 MHz, CDCl$_3$) δ 6.91-7.21 (m, 3H), 6.80-6.84 (m, 1H), 4.97 (br s, 1H), 4.00 (t, J=4.8 Hz, 2H), 3.52 (q, J=4.4 Hz, 2H), 2.40 (d, J=6.8 Hz, 2H), 2.07-2.17 (m, 1H), 1.80-1.87 (m, 2H), 1.48-1.70 (m, 4H), 1.45 (s, 9H), 1.29-1.40 (m, 2H).

Step 2: Deprotection of tert-butyl 2-(3-(3-cyclopentyl-prop-1-ynyl)phenoxy)ethylcarbamate with HCl in dioxane gave 2-(3-(3-cyclopentylprop-1-ynyl)phenoxy)ethanamine as a white solid. Yield (0.160 g, 45%): $^1$H NMR (400 MHz, DMSO-d$_6$) δ 7.20-7.24 (m, 1H), 6.89-6.94 (m, 3H), 4.00 (t, J=5.0 Hz, 2H), 3.00 (br s, 2H), 3.81 (d, J=6.8 Hz, 2H), 2.04 (quint, J=7.2, 1H), 1.71-1.78 (m, 2H), 1.44-1.62 (m, 4H), 1.20-1.31 (m, 2H).

Step 3: Hydrogenation of 2-(3-(3-cyclopentylprop-1-ynyl)phenoxy)ethanamine following the method used to prepare Example 13 gave Example 14 trifluoroacetate as a white solid. Yield (0.063 g, 68%): $^1$H NMR (400 MHz, DMSO-d$_6$) δ 7.89 (br s, 3H), 7.18 (t, J=8.0 Hz, 1H), 6.74-6.79 (m, 3H), 4.09 (t, J=5.2 Hz, 2H), 3.18 (m, 2H), 2.42-2.53 (m, 2H), 1.62-1.73 (m, 3H), 1.38-1.58 (m, 6H), 1.22-1.28 (m, 2H), 0.92-1.04 (m, 2H).

Example 15

Preparation of 1-(3-(3-Amino-1-Hydroxypropyl)Phenethyl)Cyclohexanol

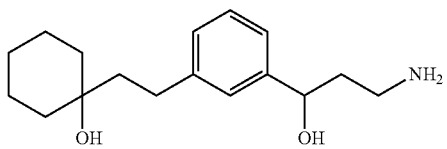 [SMILES: NCCC(O)c1cccc(CCC2(O)CCCCC2)c1]

1-(3-(3-Amino-1-hydroxypropyl)phenethyl)cyclohexanol was prepared following the method shown in Scheme 6:

SCHEME 6

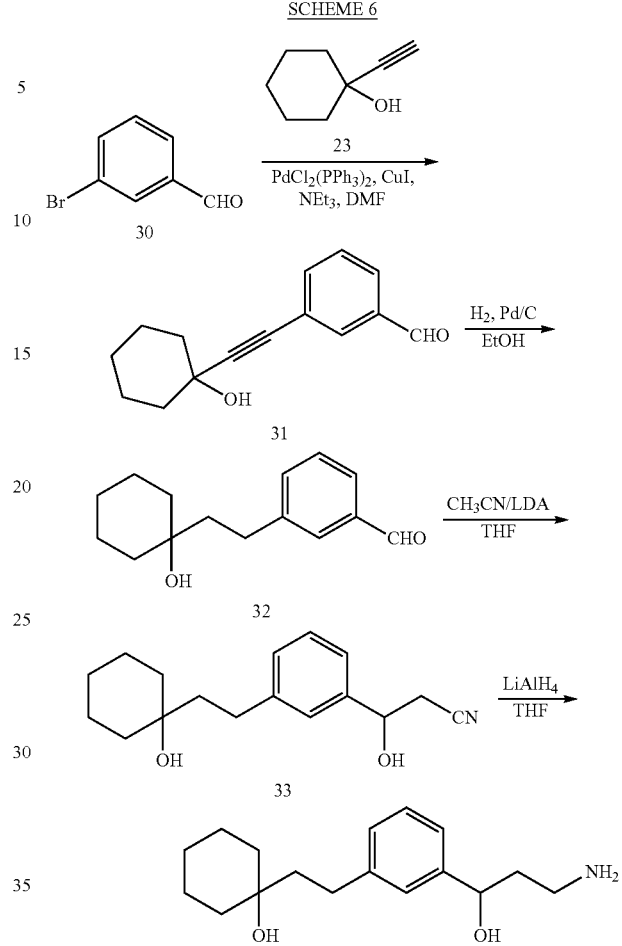

Step 1: 3-Bromobenzaldehyde was coupled with alkynol 23 following the method used in Example 7 except that the reaction was heated for 2 h. After the reaction mixture was cooled to room temperature, it was concentrated under reduced pressure and partitioned between EtOAc and water. The organics were dried over Na$_2$SO$_4$ and concentrated under reduced pressure. Purification by flash chromatography (30% EtOAc-hexanes) gave alkyne 31. Yield (3.52 g, 53%): $^1$H NMR (400 MHz, DMSO-d$_6$) δ 9.99 (s, 1H), 7.84-7.90 (m, 2H), 7.68-7.71 (m, 1H), 7.58 (t, J=7.6 Hz, 1H), 5.50 (s, 1H), 1.19-1.87 (m, 10H).

Step 2: Alkynol 31 was hydrogenated following the method used in Example 2 except that EtOAc was used as the solvent and the reaction was run for 3 h. Purification by flash chromatography (20% EtOAc-hexanes) gave aldehyde 32 as a colorless oil. Yield (2.82 g, 79%): $^1$H NMR (400 MHz, DMSO-d$_6$) δ 9.97 (s, 1H), 7.68-7.71 (m, 2H), 7.52-7.54 (m, 1H), 7.48 (t, J=7.6 Hz, 1H), 4.03 (s, 1H), 2.68-2.72 (m, 2H), 1.19-1.63 (m, 12H).

Step 3: To a −78° C. solution of LDA (13.3 mL of a 2M solution in heptane/THF/ethylbenzene, 26.51 mmol) in anhydrous THF (50 mL) was added acetonitrile (1.33 mL, 25.31 mmol) slowly and the mixture was stirred for 15 min. A solution of aldehyde 32 (2.8 g, 12.05 mmol) in THF (30 mL) was added via syringe. After warming slowly to room temperature, the reaction mixture was quenched with saturated aqueous NH$_4$Cl (30 mL). The mixture was partitioned between EtOAc and water, the organics were dried over Na₂SO₄, and the solution was concentrated under reduced pressure. Purification by flash chromatography (40% EtOAc-hexanes) gave cyanohydrin 33 as a pale yellow oil. Yield (2.21 g, 67%): ¹H NMR (400 MHz, DMSO-d₆) δ 7.07-7.24 (m, 4H), 5.86 (d, J=4.0 Hz, 1H), 4.83 (q, J=6.0 Hz, 1H), 3.99 (br s, 1H), 2.74-2.88 (m, 2H), 2.57-2.62 (m, 2H), 1.14-1.61 (m, 12H).

Step 4: To an ice cold solution of cyanohydrin 33 (2.2 g, 8.05 mmol) in anhydrous THF (50 mL) was added LiAlH₄ (10.0 mL of a 2M solution in THF, 20 mmol) slowly via syringe. During the addition, precipitates were formed and additional THF (100 mL) was added. The reaction mixture was allowed to warm to room temperature slowly over 2 h then solid Na₂SO₄.10H₂O was added slowly until gas evolution ceased. Solids were removed by filtration then the filtrate was dried over Na₂SO₄ and concentrated under reduced pressure. Purification by flash chromatography (10% 7M NH₃ in MeOH—CH₂Cl₂) gave Example 15 as an oil that solidified upon standing. Yield (1.15 g, 52%): ¹H NMR (400 MHz, DMSO-d₆) δ 7.16 (d, J=7.6 Hz, 1H), 6.99-7.12 (m, 3H), 4.59-4.62 (m, 1H), 3.98 (br s, 1H), 2.49-2.67 (m, 4H), 1.16-1.63 (m, 17H).

Example 16

Preparation of 1-(3-(3-Amino-1-Hydroxypropyl)Phenethyl)Cycloheptanol

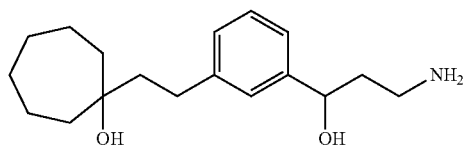 [SMILES: NCCC(O)c1cccc(CCC2(O)CCCCCC2)c1]

1-(3-(3-Amino-1-hydroxypropyl)phenethyl)cycloheptanol was prepared following the method shown in scheme 7:

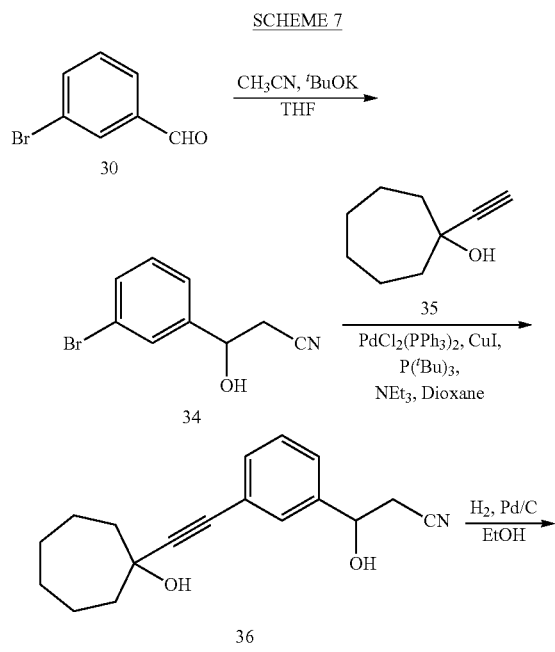

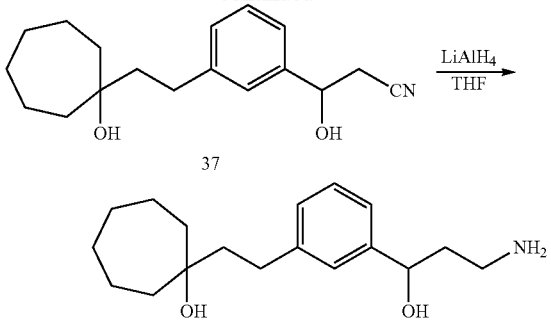

Step 1: To a -50° C. solution of potassium t-butoxide (703 mL of a 1.0 M solution in THF, 703 mmol) was added acetonitrile (27.73 g, 675.6 mmol) via syringe over 5 min. The mixture was stirred at -50° C. for 30 min, then a solution of 3-bromobenzaldehyde (22) (100 g, 540.5 mmol) in THF (50 mL) was added over 5 min. The mixture was stirred for 30 min, then allowed to warm to 0° C. The reaction mixture was quenched with saturated aqueous NH₄Cl (250 mL) and the layers were separated. The organics were washed with brine, dried over Na₂SO₄ and concentrated under reduced pressure to afford 3-(3-bromophenyl)-3-hydroxypropanenitrile (34) as a pale yellow oil. This material was used in the next synthetic step without further purification. Yield (117.6 g, 96%): ¹H NMR (400 MHz, DMSO-d₆) δ 7.60 (t, J=1.6 Hz, 1H), 7.46 (ddd, J=7.6, 2.0, 1.2 Hz, 1H), 7.40 (dd, J=7.6, 2.0 Hz, 1H), 7.31 (t, J=7.6 Hz, 1H), 6.05 (d, J=4.8 Hz, 1H), 2.80-2.94 (m, 2H).

Step 2: To a solution of nitrile 34 (2.15 g, 9.5 mmol), 1-ethynylcycloheptanol (35) (2.62 g, 19 mmol), and P(t-Bu)₃ (0.95 mL of a 1M solution in dioxane, 0.95 mmol) in diisopropylamine (6 mL) and dioxane (30 mL) was added PdCl₂(PPh₃)₂ (0.33 g, 0.47 mmol) and CuI (0.090 g, 0.47 mmol). The mixture was degassed (argon/vacuum) then heated at 45° C. overnight. After cooling to room temperature, the mixture was concentrated under reduced pressure. Purification by flash chromatography (1:2 to 1:1 EtOAc-hexanes) twice gave alkyne 36 as a pale yellow oil. Yield (2.35 g, 87%): ¹H NMR (400 MHz, CDCl₃) δ 7.33-7.46 (m, 4H), 4.99-5.04 (m, 1H), 3.66-3.74 (m, 1H), 2.72-2.78 (m, 2H), 1.56-2.13 (m, 12H).

Step 3: Alkyne 36 was hydrogenated following the method used in Example 2 except that EtOAc was used as the solvent and the reaction was stirred for 1.5 h. The product, diol 37, was used without purification. Yield (1.26 g, 97%): ¹H NMR (400 MHz, CDCl₃) δ 7.11-7.26 (m, 4H), 4.95 (t, J=6.4 Hz, 1H), 3.55-3.60 (m, 2H), 2.63-2.71 (m, 4H), 1.32-1.72 (m, 12H).

Step 4: Diol 37 was reduced following the method used in Example 15. The reaction was quenched with NaOH (0.3 mL of a 50% w/w solution), then filtered and concentrated under reduced pressure. Purification by flash chromatography (10% MeOH—CH₂Cl₂ then 10 to 20% 7M NH₃ in MeOH/CH₂Cl₂) gave Example 16 as a colorless oil that solidified to a white solid upon standing. Yield (ca. 0.149 g, 67%): ¹H NMR (400 MHz, DMSO-d₆) δ 7.16 (t, J=7.6 Hz, 1H), 7.12 (s, 1H), 7.07 (d, J=7.6 Hz, 1H), 6.99 (t, J=7.6 Hz, 1H), 4.60 (dd, J=7.6, 5.6 Hz, 1H), 3.97 (br s, 1H), 3.25 (br s, 2H), 2.56-2.66 (m, 4H), 1.26-1.64 (m, 16H).

Example 17

Preparation of 3-Amino-1-(3-(2-Cyclopentylethyl)Phenyl)Propan-1-ol

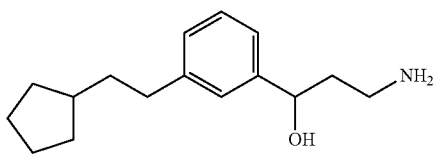 [SMILES: NCCC(O)c1cccc(CCC2CCCC2)c1]

3-Amino-1-(3-(2-cyclopentylethyl)phenyl)propan-1-ol was prepared following the method shown in scheme 8:

SCHEME 8

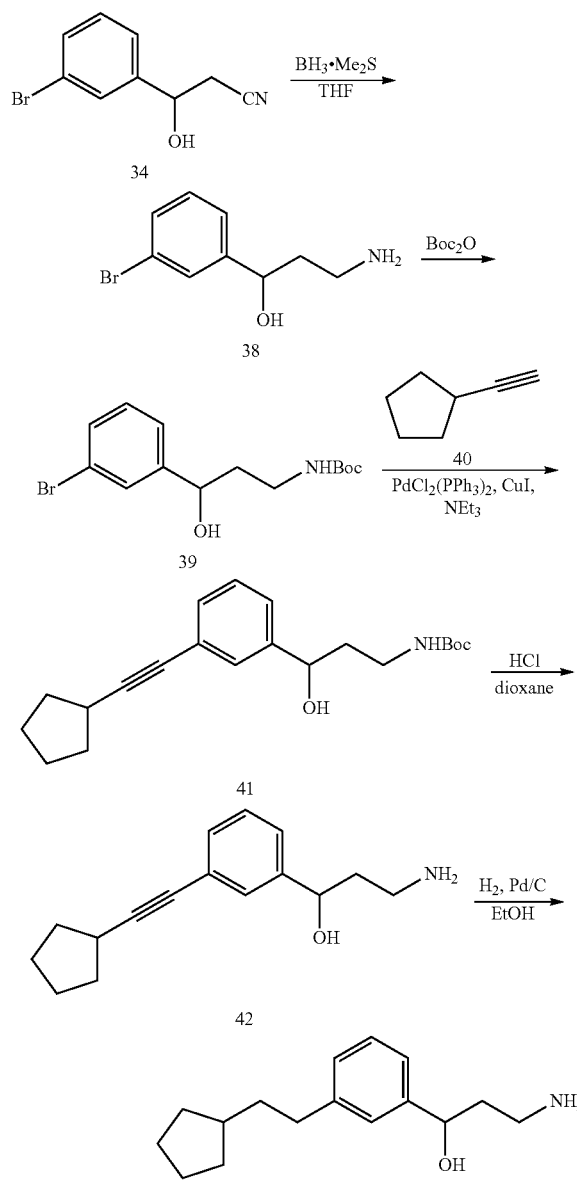

Step 1: To a solution of 3-(3-bromophenyl)-3-hydroxypropanenitrile (34) (117.5 g, 519.8 mmol) in THF (300 mL) under argon was added borane-dimethylsulfide complex (68 mL; 10.0 M in $BH_3$, 675.7 mmol) via an addition funnel over 30 min. The reaction mixture was heated at reflux for 2.5 h. After cooling to room temperature, the reaction was quenched with the addition of HCl—MeOH (350 mL of a 1.25 M solution) over 30 min. The mixture was concentrated under reduced pressure then water was added and the mixture was adjusted to pH~12 with 50% aqueous NaOH solution. The aqueous mixture was extracted with $CH_2Cl_2$ and the combined organics were dried over $Na_2SO_4$ and concentrated under reduced pressure. The residue was dissolved in 10% MeOH—$CH_2Cl_2$ and eluted through a pad of silica with 10% MeOH—$CH_2Cl_2$ then 10% 7 M $NH_3$ in MeOH/$CH_2Cl_2$ to give amine 38. This material was used in subsequent synthetic steps without further purification. Yield (106 g, 87%): $^1$H NMR (400 MHz, DMSO-$d_6$) δ 7.49 (m, 1H), 7.37 (dt, J=7.2, 1.6 Hz, 1H), 7.23-7.31 (m, 2H), 4.66 (t, J=6.8 Hz, 1H), 2.61 (m, 2H), 1.61 (q, J=6.8 Hz, 2H).

Step 2: To a solution of amine 38 (5.628 g, 26.0 mmol) in $CH_2Cl_2$ (20 mL) was added $Et_3N$ (5.43 mL, 39.0 mmol) and di-tert-butyl dicarbonate (8.52 g, 39.0 mmol). The reaction mixture was stirred overnight at room temperature then concentrated under reduced pressure. The residue was dissolved in EtOAc, washed with brine, dried over $Na_2SO_4$ and concentrated under reduced pressure. Purification by flash chromatography (13% EtOAc-hexanes) provided tert-butyl 3-(3-bromophenyl)-3-hydroxypropylcarbamate (39) as a thick brown oil. Yield (4.0 g, 48%): $^1$H NMR (400 MHz, $CDCl_3$) δ 7.53 (s, 1H), 7.39 (d, J=8.0 Hz, 1H), 7.29 (d, J=7.6 Hz, 1H), 7.20 (t, J=7.6 Hz, 1H), 4.87 (br s, 1H), 4.71 (d, J=6.4 Hz, 1H), 3.64 (br s, 1H), 3.50-3.59 (m, 1H), 3.12-3.19 (m, 1H), 1.77-1.87 (m, 2H), 1.46 (s, 9H).

Step 3: Coupling of ethynylcyclopentane (40) with tert-butyl 3-(3-bromophenyl)-3-hydroxypropylcarbamate (39) following the method used in the synthesis of Example 13 gave tert-butyl 3-(3-(cyclopentylethynyl)phenyl)-3-hydroxypropylcarbamate (41) as a brown oil. Yield (0.386 g, 92%).

Step 4: Deprotection of tert-butyl 3-(3-(cyclopentylethynyl)phenyl)-3-hydroxypropylcarbamate (41) following the method used in Example 13 and purification by preparative HPLC (Method 1P) gave compound 42 trifluoroacetate as a white solid. Yield (0.15 g, 74%): $^1$H NMR (400 MHz, $CDCl_3$) δ 7.17-7.31 (m, 4H), 4.85 (dd, J=7.6, 4.0 Hz, 1H), 3.11-3.17 (m, 2H), 2.69 (quint, J=7.2 Hz, 1H), 1.56-2.02 (m, 10H).

Step 5: Compound 42 trifluoroacetate was hydrogenated by the method used in Example 13 except that the reaction was run overnight at room temperature. Example 17 trifluoroacetate was isolated as a white sticky solid. Yield (0.094 g, 84%): $^1$H NMR (400 MHz, DMSO-$d_6$) δ 7.64 (br s, 3H), 7.20 (t, J=7.6 Hz, 1H), 7.03-7.11 (m, 3H), 5.48 (br s, 1H), 4.61 (t, J=5.6 Hz, 1H), 2.76-2.87 (m, 2H), 2.54 (t, J=8.0 Hz, 2H), 1.63-1.84 (m, 5H), 1.38-1.58 (m, 6H), 1.02-1.14 (m, 2H).

Example 18

Preparation of 3-Amino-1-(3-(3-Phenylpropyl)Phenyl)Propan-1-ol

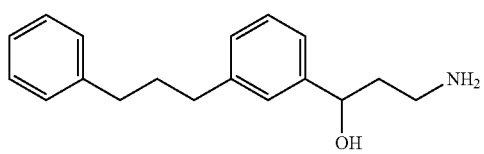 [SMILES: NCCC(O)c1cccc(CCCc2ccccc2)c1]

3-Amino-1-(3-(3-phenylpropyl)phenyl)propan-1-ol was prepared following the method used in Example 17:

Step 1: Coupling of prop-2-ynylbenzene with bromide 39 gave tert-butyl 3-hydroxy-3-(3-(3-phenylprop-1-ynyl)phenyl)propylcarbamate as a brown oil. Yield (0.404 g, 91%): $^1$H NMR (400 MHz, CDCl$_3$) δ 7.40-7.45 (m, 3H), 7.32-7.36 (m, 3H), 7.20-7.29 (m, 3H), 4.87 (br s, 1H), 4.72 (br s, 1H), 3.83 (s, 2H), 3.51-3.54 (m, 1H), 3.35 (br s, 1H), 3.12-3.19 (m, 1H), 1.81-1.84 (m, 2H), 1.45 (s, 9H).

Step 2: Deprotection of tert-butyl 3-hydroxy-3-(3-(3-phenylprop-1-ynyl)phenyl)propylcarbamate followed by purification by preparative HPLC (Method 1P) gave 3-amino-1-(3-(3-phenylprop-1-ynyl)phenyl)propan-1-ol trifluoroacetate as a white solid. Yield (0.114 g, 27%): $^1$H NMR (400 MHz, CDCl$_3$) δ 7.92 (br s, 2H), 7.26-7.37 (m, 5H), 7.16-7.23 (m, 4H), 4.79 (dd, J=8.4, 3.6 Hz, 1H), 3.75 (s, 2H), 3.02-3.16 (m, 2H), 1.93-1.98 (m, 2H).

Step 3: 3-Amino-1-(3-(3-phenylprop-1-ynyl)phenyl)propan-1-ol trifluoroacetate was hydrogenated by the method used in Example 13, except that the reaction was conducted for 1 h at 50° C., to give Example 18 trifluoroacetate as a white solid. Yield (33%): $^1$H NMR (400 MHz, DMSO-d$_6$) δ 7.76 (br s, 3H), 7.24-7.31 (m, 3H), 7.09-7.21 (m, 6H), 5.52 (br s, 1H), 4.65 (t, J=5.6 Hz, 1H), 2.67-2.89 (m, 2H), 2.52-2.64 (m, 4H), 1.78-1.91 (m, 4H).

Example 19

Preparation of 4-(3-(3-Amino-1-Hydroxypropyl)Phenethyl)Heptan-4-ol

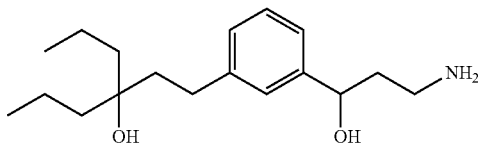 [SMILES: CCCC(O)(CCC)CCc1cccc(C(O)CCN)c1]

4-(3-(3-Amino-1-hydroxypropyl)phenethyl)heptan-4-ol was prepared following the method shown in scheme 9:

SCHEME 9

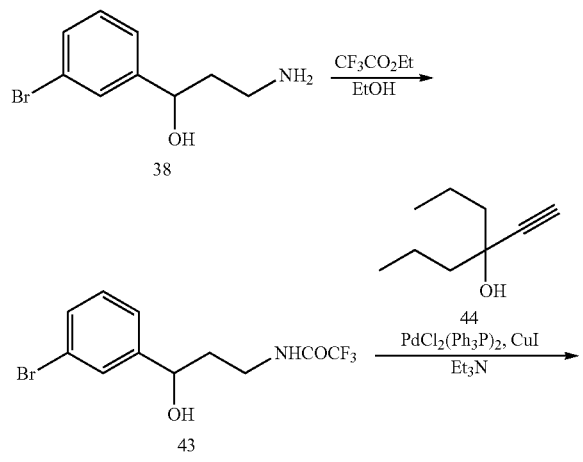

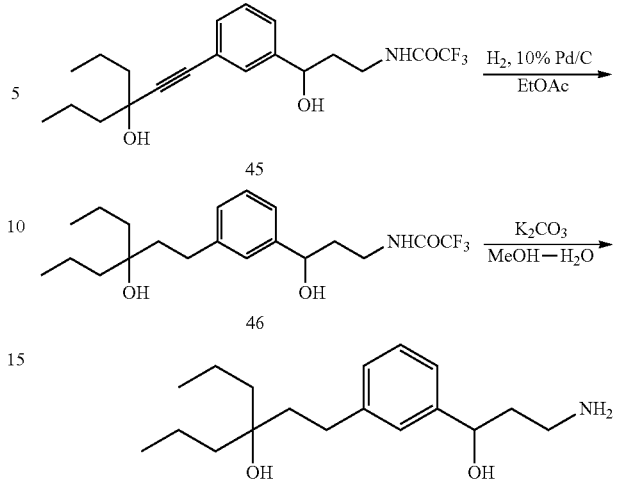

Step 1: To a solution of amine 38 (1.70 g, 7.39 mmol) in EtOH (10 mL) was added ethyl trifluoroacetate (10 mL). The mixture was stirred for 4 h then concentrated under reduced pressure. Purification by flash chromatography (20% EtOAc-hexanes) gave aryl bromide 43 as a clear oil. Yield (0.820 g, 34%): $^1$H NMR (400 MHz, DMSO-d$_6$) δ 9.33 (s, 1H), 7.51 (t, J=2.0 Hz, 1H), 7.41 (dt, J=7.6, 2.0 Hz, 1H), 7.25-7.32 (m, 2H), 5.46 (d, J=6.4 Hz, 1H), 4.55-4.60 (m, 1H), 3.20-3.23 (m, 2H), 1.75-1.82 (m, 2H).

Step 2: Coupling of 4-ethynylheptan-4-ol (44) with bromide 43 was conducted following the method used to prepare Example 7. Purification by flash chromatography (40% EtOAc-hexanes) gave alkyne 45 as a clear oil. Yield (0.520 g, 54%): $^1$H NMR (400 MHz, DMSO-d$_6$) δ 9.35 (m, 1H), 7.29-7.34 (m, 3H), 7.22-7.26 (m, 1H), 5.39 (d, J=4.4 Hz, 1H), 5.12 (s, 1H), 4.59 (dt, J=8.4, 4.8 Hz, 1H), 3.25 (quint, J=7.6 Hz, 2H), 1.80 (quint, J=8.0 Hz, 2H), 1.44-1.63 (m, 8H), 0.92 (t, J=7.2 Hz, 6H).

Step 3: Hydrogenation of alkyne 45 was conducted following the method used in Example 2 except that the reaction solvent used was EtOAc and reaction time was 2 h. Alcohol 46 was isolated as an oil and used in the next step without purification. Yield (0.519 g, quant.): $^1$H NMR (400 MHz, CDCl$_3$) δ 9.29 (t, J=5.2 Hz, 1H), 7.16 (t, J=7.2 Hz, 1H), 7.05-7.09 (m, 2H), 6.99 (d, J=7.2 Hz, 1H), 5.23 (br s, 1H), 4.50 (t, J=6.0 Hz, 1H), 3.93 (br s, 1H), 3.20 (q, J=6.8 Hz, 2H), 2.44-2.50 (m, 2H), 1.72-1.77 (m, 2H), 1.19-1.33 (m, 10H), 0.82 (t, J=6.8 Hz, 6H).

Step 4: To a solution of alcohol 46 (0.510 g, 1.31 mmol) in 10% H$_2$O—MeOH (20 mL) was added K$_2$CO$_3$ (0.905 g, 6.55 mmol) and the mixture was stirred overnight at room temperature. The mixture was concentrated under reduced pressure then partitioned between EtOAc and water. The combined organics were dried over Na$_2$SO$_4$ and concentrated under reduced pressure. Purification by flash chromatography (10% 7 M NH$_3$ in MeOH/CH$_2$Cl$_2$) gave Example 19 as a clear oil. Yield (0.202 g, 53%): $^1$H NMR (400 MHz, CDCl$_3$) δ 7.17 (t, J=7.2 Hz, 1H), 7.12 (m, 1H), 7.07-7.09 (m, 1H), 6.98-7.00 (m, 1H), 4.59-4.62 (m, 1H), 3.96 (br s, 1H), 2.57-2.66 (m, 2H), 2.48-2.53 (m, 2H), 1.53-1.65 (m, 4H), 1.22-1.36 (m, 10H), 0.84-0.86 (m, 6H).

Example 20

Preparation of 1-(3-(3-Aminopropyl)Phenethyl)Cycloheptanol

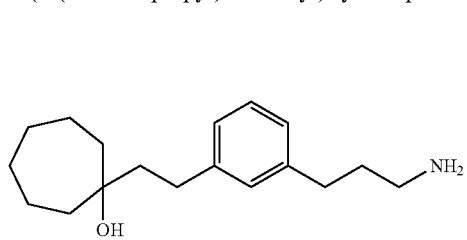

1-(3-(3-Aminopropyl)phenethyl)cycloheptanol was prepared following the method used to prepare Example 7:

Step 1: Coupling of 1-ethynylcycloheptanol with bromide 10 following the method used to prepare Example 7. Purification by flash chromatography (20% EtOAc-hexanes) gave 2,2,2-trifluoro-N-(3-(3-((1-hydroxycycloheptyl)ethynyl)phenyl)propyl)acetamide as a pale yellow oil. Yield (1.78 g, 60%): $^1$H NMR (400 MHz, DMSO-$d_6$) δ 9.40 (s, 1H), 7.26 (t, J=7.6 Hz, 1H), 7.17-7.22 (m, 3H), 5.26 (s, 1H), 3.16 (q, J=6.0 Hz, 2H), 2.56 (t, J=7.2 Hz, 2H), 1.91-1.97 (m, 2H), 1.73-1.79 (m, 4H), 1.45-1.63 (m, 8H).

Step 2: Deprotection of 2,2,2-trifluoro-N-(3-(3-((1-hydroxycycloheptyl)ethynyl)phenyl)propyl)acetamide was conducted following the method used to prepare Example 2 except that 5 equivalents of $K_2CO_3$ were used and the reaction was stirred at room temperature overnight. Purification by flash chromatography (10% 7M $NH_3$ in MeOH/$CH_2Cl_2$) gave 2,2,2-trifluoro-N-(3-(3-(2-(1-hydroxycycloheptyl)ethyl)phenyl)propyl)acetamide as a clear oil. Yield (0.635 g, 86%): $^1$H NMR (400 MHz, DMSO-$d_6$) δ 7.16-7.32 (m, 4H), 5.13 (s, 1H), 4.65 (t, J=6.0 Hz, 1H), 2.56-2.64 (m, 2H), 1.44-1.63 (m, 12H), 0.90 (t, J=7.6 Hz, 6H).

Step 3: Hydrogenation of 2,2,2-trifluoro-N-(3-(3-(2-(1-hydroxycycloheptyl)ethyl)phenyl)propyl)acetamide following the method used to prepare Example 7 gave Example 19 as a colorless oil. Yield (0.305 g, 100%): $^1$H NMR (400 MHz, DMSO-$d_6$) δ 7.13 (t, J=7.2 Hz, 1H), 6.94-6.98 (m, 3H), 4.01 (br s, 1H), 2.47-2.58 (m, 4H), 1.32-1.62 (m, 20H).

Example 21

Preparation of 3-(3-(2-(Naphthalen-2-yl)Ethyl)Phenyl)propan-1-Amine

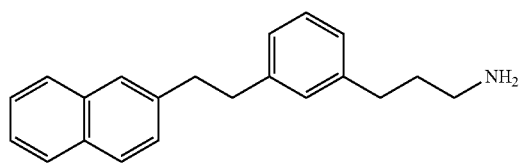 [SMILES: NCCCc1cccc(CCc2ccc3ccccc3c2)c1]

3-(3-(2-(Naphthalen-2-yl)ethyl)phenyl)propan-1-amine was prepared following the method shown in scheme 10:

SCHEME 10

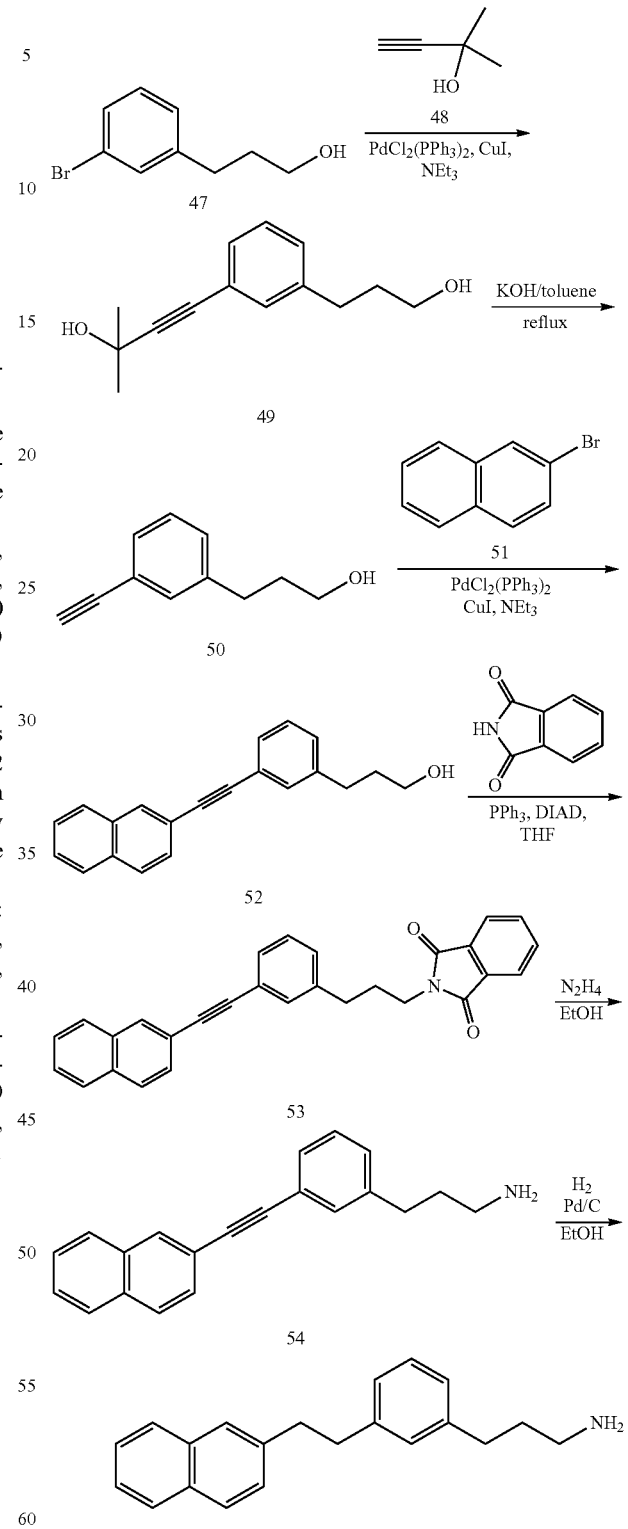

Step 1: To a degassed solution of 3-(3-bromophenyl)propan-1-ol (47) (0.95 g, 4.5 mmol) and 2-methyl-3-butyn-2-ol (48) (1.6 mL, 16 mmol) in triethylamine (25 mL) was added $PdCl_2(PPh_3)_3$ (0.095 g, 0.14 mmol) and CuI (0.027 g, 0.14 mmol). The resulting mixture was degassed and stirred under argon at 70° C. for 15 h. After cooling to room temperature, the reaction mixture was concentrated under reduced pressure and diluted with EtOAc (50 mL). Trace solids were removed by filtration then the filtrate was washed with water and brine, dried over Na$_2$SO$_4$, and concentrated under reduced pressure. Purification by flash chromatography (10 to 100% EtOAc-hexanes gradient) gave 4-(3-(3-hydroxypropyl)phenyl)-2-methylbut-3-yn-2-ol (49) as a light brown oil: Yield (0.78 g, 80%): $^1$H NMR (400 MHz, DMSO-d$_6$) δ 7.18-7.29 (m, 4H), 5.46 (s, 1H), 4.48 (t, J=4.0 Hz, 1H), 3.38 (q, J=4.0 Hz, 2H), 2.59 (t, J=6.0 Hz, 2H), 2.46 (m, 2H), 1.46 (s, 6H).

Step 2: To a solution of 4-(3-(3-hydroxypropyl)phenyl)-2-methylbut-3-yn-2-ol (49) (0.750 g, 3.4 mmol) in toluene (50 mL) was added powdered KOH (0.390 g, 7 mmol). The resulting mixture was heated at reflux for 45 min. After cooling to room temperature, the reaction mixture was concentrated under reduced pressure to 10-15 mL volume and partitioned between EtOAc and water. The combined organics were washed with water and brine, dried over MgSO$_4$ and concentrated under reduced pressure. Purification by flash chromatography (15% EtOAc-hexanes) gave 3-(3-ethynylphenyl)propan-1-ol (50) as a light brown oil. Yield (0.272 g, 49%).

Step 3: To a degassed solution of alcohol 50 (0.5 g, 3.12 mmol) and 2-bromonapthalene (51) (0.54 g, 2.60 mmol) in Et$_3$N (13 mL) was added PdCl$_2$(PPh$_3$)$_2$ (0.055 g, 0.078 mmol) and CuI (0.015 g, 0.078 mmol). The reaction mixture was stirred overnight at 70° C. After cooling to room temperature, the mixture was concentrated under reduced pressure. The residue was dissolved in EtOAc and the solids filtered off. The filtrate was washed with water and brine, dried over Na$_2$SO$_4$ and concentrated under reduced pressure. Purification by flash chromatography (8% EtOAc-hexanes) provided alcohol 52 as a brown oil. Yield (0.40 g, 45%): $^1$H NMR (400 MHz, CDCl$_3$) δ 8.06 (br s, 1H), 7.80-7.83 (m, 2H), 7.58 (dd, J=8.8, 2.0 Hz, 1H), 7.47-7.51 (m, 2H), 7.41-7.43 (m, 2H), 7.26-7.31 (m, 2H), 7.18 (d, J=7.6 Hz, 1H), 4.77 (br s, 1H), 4.11 (t, J=6.4 Hz, 2H), 2.71 (t, J=7.6 Hz, 2H), 1.99 (quint, J=6.8 Hz, 2H).

Step 4: To a solution of alcohol 52 (0.35 g, 1.22 mmol) in THF (20 mL) was added phthalimide (0.18 g, 1.28 mmol) and PPh$_3$ (0.40 g, 1.52 mmol). The reaction mixture was cooled to 0° C. and a solution of diisopropyl azodicarboxylate (0.32 g, 1.61 mmol) in THF (5 mL) was added dropwise. The reaction was stirred at room temperature for 1 h. The mixture was concentrated under reduced pressure and 20% EtOAc-heptane was added. The mixture was sonicated for 10 min then the precipitate was filtered off. The filtrate was concentrated under reduced pressure. Purification by flash chromatography (10% EtOAc-hexanes) gave alkyne 53 as a yellow solid. Yield (0.40 g, 80%): $^1$H NMR (400 MHz, CDCl$_3$) δ 8.44 (d, J=8.0 Hz, 1H), 7.82-7.88 (m, 4H), 7.76 (dd, J=7.2, 1.2 Hz, 1H), 7.70 (dd, J=5.2, 3.2 Hz, 2H), 7.59-7.64 (m, 1H), 7.52-7.56 (m, 1H), 7.42-7.49 (m, 3H), 7.29 (d, J=7.6 Hz, 1H), 7.22 (d, J=8.0 Hz, 1H), 3.79 (t, J=7.2 Hz, 2H), 2.73 (t, J=7.2 Hz, 2H), 2.09 (quint, J=7.2 Hz, 2H).

Step 5: To a solution of alkyne 53 (0.40 g, 0.96 mmol) in EtOH (4 mL) was added hydrazine hydrate (0.17 mL, 2.89 mmol). The reaction was stirred at room temperature overnight. Diethyl ether was added and the solids were removed by filtration. The filtrate was concentrated under reduced pressure. Purification by Prep HPLC using Method 2P gave amine 54 as a white solid. Yield (0.12 g, 44%): $^1$H NMR (400 MHz, DMSO-d$_6$) δ 8.18 (s, 1H), 7.80-7.95 (m, 3H), 7.69 (br s, 2H), 7.57-7.62 (m, 3H), 7.45-7.49 (m, 2H), 7.40 (t, J=7.6 Hz, 1H), 7.30 (d, J=7.6 Hz, 1H), 2.80 (t, J=7.2 Hz, 2H), 2.69 (t, J=7.6 Hz, 2H), 1.87 (quint, J=7.6 Hz, 2H).

Step 6: Hydrogenation of alkyne 54 following the method used in Example 13 gave Example 21 trifluoroacetate as a white solid. Yield (0.019 g, 23%): $^1$H NMR (400 MHz, DMSO-d$_6$) δ 7.81-7.88 (m, 3H), 7.71 (s, 1H), 7.68 (br s, 2H), 7.42-7.50 (m, 3H), 7.22 (t, J=7.4 Hz, 1H), 7.10-7.12 (m, 2H), 7.03 (d, J=7.6 Hz, 1H), 3.02-3.06 (m, 2H), 2.94-2.98 (m, 2H), 2.78 (t, J=7.4 Hz, 2H), 2.61 (t, J=7.6, 2H), 1.81 (quint, J=7.6 Hz, 2H).

Example 22

Preparation of 3-(3-Phenethylphenyl)Propan-1-Amine

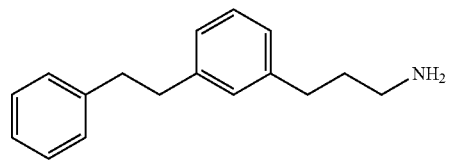 [SMILES: NCCCc1cccc(CCc2ccccc2)c1]

3-(3-Phenethylphenyl)propan-1-amine was prepared following the method shown in Scheme 11:

SCHEME 11

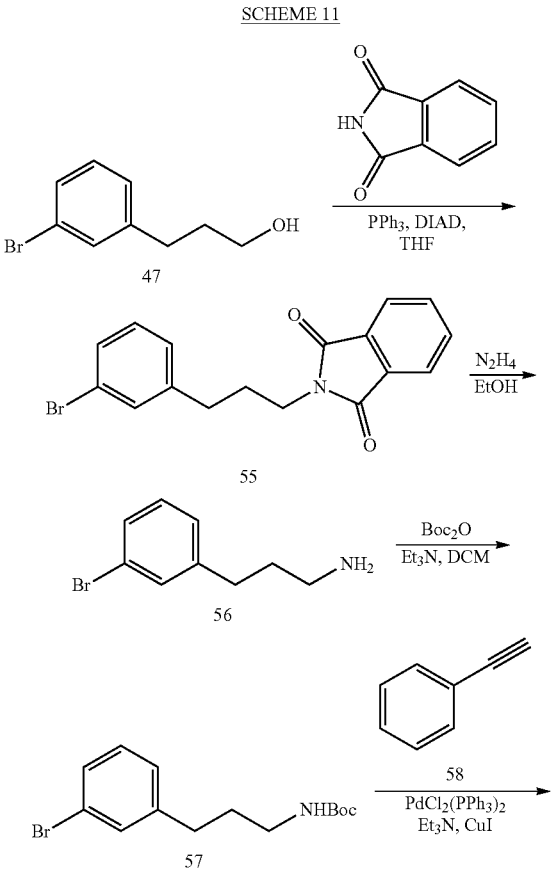

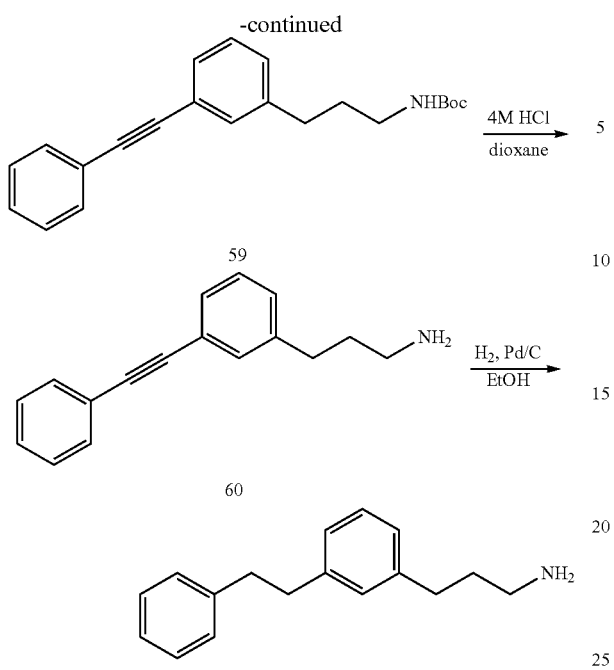

Step 1: Coupling of alcohol 47 with phthalimide was conducted following the procedure described in Example 13, except that the reaction was run at room temperature. Purification by flash chromatography (6% EtOAc-hexanes) gave phthalimide 55 as a cream-colored solid. Yield (8.6 g, 92%). $^1$H NMR (400 MHz, DMSO-$d_6$) δ 7.81-7.87 (m, 4H), 7.44 (s, 1H), 7.31-7.33 (m, 1H), 7.19-7.24 (m, 2H), 3.60 (t, J=6.8 Hz, 2H), 2.63 (t, J=7.6 Hz, 2H), 1.87-1.94 (m, 2H).

Step 2: Deprotection of phthalimide 55 following the method used in Example 21, except that the reaction mixture was heated at reflux for 1.5 h, gave amine 56 as a yellow oil. This compound was taken on to the next synthetic step without purification. Yield (5.4 g, 98%).

Step 3: Protection of amine 56 with di-tent-butyl dicarbonate following the method used in Example 17 gave carbamate 57 as a light yellow oil. Carbamate 57 was used in the next synthetic step without further purification. Yield (6.97 g, 86%): $^1$H NMR (400 MHz, DMSO-$d_6$) δ 7.33 (s, 1H), 7.26-7.34 (m, 1H), 7.08-7.20 (m, 2H), 4.55 (br s, 1H), 3.15 (q, J=6 Hz, 2H), 2.61 (t, J=8.0 Hz, 2H), 1.79 (quint, J=7.6 Hz, 2H), 1.44 (s, 9H).

Step 4: Coupling of phenylacetylene (58) with bromide 57 was conducted following the method used in Example 13. Purification by flash chromatography (5% EtOAc-hexanes) gave tert-butyl 3-(3-(phenylethynyl)phenyl)propylcarbamate (59) as a brown oil. Yield (0.32 g, 50%): $^1$H NMR (400 MHz, CDCl$_3$) δ 7.53 (dd, J=7.2, 2 Hz, 2H), 7.42-7.47 (m, 1H), 7.36-7.38 (m, 1H), 7.20-7.26 (m, 2H), 7.11 (d, J=8.0 Hz, 1H), 6.98 (t, J=7.6 Hz, 1H), 6.86 (m, 1H), 4.54 (br s, 1H), 3.14-3.17 (m, 2H), 2.63 (quint, J=7.6 Hz, 2H), 1.76-1.86 (m, 2H), 1.38 (s, 9H).

Step 5: Deprotection of tert-butyl 3-(3-(phenylethynyl)phenyl)propylcarbamate (59) was conducted following the procedure used in the preparation of Example 13. Trituration from diethyl ether gave 3-(3-(phenylethynyl)phenyl)propan-1-amine hydrochloride (60) as an off white solid. Yield (0.19 g, 73%): $^1$H NMR (400 MHz, DMSO-$d_6$) δ 8.08 (br s, 2H), 7.55-7.57 (m, 1H), 7.21-7.46 (m, 6H), 7.21-7.30 (m, 2H), 2.77 (q, J=7.6 Hz, 2H), 2.66 (q, J=7.6 Hz, 2H), 1.82-1.93 (m, 2H).

Step 6: Hydrogenation of 3-(3-(phenylethynyl)phenyl)propan-1-amine was conducted following the method used to prepare Example 18. This compound was purified by Prep HPLC using Method 1P to give Example 23 trifluoroacetate as a cream-colored solid. Yield (0.080 g, 36%): $^1$H NMR (400 MHz, CDCl$_3$) δ 7.87 (br s, 2H), 7.24-7.28 (3H), 7.16-7.20 (m, 3H), 6.93-7.03 (m, 3H), 2.85-2.87 (m, 5H (apparent low integration)), 2.61 (t, J=7.6 Hz, 2H), 1.94 (quint, J=7.6 Hz, 2H); $^{13}$C NMR (300 MHz, CDCl$_3$) δ 142.20, 141.71, 139.72, 128.62, 128.46, 128.44, 128.30, 126.55, 125.88, 125.77, 39.35, 37.84, 37.79, 32.28, 28.90.

Example 23

Preparation of 4-(3-(3-Aminopropyl)Phenyl)Butan-1-ol

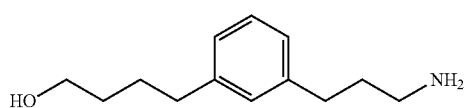 [SMILES: NCCCc1cccc(CCCCO)c1]

4-(3-(3-Aminopropyl)phenyl)butan-1-ol was prepared following the method used for the preparation of Example 2:

Step 1: Coupling of but-3-yn-1-ol with bromide 10 gave 2,2,2-trifluoro-N-(3-(3-(4-hydroxybut-1-ynyl)phenyl)propyl)acetamide as a pale yellow oil. Yield (0.9 g, 62%): $^1$H NMR (400 MHz, DMSO-$d_6$) δ 9.40 (br s, 1H), 7.15-7.26 (m, 4H), 4.86 (br s, 1H), 3.56 (app t, J=6.8 Hz, 2H), 3.16 (q, J=6.8 Hz, 2H), 2.47-2.56 (m, 4H), 1.76 (quint, J=7.6 Hz, 2H).

Step 2: Deprotection of 2,2,2-trifluoro-N-(3-(3-(4-hydroxybut-1-ynyl)phenyl)propyl)acetamide following the method used in Example 2, except that the product was purified by flash chromatography (CH$_2$Cl$_2$/EtOH/NH$_4$OH 85:14:1) gave 4-(3-(3-aminopropyl)phenyl)but-3-yn-1-ol as a clear oil. Yield (0.236 g, 65%): $^1$H NMR (400 MHz, DMSO-$d_6$) δ 7.12-7.24 (m, 4H), 3.56 (t, J=6.9 Hz, 2H), 2.47-2.57 (m, 6H), 1.59 (quint, J=6.9 Hz, 2H).

Step 3: Hydrogenation of 4-(3-(3-aminopropyl)phenyl)but-3-yn-1-ol following the method used to prepare example 18 gave Example 23 trifluoroacetate as a white solid. Yield (0.040 g, 56%): $^1$H NMR (400 MHz, DMSO-$d_6$) δ 7.74 (br s, 3H), 7.20 (t, J=8.0 Hz, 1H), 7.00-7.06 (m, 3H), 4.37 (m, 1H), 3.27-3.41 (m, 2H), 2.76 (t, J=7.6 Hz, 2H), 2.45-2.62 (m, 4H), 1.78-1.86 (m, 2H), 1.54-1.61 (m, 2H), 1.39-1.46 (m, 2H).

Example 24

Preparation of 3-(3-(2-Cyclopentylethyl)Phenyl)Propan-1-Amine

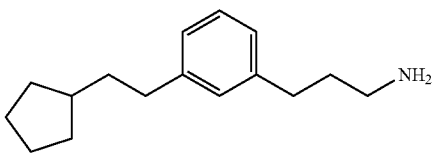 [SMILES: NCCCc1cccc(CCC2CCCC2)c1]

3-(3-(2-Cyclopentylethyl)phenyl)propan-1-amine was prepared following the method used for the preparation of Example 22:

Step 1: Coupling ethynylcyclopentane with bromide 57 was conducted following the method used in Example 22. Purification by flash chromatography (6% EtOAc-hexanes) gave tert-butyl 3-(3-(cyclopentylethynyl)phenyl)propylcarbamate as a brown oil. Yield (0.70 g, 84%): $^1$H NMR (400 MHz, DMSO-$d_6$) δ 7.06-7.33 (m, 4H), 2.85 (quint, J=7.4 Hz, 1H), 2.57-2.66 (m, 2H), 2.62 (t, J=8.0 Hz, 2H), 1.93-2.01 (m, 2H), 1.82 (quint, J=7.6 Hz, 2H), 1.66-1.75 (m, 2H), 1.55-1.64 (m, 4H), 1.45 (m, 9H).

Step 2: Deprotection of tert-butyl 3-(3-(cyclopentylethynyl)phenyl)propylcarbamate following purification by preparative HPLC (Method 1P) gave 3-(3-(cyclopentylethynyl)phenyl)propan-1-amine trifluoroacetate as a white solid. Yield (0.22 g, 30%): $^1$H NMR (400 MHz, DMSO-$d_6$) δ 7.68 (br s, 2H), 7.27 (t, J=7.6 Hz, 1H), 7.16-7.24 (m, 3H), 2.85 (quint, J=7.6 Hz, 1H), 2.75 (br s, 2H), 2.62 (t, J=7.2 Hz, 2H), 1.93-2.01 (m, 2H), 1.82 (quint, J=7.6 Hz, 2H), 1.67-1.71 (m, 2H), 1.56-1.66 (m, 4H).

Step 3: Hydrogenation of 3-(3-(cyclopentylethynyl)phenyl)propan-1-amine following the method used to prepare example 18 gave Example 24 trifluoroacetate as a white solid. Yield (80 mg, 79%): $^1$H NMR (400 MHz, DMSO-$d_6$) δ 7.67 (br s, 3H), 7.20 (t, J=8.0 Hz, 1H), 7.00-7.15 (m, 3H), 2.78 (t, J=8.4 Hz, 2H), 2.54-2.62 (m, 4H), 1.66-1.85 (m, 4H), 1.42-1.64 (m, 7H), 1.18-1.15 (m, 2H).

Example 25

Preparation of 3-(3-(2-Cyclohexylethyl)Phenyl)Propan-1-Amine

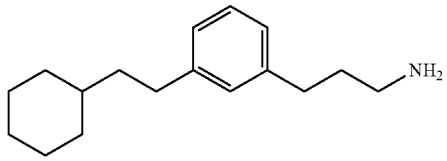 [SMILES: NCCCc1cccc(CCC2CCCCC2)c1]

3-(3-(2-Cyclohexylethyl)phenyl)propan-1-amine was prepared following the method used for the preparation of Example 22:

Step 1: Coupling of ethynylcyclohexane with bromide 57 was conducted following the method used in Example 22. Purification by flash chromatography (5% EtOAc-hexanes) gave tert-butyl 3-(3-(cyclohexylethynyl)phenyl)propylcarbamate as a brown oil. Yield (0.50 g, 57%).

Step 2: Deprotection of tert-butyl 3-(3-(cyclohexylethynyl)phenyl)propylcarbamate followed by purification by preparative HPLC (Method 1P) gave 3-(3-(cyclohexylethynyl)phenyl)propan-1-amine trifluoroacetate as a cream-colored solid. Yield (0.21 g, 40%): $^1$H NMR (400 MHz, DMSO-$d_6$) δ 7.67 (br s, 2H), 7.28 (t, J=7.6 Hz, 1H), 7.17-7.24 (m, 3H), 2.74-2.79 (m, 1H), 2.64 (t, J=7.6 Hz, 4H), 1.82 (quint, J=7.2 Hz, 4H), 1.67-1.68 (m, 2H), 1.32-1.52 (m, 6H).

Step 3: Hydrogenation of 3-(3-(cyclohexylethynyl)phenyl)propan-1-amine was conducted following the method used to prepare Example 18. Purification by Prep HPLC using Method 1P gave Example 24 trifluoroacetate as a white solid. Yield (0.050 g, 33%): $^1$H NMR (400 MHz, CDCl$_3$) δ 7.87 (br s, 3H), 7.16 (t, J=7.6 Hz, 1H), 7.01 (d, J=7.6 Hz, 1H), 6.92-6.94 (m, 2H), 2.87 (m, 2H), 2.53-2.62 (m, 4H), 1.63-1.76 (m, 5H), 1.43-1.49 (m, 2H), 1.13-1.29 (m, 6H), 0.87-0.96 (m, 2H).

Example 26

Preparation of 3-(3-(3-Phenylpropyl)Phenyl)Propan-1-Amine

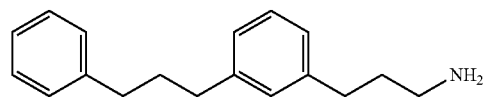 [SMILES: NCCCc1cccc(CCCc2ccccc2)c1]

3-(3-(3-Phenylpropyl)phenyl)propan-1-amine was prepared following the method used for the preparation of Example 22:

Step 1: Coupling of prop-2-ynylbenzene with bromide 57 was conducted following the method used in Example 22. Purification by flash chromatography (6% EtOAc-hexanes) gave tert-butyl 3-(3-(3-phenylprop-1-ynyl)phenyl)propylcarbamate as a brown oil. Yield (0.85 g, 73%): $^1$H NMR (400 MHz, CDCl$_3$) δ 7.41-7.43 (m, 2H), 7.35 (t, J=8.0 Hz, 2H), 7.10-7.28 (m, 5H), 4.52 (br s, 1H), 3.84 (s, 2H), 3.14-3.16 (m, 2H), 2.61 (t, J=7.6 Hz, 2H), 1.80 (quint, J=7.6 Hz, 2H), 1.48 (s, 9H).

Step 2: Deprotection of tert-butyl 3-(3-(3-phenylprop-1-ynyl)phenyl)propylcarbamate followed by purification by preparative HPLC (Method -001P) gave 3-(3-(3-phenylprop-1-ynyl)phenyl)propan-1-amine trifluoroacetate as a white solid. Yield (0.45 g, 51%): $^1$H NMR (400 MHz, DMSO-$d_6$) δ 7.69 (br s, 2H), 7.35-7.42 (m, 4H), 7.25-7.31 (m, 4H), 7.20-7.22 (m, 1H), 3.89 (s, 2H), 2.76 (t, J=7.2 Hz, 2H), 2.63 (t, J=7.6 Hz, 2H), 1.82 (quint, J=7.6 Hz, 2H).

Step 3: Hydrogenation of 3-(3-(3-phenylprop-1-ynyl)phenyl)propan-1-amine trifluoroacetate following the method used to prepare Example 18 gave Example 26 which was HPLC purified using Method 1P to give Example 26 trifluoroacetate as a colorless oil. Yield (0.180 g, 88%): $^1$H NMR (400 MHz, DMSO-$d_6$) δ 7.69 (br s, 3H), 7.29 (t, J=7.2 Hz, 2H), 7.16-7.24 (m, 4H), 7.01-7.05 (m, 3H), 2.88 (t, J=8.0 Hz, 2H), 2.56-2.62 (m, 6H), 1.88-1.91 (m, 4H).

Example 27

Preparation of 3-(3-Pentylphenyl)Propan-1-Amine

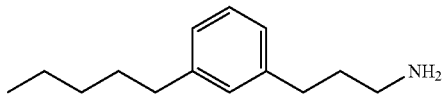

3-(3-Pentylphenyl)propan-1-amine was prepared following the method used for the preparation of Example 22:

Step 1: Coupling of 1-pent-1-yne with bromide 57 was conducted following the method used in Example 22. Purification by flash chromatography (5% EtOAc-hexanes) gave tert-butyl 3-(3-(pent-1-ynyl)phenyl)propylcarbamate as a brown oil. Yield (0.35 g, 58%): $^1$H NMR (400 MHz, CDCl$_3$) δ 7.07-7.33 (m, 4H), 4.52 (br s, 1H), 3.14-3.15 (m, 2H), 2.58-2.66 (m, 2H), 2.38 (t, J=7.2 Hz, 2H), 1.79 (quint, J=7.6 Hz, 2H), 1.64 (q, J=7.2 Hz, 2H), 1.45 (s, 9H), 1.05 (t, J=6.8 Hz, 3H).

Step 2: Deprotection of tert-butyl 3-(3-(pent-1-ynyl)phenyl)propylcarbamate followed by purification by preparative HPLC (Method 1P) gave 3-(3-(pent-1-ynyl)phenyl)propan-1-amine trifluoroacetate as a white solid. Yield (0.17 g, 32%): $^1$H NMR (400 MHz, DMSO-d$_6$) δ 7.71 (br s, 2H), 7.28 (t, J=7.6 Hz, 1H), 7.17-7.25 (m, 3H), 2.76 (t, J=7.2 Hz, 2H), 2.62 (t, J=7.2 Hz, 2H), 2.39 (t, J=6.8 Hz, 2H), 1.82 (quint, J=7.6 Hz, 2H), 1.51-1.60 (m, 2H), 1.00 (t, J=7.6 Hz, 3H).

Step 3: Hydrogenation of 3-(3-(pent-1-ynyl)phenyl)propan-1-amine trifluoroacetate following the method used to prepare example 18 gave Example 27 which was HPLC purified to give Example 27 trifluoroacetate as a cream-colored solid. Yield (0.050 g, 20%): $^1$H NMR (400 MHz, DMSO-d$_6$) δ 7.72 (br s, 3H), 7.20 (t, J=7.6 Hz, 1H), 7.00-7.03 (m, 3H), 2.88 (m, 2H), 2.60 (t, J=7.6 Hz, 2H), 2.46-2.56 (m, 2H), 1.78-1.85 (m, 2H), 1.52-1.59 (m, 2H), 1.22-1.34 (m, 4H), 0.86 (t, J=7.2 Hz, 3H).

Example 28

Preparation of 3-(3-Hexylphenyl)Propan-1-Amine

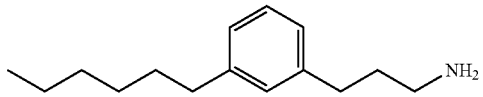 [SMILES: CCCCCCc1cccc(CCCN)c1]

3-(3-Hexylphenyl)propan-1-amine was prepared following the method used for the preparation of Example 22:

Step 1: Coupling of hex-1-yne with bromide 57 was conducted following the method used in Example 22. Purification by flash chromatography (5% EtOAc-hexanes) gave tert-butyl 3-(3-(hex-1-ynyl)phenyl)propylcarbamate as a brown oil. Yield (0.64 g, 64%).

Step 2: Deprotection of tert-butyl 3-(3-(hex-1-ynyl)phenyl)propylcarbamate gave followed by purification by preparative HPLC (Method 4P) gave 3-(3-(hex-1-ynyl)phenyl)propan-1-amine hydrochloride as a white solid. Yield (0.17 g, 33%): $^1$H NMR (400 MHz, DMSO-d$_6$) δ 7.71 (br s, 2H), 7.28 (t, J=7.2 Hz, 1H), 7.17-7.25 (m, 3H), 2.76 (t, J=7.6 Hz, 2H), 2.62 (t, J=7.2 Hz, 2H), 2.42 (t, J=7.0 Hz, 2H), 1.82 (quint, J=7.6 Hz, 2H), 1.52 (quint, J=7.0 Hz, 2H), 1.44 (quint, J=7.0 Hz, 2H), 0.92 (t, J=7.6 Hz, 3H).

Step 3: Hydrogenation of 3-(3-(hex-1-ynyl)phenyl)propan-1-amine hydrochloride following the method used to prepare Example 18 gave Example 28 hydrochloride as a colorless oil. Yield (0.085 g, 98%): $^1$H NMR (400 MHz, DMSO-d$_6$) δ 7.76 (br s, 3H), 7.20 (t, J=7.6 Hz, 1H), 7.00-7.03 (m, 3H), 2.78 (t, J=7.6 Hz, 2H), 2.60 (t, J=7.6 Hz, 2H), 2.46-2.56 (m, 2H), 1.82 (quint, J=7.6 Hz, 2H), 1.51-1.56 (m, 2H), 1.20-1.30 (m, 6H), 0.85 (t, J=7.2 Hz, 3H).

Example 29

Preparation of 3-(3-(3,3-Dimethylbutyl)Phenyl)Propan-1-Amine

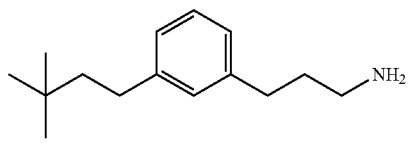

3-(3-(3,3-Dimethylbutyl)phenyl)propan-1-amine was prepared following the method used for the preparation of Example 22:

Step 1: Coupling of 3,3-dimethylbut-1-yne with bromide 57 was conducted following the method used in Example 22. Purification by flash chromatography (6% EtOAc-hexanes) gave tert-butyl 3-(3-(3,3-dimethylbut-1-ynyl)phenyl)propylcarbamate as a brown oil. Yield (0.43 g, 54%).

Step 2: Deprotection of tert-butyl 3-(3-(3,3-dimethylbut-1-ynyl)phenyl)propylcarbamate following purification by preparative HPLC (Method 1P) gave 3-(3-(3,3-dimethylbut-1-ynyl)phenyl)propan-1-amine trifluoroacetate as a pale yellow solid. Yield (0.08 g, 18%): $^1$H NMR (400 MHz, DMSO-d$_6$) δ 7.79 (br s, 2H), 7.27 (t, J=7.6 Hz, 1H), 7.16-7.22 (m, 3H), 2.75-2.77 (m, 2H), 2.61 (t, J=7.6 Hz, 2H), 1.82 (quint, J=7.2 Hz, 2H), 1.29 (s, 9H).

Step 3: Hydrogenation of 3-(3-(hex-1-ynyl)phenyl)propan-1-amine trifluoroacetate following the method used to prepare Example 18 gave Example 29 trifluoroacetate as a cream-colored solid. Yield (0.040 g, 50%): $^1$H NMR (400 MHz, DMSO-d$_6$) δ 7.69 (br s, 3H), 7.18-7.22 (m, 1H), 6.99-7.28 (m, 3H), 2.78 (t, J=5.2 Hz, 2H), 2.61 (t, J=5.2 Hz, 2H), 2.50-2.55 (m, 2H), 1.79-1.84 (m, 2H), 1.41-1.46 (m, 2H), 0.95 (s, 9H).

Example 30

Preparation of 6-(3-(3-Aminopropyl)Phenyl)Hexan-1-ol

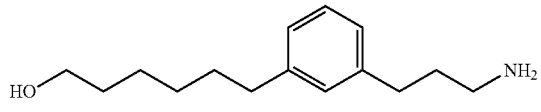 [SMILES: NCCCc1cccc(CCCCCCO)c1]

6-(3-(3-Aminopropyl)phenyl)hexan-1-ol was prepared following the method used for the preparation of Example 22:

Step 1: Coupling of hex-5-yn-1-ol with bromide 57 was conducted following the method used in Example 22. Purification by flash chromatography (30% EtOAc-hexanes) gave tert-butyl 3-(3-(6-hydroxyhex-1-ynyl)phenyl)propylcarbamate as a white solid. Yield (0.350 g, 66%): $^1$H NMR (400 MHz, CDCl$_3$) δ 7.17-7.23 (m, 3H), 7.07-7.10 (m, 1H), 6.81-6.84 (m, 1H), 4.53 (br s, 1H), 3.72 (q, J=6.0 Hz, 2H), 3.10-3.18 (m, 2H), 2.60 (t, J=8.0 Hz, 2H), 2.46 (t, J=6.8 Hz, 2H), 1.63-1.83 (m, 6H), 1.44 (s, 9H).

Step 2: Deprotection of tert-butyl 3-(3-(6-hydroxyhex-1-ynyl)phenyl)propylcarbamate following purification by prep HPLC using Method 1P gave 3-(3-(3,3-dimethylbut-1-ynyl)phenyl)propan-1-amine trifluoroacetate as a white solid. Yield (0.140 g, 34%): $^1$H NMR (400 MHz, CDCl$_3$) δ 7.21 (d, J=7.6 Hz, 2H), 7.17 (t, J=7.6 Hz, 1H), 7.07 (dm, J=7.2 Hz, 1H), 3.68 (t, J=6.4 Hz, 2H), 2.95 (t, J=7.6 Hz, 2H), 2.67 (t, J=7.6, 2H), 2.43 (t, J=6.4, 2H), 2.06 (quint, J=7.6 Hz, 2H), 1.71-1.79 (m, 2H), 1.61-1.68 (m, 2H).

Step 3: 6-(3-(3-Aminopropyl)phenyl)hex-5-yn-1-ol trifluoroacetate was hydrogenated following the procedure used in Example 18 to give Example 30 trifluoroacetate as a white solid. Yield (33%): $^1$H NMR (400 MHz, DMSO-d$_6$) δ 7.88 (br s, 3H), 7.20 (t, J=7.6 Hz, 1H), 6.95-7.20 (m, 3H), 4.38 (br s, 1H), 3.37 (t, J=6.0 Hz, 2H), 2.76 (t, J=7.6 Hz, 2H), 2.59 (t, J=7.6 Hz, 2H), 2.54 (t, J=7.2 Hz, 2H), 1.80-1.87 (m, 2H), 1.53-1.58 (m, 2H), 1.38-1.42 (m, 2H), 1.24-1.32 (m, 4H).

Example 31

Preparation of 3-(3-(2-Methylphenethyl)Phenyl)Propan-1-Amine

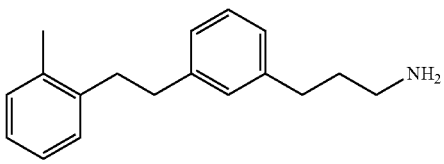 [SMILES: Cc1ccccc1CCc1cccc(CCCN)c1]

3-(3-(2-Methylphenethyl)phenyl)propan-1-amine was prepared following the method shown in scheme 12:

SCHEME 12

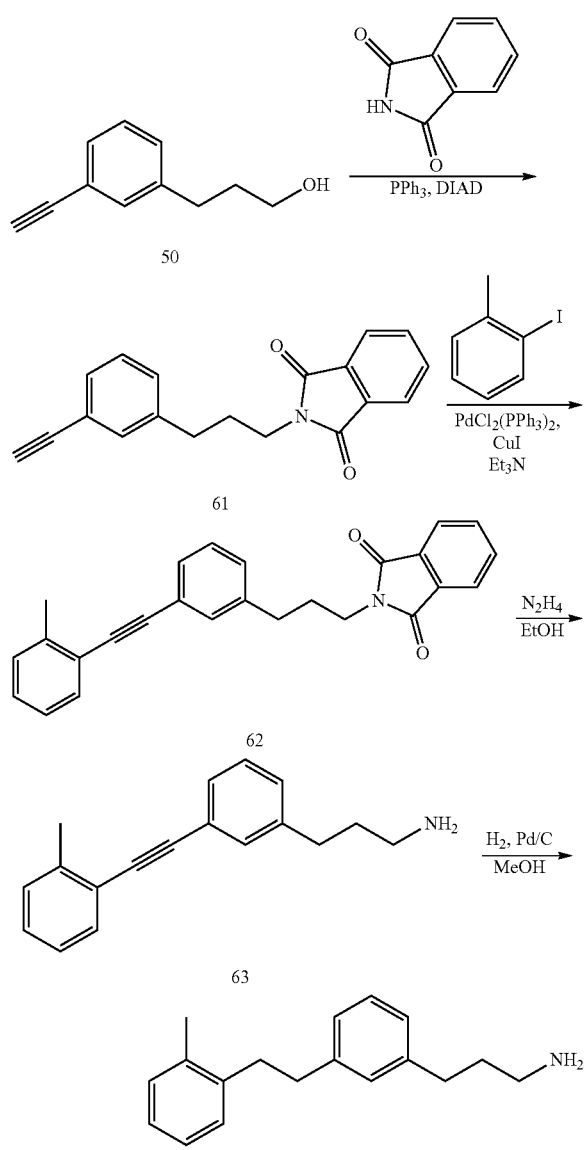

Step 1: Coupling of alcohol 50 with phthalimide following the procedure described in Example 21 gave alkyne 61 as a yellow solid. Yield (6.0 g, 76%): $^1$H NMR (400 MHz, CDCl$_3$) δ 7.83 (dd, J=5.2, 2.8 Hz, 2H), 7.70 (dd, J=5.6, 3.2 Hz, 2H), 7.33 (s, 1H), 7.29-7.24 (m, 1H), 7.16-7.22 (m, 2H), 3.74 (t, J=7.2 Hz, 2H), 3.04 (s, 1H), 2.66 (t, J=8.0 Hz, 2H), 2.02 (quint, J=7.2 Hz, 2H).

Step 2: To a degassed solution of alkyne 61 (0.6 g, 2.07 mmol) and 2-iodo toluene (0.543 g, 2.49 mmol) in triethyl amine (25 mL) was added PdCl$_2$(PPh$_3$)$_2$ (0.0435 g, 0.062 mmol) and CuI (0.0117 g, 0.062 mmol). The reaction was stirred overnight at 70° C. After cooling to room temperature, the mixture was concentrated under reduced pressure. The residue was dissolved in EtOAc and the solids were removed by filtration. The filtrate was washed with water and brine, dried over Na$_2$SO$_4$ and concentrated under reduced pressure. Purification by flash chromatography (15% EtOAc-hexanes) provided alkyne 62 as a brown oil. Yield (0.48 g, 61%): $^1$H NMR (400 MHz, CDCl$_3$) δ 7.83 (dd, J=5.6, 3.2 Hz, 2H), 7.76 (dd, J=5.6, 3.2 Hz, 2H), 7.48 (d, J=7.2 Hz, 1H), 7.37 (m, 1H), 7.31-7.32 (m, 1H), 7.15-7.24 (m, 5H), 3.77 (t, J=7.2 Hz, 2H), 2.70 (t, J=7.2 Hz, 2H), 2.50 (s, 3H), 2.02-2.09 (m, 2H).

Step 3: To alkyne 62 (0.48 g, 1.26 mmol) in EtOH (25 mL) was added hydrazine hydrate (0.23 mL, 3.79 mmol). The reaction mixture was stirred at room temperature overnight. Diethyl ether was added to the reaction mixture. The solid formed was filtered off and the filtrate was concentrated under reduced pressure. Purification by prep HPLC (Method 2P) gave amine 63 as a pale yellow oil. Yield (80 mg, 25%): $^1$H NMR (400 MHz, DMSO-d$_6$) δ 7.24-7.53 (m, 8H), 2.65 (t, J=8.0 Hz, 2H), 2.57 (t, J=6.8 Hz, 2H), 2.49 (s, 3H), 1.65-1.72 (m, 2H).

Step 4: 3-(3-(o-Tolylethynyl)phenyl)propan-1-amine was hydrogenated following the method used in Example 17 to give Example 31 which was HPLC purified to give Example 31 trifluoroacetamide as a white semi-solid. Yield (0.021 g, 30%): $^1$H NMR (400 MHz, DMSO-d$_6$) δ 7.66 (br s, 3H), 7.19 (t, J=7.6 Hz, 1H), 6.99-7.13 (m, 7H), 2.72-2.83 (m, 6H), 2.57 (t, J=7.6 Hz, 2H), 2.22 (s, 3H), 1.74-1.81 (m, 2H).

Example 32

Preparation of 3-(3-(2-(Biphenyl-3-yl)Ethyl)Phenyl-propan-1-Amine

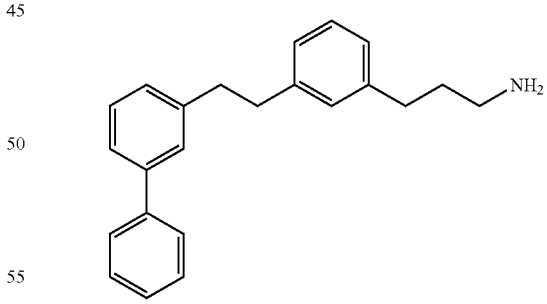

3-(3-(2-(Biphenyl-3-yl)ethyl)phenyl)propan-1-amine was prepared following the method used for the preparation of Example 21:

Step 1: Coupling of alcohol 50 with 3-bromobiphenyl was conducted following the method described in Example 21 to give 3-(3-(biphenyl-3-ylethynyl)phenyl)propan-1-ol. Purification by flash chromatography (5% EtOAc-hexanes) gave a brown oil. Yield (0.560 g, 67%): $^1$H NMR (400 MHz, CDCl$_3$) δ 7.78 (br s, 1H), 7.61 (d, J=7.2 Hz, 2H), 7.56 (d, J=7.6 Hz, 1H), 7.51 (d, J=8.0 Hz, 1H), 7.37-7.48 (m, 6H), 7.29 (d, J=7.6

Hz, 1H), 7.19 (d, J=7.6 Hz, 1H), 3.70 (dt, J=6.2, 5.2 Hz, 2H), 2.73 (t, J=7.6 Hz, 2H), 1.92 (quint, J=6.8 Hz, 2H), 1.27 (t, J=5.2 Hz, 1H).

Step 2: Coupling of 3-(3-(biphenyl-3-ylethynyl)phenyl)propan-1-ol with phthalimide was conducted following the method described in Example 21. Purification by flash chromatography (6% EtOAc-hexanes) gave 2-(3-(3-(biphenyl-3-ylethynyl)phenyl)propyl)isoindoline-1,3-dione. Yield (0.320 g, 42%): $^1$H NMR (400 MHz, CDCl$_3$) δ 7.84 (dd, J=5.6, 3.2 Hz, 2H), 7.77 (m, 1H), 7.71 (dd, J=5.6, 3.2 Hz, 2H), 7.61-7.63 (m, 2H), 7.32-7.57 (m, 8H), 7.18-7.25 (m, 2H), 3.77 (t, J=7.2 Hz, 2H), 2.70 (t, J=7.2 Hz, 2H), 2.02-2.09 (m, 2H).

Step 3: Deprotection of 2-(3-(3-(biphenyl-3-ylethynyl)phenyl)propyl)isoindoline-1,3-dione following the method described in Example 21 followed by purification by preparative HPLC (Method 1P) gave 3-(3-(Biphenyl-3-ylethynyl)phenyl)propan-1-amine trifluoroacetate trifluoroacetate as a white sticky solid. Yield (0.16 g, 52%): $^1$H NMR (400 MHz, DMSO-d$_6$) δ 7.83 (br s, 1H), 7.71-7.15 (m, 3H), 7.67 (br s, 2H), 7.38-7.55 (m, 8H), 7.28-7.30 (m, 1H), 2.77-2.82 (m, 2H), 2.68 (t, J=7.2 Hz, 2H), 1.86 (quint, J=7.6 Hz, 2H).

Step 4: 3-(3-(Biphenyl-3-ylethynyl)phenyl)propan-1-amine trifluoroacetate was hydrogenated using the method in Example 13 to give Example 32 trifluoroacetate as a white solid. Yield (0.019 g, 23%): $^1$H NMR (400 MHz, DMSO-d$_6$) δ 7.58-7.60 (m, 2H), 7.40-7.45 (m, 4H), 7.30-7.34 (m, 4H), 7.12-7.20 (m, 2H), 6.96-7.04 (m, 3H), 2.84-2.93 (m, 6H), 2.48-2.53 (m, 2H), 1.52-1.11 (m, 2H).

Example 33

Preparation of 3-(3-(6-Methoxyhexyl)Phenyl)Propan-1-Amine

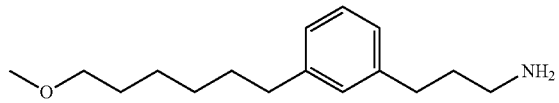 [SMILES: COCCCCCCc1cccc(CCCN)c1]

3-(3-(6-Methoxyhexyl)phenyl)propan-1-amine was prepared following the method used for the preparation of Example 22:

Step 1: Aryl bromide 57 was coupled with 6-methoxyhex-1-yne following the method used for the preparation of Example 13. Purification by flash chromatography (10% EtOAc-hexanes) gave tert-butyl 3-(3-(6-methoxyhex-1-ynyl)phenyl)propylcarbamate as a brown oil. Yield (0.20 g, 36%).

Step 2: tert-Butyl 3-(3-(6-methoxyhex-1-ynyl)phenyl)propylcarbamate was deprotected following the method used in Example 13 except that CH$_2$Cl$_2$ was used as a cosolvent in the reaction (HCl-dioxane solution: CH$_2$Cl$_2$ 7:5). Purification by prep HPLC (Method 2P) gave 3-(3-(6-methoxyhex-1-ynyl)phenyl)propan-1-amine hydrochloride as an off white solid. Yield (0.050 g, 30%): $^1$H NMR (400 MHz, CDCl$_3$) δ 8.37 (br s, 3H), 7.10-7.24 (m, 4H), 4.02 (t, J=6.4 Hz, 2H), 3.78 (s, 3H), 2.98 (t, J=7.6 Hz, 2H), 2.69 (t, J=7.6 Hz, 2H), 2.44 (t, J=7.6 Hz, 2H), 2.04-2.12 (m, 2H), 1.82-1.89 (m, 2H), 1.63-1.73 (m, 2H).

Step 3: 3-(3-(6-Methoxyhexyl)phenyl)propan-1-amine hydrochloride was hydrogenated using the method in Example 17 to give Example 33 hydrochloride as a white semi-solid. Yield (0.025 g, 82%): $^1$H NMR (400 MHz, DMSO-d$_6$) δ 7.89 (br s, 3H), 7.16 (t, J=7.6 Hz, 1H), 6.96-7.01 (m, 3H), 4.02 (t, J=6.8 Hz, 2H), 3.64 (s, 3H), 2.72 (t, J=7.6 Hz, 2H), 2.57 (t, J=7.6 Hz, 2H), 2.50 (t, J=7.6 Hz, 2H), 1.76-1.83 (m, 2H), 1.48-1.57 (m, 4H), 1.25-1.33 (m, 4H).

Example 34

Preparation of 3-(3-(Octan-4-yl)Phenyl)Propan-1-Amine

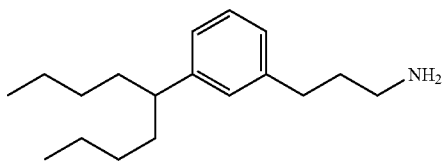 [SMILES: CCCCC(CCCC)c1cccc(CCCN)c1]

3-(3-(Octan-4-yl)phenyl)propan-1-amine was prepared following the method shown in scheme 13:

SCHEME 13

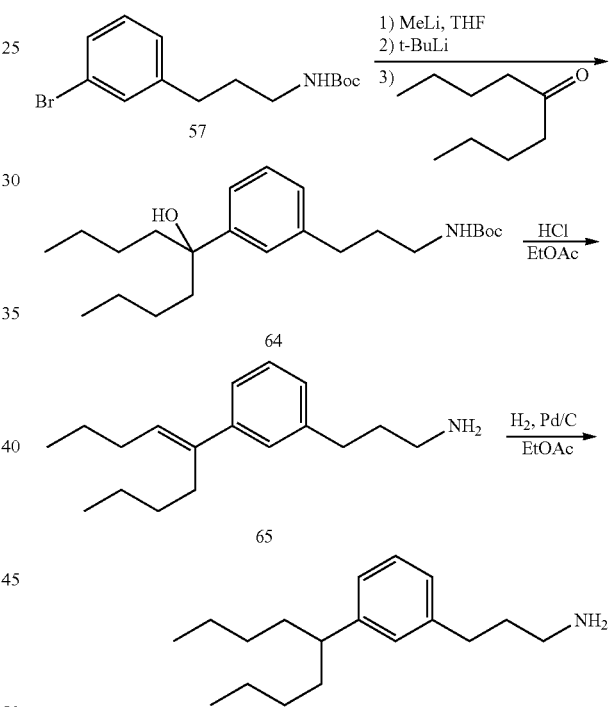

Step 1: To a −78° C. solution of compound 57 (0.650 g, 2.07 mmol, crude) in anhydrous THF (20 mL) was added MeLi (1.36 mL of a 1.6 M solution in diethyl ether, 2.17 mmol) and the mixture was stirred for 10 min tert-Butyl lithium (2.5 mL of a 1.7 M solution in pentane, 4.24 mmol) was added and the reaction mixture was stirred at −78° C. for 45 min 5-Nonanone (0.324 g, 2.28 mmol) was added to the mixture. After allowing the mixture to warm to room temperature, the reaction was quenched with the addition of saturated aqueous NH$_4$Cl (15 mL) and the pH was adjusted to 5 with 1M HCl. The mixture was extracted with EtOAc and the combined organics were dried over Na$_2$SO$_4$ and concentrated under reduced pressure to give alcohol 64 as an oil. Yield (0.090 g, 12%): $^1$H NMR (400 MHz, DMSO-d$_6$) δ 7.14-7.19 (m, 3H), 6.97 (d, J=8.0 Hz, 1H), 6.87 (t, J=4.0 Hz, 1H), 4.48 (s, 1H), 2.92 (q, J=8.0 Hz, 2H), 2.53 (t, J=8.0 Hz, 2H), 1.59-1.74 (m, 6H), 1.37 (s, 9H), 1.15-1.23 (m, 6H), 0.84-0.91 (m, 2H), 0.77 (t, J=8.0 Hz. 6H).

Step 2: A solution of alcohol 64 (0.081 g, 0.215 mmol) in HCl (2 mL of a 4.2 M solution in EtOAc, 8.4 mmol) was stirred at room temperature overnight. After concentration under reduced pressure, alkene 65 hydrochloride was obtained as an oil and used without purification. (Yield 0.066 g, quant.): $^1$H NMR (400 MHz, DMSO-$d_6$) δ 7.94 (br s, 3H), 7.11-7.37 (m, 3H), 7.07 (d, J=8.0 Hz, 1H), 5.63 (t, J=8.0 Hz, 1H), 2.77-2.80 (m, 2H), 2.64 (t, J=8.0 Hz, 2H), 2.47 (t, J=8.0 Hz, 2H), 2.15 (q, J=8.0 Hz, 2H), 1.81-1.91 (m, 2H), 1.44 (q, J=8.0 Hz, 2H), 1.17-1.27 (m, 4H), 0.93 (t, J=8.0 Hz, 3H), 0.83 (t, J=8.0 Hz, 3H).

Step 3: Hydrogenation of compound 65 was conducted following the method used in Example 2 except that EtOAc was used as the solvent. Purification by flash chromatography (10% 7M $NH_3$ in MeOH—$CH_2Cl_2$) gave Example 34 as an oil. Yield (0.013 g, 30%): $^1$H NMR (400 MHz, CDCl$_3$) δ 7.21 (t, J=8.0 Hz, 1H), 6.96-7.03 (m, 3H), 2.75 (t, J=8.0 Hz, 2H), 2.65 (t, J=8.0 Hz, 2H), 2.41-2.48 (m, 1H), 1.75-1.84 (m, 2H), 1.48-1.67 (m, 4H), 1.44 (br s, 2H), 1.05-1.34 (m, 8H), 0.84 (t, J=8.0 Hz, 6H).

Example 35

Preparation of 3-(3-(4-Phenylbutyl)Phenyl)Propan-1-Amine

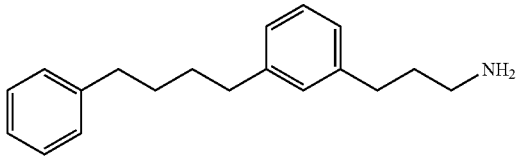 [SMILES: NCCCc1cccc(CCCCc2ccccc2)c1]

3-(3-(4-Phenylbutyl)phenyl)propan-1-amine was prepared following the method used in Example 22.

Step 1: Aryl bromide 57 was coupled with but-3-ynylbenzene following the method used in Example 22. Purification by flash chromatography (10% EtOAc-hexanes) gave tert-butyl 3-(3-(4-phenylbut-1-ynyl)phenyl)propylcarbamate as a brown oil. Yield (0.40 g, 82%).

Step 2: tert-Butyl 3-(3-(4-phenylbut-1-ynyl)phenyl)propylcarbamate was deprotected following the method used in Example 22 to give 3-(3-(4-phenylbut-1-ynyl)phenyl)propan-1-amine hydrochloride as a white solid. $^1$H NMR (400 MHz, DMSO-$d_6$) δ 7.74 (br s, 3H), 7.14-7.28 (m, 9H), 2.82 (t, J=7.2 Hz, 2H), 2.71 (t, J=7.6 Hz, 2H), 2.67 (t, J=7.2 Hz, 2H), 2.58 (t, J=7.6 Hz, 2H), 1.78 (quint, J=7.6 Hz, 2H).

Step 3: 3-(3-(4-Phenylbut-1-ynyl)phenyl)propan-1-amine hydrochloride was hydrogenated following the method used in Example 17, except that the reaction was time was 2 h, to give Example 35 hydrochloride as a white solid. Yield (0.040 g, 49%): $^1$H NMR (400 MHz, DMSO-$d_6$) δ 7.91 (br s, 3H), 7.24 (t, J=7.6 Hz, 2H), 7.12-7.19 (m, 4H), 6.98-6.99 (m, 3H), 2.73 (t, J=7.6, 2H), 2.56-2.59 (m, 6H), 1.77-1.84 (m, 2H), 1.54-1.55 (m, 4H).

Example 36

Preparation of 2-(3-(2-(Pyridin-3-yl)Ethyl)Phenoxy)Ethanamine

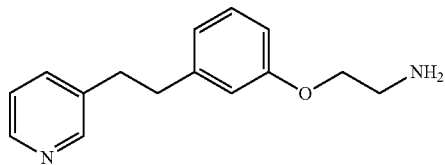 [SMILES: NCCOc1cccc(CCc2cccnc2)c1]

2-(3-(2-(Pyridin-3-yl)ethyl)phenoxy)ethanamine was prepared following the method shown in scheme 14:

SCHEME 14

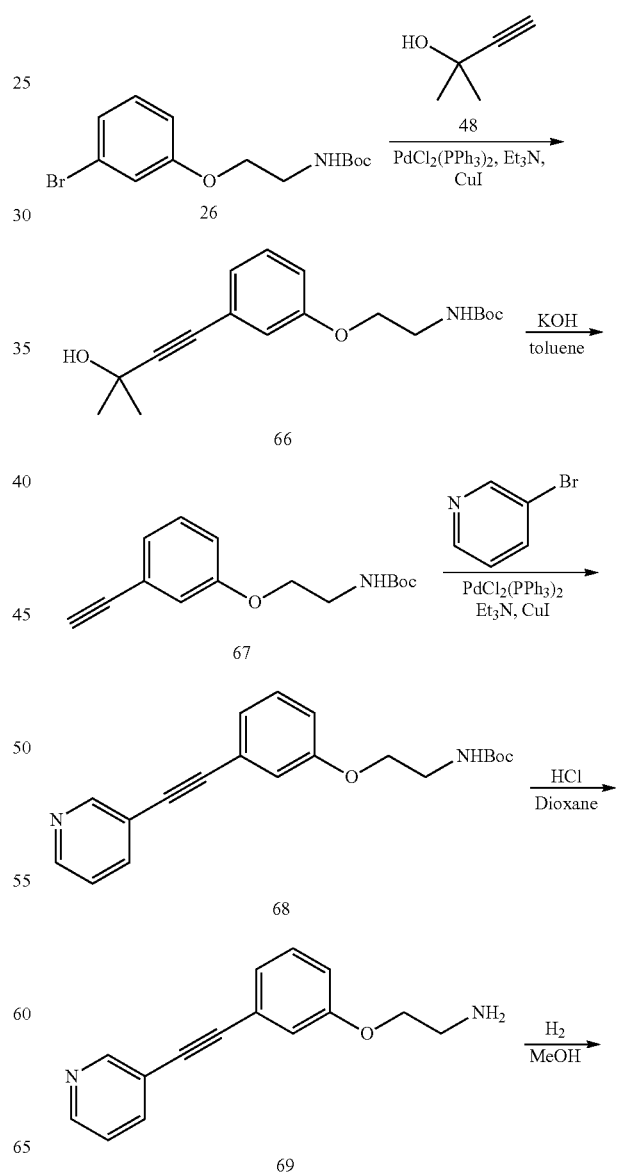

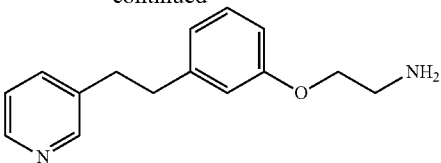

Step 1: Coupling of bromide 26 with 2-methylbut-3-yn-2-ol (48) following the method used in Example 13 gave alkyne 66 as a buff-colored solid. Yield (0.90 g, 90%): ¹H NMR (400 MHz, CDCl₃): δ 7.21 (t, J=8.0 Hz, 1H), 7.02 (d, J=7.6 Hz, 1H), 6.93-6.95 (m, 1H), 6.85 (ddd, J=8.4, 2.8, 0.8 Hz, 1 H), 4.97 (br s, 1H), 4.01 (t, J=5.2 Hz, 2H), 3.51-3.52 (m, 2H), 1.62, (s, 6H), 1.56 (s, 9H).

Step 2: Treatment of alkyne 66 with KOH following the method used in Example 21 gave alkyne 67 as a brown oil. Yield (0.20 g, 80%): ¹H NMR (400 MHz, CDCl₃) δ 7.23 (d, J=8.0 Hz, 1H), 7.10 (dt, J=7.6, 1.2 Hz, 1H), 7.00-7.02 (m, 1H), 6.90 (ddd, J=8.4, 2.8, 0.8 Hz, 1H), 4.97 (br s, 1H), 4.01 (t, J=5.2 Hz, 2H), 3.49-3.54 (m, 2H), 3.06 (s, 1H), 1.45 (s, 9H).

Step 3: Coupling of alkyne 67 with 3-bromopyridine following the method used in Example 13 gave alkyne 68 as a brown oil. Yield (0.340 g, 44%). ¹H NMR (400 MHz, CDCl₃) δ 8.76 (d, J=1.4 Hz, 1H), 8.55 (dd, J=4.8, 1.2 Hz, 1H), 7.81 (dt, J=8.0, 1.6 Hz, 1H), 7.29 (t, J=4.4 Hz, 1H), 7.28 (s, 1H), 7.16 (d, J=8.0 Hz, 1H), 7.06 (br s, 1H), 6.92 (dd, J=8.4, 2.8 Hz, 1H), 4.05 (t, J=5.2 Hz, 2H), 3.54 (q, J=5.2 Hz, 2H), 1.46 (s, 9H)

Step 4: Deprotection of alkyne 68 with HCl-dioxane following the method used in Example 13 gave amine 69 hydrochloride as an off white solid. Yield (0.230 g, 83%): ¹H NMR (400 MHz, DMSO-d₆) δ 8.78 (br s, 1H), 8.60 (dd, J=4.8, 1.6 Hz, 1H), 8.11 (br s, 3H), 8.02-8.04 (m, 1H), 7.51 (dd, J=8.0, 5.2 Hz, 1H), 7.37 (t, J=8.0 Hz, 1H), 7.20 (d, J=8.0 Hz, 1H), 7.18 (d, J=1.6 Hz, 1H), 7.06 (dd, J=8.4, 2.4 Hz, 1H), 4.20 (t, J=4.8 Hz, 2H), 3.19 (dd, J=10.4, 5.6 Hz, 2H).

Step 5: Hydrogenation of amine 69 hydrochloride was conducted following the method used in Example 35. After stirring for 2 h, the solids were removed by filtration. The filtrate was concentrated under reduced pressure and the residue was dissolved in concentrated ammonium hydroxide. The aqueous solution was extracted with CH₂Cl₂. The combined organics were concentrated under reduced pressure to give Example 36 as a colorless oil. Yield (0.080 g, 39%): ¹H NMR (400 MHz, DMSO-d₆) δ 8.39 (s, 1H), 8.36 (d, J=4.4 Hz, 1H), 7.61 (d, J=7.6 Hz, 1H), 7.26 (dd, J=7.6, 4.8, 1H), 7.14 (t, J=8.0, 1H), 6.71-6.77 (m, 3H), 3.85 (t, J=5.6 Hz, 2H), 2.82-2.84 (m, 6H).

Example 37

Preparation of 2-(3-(2-(Pyridin-2-yl)Ethyl)Phenoxy)Ethanamine

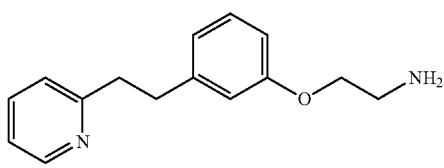 [SMILES: NCCOc1cccc(CCc2ccccn2)c1]

2-(3-(2-(Pyridin-2-yl)ethyl)phenoxy)ethanamine was prepared following the method used in Example 36:

Step 1: Coupling of alkyne 67 with 2-bromopyridine was conducted following the method used in Example 13. Purification by flash chromatography (20% EtOAc-hexanes) gave tert-butyl 2-(3-(pyridin-2-ylethynyl)phenoxy)ethylcarbamate as a yellow oil. Yield (0.50 g, 64%). ¹H NMR (400 MHz, CDCl₃): δ 8.63 (d, J=4.0 Hz, 1H), 7.69 (dt, J=7.6, 1.6 Hz, 1H), 7.53 (d, J=7.6 Hz, 1H), 7.24-7.26 (m, 2H), 7.21 (dt, J=8.0, 1.2 Hz, 1H), 7.12-7.13 (m, 1H), 6.93 (ddd, J=8.0, 2.4, 1.2 Hz, 1H), 4.98 (br s, 1H), 4.03 (t, J=5.2, 2H), 3.54-3.56 (m, 2H), 1.46 (s, 9H).

Step 2: Deprotection of tert-butyl 2-(3-(pyridin-2-ylethynyl)phenoxy)ethylcarbamate with HCl-dioxane following the method used in Example 13 gave 2-(3-(pyridin-2-ylethynyl)phenoxy)ethanamine hydrochloride as a white solid. ¹H NMR (400 MHz, DMSO-d₆) δ 8.61 (dt, J=5.2, 0.8 Hz, 1H), 8.20 (br s, 3H), 7.92 (dt, J=8.0, 2.0 Hz, 1H), 7.69 (d, J=8.0 Hz, 1H), 7.47 (ddd, J=7.6, 5.2, 1.2 Hz, 1H), 7.39 (t, J=8.0 Hz, 1H), 7.22 (d, J=7.6 Hz, 1H), 7.19-7.20 (m, 1H), 7.08 (ddd, J=8.0, 2.4, 0.8 Hz, 1H), 4.21 (t, J=5.2 Hz, 2H), 3.18 (dt, J=5.6, 5.2 Hz, 2H).

Step 3: Hydrogenation of 2-(3-(pyridin-2-ylethynyl)phenoxy)ethanamine hydrochloride following the method used in Example 17, except that the reaction time was 3 h, gave Example 37 hydrochloride as a white solid. Yield (0.150 g, 73%): ¹H NMR (400 MHz, DMSO-d₆) δ 8.69 (d, J=5.2 Hz, 1H), 8.26 (br s, 4H), 7.75 (d, J=7.6 Hz, 1H), 7.69 (t, J=6.4 Hz, 1H), 7.20 (t, J=8.0 Hz, 1H), 6.91 (s, 1H), 6.84 (d, J=7.6, 1H), 6.80 (dd, J=8.0, 2.0 Hz, 1H), 4.15 (t, J=4.8 Hz, 2H), 3.27 (t, J=8.0 Hz, 2H), 3.17 (d, J=4.4 Hz, 1H), 3.15 (d, J=4.4 Hz, 1H), 3.03 (t, J=8.0 Hz, 2H).

Example 38

Preparation of 2-(3-(2-(Thiophen-2-yl)Ethyl)Phenoxy)Ethanamine

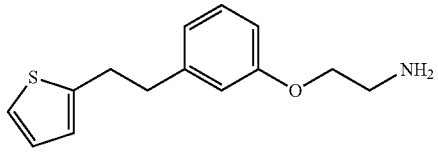 [SMILES: NCCOc1cccc(CCc2cccs2)c1]

2-(3-(2-(Thiophen-2-yl)ethyl)phenoxy)ethanamine was prepared following the method used in Example 36:

Step 1: Coupling of alkyne 67 with 2-bromothiophene was conducted following the method used in Example 13. Purification by flash chromatography (5% EtOAc-hexanes) gave tert-butyl 2-(3-(thiophen-2-ylethynyl)phenoxy)ethylcarbamate as a brown oil. Yield (0.605 g, 57%). ¹H NMR (400 MHz, CDCl₃) δ 7.30 (dd, J=5.2, 1.2 Hz, 1H), 7.28-7.29 (m, 1H), 7.25 (d, J=8.4 Hz, 1H), 7.12 (dt, J=7.6, 1.2 Hz, 1H), 7.03-7.04 (m, 1H), 7.02 (dd, J=5.2, 3.6 Hz, 1H), 6.89 (ddd, J=8.0, 2.4, 0.8 Hz, 1H), 4.99 (br s, 1H), 4.04 (t, J=4.8 Hz, 2H), 3.55 (dd, J=10.0, 5.2 Hz, 2H), 1.46 (s, 9H).

Step 2: Deprotection of tert-butyl 2-(3-(thiophen-2-ylethynyl)phenoxy)ethylcarbamate with HCl-dioxane following the method used in Example 13 gave 2-(3-(thiophen-2-ylethynyl)phenoxy)ethanamine hydrochloride as a white solid. ¹H NMR (400 MHz, DMSO-d₆) δ 8.14 (br s, 3H), 7.66 (dd, J=5.2, 1.2 Hz, 1H), 7.40 (dd, J=3.6, 1.2 Hz, 1H), 7.14 (t, J=7.6, 1.2 Hz, 1H), 7.10-7.12 (m, 2H), 7.03 (ddd, J=8.4, 2.4, 1.2 Hz, 1H), 4.19 (t, J=5.2 Hz, 2H), 3.17 (t, J=5.2, 2H).

Step 3: Hydrogenation of 2-(3-(thiophen-2-ylethynyl)phenoxy)ethanamine hydrochloride following the method used in Example 13 gave Example 38 hydrochloride as a white solid. Yield (0.15 g, 95%): $^1$H NMR (400 MHz, DMSO-d$_6$) δ 8.02 (br s, 3H), 7.27 (dd, J=5.2, 1.2 Hz, 1H), 7.18 (t, J=8.0 Hz, 1H), 6.89 (dd, J=5.2, 3.2 Hz, 1H), 6.81-6.84 (m, 3H), 6.77 (dd, J=8.4, 1.6 Hz, 1H), 4.11 (t, J=5.2 Hz, 2H), 3.16 (t, J=5.2 Hz, 2 H), 3.07 (t, J=7.6 Hz, 2H), 2.87 (t, J=7.6 Hz, 2H).

Example 39

Preparation of 5-(3-(3-Aminopropyl)Phenethyl)Nonan-5-ol

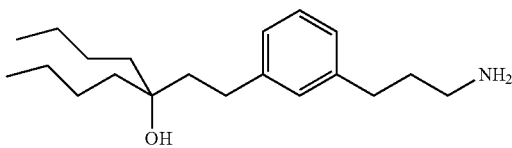 [SMILES: CCCCC(O)(CCCC)CCc1cccc(CCCN)c1]

5-(3-(3-Aminopropyl)phenethyl)nonan-5-ol was prepared following the method used in Example 2.

Step 1: Coupling of 3-ethynylnonan-5-ol with bromide 10 gave N-(3-(3-(3-butyl-3-hydroxyhept-1-ynyl)phenyl)propyl)-2,2,2-trifluoroacetamide as a brown oil. Yield (0.346 g, 22%): $^1$H NMR (400 MHz, DMSO-d$_6$) δ 9.40 (br s, 1H), 7.14-7.26 (m, 4H), 5.11 (s, 1H), 2.56 (t, J=7.6 Hz, 2H), 2.47 (m, 2H), 1.43-1.62 (m, 14H), 0.88 (t, J=7.2 Hz, 6H).

Step 2: Deprotection of N-(3-(3-(3-butyl-3-hydroxyhept-1-ynyl)phenyl)propyl)-2,2,2-trifluoroacetamide gave 5-((3-(3-aminopropyl)phenyl)ethynyl)nonan-5-ol as a light yellow oil. Yield (0.219 g, 84%): $^1$H NMR (400 MHz, DMSO-d$_6$) δ 7.22-7.26 (m, 1H), 7.14-7.17 (m, 3H), 5.11 (s, 1H), 2.56 (t, J=7.6 Hz, 2H), 2.49 (t, J=6.8 Hz, 2H), 1.25-1.62 (m, 14H), 0.88 (t, J=7.2 Hz, 6H).

Step 3: Hydrogenation of 5-((3-(3-aminopropyl)phenyl) ethynyl)nonan-5-ol gave Example 39 as a colorless oil. Yield (0.133 g, 69%): $^1$H NMR (400 MHz, CDCl$_3$) δ 7.18 (t, J=8.0 Hz, 1H), 6.97-7.03 (m, 3H), 2.72 (t, J=5.2 Hz, 2H), 2.56-2.65 (m, 4H), 1.68-1.80 (m, 4H), 1.45-1.52 (m, 4H), 1.24-1.38 (m, 11H), 0.91 (t, J=6.8 Hz, 6H). ESI MS m/z 306.7 [M+H]$^+$, 288.6 [M+H−H$_2$O]$^+$.

Example 40

Preparation of 3-(3-(3-Methoxy-3-Propylhexyl)Phenyl)Propan-1-Amine

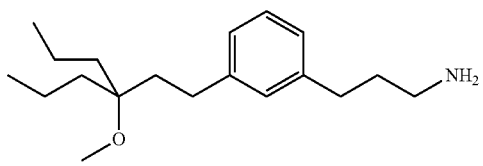 [SMILES: CCCC(CCC)(CCc1cccc(CCCN)c1)OC]

3-(3-(3-Methoxy-3-propylhexyl)phenyl)propan-1-amine was prepared following the method used in Example 2.

Step 1: Coupling of 4-ethynyl-4-methoxyheptane with bromide 10 gave 2,2,2-trifluoro-N-(3-(3-(3-methoxy-3-propylhex-1-ynyl)phenyl)propyl)acetamide as a light yellow oil.

Yield (0.596 g, 93%): $^1$H NMR (400 MHz, DMSO-d$_6$) δ 9.40 (br s, 1H), 7.18-7.29 (m, 4H), 3.25 (s, 3H), 3.14-3.20 (m, 2H), 2.56 (t, J=7.6 Hz, 2H), 1.73-1.80 (m, 2H), 1.64 (t, J=8.4 Hz, 4H), 1.34-1.44 (m, 4H), 0.88 (t, J=7.2 Hz, 6H).

Step 2: Deprotection of 2,2,2-trifluoro-N-(3-(3-(3-methoxy-3-propylhex-1-ynyl)phenyl)propyl)acetamide gave 3-(3-(3-methoxy-3-propylhex-1-ynyl)phenyl)propan-1-amine as a clear oil. Yield (0.341 g, 93%): $^1$H NMR (400 MHz, DMSO-d$_6$) δ 7.27-7.18 (m, 4H), 3.25 (s, 3H), 2.56 (t, J=7.6 Hz, 2H), 2.47 (t, J=6.8 Hz, 2H), 1.56-1.66 (m, 6H), 1.32-1.44 (m, 6H), 0.88 (t, J=7.2 Hz, 6H).

Step 3: Hydrogenation of 3-(3-(3-methoxy-3-propylhex-1-ynyl)phenyl)propan-1-amine gave Example 40 as a colorless oil. Yield (0.188 g, 71%): $^1$H NMR (400 MHz, CDCl$_3$) δ 7.18 (t, J=8.0 Hz, 1H), 6.95-7.04 (m, 3H), 3.16 (s, 3H), 2.72 (t, J=7.2 Hz, 2H), 2.62 (t, J=8.0 Hz, 2H), 2.48-2.55 (m, 2H), 1.64-1.80 (m, 4H), 1.41-1.48 (m, 4H), 1.24-1.35 (m, 4H), 1.20 (br s, 2H), 0.92 (t, J=7.2 Hz, 6H). ESI MS m/z 292.5 [M+H]+.

Example 41

Preparation of 1-(3-(3-Aminopropylphenyl)-3-Methylhexan-3-ol

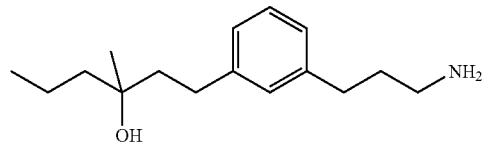 [SMILES: CCCC(C)(O)CCc1cccc(CCCN)c1]

1-(3-(3-Aminopropyl)phenyl)-3-methylhexan-3-ol was prepared following the method used in Example 2.

Step 1: Coupling of 3-methylhex-1-yn-3-ol with bromide 10 gave 2,2,2-trifluoro-N-(3-(3-(3-hydroxy-3-methylhex-1-ynyl)phenyl)propyl)acetamide contaminated with alkyne dimer Yield (0.699 g, >100%): $^1$H NMR (400 MHz, DMSO-d$_6$) δ 9.40 (br s, 1H), 7.25 (dd, J=8.8, 7.2 Hz, 1H), 7.17-7.21 (m, 3H), 5.29 (s, 1H), 3.17 (q, J=6.8 Hz, 2H), 2.56 (t, J=7.6 Hz, 2H), 1.76 (quint, J=7.2 Hz, 2 H), 1.48-1.61 (m, 4H), 1.39 (s, 3H), 0.90 (t, J=7.6 Hz, 3H).

Step 2: Deprotection of 2,2,2-trifluoro-N-(3-(3-(3-hydroxy-3-methylhex-1-ynyl)phenyl)propyl)acetamide followed by purification by flash chromatography chromatography (72:8:20 to 90:10:0 EtOAc/7 M NH$_3$ in MeOH/hexanes) gave 1-(3-(3-aminopropyl)phenyl)-3-methylhex-1-yn-3-ol as a yellow oil. Yield (0.371 g, 76%, two steps): $^1$H NMR (400 MHz, DMSO-d$_6$) δ 7.24 (t, J=8 Hz, 1H), 7.14-7.18 (m, 3H), 5.29 (br s, 1H), 2.56 (t, J=7.6 Hz, 2H), 2.47 (t, J=7.2 Hz, 2 H), 1.41-1.62 (m, 6H), 1.39 (s, 3H), 1.34 (br s, 2H), 0.90 (t, J=7.6 Hz, 3H).

Step 3: Hydrogenation of 1-(3-(3-aminopropyl)phenyl)-3-methylhex-1-yn-3-ol gave Example 41 as a pale yellow oil. Yield (0.260 g, 77%): $^1$H NMR (400 MHz, CDCl$_3$) δ 7.18 (t, J=8 Hz, 1H), 6.97-7.02 (m, 3H), 2.71 (t, J=7.2 Hz, 2H), 2.58-2.66 (m, 4H), 1.70-1.80 (m, 4H), 1.44-1.52 (m, 2H), 1.35-1.44 (m, 2H), 1.26-1.35 (br s, 3H), 1.21 (s, 3H), 0.93 (t, J=7.2 Hz, 3H). ESI MS m/z 250.5 [M+H]$^+$, 232.4 [M+H−H$_2$O]$^+$.

Example 42

Preparation of 1-(3-(3-Aminopropyl)Phenyl)-3,5-Dimethylhexan-3-ol

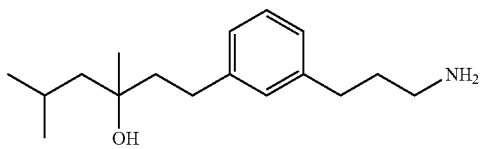 [SMILES: CC(C)CC(C)(O)CCc1cccc(CCCN)c1]

1-(3-(3-Aminopropyl)phenyl)-3,5-dimethylhexan-3-ol was prepared following the method used in Example 2 and 3.

Step 1: Coupling of 3,5-dimethylhex-1-yn-3-ol with bromide 10 following the method described in Example 3 (except that the alkynol was added after degassing) gave 2,2,2-trifluoro-N-(3-(3-(3-hydroxy-3,5-dimethylhex-1-ynyl)phenyl)propyl)acetamide as a brown oil. Yield (0.287 g, 40%): $^1$H NMR (400 MHz, DMSO-d$_6$) δ 9.41 (br s, 1H), 7.26 (t, J=7.6 Hz, 1H), 7.16-7.20 (m, 3H), 5.25 (s, 1H), 3.16 (q, J=6.8 Hz, 2H), 2.56 (t, J=7.2 Hz, 2H), 1.90-1.96 (m, 1H), 1.76 (quint, J=7.6 Hz, 2H), 1.53 (m, 2H), 1.42 (s, 3H), 0.96 (d, J=6.8 Hz, 6H).

Step 2: Deprotection of 2,2,2-trifluoro-N-(3-(3-(3-hydroxy-3,5-dimethylhex-1-ynyl)phenyl)propyl)acetamide following the method of Example 3, except that the reaction mixture was stirred at room temperature overnight, gave 1-(3-(3-aminopropyl)phenyl)-3,5-dimethylhex-1-yn-3-ol as a clear oil. Yield (0.141 g, 72%): $^1$H NMR (400 MHz, DMSO-d$_6$) δ 7.14-7.27 (m, 4H), 5.25 (s, 1H), 2.56 (t, J=7.2 Hz, 2H), 2.47 (t, J=6.0 Hz, 2H), 1.93 (quint, J=6.4 Hz, 1H), 1.60 (q, J=6.8 Hz, 2H), 1.54 (t, J=6.0 Hz, 2H), 1.42 (s, 3H), 1.35 (br s, 2H), 0.97 (d, J=6.4 Hz, 6H).

Step 3: Hydrogenation of 1-(3-(3-aminopropyl)phenyl)-3,5-dimethylhex-1-yn-3-ol following the method of Example 2 followed by flash chromatography (5% (7N NH$_3$/MeOH)/dichloromethane), gave Example 42 as a colorless oil. Yield (0.048 g, 41%): $^1$H NMR (400 MHz, CDCl$_3$) δ 7.18 (t, J=8.0 Hz, 1H), 6.97-7.03 (m, 3H), 2.71 (t, J=7.2 Hz, 2H), 2.57-2.68 (m, 4H), 1.70-1.88 (m, 5H), 1.36-1.52 (m, 5H), 1.24 (s, 3H), 0.97 (dd, J=6.4, 2.8 Hz, 6H). ESI MS m/z 264.5 [M+H]$^+$, 246.5 [M+H–H$_2$O]$^-$.

Example 43

Preparation of 1-(3-(3-Aminopropyl)Phenethyl)-2,2,6,6-Tetramethylcyclohexanol

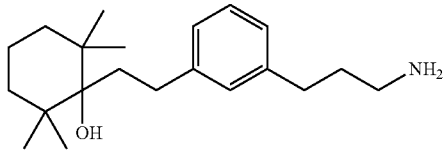 [SMILES: CC1(C)CCCC(C)(C)C1(O)CCc1cccc(CCCN)c1]

1-(3-(3-Aminopropyl)phenethyl)-2,2,6,6-tetramethylcyclohexanol was prepared following the method used in Example 2 and 4.

Step 1: Coupling of 1-ethynyl-2,2,6,6-tetramethylcyclohexanol with bromide 10 following the method used in Example 4 gave 2,2,2-trifluoro-N-(3-(3-((1-hydroxy-2,2,6,6-tetramethylcyclohexyl)ethynyl)phenyl)propyl)acetamide as a light brown foam. Yield (0.192 g, 84%): $^1$H NMR (400 MHz, DMSO-d$_6$) δ 9.40 (br s, 1H), 7.27 (t, J=7.6 Hz, 1H), 7.18-7.23 (m, 3H), 4.92 (s, 1H), 3.18 (q, J=6.8 Hz, 2H), 2.57 (t, J=7.2 Hz, 2H), 1.76 (quint, J=7.6 Hz, 2H), 1.22-1.50 (m, 6H), 1.14 (s, 6H), 1.04 (s, 6H).

Step 2: Deprotection of 2,2,2-trifluoro-N-(3-(3-((1-hydroxy-2,2,6,6-tetramethylcyclohexyl)ethynyl)phenyl)propyl)acetamide was conducted following the procedure described in Example 4, except that the product was purified by flash chromatography (10% 7 M NH$_3$ in MeOH-EtOAc), gave 1-((3-(3-aminopropyl)-phenyl)ethynyl)-2,2,6,6-tetramethylcyclohexanol as a white solid. Yield (0.016 g, 73%): $^1$H NMR (400 MHz, DMSO-d$_6$) δ 7.15-7.27 (m, 4H), 4.92 (s, 1H), 2.57 (t, J=7.2 Hz, 2H), 2.47 (t, J=7.2 Hz, 2H), 1.26-1.66 (m, 10H), 1.14 (s, 6H), 1.04 (s, 6H).

Step 3: Hydrogenation of 1-((3-(3-aminopropyl)phenyl)ethynyl)-2,2,6,6-tetramethylcyclohexanol following the method used for Example 2 gave Example 43 as a colorless oil. Yield (0.075 g, 79%): $^1$H NMR (400 MHz, CDCl$_3$) δ 7.20 (t, J=8.0 Hz, 1H), 6.97-7.06 (m, 3H), 2.60-2.77 (m, 6H), 1.86-1.92 (m, 2H), 1.73-1.82 (m, 2H), 1.54-1.69 (m, 3H), 1.49 (br s, 3H), 1.36-1.44 (m, 1H), 1.11-1.22 (m, 2H), 1.05 (s, 6H), 1.01 (s, 6H). ESI MS m/z 318.7 [M+H]$^+$, 300.7 [M+H H$_2$O]$^+$.

Example 44

Preparation of 4-(3-(3-Amino-2,2-Dimethylpropyl)Phenethyl)Heptan-4-ol

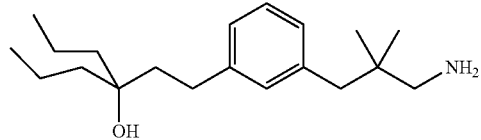 [SMILES: CCCC(O)(CCC)CCc1cccc(CC(C)(C)CN)c1]

4-(3-(3-amino-2,2-dimethylpropyl)phenethyl)heptan-4-ol was prepared following the method shown in Scheme 15:

SCHEME 15

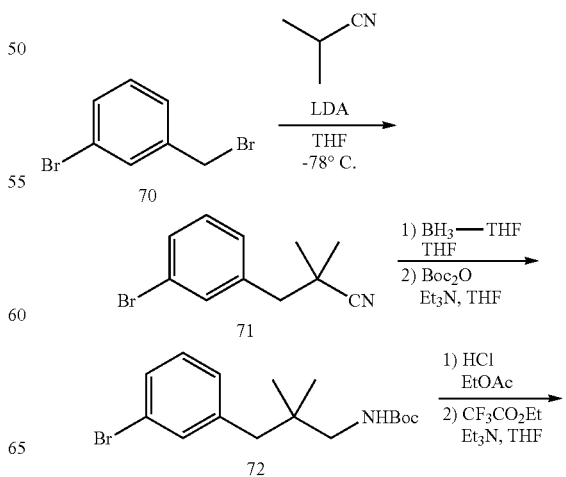

-continued

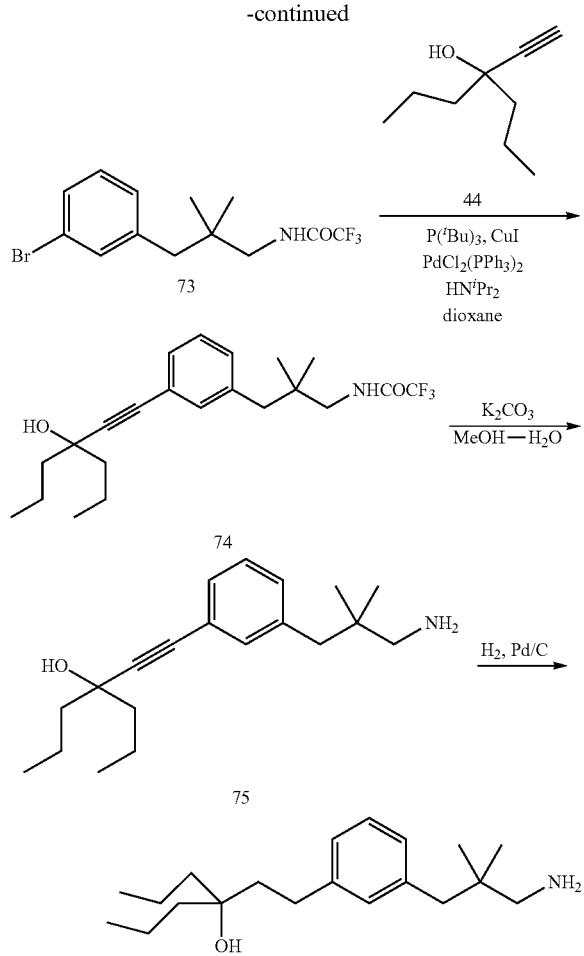

Step 1: An oven-dried flask under argon was charged with isobutyronitrile (2.15 mL, 24.0 mmol) and anhydrous THF (60 mL) and cooled to −78° C. A solution of lithium diisopropylamide (12 mL of a 2.0 M solution in heptane/THF/ethylbenzene, 24 mmol) was added in aliquots over 20 min then the reaction was stirred for 25 min 3-Bromobenzyl bromide (70) (3.98 g, 15.92 mmol) was added and the cold bath was removed. After stirring for an additional 2 h, the reaction was quenched with the slow addition of water, then EtOAc was added. The aqueous layer was partly saturated with sodium chloride. The layers were separated, and the aqueous layer was extracted with EtOAc twice. The combined organics were washed with water and brine, dried over $Na_2SO_4$ and concentrated under reduced pressure to give nitrile 71 as an orange oil which later solidified (4.16 g, quant. yield). This material was used in the next synthetic step without further purification. $^1$H NMR (400 MHz, $CDCl_3$) δ 7.40-7.45 (m, 2H), 7.20-7.25 (m, 2H), 2.78 (s, 2H), 1.36 (s, 6H).

Step 2: To an ice-cold mixture of crude 3-(3-bromophenyl)-2,2-dimethylpropanenitrile (71) (3.0 g, 12.6 mmol) in anhydrous THF (20 mL) was added $BH_3$-THF (20 mL of a 1M solution in THF, 20 mmol) slowly. The reaction was allowed to warm slowly and stirred for 19 h. The reaction was quenched with the dropwise addition of 6 M HCl then stirred for 1.5 h. Volatiles were removed under reduced pressure. The aqueous layer was extracted with diethyl ether twice then EtOAc was added and the mixture was made basic with 5 M aqueous KOH. The layers were separated and the aqueous layer was extracted with EtOAc twice. The combined organics were washed with brine, dried over $Na_2SO_4$ and concentrated under reduced pressure to give 3-(3-bromophenyl)-2,2-dimethylpropan-1-amine as a light yellow oil (2.3 g). This material was taken on to the next step without further purification. $^1$H NMR (400 MHz, $CDCl_3$) δ 7.32-7.35 (m, 1H), 7.30 (t, J=1.7 Hz, 1H), 7.13 (t, J=7.7 Hz, 1H), 7.06 (dd, J=7.6, 1.2 Hz, 1H), 2.50 (s, 2H), 2.47 (s, 2H), 0.84 (s, 6H).

Step 3: Crude 3-(3-bromophenyl)-2,2-dimethylpropan-1-amine (2.3 g) was dissolved in THF (40 mL). Di-tert-butyl dicarbonate (2.3 g, 10.5 mmol), then triethylamine (2.8 mL, 20 l mmol) were added and the mixture was stirred for 1.5 h. The reaction mixture was concentrated under reduced pressure and the product was purified by flash chromatography (0-35% EtOAc-hexanes gradient) to give aryl bromide 72 as a colorless oil. Yield (3.3 g, 77%): $^1$H NMR (400 MHz, $CDCl_3$) δ 7.34 (d, J=7.6 Hz, 1H), 7.27 (t, J=1.6 Hz, 1H), 7.14 (t, J=7.7 Hz, 1H), 7.05 (d, J=7.8 Hz, 1H), 4.58 (br s, 1H), 2.98 (d, J=6.5 Hz, 2H), 2.48 (s, 2H), 1.45 (s, 9H), 0.85 (s, 6H).

Step 4: tert-Butyl 3-(3-bromophenyl)-2,2-dimethylpropylcarbamate (72) (3.2 g, 9.35 mmol) was dissolved in EtOAc (55 mL), and a solution of HCl-EtOAc (~4.2 M, 20 mL, 84 mmol) was added. The reaction was vented with a needle and stirred at room temperature for 2.5 h. The reaction was then diluted with hexanes and the white solid was collected on a fritted glass funnel The mother liquor was concentrated under reduced pressure, suspended in ~5-10% EtOAc-hexanes, and the white solid was collected and combined with the first batch. The solid was dried in a vacuum oven at room temperature overnight to give pure 3-(3-bromophenyl)-2,2-dimethylpropan-1-amine hydrochloride as a white solid. Yield (1.52 g): $^1$H NMR (400 MHz, $CDCl_3$) δ 8.53 (br s, 2H), 7.37 (dq, J=1.2 and 8.0 Hz, 1H), 7.31 (t, J=1.6 Hz, 1H), 7.13 (t, J=7.7 Hz, 1H), 7.08 (dt, J=8.0, 1.6 Hz, 1H), 2.83-2.84 (m, 2H), 2.67 (s, 2H), 1.09 (s, 6H).

Step 5: 3-(3-Bromophenyl)-2,2-dimethylpropan-1-amine hydrochloride (1.52 g, 5.45 mmol) was dissolved in anhydrous THF (50 mL). $Et_3N$ (1.5 mL, 10.76 mmol) was added slowly to produce a white slurry. Ethyl trifluoroacetate (2 mL, 16.8 mmol) was added and the mixture was stirred at room temp for 15.5 h. Additional ethyl trifluoroacetate (~0.75 mL, 6.2 mmol) and triethylamine (0.75 mL, 5.4 mmol) were added and the mixture was stirred for 4 h. The reaction mixture was concentrated under reduced pressure. The product was taken up in EtOAc and the solution was washed with saturated aqueous $NaHCO_3$ (2×) and brine, dried over $Na_2SO_4$ and concentrated under reduced pressure to give N-(3-(3-bromophenyl)-2,2-dimethylpropyl)-2,2,2-trifluoroacetamide (73) as a yellow oil. Yield (1.84 g, 58% yield for two steps): $^1$H NMR (400 MHz, $CDCl_3$) δ 7.39 (ddd, J=8.0, 2.0, 0.8 Hz, 1H), 7.29 (t, J=1.6 Hz, 1H), 7.17 (t, J=7.6 Hz, 1H), 7.05 (dt, J=7.6, 1.6 Hz, 1H), 6.16 (br s, 1H), 3.24 (d, J=6.8 Hz, 2H), 2.53 (s, 2H), 0.93 (s, 6H).

Step 6: N-(3-(3-bromophenyl)-2,2-dimethylpropyl)-2,2,2-trifluoroacetamide (73) (0.489 g, 1.45 mmol) was coupled with 4-ethynylheptan-4-ol (44) (0.28 g, 2.0 mmol) following the method described in Example 16 and the product was purified by flash chromatography (0 to 50% EtOAc-hexanes gradient) to give 2,2,2-trifluoro-N-(3-(3-(3-hydroxy-3-propylhex-1-ynyl)phenyl)-2,2-dimethylpropyl)acetamide (74) as a yellow oil. Yield (0.350 g, 61%): $^1$H NMR (400 MHz, $CD_3OD$) δ 7.20-7.25 (m, 3H), 7.12-7.15 (m, 1H), 3.19 (s, 2H), 2.54 (s, 2H), 1.58-1.71 (m, 8H), 0.98 (t, J=7.2 Hz, 6H), 0.85 (s, 6H).

Step 7: Deprotection of 2,2,2-trifluoro-N-(3-(3-(3-hydroxy-3-propylhex-1-ynyl)phenyl)-2,2-dimethylpropyl)acetamide (74) (0.345 g, 0.87 mmol) was conducted following the method described in Example 2 and the product was purified by flash chromatography (90 to 100% EtOAc-hexanes then 10% 3.5 M NH$_3$ in MeOH-EtOAc) to give alkyne 75 as an oil along with recovered starting material. Yield (0.0847 g, 32% yield): $^1$H NMR (400 MHz, CD$_3$OD) δ 7.19-7.24 (m, 3H), 7.11-7.13 (m, 1H), 2.53 (s, 2H), 2.44 (s, 2H), 1.56-1.72 (m, 8H), 0.98 (t, J=7.2 Hz, 6H), 0.85 (s, 6H).

Step 8: Hydrogenation of alkyne 75 following the method used for Example 2 gave Example 44 as a pale yellow oil. Yield (0.077 g, 99%): 1H NMR (400 MHz, DMSO-d$_6$) δ 7.11 (t, J=7.6 Hz, 1H), 6.95 (d, J=7.8 Hz, 1H), 6.88-6.90 (m, 2H), 3.93 (s, 1H), 2.40 (s, 2H), 2.26 (s, 2H), 1.50-1.55 (m, 2H), 1.43 (br s, 2H), 1.21-1.34 (m, 8H), 0.83 (t, J=7.0 Hz, 6H), 0.71 (s, 6H). ESI MS m/z 306.4 [M+H]$^+$ Example 45

Preparation of 1-(3-(3-Aminopropyl)Phenyl)-3,4-Dimethylpentan-3-ol

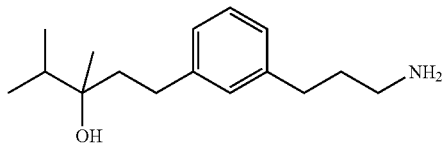 [SMILES: CC(C)C(C)(O)CCc1cccc(CCCN)c1]

1-(3-(3-Aminopropyl)phenyl)-3,4-dimethylpentan-3-ol was prepared following the method used in Example 2.

Step 1: Coupling of 3,4-dimethylpent-1-yn-3-ol with bromide 10 gave 2,2,2-trifluoro-N-(3-(3-(3-hydroxy-3,4-dimethylpent-1-ynyl)phenyl)propyl)acetamide as an amber oil. Yield (0.98 g, 89%): $^1$H NMR (400 MHz, CD$_3$OD) δ 7.15-7.25 (m, 4H), 3.27-3.31 (m, 2H), 2.62 (t, J=7.6 Hz, 2H), 1.82-1.90 (m, 3H), 1.50 (s, 3H), 1.09 (d, J=6.4 Hz, 3H), 1.05 (d, J=6.8 Hz, 3H).

Step 2: Deprotection of 2,2,2-trifluoro-N-(3-(3-(3-hydroxy-3,4-dimethylpent-1-ynyl)phenyl)propyl)acetamide gave 1-(3-(3-aminopropyl)phenyl)-3,4-dimethylpent-1-yn-3-ol as a yellow oil. Yield (0.456 g, 65%): $^1$H NMR (400 MHz, CD$_3$OD) δ 7.15-7.25 (m, 4H), 2.60-2.65 (m, 4H), 1.85 (quint, J=6.8 Hz, 1H), 1.72-1.79 (m, 2H), 1.47 (s, 3H), 1.09 (d, J=6.8 Hz, 3H), 1.05 (d, J=6.8 Hz, 3H).

Step 3: Hydrogenation of 1-(3-(3-aminopropyl)phenyl)-3,4-dimethylpent-1-yn-3-ol gave Example 45 as a colorless oil. Yield (0.384 g, 84%): $^1$H NMR (400 MHz, CDCl$_3$) δ 7.18 (t, J=8.0 Hz, 1H), 6.97-7.03 (m, 3H), 2.71 (t, J=7.2 Hz, 2H), 2.58-2.69 (m, 4H), 1.70-1.82 (m, 5H), 1.50 (br s, 3H), 1.14 (s, 3H), 0.93 (dd, J=12.4, 6.8 Hz, 6H). ESI MS m/z 250.5 [M+H]$^+$, 232.5 [M+H–H$_2$O]$^+$.

Example 46

Preparation of 4-(3-(3-Aminopropyl)Phenyl)-2-Phenylbutan-2-ol

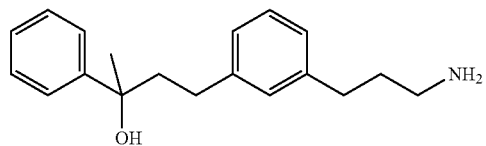 [SMILES: CC(O)(CCc1cccc(CCCN)c1)c1ccccc1]

4-(3-(3-Aminopropyl)phenyl)-2-phenylbutan-2-ol was prepared following the method used in Example 2 and 4.

Step 1: Coupling of 2-phenylbut-3-yn-2-ol with bromide 10 gave 2,2,2-trifluoro-N-(3-(3-(3-hydroxy-3-phenylbut-1-ynyl)phenyl)propyl)acetamide as a yellow oil. $^1$H NMR (400 MHz, DMSO-d$_6$) δ 9.41 (br s, 1H), 7.62 (m, 2H), 7.51 (m, 1H), 7.36 (m, 2H), 7.26 (m, 4H), 6.15 (s, 1H), 3.16 (m, 2H), 2.57 (m, 2H), 1.78 (m, 2H), 1.69 (s, 3H).

Step 2: Deprotection of 2,2,2-trifluoro-N-(3-(3-(3-hydroxy-3-phenylbut-1-ynyl)phenyl)propyl)acetamide gave 4-(3-(3-aminopropyl)phenyl)-2-phenylbut-3-yn-2-ol as a yellow oil. Yield (0.122 g, 27% for two steps): $^1$H NMR (400 MHz, DMSO-d$_6$) δ 7.60-7.63 (m, 1H), 7.33-7.38 (m, 1H), 7.18-7.28 (m, 7H), 6.16 (br s, 1H), 2.57 (m, 2H), 2.51 (m, 2H), 1.69 (s, 3H), 1.56-1.63 (m, 2H), 1.34 (br s, 2H).

Step 3: Hydrogenation of 4-(3-(3-aminopropyl)phenyl)-2-phenylbut-3-yn-2-ol gave Example 46 as a colorless oil. Yield (0.073 g, 71%): $^1$H NMR (400 MHz, CDCl$_3$) δ 7.37-7.42 (m, 2H), 7.25-7.31 (m, 2H), 7.14-7.29 (m, 1H), 7.04-7.10 (m, 1H), 6.84-6.91 (m, 3H), 2.60 (t, J=7.2 Hz, 2H), 2.46-2.57 (m, 3H), 2.29-2.38 (m, 1H), 1.96-2.10 (m, 2H), 1.60-1.80 (m, 5H), 1.51 (s, 3H). ESI MS m/z 284.5 [M+H]$^+$, 266.5 [M+H–H$_2$O]$^+$.

Example 47

Preparation of 1-(3-(3-Aminopropylphenyl)-4-Methylpentan-3-ol

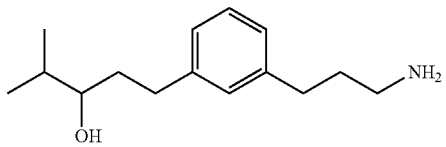 [SMILES: CC(C)C(O)CCc1cccc(CCCN)c1]

1-(3-(3-Aminopropyl)phenyl)-4-methylpentan-3-ol was prepared following the method used in Example 2 and 4.

Step 1: Coupling of 4-methylpent-1-yn-3-ol with bromide 10 gave 2,2,2-trifluoro-N-(3-(3-(3-hydroxy-4-methylpent-1-ynyl)phenyl)propyl)acetamide as a yellow oil contaminated with alkyne dimer which was used without purification in the next step. $^1$H NMR (400 MHz, DMSO-d$_6$) δ 9.40 (br s, 1H), 7.18-7.29 (m, 4H), 5.37 (d, J=5.6 Hz, 1H), 4.20 (t, J=5.6 Hz, 1H), 3.16 (dt, J=6.8, 6.0 Hz, 2H), 2.56 (t, J=7.6 Hz, 2H), 1.70-1.81 (m, 3H), 0.96 (d, J=6.8 Hz, 3H), 0.94 (d, J=6.8 Hz, 3H).

Step 2: Deprotection of 2,2,2-trifluoro-N-(3-(3-(3-hydroxy-4-methylpent-1-ynyl)phenyl)propyl)acetamide gave 1-(3-(3-aminopropyl)phenyl)-4-methylpent-1-yn-3-ol as a yellow oil. Yield (10.174 g, 47%, two steps): $^1$H NMR (400 MHz, DMSO-d$_6$) δ 7.15-7.27 (m, 4H), 4.29 (d, J=5.6 Hz, 1H), 2.63 (m, 4H), 1.88 (m, 1H), 1.76 (m, 2H), 0.96 (d, J=6.8 Hz, 3H), 0.94 (d, J=6.4 Hz, 3H).

Step 3: Hydrogenation of 1-(3-(3-aminopropyl)phenyl)-4-methylpent-1-yn-3-ol gave Example 47 as a colorless oil. Yield (0.091 g, 58%): $^1$H NMR (400 MHz, CDCl$_3$) δ 7.18 (t, J=8.0 Hz, 1H), 6.97-7.04 (m, 3H), 3.37 (ddd, J=8.8, 4.8, 3.2 Hz, 1H), 2.75-2.85 (m, 1H), 2.71 (t, J=7.2 Hz, 2H), 2.55-2.65 (m, 3H), 1.71-1.82 (m, 3H), 1.61-1.71 (m, 2H), 1.52 (br s, 3H), 0.90 (dd, J=1.2, 6.8 Hz, 6H). ESI MS m/z 236.4 [M+H]$^+$.

Example 48

Preparation of 1-(3-(3-Aminopropyl)Phenethyl)Cyclopentanol

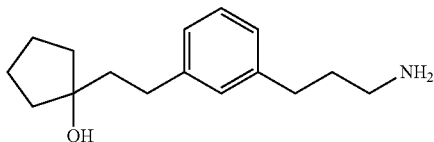 [SMILES: NCCCc1cccc(CCC2(O)CCCC2)c1]

1-(3-(3-Aminopropyl)phenethyl)cyclopentanol was prepared following the method used in Example 2 and 4.

Step 1: Coupling of 1-ethynylcyclopentanol with bromide 10 gave 2,2,2-trifluoro-N-(3-(3-((1-hydroxycyclopentyl)ethynyl)phenyl)propyl)acetamide as a yellow oil which was used without purification in the next step: $^1$H NMR (400 MHz, CD$_3$OD) δ 7.15-7.25 (m, 4H), 3.28 (t, J=7.2 Hz, 2H), 2.62 (t, J=7.2 Hz, 2H), 1.97-2.00 (m, 2H), 1.73-1.91 (m, 8H).

Step 2: Deprotection of 2,2,2-trifluoro-N-(3-(3-((1-hydroxycyclopentyl)-ethynyl)phenyl)propyl)acetamide gave 1-((3-(3-aminopropyl)phenyl)ethynyl)cyclopentanol as a yellow oil. Yield (0.478 g, 62% for two steps): $^1$H NMR (400 MHz, DMSO-d$_6$) δ 7.14-7.34 (m, 4H), 2.59-2.64 (m, 4H), 1.97-2.00 (m, 4H), 1.71-1.87 (m, 6H).

Step 3: Hydrogenation of 1-((3-(3-aminopropyl)phenyl)ethynyl)cyclopentanol gave Example 48 as a colorless oil. Yield (0.261 g, 75%): $^1$H NMR (400 MHz, CDCl$_3$) δ 7.19 (t, J=8.0 Hz, 1H), 6.98-7.05 (m, 3H), 2.69-2.76 (m, 4H), 2.62 (t, J=7.6 Hz, 2H), 1.85-1.92 (m, 2H), 1.79-1.85 (m, 2H), 1.72-1.79 (m, 2H), 1.56-1.72 (m, 6H), 1.37 (br s, 3H). ESI MS m/z 248.5 [M+H]$^+$, 230.4 [M+H–H$_2$O]$^+$.

Example 49

Preparation of 1-(3-(3-Aminopropyl)Phenyl)-3,4,4-Trimethylpentan-3-ol

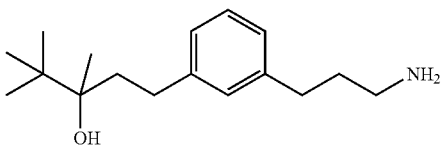 [SMILES: CC(C)(C)C(C)(O)CCc1cccc(CCCN)c1]

1-(3-(3-Aminopropyl)phenyl)-3,4,4-trimethylpentan-3-ol was prepared following the method used in Example 2.

Step 1: Coupling of 3,4,4-trimethylpent-1-yn-3-ol with bromide 10 in a 1:1 mixture of DMF and triethylamine gave 2,2,2-trifluoro-N-(3-(3-(3-hydroxy-3,4,4-trimethylpent-1-ynyl)phenyl)propyl)acetamide as an orange oil. Yield (0.84 g, 73%): $^1$H NMR (400 MHz, CD$_3$OD) δ 7.15-7.25 (m, 4H), 3.29 (t, J=7.2 Hz, 2H), 2.61 (t, J=8.0 Hz, 2H), 1.86 (quint, J=7.6 Hz, 2H), 1.49 (s, 3H), 1.09 (br s, 9H).

Step 2: Deprotection of 2,2,2-trifluoro-N-(3-(3-(3-hydroxy-3,4,4-trimethylpent-1-ynyl)phenyl)propyl)acetamide gave 1-(3-(3-aminopropyl)phenyl)-3,4,4-trimethylpent-1-yn-3-ol as a yellow oil. Yield (0.493 g, 83%): $^1$H NMR (400 MHz, DMSO-d$_6$) δ 7.15-7.24 (m, 4H), 2.60-2.65 (m, 4H), 1.72-1.79 (m, 2H), 1.49 (s, 3H), 1.09 (s, 9H).

Step 3: Hydrogenation of 1-(3-(3-aminopropyl)phenyl)-3,4,4-trimethylpent-1-yn-3-ol gave Example 49 as a colorless oil. Yield (0.388 g, 82%): $^1$H NMR (400 MHz, CDCl$_3$) δ 7.19 (t, J=8.0 Hz, 1H), 6.98-7.05 (m, 3H), 2.70-2.79 (m, 3H), 2.58-2.68 (m, 3H), 1.67-1.87 (m, 4H), 1.31 (br s, 3H), 1.21 (s, 3H), 0.94 (s, 9H). ESI MS m/z 264.6 [M+H]$^+$, 246.5 [M+H–H$_2$O]$^+$.

Example 50

Preparation of 1-(3-(2-Aminoethoxy)Phenyl)-3-Ethylpentan-3-ol

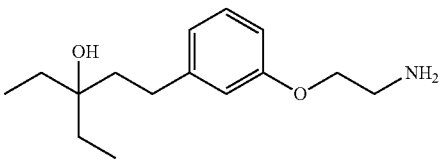 [SMILES: CCC(O)(CC)CCc1cccc(OCCN)c1]

1-(3-(2-aminoethoxy)phenyl)-3-ethylpentan-3-ol was prepared following the method used in Example 9 except that hydrogenation was conducted before deprotection of the amine Step 1: Sonogashira coupling of 3-ethylpent-1-yn-3-ol with bromide 19, followed by flash chromatography (5-50% EtOAc/hexanes gradient) gave N-(2-(3-(3-ethyl-3-hydroxypent-1-ynyl)phenoxy)ethyl)-2,2,2-trifluoroacetamide as an amber oil. Yield (2.1 g, 75%). $^1$H NMR (400 MHz, DMSO-d$_6$) δ 9.58 (m, 1H), 7.24 (t, J=8.0 Hz, 1H), 6.88-6.96 (m, 3H), 5.12 (s, 1H), 4.08 (t, J=5.6 Hz, 2H), 3.53 (q, J=6.4 Hz, 2H), 1.54-1.65 (m, 4H), 0.96 (t, J=7.6 Hz, 6H).

Step 2: Hydrogenation of N-(2-(3-(3-ethyl-3-hydroxypent-1-ynyl)phenoxy)ethyl)-2,2,2-trifluoroacetamide, followed by flash chromatography (5-20% EtoAc/hexanes gradient) gave N-(2-(3-(3-ethyl-3-hydroxypentyl)phenoxy)ethyl)-2,2,2-trifluoroacetamide as a pale yellow waxy solid. Yield (2.06 g, 97%). $^1$H NMR (400 MHz, DMSO-d$_6$) δ 9.59 (m, 1H), 7.14 (t, J=7.6 Hz, 1H), 6.68-6.76 (m, 3H), 4.04 (t, J=5.6 Hz, 2H), 3.91 (s, 1H), 3.53 (q, J=5.6 Hz, 2H), 2.45-2.50 (m, 2H), 1.49-1.55 (m, 2H), 1.36 (q, J=7.6 Hz, 4H), 0.78 (t, J=7.6 Hz, 6H).

Step 3: Deprotection of N-(2-(3-(3-ethyl-3-hydroxypentyl)phenoxy)-ethyl)-2,2,2-trifluoroacetamide followed by flash chromatography (10% (7N NH$_3$/MeOH)/dichloromethane) gave Example 50 as a yellow oil. Yield (0.557 g, 38%). $^1$H NMR (400 MHz, CDCl$_3$) δ 7.13 (t, J=7.6 Hz, 1H), 6.64-6.73 (m, 3H), 3.91 (brs, 1H), 3.85 (t, J=4.8 Hz, 2H), 2.45-2.49 (m, 2H), 1.50-1.56 (m, 2H), 1.43 (brs, 2H), 1.36 (q, J=7.6 Hz, 4H), 0.78 (t, J=7.6 Hz, 6H).

Example 51

Preparation of 1-(3-(2-aminoethoxy)phenyl)-3-isopropyl-4-methylpentan-3-ol

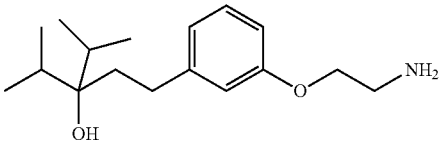 [SMILES: CC(C)C(O)(CCc1cccc(OCCN)c1)C(C)C]

1-(3-(2-Aminoethoxy)phenyl)-3-isopropyl-4-methylpentan-3-ol was prepared following the method used in Example 9.

Step 1: Coupling of 3-isopropyl-4-methylpent-1-yn-3-ol with bromide 19 following the method described in Example 9 except that the reaction was run for 20 h, gave 2,2,2-trifluoro-N-(2-(3-(3-hydroxy-3-isopropyl-4-methylpent-1-ynyl)phenoxy)ethyl)acetamide as an oil which solidified upon standing. Yield (0.94 g, 46%): $^1$H NMR (400 MHz, CDCl$_3$) δ 7.23 (t, J=8.0 Hz, 1H), 7.07 (dt, J=7.6, 1.0 Hz, 1H), 6.95 (dd, J=2.5, 1.4 Hz, 1H), 6.85 (ddd, J=8.4, 2.7, 1.0 Hz, 1H), 6.70 (br s, 1H), 4.10 (t, J=5.1 Hz, 2H), 3.79 (dt, J=5.1 Hz, 2H), 2.04 (m, 2H), 1.80 (s, 1H), 1.09 (d, J=6.7 Hz, 6H), 1.05 (d, J=6.7 Hz, 6H).

Step 2: Deprotection of 2,2,2-trifluoro-N-(2-(3-(3-hydroxy-3-isopropyl-4-methylpent-1-ynyl)phenoxy)acetamide gave 1-(3-(2-aminoethoxy)phenyl)-3-isopropyl-4-methylpent-1-yn-3-ol as a white solid. Yield (0.529 g, 76%): $^1$H NMR (400 MHz, DMSO-d$_6$) δ 7.24 (t, J=7.8 Hz, 1H), 6.90-6.95 (m, 2H), 6.87-6.88 (m, 1H), 4.83 (br s, 1H), 3.89 (t, J=5.7 Hz, 2H), 2.83 (t, J=5.7 Hz, 2H), 1.86 (m, 2H), 1.47 (br s, 2H), 0.98 (d, J=6.8 Hz, 6H), 0.93 (d, J=6.7 Hz, 6H). $^{13}$C NMR (100 MHz, DMSO-d$_6$) δ 159.29, 130.48, 124.58, 124.32, 117.46, 115.72, 92.60, 84.54, 76.74, 71.04, 41.62, 34.95, 18.98, 17.21. ESI MS m/z 276.39 [M+H]$^+$, 258.37 [M+H–H$_2$O]$^+$.

Step 3: Hydrogenation of 1-(3-(2-aminoethoxy)phenyl)-3-isopropyl-4-methylpent-1-yn-3-ol gave Example 51 as a colorless oil. Yield (0.238 g, 79%): $^1$H NMR (400 MHz, CDCl$_3$) δ 7.17 (t, J=8.0 Hz, 1H), 6.69-6.80 (m, 3H), 3.96 (t, J=5.2 Hz, 2H), 3.06 (t, J=5.2 Hz, 2H), 2.58-2.64 (m, 2H), 1.90-2.02 (m, 2H), 1.74-1.80 (m, 2H), 1.43 (br s, 3H), 0.98 (t, J=7.2 Hz, 12H). ESI MS m/z 280.6 [M+H]$^+$, 262.5 [M+H–H$_2$O]$^+$.

Example 52

Preparation of 5-(3-(2-Aminoethoxy)Phenethyl)Nonan-5-ol

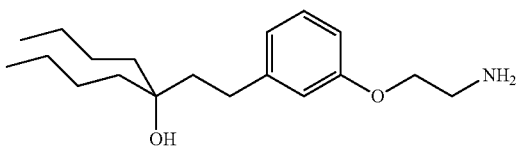 [SMILES: CCCCC(O)(CCCC)CCc1cccc(OCCN)c1]

5-(3-(2-Aminoethoxy)phenethyl)nonan-5-ol was prepared following the method used in Example 9.

Step 1: Coupling of 5-ethynylnonan-5-ol with bromide 19 gave N-(2-(3-(3-butyl-3-hydroxyhept-1-ynyl)phenoxy)ethyl)-2,2,2-trifluoroacetamide. Yield (1.06 g, 75%): $^1$H NMR (400 MHz, CDCl$_3$) δ 7.23 (t, J=8.0 Hz, 1H), 7.06 (dt, J=7.6 and 1.2 Hz, 1H), 6.94 (dd, J=2.5, 1.4 Hz, 1H), 6.86 (ddd, J=8.4, 2.7, 1.0 Hz, 1H), 6.72 (br s, 1H), 4.10 (t, J=5.3 Hz, 2H), 3.79 (dt, J=5.3 Hz, 2H), 1.96 (s, 1H), 1.70-1.75 (m, 4H), 1.50-1.58 (m, 4H), 1.34-1.43 (m, 4H), 0.94 (t, J=7.2 Hz, 6H).

Step 2: Deprotection of N-(2-(3-(3-butyl-3-hydroxyhept-1-ynyl)-phenoxy)ethyl)-2,2,2-trifluoroacetamide gave 5-((3-(2-aminoethoxy)phenyl)-ethynyl)nonan-5-ol as a colorless oil which solidified upon standing. Yield (0.695 g, 92%): $^1$H NMR (400 MHz, DMSO-d$_6$) δ 7.24 (t, J=7.8 Hz, 1H), 6.92-6.93 (m, 1H), 6.90-6.91 (m, 1H), 6.85-6.86 (m, 1H), 5.13 (br s, 1H), 3.89 (t, J=5.7 Hz, 2H), 2.83 (t, J=5.7 Hz, 2H), 1.52-1.60 (m, 6H), 1.40-1.49 (m, 4H), 1.25-1.34 (m, 4H), 0.88 (t, J=7.2 Hz, 6H). $^{13}$C NMR (100 MHz, DMSO-d$_6$) δ 159.28, 130.49, 124.50, 124.26, 117.35, 115.76, 94.87, 83.08, 71.03, 70.27, 42.19, 41.60, 26.85, 23.15, 14.74. ESI MS m/z 304.42 [M+H]$^+$, 286.42 [M+H–H$_2$O]$^-$.

Step 3: Hydrogenation of 5-((3-(2-aminoethoxy)phenyl)ethynyl)nonan-5-ol gave Example 52 as a colorless oil. Yield (0.154 g, 73%): $^1$H NMR (400 MHz, CDCl$_3$) δ 7.18 (t, J=8.0 Hz, 1H), 6.69-6.81 (m, 3H), 3.97 (t, J=5.2 Hz, 2H), 3.06 (t, J=5.2 Hz, 2H), 2.56-2.63 (m, 2H), 1.68-1.75 (m, 2H), 1.44-1.52 (m, 4H), 1.36-1.42 (br s, 3H), 1.24-1.36 (m, 8H), 0.91 (t, J=6.8 Hz, 6H). ESI MS m/z 308.6 [M+H]$^+$, 290.6 [M+H–H$_2$O]$^+$.

Example 53

Preparation of 4-(3-(2-Aminoethoxy)Phenyl)-2-Methylbutan-2-ol

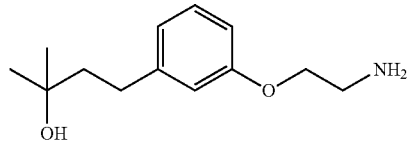 [SMILES: CC(C)(O)CCc1cccc(OCCN)c1]

4-(3-(2-Aminoethoxy)phenyl)-2-methylbutan-2-ol was prepared following the method used in Example 9.

Step 1: Coupling of 2-methylbut-3-yn-2-ol with bromide 10 following the method described in Example 9 except that the reaction was run for 19 h, gave 2,2,2-trifluoro-N-(2-(3-(3-hydroxy-3-methylbut-1-ynyl)phenoxy)ethyl)acetamide. Yield (0.667 g, 70%): $^1$H NMR (400 MHz, CDCl$_3$) δ 7.23 (t, J=7.8 Hz, 1H), 7.06 (dt, J=7.6 and 1.2 Hz, 1H), 6.94 (dd, J=2.5, 1.4 Hz, 1H), 6.86 (ddd, J=8.2, 2.5, 1.0 Hz, 1H), 6.74 (br s, 1H), 4.09 (t, J=4.9 Hz, 2H), 3.80 (dt, J=5.5 Hz, 2H), 2.04 (s, 1H), 1.61 (s, 6H).

Step 2: Deprotection of 2,2,2-trifluoro-N-(2-(3-(3-hydroxy-3-methylbut-1-ynyl)phenoxy)ethyl)acetamide gave 4-(3-(2-aminoethoxy)phenyl)-2-methylbut-3-yn-2-ol as a white solid. Yield (0.240 g, 52%): $^1$H NMR (400 MHz, DMSO-d$_6$) δ 7.23 (t, J=8.0 Hz, 1H), 6.89-6.93 (m, 2H), 6.86-6.88 (m, 1H), 5.43 (br s, 1H), 3.89 (t, J=5.9 Hz, 2H), 2.83 (t, J=5.9 Hz, 2H), 1.45 (br s, 2H), 1.44 (s, 6H). $^{13}$C NMR (100 MHz, DMSO-d$_6$) δ 159.27, 130.45, 124.38, 124.20, 117.21, 116.00, 96.57, 80.99, 71.03, 64.27, 41.59, 32.28. ESI MS m/z 220.31 [M+H]$^+$, 202.28 [M+H–H$_2$O]$^+$; HPLC (Method A) $t_R$=2.79 min.

Step 3: Hydrogenation of 4-(3-(2-aminoethoxy)phenyl)-2-methylbut-3-yn-2-ol gave Example 53 as a colorless oil. Yield (0.143 g, 73%): $^1$H NMR (400 MHz, CDCl$_3$) δ 7.18 (t, J=8.0 Hz, 1H), 6.70-6.82 (m, 3H), 3.97 (t, J=5.2 Hz, 2H), 3.07 (t, J=5.2 Hz, 2H), 2.63-2.70 (m, 2H), 1.74-1.81 (m, 2H), 1.47 (s, 3H), 1.27 (s, 6H). ESI MS m/z 224.4 [M+H]$^+$, 206.3 [M+H–H$_2$O]$^+$.

Example 54

Preparation of 1-(3-(2-Aminoethoxy)Phenethyl)Cyclopentanol

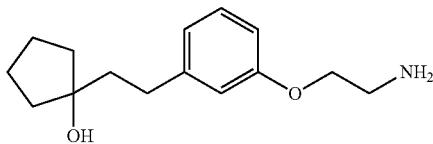 [SMILES: NCCOc1cccc(CCC2(O)CCCC2)c1]

1-(3-(2-Aminoethoxy)phenethyl)cyclopentanol was prepared following the method used in Example 9.

Step 1: Coupling of 1-ethynylcyclopentanol with bromide 19 following the method described in Example 9 except that the reaction was run for 19.5 h, gave 2,2,2-trifluoro-N-(2-(3-((1-hydroxycyclopentyl)ethynyl)phenoxy)ethyl)acetamide as a brown oil. Yield (1.055 g, 92%): $^1$H NMR (400 MHz, CDCl$_3$) δ 7.23 (t, J=8.0 Hz, 1H), 7.06 (dt, J=7.6, 1.2 Hz, 1H), 6.95 (dd, J=2.5, 1.4 Hz, 1H), 6.85 (ddd, J=8.4, 2.7, 1.0 Hz, 1H), 6.72 (br s, 1H), 4.09 (t, J=5.3 Hz, 2H), 3.78 (dt, J=5.1 Hz, 2H), 2.00-2.09 (m, 4H), 1.76-1.93 (m, 5H).

Step 2: Deprotection of 2,2,2-trifluoro-N-(2-(3-((1-hydroxycyclopentyl)ethynyl)phenoxy)ethyl)acetamide gave 1-((3-(2-aminoethoxy)phenyl)ethynyl)cyclopentanol as an oil which solidified upon standing. Yield (0.502 g, 66%): $^1$H NMR (400 MHz, DMSO-d$_6$) δ 7.23 (t, J=8.0 Hz, 1H), 6.88-6.94 (m, 3H), 5.28 (br s, 1H), 3.89 (t, J=5.7 Hz, 2H), 2.83 (t, J=5.7 Hz, 2H), 1.82-1.89 (m, 4H), 1.63-1.74 (m, 4H), 1.48 (br s, 2H). $^{13}$C NMR (100 MHz, DMSO-d$_6$) δ 159.27, 130.45, 124.50, 124.18, 117.20, 115.93, 95.65, 81.97, 73.44, 71.01, 42.66, 41.58, 23.75. ESI MS m/z 246.33 [M+H]$^+$, 228.30 [M+H–H$_2$O]$^+$; HPLC (Method A) t$_R$=4.19 min.

Step 3: Hydrogenation of 1-((3-(2-aminoethoxy)phenyl)ethynyl)cyclopentanol gave Example 54 as a colorless oil. Yield (0.353 g, 76%): $^1$H NMR (400 MHz, CDCl$_3$) δ 7.16 (t, J=8.0 Hz, 1H), 6.68-6.81 (m, 3H), 3.95 (t, J=5.2 Hz, 2H), 3.04 (t, J=5.2 Hz, 2H), 2.72 (m, 2H), 1.86 (m, 2H), 1.72-1.82 (m, 2H), 1.40-1.72 (m, 9H). ESI MS m/z 250.4 [M+H]$^+$, 232.4 [M+H–H$_2$O]$^+$.

Example 55

Preparation of 1-(3-(3-aminopropyl)phenyl)-3-isopropyl-4-methylpentan-3-ol

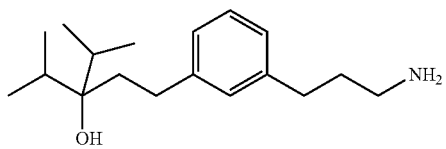 [SMILES: CC(C)C(O)(CCc1cccc(CCCN)c1)C(C)C]

1-(3-(3-Aminopropyl)phenyl)-3-isopropyl-4-methylpentan-3-ol was prepared following the method used in Example 2 and 13.

Step 1: Coupling of 3-isopropyl-4-methylpent-1-yn-3-ol with bromide 10 following the method used in Example 13 gave 2,2,2-trifluoro-N-(3-(3-(3-hydroxy-3-isopropyl-4-methylpent-1-ynyl)phenyl)propyl)acetamide as a pale yellow oil. Yield (1.375 g, 66%): $^1$H NMR (400 MHz, DMSO-d$_6$) δ 9.40 (br s, 1H), 7.26 (t, J=7.6 Hz, 1H), 7.17-7.22 (m, 3H), 4.81 (s, 1H), 3.17 (q, J=6.8 Hz, 2H), 2.56 (t, J=8.0 Hz, 2H), 1.86 (quint, J=6.8 Hz, 2H), 1.76 (quint, J=7.6 Hz, 2H), 0.99 (d, J=6.8 Hz, 6H), 0.94 (d, J=6.8 Hz, 6H).

Step 2: Deprotection of 2,2,2-trifluoro-N-(3-(3-(3-hydroxy-3-isopropyl-4-methylpent-1-ynyl)phenyl)propyl)acetamide following the method used in Example 2 followed by flash chromatography (9:1 CH$_2$Cl$_2$: 7 M NH$_3$ in MeOH) gave 1-(3-(3-aminopropyl)phenyl)-3-isopropyl-4-methylpent-1-yn-3-ol as a clear oil. Yield (0.835 g, 82%): $^1$H NMR (400 MHz, DMSO-d$_6$) δ 7.15-7.26 (m, 4H), 4.82 (br s, 1H), 2.56 (t, J=7.6 Hz, 2H), 2.47-2.52 (m, 2H), 1.86 (quint, J=6.8 Hz, 2H), 1.59 (quint, J=6.8 Hz, 2H), 1.56 (br,s, 2H), 1.05 (d, J=6.8 Hz, 6H), 1.03 (d, J=6.8 Hz, 6H).

Step 3: Hydrogenation of 1-(3-(3-aminopropyl)phenyl)-3-isopropyl-4-methylpent-1-yn-3-ol following the method used in Example 2 gave Example 55 as a colorless oil. Yield (0.538 g, 68%): $^1$H NMR (400 MHz, CDCl$_3$) δ 7.19 (t, J=8.0 Hz, 1H), 6.97-7.60 (m, 3H), 2.73 (t, J=7.2 Hz, 2H), 2.58-2.65 (m, 4H), 1.92-2.04 (m, 2H), 1.72-1.82 (m, 4H), 1.30-1.40 (br s, 3H), 0.99 (t, J=7.2 Hz, 12H). ESI MS m/z 278.6 [M+H]$^+$, 260.5 [M+H–H$_2$O]$^+$.

Example 56

Preparation of 4-(3-(3-Aminopropyl)Phenethyl)-2,6-Dimethylheptan-4-ol

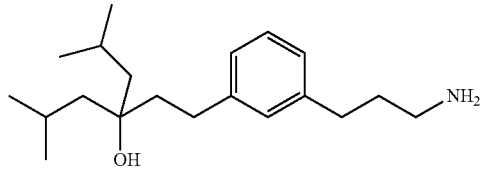 [SMILES: CC(C)CC(O)(CCc1cccc(CCCN)c1)CC(C)C]

4-(3-(3-Aminopropyl)phenethyl)-2,6-dimethylheptan-4-ol was prepared following the method used in Example 55.

Step 1: Coupling of 4-ethynyl-2,6-dimethylheptan-4-ol with bromide 10 gave 2,2,2-trifluoro-N-(3-(3-(3-hydroxy-3-isobutyl-5-methylhex-1-ynyl)phenyl)propyl)acetamide as a pale yellow oil. Yield (1.25 g, 63%): $^1$H NMR (400 MHz, DMSO-d$_6$) δ 9.40 (br s, 1H), 7.14-7.28 (m, 4H), 5.02 (s, 1H), 3.17 (q, J=6.8 Hz, 2H), 2.56 (t, J=7.6 Hz, 2H), 1.93-1.99 (m, 2H), 1.75 (quint, J=7.6 Hz, 2H), 1.47-1.56 (m, 4H), 0.86-0.98 (m, 12H).

Step 2: Deprotection of 2,2,2-trifluoro-N-(3-(3-(3-hydroxy-3-isobutyl-5-methylhex-1-ynyl)phenyl)propyl)acetamide gave 4-((3-(3-aminopropyl)phenyl)ethynyl)-2,6-dimethylheptan-4-ol as a clear oil. Yield (0.73 g, 77%): $^1$H NMR (400 MHz, DMSO-d$_6$) 7.22-7.26 (m, 1H), 7.12-7.18 (m, 3H), 5.04 (br s, 1H), 2.56 (t, J=7.2 Hz, 2H), 2.50 (t, J=6.8 Hz, 2H), 1.91-2.01 (m, 2H), 1.47-1.62 (m, 6H), 0.98 (m, 6H), 0.96 (m, 6H).

Step 3: Hydrogenation of 4-((3-(3-aminopropyl)phenyl)ethynyl)-2,6-dimethylheptan-4-ol gave Example 56 as a colorless oil. Yield (0.559 g, 77%): $^1$H NMR (400 MHz, CDCl$_3$) δ 7.18 (t, J=8.0 Hz, 1H), 6.97-7.03 (m, 3H), 2.73 (t, J=7.2 Hz, 2H), 2.56-2.65 (m, 4H), 1.72-1.88 (m, 6H), 1.40-1.48 (m, 7H), 0.98 (dd, J=6.8, 4.8 Hz, 12H). ESI MS m/z 306.7 [M+H]$^+$, 288.6 [M+H–H$_2$O]$^+$.

Example 57

Preparation of 5-(3-(3-Aminopropyl)Phenyl)Pentan-2-ol

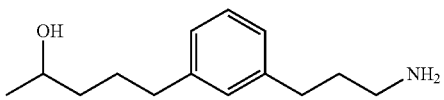 [SMILES: CC(O)CCCc1cccc(CCCN)c1]

5-(3-(3-Aminopropyl)phenyl)pentan-2-ol was prepared following the method used in Examples 2, 13, and 23.

Step 1: Coupling of pent-4-yn-2-ol with bromide 10 following the method used in Example 13 except the reaction was conducted at room temperature gave 2,2,2-trifluoro-N-(3-(3-(4-hydroxypent-1-ynyl)phenyl)propyl)acetamide as a pale yellow oil. Yield (0.95 g, 63%): $^1$H NMR (400 MHz, DMSO-$d_6$) δ 9.40 (br s, 1H), 7.14-7.26 (m, 4H), 4.80 (s, 1H), 3.81 (q, J=5.6 Hz, 1H), 3.16 (q, J=6.8 Hz, 2H), 2.54 (t, J=5.6 Hz, 2H), 2.39 (dd, J=16.8, 6.8 Hz, 2H), 1.76 (quint, J=7.2 Hz, 2H), 1.17 (d, J=5.6 Hz, 3H).

Step 2: Deprotection of 2,2,2-trifluoro-N-(3-(3-(4-hydroxypent-1-ynyl)phenyl)propyl)acetamide following the method described in Example 23 gave 5-(3-(3-aminopropyl)phenyl)pent-4-yn-2-ol as a clear oil Yield (0.34 g, 94%): $^1$H NMR (400 MHz, CDCl$_3$) δ 7.24-7.25 (m, 1H), 7.23 (t, J=1.6 Hz, 1H), 7.20 (ddd, J=7.4, 7.4, 0.6 Hz, 1H), 7.11 (dt, J=7.2, 1.6 Hz, 1H), 4.04 (dq, J=12.5, 6.3 Hz, 1H), 2.72 (t, J=6.9 Hz, 2H), 2.51-2.64 (m, 4H), 1.72-1.79 (m, 2H), 1.65 (br s, 3H), 1.32 (d, J=6.3 Hz, 3H).

Step 3: Hydrogenation of 5-(3-(3-aminopropyl)phenyl)pent-4-yn-2-ol following the method used in Example 2 gave Example 57 as a colorless oil. Yield (0.173 g, 64%): $^1$H NMR (400 MHz, CDCl$_3$) δ 7.15-7.22 (m, 1H), 6.97-7.04 (m, 3H), 3.80 (quint., J=6.4 Hz, 1H), 2.72 (t, J=7.2 Hz, 2H), 2.55-2.65 (m, 4H), 1.57-1.82 (m, 4H), 1.52 (br s, 3H), 1.40-1.54 (m, 2H), 1.17 (d, J=6.0 Hz, 3H). ESI MS m/z 222.5 [M+H]$^+$.

Example 58

Preparation of 3-(3-(2-Methoxyphenethyl)Phenyl)Propan-1-Amine

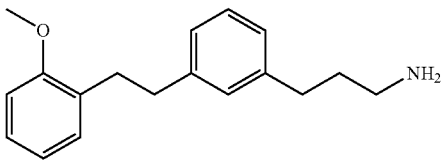 [SMILES: COc1ccccc1CCc1cccc(CCCN)c1]

3-(3-(2-Methoxyphenethyl)phenyl)propan-1-amine was prepared following the method used in Examples 22 except that the hydrogenation was conducted before the deprotection of the amine Step 1: Sonogashira reaction of bromide 57 with 2-ethynylanisole was conducted by the method used in Example 22 except that diisopropylamine was used in place of triethylamine and the reaction mixture was heated at reflux. tert-Butyl 3-(3-((2-methoxyphenyl)ethynyl)phenyl)propylcarbamate was obtained as a yellow oil. Yield (0.42 g, 72%): MS: 366 [M+1]$^+$.

Step 2: Reduction of tert-butyl 3-(3-((2-methoxyphenyl)ethynyl) phenyl) propylcarbamate gave tert-butyl 3-(3-(2-methoxyphenethyl)phenyl)propylcarbamate as an off-white solid. Yield (0.242 g, 85%): MS: 370 [M+1]$^+$.

Step 3: Deprotection of tert-butyl 3-(3-(2-methoxyphenethyl)phenyl) propylcarbamate gave Example 58 as yellow oil. Yield (0.192 g, 78%): $^1$H NMR (400 MHz, DMSO-$d_6$) δ 7.17-7.23 (m, 2H), 7.11 (d, J=7.6 Hz, 1H), 7.0-7.07 (m, 3H), 6.96 (d, J=8.4 Hz, 1H), 6.82-6.86 (m, 1H), 3.79 (s, 3H), 2.74-2.84 (m, 6H), 2.62 (t, J=7.6 Hz, 2H), 1.77-1.86 (m, 2H). $^{13}$C NMR (100 MHz, DMSO-$d_6$): 157.5, 142.4, 141.2, 130.0, 129.8, 128.8, 128.7, 127.8, 126.5, 126.2, 120.6, 111.1, 55.8, 38.8, 35.9, 32.3, 32.2, 29.2. MS: 270 [M+1]$^+$.

Example 59

Preparation of 6-(3-(3-Amino-1-Hydroxypropyl)Phenyl)Hexan-1-ol

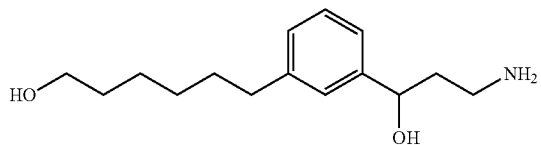 [SMILES: NCCC(O)c1cccc(CCCCCCO)c1]

6-(3-(3-Amino-1-hydroxypropyl)phenyl)hexan-1-ol was prepared following the method used in Example 17.

Step 1: Coupling of hex-5-yn-1-ol with bromide 39 gave tert-butyl 3-hydroxy-3-(3-(6-hydroxyhex-1-ynyl)phenyl)propylcarbamate as a brown oil. Yield (0.405 g, 77%).

Step 2: Deprotection of tert-butyl 3-hydroxy-3-(3-(6-hydroxyhex-1-ynyl)phenyl)propylcarbamate followed by purification by preparative HPLC (Method 2P) gave 6-(3-(3-Amino-1-hydroxypropyl)phenyl)hex-5-yn-1-ol hydrochloride as a white solid. Yield (0.12 g, 32%): $^1$H NMR (400 MHz, DMSO-$d_6$) δ 7.87 (br s, 2H), 7.25-7.35 (m, 4H), 5.51 (br s, 1H), 4.68 (dd, J=7.8, 4.4 Hz, 1H), 4.46 (t, J=6.4 Hz, 1H), 3.40-3.44 (m, 2H), 2.77-2.88 (m, 2H), 2.41-2.44 (m,2H), 1.80-1.93 (m, 2H), 1.56-1.62 (m, 4H).

Step 3: Hydrogenation of 6-(3-(3-amino-1-hydroxypropyl)phenyl)hex-5-yn-1-ol hydrochloride following the method used in Example 13 followed by purification by preparative HPLC (Method 1P) gave Example 59 trifluoroacetate as a white solid. Yield (21 mg, 14%): $^1$H NMR (400 MHz, DMSO-$d_6$) δ0 7.63 (br s, 3H), 7.23 (t, J=7.5 Hz, 1H), 7.12 (s, 1 H), 7.11 (d, J=7.5 Hz, 1 H), 7.06 (d, J=7.5 Hz, 1H), 5.49 (br s, 1H), 4.63 (t, J=6.3 Hz, 1H), 4.31 (t, J=4.9 Hz, 1H), 3.35 (dd, J=11.1, 6.1 Hz, 2H), 2.78-2.90 (m, 2H), 2.54 (t, J=7.7, 2H), 1.78-1.84 (m, 2H), 1.50-1.58 (m, 2H), 1.27-1.40 (m, 6H).

Example 60

Preparation of 4-(3-(3-Amino-1-Hydroxypropyl)Phenyl)Obutan-1-ol

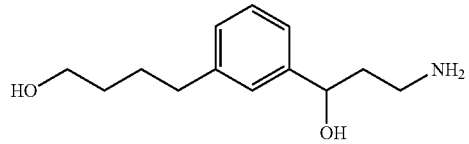 [SMILES: NCCC(O)c1cccc(CCCCO)c1]

4-(3-(3-Amino-1-hydroxypropyl)phenyl)butan-1-ol was prepared following the method used in Example 19 except that the amine deprotection was conducted before the hydrogenation.

Step 1: Sonogashira reaction of bromide 19 with but-3-yn-1-ol gave 2,2,2-trifluoro-N43-hydroxy-3-(3-(4-hydroxybut-1-ynyl)phenyl)propyl)acetamide as brown oil. Yield (0.908 g, 90%): $^1$H NMR (400 MHz, CDCl$_3$) δ 7.41 (s, 1H), 7.23-7.36 (m, 3H), 4.84-4.87 (m, 1H), 3.81 (t, J=6.4 Hz, 2H), 3.66-3.69 (m, 1H), 3.39-3.42 (m, 1H), 2.69 (t, J=6.4 Hz, 2H), 1.93-1.99 (m, 2H).

Step 2: A mixture of, 2,2,2-trifluoro-N43-hydroxy-3-(3-(4-hydroxybut-1-ynyl)phenyl)propyl)acetamide, potassium carbonate (1.6 g, 11.5 mmol) and water (3 mL) in MeOH (15 mL) was heated under reflux for 4 h. Reaction mass was concentrated to dryness under reduced pressure to give 4-(3-(3-amino-1-hydroxypropyl)phenyl)but-3-yn-1-ol as pale yellow oil after purification by flash chromatography with 15% MeOH—NH$_3$ (9.5:0.5)-DCM. Yield (0.38 g, 60%). This compound was utilized as such for the next transformation.

Step 3: A solution of 4-(3-(3-amino-1-hydroxypropyl)phenyl)but-3-yn-1-ol (5) in 2-PrOH (10 mL) was degassed and purged with nitrogen. To this was added Pd on C (0.08 g, 10%). The flask was evacuated and filled with hydrogen. After repeating this procedure thrice, the reaction mixture was stirred under H$_2$ balloon at RT. After about 72 h, this mixture was filtered through Celite and concentrated under reduced pressure to yield yellow oil. The crude product was purified by flash chromatography (0-15% MeOH—NH$_3$ (9.5:0.5)-DCM gradient) to obtain Example 60 as yellow oil. Yield (0.14 g, 37%): $^1$H NMR (400 MHz, DMSO-d$_6$) δ 7.19 (t, J=7.6, 1H), 7.13 (s, 1H), 7.11 (d, J=7.6 Hz, 1H), 7.03 (d, J=7.6 Hz, 1H), 4.60-4.63 (m, 1H), 4.36 (bs, 1H), 3.39 (t, J=7.6 Hz, 2H), 2.58-2.68 (m, 2H), 2.55 (t, J=7.6 Hz, 2H), 1.55-1.68 (m, 4H), 1.44-1.46 (m, 2H). $^{13}$C NMR (100 MHz, DMSO-d$_6$) δ 146.0, 141.8, 127.7, 126.4, 125.6, 123.0, 71.4, 60.5, 42.4, 38.9, 35.1, 32.1, 27.5. MS: 224 [M+1]$^+$.

Example 61

Preparation of 3-Amino-1-(3-(2-Methoxyphenethyl)Phenyl)Propan-1-ol

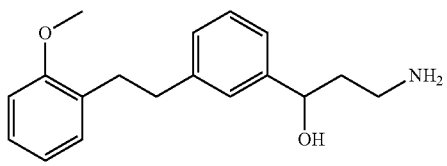 [SMILES: COc1ccccc1CCc1cccc(C(O)CCN)c1]

3-Amino-1-(3-(2-methoxyphenethyl)phenyl)propan-1-ol was prepared following the method used in Example 19.

Step 1: Sonogashira reaction of bromide 43 with 1-ethynyl-2-methoxybenzene gave 2,2,2-trifluoro-N-(3-hydroxy-3-(3-((2-methoxyphenyl)ethynyl)phenyl)propyl)acetamide as brown oil. Yield (1.12 g, 96%): $^1$H NMR (400 MHz, CDCl$_3$) δ 7.55 (s, 1H), 7.50 (d, J=5.6 Hz, 2H), 7.28-7.37 (m, 3H), 6.90-6.96 (m, 2H), 4.84-4.87 (m, 1H), 3.92 (s, 3H), 3.66-3.69 (m, 1H), 3.39-3.42 (m, 1H), 2.32 (bs, 1H), 1.93-1.99 (m, 2H).

Step 2: Reduction of 2,2,2-trifluoro-N-(3-hydroxy-3-(3-((2-methoxy phenyl)ethynyl)phenyl)propyl)acetamide gave 2,2,2-trifluoro-N-(3-hydroxy-3-(3-(2-methoxyphenethyl)phenyl)propyl)acetamide as yellow oil. Yield (1.1 g, crude): $^1$H NMR (400 MHz, CDCl$_3$) δ 7.36 (bs, 1H), 7.24-7.30 (m, 1H), 7.13-7.20 (m, 3H), 7.08 (s, 1H), 7.04 (d, J=1.6 Hz, 7.2 Hz, 1H), 6.82-6.87 (m, 2H), 4.83-4.86 (m,1H), 3.81 (s, 3H), 3.61-3.66 (m, 1H), 3.36-3.42 (m, 1H), 2.17 (bs, 1H), 1.93-1.99 (m, 2H). This compound was utilized as such for the next transformation.

Step 3: Deprotection of 2,2,2-trifluoro-N-(3-hydroxy-3-(3-(2-methoxyphenethyl)-phenyl)propyl)acetamide gave a dark oil, which upon purification by flash chromatography (0-10% MeOH—NH$_3$ (9.5:0.5)-DCM gradient) yielded Example 61 as pale green oil. Yield (0.616 g, 75%): $^1$H NMR (400 MHz, DMSO-d$_6$) δ 7.04-7.23 (m, 6H), 6.94 (d, J=8.0 Hz, 1H), 6.82 (t, J=7.2 Hz, 1H), 4.59 (t, J=6.4 Hz, 1H), 3.75 (s, 3H), 2.78 (s, 4H), 2.66-2.73 (m, 2H), 1.70-1.75 (m, 2H). $^{13}$C NMR (100 MHz, DMSO-d$_6$) δ 157.1, 145.7, 141.6, 129.6, 129.3, 128.0, 127.3, 126.7, 125.5, 123.1, 120.2, 110.6, 70.5, 55.3, 37.6, 35.6, 31.8. MS: 286 [M+1]$^+$.

Example 62

Preparation of 3-(3-(2-(Thiophen-2-yl)Ethyl)Phenyl)Propan-1-AMINE

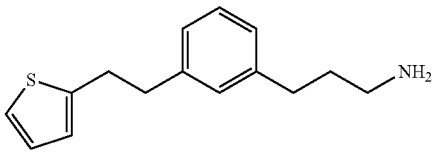 [SMILES: NCCCc1cccc(CCc2cccs2)c1]

3-(3-(2-(Thiophen-2-yl)ethyl)phenyl)propan-1-amine was prepared following the method used in Example 31.

Step 1: Alkyne 61 was coupled with 2-bromothiophene and purified by flash chromatography (15% EtOAc-hexanes) to give 2-(3-(3-(thiophen-2-ylethynyl)phenyl)propyl)isoindoline-1,3-dione as a yellow solid. Yield (0.490 g, 50%): $^1$H NMR (400 MHz, CDCl$_3$) δ 7.84 (dd, J=5.6, 3.2 Hz, 2H), 7.71 (dd, J=5.2, 3.2 Hz, 2H), 7.35 (s, 1H), 7.26-7.30 (m, 3H), 7.23 (t, J=7.6 Hz, 1H), 7.18 (d, J=7.6 Hz, 1H), 7.01 (dd, J=5.2, 3.6 Hz, 1H), 3.76 (t, J=7.2 Hz, 2H), 2.69 (t, J=7.6 Hz, 2H), 2.05 (quint., J=7.6 Hz, 2H).

Step 2: 2-(3-(3-(Thiophen-2-ylethynyl)phenyl)propyl)isoindoline-1,3-dione was deprotected and the reaction mixture diluted with diethyl ether and the precipitate removed by filtration. The filtrate was concentrated under reduced pressure and the diethyl ether precipitation step was repeated. Purification by preperative HPLC (Method 1P) gave 3-(3-(thiophen-3-ylethynyl)phenyl)propan-1-amine trifluoroacetate as a cream-colored solid. Yield (0.210 g, 65%): $^1$H NMR (400 MHz, CDCl$_3$) δ 7.94 (br s, 3H), 7.33 (d, J=7.6 Hz, 1H), 7.25-7.28 (m, 2H), 7.22 (d, J=7.6 Hz, 1H), 7.09 (d, J=7.6 Hz, 1H), 6.99 (dd, J=5.2, 3.6 Hz, 1H), 2.89 (t, J=7.2 Hz, 2H), 2.63 (t, J=7.6 Hz, 2H), 1.92-1.99 (m, 2H).

Step 3: Hydrogenation followed by purification by preperative HPLC (Method 1P) gave Example 62 trifluoroacetate as a off-white solid. Yield (170 mg, 29%): $^1$H NMR (400 MHz, DMSO-d$_6$) δ 7.66 (br s, 3H), 7.28 (d, J=5.0 Hz, 1H), 7.20 (t, J=7.5 Hz, 1H), 7.07 (d, J=7.7 Hz, 1H), 7.06 (s, 1H), 7.01 (d, J=7.6 Hz, 1H), 6.90 (dd, J=5.0, 3.4 Hz, 1H), 6.82 (d, J=3.4 Hz, 1H), 3.08 (t, J=7.8 Hz, 2H), 2.88 (t, J=7.8 Hz, 2H), 2.71-2.79 (m, 2H), 2.58 (t, J=7.7 Hz, 2H), 1.79 (quint, J=7.7 Hz, 2H).

Example 63

Preparation of 3-Amino-1-(3-(4-Phenylbutyl)Phenyl) Propan-1-ol

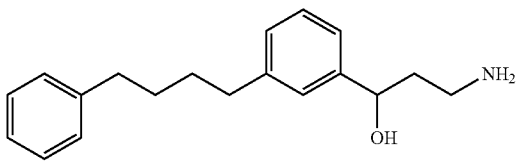 [SMILES: NCCC(O)c1cccc(CCCCc2ccccc2)c1]

3-Amino-1-(3-(4-phenylbutyl)phenyl)propan-1-ol was prepared following the method used in Example 19 except that the amine deprotection was conducted before the hydrogenation.

Step 1: Coupling of aryl bromide 43 with but-3-ynylbenzene following the method used in Example 19 and purification by flash chromatography (20% EtOAc-hexanes) gave 2,2,2-trifluoro-N-(3-hydroxy-3-(3-(4-phenylbut-1-ynyl) phenyl)propyl)acetamide as a brown oil. Yield (0.340 g, 52%): $^1$H NMR (400 MHz, CDCl$_3$) δ 7.28-7.36 (m, 7H), 7.24-7.27 (m, 2H), 4.84-4.88 (m, 1H), 3.66-3.74 (m, 1H), 3.41 (ddd, J=17.6, 8.0, 4.4 Hz, 1H), 2.93 (t, J=7.6 Hz, 2H), 2.70 (t, J=7.6 Hz, 2H), 2.27 (d, J=1.6 Hz, 1H), 1.90-2.03 (m, 2H).

Step 2: Deprotection of 2,2,2-trifluoro-N-(3-hydroxy-3-(3-(4-phenylbut-1-ynyl)phenyl)propyl)acetamide was conducted following the method used in Example 19, except that the reaction was heated overnight. Purification by prep HPLC (method 004P) gave 3-amino-1-(3-(4-phenylbut-1-ynyl)phenyl)propan-1-ol as a brown solid. Yield (0.085 g, 33%): $^1$H NMR (400 MHz, DMSO-d$_6$) δ 7.21-7.34 (m, 9H), 4.67 (t, J=6.0 Hz, 1H), 2.88 (t, J=7.2 Hz, 2H), 2.68-2.74 (m, 4H), 1.68 (q, J=6.4 Hz, 2H), 0.86-0.92 (m, 1H).

Step 3: Reduction of 3-amino-1-(3-(4-phenylbutyl)phenyl)propan-1-ol (6) in 2-PrOH at RT for 14 h gave a yellow oil after work-up. The crude product was purified by flash chromatography (0-15% MeOH—NH$_3$ (9.5:0.5)-DCM gradient). This was then dissolved in 2-PrOH (10 mL) and stirred for an hour with HCl in Dioxane (1 mL, 4M). The mixture was concentrated to dryness under reduced pressure. Purification by flash chromatography (0-15% MeOH-DCM gradient) gave Example 63 as white semi-solid. Yield (0.13 g, 19%): $^1$H NMR (400 MHz, DMSO-d$_6$) δ 7.20-7.26 (m, 3H), 7.09-7.15 (m, 5H), 7.05 (d, J=7.2 Hz, 1H), 4.60 (t, J=7.2 Hz, 1H), 2.78-2.88 (m, 2H), 2.55 (m, 4H), 1.78-1.84 (m, 2H), 1.53-1.55 (m, 4H). $^{13}$C NMR (100 MHz, DMSO-d$_6$) δ 145.3, 142.2, 142.0, 128.3, 128.1, 126.9, 125.6, 125.5, 123.0, 69.7, 36.7, 36.4, 35.0, 34.9, 30.7. MS: 284 [M+1]$^+$.

Example 64

Preparation of 2-(3-(4-Methylpentyl)Phenoxy)Ethanamine

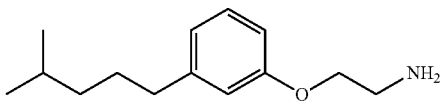

2-(3-(4-Methylpentyl)phenoxy)ethanamine was prepared following the method used in Example 9 except that the hydrogenation was conducted before the deprotection of the amine Step 1: Sonogashira reaction of bromide 19 with 4-methyl-1-pentyne gave 2,2,2-trifluoro-N-(2-(3-(4-methylpent-1-ynyl)phenoxy)ethyl) acetamide as a brown oil. Yield (0.955 g, 63%): $^1$H NMR (400 MHz, DMSO-d$_6$) δ 7.22-7.27 (m, 1H), 6.97 (d, J=7.6 Hz, 1H), 6.90-6.94 (m, 2H), 4.10 (t, J=5.6 Hz, 2H), 3.53-3.57 (m, 2H), 2.31 (d, J=6.4 Hz, 2H), 1.80-1.90 (m, 1H), 1.0 (d, J=6.8 Hz, 6H).

Step 2: The reduction of 2,2,2-trifluoro-N-(2-(3-(4-methylpent-1-ynyl)phenoxy)ethyl)acetamide afforded 2,2,2-trifluoro-N-(2-(3-(4-methylpentyl) phenoxy)ethyl)acetamide as yellow oil. Yield (0.815 g, 85%): $^1$H NMR (400 MHz, DMSO-d$_6$) δ 7.21-7.25 (m, 1H), 6.83 (d, J=7.6 Hz, 1H), 6.70-6.73 (m, 2H), 4.10 (t, J=5.0 Hz, 2H), 3.76-3.80 (m, 2H), 2.56 (t, J=7.8 Hz, 2H), 1.53-1.64 (m, 2H), 1.30-1.38 (m, 3H), 0.87 (d, J=6.4 Hz, 6H).

Step 3: Deprotection of 5-(3-(2-(2,2,2-trifluoroacetamido) ethoxy)phenyl)pentanamide gave Example 64 as yellow oil. Yield (0.415 g, 73%): $^1$H NMR (400 MHz, DMSO-d$_6$) δ 7.19-7.23 (m, 1H), 6.77-6.82 (m, 3H), 4.11 (t, J=5.2 Hz, 2H), 3.16 (t, J=5.2 Hz, 2H), 2.53 (t, J=7.6 Hz, 2H), 1.50-1.60 (m, 3H), 1.14-1.20 (m, 2H), 0.85 (d, J=6.8 Hz, 6H). $^{13}$C NMR (100 MHz, DMSO-d$_6$) δ 157.9, 144.1, 129.3, 121.2, 114.6, 111.8, 64.6, 38.5, 38.0, 35.4, 28.7, 27.3, 22.5. MS: 222 [M+1]$^+$.

Example 65

Preparation of 2-(3-(3-Phenylprop-1-Ynyl)Phenoxy)Ethanamine

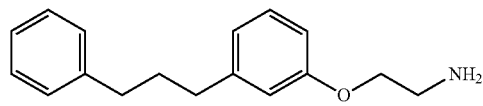 [SMILES: NCCOc1cccc(CCCc2ccccc2)c1]

2-(3-(3-Phenylpropyl)phenoxy)ethanamine was prepared following the method used in Example 9.

Step 1: Sonogashira reaction of bromide 19 with 3-phenyl-1-propyne gave 2,2,2-trifluoro-N-(2-(3-(3-phenylprop-1-ynyl)phenoxy)ethyl) acetamide as a brown oil. Yield (1.1 g, crude). The crude material was directly utilized for further deprotection reaction.

Step 2: Deprotection of 2,2,2-trifluoro-N-(2-(3-(3-phenyl-prop-1-ynyl)phenoxy)ethyl)acetamide gave 2-(3-(3-phenyl-prop-1-ynyl)phenoxy)ethanamine as brown oil. Yield (0.74 g, 94%). The crude material was directly utilized for further reduction reaction.

Step 3: The reduction of 2-(3-(3-phenylprop-1-ynyl)phenoxy)ethanamine afforded Example 65 as brown oil. Yield (0.078 g, 23%): $^1$H NMR (400 MHz, DMSO-d$_6$) δ 7.26-7.30 (m, 2H), 7.17-7.25 (m, 4H), 6.77-6.83 (m, 3H), 4.09 (t, J=5.2 Hz, 2H), 3.15 (t, J=5.2 Hz, 2H), 2.56-2.60 (m, 4H), 1.82-1.90 (m, 2H). $^{13}$C NMR (100 MHz, DMSO-d$_6$) δ 158.5, 144.1, 142.3, 129.8, 128.8, 128.7, 126.2, 121.7, 115.1, 112.4, 65.2, 39.1, 35.2, 33.0. MS: 256 [M+1]$^-$.

Example 66

Preparation of 4-(3-(2-Aminoethoxy)Phenyl)Butan-1-ol

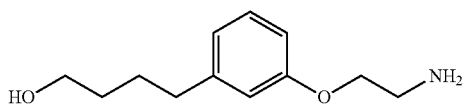 [SMILES: NCCOc1cccc(CCCCO)c1]

4-(3-(2-Aminoethoxy)phenyl)butan-1-ol was prepared following the method used in Example 64.

Step 1: Sonogashira reaction of bromide 19 with but-3-yn-1-ol gave 2,2,2-trifluoro-N-(2-(3-(4-hydroxybut-1-ynyl)phenoxy)ethyl)acetamide as a brown oil. Yield (0.9 g, 93%): $^1$H NMR (400 MHz, DMSO-d$_6$) δ 7.21-7.25 (m, 1H 7.06 (d, J=7.6 Hz, 1H), 6.94 (bs, 1H), 6.85 (dd, J=8.4, 2.4 Hz, 1H), 4.09 (t, J=5.0 Hz, 2H), 3.76-3.85 (m, 4H), 2.70 (t, J=6.4 Hz, 2H).

Step 2: The reduction of 2,2,2-trifluoro-N-(2-(3-(4-hydroxybut-1-ynyl) phenoxy)ethyl)acetamide afforded 2,2,2-trifluoro-N-(2-(3-(4-hydroxybutyl)phenoxy)ethyl)acetamide as yellow oil. Yield (0.42 g, 63%). MS: 304 [M–1].

Step 3: Deprotection of 2,2,2-trifluoro-N-(2-(3-(4-hydroxybutyl)phenoxy) ethyl)acetamide gave Example 66 as yellow oil. Yield (0.121 g, 44%): $^1$H NMR (400 MHz, DMSO-d$_6$) δ 7.14-7.18 (m, 1H), 6.71-6.76 (m, 3H), 3.88 (t, J=5.8 Hz, 2H), 3.39 (t, J=6.6 Hz, 2H), 2.85 (t, J=5.8 Hz, 2H), 2.53 (t, J=6.8 Hz, 2H), 1.53-1.60 (m, 2H), 1.38-1.45 (m, 2H). $^{13}$C NMR (100 MHz, DMSO-d$_6$) δ 159.1, 144.4, 129.6, 121.0, 115.0, 112.0, 70.4, 61.0, 41.4, 35.5, 32.6, 27.8. MS: 210 [M+1]$^+$.

Example 67

Preparation of 2-(3-Phenethylphenoxy)Ethanamine ol

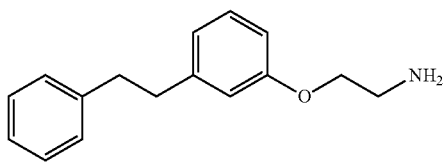 [SMILES: NCCOc1cccc(CCc2ccccc2)c1]

2-(3-Phenethylphenoxy)ethanamine was prepared following the method used in Example 64.

Step 1: Sonogashira reaction of bromide 19 with ethynylbenzene gave 2,2,2-trifluoro-N-(2-(3-(phenylethynyl)phenoxy)ethyl)acetamide as brown oil. Yield (0.755 g, 70%): $^1$H NMR (400 MHz, DMSO-d$_6$) δ 9.65 (bs, 1H), 7.53-7.57 (m, 2H), 7.41-7.47 (m, 3H), 7.34-7.36 (m, 1H), 7.15 (d, J=7.6 Hz, 1H), 7.12 (s, 1H), 7.0 (dd, J=7.6, 2.0 Hz, 1H), 4.14 (t, J=5.4 Hz, 2H), 3.55-3.60 (m, 2H).

Step 2: The reduction of 2,2,2-trifluoro-N-(2-(3-(phenylethynyl)phenoxy) ethyl)acetamide afforded 2,2,2-trifluoro-N-(2-(3-phenethylphenoxy)ethyl)acetamide as yellow oil. Yield (0.61 g, 80%): $^1$H NMR (400 MHz, DMSO-d$_6$) δ 9.66 (bs, 1H), 7.15-7.21 (m, 4H), 7.15-7.20 (m, 2H), 6.80-6.83 (m, 2H), 6.75 (d, J=7.6 Hz, 1H), 4.06 (t, J=5.6 Hz, 2H), 3.54-3.60 (m, 2H), 2.81-2.90 (m, 4H).

Step 3: Deprotection of 2,2,2-trifluoro-N-(2-(3-phenethylphenoxy)ethyl) acetamide gave Example 67 as off-white solid. Yield (0.205 g, 41%): $^1$H NMR (400 MHz, DMSO-d$_6$) δ 7.14-7.28 (m, 6H), 6.83-6.85 (m, 2H), 6.79 (d, J=8.4 Hz, 1H), 4.11 (t, J=5.0 Hz, 2H), 3.18 (t, J=5.0 Hz, 2H), 2.83-2.87 (m, 4H). $^{13}$C NMR (100 MHz, DMSO-d$_6$) δ 157.8, 143.2, 141.4, 129.3, 128.3, 128.2, 125.8, 121.3, 114.7, 112.1, 64.6, 38.2, 37.0, 36.9. MS: 242 [M+1]$^-$.

Example 68

Preparation of 2-(3-(4-Phenylbutyl)Phenoxy)Ethanamine

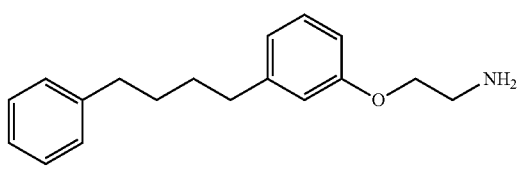 [SMILES: NCCOc1cccc(CCCCc2ccccc2)c1]

2-(3-(4-Phenylbutyl)phenoxy)ethanamine was prepared following the method used in Example 9.

Step 1: Sonogashira reaction of bromide 19 with but-3-ynyl-benzene gave 2,2,2-trifluoro-N-(2-(3-(4-phenylbut-1-ynyl)phenoxy)ethyl)acetamide as a clear oil. Yield (2.8 g, crude). The crude material was directly utilized for further deprotection reaction.

Step 2: Deprotection of 2,2,2-trifluoro-N-(2-(3-(4-phenylbut-1-ynyl)phenoxy)ethyl)acetamide gave 2-(3-(4-phenylbut-1-ynyl)phenoxy)ethanamine as yellow oil. Yield (0.700 g, 35%): $^1$H NMR (400 MHz, DMSO-d$_6$) δ 7.29-7.33 (m, 4H), 7.20-7.26 (m, 2H), 6.88-6.93 (m, 2H), 6.84-6.87 (m, 1H), 3.89 (t, J=5.6, 2H), 2.80-2.88 (m, 4H), 2.69 (t, J=7.2, 2H). $^{13}$C NMR (100 MHz, DMSO-d$_6$) δ 158.5, 140.5, 129.7, 128.6, 128.2, 126.2, 124.2, 123.5, 116.6, 114.9, 90.0, 81.1, 70.3, 40.9, 34.3, 20.9. MS: 266 [M+1]$^+$.

Step 8: The reduction of 2-(3-(4-Phenylbut-1-ynyl)phenoxy)ethanamine afforded Example 68 as yellow oil. Yield (0.178 g, 89%): $^1$H NMR (400 MHz, DMSO-d$_6$) δ 7.12-7.27 (m, 6H), 6.76-6.80 (m, 3H), 4.09 (t, J=5.0 Hz, 2H), 3.15 (t, J=5.0 Hz, 2H), 2.49-2.57 (m, 4H), 1.53-1.58 (m, 4H). $^{13}$C NMR (100 MHz, DMSO-d$_6$) δ 157.9, 143.9, 142.1, 129.3, 128.3, 128.2, 125.6, 121.2, 114.6, 111.8, 64.5, 38.5, 34.9, 30.6, 30.5. MS: 270 [M+1]$^+$.

Example 69

Preparation of 2-(3-(2-Methoxyphenethyl)Phenoxy)Ethanamine

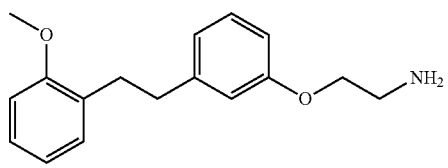 [SMILES: COc1ccccc1CCc1cccc(OCCN)c1]

2-(3-(2-Methoxyphenethyl)phenoxy)ethanamine amine was prepared following the method used in Example 64.

Step 1: Sonogashira reaction of bromide 19 with 2-ethynylanisole gave 2,2,2-trifluoro-N-(2-(3-((2-methoxyphenyl)

ethynyl)phenoxy)ethyl)acetamide as a brown oil. Yield (0.4 g, 62%): $^1$H NMR (400 MHz, DMSO-d$_6$) δ 7.48 (dd, J=7.6, 1.6 Hz, 1H), 7.37-7.42 (m, 1H), 7.31-7.36 (m, 1H), 7.09-7.12 (m, 2H), 7.08 (s, 1H), 6.95-7.01 (m, 2H), 4.13 (t, J=5.6 Hz, 2H), 3.86 (s, 3H), 3.55-3.60 (m, 2H).

Step 2: The reduction of 2,2,2-trifluoro-N-(2-(3-((2-methoxyphenyl)ethynyl)phenoxy)ethyl)acetamide afforded 2,2,2-trifluoro-N-(2-(3-(2-methoxyphenethyl) phenoxy)ethyl)acetamide as yellow oil. Yield (0.253 g, 63%): $^1$H NMR (400 MHz, DMSO-d$_6$) δ 7.15-7.20 (m, 2H), 7.12 (d, J=7.2 Hz, 1H), 6.95 (d, J=8.4 Hz, 1H), 6.73-6.86 (m, 4H), 4.06 (t, J=5.6 Hz, 2H), 3.79 (s, 3H), 3.56 (t, J=5.4 Hz, 2H), 2.75-2.83 (m, 4H).

Step 3: Deprotection of 2,2,2-trifluoro-N-(2-(3-(2-methoxyphenethyl) phenoxy)ethyl)acetamide gave Example 69 as yellow oil. Yield (0.122 g, 66%): $^1$H NMR (400 MHz, DMSO-d$_6$) δ 7.16-7.20 (m, 2H), 7.12 (d, J=7.2 Hz, 1H), 6.95 (d, J=8.0 Hz, 1H), 6.82-6.86 (m, 1H), 6.74-6.79 (m, 3H), 3.92 (t, J=5.6 Hz, 2H), 3.79 (s, 3H), 2.92 (t, J=5.6 Hz, 2H), 2.76-2.84 (m, 4H). $^{13}$C NMR (100 MHz, DMSO-d$_6$) δ 158.8, 157.5, 144.0, 130.0, 129.7, 129.6, 127.7, 121.3, 120.6, 115.0, 112.3, 111.1, 68.1, 55.8, 40.6, 35.9, 32.0. MS: 272 [M+1]$^+$.

Example 70

Preparation of (S)-4-(3-(3-Amino-1-Hydroxypropyl) Phenethyl)Heptan-4-ol

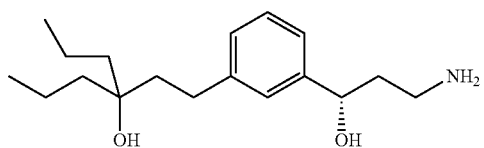 [SMILES: CCCC(O)(CCC)CCc1cccc([C@@H](O)CCN)c1]

(S)-4-(3-(3-Amino-1-hydroxypropyl)phenethyl)heptan-4-ol was prepared following the method shown in Scheme 16.

SCHEME 16

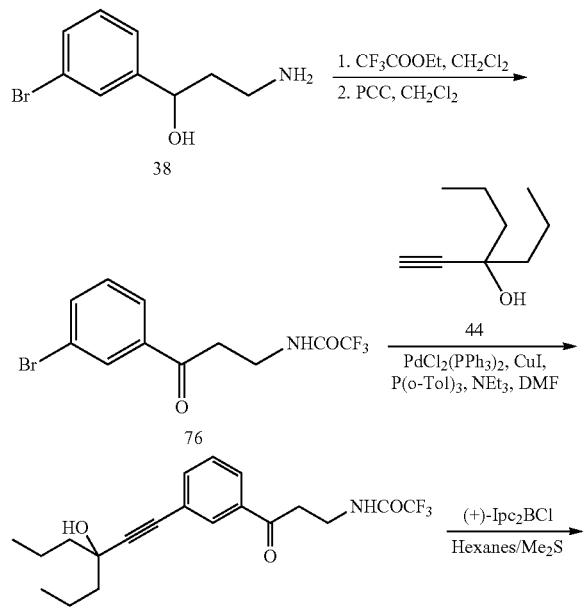

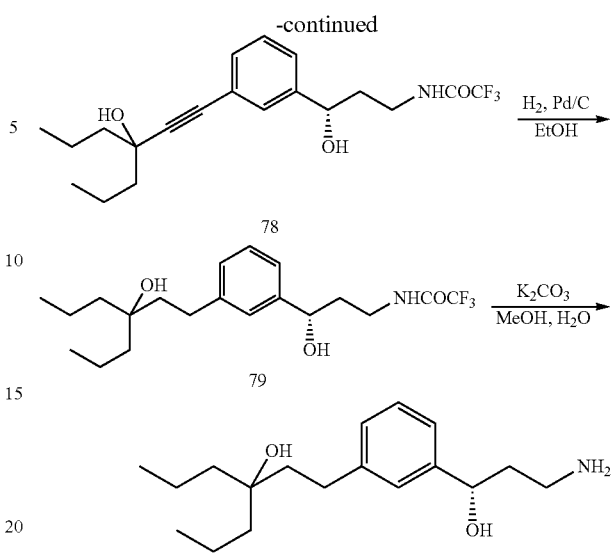

Step 1: To a solution of hydroxyamine 38 (37.61 g, 163 4 mmol) in CH$_2$Cl$_2$ (250 mL) was added ethyl trifluoroacetate (28 mL, 209.6 mmol) and the reaction mixture was stirred at room temperature for 1 h. After that Celite (70 g) was added followed by pyridinium chlorochromate (75.65 g, 350 9 mmol) and CH$_2$Cl$_2$ (200 mL). The reaction mixture was stirred at room temperature for 18 hrs, the solvent was removed under reduced pressure to give a brown solid which was transferred in a glass filter and washed extensively with MTBE:Hexanes (1:1). The filtrate was concentrated under reduced pressure and the residue was crystallized from hexanes:EtOAc (95:5) to give ketone 76 as a white solid. Yield (26.52 g, 50%). $^1$H NMR (400 MHz, DMSO-d$_6$) δ 9.41 (br, t, 1H), 8.06 (t, J=1.8 Hz, 1H), 7.91-7.95 (m, 1H), 7.80-7.85 (m, 1H), 7.48 (t, J=8.0 Hz, 1H), 3.50 (q, J=6.5 Hz, 2H), 3.30 (t, J=6.5 Hz, 2H).

Step 2: Coupling of 4-ethynylheptan-4-ol (44) with bromide 76 was conducted following the method used to prepare Example 2 except that the reaction was stirred at +80° C. for 3 hrs. Purification by flash chromatography (10% to 70% EtOAc-hexanes gradient) gave alkyne 77 as a dark yellow oil. Yield (3.15 g, quant.). $^1$H NMR (400 MHz, DMSO-d$_6$) δ 9.40 (br. t, 1H), 7.84-7.92 (m, 2H), 7.58-7.63 (m, 1H), 7.50 (t, J=7.6 Hz, 1H), 5.19 (s, 1H), 3.51 (q, J=5.7 Hz, 2H), 3.30 (t, J=6.7 Hz, 2H), 1.40-1.64 (m, 8H), 0.90 (t, J=7.2 Hz, 6H).

Step 3:Preparation of (+)-diisopinocampheylchloroborane ((+)-Ipc$_2$B—Cl) solution.: To an ice-cold solution of (+)-α-pinene (26.38 g, 193.6 mmol) in hexanes (18 mL) under argon was added monochloroborane-methyl sulfide complex (9.5 mL, 91.12 mmol) over 5 min The mixture was stirred for 5 min then allowed to warm to room temperature. The reaction mixture was heated at 30° C. for 3 h. The resulting solution was approximately 1.67 M.

To a 0° C. solution of ketone 77 (14.34 g, 37.4 mmol) and diisopropyl ethylamine (6.5 mL, 37.31 mmol) in anhydrous THF (60 mL) under argon was added a solution of (+)-Ipc$_2$B—Cl (55 mL of the 1.67 M solution prepared above, 91.12 mmol). The reaction mixture was stirred at 0° C. over 5 min, and then at room temperature for 3.5 hrs. The reaction mixture was cooled again to 0° C. and a saturated aqueous NaHCO$_3$ (80 mL) was carefully added. The reaction mixture was stirred at 0° C. for 1 h and then placed to −20° C. overnight. The layers were separated, aqueous layer was extracted with MTBE, combined organic layers were washed with NaHCO$_3$, then brine, and then concentrated under reduced pressure. Purification by flash chromatography (10% to 100% EtOAc-hexanes gradient) gave (S)-alkyne 78 as a yellowish oil. Yield (10.55 g, 70%). $^1$H NMR (400 MHz, DMSO-d$_6$) δ 9.32 (br, s, 1H), 7.30-7.33 (m, 1H), 7.26-7.29 (m, 2H), 7.19-7.23 (m, 1H), 5.36 (br, s, 1H), 5.12 (s, 1H), 4.56 (dd, J=4.7, 7.6 Hz, 1H), 3.15-3.27 (m, 2H), 1.70-1.82 (m, 2H), 1.40-1.61 (m, 8H), 0.91 (t, J=7.2 Hz, 6H).

Step 4. (S)-Alkyne 78 was hydrogenated by the method used in Example 13 except that the reaction was run at room temperature for 2 hrs. Purification by flash chromatography (20% to 80% EtOAc-hexanes gradient) gave alkane 79 as a yellow oil. (Yield 5.13 g, 98%). $^1$H NMR (400 MHz, DMSO-d$_6$) δ 9.32 (br. s, 1H), 7.18 (t, J=7.4 Hz, 1H), 7.06-7.12 (m, 2H), 6.99-7.03 (m, 1H), 5.25 (d, J=4.3 Hz, 1H), 4.52 (q, J=4.7 Hz, 1H), 3.95 (s, 1H), 3.23 (q, J=7.0 Hz, 2H), 2.48-2.53 (m, 2H), 1.72-1.80 (m, 2H), 1.50-1.56 (m, 2H), 1.20-1.36 (m, 8H), 0.84 (t, J=6.9 Hz, 6H).

Step 5. Deprotection of trifluoroacetamide 79 was conducted following the method used to prepare Example 9 except that 3 equivalents of K$_2$CO$_3$ were used and the reaction was stirred at +40° C. for 4 hrs. Purification by flash chromatography (50% to 100% of 20% 7M NH$_3$ in MeOH/EtOAc-hexane gradient) gave Example 70 as a light yellow oil. Yield (3.18 g, 82%). $^1$H NMR (400 MHz, DMSO-d$_6$) δ 7.16 (t, J=7.6 Hz, 1H), 7.04-7.12 (m, 2H), 6.96-7.00 (m, 1H), 4.59 (dd, J=5.3, 7.4 Hz, 1H), 3.95 (s, 1H), 2.54-2.66 (m, 2H), 2.48-2.52 (m, 2H), 1.50-1.64 (m, 4H), 1.20-1.35 (m, 8H), 0.84 (t, J=7.0 Hz, 6H). Chiral HPLC 95.3% (AUC), t$_R$=22.2 min Example 71

Preparation of (R)-4-(3-(3-Amino-1-Hydroxypropyl) Phenethyl)Heptan-4-ol

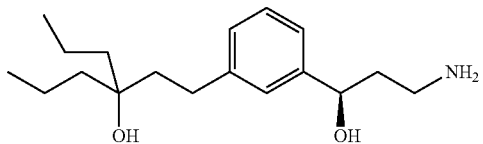 [SMILES: CCCC(O)(CCC)CCc1cccc([C@H](O)CCN)c1]

(R)-4-(3-(3-Amino-1-hydroxypropyl)phenethyl)heptan-4-ol was prepared following the method used in Example 70.

Step 1. Reduction of ketone 77 with (−)-Ipc$_2$B—Cl gave (R)-2,2,2-trifluoro-N-(3-hydroxy-3-(3-(3-hydroxy-3-propylhex-1-ynyl)phenyl)propyl)acetamide as a colorless oil. Yield (9.53 g, 69%); $^1$H NMR (400 MHz, DMSO-d$_6$) δ 9.32 (br. s, 1H), 7.30-7.33 (m, 1H), 7.26-7.29 (m, 2H), 7.19-7.23 (m, 1H), 5.36 (br. s, 1H), 5.12 (s, 1H), 4.56 (dd, J=4.7, 7.6 Hz, 1H), 3.15-3.27 (m, 2H), 1.70-1.82 (m, 2H), 1.40-1.61 (m, 8H), 0.91 (t, J=7.2 Hz, 6H).

Step 2. Hydrogenation of (R)-2,2,2-trifluoro-N-(3-hydroxy-3-(3-(3-hydroxy-3-propylhex-1-ynyl)phenyl)propyl)acetamide gave (R)-2,2,2-trifluoro-N-(3-hydroxy-3-(3-(3-hydroxy-3-propylhexyl)phenyl)propyl)acetamide as a light-yellow oil. Yield (4.81 g, 94%). $^1$H NMR (400 MHz, DMSO-d$_6$) δ 9.32 (br. s, 1H), 7.18 (t, J=7.4 Hz, 1H), 7.06-7.12 (m, 2H), 6.99-7.03 (m, 1H), 5.25 (d, J=4.3 Hz, 1H), 4.52 (q, J=4.7 Hz, 1H), 3.95 (s, 1H), 3.23 (q, J=7.0 Hz, 2H), 2.48-2.53 (m, 2H), 1.72-1.80 (m, 2H), 1.50-1.56 (m, 2H), 1.20-1.36 (m, 8H), 0.84 (t, J=6.9 Hz, 6H).

Step 3. Deprotection of (R)-2,2,2-trifluoro-N-(3-hydroxy-3-(3-(3-hydroxy-3-propylhexyl)phenyl)propyl)acetamide gave Example 71 as yellow oil. Yield (2.87 g, 79%). $^1$H NMR (400 MHz, DMSO-d$_6$) δ 7.16 (t, J=7.6 Hz, 1H), 7.04-7.12 (m, 2H), 6.96-7.00 (m, 1H), 4.59 (dd, J=5.3, 7.4 Hz, 1H), 3.95 (s, 1H), 2.54-2.66 (m, 2H), 2.44-2.66 (m, 2H), 1.50-1.64 (m, 4H), 1.20-1.35 (m, 8H), 0.84 (t, J=7.0 Hz, 6H). RP-HPLC (Method 2) t$_R$=6.21 min, 96.5% (AUC); ESI MS m/z 294.51 [M+H$^+$]$^+$. Chiral HPLC 95.1% (AUC), t$_R$=16.6 min.

Example 72

Preparation of 3-Amino-1-(3-(3-Methoxypropyl) Phenyl)Propan-1-ol

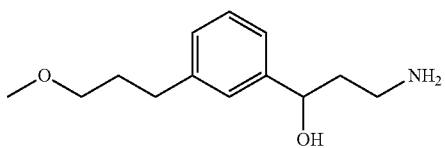 [SMILES: COCCCc1cccc(C(O)CCN)c1]

3-Amino-1-(3-(3-methoxypropyl)phenyl)propan-1-ol was prepared following the method used in Example 19.

Step 1: Sonogashira reaction of 43 with methyl propargyl ether gave 2,2,2-trifluoro-N-(3-hydroxy-3-(3-(3-methoxyprop-1-ynyl)phenyl)propyl)acetamide as brown oil. Yield (0.401 g, 82%): $^1$H NMR (400 MHz, CDCl$_3$) δ 7.51 (s, 1H), 7.38-7.44 (m, 1H), 7.31-7.35 (m, 2H), 4.84-4.88 (m, 1H), 4.32 (s, 2H), 3.66-3.69 (m, 1H), 3.44 (s, 3H), 3.39-3.42 (m, 1H), 2.37 (bs, 1H), 1.94-1.99 (m, 2H).

Step 2: Reduction of 2,2,2-trifluoro-N-(3-hydroxy-3-(3-(3-methoxyprop-1-ynyl)phenyl)propyl)acetamide yielded 2,2,2-trifluoro-N-(3-hydroxy-3-(3-(3-methoxypropyl)phenyl)propyl)acetamide as yellow oil. Yield (0.298 g, 73%). $^1$H NMR (400 MHz, CDCl$_3$) δ 7.31 (s, 1H), 7.13-7.24 (m, 3H), 4.84-4.88 (m, 1H), 3.66-3.70 (m, 1H), 3.49 (m, 1H), 3.38 (t, J=6.4 Hz, 2H), 3.34 (s, 3H), 2.69 (t, J=7.6 Hz, 2H), 1.90-1.95 (m, 2H), 1.86-1.89 (m, 2H).

Step 3: Deprotection of 2,2,2-trifluoro-N-(3-hydroxy-3-(3-(3-methoxy propyl)phenyl)propyl)acetamide gave a yellow gel which upon purification by flash chromatography (0-10% MeOH—NH$_3$ (9.5:0.5)-DCM gradient) yielded Example 72 as yellow semi-solid. Yield (0.597 g, 82%): $^1$H NMR (400 MHz, DMSO-d$_6$) δ 7.22 (t, J=7.6 Hz, 1H), 7.13 (s, 1H), 7.11 (d, J=7.6 Hz, 1H), 7.04 (d, J=7.6 Hz, 1H), 4.61 (t, J=6.4 Hz, 1H), 3.29 (t, J=6.4 Hz, 2H), 3.21 (s, 3H), 2.72-2.77 (m, 2H), 2.58 (t, J=7.2 Hz, 2H), 1.66-1.79 (m, 4H). $^{13}$C NMR (100 MHz, DMSO-d$_6$) δ 146.1, 142.0, 128.5, 127.3, 126.0, 123.5, 71.6, 70.8, 58.3, 38.7, 37.7, 32.2, 31.4. MS: 224 [M+1].

Example 73

Preparation of 3-Amino-1-(3-Hexylphenyl)Propan-1-ol

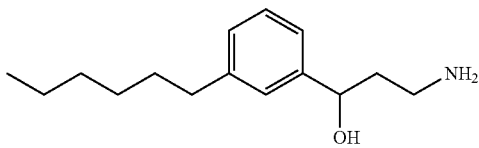 [SMILES: CCCCCCc1cccc(C(O)CCN)c1]

3-Amino-1-(3-hexylphenyl)propan-1-ol was prepared following the method used in Example 19.

Step 1: Sonogashira reaction of 43 with 1-hexyne gave 2,2,2-trifluoro-N-(3-(3-(hex-1-ynyl)phenyl)-3-hydroxypropyl)acetamide as yellow oil. Yield (1.53 g, 76%): $^1$H NMR (400 MHz, CDCl$_3$) δ 7.38 (s, 1H), 7.25-7.34 (m, 3H), 4.88 (m, 1H), 3.65-3.73 (m, 1H), 3.38-3.42 (m, 1H), 2.40 (t, J=7.2 Hz, 2H), 2.25 (d, J=2.0, 1H) 1.93-1.99 (m, 2H), 1.45-1.61 (m, 4H), 0.94 (t, J=7.2 Hz, 3H).

Step 2: A solution of 2,2,2-trifluoro-N-(3-(3-(hex-1-ynyl)phenyl)-3-hydroxypropyl)acetamide in EtOAc (20 mL) was degassed and purged with nitrogen. To this was added Pd on C (0.2 g, 10%). The flask was evacuated and filled with hydrogen. After repeating this procedure thrice, the reaction mixture was stirred under H$_2$ balloon for 14 h following which this mixture was filtered through a Celite bed and concentrated under reduced pressure to obtain 2,2,2-trifluoro-N-(3-(3-hexylphenyl)-3-hydroxypropyl)acetamide as yellow oil. Yield (0.93 g, 75%): $^1$H NMR (400 MHz, CDCl$_3$) δ 7.40 (bs, 1H), 7.28-7.31 (m, 2H), 7.12-7.16 (m, 2H), 4.86-4.88 (m, 1H), 3.66-3.71 (m, 1H), 3.40-3.43 (m, 1H), 2.58 (t, J=7.6 Hz, 2H), 1.96-1.99 (m, 2H), 1.56-1.60 (m. 4H), 1.30-1.35 (m, 4H), 0.88 (t, J=6.8 Hz, 3H).

Step 3: A mixture of 2,2,2-trifluoro-N-(3-(3-hexylphenyl)-3-hydroxypropyl)acetamide, potassium carbonate (1.55 g, 11.2 mmol) and water (4 mL) in 2-PrOH (20 mL) was heated under reflux for overnight. The reaction mass was concentrated to dryness under reduced pressure to yield a yellow oil. This crude product was dissolved in methanol (5 mL) and to it was added HCl in Dioxane (1 mL, 4M). The mixture stirred for about 30 min after which it was concentrated to dryness under reduced pressure. Purification by flash chromatography (0-10% MeOH-DCM gradient) gave Example 73 hydrochloride as pale yellow semi-solid. Yield (0.174 g, 21%): $^1$H NMR (400 MHz, DMSO-d$_6$) δ 7.67 (bs, 3H), 7.23 (t, J=7.2 Hz, 1H), 7.11 (m, 2H), 7.07 (d, J=7.2 Hz, 1H), 4.62-4.65 (m, 1H), 2.78-2.87 (m, 2H), 2.49 (m, 2H), 1.80-1.84 (m, 2H), 1.54 (m, 2H), 1.27 (m, 6H), 0.85 (t, J=6.8, 3H). $^{13}$C NMR (100 MHz, DMSO-d$_6$) δ 145.3, 142.2, 128.1, 126.9, 125.5, 122.9, 69.7, 36.7, 36.4, 35.3, 31.1, 31.0, 28.4, 22.1. MS: 236 [M+1]$^+$.

Example 74

Preparation of 2-(3-(2-Cyclopropylethyl)Phenoxy)Ethanamine

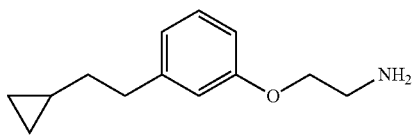 [SMILES: NCCOc1cccc(CCC2CC2)c1]

2-(3-(2-Cyclopropylethyl)phenoxy)ethanamine was prepared following the method used in Example 64.

Step 1: Sonogashira reaction of bromide 19 with cyclopropyl acetylene gave N-(2-(3-(2-cyclopropylethynyl)phenoxy)ethyl)-2,2,2-trifluoroacetamide as a clear oil. Yield (2.0 g, 71%): The crude material was directly hydrogenated.

Step 2: The reduction of N-(2-(3-(cyclopropylethynyl)phenoxy)ethyl)-2,2,2-trifluoroacetamide gave N-(2-(3-(2-cyclopropylethyl)phenoxy)ethyl)-2,2,2-trifluoroacetamide as yellow oil. Yield (0.205 g, 45%): $^1$H NMR (400 MHz, DMSO-d$_6$) δ 9.70 (bs, 1H), 7.14-7.19 (m, 1H), 6.72-6.80 (m, 3H), 4.06 (t, J=5.6 Hz, 2H), 3.53-3.58 (m, 2H), 2.62 (t, J=7.8 Hz, 2H), 1.42-1.48 (m, 2H), 0.62-0.70 (m, 1H), 0.37-0.40 (m, 2H), 0.02-0.10 (m, 2H). MS: 300 [M−1].

Step 3: Deprotection of N-(2-(3-(2-cyclopropylethyl)phenoxy)ethyl)-2,2,2-trifluoroacetamide gave Example 74 as green oil. Yield (0.121 g, 87%): $^1$H NMR (400 MHz, DMSO-d$_6$) δ 7.13-7.19 (m, 1H), 6.71-6.77 (m, 3H), 3.88 (t, J=5.8 Hz, 2H), 2.85 (t, J=5.8 Hz, 2H), 2.61 (t, J=7.8 Hz, 2H), 1.43-1.50 (m, 2H), 0.64-0.72 (m, 1H), 0.47-0.50 (m, 2H), 0.02-0.06 (m, 2H). $^{13}$C NMR (100 MHz, DMSO-d$_6$) δ 158.6, 143.7, 129.1, 120.5, 114.5, 111.6, 69.8, 40.9, 36.0, 35.4, 10.6, 4.4. MS: 206 [M+1]$^+$.

Example 75

Preparation of 5-(3-(2-Aminoethoxy)Phenylpentan-1-ol

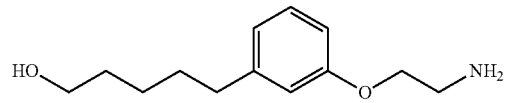 [SMILES: NCCOc1cccc(CCCCCO)c1]

5-(3-(2-Aminoethoxy)phenyl)pentan-1-ol was prepared following the method used in Example 64.

Step 1: A mixture of bromide 19 (2.5 g, 8 mmol), pentyn-1-ol (1.34 g, 16 mmol) in triethylamine (6 mL, 60 mmol) and DMF (18 mL) was purged with nitrogen for 10 minutes. This was followed by the addition of PdCl$_2$(PPh$_3$)$_2$ (0.28 g, 0.4 mmol), P(o-Tol)$_3$ (0.122 g, 0.4 mmol) and CuI (0.076 g, 0.4 mmol) and the flask was purged once again with nitrogen and the resulting mixture was heated at 90° C. overnight. This was then poured into water, extracted with ethyl acetate. The organic layer was washed with water, dried over anhydrous Na$_2$SO$_4$, filtered and concentrated under reduced pressure. Purification by flash chromatography (0 to 30% EtOAc-hexanes gradient) gave 2,2,2-trifluoro-N-(2-(3-(5-hydroxypent-1-ynyl)phenoxy)ethyl)acetamide as yellow oil. Yield (1.61 g, 63%): $^1$H NMR (400 MHz, CDCl$_3$) δ 7.18-7.24 (m, 1H), 7.03 (d, J=7.6 Hz, 1H), 6.91 (dd, J=0.8, 1.2 Hz, 1H), 6.83 (dd, J=5.6, 2.0 Hz, 1H), 6.76 (bs, 1H), 4.06-4.10 (m, 2H), 3.76-3.84 (m, 4H), 2.53 (t, J=7.2 Hz, 2H), 1.82-1.90 (m, 2H).

Step 2: Reduction of 2,2,2-trifluoro-N-(2-(3-(5-hydroxypent-1-ynyl)phenoxy)ethyl)acetamide afforded 2,2,2-trifluoro-N-(2-(3-(5-hydroxypentyl) phenoxy)ethyl)acetamide as yellow oil. Yield (0.513 g, 72%): $^1$H NMR (400 MHz, DMSO-d$_6$) δ 7.15-7.20 (m, 1H), 6.72-6.78 (m, 3H), 4.34 (t, J=5.0 Hz, 2H), 4.06 (t, J=5.6 Hz, 2H), 3.52-3.59 (m, 2H), 3.37 (t, J=6.4 Hz, 2H), 1.51-1.60 (m, 2H), 1.40-1.47 (m, 2H), 1.24-1.32 (m, 2H). MS: 318 [M−1].

Step 3: Deprotection of 2,2,2-trifluoro-N-(2-(3-(5-hydroxypentyl) phenoxy)ethyl)acetamide gave Example 75 as yellow oil. Yield (0.175 g, 49%): $^1$H NMR (400 MHz, DMSO-d$_6$) δ 7.14-7.19 (m, 1H), 6.71-6.76 (m, 3H), 3.94 (t, J=5.6 Hz, 2H), 3.34 (t, J=6.6 Hz, 2H), 2.90 (t, J=5.6 Hz, 2H), 2.50 (t, J=8.0 Hz, 2H), 1.48-1.56 (m, 2H), 1.36-1.46 (m, 2H), 1.22-1.30 (m, 2H). $^{13}$C NMR (100 MHz, DMSO-d$_6$) δ 158.5, 144.0, 129.2, 120.7, 114.6, 111.6, 68.4, 60.7, 40.3, 35.3, 32.4, 30.8, 25.2. MS: 224 [M+1]$^−$.

Example 76

Preparation of 3-(3-(2-Cyclopropylethyl)Phenyl-Propan-1-Amine

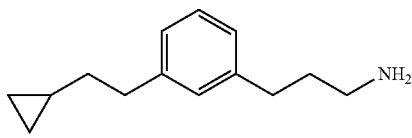

3-(3-(2-Cyclopropylethyl)phenyl-propan-1-amine was prepared following the method used for Examples 13 and 22 except that the hydrogenation was conducted before the deprotection of the amine.

Step 1: To a degassed solution of tert-butyl 3-(3-bromophenyl)propylcarbamate (57) (1.0 g, 3.1 mmol) and cyclopropyl acetylene (2.9 mL, 3.4 mmol, 70% soln in toluene) in diisopropylamine (4 mL) was added PdCl$_2$(PPh$_3$)$_2$ (0.120 g, 0.17 mmol), tri-o-tolylphosphine (0.048 g, 0.16 mmol) and CuI (0.026 g, 0.16 mmol). The resulting mixture was degassed and stirred under nitrogen at 90° C. for overnight. The mixture was cooled to room temperature and concentrated under reduced pressure. The residue was partitioned between water and ethyl acetate. The organic layer was dried over anhydrous Na$_2$SO$_4$, filtered, and concentrated under reduced pressure. Purification by flash chromatography (10-40% ethyl acetate-hexane gradient) gave tert-butyl 3-(3-(cyclopropylethynyl)phenyl)propylcarbamate. Yield (0.756 g, 79%). This alkyne was used for deprotection without further purification.

Step 2: Reduction of tert-butyl 3-(3-(cyclopropylethynyl)phenyl)propyl carbamate following the method used in Example 22 gave tert-butyl 3-(3-(2-cyclopropylethyl)phenyl)propylcarbamate as yellow oil. Yield (0.404 g, 98%): MS: 304 [M+1]$^+$.

Step 3: BOC deprotection of tert-butyl 3-(3-(2-cyclopropylethyl)phenyl) propylcarbamate following the method used in Example 13 gave Example 76 as yellow oil. Yield (0.19 g, 90%): $^1$H NMR (400 MHz, DMSO-d$_6$) δ 7.17-7.21 (m, 1H), 6.99-7.04 (m, 3H), 2.72 (t, J=7.2 Hz, 2H), 2.58-2.66 (m, 4H), 1.75-1.83 (m, 2H), 1.42-1.48 (m, 2H), 0.64-0.71 (m, 1H), 0.36-0.41 (m, 2H), 0.01-0.06 (m, 2H). $^{13}$C NMR (100 MHz, DMSO-d$_6$): 142.7, 141.1, 128.8, 128.7, 126.5, 126.0, 38.8, 36.6, 35.8, 32.3, 29.3, 11.1, 4.9. MS: 204 [M+1]$^+$.

Example 77

Preparation of 2-(3-Hexylphenoxy)Ethanamine

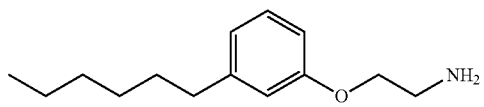 [SMILES: CCCCCCc1cccc(OCCN)c1]

2-(3-Hexylphenoxy)ethanamine was prepared following the method used in Example 9.

Step 1: Sonogashira reaction of bromide 19 with 1-hexyne gave 2,2,2-trifluoro-N-(2-(3-(hex-1-ynyl)phenoxy)ethyl)acetamide as a clear oil. Yield (1.8 g, 72%): $^1$H NMR (400 MHz, CDCl$_3$) δ 7.19-7.23 (m, 1H), 7.05 (d, J=7.6 Hz, 1H), 6.84 (s, 1H), 6.80 (dd, J=8.0, 2.4 Hz, 1H), 4.10 (t, J=5.2 Hz, 2H), 3.77-3.80 (m, 2H), 2.40 (t, J=7.2 Hz, 2H), 1.53-1.61 (m, 2H), 1.43-1.50 (m, 2H), 0.95 (t, J=7.2 Hz, 3H).

Step 2: Deprotection of 2,2,2-trifluoro-N-(2-(3-(hex-1-ynyl)phenoxy)-ethyl)acetamide gave 2-(3-(hex-1-ynyl)phenoxy)ethanamine as yellow oil. Yield (0.620 g, 90%): $^1$H NMR (400 MHz, DMSO-d$_6$) δ 7.20-7.25 (m, 1H), 6.87-6.93 (m, 3H), 3.91 (t, J=5.2 Hz, 2H), 2.79-2.87 (m, 2H), 2.38 (t, J=6.4 Hz, 2H), 1.42-1.53 (m, 2H), 1.30-1.40 (m, 2H), 0.88 (t, J=7.2 Hz, 3H). $^{13}$C NMR (100 MHz, DMSO-d$_6$) δ 158.9, 130.1, 124.8, 124.1, 117.2, 115.3, 90.9, 80.9, 70.3, 41.1, 30.7, 21.9, 18.7, 13.9. ESI MS m/z 218 [M+1]$^+$.

Step 3: The reduction of 2-(3-hex-1-ynyl-phenoxy)-ethanamine afforded Example 77 as yellow oil. Yield (0.154 g, 57%): $^1$H NMR (400 MHz, DMSO-d$_6$) δ 7.13-7.18 (m, 1H), 6.70-6.75 (m, 3H), 3.91 (t, J=5.6 Hz, 2H), 2.86 (t, J=5.6 Hz, 2H), 1.20-1.28 (m, 6H), 1.52 (t, J=7 Hz, 2H), 0.82 (t, J=6.6 Hz, 3H). $^{13}$C NMR (100 MHz, DMSO-d$_6$) δ 159.1, 144.4, 129.6, 121.0, 114.9, 112.0, 69.9, 35.7, 31.6, 31.3, 28.8, 22.5, 14.6. MS: 222 [M+1]$^+$.

Example 78

Preparation of 2-(3-(3-Methoxypropylphenoxy)Ethanamine

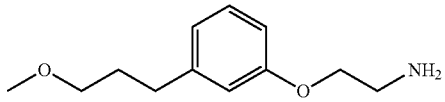

2-(3-(3-Methoxypropyl)phenoxy)ethanamine was prepared following the method used in Example 64.

Step 1: Sonogashira reaction of bromide 19 with 3-methoxy-propyne gave 2,2,2-trifluoro-N-(2-(3-(3-methoxyprop-1-ynyl)phenoxy)ethyl)acetamide as a clear oil. Yield (0.51 g, 21%): $^1$H NMR (400 MHz, CDCl$_3$) δ 7.22-7.27 (m, 1H), 7.10 (d, J=7.6 Hz, 1H), 6.98 (s, 1H), 6.88 (dd, J=6.8, 1.6 Hz, 1H), 6.71 (bs, 1H), 4.32 (s, 2H), 4.10 (t, J=5.2 Hz, 2H), 3.77-3.82 (m, 2H), 3.45 (s, 3H).

Step 2: The reduction of 2,2,2-trifluoro-N-(2-(3-(3-methoxyprop-1-ynyl)phenoxy)ethyl)acetamide afforded 2,2,2-trifluoro-N-(2-(3-(3-methoxypropyl)phenoxy)ethyl)acetamide as yellow oil. Yield (0.355 g, 76%). $^1$H NMR (400 MHz, DMSO-d$_6$) δ 7.16-7.22 (m, 1H), 6.74-6.79 (m, 3H), 4.07 (t, J=5.6 Hz, 2H), 3.54-3.58 (m, 2H), 3.33 (s, 3H), 3.28 (t, J=6.2 Hz, 2H), 2.57 (t, J=7.8 Hz, 2H), 1.73-1.81 (m, 2H).

Step 3: Deprotection of 2,2,2-trifluoro-N-(2-(3-(3-methoxypropyl)phenoxy)ethyl)acetamide gave Example 78 as yellow oil. Yield (0.125 g, 52%): $^1$H NMR (400 MHz, DMSO-d$_6$) δ 8.03 (bs, 2H), 7.20-7.24 (m, 1H), 6.78-6.83 (m, 3H), 4.14 (t, J=5.6 Hz, 2H), 2.94 (t, J=5.6 Hz, 2H), 2.53 (t, J=7.2 Hz, 2H), 2.05 (t, J=7.2 Hz, 2H), 1.44-1.54 (m, 4H). $^{13}$C NMR (100 MHz, DMSO-d$_6$) δ 158.4, 144.0, 129.8, 121.7, 115.1, 112.4, 71.6, 64.6, 58.3, 38.8, 32.2, 31.2. MS: 210 [M+1]$^+$.

Example 79

Preparation of 3-Amino-1-(3-(3-Hydroxypropyl)Phenyl)Propan-1-ol

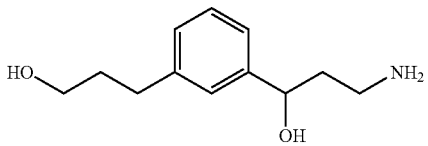 [SMILES: NCCC(O)c1cccc(CCCO)c1]

3-Amino-1-(3-(3-hydroxypropyl)phenyl)propan-1-ol was prepared following the method used in Example 17 except that the hydrogenation was conducted before the deprotection of the amine Step 1: Sonogashira reaction of bromide 39 with propargyl alcohol gave tert-butyl 3-hydroxy-3-(3-(3-hydroxyprop-1-ynyl)phenyl)propylcarbamate as brown oil. Yield (0.880 g, 94%): $^1$H NMR (400 MHz, CDCl$_3$) δ 7.45 (s, 1H), 7.28-7.36 (m, 3H), 4.85-4.87 (bs, 1H), 4.70-4.72 (m, 1H), 4.49 (d, J=5.2 Hz, 2H), 3.47-3.50 (m, 1H), 3.44 (bs, 1H), 3.12-3.17 (m, 1H), 1.93-1.99 (m, 2H), 1.45 (s, 9H).

Step 2: Reduction reaction of tert-butyl 3-hydroxy-3-(3-(3-hydroxyprop-1-ynyl)phenyl)propylcarbamate gave tert-butyl 3-hydroxy-3-(3-(3-hydroxypropyl)phenyl)propylcarbamate as yellow oil. Yield (0.731 g, 82%): $^1$H NMR (400 MHz, DMSO-d$_6$) δ 7.20 (t, J=7.6 Hz, 1H), 7.13 (s, 1H), 7.11 (d, J=7.6 Hz, 1H), 7.04 (d, J=7.6 Hz, 1H), 6.77 (d, J=5.2 Hz, 1H) 5.15 (d, J=4.4 Hz, 1H), 4.51 (m, 1H), 4.46 (t, J=4.4 Hz, 1H), 3.32-3.44 (m, 2H), 2.94-2.98 (m, 2H), 2.58 (t, J=7.6 Hz, 2H), 1.64-1.73 (m, 4H), 1.45 (s, 9H).

Step 3: Deprotection of tert-butyl 3-hydroxy-3-(3-(3-hydroxypropyl)phenyl)propylcarbamate resulted in the hydrochloride salt. The crude product was subjected to flash chromatography (0-15% MeOH—NH$_3$ (9.5:0.5)-DCM gradient) to obtain Example 79 as pale yellow semi-solid. Yield (0.364 g, 61%): $^1$H NMR (400 MHz, DMSO-d$_6$) δ 7.20 (t, J=7.6 Hz, 1H), 7.10 (s, 1H), 7.07 (d, J=7.6 Hz, 1H), 7.02 (d, J=7.6 Hz, 1H), 4.56 (t, J=6.8 Hz, 1H), 3.38 (t, J=6.4 Hz, 2H), 2.62-2.64 (m, 2H), 2.54-2.56 (m, 2H), 1.53-1.72 (m, 4H). $^{13}$C NMR (100 MHz, DMSO-d$_6$) δ 145.7, 142.5, 128.5, 127.4, 126.0, 123.4, 70.1, 60.5, 37.1, 36.8, 34.8, 32.2. MS: 210 [M+1]$^+$.

Example 80

Preparation of 1-(3-(3-Amino-1-Hydroxypropyl)Phenyl)Hexan-3-ol

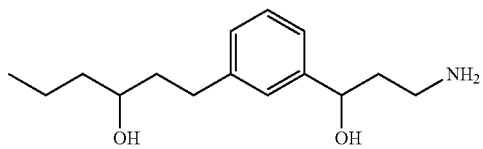 [SMILES: CCCC(O)CCc1cccc(C(O)CCN)c1]

1-(3-(3-Amino-1-hydroxypropyl)phenyl)hexan-3-ol was prepared following the method used in Example 19.

Step 1: Sonogashira reaction of 43 (3 g, 9.2 mmol) with hex-1-yn-3-ol yielded 2,2,2-trifluoro-N-(3-hydroxy-3-(3-(3-hydroxyhex-1-ynyl)phenyl)propyl)acetamide as yellow oil. Yield (2.31 g, 73%): $^1$H NMR (400 MHz, CDCl$_3$) δ 7.42 (s, 1H), 7.26-7.38 (m, 3H), 4.86 (m, 1H), 4.61 (dd, J=2.0, 5.6 Hz, 1H), 3.67-3.71 (m, 1H), 3.37-3.46 (m, 1H), 2.38 (d, J=2.0 Hz, 1H), 1.95-1.99 (m, 2H), 1.75-1.88 (m, 2H), 1.53-1.57 (m, 2H), 0.97 (t, J=7.2 Hz, 3H).

Step 2: Reduction reaction of 2,2,2-trifluoro-N-(3-hydroxy-3-(3-(3-hydroxyhex-1-ynyl)phenyl)propyl)acetamide yielded 2,2,2-trifluoro-N-(3-hydroxy-3-(3-(3-hydroxyhexyl)phenyl)propyl)acetamide as yellow oil. Yield (0.911 g, 83%). This compound was utilized as such for the next transformation.

Step 3: Deprotection of 2,2,2-trifluoro-N-(3-hydroxy-3-(3-(3-hydroxyhexyl)phenyl)propyl)acetamide and purification by flash chromatography (0-10% MeOH—NH$_3$ (9.5:0.5)-DCM gradient) gave Example 80 as yellow oil (the HCl salt was not prepared in this case). Yield (0.325 g, 49%): $^1$H NMR (400 MHz, DMSO-d$_6$) δ 7.23 (t, J=7.2 Hz, 1H), 7.17 (s, 1H), 7.10 (d, J=7.6 Hz, 1H), 7.01 (d, J=7.2 Hz, 1H), 4.61 (t, J=6.0 Hz, 1H), 4.39 (bs, 1H), 2.55-2.70 (m, 4H), 1.53-1.65 (m, 4H), 1.26-1.39 (m, 4H), 0.85 (t, J=6.4 Hz, 3H). $^{13}$C NMR (100 MHz, DMSO-d$_6$) δ 146.4, 142.1, 127.8, 126.4, 125.6, 122.9, 71.3, 68.7, 42.3, 38.9, 31.6, 18.4, 14.1. MS: 252 [M+1]$^+$.

Example 81

Preparation of 1-(3-(2-Aminoethoxy)Phenyl)Hexan-3-ol

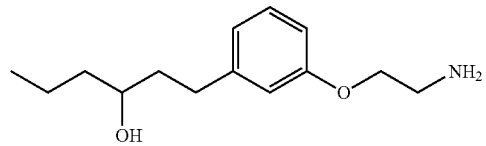 [SMILES: CCCC(O)CCc1cccc(OCCN)c1]

1-(3-(2-Aminoethoxy)phenyl)hexan-3-ol was prepared following the method used in Example 9.

Step 1: Sonogashira reaction of bromide 19 with 4-methylpent-1-yn-3-ol gave 2,2,2-trifluoro-N-(2-(3-(3-hydroxyhex-1-ynyl)phenoxy)ethyl)acetamide as a clear oil. Yield (3 g, crude): The crude material was directly utilized for further deprotection reaction.

Step 2: Deprotection of 2,2,2-trifluoro-N-(2-(3-(3-hydroxyhex-1-ynyl)phenoxy)ethyl)acetamide gave 1-(3-(2-aminoethoxy)phenyl)hex-1-yn-3-ol as a yellow oil. Yield (1.858 g, 88%): $^1$H NMR (400 MHz, DMSO-d$_6$) δ 7.23-7.29 (m, 1H), 6.90-6.98 (m, 3H), 4.42 (t, J=6.4 Hz, 2H), 3.92 (t, J=4.8 Hz, 2H), 2.86 (bs, 2H), 1.56-1.68 (m, 2H), 1.40-1.49 (m, 2H), 0.91 (t, J=7.6 Hz, 3H). $^{13}$C NMR (100 MHz, DMSO-d$_6$) δ 159.0, 130.3, 124.0, 117.1, 115.8, 92.8, 833, 70.4, 61.0, 41.2, 40.1, 18.6, 14.2. ESI MS m/z 234 [M+1]$^+$.

Step 3: The reduction of 1-(3-(2-aminoethoxy)phenyl)hex-1-yn-3-ol afforded Example 81 as yellow oil. Yield (0.55 g, 68%): $^1$H NMR (400 MHz, DMSO-d$_6$) δ 7.13-7.18 (m, 1H), 6.71-6.76 (m, 3H), 4.36-4.42 (m, 1H), 3.91 (t, J=5.6 Hz, 2H), 2.87 (t, J=5.6 Hz, 2H), 2.62-2.70 (m, 2H), 1.50-1.64 (m, 2H), 1.24-1.40 (m, 4H), 0.85 (s, 3H). $^{13}$C NMR (100 MHz, DMSO-d$_6$) δ 158.6, 144.2, 129.2, 120.5, 114.5, 111.5, 69.5, 68.7, 40.8, 39.3, 39.0, 31.6, 18.4, 14.1. MS: 238 [M+1]+

Example 82

Preparation of 3-Amino-1-(3-(4-Methoxybutyl)Phenyl)Propan-1-ol

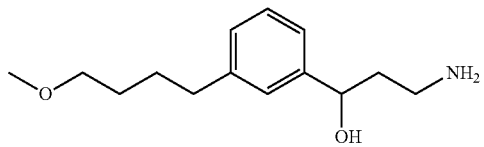 [SMILES: COCCCCc1cccc(C(O)CCN)c1]

3-Amino-1-(3-(4-methoxybutyl)phenyl)propan-1-ol was prepared following the method used in Example 19.

Step 1: Sonogashira reaction of 43 with 4-methoxybut-1-yne gave 2,2,2-trifluoro-N-(3-hydroxy-3-(3-(4-methoxybut-1-ynyl)phenyl)propyl)acetamide as brown oil. Yield (0.351 g, 81%): $^1$H NMR (400 MHz, CDCl$_3$) δ 7.40 (s, 1H), 7.27-7.37 (m, 3H), 4.83-4.85 (m, 1H), 3.68-3.71 (m, 1H), 3.63 (t, J=6.8 Hz, 2H), 3.39 (s, 3H), 3.34-3.38 (m, 1H), 2.69 (t, J=6.8 Hz, 2H), 2.38 (bs, 1H), 1.91-2.02 (m, 2H).

Step 2: Reduction of 2,2,2-trifluoro-N-(3-hydroxy-3-(3-(4-methoxybut-1-ynyl)phenyl)propyl)acetamide yielded 2,2,2-trifluoro-N-(3-hydroxy-3-(3-(4-methoxybutyl)phenyl)propyl)acetamide as yellow oil. Yield (0.332 g, 94%). This compound was utilized as such for the next transformation. MS: 334 [M+1]$^+$.

Step 3: Deprotection of 2,2,2-trifluoro-N-(3-hydroxy-3-(3-(4-methoxybutyl)phenyl)propyl)acetamide and subsequent purification by flash chromatography (0-10% (MeOH—NH$_3$ (9.5:0.5))-DCM) gave Example 82 as pale green oil. Yield (0.156 g, 61%): $^1$H NMR (400 MHz, DMSO-d$_6$) δ 7.20 (t, J=7.6 Hz, 1H), 7.11 (s, 1H), 7.09 (d, J=7.6 Hz, 1H), 7.04 (d, J=7.6 Hz, 1H), 4.58-4.61 (m, 1H), 3.30 (t, J=6.4 Hz, 2H), 3.18 (s, 3H), 2.61 (t, J=6.8 Hz, 2H), 2.58 (t, J=7.2 Hz, 2H), 1.63-1.69 (m, 2H), 1.45-1.56 (m, 4H). $^{13}$C NMR (100 MHz, DMSO-d$_6$) δ 146.6, 142.2, 128.3, 127.0, 126.0, 123.5, 72.2, 71.4, 58.3, 41.4, 38.7, 35.5, 29.1, 28.1. MS: 238 [M+1]$^+$.

Example 83

Preparation of (S)-1-(3-(1-Aminopropan-2-Yloxy)Phenethyl)Cyclohexanol

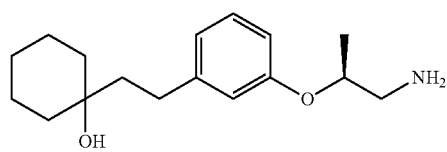 [SMILES: C[C@@H](CN)Oc1cccc(CCC2(O)CCCCC2)c1]

(S)-1-(3-(1-Aminopropan-2-yloxy)phenethyl)cyclohexanol was prepared following the method shown in Scheme 17.

SCHEME 17

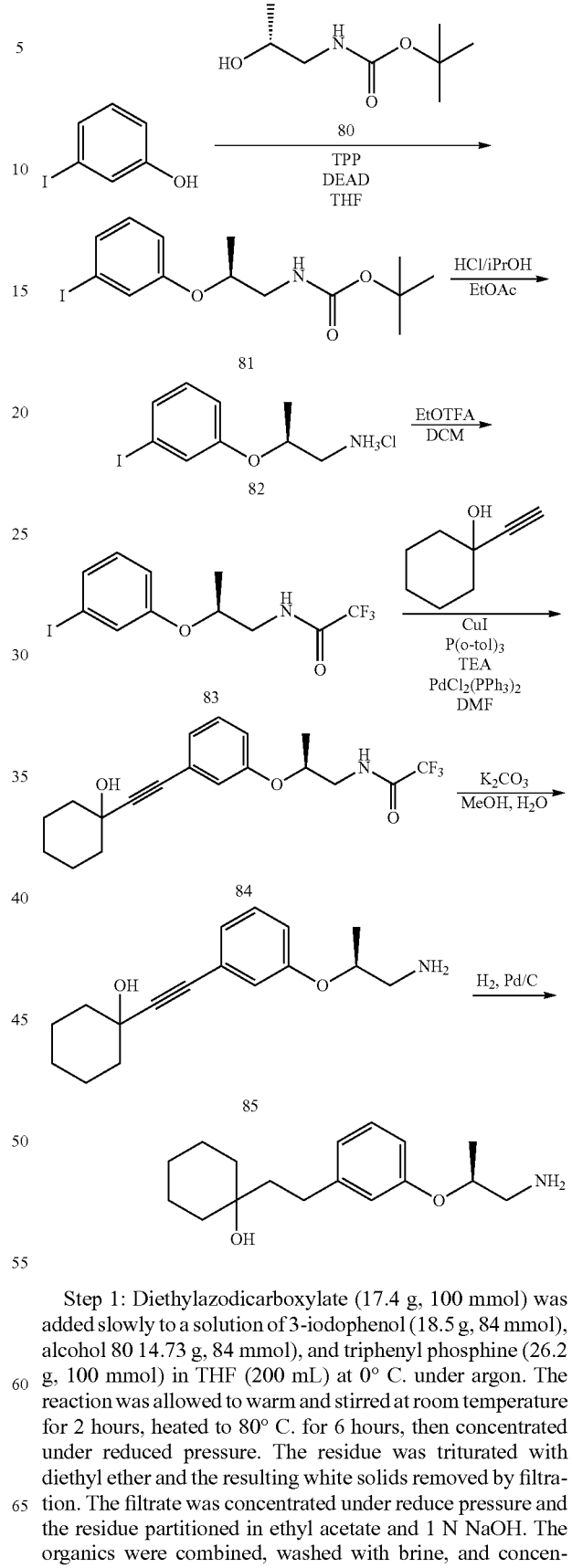

Step 1: Diethylazodicarboxylate (17.4 g, 100 mmol) was added slowly to a solution of 3-iodophenol (18.5 g, 84 mmol), alcohol 80 14.73 g, 84 mmol), and triphenyl phosphine (26.2 g, 100 mmol) in THF (200 mL) at 0° C. under argon. The reaction was allowed to warm and stirred at room temperature for 2 hours, heated to 80° C. for 6 hours, then concentrated under reduced pressure. The residue was triturated with diethyl ether and the resulting white solids removed by filtration. The filtrate was concentrated under reduce pressure and the residue partitioned in ethyl acetate and 1 N NaOH. The organics were combined, washed with brine, and concentrated under reduced pressure. The residue was purified by flash chromatography (5-20% ethyl acetate/hexanes gradient) on silica gel, giving the carbamate 81 as an impure yellow oil which was carried on to the next step without further purification. Yield (17.3 g, 54%).

Step 2: HCl (12 mL of a 4.8 M solution in iPrOH, 56 mmol) was added to a solution of carbamate 81 (10 g, 28 mmol) in ethyl acetate (25 mL). After stirring 1 h, the reaction mixture was filtered and the solids dried under reduced pressure, giving the hydrochloride salt 82 as a white solid which was carried on to the next step without purification or analysis. Yield (2.9 g, 30%).

Step 3: Protection of amine hydrochloride 82 with ethyltrifluoroacetate according the method used in Example 9, except that 1 equivalent of TEA was used and the reaction was carried out in dichloromethane, gave trifluoroamide 83 as a yellow oil. Yield (3.4 g, quantitative). $^1$H NMR (400 MHz, CDCl$_3$) δ 7.29-7.33 (m, 1H), 7.24-7.26 (m, 1H), 6.99 (t, J=8.0 Hz, 1H), 6.83-6.87 (m, 1H), 6.75 (brs, 1H), 4.45-4.55 (m, 1H), 3.52-3.53 (m, 1H), 3.40-3.50 (m, 1H), 1.29 (d, J=6.4 Hz, 3H).

Step 4: A mixture of trifluoroamide 83 (500 mg, 1.34 mmol), 1-ethynylcyclohexanol (250 mg, 2.01 mmol), copper iodide (25 mg, 0.13 mmol), tri-o-tolylphosphine (40 mg, 0.13 mmol), TEA (0.279 mL, 2.01 mL), and bis-chloro-triphenylphosphine palladium (91 mg, 0.13 mmol) in DMF (13 mL) was degassed, placed under argon atmosphere, and stirred overnight at 90° C. The reaction mixture was filtered and the filtrate partitioned in EtOAc/water. The organic layers were combined and washed with brine, dried over sodium sulfate, filtered, and concentrated under reduced pressure. The residue was purified by flash chromatography (10-30% EtOAc/hexanes gradient) giving alkyne 84 as a yellow glassy oil. Yield (0.322 g, 65%). %). $^1$H NMR (400 MHz, CDCl$_3$) δ 7.21 (t, J=8.0 Hz, 1H), 7.04-7.08 (m, 1H), 6.94-6.96 (m, 1H), 6.83-6.87 (m, 1H), 6.81 (brs, 1H), 4.48-4.57 (m, 1H), 3.72-3.80 (m, 1H), 3.39-3.49 (m, 1H), 1.85-2.04 (m, 3H), 1.50-1.80 (m, 8H), 1.29 (d, J=6.4 Hz, 3H).

Step 5: Deprotection of alkyne 84 according to the method used in Example 2 gave amine 85l as a yellow oil. Yield (0.200 g, 85%). $^1$H NMR (400 MHz, CDCl$_3$) δ 7.18 (t, J=8.0 Hz, 1H), 6.96-7.02 (m, 2H), 6.84-6.88 (m, 1H), 4.30-4.38 (m, 1H), 2.87 (d, J=5.2 Hz, 2H), 1.85-2.02 (m, 2H), 1.50-1.80 (m, 11H), 1.25 (d, J=6.4 Hz, 3H). ESI MS m/z 274.3 [m +H]$^+$.

Step 6: Hydrogenation of amine 85 according to the method used in Example 2 followed by flash chromatography (2% (7N NH$_3$/CH$_3$OH)/CH$_2$Cl$_2$) gave Example 83 as a colorless oil. Yield (0.045 g, 51%). $^1$H NMR (400 MHz, CDCl$_3$) δ 7.10 (t, J=8.0 Hz, 1H), 6.64-7.73 (m, 3H), 4.27 (dddd, J=6.0 Hz, 1H), 2.81 (d, J=2.8 Hz, 2H), 2.59 (m, 2H), 1.67 (m, 2H), 1.30-1.60 (m, 12H), 1.15-1.30 (m, 4H). ESI MS m/z 278.4 [m +H]$^+$, 260.3 [m+H−OH]$^+$.

Example 84

Preparation of 1-(3-(2-Aminoethoxy)Phenyl)-4-Methylpentan-3-ol

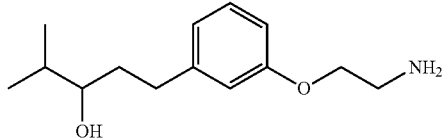 [SMILES: CC(C)C(O)CCc1cccc(OCCN)c1]

1-(3-(2-Aminoethoxy)phenyl)-4-methylpentan-3-ol was prepared following the method used in Example 9.

Step 1: Sonogashira reaction of bromide 19 with 4-methylpent-1-yn-3-ol gave 2,2,2-trifluoro-N-(2-(3-(3-hydroxy-4-methylpent-1-ynyl)phenoxy)ethyl)acetamide as yellow oil. Yield (0.51 g, 21%): $^1$H NMR (400 MHz, CDCl$_3$) δ 7.22-7.27 (m, 1H), 7.08-7.12 (d, J=7.6 Hz, 1H), 6.98 (s, 1H), 6.88 (dd, 1H, J=6.8 Hz, 1.6, 1H), 6.71 (bs, 1H), 4.32 (s, 2H), 4.09 (t, J=5.2 Hz, 2H), 3.77-3.82 (m, 2H), 1.77-1.83 (m, 1H), 0.94-0.99 (m, 6H).

Step 2: Deprotection of 2,2,2-trifluoro-N-(2-(3-(3-hydroxy-4-methylpent-1-ynyl)phenoxy)ethyl)acetamide gave 1-(3-(2-Aminoethoxy)phenyl)-4-methylpent-1-yn-3-ol as yellow oil. Yield (0.160 g, 47%): $^1$H NMR (400 MHz, DMSO-d$_6$) δ 7.22-7.30 (m, 1H), 6.90-7.00 (m, 3H), 4.21 (d, J=5.6 Hz, 1H), 3.93 (t, J=5.2 Hz, 2H), 2.87 (bs, 2H), 1.77-1.83 (m, 1H), 0.94-0.99 (m, 6H). $^{13}$C NMR (100 MHz, DMSO-d$_6$) δ 158.5, 129.8, 123.7, 116.7, 115.2, 91.0, 83.6, 69.9, 66.3, 40.7, 34.3, 18.3, 17.7. ESI MS m/z 234 [M+1]$^+$.

Step 2: A solution of 1-(3-(2-Aminoethoxy)phenyl)-4-methylpent-1-yn-3-ol (0.56 g, 2.4 mmol) in EtOH (30 mL) was degassed and purged with nitrogen. To this was added Pd on C (0.05 g, 10%). The flask was evacuated and purged with hydrogen thrice. This suspension was then stirred at room temperature under hydrogen balloon for overnight. The reaction mixture was filtered through a pad of Celite and the filter cake was washed with ethanol. The filtrate was concentrated to afford Example 1. Yield (0.38, 66%): $^1$H NMR (400 MHz, DMSO-d$_6$) δ 7.14-7.18 (m, 1H), 6.71-6.76 (m, 3H), 3.91 (t, J=5.6 Hz, 2H), 3.12-3.17 (m, 1H), 2.89 (t, J=5.6 Hz, 2H), 2.65-2.73 (m, 1H), 2.46-2.50 (m, 1H), 1.46-1.64 (m, 3H), 0.8 (t, J=5.6 Hz, 2H). $^{13}$C NMR (100 MHz, DMSO-d$_6$) δ 159.0, 144.8, 129.7, 121.1, 115.0, 112.0, 74.2, 69.6, 41.1, 36.2, 33.7, 32.4, 19.4, 18.0. MS: 238 [M+1]+.

Example 85

Preparation of 3-Amino-1-(3-Phenethylphenyl)Propan-1-ol

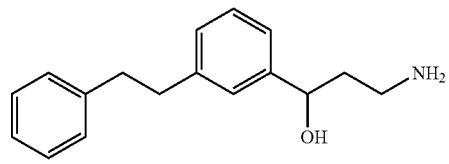 [SMILES: NCCC(O)c1cccc(CCc2ccccc2)c1]

3-Amino-1-(3-phenethylphenyl)propan-1-ol was prepared following the method used in Example 79.

Step 1: Sonogashira reaction of 39 with ethynylbenzene gave tert-butyl 3-hydroxy-3-(3-(phenylethynyl)phenyl)propylcarbamate as brown oil. Yield (0.911 g, 85%): $^1$H NMR (400 MHz, CDCl$_3$) δ 7.51-7.55 (m, 3H), 7.42-7.44 (m, 1H), 7.30-7.37 (m, 5H), 4.87 (bs, 1H), 4.74-4.76 (m, 1H), 3.46-3.51 (m, 1H), 3.41 (bs, 1H), 3.13-3.19 (m, 1H), 1.79-1.88 (m, 2H), 1.44 (s, 9H).

Step 2: Reduction of tert-butyl 3-hydroxy-3-(3-(phenylethynyl)phenyl)propylcarbamate gave tert-butyl 3-hydroxy-3-(3-phenethylphenyl)propyl carbamate as yellow oil. Yield (0.824 g, 91%): $^1$H NMR (400 MHz, CDCl$_3$) δ 7.24-7.29 (m, 3H), 7.16-7.21 (m, 5H), 7.10 (d, J=7.2 Hz, 1H), 4.86 (bs, 1H), 4.69-4.73 (m, 1H), 3.46-3.49 (m, 1H), 3.13-3.19 (m, 1H), 3.10 (bs, 1H), 2.91 (s, 4H), 1.80-1.88 (m, 2H), 1.46 (s, 9H).

Step 3: Deprotection of tert-butyl 3-hydroxy-3-(3-phenethyl phenyl) propyl carbamate gave Example 85 as off-white semi-solid. Yield (0.391 g, 59%): $^1$H NMR (400 MHz, DMSO-d$_6$) δ 7.11-7.29 (m, 9H), 4.64 (t, J=7.2 Hz, 1H), 2.79-2.86 (m, 6H), 1.79-1.84 (m, 2H). $^{13}$C NMR (100 MHz, DMSO-d$_6$) δ 145.7, 142.0, 141.8, 128.8, 128.7, 128.5, 127.5, 126.3, 126.0, 123.6, 70.2, 37.7, 37.6, 37.1, 36.8. MS: 256 [M+1]$^+$.

Example 86

Preparation of 5-(3-(3-Amino-1-Hydroxypropyl) Phenyl)-N,N-Dimethylpentanamide

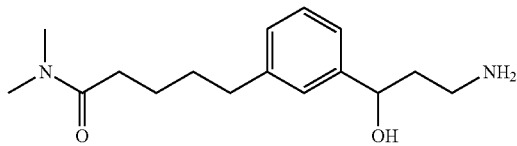 [SMILES: CN(C)C(=O)CCCCc1cccc(C(O)CCN)c1]

5-(3-(3-Amino-1-hydroxypropyl)phenyl)-N,N-dimethylpentanamide was prepared following the method used in Example 19.

Step 1: Sonogashira reaction of 43 with pent-4-ynoic acid dimethylamide yielded 5-(3-(1-hydroxy-3-(2,2,2-trifluoroacetamido)propyl)phenyl)-N,N-dimethylpent-4-ynamide as dark yellow oil. Yield (0.33 g, 48%). This compound had some traces of the starting material and was used without further purification.

Step 2: Reduction reaction of 5-(3-(1-hydroxy-3-(2,2,2-trifluoro acetamido) propyl)phenyl)-N,N-dimethylpent-4-ynamide in EtOH gave 5-(3-(1-hydroxy-3-(2,2,2-trifluoroacetamido)propyl)phenyl)-N,N-dimethylpentanamide as yellow oil. Yield (0.63 g, 99%): $^1$H NMR (400 MHz, CDCl$_3$) δ 7.62 (bs, 1H), 7.24-7.28 (m, 1H), 7.19 (s, 1H), 7.12 (m, 2H), 4.85 (t, J=6.8 Hz, 1H), 3.57-3.65 (m, 1H), 3.35-3.44 (m, 1H), 2.99 (s, 3H), 2.92 (s, 3H), 2.65 (t, J=6.8 Hz, 2H), 2.29 (t, J=6.8 Hz, 2H), 1.98-2.03 (m, 2H), 1.62-1.68 (m, 4H).

Step 3: Deprotection reaction of 5-(3-(1-hydroxy-3-(2,2,2-trifluoro acetamido)propyl)phenyl)-N,N-dimethylpentanamide in MeOH—H$_2$O system at RT for 16 h, gave a yellow oil which upon purification by flash chromatography (0-10% MeOH—NH$_3$ (9.5:0.5)-DCM gradient) yielded Example 86 as pale yellow oil. Yield (0.24 g, 54%): $^1$H NMR (400 MHz, DMSO-d$_6$) δ 7.19 (t, J=7.6 Hz, 1H), 7.11 (s, 1H), 7.08 (d, J=7.6 Hz, 1H), 7.04 (d, J=7.6 Hz, 1H), 4.55-4.59 (m, 1H), 2.91 (s, 3H), 2.76 (s, 3H), 2.52-2.59 (m, 4H), 2.26 (t, J=7.6 Hz, 2H), 1.61-1.71 (m, 2H), 1.44-1.56 (m, 4H). $^{13}$C NMR (100 MHz, DMSO-d$_6$) δ 171.8, 146.4, 141.7, 127.8, 126.4, 125.5, 123.0, 71.3, 42.1, 36.7, 35.1, 34.7, 32.2, 30.6, 24.3. MS: 279 [M+1]$^+$.

Example 87

Preparation of 5-(3-(3-Aminopropyl)Phenyl)Pentan-1-ol

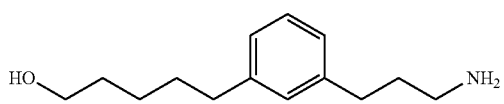 [SMILES: NCCCc1cccc(CCCCCO)c1]

5-(3-(3-Aminopropyl)phenyl)pentan-1-ol was prepared following the method used in Example 76.

Step 1: Sonogashira reaction of bromide 57 with 4-pentyn-1-ol gave tert-butyl 3-(3-(5-hydroxypent-1-ynyl)phenyl)propylcarbamate as yellow oil. Yield (0.653 g, 59%): $^1$H NMR (400 MHz, CDCl$_3$) δ 7.17-7.23 (m, 3H), 7.08 (d, J=7.2 Hz, 1H), 4.53 (bs, 1H), 3.83 (t, J=6.0 Hz, 2H), 3.10-3.18 (m, 2H), 2.60 (t, J=7.8 Hz, 2H), 2.54 (t, J=7.0 Hz, 2H), 1.83-1.90 (m, 2H), 1.74-1.82 (m, 2H), 1.44 (s, 9H).

Step 2: Reduction of tert-butyl 3-(3-(5-hydroxypent-1-ynyl)phenyl)propyl carbamate gave tert-butyl 3-(3-(5-hydroxypentyl)phenyl)propylcarbamate as yellow oil. Yield (0.628 g, 95%): $^1$H NMR (400 MHz, CDCl$_3$) δ 7.16-7.21 (m, 1H), 6.97-7.02 (m, 3H), 4.54 (bs, 1H), 3.71 (t, J=7.0 Hz, 2H), 3.12-3.17 (m, 2H), 2.58-2.64 (m, 4H), 1.77-1.84 (m, 2H), 1.56-1.67 (m, 4H), 1.44 (s, 9H), 1.37-1.42 (m, 2H).

Step 3: BOC-deprotection of tert-butyl 3-(3-(5-hydroxypentyl)phenyl) propylcarbamate gave Example 8 as brown oil. Yield (0.19 g, 43%): $^1$H NMR (400 MHz, DMSO-d$_6$) δ 7.12-7.17 (m, 1H), 6.94-6.98 (m, 3H), 3.37 (t, J=6.4 Hz, 2H), 2.49-2.57 (m, 6H), 1.58-1.65 (m, 2H), 1.50-1.57 (m, 2H), 1.40-1.47 (m, 2H), 1.27-1.33 (m, 2H). $^{13}$C NMR (100 MHz, DMSO-d$_6$): 142.6, 142.5, 128.8, 128.5, 126.0, 61.1, 41.4, 35.7, 35.2, 33.0, 32.8, 31.4, 25.7. MS: 222 [M+1]$^+$.

Example 88

Preparation of 2-(3-(4-Methoxybutyl)Phenoxy)Ethanamine

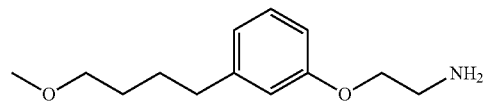

2-(3-(4-Methoxybutyl)phenoxy)ethanamine was prepared following the method used in Example 64.

Step 1: Sonogashira reaction of bromide 19 with 4-methoxybut-1-yne gave 2,2,2-trifluoro-N-(2-(3-(4-methoxybut-1-ynyl)phenoxy)ethyl)acetamide as yellow oil. Yield (0.45 g, 45%): This material was directly utilized for the deprotection reaction.

Step 2: The reduction of 2,2,2-trifluoro-N-(2-(3-(4-methoxybut-1-ynyl)phenoxy)ethyl)acetamide afforded 2,2,2-trifluoro-N-(2-(3-(4-methoxybutyl)phenoxy)ethyl)acetamide as yellow oil. Yield (0.34 g, 75%): $^1$H NMR (400 MHz, DMSO-d$_6$) δ 7.15-7.20 (m, 1H), 6.71-6.78 (m, 3H), 4.06 (t, J=5.6 Hz, 2H), 3.53-3.58 (m, 2H), 3.31 (t, J=6.8 Hz, 2H), 3.20 (s, 3H), 2.54 (t, J=7.6 Hz, 2H), 1.54-1.62 (m, 2H), 1.44-1.52 (m, 2H). MS: 318 [M−1].

Step 3: Deprotection of 2,2,2-trifluoro-N-(2-(3-(4-methoxybutyl)phenoxy)ethyl)acetamide gave Example 88 as yellow oil. Yield (0.18 g, 76%): $^1$H NMR (400 MHz, DMSO-d$_6$) δ 7.15-7.20 (m, 1H), 6.71-6.78 (m, 3H), 3.93 (t, J=5.6 Hz, 2H), 3.31 (t, J=6.2 Hz, 2H), 3.20 (s, 3H), 2.93 (t, J=5.6 Hz, 2H), 2.54 (t, J=7.4 Hz, 2H), 1.52-1.60 (m, 2H), 1.43-1.50 (m, 2H). $^{13}$C NMR (100 MHz, DMSO-d$_6$) δ 159.0, 144.2, 129.7, 121.1, 115.0, 112.1, 72.1, 69.1, 58.3, 40.9, 35.4, 29.1, 27.9. MS: 224 [M+1]$^+$

Example 89

Preparation of 1-(3-(2-Aminoethoxy)Phenethyl)Cyclooctanol

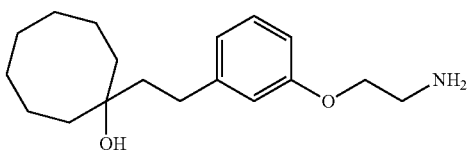

1-(3-(2-Aminoethoxy)phenethyl)cyclooctanol was prepared following the method used in Example 64.

Step 1: Sonogashira reaction of bromide 19 with 1-ethynylcyclooctanol gave 2,2,2-trifluoro-N-(2-(3-(2-(1-hydroxycyclooctyl)ethynyl)phenoxy)ethyl)acetamide as a clear oil. Yield (1.3 g, 72%): $^1$H NMR (400 MHz, DMSO-$d_6$) δ 7.22 (d, J=8.0 Hz, 1H), 7.07 (d, J=7.6 Hz, 1H), 6.91-6.96 (m, 2H), 4.09-4.13 (m, 2H), 2.00-2.06 (m, 6H), 1.48-1.72 (m, 11H).

Step 2: The reduction of 2,2,2-trifluoro-N-(2-(3-((1-hydroxycyclooctyl)ethynyl)phenoxy)ethyl)acetamide afforded 2,2,2-trifluoro-N-(2-(3-(2-(1-hydroxycyclo octyl)ethyl)phenoxy)ethyl)acetamide as yellow oil. Yield (0.36 g, 78%): $^1$H NMR (400 MHz, DMSO-$d_6$) δ 7.14-7.18 (m, 1H), 6.72-6.78 (m, 3H), 4.06 (t, J=6.0 Hz, 2H), 3.42-3.45 (m, 2H), 2.55-2.59 (m, 2H), 1.30-1.71 (m, 16H). MS: 386 [M−1].

Step 3: Deprotection of 2,2,2-trifluoro-N-(2-(3-(2-(1-hydroxycyclooctyl) ethyl)phenoxy)ethyl)acetamide gave Example 89 as yellow oil. Yield (0.097 g, 37%): $^1$H NMR (400 MHz, DMSO-$d_6$) δ 7.14-7.18 (m, 1H), 6.70-6.76 (m, 3H), 3.93 (t, J=5.6 Hz, 2H), 2.92 (t, J=5.6 Hz, 2H), 2.54-2.59 (m, 2H), 1.31-1.70 (m, 16H). $^{13}$C NMR (100 MHz, DMSO-$d_6$) δ 158.5, 144.9, 129.2, 120.6, 114.5, 111.4, 72.6, 68.6, 43.5, 40.4, 35.6, 29.3, 27.9, 24.6, 22.0. MS: 292 [M+1]$^+$.

Example 90

Preparation of 3-Amino-1-(3-(4-Methylpentyl)Phenyl)Propan-1-ol

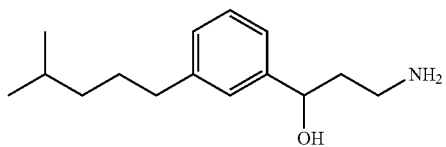 [SMILES: CC(C)CCCc1cccc(C(O)CCN)c1]

3-Amino-1-(3-(4-methylpentyl)phenyl)propan-1-ol was prepared following the method used in Example 63.

Step 1: Sonogashira reaction of 43 with 4-methyl-pent-1-yne yielded 2,2,2-trifluoro-N-(3-hydroxy-3-(3-(4-methylpent-1-ynyl)phenyl)propyl)acetamide as dark brown oil. Yield (0.94 g, 94%): $^1$H NMR (400 MHz, CDCl$_3$) δ 7.38 (s, 1H), 7.25-7.35 (m, 3H), 4.86 (m, 1H), 3.67-3.72 (m, 1H), 3.38-3.44 (m, 1H), 2.30 (d, J=6.4 Hz, 2H), 2.28 (bs, 1H), 1.87-1.99 (m, 3H), 1.05 (d, J=6.8 Hz, 6H).

Step 2: Deprotection of 2,2,2-trifluoro-N-(3-hydroxy-3-(3-(4-methylpent-1-ynyl)phenyl)propyl)acetamide gave 3-(3-amino-1-hydroxypropyl)phenyl)prop-2-yn-1-ol as yellow oil. Yield (0.508 g, 76%): $^1$H NMR (400 MHz, DMSO-$d_6$) δ 7.33 (s, 1H), 7.23-7.29 (m, 3H), 5.12 (bs, 2H), 4.66 (t, J=6.4 Hz, 1H), 2.68 (t, J=6.8 Hz, 2H), 2.32 (d, J=6.4 Hz, 2H), 1.82-1.86 (m, 1H), 1.67-1.72 (m, 2H), 0.95 (d, J=6.8 Hz, 6H). $^{13}$C NMR (100 MHz, DMSO-$d_6$) δ 146.8, 130.0, 128.9, 128.8, 125.7, 123.4, 89.6, 82.1, 70.7, 40.6, 38.3, 28.1, 28.0, 22.3. ESI MS m/z 232 [M+1]$^−$.

Step 3: A mixture of 3-amino-1-(3-(4-methylpent-1-ynyl)phenyl)propan-1-ol (0.3 g, 1.3 mmol) and HCl in Dioxane (1 mL, 4M) in 2-PrOH was stirred at RT for 30 min The solvent was removed under reduced pressure and the hydrochloride salt thus obtained was dissolved in EtOH (10 mL). After purging the flask with nitrogen, Pd on C (0.040 g, 10%) was added. The flask was evacuated and re-filled with hydrogen after which it was stirred under H$_2$ balloon for about 14 h. The reaction mixture was filtered through a pad of Celite and the filtrate was evaporated to dryness under reduced pressure. The product obtained was purified by flash chromatography (0-10% MeOH-DCM gradient) to yield Example 90 hydrochloride as white solid. Yield (0.231 g, 65%): $^1$H NMR (400 MHz, DMSO-$d_6$) δ 7.23 (t, J=7.2 Hz, 1H), 7.12 (s, 1H), 7.10 (d, J=7.6 Hz, 1H), 7.05 (d, J=7.6 Hz, 1H), 4.62 (t, J=7.6 Hz, 1H), 2.77-2.89 (m, 2H), 2.50-2.54 (m, 2H), 1.78-1.84 (m, 2H), 1.48-1.57 (m, 3H), 1.13 (m, 2H), 0.83 (d, J=6.8 Hz, 6H). $^{13}$C NMR (100 MHz, DMSO-$d_6$) δ 145.7, 142.6, 128.5, 127.3, 125.9, 123.4, 70.2, 38.5, 37.1, 36.8, 36.0, 29.4, 27.7, 23.0. MS: 236 [M+1]$^+$.

Example 91

Preparation of 5-(3-(3-Amino-1-Hydroxypropyl)Phenylpentan-1-ol

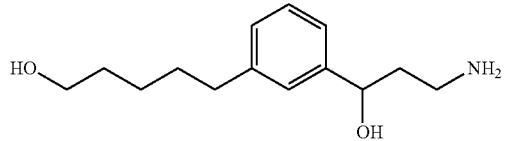 [SMILES: NCCC(O)c1cccc(CCCCCO)c1]

5-(3-(3-Amino-1-hydroxypropyl)phenyl)pentan-1-ol was prepared following the method used in Example 63.

Step 1: Sonogashira reaction of 43 with pent-4-yn-1-ol gave 2,2,2-trifluoro-N43-hydroxy-3-(3-(5-hydroxypent-1-ynyl)phenyl)propyl)acetamide as brown oil. Yield (1.46 g, 69%): $^1$H NMR (400 MHz, CDCl$_3$) δ 7.38 (s, 1H), 7.22-7.34 (m, 3H), 4.86 (d, J=8.0 Hz, 1H), 3.83 (t, J=5.2 Hz, 2H), 3.65-3.69 (m, 1H), 3.38-3.42 (m, 1H), 2.56 (t, J=7.2 Hz, 2H), 2.38 (bs, 1H) 1.93-1.99 (m, 2H), 1.83-1.88 (m, 2H).

Step 2: Deprotection of 2,2,2-trifluoro-N-(3-hydroxy-3-(3-(5-hydroxypent-1-ynyl)phenyl)propyl)acetamide gave 5-(3-(3-amino-1-hydroxypropyl)phenyl)pent-4-yn-1-ol as yellow oil. Yield (0.64 g, 65%): $^1$H NMR (400 MHz, DMSO-$d_6$) δ 7.32 (s, 1H), 7.25-7.28 (m, 2H), 7.20-7.22 (m, 1H) 4.66 (t, J=6.4 Hz, 1H), 4.55 (bs, 1H), 3.52 (t, J=6.4 Hz, 2H), 2.57-2.66 (m, 2H), 2.44 (t, J=7.2 Hz, 2H), 1.60-1.70 (m, 4H). $^{13}$C NMR (100 MHz, DMSO-$d_6$) δ 147.2, 129.8, 129.0, 128.7, 125.7, 123.3, 90.6, 81.1, 71.1, 59.9, 41.8, 38.9, 32.0, 15.7; ESI MS m/z 234 [M+1]$^+$.

Step 3: A solution of 5-(3-(3-amino-1-hydroxypropyl)phenyl) pent-4-yn-1-ol in IPA (20 mL) was degassed and purged with nitrogen. To this was added Pd on C (0.2 g, 10%). The flask was evacuated and filled with hydrogen. After repeating this procedure thrice, the reaction mixture was stirred under H$_2$ balloon for about 14 h following which it was filtered through Celite and concentrated under reduced pressure. Upon purification by flash chromatography (0-10% MeOH—NH$_3$ (9.5:0.5)-DCM gradient) Example 91 was obtained as yellow oil. Yield (0.208 g, 85%): $^1$H NMR (400 MHz, DMSO-d$_6$) δ 7.23 (t, J=7.6 Hz, 1H), 7.10-7.13 (m, 2H), 7.05 (d, J=7.6 Hz, 1H), 4.63 (t, J=6.4 Hz, 1H), 3.36 (t, J=6.8 Hz, 2H), 2.72 (t, J=6.8 Hz, 2H), 2.55 (t, J=7.6 Hz, 2H), 1.73 (m, 2H), 1.59 (m, 2H), 1.45 (m, 2H), 1.39 (m, 2H). $^{13}$C NMR (100 MHz, DMSO-d$_6$) δ 145.8, 142.0, 127.9, 126.7, 125.5, 122.9, 70.6, 60.6, 37.7, 35.3, 32.3, 31.0, 25.2. MS: 238 [M+1]$^+$.

Example 92

Preparation of 3-(3-(4-Methylpentyl)Phenyl-Propan-1-Amine

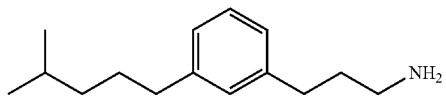 [SMILES: CC(C)CCCc1cccc(CCCN)c1]

3-(3-(4-Methylpentyl)phenyl-propan-1-amine was prepared following the method used in Example 76.

Step 1: Sonogashira coupling of bromide 57 (0.5 g, 1.5 mmol) with 4-methyl-1-pentyne (0.2 mL, 2.4 mmol) gave tert-butyl 3-(4-methylpent-1-ynyl)phenylcarbamate. Yield (0.35 g, 69%). $^1$H NMR (400 MHz, CDCl$_3$) δ 7.16-7.28 (m, 3H), 7.07 (d, J=7.2 Hz, 1H), 4.50 (bs, 1H), 3.12-3.15 (m, 2H), 2.60 (d, J=7.6 Hz, 2H), 2.29 (d, J=6.8 Hz, 2H), 1.84-1.94 (m, 2H), 1.74-1.82 (m, 1H), 1.44 (s, 9H), 1.04 (d, J=6.8 Hz, 6H).

Step 2: Reduction of tert-butyl 3-(3-(4-methylpent-1-ynyl) phenyl)propyl carbamate gave tert-butyl 3-(3-(4-methylpentyl)phenyl)propylcarbamate as yellow oil. Yield (0.309 g, 88%): $^1$H NMR (400 MHz, CDCl$_3$) δ 7.17-7.21 (m, 1H), 6.98-7.02 (m, 3H), 3.12-3.18 (m, 2H), 2.61 (t, J=7.8 Hz, 2H), 2.55 (t, J=7.8 Hz, 2H), 1.74-1.83 (m, 2H), 1.51-1.62 (m, 2H), 1.44 (s, 9H), 1.18-1.26 (m, 3H), 0.87 (d, J=6.8 Hz, 6H).

Step 3: BOC-deprotection of tert-butyl 3-(3-(4-methylpentyl)phenyl)propylcarbamate gave Example 92 hydrochloride as an off-white solid. Yield (0.1 g, 53%): $^1$H NMR (400 MHz, DMSO-d$_6$) δ 7.18-7.22 (m, 1H), 7.0-7.03 (m, 3H), 2.76 (t, J=7.6 Hz, 2H), 2.61 (t, J=7.8 Hz, 2H), 2.52 (t, J=7.6 Hz, 2H), 1.79-1.87 (m, 2H), 1.50-1.59 (m, 3H), 1.14-1.20 (m, 2H), 0.85 (d, J=6.8 Hz, 6H). $^{13}$C NMR (100 MHz, DMSO-d$_6$): 142.4, 140.7, 128.3, 128.2, 125.9, 125.5, 38.3, 38.1, 35.4, 31.8, 28.8, 28.7, 27.2, 22.5. MS: 220 [M+1]$^+$.

Example 93

Preparation of 5-(3-(2-Aminoethoxy)Phenyl)-N-Methylpentanamide

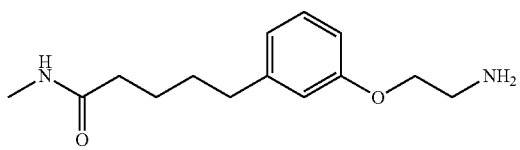 [SMILES: CNC(=O)CCCCc1cccc(OCCN)c1]

5-(3-(2-Aminoethoxy)phenyl)-N-methylpentanamide was prepared following the method used in Example 64.

Step 1: Sonogashira reaction of bromide 19 with pent-4-ynoic acid N-methyl amide gave N-methyl-5-(3-(2-(2,2,2-trifluoroacetamido)ethoxy)phenyl)pent-4-ynamide as a brown oil. Yield (0.45 g, 58%): $^1$H NMR (400 MHz, DMSO-d$_6$) δ 8.02 (bs, 1H), 7.18-7.24 (m, 1H), 7.02 (d, J=8.0 Hz, 1H), 6.91 (s, 1H), 6.83 (dd, J=8.0, 2.4 Hz, 1H), 6.76 (bs, 1H), 4.09 (t, J=5.2 Hz, 2H), 3.76-3.81 (m, 2H), 2.85 (d, J=4.8 Hz, 3H), 2.76 (t, J=7.4 Hz, 2H), 2.47 (t, J=7.4 Hz, 2H).

Step 2: The reduction of N-methyl-5-(3-(2-(2,2,2-trifluoroacetamido) ethoxy)phenyl)pent-4-ynamide afforded N-methyl-5-(3-(2-(2,2,2-trifluoroacetamido)ethoxy)phenyl) pentanamide as yellow oil. Yield (0.22 g, 47%): MS: 345 [M−1]. This product was utilized as such for the next transformation.

Step 3: Deprotection of N-methyl-5-(3-(2-(2,2,2-trifluoroacetamido)ethoxy)phenyl)pentanamide gave 5-(3-(2-aminoethoxy)phenyl)-N-methylpentanamide. Treatment of 5-(3-(2-aminoethoxy)phenyl)-N-methylpentanamide with HCl in dioxane (4 M) gave Example 93 hydrochloride as a white solid. Yield (0.08 g, 44%): $^1$H NMR (400 MHz, DMSO-d$_6$) δ 7.18-7.23 (m, 1H), 6.77-6.81 (m, 3H), 4.12 (t, J=4.8 Hz, 2H), 3.19 (t, J=4.8 Hz, 2H), 2.50-2.53 (m, 5H), 2.05 (t, J=6.8 Hz, 2H), 1.43-1.52 (m, 4H). $^{13}$C NMR (100 MHz, DMSO-d$_6$) δ 172.4, 157.8, 143.8, 129.3, 121.2, 114.7, 111.8, 64.0, 38.2, 35.1, 34.8, 30.5, 25.4, 24.9. MS: 251 [M+1].

Example 94

Preparation of 5-(3-(2-Aminoethoxy)Phenyl)-N,N-Dimethylpentanamide

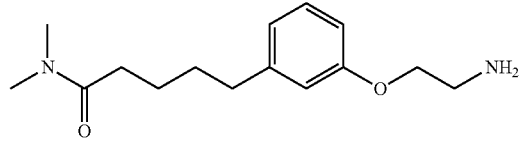

5-(3-(2-Aminoethoxy)phenyl)-N,N-dimethylpentanamide was prepared following the method used in Example 64.

Step 1: Sonogashira reaction of bromide 19 with pent-4-ynoic acid N,N-dimethyl amide gave N,N-dimethyl-5-(3-(2-(2,2,2-trifluoroacetamido)ethoxy)phenyl)pent-4-ynamide as a brown oil. Yield (0.9 g, 50%): $^1$H NMR (400 MHz, DMSO-d$_6$) δ 7.18-7.23 (m, 1H), 7.03 (d, J=7.2 Hz, 1H), 6.92 (s, 1H), 6.83 (dd, J=8.4, 2.4 Hz, 1H), 4.09 (t, J=5.0 Hz, 2H), 3.76-3.80 (m, 2H), 2.98 (s, 3H), 2.96 (s, 3H), 2.76 (t, J=7.6 Hz, 2H), 2.64 (t, J=7.6 Hz, 2H).

Step 2: The reduction of N,N-dimethyl-5-(3-(2-(2,2,2-trifluoroacetamido)ethoxy)phenyl)pent-4-ynamide afforded N,N-dimethyl-5-(3-(2-(2,2,2-trifluoroacetamido)ethoxy) phenyl)pentanamide as yellow oil. Yield (0.4 g, 88%): MS: 361 [M+1]$^+$. This product was pure enough to be utilized as such for the next transformation.

Step 3: Deprotection of N,N-dimethyl-5-(3-(2-(2,2,2-trifluoroacetamido) ethoxy)phenyl)pentanamide gave Example 94 as yellow oil. Yield (0.18 g, 61%): $^1$H NMR (400 MHz, DMSO-d$_6$) δ 7.16-7.21 (m, 1H), 6.74-6.79 (m, 3H), 4.0 (t, J=5.4 Hz, 2H), 3.02 (t, J=5.4 Hz, 2H), 2.93 (s, 3H), 2.79 (s, 3H), 2.54 (t, J=7.2 Hz, 2H), 2.28 (t, J=7.4 Hz, 2H), 1.51-1.60 (m, 2H), 1.44-1.50 (m, 2H). $^{13}$C NMR (100 MHz, DMSO-d$_6$) δ 172.3, 158.7, 144.3, 129.7, 121.4, 115.1, 112.1, 67.6, 37.2, 35.4, 35.2, 32.6, 30.9, 24.7. MS: 265 [M+1]$^+$

Example 95

Preparation of 1-(3-(3-Amino-1-Hydroxypropyl)Phenethyl)Cyclooctanol

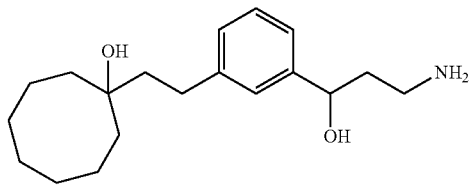 [SMILES: NCCC(O)c1cccc(CCC2(O)CCCCCCC2)c1]

1-(3-(3-Amino-1-hydroxypropyl)phenethyl)cyclooctanol was prepared following the method used in Example 19.

Step 1: Sonogashira reaction of 43 with 3-methylhex-1-yn-3-ol gave 2,2,2-trifluoro-N-(3-hydroxy-3-(3-(3-hydroxy-3-methylhex-1-ynyl)phenyl)propyl)acetamide as brown oil. Yield (0.908 g, 90%): $^1$H NMR (400 MHz, CDCl$_3$) δ 7.37 (s, 1H), 7.30-7.35 (m, 1H), 7.26-7.28 (m, 2H), 4.83-4.86 (m, 1H), 3.66-3.69 (m, 1H), 3.39-3.42 (m, 1H), 2.60 (bs, 1H), 2.11 (bs, 1H), 1.94-1.99 (m, 2H), 1.69-1.74 (m, 2H), 1.65 (s, 3H), 1.54-1.57 (m, 2H), 0.97 (t, J=7.2 Hz, 3H).

Step 2: Reduction of 2,2,2-trifluoro-N-(3-hydroxy-3-(3-(3-hydroxy-3-methylhex-1-ynyl)phenyl)propyl)acetamide yielded 2,2,2-trifluoro-N-(3-hydroxy-3-(3-(3-hydroxy-3-methylhexyl)phenyl)propyl)acetamide as yellow oil. Yield (0.99 g, 90%). This compound was utilized as such for the next transformation.

Step 3: Deprotection of 2,2,2-trifluoro-N-(3-hydroxy-3-(3-(3-hydroxy-3-methylhexyl)phenyl)propyl)acetamide gave a yellow oil, which upon purification by flash chromatography (0-10% MeOH—NH$_3$ (9.5:0.5)-DCM gradient) yielded Example 95 as a clear oil. Yield (0.597 g, 82%): $^1$H NMR (400 MHz, DMSO-d$_6$) δ 7.22 (t, J=7.2 Hz, 1H), 7.12 (s, 1H), 7.08 (d, J=7.2 Hz, 1H), 7.04 (d, J=7.2 Hz, 1H), 4.60 (t, J=6.4 Hz, 1H), 2.70-2.73 (m, 2H), 2.55-2.58 (m, 2H), 1.69-1.74 (dd, J=6.4 Hz, 12.8 Hz, 2H), 1.55-1.58 (m, 2H), 1.17-1.37 (m, 4H), 1.07 (s, 3H), 0.86 (t, J=7.2 Hz, 3H). $^{13}$C NMR (100 MHz, DMSO-d$_6$) δ 146.0, 142.8, 128.0, 126.7, 125.4, 122.8, 70.6, 70.5, 44.1, 43.9, 37.7, 30.0, 26.8, 16.8, 14.8. MS: 266 [M+1].

Example 96

Preparation of 5-(3-(2-Aminoethoxy)Phenylpentanamide

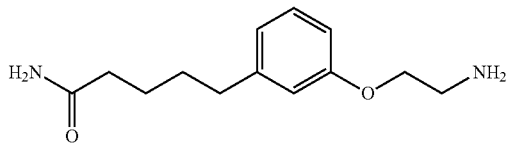

5-(3-(2-Aminoethoxy)phenyl)pentanamide was prepared following the method used in Example 64.

Step 1: Sonogashira reaction of bromide 19 with pent-4-ynoic acid amide gave 5-(3-(2-(2,2,2-trifluoroacetamido)ethoxy)phenyl)pent-4-ynamide as a clear oil. Yield (0.8 g, 50%): This compound was used without further purification in the next step.

Step 2: The reduction of 5-(3-(2-(2,2,2-trifluoroacetamido)ethoxy)phenyl)pent-4-ynamide afforded 5-(3-(2-(2,2,2-trifluoroacetamido)ethoxy)phenyl)pentanamide as yellow oil. Yield (0.6 g, 54%): MS: 331 [M−1].

Step 3: Deprotection of 5-(3-(2-(2,2,2-trifluoroacetamido)ethoxy)phenyl)pentanamide gave Example 96 as yellow oil. Yield (0.2 g, 47%): $^1$H NMR (400 MHz, DMSO-d$_6$) δ 7.15-7.20 (m, 1H), 6.73-6.77 (m, 3H), 3.96 (t, J=5.6 Hz, 2H), 2.94 (t, J=5.6 Hz, 2H), 2.53 (t, J=7.2 Hz, 2H), 2.05 (t, J=7.2 Hz, 2H), 1.44-1.54 (m, 4H). $^{13}$C NMR (100 MHz, DMSO-d$_6$) δ 174.7, 158.5, 144.3, 129.7, 121.6, 115.1, 112.2, 65.5, 39.2, 35.4, 31.0, 25.2. MS: 237 [M+1]$^+$.

Example 97

Preparation of 5-(3-(3-Aminopropyl)Phenyl)-N,N-Dimethylpentanamide

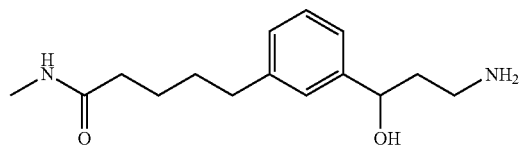

5-(3-(3-Aminopropyl)phenyl)-N,N-dimethylpentanamide was prepared following the method used in Example 19.

Step 1: Sonogashira reaction of 43 with N-methylpent-4-ynamide gave 5-(3-(1-hydroxy-3-(2,2,2-trifluoroacetamido)propyl)phenyl)-N-methylpent-4-ynamide as brown oil. Yield (0.661 g, 60%): $^1$H NMR (400 MHz, CDCl$_3$) δ 8.0 (bs, 1H), 7.43-7.48 (m, 1H), 7.37 (s, 1H), 7.30 (d, J=6.8 Hz, 2H), 5.66 (bs, 1H), 4.83-4.85 (m, 1H), 3.63-3.69 (m, 1H), 3.37-3.44 (m, 1H), 2.84 (d, J=4.8 Hz, 3H), 2.72 (t, J=7.6 Hz, 2H), 2.46 (t, J=7.6 Hz, 2H), 1.92-2.02 (m, 2H).

Step 2: Reduction of 5-(3-(1-hydroxy-3-(2,2,2-trifluoro acetamido) propyl)phenyl)-N-methylpent-4-ynamide using EtOH as the solvent yielded 5-(3-(1-hydroxy-3-(2,2,2-trifluoro acetamido)propyl)phenyl)-N-methyl pentanamide as yellow oil. Yield (0.911 mg, 83%). $^1$H NMR (400 MHz, CDCl$_3$) δ 8.0 (bs, 1H), 7.27 (t, J=7.2 Hz, 1H), 7.16 (s, 1H), 7.14 (d, J=7.6 Hz, 1H), 7.10 (d, J=7.6 Hz, 1H), 5.56 (bs, 1H), 4.83-4.86 (m, 1H), 3.54-3.60 (m, 1H), 3.37-3.44 (m, 1H), 2.76 (d, J=4.8 Hz, 3H), 2.63 (t, J=7.6 Hz, 2H), 2.12 (t, J=7.6 Hz, 2H), 1.96-2.0 (m, 2H), 1.58-1.67 (m, 4H).

Step 3: Deprotection of 5-(3-(1-hydroxy-3-(2,2,2-trifluoro acetamido)propyl)phenyl)-N-methyl pentanamide in MeOH—H$_2$O system at RT for 16 h, gave a yellow oil which upon purification by flash chromatography (0-10% MeOH—NH$_3$ (9.5:0.5)-DCM gradient) yielded Example 97 as yellow semi-solid. Yield (0.325 g, 49%): $^1$H NMR (400 MHz, DMSO-d$_6$) δ 7.19 (t, J=7.2 Hz, 1H), 7.13 (s, 1H), 7.08 (d, J=7.2 Hz, 1H), 7.00 (d, J=7.2 Hz, 1H), 4.57 (t, J=6.4 Hz, 1H), 2.57 (t, J=7.2 Hz, 2H), 2.53 (d, J=4.8 Hz, 3H), 2.35 (m, 2H), 2.07 (m, 2H), 1.70 (m, 2H), 1.48-1.55 (m, 4H). $^{13}$C NMR (100 MHz, DMSO-d$_6$) δ 172.9, 146.9, 142.1, 128.3, 126.9, 126.2, 123.6, 71.8, 42.7, 35.6, 35.5, 31.2, 25.9, 25.5. MS: 265 [M+1]$^+$.

Example 98

Preparation of 1-(3-(3-Amino-1-Hydroxypropyl) Phenethyl)Cyclobutanol

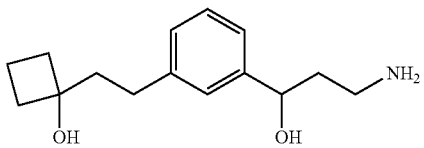 [SMILES: NCCC(O)c1cccc(CCC2(O)CCC2)c1]

1-(3-(3-Amino-1-hydroxypropyl)phenethyl)cyclobutanol was prepared following the method used in Example 79.

Step 1: Sonogashira reaction of 39 with 1-ethynyl-cyclobutanol yielded tert-butyl 3-hydroxy-3-(3-(2-(1-hydroxycyclobutyl)ethynyl)phenyl)propylcarbamate as yellow oil. Yield (1.5 g, 70%): $^1$H NMR (400 MHz, DMSO-$d_6$) δ 7.45 (s, 1H), 7.27-7.34 (m, 3H), 4.85 (bs, 1H), 4.71 (m, 1H), 3.48-3.51 (m, 2H), 3.14-3.16 (m, 1H), 2.50-2.52 (m, 2H), 2.30-2.49 (m, 3H), 1.80-1.90 (m, 4H), 1.45 (s, 9H).

Step 2: Reduction of tert-butyl 3-hydroxy-3-(3-((1-hydroxycyclobutyl)ethynyl)phenyl)propylcarbamate in EtOH for 72 h gave tert-butyl 3-hydroxy-3-(3-(2-(1-hydroxycyclobutyl)ethyl)phenyl)propylcarbamate as yellow oil. Yield (0.694 g, 92%): $^1$H NMR (400 MHz, CDCl$_3$) δ 7.24-7.26 (m, 2H), 7.12-7.18 (m, 2H), 4.73 (bs, 1H), 4.68-4.75 (m, 1H), 3.46-3.51 (m, 1H), 3.13-3.20 (m, 1H), 2.69-2.72 (m, 2H), 2.06-2.11 (m, 2H), 1.96-1.99 (m, 2H), 1.56-1.93 (m. 4H), 1.45 (s, 9H).

Step 3: A mixture of tert-butyl 3-hydroxy-3-(3-(2-(1-hydroxycyclobutyl)ethyl)phenyl)propylcarbamate and HCl in Dioxane (2 mL, 4M) in ethyl acetate was stirred at RT for 20 h. The mixture was concentrated to dryness under reduced pressure. Purification by flash chromatography (0-10% MeOH-DCM gradient) gave Example 98 hydrochloride as pale yellow semi-solid. Yield (0.235 g, 47%): $^1$H NMR (400 MHz, DMSO-$d_6$) δ 7.67-7.71 (bs, 3H), 7.23 (t, J=7.6, 1H), 7.18 (s, 1H), 7.10 (d, J=7.6 Hz, 1H), 7.08 (d, J=7.6 Hz, 1H), 4.93 (bs, 1H), 4.63-4.66 (m, 1H), 2.80-2.85 (m, 2H), 2.50-2.59 (m, 2H), 1.93-1.97 (m, 4H), 1.81-1.85 (m, 2H), 1.71-1.76 (m, 2H), 1.62-1.64 (m, 1H), 1.44-1.49 (m, 1H). $^{13}$C NMR (100 MHz, DMSO-$d_6$) δ 145.7, 143.2, 128.5, 127.4, 125.9, 123.2, 73.7, 70.2, 42.0, 37.2, 36.9, 36.1, 30.1, 12.3. MS: 250 [M+1]$^+$.

Example 99

Preparation of 2-(3-(2-Aminoethoxy)Phenethyl)Cyclohexanol

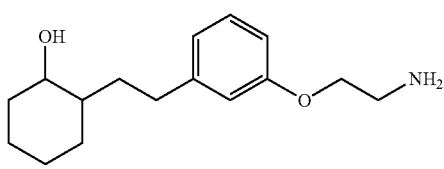 [SMILES: NCCOc1cccc(CCC2CCCCC2O)c1]

2-(3-(2-Aminoethoxy)phenethyl)cyclohexanol was prepared following the method used in Example 9.

Step 1: Sonogashira coupling of bromide 19 with 2-ethynylcyclohexanol followed by flash chromatography (5-50% EtOAc/hexanes gradient), gave 2,2,2-trifluoro-N-(2-(3-((2-hydroxycyclohexyl)ethynyl)phenoxy)ethyl)acetamide as a yellow oil. Yield (0.88 g, 31%): $^1$H NMR (400 MHz, CDCl$_3$) δ 7.18 (t, J=8.0 Hz, 1H), 7.01-7.04 (m, 1H), 6.90-6.98 (brs, 1H), 6.91-6.92 (m, 1H), 6.79-6.83 (m, 1H), 4.05-4.07 (m, 2H), 3.74 (app q, J=5.2 Hz, 2H), 3.48-3.56 (m, 1H), 2.35-2.46 (m, 2H), 2.00-2.08 (m, 1H), 1.64-1.80 (m, 2H), 1.40-1.52 (m, 1H), 1.14-1.40 (m, 4H).

Step 2: Deprotection of 2,2,2-trifluoro-N-(2-(3-(2-hydroxycyclohexyl)-ethynyl)phenoxy)ethyl)acetamide followed by purification by flash chromatography (10% (7N NH$_3$/MeOH)/dichloromethane) gave 2-((3-(2-aminoethoxy)phenyl)ethynyl)cyclohexanol as a white solid. Yield (0.29 g, 45%): $^1$H NMR (400 MHz, CDCl$_3$) δ 7.18 (t, J=7.6 Hz, 1H), 6.98-7.03 (m, 1H), 6.93-6.95 (m, 1H), 6.83-6.86 (m, 1H), 3.96 (t, J=5.2 Hz, 2H), 3.49-3.57 (m, 1H), 3.08 (brs, 2H), 2.38-2.46 (m, 1H), 2.01-2.10 (m, 2H), 1.55-2.00 (brs, 1H), 1.74-1.82 (m, 2H), 1.65-1.74 (m, 2H), 1.40-1.52 (m, 1H), 1.16-1.40 (m, 3H).

Step 3: Hydrogenation of 2-((3-(2-aminoethoxy)phenyl)ethynyl)cyclohexanol followed by flash chromatography (10% (7N NH$_3$/MeOH)/dichloromethane) gave example 99 as a yellow-green oil. Yield (0.99 g, 67%): $^1$H NMR (400 MHz, CDCl$_3$) δ 7.17 (t J=8.0 Hz, 1H), 6.75-6.80 (m, 2H), 6.69-6.73 (m, 1H), 3.70 (t, J=5.2 Hz, 2H), 3.19-3.27 (m, 1H), 3.06 (t, J=5.2 Hz, 2H), 2.66-2.79 (m, 1H), 2.47-2.56 (m, 1H), 2.05-2.14 (m, 1H), 1.87-1.97 (m, 2H), 1.69-1.77 (m, 1H), 1.61-1.69 (m, 1H), 1.53 (brs, 3H), 1.36-1.46 (m, 1H), 1.11-1.34 (m, 4H), 0.91-1.03 (m, 1H).

Example 100

Preparation of 2-(3-(3-Amino-1-Hydroxypropyl) Phenethyl)Cyclohexanol

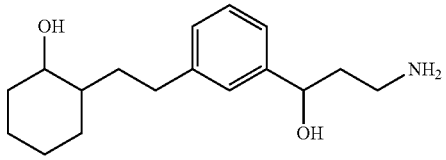 [SMILES: NCCC(O)c1cccc(CCC2CCCCC2O)c1]

2-(3-(3-Amino-1-hydroxypropyl)phenethyl)cyclohexanol was prepared following the method used in Example 63.

Step 1: Sonogashira coupling of bromide 43 with 2-ethynylcyclohexanol followed by flash chromatography (5-50% EtOAc/hexanes gradient), gave 2,2,2-trifluoro-N-(3-hydroxy-3-(3-((2-hydroxycyclohexyl)ethynyl)phenyl)propyl)acetamide as a yellow oil. Yield (1.9 g, 63%): $^1$H NMR (400 MHz, CDCl$_3$) δ 7.39-7.41 (m, 1H), 7.23-7.36 (m, 4H), 4.84 (q, J=4.0 Hz, 1H), 3.62-3.72 (m, 1H), 3.50-3.57 (m, 1H), 3.34-3.44 (m, 1H), 2.38-2.46 (m 1H), 2.18 (brs, 2H), 1.90-2.10 (m, 4H), 1.66-1.84 (m, 2H), 1.40-1.53 (m, 1H), 1.16-1.40 (m, 3H).

Step 2: Deprotection of 2,2,2-trifluoro-N-(3-hydroxy-3-(3-((2-hydroxycyclohexyl)ethynyl)phenyl)propyl)acetamide followed by flash chromatography (10% (7N NH$_3$/MeOH)/dichloromethane) gave 2-((3-(3-amino-1-hydroxypropyl)phenyl)ethynyl)cyclohexanol as a light yellow glassy solid. Yield (0.402 g, 29%): $^1$H NMR (400 MHz, CDCl$_3$) δ 7.44-7.46 (m, 1H), 7.21-7.31 (m, 3H), 4.92 (dd, J=8.8, 3.2 Hz, 1H), 3.47-3.56 (m, 1H), 3.05-3.12 (m, 1H), 3.01 (brs, 4H), 2.90-2.99 (m, 1H), 2.37-2.44 (m, 1H), 2.00-2.09 (m, 2H), 1.81-1.90 (m, 1H), 1.64-1.81 (m, 3H), 1.40-1.52 (m, 1H), 1.14-1.40 (m, 3H).

Step 3: Hydrogenation of 2-((3-(3-amino-1-hydroxypropyl)phenyl)ethynyl)cyclohexanol followed by flash chromatography (10% (7N NH$_3$/MeOH)/dichloromethane) gave Example 100 as a yellow oil. Yield (0.153 g, 67%): $^1$H NMR (400 MHz, CDCl$_3$) δ 7.19-7.26 (m, 2H), 7.13-7.17 (m, 1H), 7.05-7.08 (m, 1H), 4.88-4.93 (dd, J=3.2, 8.8 Hz, 1H), 3.17-3.25 (m, 1H), 3.01-3.10 (m, 1H), 2.88-2.97 (m, 1H), 2.60-2.88 (m, 5H), 2.49-2.58 (m, 1H), 2.05-2.15 (m, 1H), 1.54-1.96 (m, 6H), 1.35-1.47 (m, 1H), 1.10-1.33 (m, 4H), 0.91-1.02 (m, 1H).

Example 101

Preparation of 1-(3-(2-Aminoethoxy)Phenethyl)Cyclobutanol

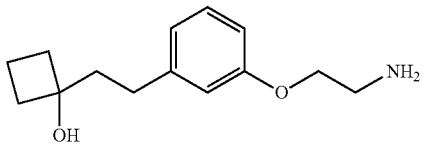 [SMILES: NCCOc1cccc(CCC2(O)CCC2)c1]

1-(3-(2-Aminoethoxy)phenethyl)cyclobutanol was prepared following the method used in Example 64.

Step 1: Sonogashira reaction of bromide 19 with 1-ethynylcyclobutanol gave 2,2,2-trifluoro-N-(2-(3-(2-(1-hydroxycyclobutyl)ethynyl)phenoxy) ethyl)acetamide as a brown oil. Yield (0.85 g, 39%): $^1$H NMR (400 MHz, DMSO-d$_6$) δ 7.27-7.30 (m, 1H), 6.92-7.03 (m, 3H), 4.09-4.13 (m, 4H), 3.54-3.58 (m, 2H), 2.33-2.37 (m, 2H), 2.16-2.24 (m, 2H), 1.74-1.81 (m, 2H).

Step 2: A solution of 2,2,2-Trifluoro-N-(2-(3-(2-(1-hydroxy cyclobutyl)ethynyl)phenoxy)ethyl)acetamide (0.45 g, 1.9 mmol) in EtOH (20 mL) was degassed and purged with nitrogen. To this was added Pd on C (0.09 g, 10%) and the flask was evacuated and filled with hydrogen. The resulting reaction mixture was stirred at room temperature under hydrogen balloon overnight. This was followed by filteration through a pad of Celite. The filter cake was washed with ethanol and the filtrate concentrated to afford 2,2,2-trifluoro-N-(2-(3-(2-(1-hydroxycyclobutyl)ethyl)phenoxy)ethyl)acetamide as yellow oil. Yield (0.3 g, 66%): $^1$H NMR (400 MHz, DMSO-d$_6$) δ 7.20-7.25 (m, 1H), 6.87 (d, J=7.6 Hz, 1H), 6.78 (s, 1H), 6.72 (dd, J=8.0, 2.4 Hz, 1H), 4.11 (t, J=5.0 Hz, 2H), 3.76-3.81 (m, 2H), 2.67-2.72 (m, 2H), 2.01-2.14 (m, 4H), 1.92-1.96 (m, 2H), 1.22-1.26 (m, 2H).

Step 3: To a stirred solution of 2,2,2-trifluoro-N-(2-(3-(2-(1-hydroxy cyclobutyl)ethyl)phenoxy)ethyl)acetamide (0.3 g, 0.9 mmol) in MeOH-water (6:0.5) mL was added K$_2$CO$_3$ (0.187 g, 1.4 mmol). The resulting mixture was stirred overnight following which the solvent was removed under reduced pressure. The residue was partitioned between DCM and water and the combined organics were washed with water followed by drying over Na$_2$SO$_4$. The filtrate was concentrated under reduced pressure to give Example 101 as brown oil. Yield (0.12 g, 56%): $^1$H NMR (400 MHz, DMSO-d$_6$) δ 7.17-7.22 (m, 1H), 6.81-6.85 (m, 2H), 6.77 (dd, J=7.6, 2.0 Hz, 2H), 4.12 (t, J=5.2 Hz, 2H), 3.18 (t, J=5.2 Hz, 2H), 2.52-2.60 (m, 2H), 1.91-1.97 (m, 4H), 1.70-1.76 (m, 2H), 1.58-1.66 (m, 1H), 1.40-1.50 (m, 1H). $^{13}$C NMR (100 MHz, DMSO-d$_6$) δ 158.4, 145.1, 129.8, 121.7, 115.1, 112.2, 73.7, 64.6, 41.8, 38.8, 36.1, 30.1, 12.3. MS: 236 [M+1]$^+$.

Example 102

Preparation of 1-(3-(3-Amino-1-Hydroxypropyl)Phenyl)-4-Methylpentan-3-ol

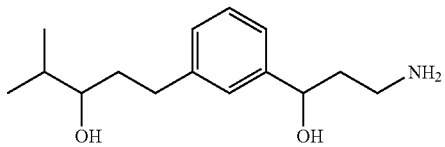 [SMILES: CC(C)C(O)CCc1cccc(C(O)CCN)c1]

1-(3-(3-Amino-1-hydroxypropyl)phenyl)-4-methylpentan-3-ol was prepared following the method used in Example 79.

Step 1: Sonogashira reaction of 39 with 4-methyl-pent-1-yn-3-ol yielded tert-butyl 3-hydroxy-3-(3-(3-hydroxy-4-methylpent-1-ynyl)phenyl)propylcarbamate as dark brown oil. Yield (1.73 g, 81%): $^1$H NMR (400 MHz, CDCl$_3$) δ 7.44 (s, 1H), 7.28-7.34 (m, 3H), 4.86 (bs, 1H), 4.72 (bs, 1H), 4.39 (t, J=6.0 Hz, 1H), 3.46-3.51 (m, 2H), 3.11-3.19 (m, 1H), 1.78-2.04 (m, 4H), 1.45 (s, 9H), 1.02 (d, J=7.2 Hz, 3H), 1.06 (d, J=7.2 Hz, 3H).

Step 2: Reduction of tert-butyl 3-hydroxy-3-(3-(3-hydroxy-4-methylpent-1-ynyl)phenyl)propylcarbamate resulted in tert-butyl 3-hydroxy-3-(3-(3-hydroxy-4-methylpentyl)phenyl)propylcarbamate as yellow oil. Yield (0.847 g, 91%): $^1$H NMR (400 MHz, CDCl$_3$) δ 7.24-7.28 (m, 1H), 7.22 (s, 1H), 7.18 (d, J=7.2 Hz, 1H), 7.12 (d, J=7.2 Hz, 1H), 4.89 (bs, 1H), 4.70-4.72 (m, 1H), 3.46-3.51 (m, 1H), 3.35-3.40 (bs, 1H), 3.15-3.18 (m, 2H), 2.81-2.84 (m, 1H), 2.64-2.67 (m, 1H), 1.80-1.87 (m, 2H), 1.64-1.79 (m, 3H), 1.45 (s, 9H), 0.92 (d, J=6.8, 6H).

Step 3: Deprotection of tert-butyl 3-hydroxy-3-(3-(3-hydroxy-4-methylpentyl)phenyl)propylcarbamate gave Example 102 hydrochloride as pale yellow semi-solid. Yield (0.205 g, 30%): $^1$H NMR (400 MHz, DMSO-d$_6$) δ 7.22 (t, J=7.6 Hz, 1H), 7.13 (s, 1H), 7.18 (d, J=7.6 Hz, 1H), 7.12 (d, J=7.6 Hz, 1H), 4.61 (t, J=6.8 Hz, 1H), 3.81 (m, 1H) 3.14-3.18 (m, 1H), 2.83-2.90 (m, 2H), 2.77-2.80 (m, 1H), 1.81-1.85 (m, 2H), 1.48-1.61 (m, 3H), 0.92 (d, J=6.8 Hz, 6H). $^{13}$C NMR (100 MHz, DMSO-d$_6$) δ 145.7, 143.0, 128.5, 127.4, 126.0, 125.9, 123.3, 74.3, 70.2, 36.8, 36.4, 33.7, 32.5, 19.4, 18.0. MS: 252 [M+1]$^+$.

Example 103

Preparation of 1-(3-(3-Aminopropyl)Phenethyl)Cyclooctanol

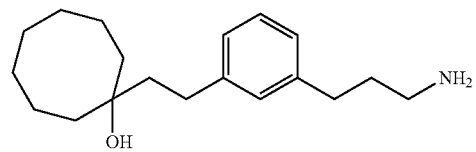

1-(3-(3-Aminopropyl)phenethyl)cyclooctanol was prepared following the method used in Example 57 except that the hydrogenation was conducted before the deprotection of the amine.

Step 1: Sonogashira coupling of bromide 10 with 1-ethynyl-cyclooctanol gave 2,2,2-trifluoro-N-(3-(3-(2-(1-hydroxycyclooctyl)ethynyl)phenyl)propyl)acetamide. Yield (0.344 g, 47%). $^1$H NMR (400 MHz, CDCl$_3$) δ 7.22-7.29 (m, 2H), 7.15-7.19 (m, 1H), 7.11-7.13 (m, 1H), 6.23 (bs, 1H), 3.36-3.42 (m, 2H), 1.48-2.07 (m, 18H).

Step 2: Reduction of 2,2,2-trifluoro-N-(3-(3-((1-hydroxycyclooctyl)ethynyl)phenyl)propyl)acetamide gave 2,2,2-trifluoro-N-(3-(3-(2-(1-hydroxycyclooctyl)ethyl)phenyl)propyl) acetamide as yellow oil. Yield (0.895 g, 98%): $^1$H NMR (400 MHz, CDCl$_3$) δ 7.19-7.24 (m, 1H), 7.06 (d, J=7.2 Hz, 1H), 7.02 (s, 1H), 6.99 (d, J=7.2 Hz, 1H), 3.36-3.42 (m, 2H), 2.64-2.70 (m, 4H), 1.89-1.96 (m, 2H), 1.32-1.87 (m, 16H).

Step 7: Deprotection of 2,2,2-trifluoro-N-(3-(3-(2-(1-hydroxycyclooctyl)ethyl)phenyl)propyl)acetamide gave Example 103 as yellow oil. Yield (0.277 g, 42%): $^1$H NMR (400 MHz, DMSO-d$_6$) δ 7.12-7.16 (m, 1H), 6.94-6.98 (m, 3H), 2.50-2.56 (m, 6H), 1.32-1.70 (m, 18H). $^{13}$C NMR (100 MHz, DMSO-d$_6$): 143.3, 142.1, 128.2, 128.1, 125.6, 125.4, 72.6, 43.7, 40.9, 35.7, 34.5, 32.5, 29.3, 28.0, 24.7, 22.0. MS: 290 [M+1]$^+$.

Example 104

Preparation of 5-(3-(3-Amino-1-Hydroxypropyl)Phenylpentanamide

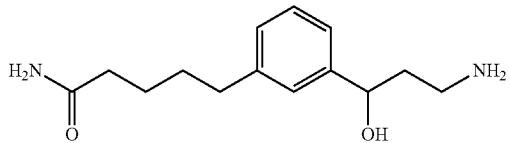 [SMILES: NCCC(O)c1cccc(CCCCC(N)=O)c1]

5-(3-(3-Amino-1-hydroxypropyl)phenyl)pentanamide was prepared following the method used in Example 19.

Step 1: Sonogashira reaction of 43 with pent-4-ynamide gave 5-(3-(1-hydroxy-3-(2,2,2-trifluoroacetamido)propyl) phenyl)pent-4-ynamide as brown oil. Yield (0.6 g, 57%). This compound was utilized as such for the next transformation. MS: 343 [M+1]$^+$.

Step 2: Reduction of 5-(3-(1-hydroxy-3-(2,2,2-trifluoro acetamido)propyl)phenyl)pent-4-ynamide yielded 5-(3-(1-hydroxy-3-(2,2,2-trifluoro acetamido)propyl)phenyl)pentanamide as yellow oil. Yield (0.51 g, 83%). This compound was also utilized as such for the next transformation. MS: 347 [M+1]$^+$.

Step 3: Deprotection of 5-(3-(1-hydroxy-3-(2,2,2-trifluoroacetamido)propyl)phenyl)pentanamide and subsequent purification by flash chromatography (0-10% (MeOH—NH$_3$ (9.5:0.5))-DCM gradient) gave Example 104 as clear oil. Yield (0.125 g, 35%): $^1$H NMR (400 MHz, DMSO-d$_6$) δ 7.23 (t, J=7.6 Hz, 1H), 7.12 (s, 1H), 7.10 (d, J=7.6 Hz, 1H), 7.04 (d, J=7.6 Hz, 1H), 4.60 (t, J=6.4 Hz, 1H), 2.77-2.89 (m, 2H), 2.56 (t, J=6.8 Hz, 2H), 2.05 (t, J=6.8 Hz, 2H), 1.79-1.85 (m, 2H), 1.48-1.52 (m, 4H). $^{13}$C NMR (100 MHz, DMSO-d$_6$) δ 174.7, 145.7, 142.5, 128.5, 127.4, 125.9, 123.4, 70.3, 37.1, 37.0, 35.5, 35.4, 31.2, 25.2. MS: 251 [M+1]$^-$.

Example 105

Preparation of 3-Amino-1-(3-(2-Cyclooctylethyl) Phenyl)Propan-1-OL

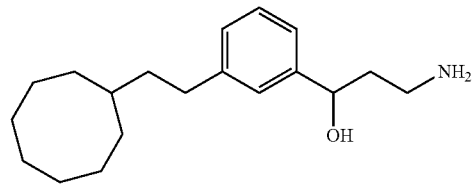 [SMILES: NCCC(O)c1cccc(CCC2CCCCCCC2)c1]

3-Amino-1-(3-(2-cyclooctylethyl)phenyl)propan-1-ol was prepared following the method used in Example 79.

Step 1: Sonogashira reaction of 39 with ethynyl cyclooctane yielded tert-butyl 3-(3-(2-cyclooctylethynyl)phenyl)-3-hydroxypropylcarbamate as light yellow oil. Yield (470 mg, 91%): $^1$H NMR (400 MHz, CDCl$_3$) δ 7.39 (s, 1H), 7.22-7.29 (m, 3H), 4.86 (bs, 1H), 4.72 (m, 1H), 3.23 (bs, 1H), 3.11-3.19 (m, 1H), 2.76-2.79 (m, 2H), 1.92-1.96 (m, 2H), 1.74-1.81 (m, 6H), 1.53-1.60 (m, 6H), 1.45 (s, 9H), 1.27 (m, 2H).

Step 2: Reduction of tert-butyl 3-(3-(cyclooctylethynyl) phenyl)-3-hydroxypropylcarbamate gave tert-butyl 3-(3-(2-cyclooctylethyl)phenyl)-3-hydroxypropylcarbamate as yellow oil. Yield (0.232 g, 89%). $^1$H NMR (400 MHz, CDCl$_3$) δ 7.22 (t, J=7.6 Hz, 1H), 7.18 (s, 1H), 7.16 (d, J=7.6 Hz, 1H), 7.09 (d, J=7.6 Hz, 1H), 4.89 (bs, 1H), 4.72 (m, 1H), 3.49-3.54 (m, 1H), 3.13-3.21 (m, 1H), 3.07 (bs, 1H), 2.58-2.62 (m, 2H), 1.82-1.87 (m, 2H), 1.63-1.68 (m, 4H), 1.49-1.57 (m, 5H), 1.46-1.48 (m, 3H), 1.45 (s, 9H), 1.28-1.33 (m, 2H).

Step 3: Deprotection of tert-butyl 3-hydroxy-3-(3-(2-(tetrahydro-2H-pyran-2-yl)ethyl)phenyl)propylcarbamate gave a semi-solid product which was purified by flash chromatography (0-10% MeOH-DCM gradient) to obtain Example 105 hydrochloride as off-white solid. Yield (0.194 g, 40%): $^1$H NMR (400 MHz, DMSO-d$_6$) δ 7.60 (bs, 1H), 7.23 (t, J=7.6 Hz, 1H), 7.14 (s, 1H), 7.11 (d, J=7.6 Hz, 1H), 7.08 (d, J=7.6 Hz, 1H), 4.64 (m, 1H), 2.81-2.86 (m, 2H), 2.56-2.58 (m, 2H), 1.79-1.83 (m, 2H), 1.54-1.65 (m, 7H), 1.40-1.47 (m, 9H), 1.28-1.33 (m, 2H). $^{13}$C NMR (100 MHz, DMSO-d$_6$) δ 145.7, 142.9, 128.5, 127.3, 125.9, 123.3, 70.2, 37.2, 36.9, 36.8, 33.7, 32.2, 27.3, 26.3, 25.4. MS: 290 [M+1]$^+$.

Example 106

Preparation of 3-Amino-1-(3-(5-Methoxypentyl) Phenyl)Propan-1-ol

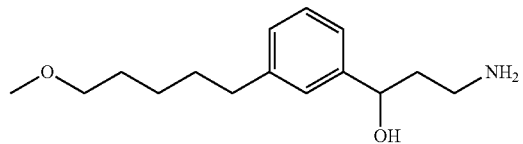 [SMILES: COCCCCCc1cccc(C(O)CCN)c1]

3-Amino-1-(3-(5-methoxypentyl)phenyl)propan-1-ol was prepared following the method used in Example 79.

Step 1: Sonogashira reaction of 39 with 5-methoxypent-1-yne gave tert-butyl 3-hydroxy-3-(3-(5-methoxypent-1-ynyl) phenyl)propylcarbamate as brown oil. Yield (0.347 g, 66%): $^1$H NMR (400 MHz, CDCl$_3$) δ 7.39 (s, 1H), 7.27-7.37 (m, 3H), 4.83-4.85 (bs, 1H), 4.69-4.71 (m, 1H), 3.66-3.71 (m, 1H), 3.52 (t, J=6.4 Hz, 2H), 3.48 (m, 1H), 3.36 (s, 3H), 3.29 (bs, 1H), 2.49 (t, J=6.4 Hz, 2H), 1.80-2.02 (m, 4H), 1.45 (s, 9H).

Step 2: Reduction of tert-butyl 3-hydroxy-3-(3-(5-methoxypent-1-ynyl)phenyl)propylcarbamate yielded tert-butyl 3-hydroxy-3-(3-(5-methoxypentyl)phenyl)propylcarbamate as yellow oil. Yield (0.299 g, 88%). $^1$H NMR (400 MHz, DMSO-$d_6$) δ 7.19 (t, J=7.6 Hz, 1H), 7.09 (s, 1H), 7.07 (d, J=7.6 Hz, 1H), 7.02 (d, J=7.6 Hz, 1H), 4.48 (t, J=6.4 Hz, 1H), 3.27 (t, J=6.4 Hz, 2H), 3.16 (s, 3H), 2.91-2.94 (m, 2H), 2.50-2.54 (m, 2H), 1.62-1.67 (m, 2H), 1.47-1.56 (m, 4H), 1.33 (s, 9H), 1.23-1.28 (m, 2H).

Step 3: Deprotection of tert-butyl 3-hydroxy-3-(3-(5-methoxypentyl)phenyl)propylcarbamate and subsequent purification by flash chromatography (0-10% MeOH—NH$_3$ (9.5:0.5)-DCM) gave Example 106 as clear oil. Yield (0.178 g, 72%): $^1$H NMR (400 MHz, DMSO-$d_6$) δ 7.20 (t, J=7.6 Hz, 1H), 7.11 (s, 1H), 7.09 (d, J=7.6 Hz, 1H), 7.04 (d, J=7.6 Hz, 1H), 4.58-4.61 (m, 1H), 3.30 (t, J=6.4 Hz, 2H), 3.18 (s, 3H), 2.78-2.87 (m, 2H), 2.53-2.55 (m, 2H), 1.79-1.84 (m, 2H), 1.47-1.57 (m, 4H), 1.23-1.28 (m, 2H). $^{13}$C NMR (100 MHz, DMSO-$d_6$) δ 146.4, 141.7, 127.7, 126.4, 125.6, 123.0, 71.8, 71.4, 57.7, 42.5, 38.9, 35.2, 30.8, 28.8, 25.4. MS: 252 [M+1]$^+$.

Example 107

Preparation of 2-(3-(5-Methoxypentyl)Phenoxy)Ethanamine

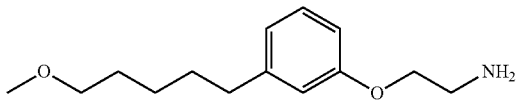 [SMILES: COCCCCCc1cccc(OCCN)c1]

2-(3-(5-Methoxypentyl)phenoxy)ethanamine was prepared following the method used in Example 64.

Step 1: Sonogashira reaction of bromide 19 with 5-methoxypent-1-yne gave 2,2,2-trifluoro-N-(2-(3-(5-methoxypent-1-ynyl)phenoxy)ethyl)acetamide as a brown oil. Yield (0.305 g, 29%): $^1$H NMR (400 MHz, DMSO-$d_6$) δ 7.22-7.27 (m, 1H), 6.97 (d, J=7.6 Hz, 1H), 6.90-6.94 (m, 2H), 4.10 (t, J=5.6 Hz, 2H), 3.53-3.58 (m, 2H), 3.43 (t, J=6.4 Hz, 2H), 3.25 (s, 3H), 2.45 (t, J=7.2 Hz, 2H), 1.72-1.79 (m, 2H).

Step 2: The reduction of 2,2,2-trifluoro-N-(2-(3-(5-methoxypent-1-ynyl)phenoxy)ethyl)acetamide afforded 2,2,2-trifluoro-N-(2-(3-(5-methoxypentyl)phenoxy)ethyl)acetamide as yellow oil. Yield (0.265 g, 87%): $^1$H NMR (400 MHz, DMSO-$d_6$) δ 7.15-7.20 (m, 1H), 6.72-6.78 (m, 3H), 4.06 (t, J=5.6 Hz, 2H), 3.53-3.58 (m, 2H), 3.30 (t, J=6.4 Hz, 2H), 3.19 (s, 3H), 2.53 (t, J=7.2 Hz, 2H), 1.48-1.60 (m, 4H), 1.26-1.32 (m, 2H).

Step 3: Deprotection of 2,2,2-trifluoro-N-(2-(3-(5-methoxypentyl)phenoxy)ethyl)acetamide gave Example 107 as yellow oil. Yield (0.115 g, 62%): $^1$H NMR (400 MHz, DMSO-$d_6$) δ 7.14-7.18 (m, 1H), 6.71-6.75 (m, 3H), 3.89 (t, J=5.8 Hz, 2H), 3.28 (t, J=6.4 Hz, 2H), 3.20 (s, 3H), 2.87 (t, J=5.8 Hz, 2H), 2.52 (t, J=7.2 Hz, 2H), 1.47-1.60 (m, 4H), 1.26-1.32 (m, 2H). $^{13}$C NMR (100 MHz, DMSO-$d_6$) δ 158.3, 144.4, 129.7, 121.7, 115.1, 112.2, 72.3, 64.5, 58.2, 38.7, 35.6, 31.1, 29.3, 25.8. MS: 238 [M+1]$^+$ Example 108

Preparation of 2-(3-(2-Cyclooctylethyl)Phenoxy)Ethanamine

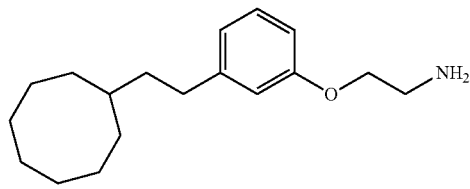 [SMILES: NCCOc1cccc(CCC2CCCCCCC2)c1]

2-(3-(2-Cyclooctylethyl)phenoxy)ethanamine was prepared following the method used in Example 64.

Step 1: Sonogashira reaction of bromide 19 with ethynylcyclooctane gave N-(2-(3-(cyclooctylethynyl)phenoxy)ethyl)-2,2,2-trifluoroacetamide as a brown oil. Yield (0.505 g, 50%): $^1$H NMR (400 MHz, DMSO-$d_6$) δ 7.21-7.27 (m, 1H), 6.94 (d, J=7.2 Hz, 1H), 6.88-6.92 (m, 2H), 4.09 (t, J=5.4 Hz, 2H), 3.52-3.57 (m, 2H), 2.79-2.84 (m, 1H), 1.86-1.92 (m, 2H), 1.67-1.76 (m, 4H), 1.47-1.58 (m, 8H).

Step 2: Reduction of 2,2,2-trifluoro-N-(2-(3-((1-hydroxycyclooctyl)ethynyl)phenoxy)ethyl)acetamide afforded 2,2,2-trifluoro-N-(2-(3-(2-(1-hydroxycyclooctyl)ethyl)phenoxy)ethyl)acetamide as yellow oil. Yield (0.215 g, 70%): $^1$H NMR (400 MHz, DMSO-$d_6$) δ 7.14-7.19 (m, 1H), 6.74-6.78 (m, 3H), 4.05 (t, J=5.6 Hz, 2H), 3.53-3.58 (m, 2H), 2.50-2.55 (m, 2H), 1.22-1.68 (m, 17H). MS: 372 [M+1]$^+$.

Step 3: Deprotection of 2,2,2-trifluoro-N-(2-(3-(2-(1-hydroxycyclooctyl)ethyl)phenoxy)ethyl)acetamide gave Example 108 as yellow oil. Yield (0.07 g, 45%): $^1$H NMR (400 MHz, DMSO-$d_6$) δ 7.13-7.18 (m, 1H), 6.70-6.75 (m, 3H), 3.91 (t, J=5.6 Hz, 2H), 2.87 (t, J=5.6 Hz, 2H), 2.50-2.54 (m, 2H), 1.22-1.66 (m, 17H). $^{13}$C NMR (100 MHz, DMSO-$d_6$) δ 158.3, 144.8, 129.8, 121.7, 115.1, 112.3, 64.6, 40.6, 38.8, 36.7, 33.6, 32.2, 27.3, 26.3, 25.4. MS: 276 [M+1]$^+$ Example 109

Preparation of 1-(3-(3-Amino-1-Hydroxypropyl) Phenyl)-3-Methylhexan-3-ol

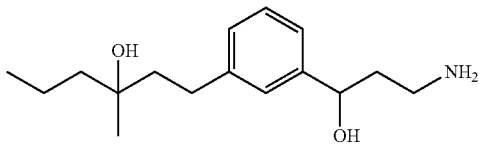 [SMILES: CCCC(C)(O)CCc1cccc(C(O)CCN)c1]

1-(3-(3-Amino-1-hydroxypropyl)phenyl)-3-methylhexan-3-ol was prepared following the method used in Example 19.

Step 1: Sonogashira reaction of 43 with 3-methylhex-1-yn-3-ol gave 2,2,2-trifluoro-N-(3-hydroxy-3-(3-(3-hydroxy-3-methylhex-1-ynyl)phenyl)propyl)acetamide as brown oil. Yield (0.908 g, 90%): $^1$H NMR (400 MHz, CDCl$_3$) δ 7.37 (s, 1H), 7.30-7.35 (m, 1H), 7.26-7.28 (m, 2H), 4.83-4.86 (m, 1H), 3.66-3.69 (m, 1H), 3.39-3.42 (m, 1H), 2.60 (bs, 1H), 2.11 (bs, 1H), 1.94-1.99 (m, 2H), 1.69-1.74 (m, 2H), 1.65 (s, 3H), 1.54-1.57 (m, 2H), 0.97 (t, J=7.2 Hz, 3H).

Step 2: Reduction of 2,2,2-trifluoro-N-(3-hydroxy-3-(3-(3-hydroxy-3-methylhex-1-ynyl)phenyl)propyl)acetamide yielded 2,2,2-trifluoro-N-(3-hydroxy-3-(3-(3-hydroxy-3-methylhexyl)phenyl)propyl)acetamide as yellow oil. Yield (0.99 g, 90%). This compound was utilized as such for the next transformation.

Step 3: Deprotection of 2,2,2-trifluoro-N-(3-hydroxy-3-(3-(3-hydroxy-3-methylhexyl)phenyl)propyl)acetamide gave a yellow oil, which upon purification by flash chromatography (0-10% MeOH—NH₃ (9.5:0.5)-DCM gradient) yielded Example 109 as clear oil. Yield (0.597 g, 82%): $^1$H NMR (400 MHz, DMSO-d$_6$) δ 7.22 (t, J=7.2 Hz, 1H), 7.12 (s, 1H), 7.08 (d, J=7.2 Hz, 1H), 7.04 (d, J=7.2 Hz, 1H), 4.60 (t, J=6.4 Hz, 1H), 2.70-2.73 (m, 2H), 2.55-2.58 (m, 2H), 1.69-1.74 (dd, J=6.4 Hz, 12.8 Hz, 2H), 1.55-1.58 (m, 2H), 1.17-1.37 (m, 4H), 1.07 (s, 3H), 0.86 (t, J=7.2 Hz, 3H). $^{13}$C NMR (100 MHz, DMSO-d$_6$) δ 146.0, 142.8, 128.0, 126.7, 125.4, 122.8, 70.6, 70.5, 44.1, 43.9, 37.7, 30.0, 26.8, 16.8, 14.8. MS: 266 [M+1].

Example 110

Preparation of 3-Amino-1-(3-(2-(Tetrahydro-2H-Pyran-2-yl)Ethyl)Phenylpropan-1-ol

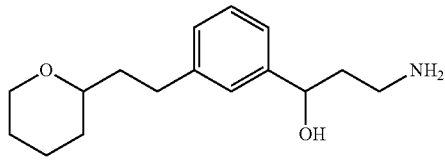 [SMILES: NCCC(O)c1cccc(CCC2CCCCO2)c1]

3-Amino-1-(3-(2-(tetrahydro-2H-pyran-2-yl)ethyl)phenyl)propan-1-ol was prepared following the method shown in Scheme 18 and used for Examples 3, 13, 16 and 17.

SCHEME 18

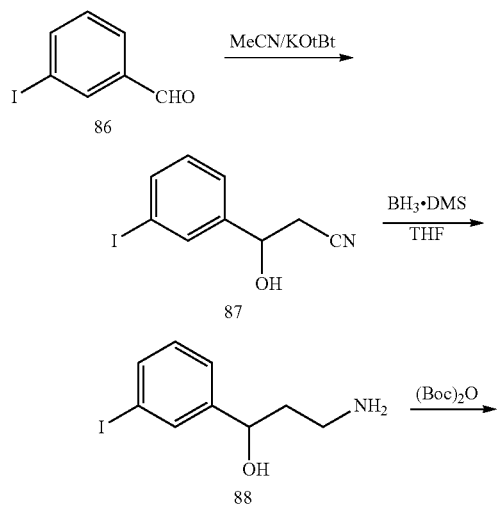

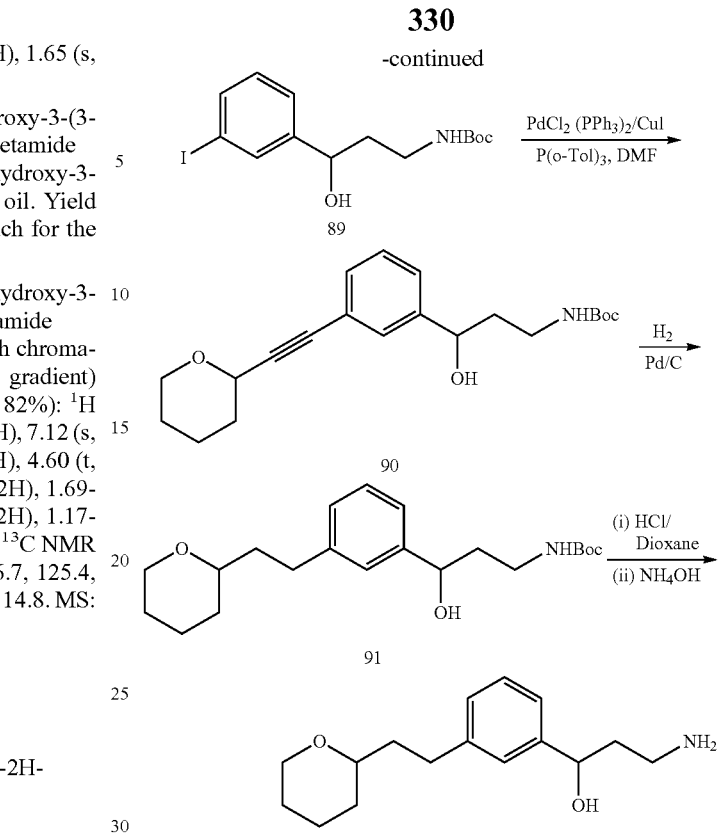

Step 1: Acetonitrile addition to 3-iodobenzaldehyde (86) according to the method used for Example 16 yielded 3-hydroxy-3-(3-iodophenyl)propanenitrile (87) as yellow oil. Yield (2.58 g, 55%): $^1$H NMR (400 MHz, CDCl$_3$) δ 7.82 (s, 1H), 7.70 (d, J=8.0 Hz, 1H), 7.38 (d, J=8.0 Hz, 1H), 7.14 (t, J=8.0 Hz, 1H), 5.01 (m, 1H), 2.80 (d, J=6.4, 2H), 2.40 (bs, 1H).

Step 2: Nitrile reduction of 87 according to the method used in Example 17 yielded 3-amino-1-(3-iodophenyl)propan-1-ol (88) as pale yellow oil. Yield (2.63 g, quantitative yield). This compound was utilized as such for the next transformation. $^1$H NMR (400 MHz, CDCl$_3$) δ 7.76 (s, 1H), 7.58 (d, J=7.6, 1H), 7.33 (d, J=7.6, 1H), 7.06 (t, J=8.0, 1H), 4.92 (dd, J=8.8,2.8 Hz, 1H), 3.09-3.14 (m, 1H), 2.93-2.99 (m, 1H), 1.81-1.85 (m, 1H), 1.64-1.73 (m, 1H).

Step 3: BOC protection of amine 88 as in Example 17 gave tert-butyl 3-hydroxy-3-(3-iodophenyl)propylcarbamate (89) as yellow oil. Yield (1.39 g, 40%). This compound was utilized as such for the next transformation. $^1$H NMR (400 MHz, CDCl$_3$) δ 7.73 (s, 1H), 7.58 (d, J=7.6, 1H), 7.33 (d, J=7.6, 1H), 7.07 (t, J=8.0, 1H), 4.86 (bs, 1H), 4.67 (m, 1H), 3.45-3.51 (m, 2H), 3.11-3.18 (m, 1H), 1.76-1.83 (m, 2H), 1.51 (s, 9H).

Step 4: Sonogashira reaction of 89 with 2-ethynyltetrahydro-2H-pyran according to the method in Example 3 yielded tert-butyl 3-hydroxy-3-(3-((tetrahydro-2H-pyran-2-yl)ethynyl)phenyl)propylcarbamate (90) as dark brown oil. Yield (1.21 g, 83%): $^1$H NMR (400 MHz, CDCl$_3$) δ 7.45 (s, 1H), 7.27-7.35 (m, 3H), 4.87 (bs, 1H), 4.69-4.71 (m, 1H), 4.49-4.51 (m, 1H), 4.02-4.07 (m, 1H), 3.50-3.52 (m, 1H), 3.56-3.61 (m, 1H), 3.13-3.18 (m, 1H), 1.91-1.93 (m, 2H), 1.74-1.86 (m, 4H), 1.51 (m, 2H), 1.43 (s, 9H).

Step 5: Reduction of tert-butyl 3-hydroxy-3-(3-((tetrahydro-2H-pyran-2-yl)ethynyl)phenyl)propylcarbamate according to the method used for Example 13 gave tert-butyl 3-hydroxy-3-(3-(2-(tetrahydro-2H-pyran-2-yl)ethyl)phenyl) propylcarbamate (91) as yellow oil. Yield (0.592 g, crude). $^1$H NMR (400 MHz, CDCl$_3$) δ 7.23 (t, J=7.2 Hz, 1H), 7.19 (s, 1H), 7.10 (d, J=7.2 Hz, 1H), 7.02 (d, J=7.2 Hz, 1H), 4.89 (bs, 1H), 4.64 (t, J=7.6 Hz, 1H), 3.98-4.0 (m, 1H), 3.38-3.43 (m, 2H), 3.14-3.32 (m, 3H), 2.60-2.76 (m, 2H), 1.80-1.85 (m, 4H), 1.59-1.61 (m, 1H), 1.50-1.53 (m, 2H), 1.45 (s, 9H), 1.20-1.33 (m, 3H).

Step 6: Deprotection of 91 according to the method used in Example 13 gave a crude product which was purified by flash chromatography (0-10% MeOH-DCM gradient) to obtain Example 110 hydrochloride as an off-white solid. Yield (0.194 g, 40%): $^1$H NMR (400 MHz, DMSO-d$_6$) δ 7.24 (t, J=7.2 Hz, 1H), 7.14 (s, 1H), 7.10 (d, J=7.2 Hz, 1H), 7.07 (d, J=7.2 Hz, 1H), 4.64 (t, J=7.6 Hz, 1H), 3.82-3.87 (m, 2H), 3.17-3.21 (m, 2H), 2.76-2.84 (m, 2H), 2.58-2.63 (m, 1H), 1.80-1.84 (m, 2H), 1.54-1.67 (m, 3H), 1.43-1.51 (m, 3H), 1.16 (m, 1H). $^{13}$C NMR (100 MHz, DMSO-d$_6$) δ 145.8, 142.4, 128.5, 127.3, 125.9, 123.4, 76.6, 70.1, 67.9, 38.4, 37.1, 36.8, 31.9, 31.7, 26.2, 23.5. MS: 264 [M+1]$^+$.

Example 111

Preparation of 5-(3-(3-Aminopropyl)Phenyo-N-Methylpentanamide

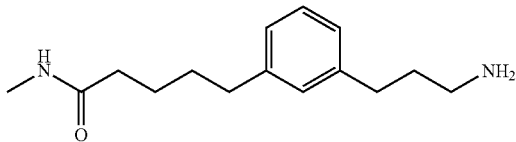

5-(3-(3-Aminopropyl)phenyl)-N-methylpentanamide was prepared following the method used in Example 76.

Step 1: Sonogashira coupling of bromide 57 with N-methylpent-4-ynamide gave tert-butyl 3-(3-(5-(methylamino)-5-oxopent-1-ynyl)phenyl)propyl carbamate. Yield (1.03 g, crude). $^1$H NMR (400 MHz, CDCl$_3$) δ 7.64-7.70 (m, 1H), 7.48 (d, J=6.6 Hz, 1H), 7.21 (s, 1H), 7.10 (d, J=6.4 Hz, 1H), 5.68 (bs, 1H), 4.52 (bs, 1H), 3.10-3.18 (m, 2H), 2.85 (d, J=6.8 Hz, 3H), 2.75 (t, J=7.2 Hz, 2H), 2.60 (t, J=7.6 Hz, 2H), 2.47 (t, J=7.2 Hz, 2H), 1.75-1.82 (m, 2H), 1.44 (s, 9H).

Step 2: Reduction of 5-(3-(3-Aminopropyl)phenyl)-N-methylpent-4-ynamide gave tert-butyl 3-(3-(5-(methylamino)-5-oxopentyl)phenyl)propylcarbamate as yellow oil. Yield (0.55 g, 88%): MS: 349 [M+1]$^+$.

Step 3: BOC deprotection of tert-butyl 3-(3-(5-(methylamino)-5-oxopentyl)phenyl)propylcarbamate gave 5-(3-(3-aminopropyl)phenyl)-N-methylpentanamide hydrochloride The product was isolated by adjusting the pH with conc. ammonia and extration with DCM. The organic layer was washed with water, dried over anhydrous Na$_2$SO$_4$, filtered and concentrated under reduced pressure. Purification by flash chromatography (0-(9.5-0.5) MeOH—NH$_3$)-DCM gradient) gave Example 111 as brown oil. Yield (0.107 g, 27%): $^1$H NMR (400 MHz, DMSO-d$_6$) δ 7.13-7.18 (m, 1H), 6.94-6.99 (m, 3H), 2.48-2.56 (m, 9H), 2.05 (t, J=6.8 Hz, 2H), 1.60-1.68 (m, 2H), 1.42-1.50 (m, 4H). $^{13}$C NMR (100 MHz, DMSO-d$_6$): 172.8, 142.5, 142.4, 128.8, 128.6, 126.1, 41.2, 35.6, 34.6, 32.9, 31.2, 25.8, 25.4. MS: 249 [M+1]$^+$.

Example 112

Preparation of 5-(3-(3-Aminopropyl)Phenyl)Pentanamide

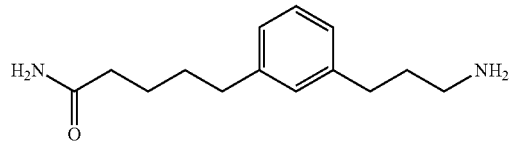 [SMILES: NCCCc1cccc(CCCCC(N)=O)c1]

5-(3-(3-Aminopropyl)phenyl)pentanamide was prepared following the method used in Example 111.

Step 1: Sonogashira coupling of bromide 57 with pent-4-ynamide gave tert-butyl 3-(3-(5-amino-5-oxopent-1-ynyl)phenyl)propylcarbamate. Yield (0.967 g, crude). $^1$H NMR (400 MHz, CDCl$_3$) δ 7.64-7.70 (m, 1H), 7.47 (d, J=6.4 Hz, 1H), 7.18 (s, 1H), 7.10 (d, J=6.4 Hz, 1H), 5.60-5.80 (m, 2H), 4.53 (bs, 1H), 3.10-3.18 (m, 2H), 2.75 (d, J=7.2 Hz, 2H), 2.60 (t, J=7.6 Hz, 2H), 2.54 (t, J=7.2 Hz, 2H), 1.76-1.80 (m, 2H), 1.44 (s, 9H).

Step 2: Reduction of 5-(3-(3-Aminopropyl)phenyl)pent-4-ynamide gave tert-butyl 3-(3-(5-amino-5-oxopentyl)phenyl) propylcarbamate as yellow oil. Yield (0.310 g, 83%): MS: 335 [M+1]$^+$. The compound was pure enough to be utilized for the next transformation.

Step 3: BOC deprotection of tert-butyl 3-(3-(5-amino-5-oxopentyl)phenyl)propylcarbamate gave Example 112 as off-white solid. Yield (0.08 g, 38%): $^1$H NMR (400 MHz, DMSO-d$_6$) δ 7.14-7.19 (m, 1H), 6.97-7.0 (m, 3H), 2.50-2.60 (m, 6H), 2.05 (t, J=6.8 Hz, 2H), 1.60-1.70 (m, 2H), 1.43-1.55 (m, 4H). $^{13}$C NMR (100 MHz, DMSO-d$_6$): 174.2, 142.0, 141.9, 128.3, 128.1, 125.6, 40.7, 34.9, 34.0, 32.4, 30.7, 24.8. MS: 235 [M+1]$^+$.

Example 113

Preparation of 1-(3-(3-Amino-1-Hydroxypropyl) Phenyl)-3-Ethylpentan-3-ol

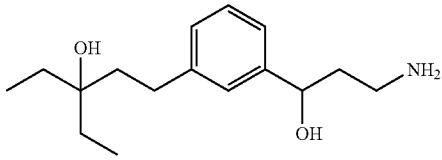 [SMILES: CCC(O)(CC)CCc1cccc(C(O)CCN)c1]

1-(3-(3-Amino-1-hydroxypropyl)phenyl)-3-ethylpentan-3-ol was prepared following the method used in Example 63.

Step 1: Sonogashira coupling of bromide 43 with 3-ethylpent-1-yn-3-ol gave N-(3-(3-(3-ethyl-3-hydroxypent-1-ynyl) phenyl)-3-hydroxypropyl)-2,2,2-trifluoroacetamide. Yield (0.825 g, 77%). $^1$H NMR (400 MHz, CDCl$_3$) δ 7.41 (s, 1H), 7.28-7.39 (m, 3H), 4.83-4.87 (m, 1H), 3.66-3.73 (m, 1H), 3.37-3.44 (m, 1H), 1.90-2.02 (m, 2H), 1.70-1.81 (m, 4H), 1.10 (t, J=7.4 Hz, 6H).

Step 2: Deprotection of N-(3-(3-(3-ethyl-3-hydroxypent-1-ynyl)phenyl)-3-hydroxypropyl)-2,2,2-trifluoroacetamide gave 1-(3-(3-amino-1-hydroxypropyl)phenyl)hex-1-yn-3-ol as yellow oil. Yield (0.52 g, 91%): $^1$H NMR (400 MHz, DMSO-d$_6$) δ 7.36 (s, 1H), 7.29-7.33 (m, 2H), 7.26 (d, J=6.4 Hz, 1H), 4.68 (t, J=4.8 Hz, 1H), 2.74-2.82 (m, 2H), 1.76-1.82 (m, 2H), 1.60-1.69 (m, 4H), 0.99 (t, J=7.4 Hz, 6H). $^{13}$C NMR (100 MHz, DMSO-d$_6$): 146.5, 130.1, 128.9, 126.0, 125.0, 123.0, 100.0, 94.0, 83.3, 75.0, 71.0, 70.2, 34.5, 9.2. ESI MS m/z 262 [M+1]$^+$.

Step 3: Reduction of 1-(3-(3-amino-1-hydroxypropyl)phenyl)-3-ethylpent-1-yn-3-ol gave Example 113 as yellow oil. Yield (0.15 g, 49%). $^1$H NMR (400 MHz, DMSO-$d_6$) δ 7.17-7.21 (m, 1H), 7.14 (s, 1H), 7.07 (d, J=8.4 Hz, 1H), 7.02 (d, J=7.2 Hz, 1H), 4.60-4.64 (m, 1H), 2.58 (t, J=7.2 Hz, 2H), 2.42-2.50 (m, 2H), 1.60-1.68 (m, 2H), 1.50-1.56 (m, 2H), 1.37 (q, J=7.6 Hz, 4H), 0.81 (t, J=7.6 Hz, 6H). $^{13}$C NMR (100 MHz, DMSO-$d_6$): 146.5, 142.7, 127.9, 126.4, 125.4, 122.9, 72.4, 71.3, 42.0, 40.1, 38.8, 30.4, 29.6, 7.9. MS: 266 [M+1]$^-$ Example 114

Preparation of 2-(3-(2-(Tetrahydro-2H-Pyran-2-yl)Ethyl)Phenoxy)Ethanamine

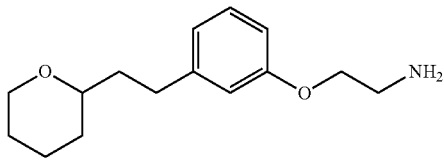 [SMILES: NCCOc1cccc(CCC2CCCCO2)c1]

2-(3-(2-Tetrahydro-2H-pyran-2-yl)ethyl)phenoxy)ethanamine was prepared following the method used in Example 64.

Step 1: Sonogashira reaction of bromide 19 with 2-ethynyltetrahydro-2H-pyran gave 2,2,2-trifluoro-N-(2-(3-((tetrahydro-2H-pyran-2-yl)ethynyl)phenoxy)ethyl)acetamide as a brown oil. Yield (0.753 g, 79%): $^1$H NMR (400 MHz, DMSO-$d_6$) δ 7.26-7.32 (m, 1H), 7.05 (d, J=7.6 Hz, 1H), 6.95-6.98 (m, 2H), 4.50-4.53 (m, 1H), 4.11 (t, J=5.4 Hz, 2H), 3.83-3.90 (m, 1H), 3.54-3.58 (m, 2H), 3.46-3.53 (m, 1H), 1.78-1.86 (m, 2H). 1.46-1.66 (m, 4H).

Step 2: The reduction of 2,2,2-trifluoro-N-(2-(3-((tetrahydro-2H-pyran-2-yl)ethynyl)phenoxy)ethyl)acetamide afforded 2,2,2-trifluoro-N-(2-(3-(2-(tetrahydro-2H-pyran-2-yl)ethyl)phenoxy)ethyl)acetamide as brown oil. Yield (0.315 g, 77%): $^1$H NMR (400 MHz, DMSO-$d_6$) δ 7.15-7.20 (m, 1H), 6.72-6.78 (m, 3H), 4.07 (t, J=5.6 Hz, 2H), 3.86-3.90 (m, 1H), 3.52-3.58 (m, 2H), 3.26-3.30 (m, 1H), 3.12-3.18 (m, 1H), 2.51-2.68 (m, 2H), 1.52-1.78 (m, 4H), 1.38-1.48 (m, 4H), Step 3: Deprotection of 2,2,2-trifluoro-N-(2-(3-(2-(tetrahydro-2H-pyran-2-yl)ethyl)phenoxy)ethyl)acetamide gave Example 114 as yellow oil. Yield (0.141 g, 63%): $^1$H NMR (400 MHz, DMSO-$d_6$) δ 7.19-7.23 (m, 1H), 6.77-6.82 (m, 3H), 4.10 (t, J=5.2 Hz, 2H), 3.83-3.86 (m, 1H), 3.24-3.30 (m, 1H), 3.12-3.20 (m, 3H), 2.50-2.70 (m, 2H), 1.50-1.74 (m, 4H), 1.36-1.46 (m, 3H), 1.10-1.20 (m, 1H). $^{13}$C NMR (100 MHz, DMSO-$d_6$) δ 158.4, 144.3, 129.3, 121.6, 115.0, 112.4, 76.6, 67.9, 64.5, 38.7, 38.2, 31.9, 31.6, 26.2, 23.5. MS: 250 [M+1]$^+$.

Example 115

Preparation of 1-(3-(3-Amino-1-Hydroxypropyl)Phenethyl)Cyclopentanol

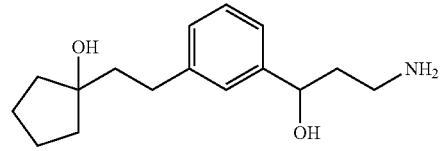 [SMILES: NCCC(O)c1cccc(CCC2(O)CCCC2)c1]

1-(3-(3-Amino-1-hydroxypropyl)phenethyl)cyclopentanol was prepared following the method used in Example 19.

Step 1: Sonogashira reaction of bromide 43 with 1-ethynylcyclopentanol yielded 2,2,2-trifluoro-N-(3-hydroxy-3-(3-((1-hydroxycyclopentyl)ethynyl)phenyl)propyl)-acetamide as brown oil. Yield (0.55 g, 55%): $^1$H NMR (400 MHz, CDCl$_3$) δ 7.41 (s, 1H), 7.28-7.35 (m, 3H), 4.85-4.87 (m, 1H), 3.66-3.70 (m, 1H), 3.38-3.44 (m, 1H), 2.41 (bs, 1H), 1.76-2.08 (m, 10H).

Step 2: Reduction of 2,2,2-trifluoro-N-(3-hydroxy-3-(3-((1-hydroxy cyclopentyl)ethynyl)phenyl)propyl)acetamide gave 2,2,2-trifluoro-N-(3-hydroxy-3-(3-(2-(1-hydroxycyclopentyl)ethyl)phenyl)propyl)acetamide as yellow oil. Yield (0.248 g, 62%). $^1$H NMR (400 MHz, CDCl$_3$) δ 7.27-7.31 (m, 1H), 7.20 (s, 1H), 7.14-7.18 (m, 2H), 4.86-4.90 (m, 1H), 3.68-3.73 (m, 1H), 3.38-3.46 (m, 1H), 2.76-2.80 (m, 2H), 2.25 (s, 1H), 1.96-2.02 (m, 3H), 1.80-1.90 (m, 4H), 1.60-1.72 (m, 5H).

Step 3: Deprotection of 2,2,2-trifluoro-N-(3-hydroxy-3-(3-(2-(1-hydroxycyclopentyl)ethyl)phenyl)propyl)acetamide gave Example 115 as yellow oil. Yield (0.12 g, 68%). $^1$H NMR (400 MHz, CDCl$_3$) δ 7.20-7.24 (m, 1H), 7.13 (s, 1H), 7.06-7.11 (m, 2H), 4.61 (t, J=6.4 Hz, 1H), 2.78-2.92 (m, 2H), 2.60-2.65 (m, 2H), 1.80-1.87 (m, 2H), 1.64-1.74 (m, 4H), 1.40-1.60 (m, 6H). $^{13}$C NMR (100 MHz, DMSO-$d_6$) δ 145.9, 143.4, 128.5, 127.3, 125.8, 123.2, 80.6, 70.6, 44.1, 38.6, 37.4, 31.3, 24.0. MS: 264 [M+1]$^+$ Example 116

Preparation of 3-(3-(3-Aminopropyl)Phenyl)-1-Phenylpropan-1-ol

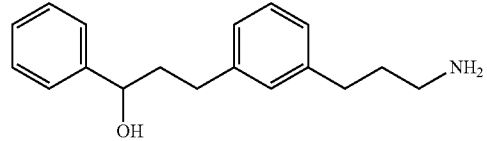 [SMILES: NCCCc1cccc(CCC(O)c2ccccc2)c1]

3-(3-(3-Aminopropyl)phenyl)-1-phenylpropan-1-ol was prepared following the method used in Example 103.

Step 1: Sonogashira reaction of bromide 10 with 1-phenylprop-2-yn-1-ol gave 2,2,2-trifluoro-N-(3-hydroxy-3-(3-(3-hydroxy-3-phenylprop-1-ynyl)phenyl)propyl)acetamide as brown oil. Yield (0.408 g, 80%). This compound was utilized as such for the next transformation.

Step 2: Reduction of 2,2,2-trifluoro-N-(3-hydroxy-3-(3-(3-hydroxy-3-phenylprop-1-ynyl)phenyl)propyl)acetamide yielded 2,2,2-trifluoro-N-(3-hydroxy-3-(3-(3-hydroxy-3-phenylpropyl)phenyl)propyl)acetamide as yellow oil. Yield (0.365 g, 91%). This compound was utilized as such for the next transformation.

Step 3: Deprotection of 2,2,2-trifluoro-N-(3-hydroxy-3-(3-(3-hydroxy-3-phenylpropyl)phenyl)propyl)acetamide and subsequent purification by flash chromatography (0-10% MeOH—NH$_3$ (9.5:0.5)-DCM gradient) gave Example 116 as pale yellow oil. Yield (0.20 g, 74%): $^1$H NMR (400 MHz, DMSO-$d_6$) δ 7.30-7.33 (m, 4H), 7.20-7.25 (m, 2H), 7.13 (s, 1H), 7.13 (d, J=8.0 Hz, 1H), 7.08 (d, J=8.0 Hz, 1H), 5.28 (d, J=4.4 Hz, 1H), 4.62 (t, J=7.2 Hz, 1H), 4.52-4.63 (m, 1H), 2.79-2.87 (m, 2H), 2.50-2.59 (m, 2H), 1.79-1.89 (m, 4H). $^{13}$C NMR (100 MHz, DMSO-$d_6$) δ 146.6, 145.7, 142.4, 128.6, 128.5, 127.4, 127.1, 126.2, 125.9, 123.4, 72.2, 70.3, 41.6, 37.1, 32.1. MS: 286 [M+1]$^+$.

Example 117

Preparation of 3-(3-(3-Aminopropyl)Phenyl)-2,2-Dimethylpropyl Acetate

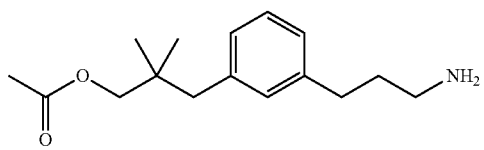 [SMILES: CC(=O)OCC(C)(C)Cc1cccc(CCCN)c1]

3-(3-(3-Aminopropyl)phenyl)-2,2-dimethylpropyl acetate was prepared following the method shown in Scheme 19.

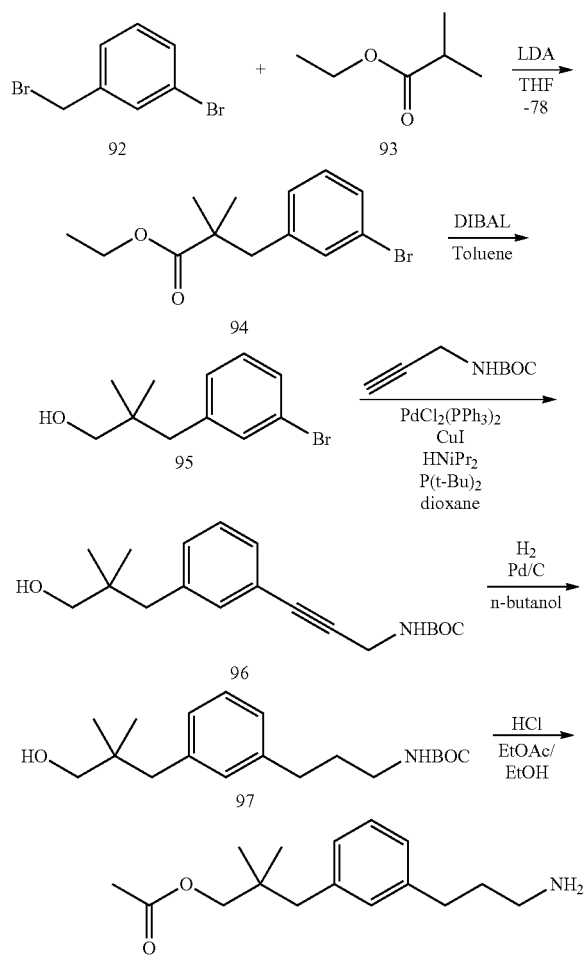

SCHEME 19

Step 1: Alkylation of 3-bromobenzylbromide (92) with ethyl isobutyrate (93) following the method used in Example 44 (except that saturated aqueous ammonium chloride was used to quench the reaction instead of water), followed by flash chromatography (0-20% EtOAc/hexanes gradient) gave the ester 94 as a light yellow oil. Yield (2.9 g, 87%): $^1$H NMR (400 MHz, CDCl$_3$) δ 7.31-7.35 (m, 1H), 7.27 (t, J=2.0 Hz, 1H), 7.11 (t, J=7.6 Hz, 1H), 7.01-7.05 (m, 1H), 4.11 (q, J=7.2 Hz, 2H), 2.80 (s, 2H), 1.23 (t, J=7.2 Hz, 3H), 1.67 (s, 6H).

Step 2: DIBALH (8.8 mL of a 1.0 M solution in THF, 8.8 mmol) was added to a stirring solution of the ester 94 (2.1 g, 7.36 mmol) in toluene at 0° C. under argon. After 1 h, a second aliquot of DIBALH (4.2 mL, 4.2 mmol) was added. After overnight stirring the reaction was quenched with saturated aqueous ammonium chloride, diluted with 1M HCl, and extracted with ethyl acetate. Combined organic layers were washed with more 1M HCl, water, saturated aqueous sodium bicarbonate and brine, dried over sodium sulfate, filtered, and concentrated, giving the alcohol 95 as a colorless oil, Yield (1.84 g, quantitative): $^1$H NMR (400 MHz, CDCl$_3$) δ 7.30-7.35 (m, 2H), 7.13 (t, J=7.6 Hz, 1H), 7.06-7.10 (m, 1H), 3.29 (d, J=4.8 Hz, 2H), 2.54 (s, 2H), 1.38-1.40 m, 1H), 0.87 (s, 6H).

Step 3: A solution of tri-t-butyl phospine (0.13 mL of a 1M solution in dioxane, 0.13 mmol) was added to a degassed mixture of bis-chloro-triphenylphosphine palladium (49 mg, 0.07 mmol), copper iodide (4.9 mg, 0.026 mmol), di-isopropylamine (0.31 mL, 2.2 mmol), alcohol 95 (0.422 g, 1.73 mmol), and tert-butyl prop-2-ynylcarbamate (0.4 g, 2.6 mmol) in anhydrous dioxane (20 mL). The reaction was heated to 50° C. overnight, filtered, and purified by flash chromatography (4-60% EtOAc/hexanes gradient), giving alkyne 96 as a yellow oil. Yield (0.162 g, 29%): $^1$H NMR (400 MHz, CDCl$_3$) δ 7.23-7.27 (m, 1H), 7.17-7.23 (m, 2H), 7.09-7.13 (m, 1H), 4.74 (brs, 1H), 4.10-4.15 (m, 2H), 3.29 (s, 2H), 2.54 (s, 2H), 1.45 (s, 10H), 0.88 (s, 6H).

Step 4: Reduction of the alkyne 96 following the method used in Example 2 exept that n-butanol was used as the solvent, followed by flash chromatography (10-60% ethyl acetate/hexanes gradient), gave the alkane 97 as a colorless oil. Yield (0.1 g, 63%): $^1$H NMR (400 MHz, CDCl$_3$) δ 7.17 (t, J=7.6 Hz, 1H), 6.95-7.02 (m, 3H), 4.53 (m, 1H), 3.27 (s, 2H), 3.05-3.15 (m, 2H), 2.60 (t, J=7.2 Hz, 2H), 2.54 (s, 2H), 2.08 (s, 1H), 1.57-1.82 (m, 2H), 1.44 (s, 9H), 0.87 (s, 6H).

Step 5: HCl (0.25 mL of a 6.95 M solution in ethanol, 1.74 mmol) was added to a solution of alcohol 97 in ethyl acetate (2 mL). The reaction was stirred overnight, concentrated under reduced pressure, and the residue extracted from saturated aqueous sodium bicarbonate with ethyl acetate. Combined organic layers were washed with water and brine, dried over sodium sulfate, filtered, and concentrated under reduced pressure. The residue was purified by flash chromatography (5% (7 N ammonia/methanol)/ethyl acetate), giving Example 117 as a colorless oil. Yield (0.035 g, %): $^1$H NMR (400 MHz, CDCl$_3$) δ 7.16 (t, J=8.0 Hz, 1H), 6.99-7.04 (m, 1H), 6.89-6.93 (m, 2H), 3.74 (s, 2H), 2.70 (t, J=7.2 Hz, 2H), 2.61 (t, J=8.0 Hz, 2H), 2.54 (s, 2H), 2.09 (s, 3H), 1.69-1.78 (m, 2H), 1.27 (brs, 2H), 0.89 (s, 6H). ESI MS m/z 264.3 [m+H]$^+$

Example 118

Preparation of 3-(3-(3-Aminopropylphenyl)-2,2-Dimethylpropan-1-ol

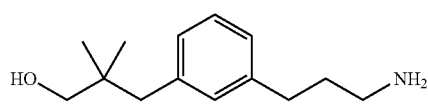 [SMILES: CC(C)(CO)Cc1cccc(CCCN)c1]

3-(3-(3-Aminopropyl)phenyl)-2,2-dimethylpropan-1-ol was prepared following the method shown in Scheme 20.

SCHEME 20

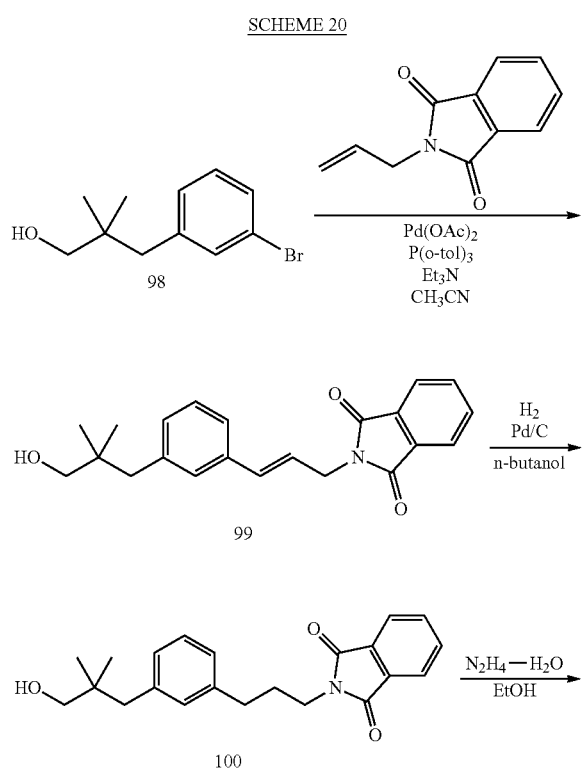

Step 1: To a solution of aryl bromide 98 (0.63 g, 2 6 mmol) in acetonitrile (5 mL) was added allyl phthalimide (0.58 g, 3.1 mmol), tri-o-tolyl phosphine (0.079 g, 0.26 mmol), and palladium acetate (0.036 g, 0.16 mmol). The mixture was evacuated and purged with argon three times, then triethylamine (0.51 mL, 3.65 mmol), was added and the evacuation—purge procedure was repeated three times. The reaction was heated at reflux overnight, then diluted with aqueous NH$_4$OAc and extracted with EtOAc. The combined organics were washed with water, aqueous NH$_4$OAc, saturated aqueous NaHCO$_3$ and brine, then dried over MgSO$_4$, filtered and concentrated. Flash chromatography of the residue (5-60% EtOAc/Hexanes gradient) gave the alcohol 99 as a white solid. Yield (0.58 g, 64%). $^1$H NMR (400 MHz, CDCl$_3$) δ 7.80-7.88 (m, 2H), 7.66-7.72 (m, 2H), 7.10-7.22 (m, 3H), 7.0-7.04 (m, 1H), 6.62 (d, J=16 Hz, 1H), 6.18-6.26 (m, 1H), 4.42 (dd, J=1.6, 6.8 Hz, 2H), 3.27 (s, 2H), 2.52 (s, 2H), 1.59 (brs, 1H), 0.85 (s, 6H).

Step 2: Reduction of alkene 99 following the method used in Example 117, followed by flash chromatography (20-50% ethyl acetate/hexanes gradient) gave alkane 100 as a colorless oil. $^1$H NMR (400 MHz, CDCl$_3$) δ 7.79-7.85 (m, 2H), 7.66-7.72 (m, 2H), 7.15 (t, J=7.6 Hz, 1H), 7.0-7.05 (m, 2H), 6.92-6.96 (m, 1H), 3.72 (t, J=7.2 Hz, 2H), 3.29 (s, 2H), 2.66 (t, J=7.2 Hz, 2H), 2.53 (s, 2H), 1.59-2.05 (m, 2H), 1.54 (s, 1H), 0.87 (s, 6H).

Step 3: Deprotection of alkane 100 following the method used in Example 9, followed by flash chromatography (0-10% (7N NH3/MeOH)/ethyl acetate) gradient), gave Example 118 as a colorless oil. Yield (0.068 g, 33%): 7.13-7.18 (m, 1H), 6.94-7.02 (m, 3H), 3.25 (s, 2H), 2.69 (t, J=6.8 Hz, 2H), 2.61 (t, 7.6 Hz, 2H), 2.53 (s, 2H), 1.89 (brs, 3H), 1.75 (quint, J=7.2 Hz, 2H), 0.85 (s, 6H). ESI MS m/z 222.2 [m+H]$^+$.

Example 119

Preparation of 2-(3-(3-Aminopropyl)Phenyl)Decan-2-ol

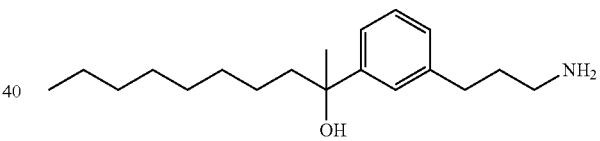

2-(3-(3-Aminopropyl)phenyl)decan-2-ol was prepared following the method shown in Scheme 21.

SCHEME 21

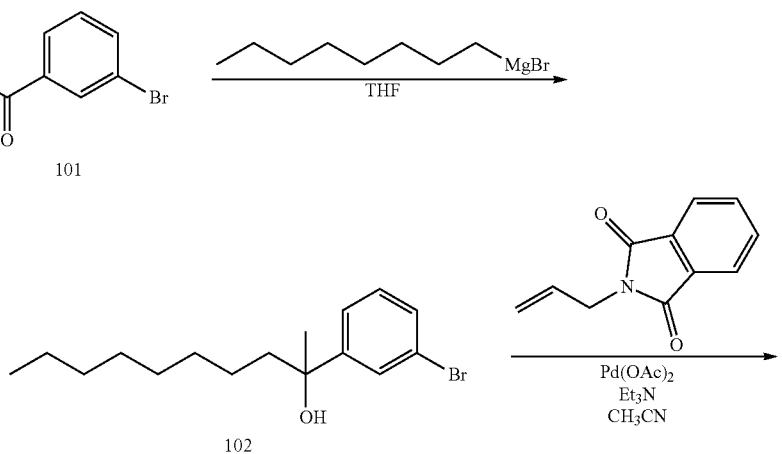

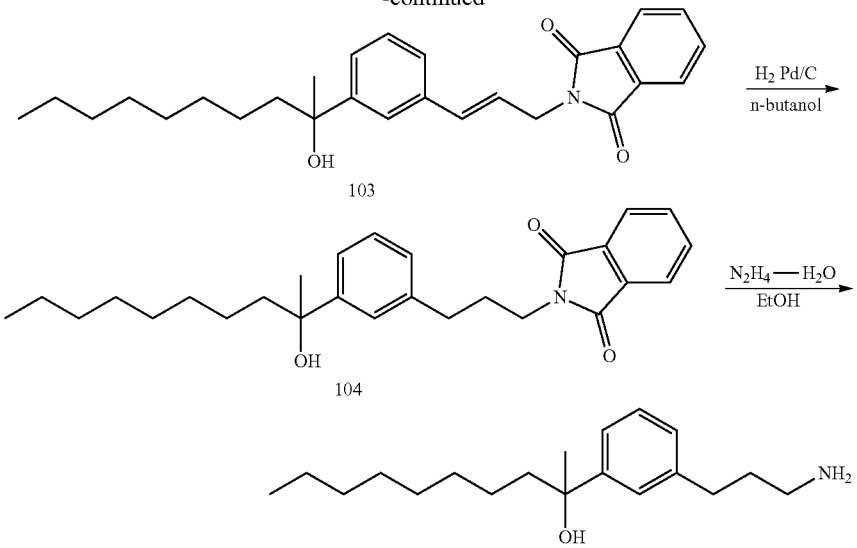

Step 1: To a solution of 1-(3-bromophenyl)ethanone (101) (2.0 mL, 15 mmol) in anhydrous THF (10 mL) under argon at −78° C. was added octylmagnesium bromide. The reaction was allowed to warm to room temperature and stirred overnight. The reaction solution was decanted into saturated aqueous ammonium chloride and stirred for 20 min The aqueous was extracted with ethyl acetate and the combined organics washed with water, saturated aqueous sodium bicarbonate and brine, dried over MgSO4, filtered through celite and concentrated under reduced pressure. Flash chromatography of the residue gave the benzyl hydroxide 102 as a colorless oil. Yield (2.7 g, 57%): $^1$H NMR (400 MHz, CDCl$_3$) δ 7.59 (t, 2.0 Hz, 1H), 7.30-7.37 (m, 2H), 7.19 (t, J=8.0 Hz, 1H), 1.68-1.82 (m, 2H), 1.64 (brs, 1H), 1.52 (s, 3H), 1.18-1.30 (m, 11H), 1.0-1.16 (m, 1H), 0.85 (t, J=7.2 Hz, 3H).

Step 2: Heck coupling of bromide 102 with allyl phthalimide following the method used in Example 118, followed by chromatography (5-40% ethyl acetate/hexanes gradient), gave the alkene 103 as a yellow oil. Yield (0.67 g, 84%): $^1$H NMR (400 MHz, CDCl$_3$) δ 7.80-7.88 (m, 2H), 7.66-7.74 (m, 2H), 7.39-7.42 (m, 1H), 7.20-7.28 (m, 3H), 6.63-6.69 (m, 1H), 6.26 (dt, J=6.4, 15.6 Hz, 1H), 4.44 (dd, 1.2, 6.0 Hz, 2H), 1.70-1.80 (m, 2H), 1.62 (brs, 1H), 1.51 (s, 3H), 1.30-1.60 (m, 12 H), 0.84 (t, J=3.2 Hz, 3H).

Step 3: Reduction of alkene 103 following the method used in Example 117, followed by flash chromatography (0-40% ethyl acetate/hexanes gradient) gave alkane 104 as a colorless oil. Yield (0.43 g, 65%): $^1$H NMR (400 MHz, CDCl$_3$) δ 7.79-7.85 (m, 2H), 7.68-7.72 (m, 2H), 7.16-7.28 (m, 3H), 7.04-7.07 (m, 1H), 3.73 (t, J=7.2 Hz, 2H), 2.69 (t, J=8.0 Hz, 2H), 1.99-2.10 (m, 2H), 1.65-1.70 (m, 3H), 1.52 (s, 3H), 1.05-1.30 (m, 12), 0.83 (t, J=7.2 Hz, 3H).

Step 4: Deprotection of alkane 104 following the method used in Example 9, followed by flash chromatography (0-10% (7N NH3/MeOH)/ethyl acetate) gradient gave Example 119 as a colorless oil. Yield (0.068 g, 25%): $^1$H NMR (400 MHz, CDCl$_3$) δ 7.21-7.27 (m, 3H), 7.03-7.07 (m, 1H), 2.74 (t, J=6.8 Hz, 2H), 2.66 (t, 8.0 Hz, 2H), 1.72-1.83 (m, 4H), 1.53 m, 6H), 1.06-1.30 (m, 12 H), 0.85 (t, J=7.2 Hz, 3H). ESI MS m/z 292.4 [m+H]$^+$, 274.4 [m+H−H$_2$O].

Example 120

Preparation of 2-(3-(3-Aminopropyl)Phenyl)Hexan-2-ol

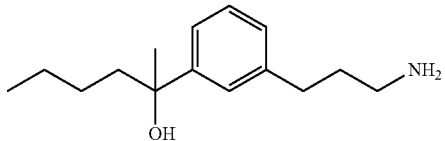 [SMILES: CCCCC(C)(O)c1cccc(CCCN)c1]

2-(3-(3-Aminopropyl)phenyl)hexan-2-ol was prepared following the method used in Example 119.

Step 1: Grignard coupling of butylmagnesium chloride with 1-(3-bromophenyl)ethanone followed by flash chromatography (0-25% ethyl acetate/hexanes gradient), gave 2-(3-bromophenyl)hexan-2-ol as a yellow oil. Yield (0.99 g, 51%): $^1$H NMR (400 MHz, CDCl$_3$) δ 7.59 (t, J=2.0 Hz, 1H), 7.30-7.37 (m, 2H), 7.19 (t, J=8.0 Hz, 1H), 1.70-1.84 (m, 2H), 1.52 (s, 3H), 1.64 (brs, 1H), 1.18-1.30 (m, 3H), 1.02-1.14 (m, 1H), 0.84 (t, J=7.2 Hz, 3H).

Step 2: Heck coupling of 2-(3-bromophenyl)hexan-2-ol with allyl phthalimide, followed by chromatography (5-30% ethyl acetate/hexanes gradient), gave (E)-2-(3-(3-(2-hydroxyhexan-2-yl)phenyl)allyl)isoindoline-1,3-dione as a colorless oil. Yield (0.46 g, 47%): $^1$H NMR (400 MHz, CDCl$_3$) δ 7.78-7.86 (m, 2H), 7.66-7.72 (m, 2H), 7.40 (s, 1H), 7.18-7.28 (m, 3H), 6.61-6.68 (m, 1H), 6.24 (dt, J=6.4, 15.6 Hz, 1H), 4.42 (dd, J=1.2, 6.4 Hz, 2H), 1.85 (brs, 1H), 1.54-1.56 (m, 2H), 1.50 (s, 3H), 1.15-1.30 (m, 3H), 1.00-1.10 (m, 1H), 0.75-0.85 (m, 3H).

Step 3: Reduction of (E)-2-(3-(3-(2-hydroxyhexan-2-yl)phenyl)allyl)isoindoline-1,3-dione, followed by flash chromatography (0-40% ethyl acetate/hexanes gradient) gave 2-(3-(3-(2-hydroxyhexan-2-yl)phenyl)propyl)isoindoline-1,3-dione as a colorless oil. Yield (0.43 g, 65%): $^1$H NMR (400 MHz, CDCl$_3$) δ 7.80-7.84 (m, 2H), 7.68-7.72 (m, 2h), 7.27

(brs, 1H), 7.16-7.23 (m, 2H), 7.04-7.08 (m, 1H), 3.73 (t, J=7.2 Hz, 2H), 2.69 (t, J=8.0 Hz, 2H), 2.03 (quint, J=7.6 Hz, 2H), 1.54-1.56 (m, 2H), 1.65 (brs, 1H), 1.52 (s, 3H), 1.15-1.30 (m, 3H), 1.10-1.30 (m, 1H), 0.83 (t, J=7.2 Hz, 3H).

Step 4: Deprotection of 2-(3-(3-(2-hydroxyhexan-2-yl)phenyl)propyl)isoindoline-1,3-dione followed by flash chromatography (0-10% (7N NH3/MeOH)/ethyl acetate gradient), gave Example 120 a colorless oil. Yield (0.157 g, 90%): $^1$H NMR (400 MHz, CDCl$_3$) δ 7.20-7.27 (m, 3H), 7.03-7.07 (m, 1H), 2.73 (t, J=7.2 Hz, 2H), 2.66 (t, J=8.0 Hz, 2H), 1.70-1.84 (m, 4H), 1.53 (s, 3H), 1.42 (brs, 3H), 1.18-1.30 (m, 3H), 1.06-1.16 (m, 1H), 0.84 (t, J=7.2 Hz, 3H). ESI MS m/z 236.2 [m+H]$^+$, 218.2 [m+H–H$_2$O].

Example 121

Preparation of 1-(3-(3-Aminopropyl)Phenyl)-2-Methylhexan-2-ol

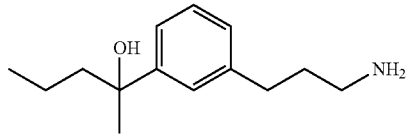 [SMILES: CCCC(C)(O)c1cccc(CCCN)c1]

1-(3-(3-Aminopropyl)phenyl)-2-methylhexan-2-ol was prepared following the method used in Example 119.

Step 1: Grignard coupling of n-butylmagnesium chloride with 1-(3-bromophenyl)propan-2-one, followed by flash chromatography (0-25% ethyl acetate/hexanes gradient), gave 1-(3-bromophenyl)-2-methylhexan-2-ol as a yellow oil. Yield (0.99 g, 51%): $^1$H NMR (400 MHz, CDCl$_3$) δ 7.35-7.38 (m, 2H), 7.11-7.19 (m, 2H), 2.70 (dd, J=13.4, 28.8 Hz, 2H), 1.24-1.48 (m, 7H), 1.13 (s, 3H), 0.91 (t, J=7.2 Hz, 3H).

Step 2: Heck coupling of 1-(3-bromophenyl)-2-methylhexan-2-ol with allyl phthalimide, followed by chromatography (5-30% ethyl acetate/hexanes gradient), gave (E)-2-(3-(3-(2-hydroxy-2-methylhexyl)phenyl)allyl)isoindoline-1,3-dione as a white solid. Yield (0.55 g, 50%): $^1$H NMR (400 MHz, CDCl$_3$) δ 7.80-7.88 (m, 2H), 7.68-7.74 (m, 2H), 7.16-7.26 (m, 3H), 7.04-7.08 (m, 1H), 6.60-6.66 (m, 1H), 6.24 (dt, J=6.4, 16 Hz, 1H), 4.43 (dd, J=1.2, 6.4 Hz, 2H), 2.69 (dd, J=13.2, 28 Hz, 2H), 1.30-1.50 (m, 7H), 1.10 (s, 3H), 0.89 (t, J=7.2 Hz, 3H).

Step 3: Reduction of (E)-2-(3-(3-(2-hydroxy-2-methylhexyl)phenyl)allyl)isoindoline-1,3-dione, followed by flash chromatography (0-40% ethyl acetate/hexanes gradient) gave 2-(3-(3-(2-hydroxy-2-methylhexyl)phenyl)propyl)isoindoline-1,3-dione as a colorless oil. Yield (0.43 g, 65%): $^1$H NMR (400 MHz, CDCl$_3$) δ 7.78-7.84 (m, 2H), 7.66-7.72 (m, 2H), 7.16 (t, J=8.0 Hz, 1H), 7.04-7.08 (m, 2H), 6.95-6.99 (m, 1H), 3.72 (t, J=7.2 Hz, 2H), 2.62-2.76 (m, 4H), 2.03 (quint, J=7.6 Hz, 2H), 1.25-1.50 (m, 7H), 1.12 (s, 3H), 0.91 (t, J=7.2 Hz, 3H).

Step 4: Deprotection of 2-(3-(3-(2-hydroxy-2-methylhexyl)phenyl)propyl)isoindoline-1,3-dione followed by flash chromatography (0-10% (7N NH3/MeOH)/ethyl acetate) gradient gave Example 121 a colorless oil. Yield (0.144 g, 85%): $^1$H NMR (400 MHz, CDCl$_3$) δ 7.18-7.24 (m, 1H), 7.00-7.08 (m, 3H), 2.68-2.78 (m, 4H), 2.60-2.68 (m, 2H), 1.71-1.80 (m, 2H), 1.24-1.50 (m, 9H), 1.12 (s, 3H), 0.91 (t, J=7.2 Hz, 3H). ESI MS m/z 250.3 [m+H]$^+$, 232.3 [m+H–H$_2$O]

Example 122

Preparation of 3-(3-(4-Methoxybutyl)Phenyl)Propan-1-Amine

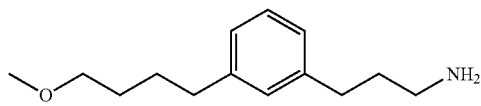 [SMILES: COCCCCc1cccc(CCCN)c1]

3-(3-(4-Methoxybutyl)phenyl)propan-1-amine was prepared following the method used in Example 76.

Step 1: Sonogashira reaction of bromide 57 with 4-methoxybut-1-yne gave tert-butyl 3-(3-(4-methoxybut-1-ynyl)phenyl)propylcarbamate as yellow oil. Yield (0.83 g, 77%): $^1$H NMR (400 MHz, CDCl$_3$) δ 7.22-7.25 (m, 2H), 7.16-7.21 (m, 1H), 7.09 (d, J=7.6 Hz, 1H), 4.51 (bs, 1H), 3.60 (t, J=7.8 Hz, 2H), 3.41(s, 3H), 3.10-3.16 (m, 2H), 2.69 (t, J=7.0 Hz, 2H), 2.59 (t, J=7.6 Hz, 2H), 1.76-1.84 (m, 2H), 1.44 (s, 9H).

Step 2: Reduction of tert-butyl 3-(3-(4-methoxybut-1-ynyl)phenyl)propyl carbamate gave tert-butyl 3-(3-(4-methoxybutyl)phenyl)propylcarbamate as yellow oil. Yield (0.81 g, 83%): $^1$H NMR (400 MHz, CDCl$_3$) δ 7.16-7.20 (m, 1H), 6.97-7.02 (m, 3H), 4.53 (bs, 1H), 3.39 (t, J=6.4 Hz, 2H), 3.32 (s, 3H), 3.10-3.17 (m, 2H), 2.58-2.64 (m, 4H), 1.76-1.84 (m, 2H), 1.59-1.70 (m, 4H), 1.44 (s, 9H).

Step 3: BOC deprotection of tert-butyl 3-(3-(4-methoxybutyl)phenyl)propylcarbamate gave Example 122 hydrochloride as an off-white solid. Yield (0.615 g, 96%): $^1$H NMR (400 MHz, DMSO-d$_6$) δ 7.16-7.19 (m, 1H), 6.99-7.02 (m, 3H), 3.29 (t, J=6.2 Hz, 2H), 3.18 (s, 3H), 2.76 (t, J=7.6 Hz, 2H), 2.58 (t, J=7.6 Hz, 2H), 2.54 (t, J=7.4 Hz, 2H), 1.77-1.83 (m, 2H), 1.50-1.59 (m, 2H), 1.44-1.49 (m, 2H). $^{13}$C NMR (100 MHz, DMSO-d$_6$) δ 142.7, 141.3, 128.8, 128.7, 126.4, 126.1, 72.1, 58.3, 38.8, 35.3, 32.3, 29.2, 29.1, 28.1. MS: 222 [M+1]$^+$.

Example 123

Preparation of 3-(3-(2-Aminoethoxy)Phenyl)-1-Phenylpropan-1-ol

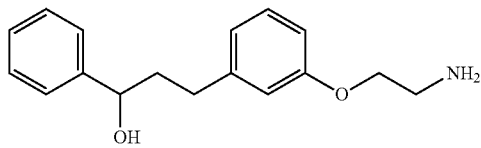 [SMILES: NCCOc1cccc(CCC(O)c2ccccc2)c1]

3-(3-(2-Aminoethoxy)phenyl)-1-phenylpropan-1-ol was prepared following the method used in Example 64.

Step 1: Sonogashira reaction of bromide 19 with 1-phenylprop-2-yn-1-ol gave 2,2,2-trifluoro-N-(2-(3-(3-hydroxy-3-phenylprop-1-ynyl)phenoxy)ethyl)acetamide as a brown oil. Yield (0.55 g, 47%): $^1$H NMR (400 MHz, DMSO-d$_6$) δ 7.61 (d, J=7.2 Hz, 1H), 7.30-7.41 (m, 5H), 7.13-7.16 (m, 1H), 7.06 (s, 1H), 6.89 (dd, J=8.4, 2.4 Hz, 1H), 5.69 (d, J=6.0 Hz, 1H), 4.10 (t, J=5.2 Hz, 2H), 3.77-3.81 (m, 2H), 2.26 (d, J=6.0 Hz, 1H).

Step 2: The reduction of 2,2,2-trifluoro-N-(2-(3-(3-hydroxy-3-phenylprop-1-ynyl)phenoxy)ethyl)acetamide gave 2,2,2-trifluoro-N-(2-(3-(3-hydroxy-3-phenylpropyl)phenoxy)ethyl)acetamide as yellow oil. Yield (0.45 g, 80%). MS: 366 [M−1].

Step 3: Deprotection of 2,2,2-trifluoro-N-(2-(3-(3-hydroxy-3-phenylpropyl)phenoxy)ethyl)acetamide gave Example 123 as off-white semi-solid. Yield (0.233 g, 73%): $^1$H NMR (400 MHz, DMSO-d$_6$) δ 7.31-7.35 (m, 4H), 7.20-7.27 (m, 1H), 7.14-7.19 (m, 1H), 6.71-6.75 (m, 3H), 5.25 (d, J=4.4 Hz, 1H), 4.49-4.54 (m, 1H), 3.87 (t, J=5.8 Hz, 2H), 2.84 (t, J=5.8 Hz, 2H), 2.50-2.66 (m, 2H), 1.820-1.90 (m, 2H), 1.52-1.60 (m, 2H). $^{13}$C NMR (100 MHz, DMSO-d$_6$) δ 159.2, 146.6, 144.1, 129.7, 128.5, 127.1, 126.3, 120.9, 114.9, 112.1, 72.1, 70.4, 41.5, 41.4, 40.6, 32.1. MS: 272 [M+1]$^+$ Example 124

Preparation of 3-Amino-1-(3-(3-Hydroxy-3-Phenylpropyl)Phenyl)Propan-1-ol

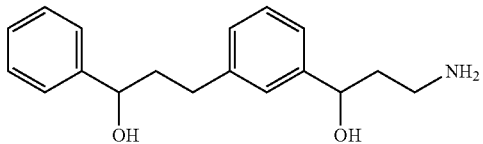 [SMILES: NCCC(O)c1cccc(CCC(O)c2ccccc2)c1]

3-Amino-1-(3-(3-hydroxy-3-phenylpropyl)phenyl)propan-1-ol was prepared following the method used in Example 19.

Step 1: Sonogashira reaction of 43 with 1-phenylprop-2-yn-1-ol gave 2,2,2-trifluoro-N-(3-hydroxy-3-(3-(3-hydroxy-3-phenylprop-1-ynyl)phenyl)propyl)acetamide as brown oil. Yield (0.408 g, 80%). This compound was utilized as such for the next transformation.

Step 2: Reduction of 2,2,2-trifluoro-N-(3-hydroxy-3-(3-(3-hydroxy-3-phenylprop-1-ynyl)phenyl)propyl)acetamide yielded 2,2,2-trifluoro-N-(3-hydroxy-3-(3-(3-hydroxy-3-phenylpropyl)phenyl)propyl)acetamide as yellow oil. Yield (0.365 g, 91%). This compound was utilized as such for the next transformation.

Step 3: Deprotection of 2,2,2-trifluoro-N-(3-hydroxy-3-(3-(3-hydroxy-3-phenylpropyl)phenyl)propyl)acetamide and subsequent purification by flash chromatography (0-10% MeOH—NH$_3$ (9.5:0.5)-DCM gradient) gave Example 124 as pale yellow oil. Yield (0.20 g, 74%): $^1$H NMR (400 MHz, DMSO-d$_6$) δ 7.30-7.33 (m, 4H), 7.20-7.25 (m, 2H), 7.13 (s, 1H), 7.13 (d, J=8.0 Hz, 1H), 7.08 (d, J=8.0 Hz, 1H), 5.28 (d, J=4.4 Hz, 1H), 4.62 (t, J=7.2 Hz, 1H), 4.52-4.63 (m, 1H), 2.79-2.87 (m, 2H), 2.50-2.59 (m, 2H), 1.79-1.89 (m, 4H). $^{13}$C NMR (100 MHz, DMSO-d$_6$) δ 146.6, 145.7, 142.4, 128.6, 128.5, 127.4, 127.1, 126.2, 125.9, 123.4, 72.2, 70.3, 41.6, 37.1, 32.1. MS: 286 [M+1]$^+$.

Example 125

Preparation of 3-(3-(2-Aminoethoxy)Phenyl)Propan-1-ol

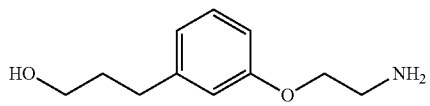 [SMILES: NCCOc1cccc(CCCO)c1]

3-(3-(2-Aminoethoxy)phenyl)propan-1-ol was prepared following the method used in Example 64.

Step 1: Sonogashira reaction of bromide 19 with propargyl alcohol gave 2,2,2-trifluoro-N-(2-(3-(3-hydroxyprop-1-ynyl)phenoxy)ethyl)acetamide as a brown oil. Yield (1.0 g, 43%). The crude material was directly utilized in the next step.

Step 2: The reduction of 2,2,2-trifluoro-N-(2-(3-(3-hydroxyprop-1-ynyl)phenoxy)ethyl)acetamide gave 2,2,2-trifluoro-N-(2-(3-(3-hydroxypropyl)phenoxy)ethyl)acetamide as yellow oil. Yield (0.563 g, 91%). MS: 290 [M−1].

Step 3: Deprotection of 2,2,2-trifluoro-N-(2-(3-(3-hydroxypropyl)phenoxy)ethyl)acetamide gave Example 125 as a yellow oil. Yield (0.21 g, 56%): $^1$H NMR (400 MHz, DMSO-d$_6$) δ 7.14-7.19 (m, 1H), 6.72-6.77 (m, 3H), 3.94 (t, J=5.6 Hz, 2H), 3.38 (t, J=6.4 Hz, 2H), 2.91 (t, J=5.6 Hz, 2H), 2.55 (t, J=7.8 Hz, 2H), 1.64-1.72 (m, 2H). $^{13}$C NMR (100 MHz, DMSO-d$_6$) δ 158.5, 143.8, 129.2, 120.7, 114.6, 111.6, 68.3, 60.1, 40.1, 34.2, 31.7. MS: 210 [M+1]$^+$.

Example 126

Preparation of 5-(3-(3-Aminopropyl)Phenyo-N,N-Dimethylpentanamide

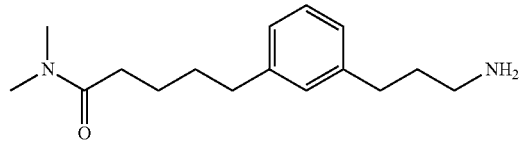

5-(3-(3-Aminopropyl)phenyl)-N,N-dimethylpentanamide was prepared following the method used in Example 76.

Step 1: Sonogashira coupling of bromide 57 with N,N-dimethylpent-4-ynamide gave tert-butyl 3-(3-(5-(methylamino)-5-oxopent-1-ynyl)phenyl)propyl carbamate. Yield (1.10 g, crude).

Step 2: Reduction of tert-butyl 3-(3-(5-(dimethylamino)-5-oxopent-1-ynyl)phenyl)propylcarbamate gave tert-butyl 3-(3-(5-(dimethylamino)-5-oxopentyl)phenyl)propylcarbamate as yellow oil. Yield (0.2 g, 96%): $^1$H NMR (400 MHz, CDCl$_3$) δ 7.15-7.20 (m, 1H), 6.97-7.01 (m, 3H), 4.59 (bs, 1H), 3.10-3.17 (m, 2H), 2.98 (s, 3H), 2.88 (s, 3H), 2.58-2.64 (m, 4H), 2.32 (t, J=6.6 Hz, 2H), 1.52-1.78 (m, 6H), 1.44 (s, 9H).

Step 3: BOC deprotection of tert-butyl 3-(3-(5-(dimethylamino)-5-oxopentyl)phenyl)propylcarbamate gave 5-(3-(3-aminopropyl)phenyl)-N,N-dimethyl pentanamide hydrochloride. Neutralization with conc. ammonia followed by purification by flash chromatography ((0-10%) MeOH:DCM gradient) gave Example 126 as yellow oil. Yield (0.09 g, 66%): $^1$H NMR (400 MHz, DMSO-d$_6$) δ 7.13-7.17 (m, 1H), 6.96-6.99 (m, 3H), 2.91 (s, 3H), 2.77 (s, 3H), 2.50-2.56 (m, 6H), 2.26 (t, J=7.2 Hz, 2H), 1.60-1.66 (m, 6H), 1.43-1.59 (m, 4H). $^{13}$C NMR (100 MHz, DMSO-d$_6$) δ 172.7, 142.5, 128.7, 128.6, 126.0, 37.2, 35.4, 35.2, 33.0, 32.6, 31.1, 24.8. MS: 263 [M+1]$^+$.

Example 127

Preparation of 4-(3-(4-Aminobutyl)Phenethyl)Heptan-4-Ol

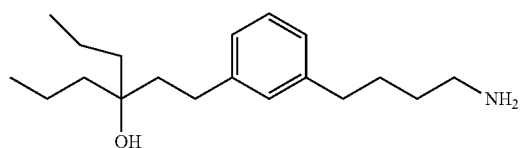 [SMILES: CCCC(O)(CCC)CCc1cccc(CCCCN)c1]

4-(3-(4-Aminobutyl)phenethyl)heptan-4-ol was prepared following the method Scheme 22.

SCHEME 22

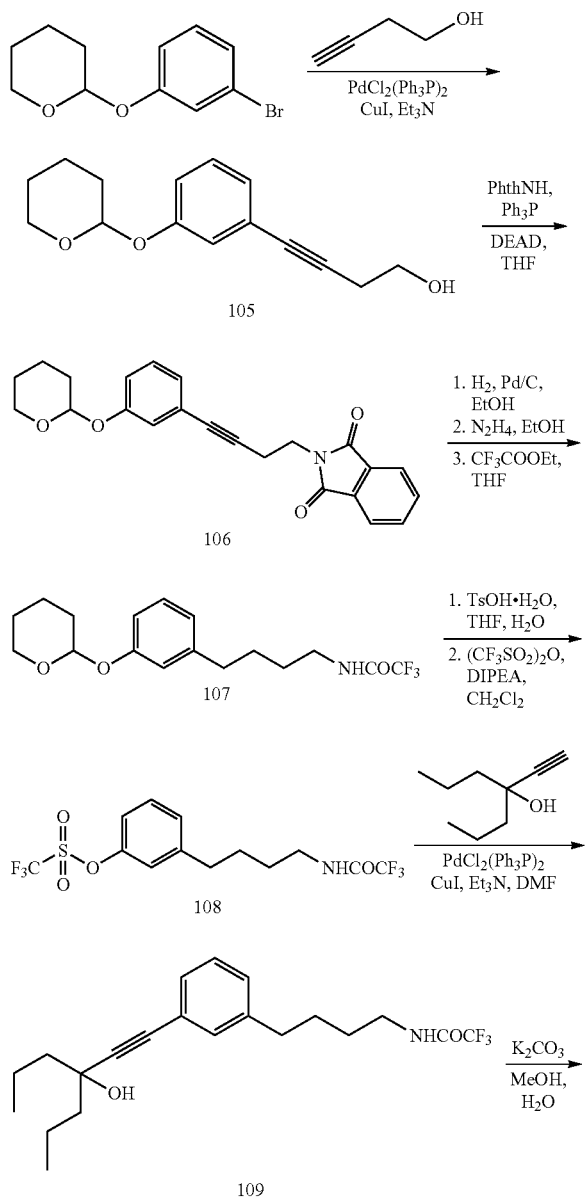

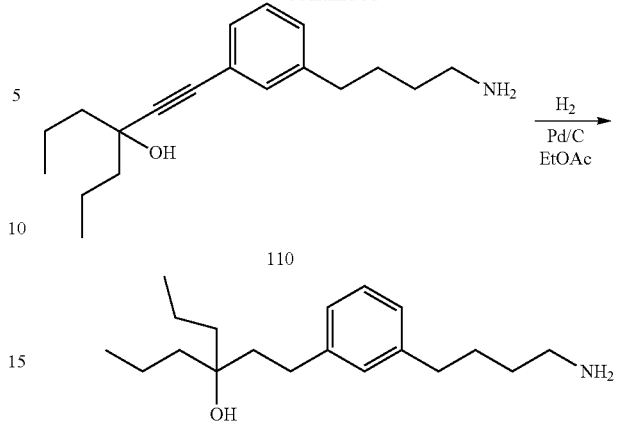

Step 1: Sonogashira coupling of 3-tetrahydropyranylbromophenol and 3-butyn-1-ol following the method used in Example 13 except that the reaction mixture was heated at 90° C. for 18 hr. Flash chromatography purification (30% to 100% EtOAc-hexanes gradient) gave alcohol 105 an orange oil. Yield (2.46 g, 85%); $^1$H NMR (400 MHz, DMSO-$d_6$) δ 7.22 (t, J=8.0 Hz, 1H), 6.93-7.01 (m, 3H), 5.45 (t, J=3.2 Hz, 1H), 4.86 (t, J=5.6 Hz, 1H), 3.66-3.75 (m, 1H), 3.48-3.58 (m, 3H), 2.51 (t, J=6.4 Hz, 2H), 1.64-1.90 (m, 3H), 1.44-1.64 (m, 3H).

Step 2: Diethyl azodicarboxylate (1.195 g, 6.86 mmol) was added under argon to a stirred solution of alcohol 105 (39 g, 5.64 mmol), phthalimide (0.90 g, 6.12 mmol) and triphenylphosphine (1.64 g, 6.25 mmol) in anhydrous THF. The reaction mixture was stirred at room temperature for 20 min and concentrated under reduced pressure. Purification by flash chromatography (10% to 40% ethyl acetate/hexanes gradient) gave phthalimide 106 a colorless oil. Yield (1.77 g, 84%); $^1$H NMR (400 MHz, CDCl$_3$) δ 7.82-7.88 (m, 2H), 7.68-7.73 (m, 2H), 7.14 (t, J=8.0 Hz, 1H), 7.02-7.04 (m, 1H), 6.92-6.97 (m, 2H), 5.36 (t, J=3.1 Hz, 1H), 3.95 (t, J=7.2 Hz, 2H), 3.87 (ddd, J=3.13, 9.6, 14.5 Hz, 1H), 3.58 (dtd, J=1.2, 4.1, 11.2 Hz, 1H), 2.80 (t, J=7.2Hz, 2H), 1.92-2.05 (m, 1H), 1.78-1.85 (m, 2H), 1.52-1.73 (m, 3H)

Step 3. A solution of butynylphthalimide 106 (1.00 g, 2.66 mmol) in EtOH (abs, 50 mL) was degassed by bubbling argon for 3 min Palladium on carbon (10%, 0.102 g) was added to the reaction mixture, which was degassed by bubbling argon for 30 sec, and then by applying vacuum/H$_2$ three times. The reaction mixture was stirred under hydrogen atmosphere for 45 min and filtered. The filtrate was used directly in the next step.

Deprotection with hydrazine monohydrate following the method used in Example 12 except that the reaction mixture was heated at +50° C. for 16 hrs, gave 4-(3-(tetrahydro-2H-pyran-2-yloxy)phenyl)but-3-yn-1-amine as a colorless oil, which was used in the next step without purification.

Protection of 4-(3-(tetrahydro-2H-pyran-2-yloxy)phenyl)but-3-yn-1-amine with ethyl trifluoroacetate following the method used in Example 19 except that the reaction was carried out in THF, gave trifluoroacetamide 107 a colorless oil. Yield (0.72 g, 78% after three steps); $^1$H NMR (400 MHz, DMSO-$d_6$) δ 9.37 (br.t, 1H), 7.12-7.18 (m, 1H), 6.75-6.83 (m 3H), 5.40 (t, J=3.2 Hz, 1H), 3.69-3.77 (m, 1H), 3.47-3.54 (m, 1H), 3.17 (q, J=6.4 Hz, 2H), 2.52 (t, J=7.2 Hz, 2H), 1.63-1.90 (m, 3H), 1.40-1.62 (m, 7H).

Step 4. A mixture of 107 (0.72 g, 2.08 mmol) and p-toluenesulfonic acid monohydrate (0.366 g) in THF: H$_2$O (3:1, 20 mL) was stirred at room temperature for 3.5 hr. The reaction mixture was partitioned between aqueous NaHCO$_3$-brine solution and EtOAc. Aqueous layer was aextracted with EtOAc. Combined organic layers were washed with brine and concentrated under reduced pressure. Purification by flash chromatography (10% to 50% EtOAc-hexanes gradient) gave 2,2,2-trifluoro-N-(4-(3-hydroxyphenyl)butyl)acetamide as a colorless oil. Yield (0.438 g, 96%).

A solution of trifluoromethanesulfonic anhydride (0.32 mL, 1.90 mmol) was added to a stirred solution of 2,2,2-trifluoro-N-(4-(3-hydroxyphenyl)butyl)acetamide (0.438 g, 1.68 mmol) and diisopropylethylamine (0.5 mL, 2.87 mmol) at 0° C. under argon in anhydrous CH$_2$Cl$_2$. The reaction mixture was stirred at 0° C. for 15 min and concentrated under reduced pressure. EtOAc was added to the residue and the mixture was washed with brine, dried over anhydrous MgSO$_4$, and the filtrate was concentrated under reduced pressure to give crude triflate 108 a light brown oil which was used in the next step without additional purification. Yield (0.683 g, quant.); $^1$H NMR (400 MHz, DMSO-d$_6$) δ 9.38 (brt, 1H), 7.45 (t, J=8.0 Hz, 1H), 7.24-7.34 (m, 3H), 3.17 (q, 6.4 Hz, 2H), 2.64 (t, J=7.2 Hz, 2H), 1.40-1.60 (m, 4H).

Step 5. Sonogashira coupling of triflate 108 with 4-ethynylheptan-4-ol following the method used in Example 2 except that the reaction was run for 15 hrs, after flash chromatography purification (5% to 40% EtOAc-hexanes gradient) gave alkynol 109 a light brown oil. Yield (0.327 g, 51%); $^1$H NMR (400 MHz, DMSO-d$_6$) δ 9.38 (brt, 1H), 7.20-7.34 (m, 1H), 7.13-7.18 (m, 2H), 5.10 (s, 1H), 3.17 (q, J=6.4 Hz, 1H), 2.54 (t, J=7.2 Hz, 2H), 1.38-1.62 (m, 12H), 0.88 (t, J=7.6 Hz, 6H).

Step 6. Deprotection of trifluoroacetamide 109 following the method used in Example 19 except that the reaction mixture was stirred at 50° C. for 3.5 hr after purification by flash chromatography (10% -100% 7N NH$_3$/MeOH/CH$_2$Cl$_2$—CH$_2$Cl$_2$) gave amine 110 a white solid. Yield (0.175 g, 71%); $^1$H NMR (400 MHz, CD$_3$OD) δ 7.12-7.24 (m, 4H), 2.46-2.66 (m, 4H), 1.42-1.73 (m, 10H), 1.43-1.42 (m, 2H), 0.97 (t, J=7.2 Hz, 6H); $^{13}$C NMR (100 MHZ, CD$_3$OD), δ 142.8, 131.3, 128.8, 128.3, 128.2, 123.6, 91.9, 83.9, 70.9, 44.5, 41.2, 35.2, 32.2, 28.6, 17.6, 13.6; RP-HPLC t$_R$=7.06 min, 92.5% (AUC); LC-MS m/z=288.25 [M+H]$^+$.

Step 7. A solution of alkyne 110 (0.0446 g, 0.155 mmol) in EtOAc (5 mL) was degassed by applying vac/argon 2×. Then Pd/C (10%, 0.0166 g) was added to the reaction mixture, degassed by applying vac/H$_2$ 2×, and the reaction mixture was stirred at room temperature for 18 hrs. Filtration followed by flash chromatography purification (10% to 50% of 20% 7N NH$_3$/MeOH/CH$_2$Cl$_2$—CH$_2$Cl$_2$ gradient) gave Example 127 as a colorless oil. Yield (0.0321 g, 71%); $^1$H NMR (400 MHz, CD$_3$OD) δ 7.13 (t, J=7.6 Hz, 1H), 6.95-7.01 (m, 3H), 2.52-2.67 (m, 6H), 1.58-1.69 (m, 4H), 1.41-1.53 (m, 6H), 1.30-1.40 (m, 4H), 0.93 (t, J=7.2 Hz, 6H); RP-HPLC (Method 2) t$_R$=7.06 min, 87.4% (AUC); LC-MS m/z=288.25 [M+H]$^+$.

Example 128

Preparation of (1S,2S)-3-Amino-1-(3-(2-(1-Hydroxycyclohexyl)Ethyl)Phenylpropane-1,2-Diol

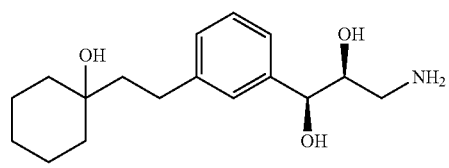 [SMILES: NC[C@H](O)[C@@H](O)c1cccc(CCC2(O)CCCCC2)c1]

(1S,2S)-3-Amino-1-(3-(2-(1-hydroxycyclohexyl)ethyl)phenyl)propane-1,2-diol was prepared following the method shown in Scheme 23

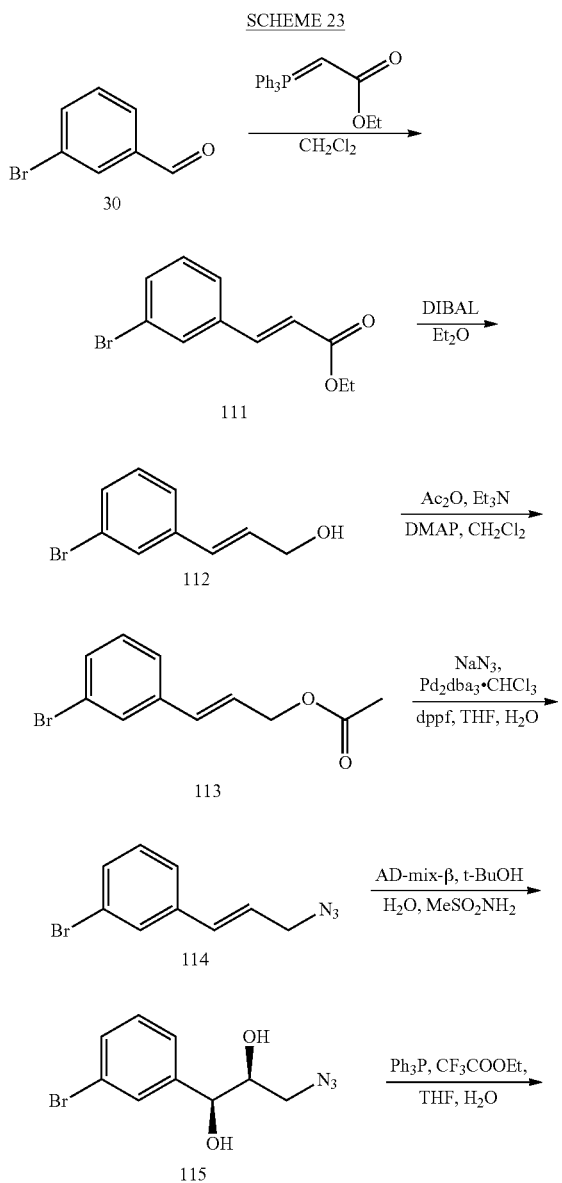

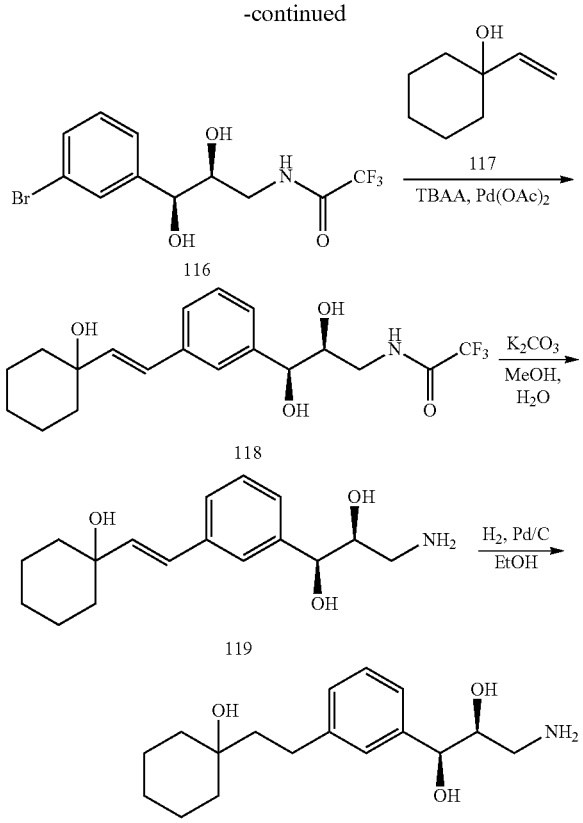

Step 1: To an ice-cold solution of 3-bromobenzaldehyde (30) (3.9 mL, 33.30 mmol) in anhydrous dichloromethane (100 mL) was added (carbethoxymethylene)triphenylphosphorane (11.65 g, 33.44 mmol). The reaction mixture was stirred at 0° C. for 5 min, then allowed to warm to room temperature over 30 min and concentrated under reduced pressure. The residue was resuspended in 5% EtOAc/hexanes, stirred for 10 min at room temperature and then filtered. Filter cake was washed with hexanes, and the filtrate was concentrated under reduced pressure. Purification of the residue by flash column chromatography (silica gel, hexanes to 10% EtOAc/hexanes gradient) gave allyl ester 111 a white solid. Yield (7.63 g, 90%). $^1$H NMR (400 MHz, DMSO-$d_6$) δ 7.95 (t, J=1.8 Hz, 1H), 7.70-7.72 (m, 1H), 7.59 (d, J=16.4 Hz, 1H), 7.58 (ddd, J=1.0, 2.0, 8.0 Hz, 1H), 7.35 (t, J=7.8 Hz, 1H), 6.69 (d, J=16.0 Hz, 1H), 4.17 (q, J=7.2 Hz, 2H), 1.23 (t, J=7.0 Hz, 3H).

Step 2. A solution of diisobutyl aluminum hydride (DIBAL-H, 60 mL of a 1.0 M solution in $CH_2Cl_2$, 60.0 mmol) was added to an ice-cold solution of ester 111 (0.63 g, 29.9 mmol) in diethyl ether (100 mL). The reaction mixture was stirred at 0° C. for 30 min after which aqueous solution of $NaHSO_4$ (2M, 42 mL) was added and the resulting mixture was stirred for 1.5 hrs while warming to room temperature. Anhydrous $MgSO_4$ was added to the stirred reaction mixture, and after 30 min the mixture was filtered and the filtrate cake washed excessively with EtOAc. Filtrate was concentrated under reduced pressure to give alcohol 112 a colorless oil. Yield (6.42 g, quant.). $^1$H NMR (400 MHz, DMSO-$d_6$) δ 7.60 (t, J=1.8 Hz, 1H), 7.40 (dt, J=1.2, 7.6 Hz, 1H), 7.38 (ddd, J=1.0, 2.0, 8.0 Hz, 1H), 7.25 (t, J=7.6 Hz, 1H), 6.48-6.54 (m, 1H), 6.43 (dt, J=4.3, 16.0 Hz, 1H), 4.88 (t, J=5.5 Hz, 1H), 4.08-4.12 (m, 2H).

Step 3. Acetic anhydride (1.2 mL, 12.7 mmol) was added to a stirred solution of alcohol 112 (2.535 g, 11.90 mmol), $Et_3N$ (2.0 mL, 14.3 mmol) and DMAP (0.141 g, 1.15 mmol) in anhydrous $CH_2Cl_2$. The reaction mixture was stirred at room temperature for 30 min and concentrated under reduced pressure. Purification by flash column chromatography (silica gel, 5% to 20% EtOAc/hexanes gradient) gave acetate 113 a colorless oil. Yield (2.71 g, 89%). $^1$H NMR (400 MHz, DMSO-$d_6$) δ 7.66 (t, J=1.8 Hz, 1H), 7.40-7.46 (m, 2H), 7.27 (t, J=7.8 Hz, 1H), 6.58-6.65 (m, 1H), 6.42 (dt, J=5.9, 16.0 Hz, 1H), 4.66 (dd, J=1.4, 5.9 Hz, 1H), 2.04 (s, 3H).

Step 4. A mixture of allyl acetate 113 (0.71 g, 10.6 mmol), sodium azide (0.787 g, 12.1 mmol), water (20 mL) and THF (50 mL) was degassed by bubbling argon for 3 min tris-Dibenzylideneacetonyl-bis-palladium—chloroform adduct (0.158 g, 0.17 mmol) and diphenylphosphinoferrocene (0.1773 g, 0.32 mmol) were added to the reaction mixture. Air was evacuated by applying vacuum/argon 3× and then the reaction mixture was heated at 60° C. under argon for 4 hrs. The reaction mixture was concentrated under reduced pressure, water was added to the residue and the product was extracted twice with hexanes. Combined hexane layers were washed with saturated brine, dried with anhydrous $MgSO_4$, filtered and the filtrate was concentrated under reduced pressure. Purification of the residue by flash column chromatography (silica gel, 5% to 30% EtOAc/hexanes gradient) gave allyl azide 114 as a colorless oil. Yield (1.90 g, 75%). $^1$H NMR (400 MHz, DMSO-$d_6$) δ 7.69 (t, J=1.8 Hz, 1H), 7.42-7.48 (m, 2H), 7.28 (t, J=7.8 Hz, 1H), 6.62-6.68 (m, 1H), 6.45 (dt, J=6.3, 15.8 Hz, 1H), 4.02 (dd, J=1.2, 6.3 Hz, 1H).

Step 5. To a 100-ml round bottomed flask was placed $H_2O$ (19 mL) and tert-BuOH (19 mL) followed by AD-mix-β (5.61 g). The mixture was stirred at room temperature for 10 min after which $MeSO_2NH_2$ (0.36 g, 3.79 mmol) was added. The reaction mixture was cooled to 0° C., allyl azide 114 (0.90 g, 3.78 mmol) was added and the reaction mixture was stirred at 0° C. for 24 hrs. $Na_2S_2O_3$ (6.30 g) was added and the mixture was stirred for another hour after which EtOAc (50 mL) was added followed by saturated NaCl (50 mL). Layers were separated and aqueous layer was extracted with EtOAc (3×25 mL). Combined organic layers were washed with brine (50 mL), dried over anhydrous $MgSO_4$ and filtered. Filtrate was concentrated under reduced pressure and the residue was purified by flash column chromatography (silica gel, 10% to 90% EtOAc/hexanes gradient) to give azido diol 115 as a thick colorless oil. Yield (1.02 g, 99%). $^1$H NMR (400 MHz, DMSO-$d_6$) δ 7.50 (t, J=1.6 Hz, 1H), 7.40 (ddd, J=1.2, 2.0, 7.6 Hz, 1H), 7.29-7.33 (m, 1H), 7.25 (t, J=7.6 Hz, 1H), 5.52 (d, J=5.1 Hz, 1H), 5.26 (d, J=5.9 Hz, 1H), 4.51 (t, J=4.7 Hz, 1H), 3.15 (dd, J=3.3, 12.5 Hz, 1H), 3.02 (dd, J=8.0, 12.7 Hz, 1H).

Step 6. A mixture of azido diol 115 (0.826 g, 3.037 mmol), triphenylphosphine (0.84 g, 3.20 mmol), THF (10 mL), water (0.2 mL) and ethyl trifluoroacetate (1 mL) was heated at 50° C. for 5 hrs and then concentrated under reduced pressure. Purification of the residue by flash column chromatography (silica gel, 20% to 90% EtOAc/hexanes gradient) gave trifluoroacetamide 116 as white solid. Yield (0.73 g, 70%). $^1$H NMR (400 MHz, DMSO-$d_6$) δ 9.21 (t, J=5.3 Hz, 1H), 7.52 (t, J=1.6 Hz, 1H), 7.40 (ddd, J=1.2, 2.0, 7.8 Hz, 1H), 7.30-7.33 (m, 1H), 7.25 (t, J=7.6 Hz, 1H), 5.48 (d, J=5.1 Hz, 1H), 5.00 (d, J=5.9 Hz, 1H), 4.51 (t, J=4.7 Hz, 1H), 3.70-3.76 (m, 1H), 3.24 (dt, J=4.9, 13.3 Hz, 1H), 2.98 (ddd, J=5.7, 8.8, 13.3 Hz, 1H).

Step 7. A mixture of alkene 116 (0.116 g, 0.922 mmol), bromide 117 (0.242 g, 0.708 mmol), tetrabutylammonium acetate (1.19 g) and $Pd(OAc)_2$ (0.029 g, 0.127 mmol) was heated under argon at 90° C. for 5 hrs. Water and brine were added to the reaction mixture which was extracted three times with EtOAc. The combined organic layers were washed with brine, dried over anhydrous MgSO$_4$ and concentrated under reduced pressure. Purification by flash column chromatography (silica gel, 20% to 70% EtOAc/hexanes gradient) gave alkene 118 as a white foam. Yield (0.2128 g, 78%). $^1$H NMR (400 MHz, DMSO-d$_6$) δ 9.19 (t, J=5.3 Hz, 1H), 7.35-7.37 (m, 1H), 7.20-7.26 (m, 2H), 7.13-7.18 (m, 1H), 6.51 (d, J=16.2 Hz, 1H), 6.33 (d, J=16.0 Hz, 1H), 5.33 (d, J=4.9 Hz, 1H), 4.94 (d, J=5.7 Hz, 1H), 4.46 (t, J=4.8 Hz, 1H), 4.41 (s, 1H), 3.70-3.76 (m, 1H), 3.18 (dt, J=4.5, 13.3 Hz, 1H), 2.99 (ddd, J=6.1, 8.8, 14.3 Hz, 1H), 1.54-1.66 (m, 2H), 1.36-1.54 (m, 7H), 1.18-1.26 (m, 1H).

Step 8. N-((2S,3S)-2,3-dihydroxy-3-(3-((E)-2-(1-hydroxycyclohexyl)vinyl)phenyl)propyl)-2,2,2-trifluoroacetamide (118) was deprotected according to the method used in Example 19 except that three equivalents of K$_2$CO$_3$ were used in a MeOH:H$_2$O (2:1) mixture and the reaction mixture was heated at 50° C. for 5 hrs. Following the reaction, reaction mixture was concentrated under reduced pressure, resuspended in EtOAc/EtOH and purified by flash chromatography using a gradient of 50% 7N NH$_3$/MeOH in EtOAc/hexanes to give alkene 119 as a colorless oil. Yield (0.118 g, 74%). $^1$H NMR (400 MHz, MeOH-d$_4$) δ 7.42-7.44 (m, 1H), 7.30 (dt, J=1.6, 7.6 Hz, 1H), 7.27 (t, J=7.4 Hz, 1H), 7.21 (dt, J=1.6, 7.2 Hz, 1H), 6.60 (d, J=16.0 Hz, 1H), 6.36 (d, J=16.0 Hz, 1H), 4.50 (d, J=5.9 Hz, 1H), 3.62-2.70 (m, 1H), 2.51-2.58 (m, 2H), 1.66-1.77 (m, 2H), 1.48-1.66 (m, 7H), 1.28-1.40 (m, 1H); $^{13}$C NMR (100 MHz, MeOH-d$_4$) δ 142.3, 137.9, 137.7, 128.3, 126.7, 125.7, 125.6, 124.6, 76.0, 75.8, 71.2, 43.6, 37.5, 25.5, 21.9, 20.9; RP-HPLC (Method 1) t$_R$=4.73 min, 97% (AUC); ESI MS m/z 292.3 [M+H]$^+$.

Step 9. A solution of alkene 119 (0.0612 g, 0.21 mmol) in EtOH (abs, 8 mL) was degassed by applying vac/argon 2×. Then Pd/C (10%, 0.0139 g) was added to the reaction mixture, degassed by applying vac/H$_2$ 2× and the reaction mixture was stirred at room temperature for 18 hrs. The reaction mixture was filtered and the filtrate was concentrated under reduced pressure to give Example 128 as a colorless oil. Yield (0.0454 g, 74%); $^1$H NMR (400 MHz, CD$_3$OD) δ 7.20-7.25 (m, 2H), 7.13-7.17 (m, 1H), 7.09-7.12 (m, 1H), 4.45 (d, J=6.3 Hz, 1H), 3.64 (q, J=6.1 Hz, 1H), 2.64-2.69 (m, 2H), 2.52 (d, J=5.9 Hz, 2H), 1.40-1.73 (m, 12H), 1.26-1.38 (m, 2H); RP-HPLC (Method 2) t$_R$=5.13 min, 92.2% (AUC); ESI MS m/z=294.46 [M+H]$^+$.

Example 129

Preparation of (1R,2R)-3-Amino-1-(3-(2-(1-Hydroxycyclohexyl)Ethyl)Phenylpropane-1,2-Diol

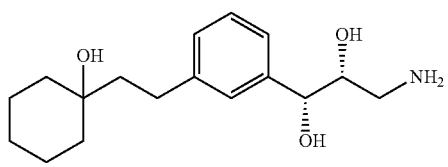 [SMILES: NC[C@@H](O)[C@H](O)c1cccc(CCC2(O)CCCCC2)c1]

(1R,2R)-3-Amino-1-(3-(2-(1-hydroxycyclohexyl)ethyl)phenyl)propane-1,2-diol was prepared following the method used in Example 128.

Step 1. Dihydroxylation of ally azide 114 was conducted using AD-mix-α to give (1R,2R)-3-azido-1-(3-bromophenyl)propane-1,2-diol. Yield (0.966 g, 96%). $^1$H NMR (400 MHz, DMSO-d$_6$) δ 7.50 (t, J=1.6 Hz, 1H), 7.40 (ddd, J=1.2, 2.0, 7.6 Hz, 1H), 7.29-7.33 (m, 1H), 7.25 (t, J=7.6 Hz, 1H), 5.52 (d, J=5.1 Hz, 1H), 5.26 (d, J=5.9 Hz, 1H), 4.51 (t, J=4.7 Hz, 1H), 3.15 (dd, J=3.3, 12.5 Hz, 1H), 3.02 (dd, J=8.0, 12.7 Hz, 1H).

Step 2. Reduction and protection of (1R,2R)-3-azido-1-(3-bromophenyl)propane-1,2-diol gave N-((2R,3R)-3-(3-bromophenyl)-2,3-dihydroxypropyl)-2,2,2-trifluoroacetamide as a white solid. Yield 0.66 g, 69%). $^1$H NMR (400 MHz, DMSO-d$_6$) δ 9.21 (t, J=5.3 Hz, 1H), 7.52 (t, J=1.6 Hz, 1H), 7.40 (ddd, J=1.2, 2.0, 7.8 Hz, 1H), 7.30-7.33 (m, 1H), 7.25 (t, J=7.6 Hz, 1H), 5.48 (d, J=5.1 Hz, 1H), 5.00 (d, J=5.9 Hz, 1H), 4.51 (t, J=4.7 Hz, 1H), 3.70-3.76 (m, 1H), 3.24 (dt, J=4.9, 13.3 Hz, 1H), 2.98 (ddd, J=5.7, 8.8, 13.3 Hz, 1H).

Step 3. Coupling of N-((2R,3R)-3-(3-bromophenyl)-2,3-dihydroxypropyl)-2,2,2-trifluoroacetamide with olefin 117 gave N-((2R,3R)-2,3-dihydroxy-3-(3-((E)-2-(1-hydroxycyclohexyl)vinyl)phenyl)propyl)-2,2,2-trifluoroacetamide as a brownish foam. Yield (0.1958 g, 82%). $^1$H NMR (400 MHz, DMSO-d$_6$) δ 9.19 (t, J=5.3 Hz, 1H), 7.35-7.37 (m, 1H), 7.20-7.26 (m, 2H), 7.13-7.18 (m, 1H), 6.51 (d, J=16.2 Hz, 1H), 6.33 (d, J=16.0 Hz, 1H), 5.33 (d, J=4.9 Hz, 1H), 4.94 (d, J=5.7 Hz, 1H), 4.46 (t, J=4.8 Hz, 1H), 4.41 (s, 1H), 3.70-3.76 (m, 1H), 3.18 (dt, J=4.5, 13.3 Hz, 1H), 2.99 (ddd, J=6.1, 8.8, 14.3 Hz, 1H), 1.54-1.66 (m, 2H), 1.36-1.54 (m, 7H), 1.18-1.26 (m, 1H).

Step 4. Deprotection of N-((2R,3R)-2,3-dihydroxy-3-(3-((E)-2-(1-hydroxycyclohexyl)vinyl)phenyl)propyl)-2,2,2-trifluoroacetamide gave (1R,2R)-3-amino-1-(3-((E)-2-(1-hydroxycyclohexyl)vinyl)phenyl)propane-1,2-diol as a colorless oil. Yield (0.16 g, quant.). $^1$H NMR (400 MHz, MeOH-d$_4$) δ 7.42-7.44 (m, 1H), 7.30 (dt, J=1.6, 7.6 Hz, 1H), 7.27 (t, J=7.4 Hz, 1H), 7.21 (dt, J=1.6, 7.2 Hz, 1H), 6.60 (d, J=16.0 Hz, 1H), 6.36 (d, J=16.0 Hz, 1H), 4.50 (d, J=5.9 Hz, 1H), 3.62-2.70 (m, 1H), 2.51-2.58 (m, 2H), 1.66-1.77 (m, 2H), 1.48-1.66 (m, 7H), 1.28-1.40 (m, 1H). $^{13}$C NMR (100 MHz, MeOH-d$_4$) δ 142.3, 137.9, 137.7, 128.3, 126.7, 125.7, 125.6, 124.6, 76.0, 75.8, 71.2, 43.6, 37.5, 25.5, 21.9, 20.9. ESI MS m/z 292.3 [M+H]$^+$; HPLC (Method 1) 96% (AUC), t$_R$=4.73 min Step 5. Hydrogenation of (1R,2R)-3-amino-1-(3-((E)-2-(1-hydroxycyclohexyl)vinyl)phenyl)propane-1,2-diol gave Example 129 as a colorless oil. Yield (0.0380 g, 77%); $^1$H NMR (400 MHz, CD$_3$OD) δ 7.20-7.25 (m, 2H), 7.13-7.17 (m, 1H), 7.09-7.12 (m, 1H), 4.45 (d, J=6.3 Hz, 1H), 3.64 (q, J=6.1 Hz, 1H), 2.64-2.69 (m, 2H), 2.52 (d, J=5.9 Hz, 2H), 1.40-1.73 (m, 12H), 1.26-1.38 (m, 2H); RP-HPLC (Method 2) t$_R$=5.17 min, 94.4% (AUC); ESI MS m/z=294.46 [M+H]$^+$.

Example 130

Preparation of (1S,2R)-3-Amino-1-(3-(2-(1-Hydroxycyclohexyl)Ethyl)Phenylpropane-1,2-Diol

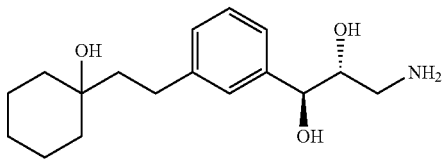 [SMILES: NC[C@@H](O)[C@@H](O)c1cccc(CCC2(O)CCCCC2)c1]

(1S,2R)-3-Amino-1-(3-(2-(1-hydroxycyclohexyl)ethyl)phenyl)propane-1,2-diol was prepared following the method shown in Scheme 24.

SCHEME 24

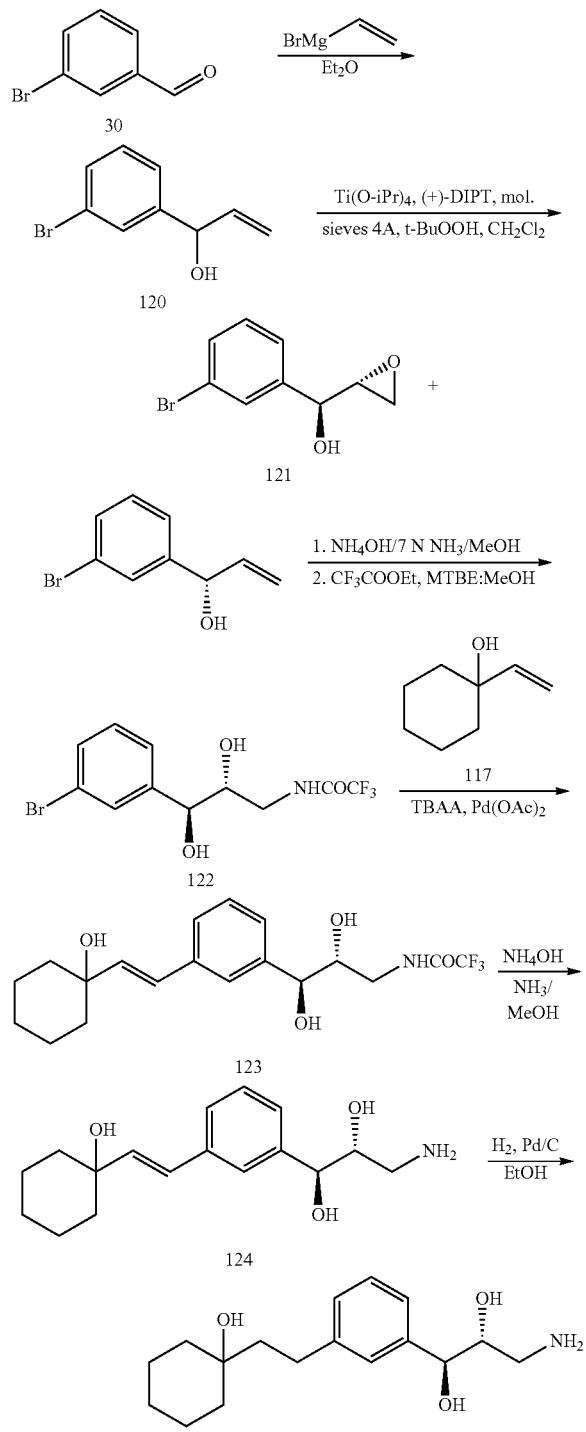

Step 1: A fresh solution of vinyl magnesium bromide (30.0 mL of a 1.0 M solution in THF, 30 mmol) was slowly added under argon to an ice-cold solution of 3-bromobenzaldehyde (30) (3.2 mL, 27.3 mmol) in anhydrous diethyl ether (50 mL). The reaction mixture was stirred at 0° C. for 20 min, after which aqueous solution of NH$_4$Cl (25%, 50 mL) was added. The mixture was allowed to warm to room temperature, layers were separated and aqueous layer was extracted with hexane. Combined organic layers were washed with brine, concentrated under reduced pressure and purified by flash column chromatography (silica gel, 5% to 300% EtOAc/hexanes gradient) to give allyl alcohol 120 as a colorless oil. Yield (4.22 g, 73%). $^1$H NMR (400 MHz, DMSO-d$_6$) δ 7.47-7.49 (m, 1H), 7.40 (dt, J=1.8, 7.4 Hz, 1H), 7.24-7.32 (m, 2H), 5.85-5.94 (m, 1H), 5.61 (d, J=4.5 Hz, 1H), 5.24 (dt, J=1.8, 17.0 Hz, 1H), 5.00-5.07 (m, 2H).

Step 2. To a cold (−23° C.) mixture of powdered 4 Å molecular sieves (6.4 g) and titanium tetraisopropoxide (5.5 mL, 18.8 mmol) in anhydrous CH$_2$Cl$_2$ (110 mL) was added L-(+)-diisopropyl tartrate (DIPT, 4.7 mL, 22.49 mmol) under inert atmosphere. The reaction mixture was stirred at −20° C. and a solution of allyl alcohol 120 (4.0 g, 18 8 mmol) in anhydrous CH$_2$Cl$_2$ (80 mL) was added over 5 mins After the reaction mixture was stirred at −20° C. for 30 min, tert-butyl hydroperoxide solution (5.0-6.0 M in nonane, 2 mL, ca 10.0 mmol) was added. The reaction mixture was stirred at −20° C. for 7.5 nrs, kept at −20° C. overnight, stirred at −20° C. for another 7 hrs and left at −20° C. and then kept at −20° C. for 43 hrs. An aqueous solution of L-tartaric acid (10%, 110 mL) was added to the reaction mixture, the mixture was stirred for 10 min at room temperature, then saturated aqueous solution of Na$_2$SO$_4$ (20 mL) was added. The mixture was stirred vigorously for 1 h at room temperature, layers were separated. Aqueous layer was extracted with diethyl ether, then with EtOAc. Combined organic layers were washed with brine, dried over anhydrous NaSO$_4$, filtered and the filtrate concentrated under reduced pressure. The residue was purified by flash column chromatography (silica gel, 30% to 70% EtOAc/hexanes gradient) to give a mixture of epoxide 121, DIPT (1:1 molar ratio) and unreacted 120 as a colorless oil. Re-purified by flash column chromatography (silica gel, 5% to 10% EtOAc/CH$_2$Cl$_2$ gradient) gave a mixture of epoxide 121 and DIPT (1:0.85 molar ratio) as a colorless oil, which was used in the next step without additional purification. Yield (3.44 g, 85.6%); $^1$H NMR (400 MHz, DMSO-d$_6$) δ 7.54 (t, J=1.6 Hz, 1H), 7.45 (ddd, J=1.2, 2.0, 7.8 Hz, 1H), 7.34-7.38 (m, 1H), 7.29 (t, J=7.6 Hz, 1H), 5.68 (d, J=4.5 Hz, 1H), 4.41 (t, J=4.7 Hz, 1H), 2.99-3.03 (m, 1H), 2.69 (ABd, J=5.5, 3.9 Hz, 1H), 2.63 (ABd, J=5.3, 2.7 Hz, 1H).

Step 3. A solution of the crude epoxide 121 (0.47 g, 0.803 mmol), ammonium hydroxide (25%, 5 mL) and NH$_3$/MeOH (7N, 5 mL) was stirred in a pressure bottle at room temperature for 20 hrs, and then concentrated under reduced pressure. The residue was dissolved in MTBE:MeOH (1:1, 10 mL) and ethyl trifluoroacetate (3.0 mL) was added. The mixture was stirred at room temperature for 1 h, concentrated under reduced pressure and the residue was purified by flash column chromatography (silica gel, 30% to 60% EtOAc/hexanes gradient) to give trifluoroacetamide 122 as a colorless oil. Yield (0.248 g, 66%); $^1$H NMR (400 MHz, DMSO-d$_6$) δ 9.17 (br. t, 1H), 7.51 (t, J=1.8 Hz, 1H), 7.40 (ddd, J=1.2, 2.0, 7.9 Hz, 1H), 7.30-7.33 (m, 1H), 7.25 (t, J=7.8 Hz, 1H), 5.57 (d, J=4.7 Hz, 1H), 4.96 (d, J=6.06 Hz, 1H), 4.39 (t, J=5.5 Hz, 1H), 3.62-3.69 (m, 1H), 3.38 (dt, J=4.1, 13.7 Hz, 1H), 3.05-3.13 (m, 1H).

Step 4. Coupling of bromide 122 with olefin 117 following the method used in Example 128 except that anhydrous degassed DMF (1 mL) was used as the reaction solvent, the reaction was heated at 90° C. for 3 hrs then at 60° C. overnight. After addition of water, the product was extracted with EtOAc (3×) to give olefin 123 as a colorless oil. Yield (0.194 g, 70%); $^1$H NMR (400 MHz, DMSO-d$_6$) δ 9.14 (t, J=5.7 Hz, 1H), 7.35-7.39 (m, 1H), 7.19-7.25 (m, 2H), 7.13-7.18 (m, 1H), 6.51 (d, J=16.0 Hz, 1H), 6.34 (d, J=16.0 Hz, 1H), 5.41 (d, J=4.5 Hz, 1H), 4.86 (d, J=6.3 Hz, 1H), 4.39-4.43 (m, 2H), 3.66-3.73 (m, 1H), 3.37 (ddd, J=3.3, 4.7, 13.3 Hz, 1H), 3.08-3.16 (m, 1H), 1.55-1.67 (m, 2H), 1.37-1.54 (m, 7H), 1.18-1.25 (m, 1H).

Step 5. A mixture of trifluoroacetamide 123 (0.189 g, 0.488 mmol), NH₃/MeOH (7N, 3.0 mL) and ammonium hydroxide (10.0 mL) was stirred at room temperature for 68 hrs and concentrated under reduced pressure. The residue was purified by flash chromatography using a gradient of 50% to 100% 7N NH₃/MeOH in EtOAc/hexanes to give crude amine as a colorless oil. The amine was re-purified by flash chromatography using 20% 7N NH₃/MeOH in CH₂Cl₂ to give alkene 124 as a colorless oil. Yield (0.065 g, 46%); $^1$H NMR (400 MHz, MeOH-d₄) δ 7.42-7.45 (m, 1H), 7.22-7.32 (m, 3H), 6.61 (d, J=16.2 Hz, 1H), 6.36 (d, J=16.0 Hz, 1H), 4.58 (d, J=6.1 Hz, 1H), 3.71-3.76 (m, 1H), 2.92 (dd, J=3.5, 13.1 Hz, 1H), 2.77 (dd, J=8.0, 13.1 Hz, 1H), 1.47-1.76 (m, 9H), 1.25-1.40 (m, 1H); $^{13}$C NMR (100 MHz, MeOH-d₄) δ 142.7, 137.8, 137.5, 128.1, 126.9, 125.8, 125.4, 124.8, 76.1, 75.7, 71.2, 43.3, 37.5, 25.5, 21.9; RP-HPLC (Method 2) 97% (AUC), $t_R$=5.44 min; ESI MS m/z 292.5 [M+H]⁺.

Step 6. Hydrogenation of alkene 124 following the method used in Example 128 gave Example 130 as a colorless oil. Yield (0.0513 g, quant); $^1$H NMR (400 MHz, CD₃OD) δ 7.19-7.25 (m, 2H), 7.15-7.19 (m, 1H), 7.07-7.11 (m, 1H), 4.52 (d, J=6.3 Hz, 1H), 3.65 (ddd, J=3.3, 6.1, 9.6 Hz, 1H), 2.82 (dd, J=3.5, 13.1 Hz, 1H), 2.63-2.70 (m, 3H), 1.42-1.74 (m, 12H), 1.26-1.37 (m, 2H); $^{13}$C NMR (100 MHz, MeOH-d₄) δ 143.1, 142.3, 128.0, 127.3, 126.8, 124.1, 76.2, 75.5, 70.9, 44.5, 43.2, 37.0, 29.4, 25.9, 22.1, 17.2; RP-HPLC (Method 2) $t_R$=5.30 min, 92.7% (AUC); ESI MS m/z=294.46 [M+H]⁺

Example 131

Preparation of (1R,2S)-3-Amino-1-(3-(2-(1-Hydroxycyclohexyl)Ethyl)Phenylpropane-1,2-Diol

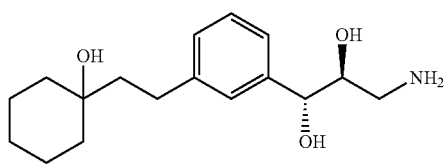 [SMILES: NC[C@H](O)[C@H](O)c1cccc(CCC2(O)CCCCC2)c1]

(1R,2S)-3-Amino-1-(3-(2-(1-hydroxycyclohexyl)ethyl)phenyl)propane-1,2-diol was prepared following the method used in Example 130.

Step 1. Epoxidation of allyl alcohol 120 using D-(−)-diisopropyl tartrate gave crude (R)-(3-bromophenyl)((S)-oxiran-2-yl)methanol as a colorless oil. Yield (4.12 g, quant.); $^1$H NMR (400 MHz, DMSO-d₆) δ 7.54 (t, J=1.6 Hz, 1H), 7.45 (ddd, J=1.2, 2.0, 7.8 Hz, 1H), 7.34-7.38 (m, 1H), 7.29 (t, J=7.6 Hz, 1H), 5.68 (d, J=4.5 Hz, 1H), 4.41 (t, J=4.7 Hz, 1H), 2.99-3.03 (m, 1H), 2.69 (ABd, J=5.5, 3.9 Hz, 1H), 2.63 (ABd, J=5.3, 2.7 Hz, 1H).

Step 3. Epoxide ring opening and protection of amine with trifluoroacetyl group gave N-((2S,3R)-3-(3-bromophenyl)-2,3-dihydroxypropyl)-2,2,2-trifluoroacetamide as a colorless oil. Yield (0.322 g, 42%); $^1$H NMR (400 MHz, DMSO-d₆) δ 9.14 (t, J=5.7 Hz, 1H), 7.35-7.39 (m, 1H), 7.19-7.25 (m, 2H), 7.13-7.18 (m, 1H), 6.51 (d, J=16.0 Hz, 1H), 6.34 (d, J=16.0 Hz, 1H), 5.41 (d, J=4.5 Hz, 1H), 4.86 (d, J=6.3 Hz, 1H), 4.39-4.43 (m, 2H), 3.66-3.73 (m, 1H), 3.37 (ddd, J=3.3, 4.7, 13.3 Hz, 1H), 3.08-3.16 (m, 1H), 1.55-1.67 (m, 2H), 1.37-1.54 (m, 7H), 1.18-1.25 (m, 1H).

Step 4. Heck coupling of N-((2S,3R)-3-(3-bromophenyl)-2,3-dihydroxypropyl)-2,2,2-trifluoroacetamide with olefin 105 gave N-((2S,3R)-2,3-dihydroxy-3-(3-((E)-2-(1-hydroxycyclohexyl)vinyl)phenyl)propyl)-2,2,2-trifluoroacetamide as a colorless oil. Yield (0.266 g, 76%); $^1$H NMR (400 MHz, DMSO-d₆) δ 9.14 (t, J=5.7 Hz, 1H), 7.35-7.39 (m, 1H), 7.19-7.25 (m, 2H), 7.13-7.18 (m, 1H), 6.51 (d, J=16.0 Hz, 1H), 6.34 (d, J=16.0 Hz, 1H), 5.41 (d, J=4.5 Hz, 1H), 4.86 (d, J=6.3 Hz, 1H), 4.39-4.43 (m, 2H), 3.66-3.73 (m, 1H), 3.37 (ddd, J=3.3, 4.7, 13.3 Hz, 1H), 3.08-3.16 (m, 1H), 1.55-1.67 (m, 2H), 1.37-1.54 (m, 7H), 1.18-1.25 (m, 1H).

Step 5. Deprotection of N-((2S,3R)-2,3-dihydroxy-3-(3-((E)-2-(1-hydroxycyclohexyl)vinyl)phenyl)propyl)-2,2,2-trifluoroacetamide gave (1R,2S)-3-amino-1-(3-((E)-2-(1-hydroxycyclohexyl)vinyl)phenyl)propane-1,2-diol as a colorless oil. Yield (0.104 g, 52%); $^1$H NMR (400 MHz, MeOH-d₄) δ 7.42-7.45 (m, 1H), 7.22-7.32 (m, 3H), 6.61 (d, J=16.2 Hz, 1H), 6.36 (d, J=16.0 Hz, 1H), 4.58 (d, J=6.1 Hz, 1H), 3.71-3.76 (m, 1H), 2.92 (dd, J=3.5, 13.1 Hz, 1H), 2.77 (dd, J=8.0, 13.1 Hz, 1H), 1.47-1.76 (m, 9H), 1.25-1.40 (m, 1H).

Step 6. Hydrogenation of (1R,2S)-3-amino-1-(3-((E)-2-(1-hydroxycyclohexyl)vinyl)phenyl)propane-1,2-diol gave Example 131 as a colorless oil. Yield (0.0834 g, 96%); $^1$H NMR (400 MHz, CD₃OD) δ 7.19-7.25 (m, 2H), 7.15-7.19 (m, 1H), 7.07-7.11 (m, 1H), 4.52 (d, J=6.3 Hz, 1H), 3.65 (ddd, J=3.3, 6.1, 9.6 Hz, 1H), 2.82 (dd, J=3.5, 13.1 Hz, 1H), 2.63-2.70 (m, 3H), 1.42-1.74 (m, 12H), 1.26-1.37 (m, 2H); RP-HPLC (Method 2) $t_R$=5.31 min, 88.0% (AUC); ESI MS m/z=294.48 [M+H]⁺

Example 132

Preparation of (R)-3-(3-(3-Aminopropyl)Phenyl)-1-Phenylpropan-1-Ol

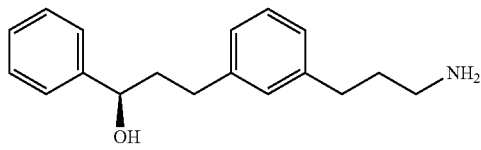

(R)-3-(3-(3-Aminopropyl)phenyl)-1-phenylpropan-1-ol was prepared following the method used in Example 2.

Step 1: Sonogashira coupling of (R)-1-phenylprop-2-yn-1-ol with N-(3-(3-bromophenyl)propyl)-2,2,2-trifluoroacetamide gave (S)-2,2,2-trifluoro-N-(3-(3-(3-hydroxy-3-phenylprop-1-ynyl)phenyl)propyl)acetamide as an amber oil. Yield (0.73 g, 62%); $^1$H NMR (400 MHz, DMSO-d₆) δ 7.57-7.59 (m, 2H), 7.17-7.40 (m, 7H), 5.60 (s, 1H), 3.26-3.29 (m, 2H), 2.62 (t, J=7.6 Hz, 2H), 1.86 (quint, J=6.8 Hz, 2H)

Step 2: Deprotection of (S)-2,2,2-trifluoro-N-(3-(3-(3-hydroxy-3-phenylprop-1-ynyl)phenyl)propyl)acetamide gave (S)-3-(3-(3-Aminopropyl)phenyl)-1-phenylprop-2-yn-1-ol as a pale yellow oil. Yield (0.239 g, 30%): $^1$H NMR (400 MHz, CD₃OD) δ 7.56-7.59 (m, 1H), 7.16-7.39 (m, 8H), 5.60 (s, 1H), 2.58-2.62 (m, 4H), 1.69-1.77 (m, 2H).

Step 3: Reduction of (S)-3-(3-(3-Aminopropyl)phenyl)-1-phenylprop-2-yn-1-ol following the method used in Example 2, followed by flash chromatography (10-100% (7N NH₃/MeOH)/DCM gradient), gave Example 132 as a colorless oil. Yield (0.103 g, 81%). $^1$H NMR (400 MHz, CDCl₃) δ 7.31-

7.36 (m, 4H), 7.24-7.30 (m, 1H), 7.15-7.21 (m, 1H), 6.97-7.03 (m, 3H), 4.66 (dd, J=5.2, 8.0 Hz, 1H), 2.56-2.76 (m, 6H), 1.96-2.16 (m, 2H), 1.69-1.79 (m, 2H), 1.50-1.70 (brs, 3H). ESI MS m/z 270.21 [m+H]$^+$, 252.17 [m+H−OH]$^+$.

Example 133

Preparation of 3-(3-(2-Cycloheptylethyl)Phenyl)Propan-1-Amine

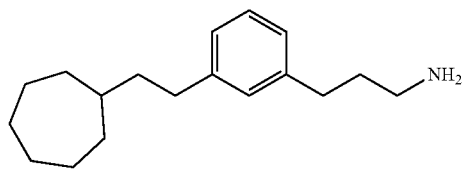 [SMILES: NCCCc1cccc(CCC2CCCCCC2)c1]

3-(3-(2-cycloheptylethyl)phenyl)propan-1-amine was prepared following the method shown in Scheme 25.

SCHEME 25

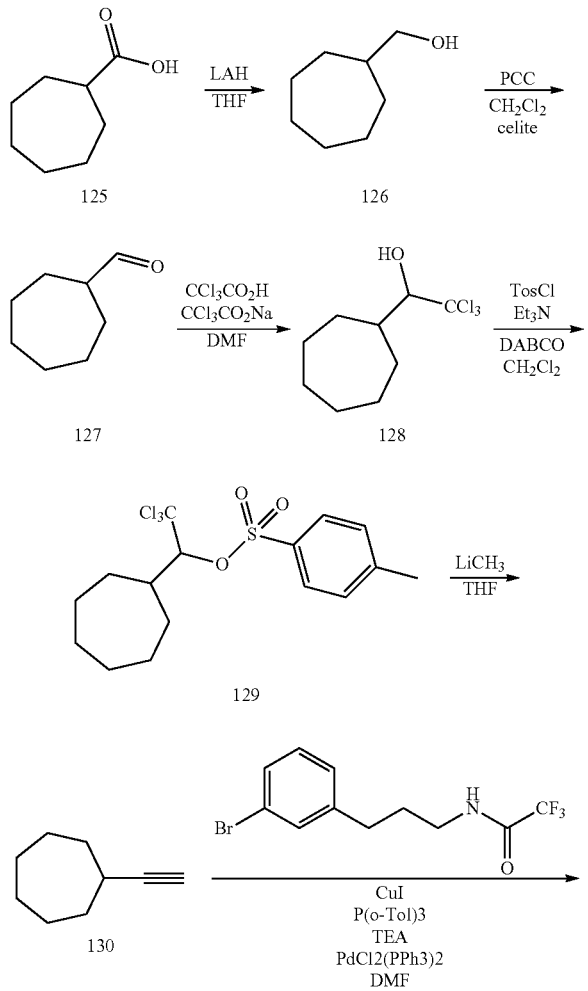

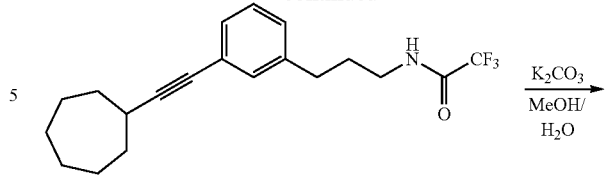

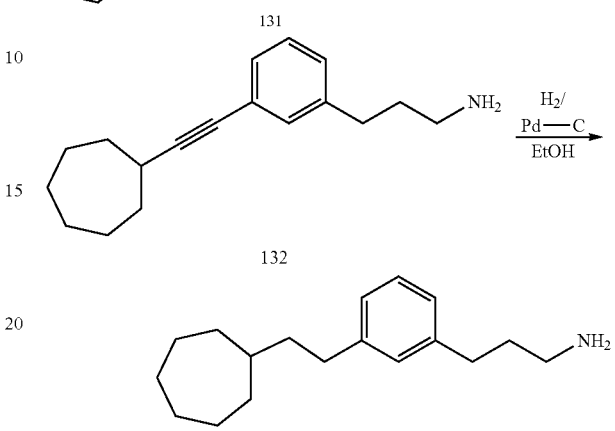

Step 1: LAH (180 mL of a 1M solution, 176 mmol) was added slowly to a solution of acid 125 (25 g, 176 mmol), in anhydrous THF (500 mL) under argon at 5° C. The reaction was allowed to warm to room temperature, stirred 1 h, cooled again to 5° C., then quenched by slow addition of saturated aqueous Na$_2$SO$_4$. The resultant precipitate was removed by filtration, then the filtrate was extracted with EtOAc, washed with water and brine, dried over Na$_2$SO$_4$, filtered and concentrated to give the alcohol 126 as a colorless oil. Yield (21 g, 98%). $^1$H NMR (400 MHz, CDCl$_3$) δ 3.38 (d, J=6.4 Hz, 2H), 1.38-1.80 (m, 12H), 1.10-1.20 (m, 2H).

Step 2: A solution of alcohol 126 (4.5 g, 35 mmol) in dichloromethane (10 mL) was added to a stirring mixture of pyridinium chlorochromate (9.4 g, 43 8 mmol) and celite (10 g) in dichloromethane (100 mL) and the reaction stirred 16 hr. The mixture was filtered through a pad of silica gel and the pad rinsed with diethyl ether. The combined filtrate was concentrated, giving impure aldehyde 127 as a green oil, which was taken on to the next step without purification. Yield (4.1 g, 93%). $^1$H NMR (400 MHz, CDCl$_3$) δ 9.58 (d, J=0.8 Hz, 1H), 2.28-2.36 (m, 1H), 1.88-1.95 (m, 2H), 1.40-1.70 (m, 10H).

Step 3: Sodium trichloroacetate was added in 3 aliquots over 10 min to a stirred solution of aldehyde 127 (14.9 g,118 mmole) and trichloroacetic acid (19.3 g, 177 mmol) in DMF (150 mL). The reaction was stirred at room temperature for 2 h, cooled in an ice bath, then quenched and diluted with water. The solution was extracted with hexanes and washed with saturated aqueous NH$_4$Cl, water, and brine. The combined organics were dried over Na$_2$SO$_4$, filtered, and concentrated under reduced pressure, giving impure alcohol 128 as a yellow oil, which was taken on to the next step without purification. Yield (23.4 g, 80%). $^1$H NMR (400 MHz, CDCl$_3$) δ 3.95 (d, J=2.0 Hz, 1H), 2.85 (br s, 1H), 2.20-2.30 (m, 1H), 1.88-2.08 (m, 1H), 1.36-1.84 (m, 11H).

Step 4: p-toluenesulfonyl chloride (3.34 g, 17 5 mmol) was added to a solution of alcohol 128 (4.3 g, 17.5 mmol), triethylamine (3.6 mL, 26.3 mmol), and diazabicyclooctane (0.586 g, 5 2 mmol) in 40 mL dichloromethane and stirred at room temperature for 90 min. The reaction was washed with water (40 mL), and 5N HCl (40 mL). The combined aqueous was extracted with dichloromethane (40 mL) and the combined organics further washed with 2N HCl, water, and brine, then dried over Na$_2$SO$_4$, filtered, and concentrated under reduced pressure. Purification by flash chromatography (0-10% EtOAc/hexanes gradient) gave the sulfonate 129 as pale yellow crystals. Yield (2.65 g, 38%): $^1$H NMR (400 MHz, CDCl$_3$) δ 7.81 (d, J=8.8 Hz, 2H), 7.32 (d, J=8 Hz, 2H), 2.43 (s, 3H), 2.24-2.32 (m, 1H), 1.98-2.06 (s, 1H), 1.78-1.88 (m, 1H), 1.60-1.73 (m, 3H), 1.28-1.60 (m, 8H).

Step 5: Methyllithium (7.0 mL of a 1.6 M solution in diethyl ether, 11.25 mmol) was added dropwise to a stirring solution of sulfonate 129 (1 g, 2.5 mmol) in anhydrous THF (15 mL) under argon at 5° C. The reaction was allowed to warm to room temperature, stirred 16 hr, then quenched by the slow addition of saturated aqueous NH$_4$Cl. The mixture was extracted with hexanes, and the combined organics washed with brine, dried over Na$_2$SO$_4$, filtered, and concentrated under reduced pressure, giving the ethynylcycloheptane (130) as a yellow oil. Yield (0.270 g, 88%) $^1$H NMR (400 MHz, CDCl$_3$) δ 2.51 (s, 1H), 1.99 (d, J=2.8 Hz, 1H), 1.73-1.83 (m, 2H), 1.55-1.70 (m, 4H), 1.35-1.55 (m, 6H).

Step 6: Sonogashira coupling of ethynylcycloheptane (130) with N-(3-(3-bromophenyl)propyl)-2,2,2-trifluoroacetamide following the method used in Example 2, followed by flash chromatography (0-25% EtOAc/hexanes gradient), gave alkyne 131 as an amber oil. Yield (0.556 g, 59%): $^1$H NMR (400 MHz, CDCl$_3$) δ 7.16-7.26 (m, 3H), 7.03-7.08 (m, 1H), 6.28 (br s, 1H), 3.36 (dt, J=6.8, 6.8 Hz, 2H), 2.75-2.83 (m, 1H), 2.63 (t, J=7.2 Hz, 2H), 1.85-1.95 (m, 4H), 1.69-1.80 (m, 4H), 1.48-1.65 (m, 6H).

Step 7: Deprotection of alkyne 131 following the method used in Example 2, followed by flash chromatography (5% (7N NH3/MeOH)/dichloromethane), gave alkyne 132 as a colorless oil. Yield (0.226 g, 56%): $^1$H NMR (400 MHz, CDCl$_3$) δ 7.13-7.25 (m, 3H), 7.03-7.08 (m, 1H), 2.74-2.82 (m, 1H), 2.69 (t, J=7.2 Hz, 2H), 2.59 (t, J=7.2 Hz, 2H), 1.84-1.94 (m, 2H), 1.68-1.80 (m, 6H), 1.46-1.64 (m, 6H), 1.30 (br s, 2H).

Step 8: Reduction of alkyne 132 following the method used in Example 2, followed by flash chromatography (10-100% (7N NH$_3$/MeOH)/DCM gradient), gave Example 133 as a colorless oil. Yield (0.081 g, 80%): $^1$H NMR (400 MHz, CD3OD) δ 7.13 (t, J=7.2 Hz, 1H), 6.92-7.00 (m, 32H), 2.52-2.65 (m, 6H), 1.70-1.80 (m, 4H), 1.60-1.70 (m, 2H), 1.36-1.60 (m, 9H), 1.18-1.28 (m, 2H). ESI MS m/z 260.25 [m+H]$^+$.

Example 134

Preparation of 4-(3-(2-Aminothyelthio)Phenethyl)Heptan-4-Ol

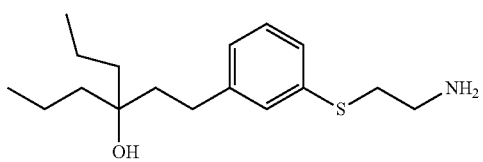 [SMILES: CCCC(O)(CCC)CCc1cccc(SCCN)c1]

4-(3-(2-Aminoethylthio)phenethyl)heptan-4-ol was prepared following the method shown in Scheme 26.

SCHEME 26

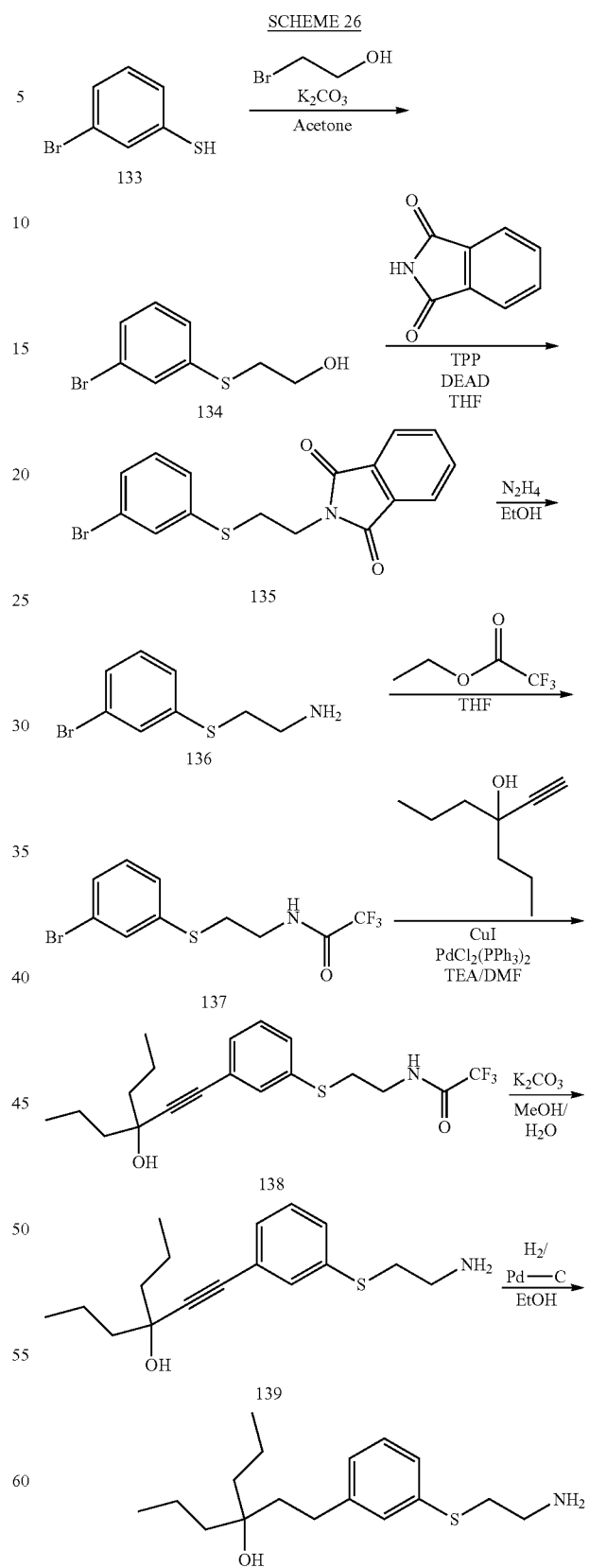

Step 1: 3-bromobenzenethiol (133) (3 g, 15.9 mmol), 2-bromoethanol (2.4 g, 19.1 mmol), and K$_2$CO$_3$ (4.4 g, 32 mmol) were combined in acetone (20 mL) and stirred at room temperature for 1 h. The acetone was removed under reduced pressure and the residue extracted from water with ethyl acetate. The ethyl acetate solution was washed with brine, dried with MgSO$_4$, filtered, and concentrated under reduced pressure, giving the alcohol 134 as a yellow oil without purification. Yield (3.6 g, 97%): $^1$H NMR (400 MHz, CDCl$_3$) δ 7.49 (t, J=2.0 Hz, 1H), 7.31 (ddd, J=0.8, 1.6, 8.0 Hz, 1H), 7.27 (ddd, J=0.8, 1.6, 8.0 Hz, 1H), 7.13 (t, J=7.6 Hz, 1H), 3.75 (t, J=6.4 Hz, 2H), 3.10 (t, J=6.4 Hz, 2H), 2.18 (brs, 1H).

Step 2: Mitsunobu coupling of 134 with phthalimide following the method used in Example 21, followed by flash chromatography (5-20% ethyl acetate/hexanes gradient) gave the bromide 135 as a white solid. Yield (4.04 g, 72%): $^1$H NMR (400 MHz, CDCl$_3$) δ 7.77-7.84 (m, 2H), 7.66-7.72 (m, 2H), 7.50 (t, J=2.0 Hz, 1H), 7.30 (ddd, J=0.8, 1.6, 7.6 Hz, 1H), 7.19 (ddd, J=0.8, 1.6, 7.6 Hz, 1H), 7.07 (t, J=7.6 Hz, 1H), 3.93 (t, J=7.2 Hz, 2H), 3.22 (J=7.2 Hz, 2H).

Step 3: Deprotection of the bromide 135 following the method used in Example 9 gave the amine 136 as a yellow oil. Yield (1.56 g, 98%): $^1$H NMR (400 MHz, CDCl$_3$) δ 7.44 (t, J=2.0 Hz, 1H), 7.26 (ddd, J=0.8, 1.6, 7.6 Hz, 1H), 7.21 (ddd, J=0.8, 1.6, 7.6 Hz, 1H), 7.09 (t, J=8.0 Hz, 1H), 2.87-3.0 (m, 2H), 2.82-2.86 (m, 2H), 1.7-2.4 (brs, 2H).

Step 4: Amidation of the amine 136 according to the method used in Example 2, followed by flash chromatography (5-20% ethyl acetate/hexanes gradient) gave the trifluoroamide 137 as a colorless oil. Yield (1.75 g, 80%): $^1$H NMR (400 MHz, CDCl$_3$) δ 7.50 (t, J=2.0 Hz, 1H), 7.35 (ddd, J=0.8, 1.6, 7.6 Hz, 1H), 7.29 (ddd, J=0.8, 1.6, 7.6 Hz, 1H), 7.16 (t, J=8.0 Hz, 1H), 6.81 (brs, 1H), 3.55 (app q, J=6.4 Hz, 2H), 3.10 (t, J=6.4 Hz, 2H).

Step 5: Sonogashira coupling of 4-ethynylheptan-4-ol with the N-(2-(3-bromophenylthio)ethyl)-2,2,2-trifluoroacetamide (137) following the method used in Example 2, followed by flash chromatography (5-50% ethyl acetate/hexanes gradient) gave alkynol 138 as a colored solid. Yield (0.22 g, 52%): $^1$H NMR (400 MHz, DMSO) δ 9.52-9.60 (m, 1H), 7.26-7.36 (m, 3H), 7.16-7.20 (m, 1H), 5.11 (s, 1H), 3.60 (ddd, J=6.4 Hz, 2H), 3.11 (t, J=7.2 Hz, 2H), 1.52-1.62 (m, 4H), 1.38-1.52 (m, 4H), 0.89 (t, J=7.2 Hz, 6H).

Step 6: Deprotection of alkynol 138 following the method used in Example 2, followed by flash chromatography (0-10% (7N NH$_3$/MeOH)/dichloromethane gradient) gave amine 139 as a yellow oil. Yield (0.89 g, 68%): $^1$H NMR (400 MHz, MeOD) δ 7.36-7.38 (m, 1H), 7.32 (dt, J=1.6, 7.6 Hz, 1H), 7.25 (t, J=7.6 Hz, 1H), 7.20 (dt, J=1.6, 7.6 Hz, 1H), 3.01 (t, J=6.4 Hz, 2H), 2.78 (brs, 2H), 1.62-1.74 (m, 4H), 1.50-1.62 (m, 4H), 0.97 (t, J=7.2 Hz, 6H).

Step 7: Reduction of amine 139 following the method used in Example 1, followed by flash chromatography (10-100% (7N NH$_3$/MeOH)/DCM gradient), gave Example 134 as a colorless oil. Yield (0.042 g, 75%): $^1$H NMR (400 MHz, CDCl$_3$) δ 7.16-7.21 (m, 3H), 6.99-7.03 (m, 1H), 2.99 (t, J=5.6 Hz, 2H), 2.91 (brs, 2H), 2.56-2.62 (m, 2H), 1.66-1.73 (m, 2H), 1.40-1.60 (m, 7H), 1.28-1.40 (m, 4H), 0.924 (t, J=7.2 Hz, 6H). ESI MS m/z 296.29 [m+H]$^+$, 278.25 [m+H−OH]$^+$.

Example 135

Preparation of 4-(3-(2-Aminoethylsulfonyl)Phenethyl)Heptan-4-Ol

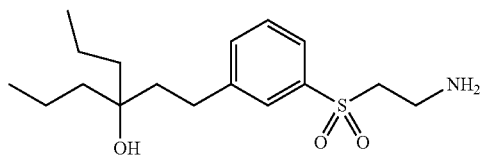 [SMILES: CCCC(O)(CCC)CCc1cccc(S(=O)(=O)CCN)c1]

4-(3-(2-Aminoethylsulfonyl)phenethyl)heptan-4-ol was prepared following the method shown in Scheme 27.

SCHEME 27

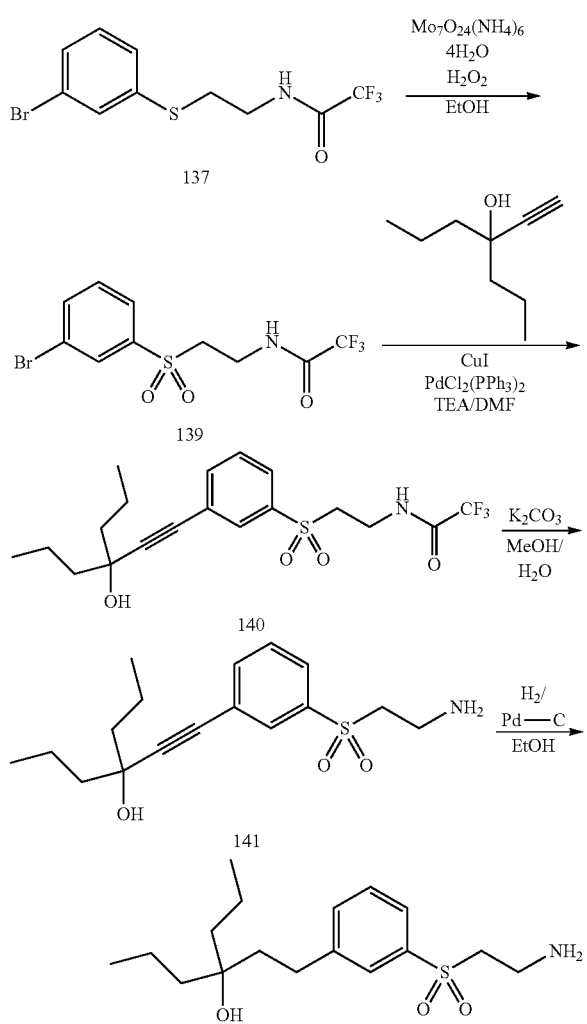

Step 1: To a solution of the bromide 137 (0.6 g, 1.83 mmol) in ethanol (10 mL) at room temperature was added ammonium molybdate tetrahydrate (0.68 g, 0.55 mmol (30%)), and hydrogen peroxide (1.9 mL of a 30% aq solution, 18.3 mmol). The reaction was stirred overnight then quenched with saturated aqueous Na$_2$S$_2$O$_3$ (4 mL). Ethanol was removed in vacuo and the residue was extracted from water with ethyl acetate. The combined organics was washed with brine, dried over MgSO$_4$, filtered, concentrated in-vacuo, and purified by flash chromatography (5-50% ethyl acetate/hexanes gradient), giving the sulfone 139 as a white waxy solid. Yield (0.615 g, 93%): $^1$H NMR (400 MHz, CDCl$_3$) δ 8.05 (t, J=2.0 Hz, 1H), 7.81-7.87 (m, 2H), 7.49 (t, J=8.0 Hz, 1H), 7.25 (brs, 1H), 3.81-3.88 (m, 2H), 3.33-3.38 (m, 2H).

Step 2: Sonogashira coupling of 139 with 4-ethynylheptan-4-ol following the method used in Example 2, followed by flash chromatography (5-50% ethyl acetate/hexanes gradient) gave alkynol 140 as a yellow oil. Yield (0.515 g, 72%): $^1$H NMR (400 MHz, DMSO) δ 7.93 (m, 1H), 7.80-7.84 (m, 1H), 7.69-7.73 (m, 1H), 7.55 (t, J=8.0 Hz, 1H), 7.27 (brs, 1H), 3.79-3.86 (m, 2H), 3.31-3.36 (m, 2H), 1.93 (brs, 1H), 1.64-1.78 (m, 4H), 1.51-1.64 (m, 4H), 0.98 (t, J=7.2 Hz, 6H).

Step 3: Deprotection of trifluoroamide 140 according to the method used in Example 2, followed by flash chromatography (0-10% (7N NH$_3$/MeOH)/dichloromethane gradient), gave alkyne 141 as a yellow oil. Yield (0.21 g, 52%): $^1$H NMR (400 MHz, MeOD) δ 7.90-7.92 (m, 1H), 7.78-7.82 (m, 1H), 7.62-7.64 (m, 1H), 7.48 (t, J=8.0 Hz, 1H), 3.20-3.25 (m, 2H), 3.07-3.15 (m, 2H), 1.81 (brs, 3H), 1.62-1.75 (m, 4H), 1.50-1.62 (m, 4H), 0.96 (t, J=7.2 Hz, 6H).

Step 4: Reduction of the alkyne 141 following the method used in Example 2, followed by flash chromatography (10-100% (7N NH$_3$/MeOH)/DCM gradient), gave Example 135 as a colorless oil. Yield (0.081 g, 80%): $^1$H NMR (400 MHz, CDCl$_3$) δ 7.69-7.74 (m, 2H), 7.44-7.49 (m, 2H), 3.20-3.24 (m, 2H), 3.08-3.13 (m, 2H), 2.69-2.75 (m, 2H), 1.68-1.74 (m, 2H), 1.43-1.52 (m, 7H), 1.26-1.40 (m, 4H), 0.92 (t, 8.0 Hz, 6H). ESI MS m/z 328.31 [m+H]$^+$, 310.27 [m+H−OH]$^+$.

Example 136

Preparation of 4-(3-(2-Aminoethylamino)Phenethyl)Heptan-4-Ol

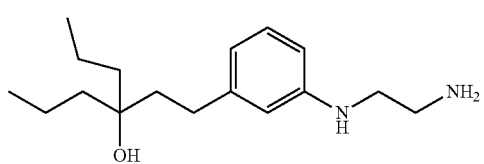 [SMILES: CCCC(O)(CCC)CCc1cccc(NCCN)c1]

4-(3-(2-Aminoethylamino)phenethyl)heptan-4-ol was prepared following the method shown in Scheme 28.

SCHEME 28

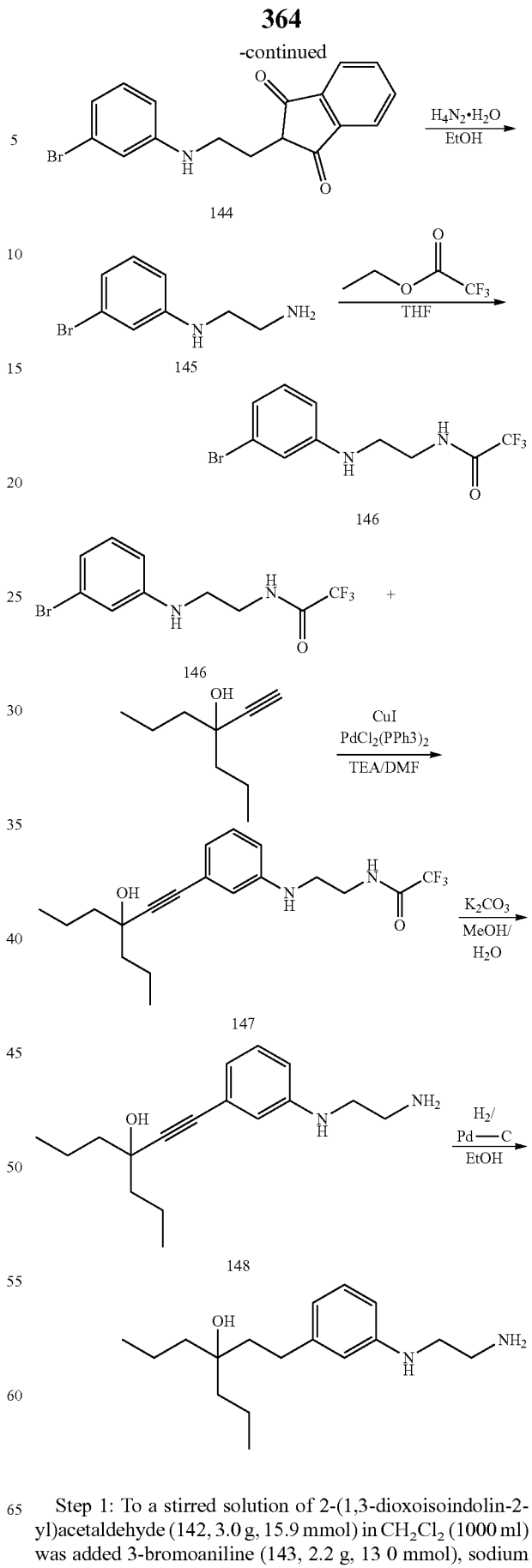

Step 1: To a stirred solution of 2-(1,3-dioxoisoindolin-2-yl)acetaldehyde (142, 3.0 g, 15.9 mmol) in CH$_2$Cl$_2$ (1000 ml) was added 3-bromoaniline (143, 2.2 g, 13 0 mmol), sodium triacetoxyborohydride (4.2 g, 20 mmol) and acetic acid (1.2 g, 20 mmol). The reaction was stirred at room temperature overnight, then washed with saturated ammonium chloride, water, and brine. The combined organics were dried over MgSO$_4$, filtered, and concentrated in-vacuo. Purification by flash chromatography (10-40% ethyl acetate/hexanes gradient) gave benzyl bromide 144 as a yellow oil. Yield (1.7 g, 38%). $^1$H NMR (400 MHz, CDCl$_3$) δ 7.80-7.88 (m, 2H), 7.68-7.78 (m, 2H), 6.93-6.99 (m, 1H), 6.72-6.77 (m, 2H), 6.49-6.54 (m, 1H), 4.23 (brs, 1H), 3.95 (t, J=6.0 Hz, 2H), 3.39 (t, J=6.0 Hz, 2H).

Step 2: Deprotection of benzyl bromide 144 following the method used in Example 9, followed by flash chromatography (0-10% (7N NH$_3$/MeOH)/dichloromethane) gradient), gave diamine 145 as a yellow oil. Yield (0.286 g, 57%). $^1$H NMR (400 MHz, CDCl$_3$) δ 6.99 (t, J=8.0 Hz, 1H), 6.76-6.81 (m, 1H), 6.74 (t, J=2.0 Hz, 1H), 6.49-6.54 (m, 1H), 4.19 (brs, 1H), 3.13 (t, J=6.0 Hz, 2H), 2.92 (t, J=6.0 Hz, 2H), 1.20 (brs, 2H).

Step 3: Amidation of diamine 145 following the method used in Example 2 gave trifluoroamide 146 as a yellow, waxy solid. Yield (0.462 g, quantitative). $^1$H NMR (400 MHz, CDCl$_3$) δ 7.01 (t, J=8.0 Hz, 1H), 6.99 (brs, 1H), 6.82-6.86 (m, 1H), 6.74 (t, J=2.4 Hz, 1H), 6.50-6.55 (m, 1H), 4.03 (brs, 1H), 3.55 (q, J=6.0, Hz, 2H), 3.33 (t, J=6.0 Hz, 2H).

Step 4: Sonogashira coupling of 146 with 4-ethynylheptan-4-ol following the method used in Example 2, followed by flash chromatography (5-30% ethyl acetate/hexanes gradient), gave alkynol 147 as an orange oil. Yield (0.30 g, 60%). $^1$H NMR (400 MHz, CDCl$_3$) δ 7.54 (brs, 1H), 7.07 (t, J=8.0 Hz, 1H), 6.75-6.78 (m, 1H), 6.61-6.64 (m, 1H), 6.52-6.56 (m, 1H), 3.51 (q, J=5.6 Hz, 2H), 3.32 (t, J=6.0 Hz, 2H), 1.63-1.71 (m, 4H), 1.50-1.63 (m, 4H), 0.95 (t, J=7.2 Hz, 6H).

Step 5: Deprotection of alkynol 147 following the method used in Example 2 followed by flash chromatography (0-10% (7N NH$_3$/MeOH)/dichloromethane) gradient), gave amine 148 as a yellow, waxy solid. Yield (0.14 g, 63%). $^1$H NMR (400 MHz, DMSO) δ 6.97-7.03 (m, 1H), 6.46-6.54 (m, 3H), 5.66 (t, J=5.2 Hz, 1H), 5.07 (s, 1H), 2.94 (q, J=6.4 Hz, 2H), 2.66 (t, J=6.4 Hz, 2H), 1.38-1.62 (m, 10H), 0.88 (t, J=7.8 Hz, 6H).

Step 6: Reduction of the amine 148 following the method used in Example 2, followed by flash chromatography (10-100% (7N NH$_3$/MeOH)/DCM gradient), gave Example 136 as a colorless oil. Yield (0.047 g, 84%): $^1$H NMR (400 MHz, CDCl$_3$) δ 7.08 (t, J=7.6 Hz, 1H), 6.53-6.57 (m, 1H), 6.44-6.49 (m, 2H), 3.18 (t, J=6.0 Hz, 2H), 2.94 (t, J=6.0 Hz, 2H), 2.51-2.57 (m, 2H), 1.68-1.74 (m, 2H), 1.42-1.50 (m, 6H), 1.28-1.40 (m, 6H), 0.93 (t, J=7.2 Hz, 6H). ESI MS m/z 279.3 [m+H]$^+$, 261.26 [m+H–OH]$^+$.

Example 137

Preparation of 3-Amino-1-(3-(2-Cycloheptylethyl)Phenyl)Propan-1-Ol

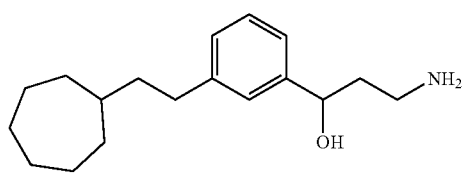 [SMILES: NCCC(O)c1cccc(CCC2CCCCCC2)c1]

3-amino-1-(3-(2-cycloheptylethyl)phenyl)propan-1-ol was prepared following the method used in Example 2.

Step 1: Sonogashira coupling of N-(3-(3-bromophenyl)-3-hydroxypropyl)-2,2,2-trifluoroacetamide (43) with ethynylcycloheptane, followed by flash chromatography (5-40% EtOAc/hexanes gradient), gave N-(3-(3-(cycloheptylethynyl)phenyl)-3-hydroxypropyl)-2,2,2-trifluoroacetamide as an amber oil. Yield (0.507 g, 51%): $^1$H NMR (400 MHz, CDCl$_3$) δ 7.42 (br s, 1H), 7.34-7.36 (m, 1H), 7.19-7.33 (m, 3H), 4.81 (q, J=4.0 Hz, 1H), 3.48-3.68 (m, 1H), 3.32-3.42 (m, 1H), 2.74-2.82 (m, 1H), 2.48 (br s, 1H), 1.85-2.00 (m, 4H), 1.70-1.80 (m, 4H), 2.46-1.64 (m, 6H).

Step 2: Deprotection of N-(3-(3-(cycloheptylethynyl)phenyl)-3-hydroxypropyl)-2,2,2-trifluoroacetamide followed by flash chromatography (5% (7N NH$_3$/MeOH)/dichloromethane) gave 3-amino-1-(3-(2-cycloheptylethynyl)phenyl)propan-1-ol as a yellow oil. Yield (0.173 g, 46%): $^1$H NMR (400 MHz, CDCl$_3$) δ 7.40 (s, 1H), 7.18-7.30 (m, 3H), 4.91 (d, J=6.8 Hz, 1H), 3.00 (br s, 5H), 2.74-2.82 (m, 1H), 1.80-1.94 (m, 3H), 1.68-1.80 (m, 5H), 1.44-1.64 (m, 6H).

Step 3: Reduction of 3-amino-1-(3-(2-cycloheptylethynyl)phenyl)propan-1-ol following the method used in Example 2, followed by flash chromatography (10-100% (7N NH$_3$/MeOH)/DCM gradient), gave Example 137 as a colorless oil. Yield (0.076 g, 69%): $^1$H NMR (400 MHz, CDCl$_3$) δ 7.13-7.26 (m, 3H), 7.03-7.07 (m, 1H), 4.88-4.94 (m, 1H), 3.03-3.10 (m, 1H), 2.88-2.98 (m, 1H), 2.77 (brs, 3H), 2.55-2.63 (m, 2H), 1.80-1.90 (m, 1H), 1.68-1.80 (m, 3H), 1.58-1.68 (m, 2H), 1.34-1.58 (m, 9H), 1.16-1.27 (m, 2H). ESI MS m/z 276.29 [m+H]$^+$, 258.25 [m+H–OH]$^+$.

Example 138

Preparation of (R)-3-Amino-1-(3(4-Phenylbutyl)Phenyl)Propan-1-Ol

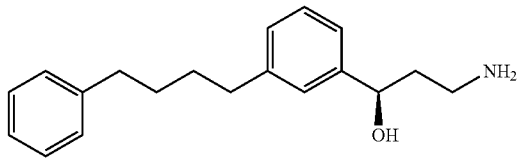 [SMILES: NCC[C@@H](O)c1cccc(CCCCc2ccccc2)c1]

(R)-3-Amino-1-(3-(4-phenylbutyl)phenyl)propan-1-ol was prepared following the method shown in Scheme 29.

SCHEME 29

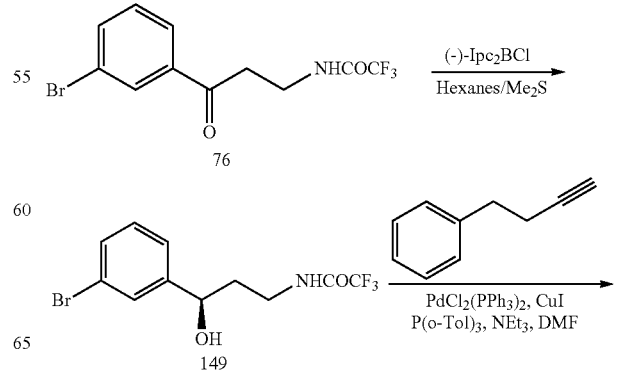

367

-continued

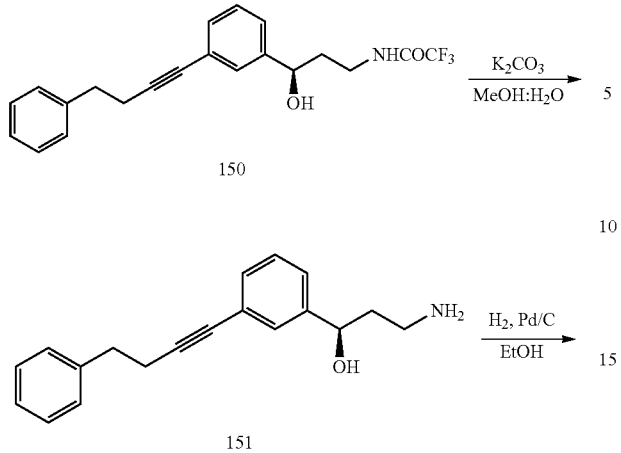

150

151

Step 1: Chiral reduction of ketone 76 with (−)-Ipc$_2$BCl following the method used in Example 70 after flash chromatography purification (gradient) gave (R)-alcohol 149 as a colorless oil. $^1$H NMR (400 MHz, CDCl$_3$) δ 7.50 (t, J=1.6 Hz, 1H), 7.43 (dt, J=7.2, 2.0 Hz, 1H), 7.21-7.27 (m, 2H), 4.84 (dr, J=8.8, 3.2 Hz, 1H), 3.65-3.73 (m, 1H), 3.36-3.43 (m, 1H), 2.47 (dd, J=2.9, 1.0 Hz, 1H), 1.80-2.00 (m, 2H).

Step 2. Sonogashira coupling between (R)-hydroxyaryl bromide 149 and 4-phenylbutyne following the method used in Example 70 except that the reaction mixture was stirred at 70° C. for 4 h, and then at 60° C. for 17 h, gave crude alkyne 150 as a light yellow oil which was used in the next step without purification. Yield (0.49 g, 77%).

Step 3. Deprotection of 150 following the method used in Example 100 (Determination of the Absolute Stereochemistry) gave amine 151 as a colorless oil. Yield (0.195 g, 60%); $^1$H NMR (400 MHz, CD$_3$OD) δ 7.31-7.33 (m, 1H), 7.15-7.29 (m, 8H), 4.67 (dd, J=8.0, 5.3 Hz, 1H), 2.87 (t, J=7.2 Hz, 2H), 2.64-2.74 (m, 4H), 1.72-1.85 (m, 2H); $^{13}$C NMR (100 MHz, CD$_3$OD) δ 145.6, 140.9, 130.1, 128.8, 128.7, 128.4, 128.2, 126.1, 125.1, 124.1, 89.0, 81.1, 72.0, 71.9, 41.5, 38.4, 35.0, 21.2; RP-HPLC, 96.4% (AUC); LC-MS m/z=280.2 [M+H]$^+$.

Step 4. Hydrogenation of alkyne 151 was done following the method used in Example 70 except that the reaction was run for 16 hrs. The reaction mixture was filtered and HCl/EtOH (7.4 M, 1 mL) was added to the filtrate. The filtrate was concentrated under reduced pressure, dissolved in EtOAc and cooled to 0° C. The precipitate formed was collected by filtration and dried in vacuo to give Example 138 hydrochloride as a white solid. Yield (0.069 g, 75%); $^1$H NMR (400 MHz, CD$_3$OD) δ 7.06-7.26 (m, 9H), 4.78 (dd, J=5.3, 7.4 Hz, 1H), 2.97-3.12 (m, 2H), 2.58-2.66 (m, 2H), 1.92-2.01 (m, 2H), 1.58-1.67 (m, 2H); LC-MS (ESI+) 284.42 [M+H]$^+$; RP-HPLC (Method 2): 97.6%, t$_R$=7.00 min.

368

Example 139

Preparation of (S)-4-(3(2-Amino-1-Hydroxyethyl)Phenethyl)Heptan-4-Ol

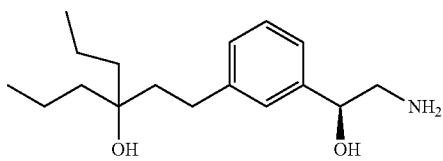 [SMILES: CCCC(O)(CCC)CCc1cccc([C@H](O)CN)c1]

(S)-4-(3-(2-Amino-1-hydroxyethyl)phenethyl)heptan-4-ol was prepared following the Scheme 30.

SCHEME 30

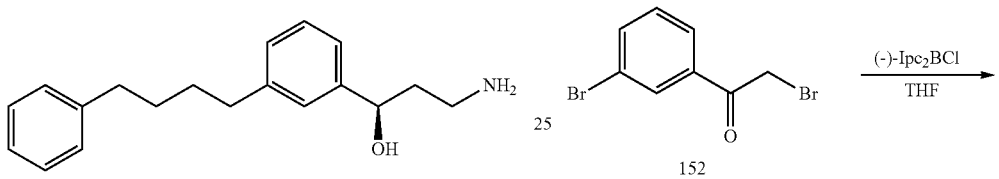

152

153

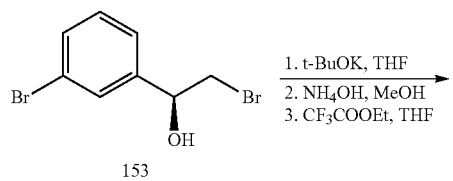

154

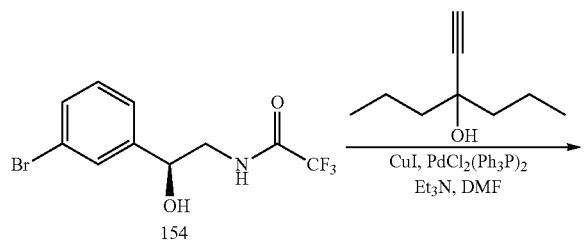

155

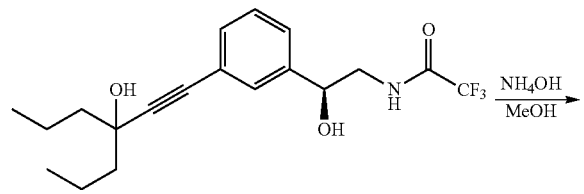

156

-continued

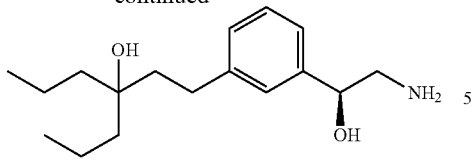

Step 1. Ketone 152 was reduced following the method used in Example 70 to give hydroxybromide 153 as a colorless oil. Yield (0.818 g, 80%): $^1$H NMR (400 MHz, DMSO-$d_6$) δ 7.57 (t, J=1.8 Hz, 1H), 7.44 (ddd, J=1.0, 2.0, 7.8 Hz, 1H), 7.35-7.39 (m, 1H), 7.28 (t, J=7.8 Hz, 1H), 5.90 (d, J=4.9 Hz, 1H), 4.80 (dd, J=4.7, 6.5 Hz, 1H), 3.66 (ABd, J=4.5, 6.5 Hz, 1H), 3.57 (ABd, J=4.5, 6.5 Hz, 1H).

Step 2. To a solution of bromide 153 (0.818 g, 2.92 mmol) in anhydrous THF (10 mL) was added a solution of potassium tert-butoxide (1M, 3.5 mL), the reaction mixture was stirred at room temperature for 15 min concentrated under reduced pressure, and the residue was treated with water. The product was extracted twice with EtOAc, organic layers were pooled, washed with brine, aq. NH$_4$Cl solution, dried over anhydrous MgSO$_4$, filtered and filtrate was concentrated under reduced pressure to give the (S)-2-(3-bromophenyl)oxirane (0.486 g) which was used in the next step without purification.

(S)-2-(3-Bromophenyl)oxirane was dissolved in 7N NH$_3$/MeOH solution (5 mL) and aqueous NH$_4$OH (25%, 5 mL) was added to the reaction mixture which was stirred at room temperature for 18 hrs. The reaction mixture was concentrated under reduced pressure to give (S)-2-amino-1-(3-bromophenyl)ethanol (0.801 g) which was used in the next step without purification.

(S)-2-Amino-1-(3-bromophenyl)ethanol was dissolved in anhydrous THF (5 mL) and ethyl trifluoroacetate (1 mL) was added. The reaction mixture was stirred at room temperature for 20 min, concentrated under reduced pressure and the residue was purified by flash chromatography to give trifluoroacetamide 154 as a colorless oil. Yield (0.608 g, 67% for 3 steps): $^1$H NMR (400 MHz, DMSO-$d_6$) δ 9.45 (br. t, 1H), 7.46-7.49 (m, 1H), 7.40-7.45 (m, 1H), 7.25-7.30 (m, 2H), 5.73 (d, J=4.7 Hz, 1H), 4.68 (dd, J=6.7, 11.3 Hz, 1H), 3.47-3.52 (m, 2H).

Step 3. Sonogashira coupling of bromide 154 with 4-ethynylheptan-4-ol following the method given in Example 70 except that P(o-tol)$_3$ was not used, gave alkynol 155 as a tan oil. Yield (0.59 g, 82%): $^1$H NMR (400 MHz, DMSO-$d_6$) δ 9.44 (br t, J=5.5 Hz, 1H), 7.22-7.32 (m, 4H), 5.65 (d, J=4.7 Hz, 1H), 4.67 (dd, J=11.7, 6.8 Hz, 1H), 3.25-3.31 (m, 2H), 1.40-1.62 (m, 8H), 0.89 (t, J=7.0 Hz, 6H).

Step 4. A solution of alkynol 155 (0.59 g, 1.59 mmol) in NH$_3$/MeOH (7N, 10 mL) and aqueous NH$_4$OH (25%, 10 mL) was stirred at room temperature for 70 hrs and the concentrated under reduced pressure. Purification by flash chromatography (0% to 100% of 10% 7N NH$_3$/MeOH/CH$_2$Cl$_2$ in CH$_2$Cl$_2$) gave amine 156 as a colorless oil. Yield (0.35 g, 80%); $^1$H NMR (400 MHz, CD$_3$OD) δ 7.39-7.41 (m, 1H), 7.26-7.32 (m, 3H), 4.58 (dd, J=4.7, 7.6 Hz, 1H), 2.65-2.81 (m, 2H), 1.51-1.73 9m, 8H), 0.97 (t, J=7.0 Hz, 6H); 143.7, 130.3, 128.9, 128.3, 125.8, 123.4, 92.4, 83.7, 74.5, 70.9, 49.0, 44.5, 17.6, 13.6; LC-MS: 276.38 [M+H]$^+$; RP-HPLC tR=6.21 min, 98% AUC.

Step 5: Hydrogenation of alkyne 156 followed by flash chromatography purification (10% to 50% of 20% 7N NH$_3$/MeOH/CH$_2$Cl$_2$—CH$_2$Cl$_2$ gradient) gave Example 139 as a colorless oil. Yield (0.042 g, 57%); $^1$H NMR (400 MHz, CD$_3$OD) δ 7.23 (t, J=7.6 Hz, 1H), 7.07-7.21 (m, 3H), 4.58 (dd, J=5.1, 7.2 Hz, 1H), 2.72-2.82 (m, 2H), 2.61 (ddd, J=4.9, 8.6, 12.7 Hz, 2H), 1.68 (ddd, J=4.7, 8.4, 12.5 Hz, 2H), 1.26-1.50 (m, 8H), 0.93 (t, J=7.2 Hz, 6H); LC-MS (ESI+) 280.41 [M+H]$^+$; RP-HPLC (Method 2): 85.1% (AUC), $t_R$=6.17 min.

Example 140

Preparation of 4-(5-(3-Amino-1-Hydroxypropyl)-2-Fluorophenethyl)Heptan-4-Ol

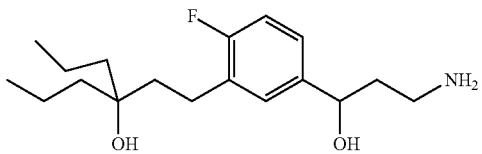 [SMILES: CCCC(O)(CCC)CCc1cc(C(O)CCN)ccc1F]

4-(5-(3-Amino-1-hydroxypropyl)-2-fluorophenethyl) heptan-4-ol was prepared following the method used in Examples 1, 7, 9, 16 and 17.

Step 1: Addition of acetonitrile to 3-bromo-4-fluorobenzaldehyde following the method used in Example 16 gave 3-(3-bromo-4-fluorophenyl)-3-hydroxypropanenitrile as a pale yellow oil. Yield (4.2 g, 70%): $^1$H NMR (400 MHz, DMSO-$d_6$) δ 7.71 (dd, J=6.8, 2.0 Hz, 1H), 7.44 (ddd, J=8.4, 5.2, 2.4 Hz, 1H), 7.35 (t, J=8.8 Hz, 1H), 6.08 (bs, 1H), 4.90 (s, 1H), 2.90 (ABd, J=16.8, 5.2 Hz, 1H), 2.83 (ABd, J=16.8, 6.4 Hz, 1H).

Step 2: Reduction of 3(3-bromo-4-fluorophenyl)-3-hydroxypropanenitrile with BH$_3$-THF following the method used in Example 17, followed by protection of the amine with ethyl trifluoroacetate following the method used in Example 9 gave N4343-bromo-4-fluorophenyl)-3-hydroxypropyl)-2,2,2-trifluoroacetamide as a clear oil. Yield (4.3 g, 73%): $^1$H NMR (400 MHz, DMSO-$d_6$) δ 9.31 (bs, 1H), 7.62 (dd, J=6.8, 2.0 Hz, 1H), 7.37-7.33 (m, 1H), 7.30 (t, J=8.8 Hz, 1H), 5.48 (d, J=4.4 Hz, 1H), 4.60-4.56 (m, 1H), 3.28-3.15 (m, 2H), 1.84-1.71 (m, 2H).

Step 3: N-(3-(3-Bromo-4-fluorophenyl)-3-hydroxypropyl)-2,2,2-trifluoroacetamide was coupled with 4-ethynyl-heptan-4-ol following the method used in Example 7 to give 2,2,2-trifluoro-N-(3-(4-fluoro-3-(3-hydroxy-3-propylhex-1-ynyl)phenyl)-3-hydroxypropyl)acetamide as a pale yellow oil. Yield (1.37 g, 78%): $^1$H NMR (400 MHz, DMSO-$d_6$) δ 9.31 (t, J=5.0 Hz, 1H), 7.37 (dd, J=6.8, 2.0 Hz, 1H), 7.34-7.30 (m, 1H), 7.18 (t, J=9.0 Hz, 1H), 5.41 (d, J=4.8 Hz, 1H), 5.19 (s, 1H), 4.58-4.54 (m, 1H), 3.28-3.16 (m, 2H), 1.82-1.69 (m, 2H), 1.63-1.41 (m, 8H), 0.89 (t, J=7.2 Hz, 6H).

Step 4: 2,2,2-Trifluoro-N-(3-(4-fluoro-3-(3-hydroxy-3-propylhex-1-ynyl)phenyl)-3-hydroxypropyl)acetamide was deprotected following the method used in Example 9 to give 4-((5-(3-amino-1-hydroxypropyl)-2-fluorophenyl)ethynyl) heptan-4-ol as a pale yellow oil. Yield (0.85 g, 82%): $^1$H NMR (400 MHz, DMSO-$d_6$) δ 7.35 (dd, J=6.8, 2.0 Hz, 1H), 7.31-7.27 (m, 1H), 7.16 (t, J=9.0 Hz, 1H), 5.19 (bs, 1H), 4.64 (t, J=6.4 Hz, 1H), 2.64-2.52 (m, 2H), 1.63-1.42 (m, 10H), 0.89 (t, J=7.2 Hz, 6H).

Step 5: 4-((5-(3-Amino-1-hydroxypropyl)-2-fluorophenyl)ethynyl)heptan-4-ol (0.107 g, 0.348 mmole) was dissolved in EtOAc (5 ml) and degassed with a stream of argon. 10% Pd/C (10 mg) was added and a vacuum was pulled for 1 min. A balloon of H$_2$ was added and stirred for 3 hr. Filtration of the catalyst followed by evaporation to dryness gave Example 140 as a pale yellow oil. Yield (0.11 g, 100%): $^1$H NMR (400 MHz, DMSO-$d_6$) δ 7.17 (dd, J=7.6, 2.0 Hz, 1H), 7.13-7.09 (m, 1H), 7.00 (dd, J=10.0, 8.4 Hz, 1H), 4.61 (m, 1H), 3.98 (bs, 1H), 2.63-2.56 (m, 2H), 2.54-2.50 (m, 2H), 1.63-1.58 (m, 2H), 1.53-1.49 (m, 2H), 1.35-1.20 (m, 8H), 0.84 (t, J=7.0 Hz, 6H).

Example 141

Preparation of (R)—N-(3-Hydroxy-3-(3-(3-Hydroxy-3-Propylhexyl)Phenyl)Propyl)Acetamide

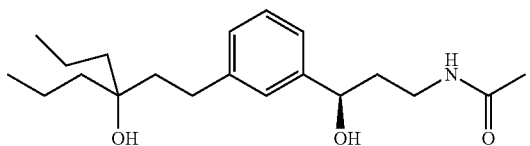 [SMILES: CCCC(O)(CCC)CCc1cccc([C@H](O)CCNC(C)=O)c1]

(R)—N-(3-Hydroxy-3-(3-(3-hydroxy-3-propylhexyl)phenyl)propyl)acetamide was prepared following the method below.

Example 71 (0.35 g, 1.19 mmol) and acetic anhydride (0.13 g, 1.25 mmole) was stirred in $CH_2Cl_2$ overnight at room temperature. The reaction mixture was partitioned between $CH_2Cl_2$ and sat $NaHCO_3$. The organic layer was dried over $Na_2SO_4$ and concentrated under reduced pressure to give Example 141 as a clear oil. Yield (0.40 g, 100%); $^1H$ NMR (400 MHz, DMSO-$d_6$) δ 7.62 (t, =5.0 Hz, 1H), 7.17 (t, J=7.4 Hz, 1H), 7.11 (s, 1H), 7.07 (d, J=8.0 Hz, 1H), 7.00 (d, J=7.6 Hz, 1H). 5.14 (d, J=4.4 Hz, 1H), 4.51-4.47 (m, 1H), 3.95 (s, 1H), 3.07-3.02 (m, 2H), 2.52-2.47 (m, 2H), 1.76 (s, 3H), 1.65 (q, J=6.8 Hz, 2H), 1.56-1.51 (m, 2H), 1.35-1.21 (m, 8H), 0.84 (t, J=7.0 Hz, 6H).

Example 142

Preparation of (R)-2,2,2-Trifluoro-N-(3-Hydroxy-3-(3-(3-Hydroxy-3-Propylhexyl)Phenyl)Propyl)Acetamide

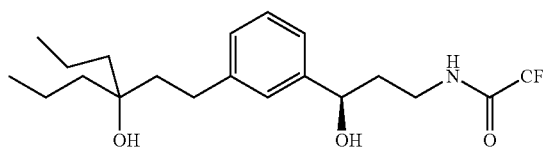

(R)-2,2,2-Trifluoro-N-(3-hydroxy-3-(3-(3-hydroxy-3-propylhexyl)phenyl)propyl)acetamide was prepared following the method below.

A mixture of Example 71 (0.29 g, 0.98 mmole) and $CF_3CO_2Et$ (2 ml) in $CH_2Cl_2$ was stirred at room temperature overnight. Concentration under reduced pressure gave Example 142 as a clear oil. Yield (0.39 g, 100%); $^1H$ NMR (400 MHz, DMSO-$d_6$) δ 9.32 (t, =5.2 Hz, 1H), 7.18 (t, J=7.6 Hz, 1H), 7.11 (s, 1H), 7.08 (d, J=7.6 Hz, 1H), 7.01 (d, J=7.6 Hz, 1H), 5.25 (bs, 1H), 4.52 (t, J=6.4 Hz, 1H), 3.94 (bs, 1H), 3.22 (q, J=6.8 Hz, 2H), 2.52-2.47 (m, 2H), 1.79-1.73 (m, 2H), 1.56-1.51 (m, 2H), 1.35-1.21 (m, 8H), 0.84 (t, J=7.0 Hz, 6H).

Example 143

Preparation of 4-(3-(3-Amino-2-Hydroxypropyl)Phenethyl)Heptan-4-Ol

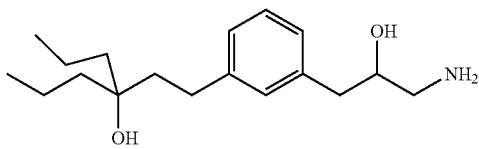 [SMILES: CCCC(O)(CCC)CCc1cccc(CC(O)CN)c1]

4-(3-(3-Amino-2-hydroxypropyl)phenethyl)heptan-4-ol was prepared following the method shown in Scheme 31.

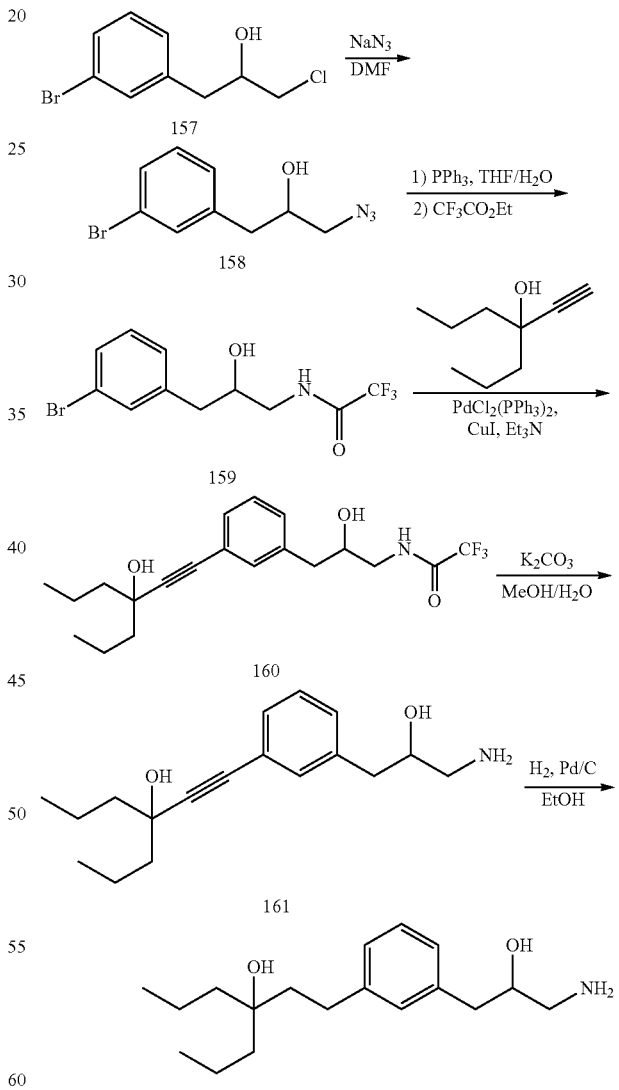

Step 1: To a solution of 1-(3-bromophenyl)-3-chloropropan-2-ol (157) (8.49 g, 34.0 mmol) in anhydrous DMF (100 mL) under $N_2$ was added $NaN_3$ (11.05 g, 170.0 mmol) and NaI (cat., 0.75 g, 5.0 mmol). The mixture was heated at 75° C. overnight. After cooling to room temperature, the mixture was diluted with ether and washed with water and brine. The solution was dried over Na₂SO₄ and concentrated under reduced pressure. The product was dried in a vacuum oven at 40° C. for 2 h to give azide 158 as a yellow oil which was used without purification. Yield (8.6 g, 98% crude).

Step 2: To a solution of azide 158 (8.59 g, 33.28 mmol) in THF (60 mL) under N₂ was added PPh₃ (8.73 g, 33.28 mmol) and water (20 mL). The reaction mixture was heated at 50° C. for 24 h. After cooling to room temperature, the mixture was diluted with brine and extracted with EtOAc. The organic layer was dried over Na₂SO₄ and concentrated under reduced pressure. The crude amine was dissolved in THF (20 ml) and ethyl trifluoroacetate (20 ml) and stirred overnight at room temperature. Evaporation under reduced pressure followed by purification by flash chromatography (5% EtOAc/CH₂Cl₂) gave trifluoroacetamide 159 as a white solid. Yield (3.72 g, 35%): ¹H NMR (400 MHz, DMSO-d₆) δ 9.33 (t, J=5.2 Hz, 1H), 7.42 (d, J=1.2 Hz, 1H), 7.38-7.35 (m, 1H), 7.24-7.20 (m, 2H), 5.00 (d, J=6.0 Hz, 1H), 3.83-3.75 (m, 1H), 3.21-3.07 (m, 2H), 2.70 (dd, J=13.6 Hz, 4.8, 1H), 2.55 (dd, =14.0, 6.0 Hz, 1H).

Step 3: Coupling of bromide 159 with 4-ethynylheptan-4-ol following the procedure described in Example 7 gave alkyne 160 as a clear oil. Yield (0.455 g, 59%): ¹H NMR (400 MHz, DMSO-d₆) δ9.32 (t, J=5.4 Hz, 1H), 7.25-7.22 (m, 2H), 7.18-7.16 (m, 2H), 5.11 (s, 1H), 4.96 (d, J=5.6 Hz, 1H), 3.81-3.74 (m, 1H), 3.21-3.07 (m, 2H), 2.68 (dd, J=14.0, 4.6 Hz, 1H), 2.54 (dd, J=14.0, 7.8 Hz, 1H), 1.61-1.40 (m, 8H), 0.89 (t, J=7.2 Hz, 6H).

Step 4: Deprotection of trifluoroacetamide 160 following the procedure described in Example 9 gave amine 161 as a pale yellow oil. Yield (0.273 g, 82%): ¹H NMR (400 MHz, DMSO-d₆) δ 7.24-7.20 (m, 2H), 7.17-7.13 (m, 2H), 5.11 (bs, 1H), 4.55 (bs, 1H), 3.51-3.46 (m, 1H), 2.67 (dd, J=13.6, 5.2 Hz, 1H), 2.50 (dd, J=13.6, 7.6 Hz, 1H), 2.45 (dd, obs., 1H), 2.37 (dd, J=12.8, 6.8 Hz, 1H), 1.61-1.40 (m, 8H), 0.89 (t, J=7.6 Hz, 6H).

Step 5: Hydrogenation of amine 161 following the method used in Example 140 gave Example 143 as a pale yellow oil. Yield (0.10 g, 100%): ¹H NMR (400 MHz, DMSO-d₆) δ 7.12 (t, J=7.4 Hz, 1H), 6.98-6.94 (m, 3H), 3.94 (bs, 1H), 3.53-3.47 (m, 1H), 2.62 (dd, J=13.6, 5.6 Hz, 1H), 2.51 (dd, J=13.2, 7.2 Hz, 1H), 2.49-2.45 (m, obs., 3H), 2.37 (dd, J=12.8, 7.2 Hz, 1H), 1.55-1.51 (m, 2H), 1.35-1.21 (m, 8H), 0.84 (t, J=7.0 Hz, 6H).

Example 144

Preparation of 4-(5-(3-Amino-1-Hydroxypropyl)-2-Methoxyphenethyl)Heptan-4-Ol

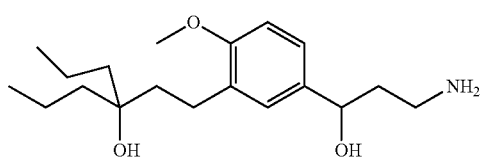 [SMILES: CCCC(O)(CCC)CCc1cc(C(O)CCN)ccc1OC]

4-(5-(3-Amino-1-hydroxypropyl)-2-methoxyphenethyl)heptan-4-ol was prepared following the method used in Example 140.

Step 1: Addition of acetonitrile to 3-bromo-4-methoxybenzaldehyde gave 3-(3-bromo-4-methoxyphenyl)-3-hydroxypropanenitrile as a pale orange oil. Yield (10.32 g, 96%): ¹H NMR (400 MHz, DMSO-d₆) δ 7.58 (d, J=2.0 Hz, 1H), 7.35 (dd, J=8.8, 2.0 Hz, 1H), 7.07 (d, J=8.8 Hz, 1H), 5.93 (d, J=4.4 Hz, 1H), 4.85-4.81 (m, 1H). 3.81 (s, 3H), 2.86 (ABd, J=16.4, 4.8 Hz, 1H), 2.79 (ABd, J=16.8, 6.8 Hz, 1H).

Step 2: Reduction of 3-(3-bromo-4-methoxyphenyl)-3-hydroxypropanenitrile with BH₃-THF followed by protection of the amine gave N-(3-(3-bromo-4-methoxyphenyl)-3-hydroxypropyl)-2,2,2-trifluoroacetamide as an orange oil. Yield (5.76 g, 40%): ¹H NMR (400 MHz, DMSO-d₆) δ 9.31 (bs, 1H), 7.49 (d, J=2.0 Hz, 1H), 7.26 (dd, J=8.8, 2.0 Hz, 1H), 7.03 (d, J=8.8 Hz, 1H), 5.32 (d, J=4.8 Hz, 1H), 4.53-4.49 (m, 1H), 3.80 (s, 3H), 3.24-3.15 (m, 2H), 1.79-1.72 (m, 2H).

Step 3: N-(3-(3-bromo-4-methoxyphenyl)-3-hydroxypropyl)-2,2,2-trifluoroacetamide was coupled with 4-ethynylheptan-4-ol to give 2,2,2-trifluoro-N-(3-hydroxy-3-(3-(3-hydroxy-3-propylhex-1-ynyl)-4-methoxyphenyl)propyl)acetamide as a yellow oil. Yield (0.92 g, 55%): ¹H NMR (400 MHz, DMSO-d₆) δ 9.31 (t, J=5.0 Hz, 1H), 7.24-7.21 (m, 2H), 6.95 (d, J=9.2 Hz, 1H), 5.25 (d, J=4.8 Hz, 1H), 5.05 (s, 1H), 4.51-4.47 (m, 1H), 3.75 (s, 3H), 3.24-3.17 (m, 2H), 1.77-1.72 (m, 2H), 1.61-1.42 (m, 8H), 0.89 (t, J=7.0 Hz, 6H).

Step 4: 2,2,2-Trifluoro-N-(3-hydroxy-3-(3-(3-hydroxy-3-propylhex-1-ynyl)-4-methoxyphenyl)propyl)acetamide was deprotected to give 4-((5-(3-amino-1-hydroxypropyl)-2-methoxyphenyl)ethynyl)heptan-4-ol as a pale yellow oil. Yield (0.53 g, 76%): ¹H NMR (400 MHz, DMSO-d₆) δ 7.22-7.19 (m, 2H), 6.92 (d, J=8.4 Hz, 1H), 5.06 (bs, 1H), 4.58-4.55 (m, 1H), 3.74 (s, 3H), 2.63-2.51 (m, 2H), 1.64-1.42 (m, 10H), 0.89 (t, J=7.0 Hz, 6H).

Step 5. Hydrogenation of 4-((5-(3-amino-1-hydroxypropyl)-2-methoxyphenyl)ethynyl)heptan-4-ol following the method used in Example 140 gave Example 144 as a pale yellow oil. Yield (0.11 g, 100%): ¹H NMR (400 MHz, DMSO-d₆) δ 7.05-7.02 (m, 2H), 6.81 (d, J=8.0 Hz, 1H), 4.55-4.52 (m, 1H), 3.84 (bs, 1H), 3.71 (s, 3H), 2.64-2.61 (m, 2H), 2.47-2.43 (m, 2H), 1.65-1.53 (m, 2H), 1.50-1.45 (m, 2H), 1.39-1.21 (m, 8H), 0.85 (t, J=6.8 Hz, 6H).

Example 145

Preparation of 4-(5-(3-Amino-1-Hydroxypropyl)-2-Methylphenethyl)Heptan-4-Ol

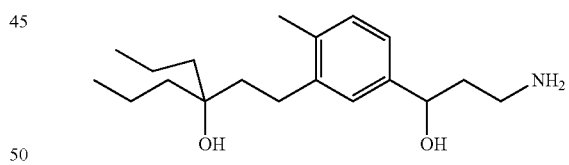

4-(5-(3-Amino-1-hydroxypropyl)-2-methylphenethyl)heptan-4-ol was prepared following the method used in Example 140.

Step 1: Alkylation of 3-bromo-4-methylbenzaldehyde with acetonitrile gave 3-(3-bromo-4-methylphenyl)-3-hydroxypropanenitrile as a pale yellow oil. Yield (5.1 g, 94%): ¹H NMR (400 MHz, DMSO-d₆) δ 7.59 (d, J=1.2 Hz, 1H), 7.31 (d, J=8.0 Hz, 1H), 7.28 (dd, J=8.0 Hz, 1.2, 1H), 5.99 (d, J=4.8 Hz, 1H), 4.87-4.84 (m, 1H), 2.88 (ABd, J=16.8, 4.8 Hz, 1H), 2.80 (ABd, J=16.8, 6.8 Hz, 1H), 2.30 (s, 3H).

Step 2: Reduction of 3(3-bromo-4-methylphenyl)-3-hydroxypropanenitrile with BH₃-THF followed by protection of the amine gave N4343-bromo-4-methylphenyl)-3-hydroxypropyl)-2,2,2-trifluoroacetamide as a clear oil. Yield (4.12 g, 57%): ¹H NMR (400 MHz, DMSO-d₆) δ 9.31 (bs, 1H), 7.50 (d, J=1.6 Hz, 1H), 7.27 (d, J=8.4 Hz, 1H), 7.20 (dd, J=8.4, 1.6

Hz, 1H), 5.38 (d, J=4.4 Hz, 1H), 4.56-4.52 (m, 1H), 3.28-3.14 (m, 2H), 2.25 (s, 3H), 1.83-1.75 (m, 2H).

Step 3: N-(3-(3-Bromo-4-methylphenyl)-3-hydroxypropyl)-2,2,2-trifluoroacetamide was coupled with 4-ethynyl-heptan-4-ol to give 2,2,2-trifluoro-N43-hydroxy-343-(3-hydroxy-3-propylhex-1-ynyl)-4-methylphenyl)propyl)acetamide as a yellow oil. Yield (0.286 g, 28%): $^1$H NMR (400 MHz, DMSO-$d_6$) δ 9.31 (t, J=5.2 Hz, 1H), 7.27 (s, 1H), 7.18 (d, J=7.6 Hz, 1H), 7.16 (dd, J=7.6, 1.8 Hz, 1H), 5.30 (d, J=4.8 Hz, 1H), 5.10 (s, 1H), 4.54-4.50 (m, 1H), 3.25-3.14 (m, 2H), 2.30 (s, 3H), 1.78-1.72 (m, 2H), 1.63-1.36 (m, 8H), 0.89 (t, J=7.2 Hz, 6H).

Step 4: 2,2,2-Trifluoro-N-(3-hydroxy-3-(3-(3-hydroxy-3-propylhex-1-ynyl)-4-methylphenyl)propyl)acetamide was deprotected to give 4-((5-(3-amino-1-hydroxypropyl)-2-methylphenyl)ethynyl)heptan-4-ol as a pale yellow oil. Yield (0.161 g, 76%): $^1$H NMR (400 MHz, DMSO-$d_6$) δ 7.25 (s, 1H), 7.17-7.12 (m, 2H), 5.11 (bs, 1H), 4.59 (t, J=6.4 Hz, 1H), 2.64-2.52 (m, 2H), 2.30 (s, 3H), 1.73-1.42 (m, 10H), 0.89 (t, J=7.2 Hz, 6H)

Step 5: Hydrogenation of 4-((5-(3-amino-1-hydroxypropyl)-2-methylphenyl)ethynyl)heptan-4-ol gave Example 145 as a pale yellow oil. Yield (0.11 g, 100%): $^1$H NMR (400 MHz, DMSO-$d_6$) δ 7.02-6.99 (m, 2H), 6.96 (dd, J=8.0, 1.6 Hz, 1H), 4.57-4.54 (m, 1H), 3.96 (bs, 1H), 2.65-2.54 (m, 2H), 2.50-2.47 (m, obs., 2H), 2.19 (s, 3H), 1.63-1.53 (m, 2H), 1.47-1.43 (m, 2H), 1.37-1.22 (m, 8H), 0.86 (t, J=7.2 Hz, 6H).

Example 146

Preparation of 4-(3-(3-Amino-1-Hydroxypropyl)-5-Methoxyphenethyl)Heptan-4-Ol

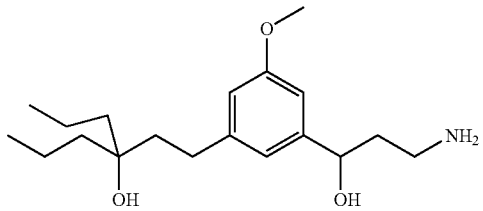 [SMILES: CCCC(O)(CCC)CCc1cc(OC)cc(C(O)CCN)c1]

4-(3-(3-Amino-1-hydroxypropyl)-5-methoxyphenethyl)heptan-4-ol was prepared following the method used in Example 140.

Step 1: Alkylation of 3-bromo-5-methoxybenzaldehyde with acetonitrile gave 3-(3-bromo-5-methoxyphenyl)-3-hydroxypropanenitrile as a pale yellow oil. Yield (4.1 g, 70%): $^1$H NMR (400 MHz, DMSO-$d_6$) δ 7.16-7.15 (m, 1H), 7.04-7.03 (m, 1H), 6.97-6.96 (m, 1H), 6.04 (d, J=4.8 Hz, 1H), 4.87-4.83 (m, 1H), 3.74 (s, 3H), 2.89 (ABd, J=16.4, 5.2 Hz, 1H), 2.81 (ABd, J=16.8, 6.8 Hz, 1H).

Step 2: Reduction of 3-(3-bromo-5-methoxyphenyl)-3-hydroxypropanenitrile with BH$_3$-THF followed by protection of the amine gave N-(3-(3-bromo-5-methoxyphenyl)-3-hydroxypropyl)-2,2,2-trifluoroacetamide as a clear oil. Yield (3.9 g, 68%): $^1$H NMR (400 MHz, DMSO-$d_6$) δ 9.30 (bs, 1H), 7.07 (t, J=1.2 Hz, 1H), 6.98-6.97 (m, 1H), 6.88-6.87 (m, 1H), 5.44 (d, J=4.8 Hz, 1H), 4.56-4.51 (m, 1H), 3.74 (m, 3H), 3.27-3.15 (m, 2H), 1.96-1.70 (m,2H).

Step 3: N-(3-(3-Bromo-5-methoxyphenyl)-3-hydroxypropyl)-2,2,2-trifluoroacetamide was coupled with alkynol 20 to give 2,2,2-trifluoro-N-(3-(hydroxy-3-(3-(3-hydroxy-3-propylhex-1-ynyl)-5-methoxyphenyl)propyl)acetamide as a pale yellow oil. Yield (0.96 g, 66%): $^1$H NMR (400 MHz, DMSO-$d_6$) δ 9.31 (t, J=4.8 Hz, 1H), 6.91 (s, 1H), 6.86-6.85 (m, 1H), 6.73-6.72 (m, 1H), 5.36 (d, J=4.8 Hz, 1H), 5.11 (s, 1H), 4.55-4.50 (m, 1H), 3.73 (s, 3H), 3.27-3.16 (m, 2H), 1.81-1.69 (m, 2H), 1.61-1.39 (m, 8H), 0.89 (t, J=7.2 Hz, 6H).

Step 4: 2,2,2-Trifluoro-N-(3-hydroxy-3-(3-(3-hydroxy-3-propylhex-1-ynyl)-5-methoxyphenyl)propyl)acetamide was deprotected to give 4-((3-(3-amino-1-hydroxypropyl)-5-methoxyphenyl)ethynyl)heptan-4-ol as a pale yellow oil. Yield (0.63 g, 86%: $^1$H NMR (400 MHz, DMSO-$d_6$) δ 6.89 (s, 1H), 6.84-6.83 (m, 1H), 6.70-6.69 (m, 1H), 5.12 (bs, 1H), 4.60 (t, J=6.2 Hz, 1H), 3.72 (s, 3H), 2.60-2.53 (m, 2H), 1.61-1.39 (m, 10H), 0.89 (t, J=7.2 Hz, 6H).

Step 5: Hydrogenation of 4-((5-(3-amino-1-hydroxypropyl)-2-methylphenyl)ethynyl)heptan-4-ol gave Example 146 as a pale yellow oil. Yield (0.10 g, 100%): $^1$H NMR (400 MHz, DMSO-$d_6$) δ 6.81 (s, 1H), 6.65 (s, 1H), 6.54 (s, 1H), 4.56 (t, J=6.4 Hz, 1H), 3.94 (bs, 1H), 3.69 (s, 3H), 2.66-2.58 (m, 2H), 2.48-2.44 (m, obs., 2H), 1.60 (q, J=6.8 Hz, 2H), 1.55-1.51 (m, 2H), 1.34-1.22 (m, 8H), 0.84 (t, J=7.2 Hz, 6H).

Example 147

Preparation of 4-(3-(3-Amino-1-Hydroxypropyl)-4-Chlorophenethyl)Heptan-4-Ol

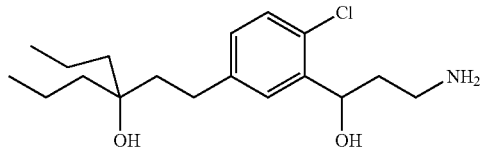 [SMILES: CCCC(O)(CCC)CCc1ccc(Cl)c(C(O)CCN)c1]

4-(3-(3-Amino-1-hydroxypropyl)-4-chlorophenethyl)heptan-4-ol was prepared following the method used in Example 140:

Step 1: Alkylation of 5-bromo-2-chlorobenzaldehyde with acetonitrile gave 3-(5-bromo-2-chlorophenyl)-3-hydroxypropanenitrile as a pale yellow liquid. Yield (4.42 g, 75%): $^1$H NMR (400 MHz, DMSO-$d_6$) δ 7.74 (d, J=2.8 Hz, 1H), 7.53 (dd, J=8.8, 2.8 Hz, 1H), 7.39 (d, J=8.8 Hz, 1H), 6.30 (d, J=4.8 Hz, 1H), 5.13-5.09 (m, 1H), 2.96 (ABd, J=16.8, 4.8 Hz, 1H), 2.83 (ABd, J=17.0, 6.0 Hz, 1H).

Step 2: Reduction of 3(5-bromo-2-chlorophenyl)-3-hydroxypropanenitrile with BH$_3$-THF followed by protection of the amine gave N-(3-(5-bromo-2-chlorophenyl)-3-hydroxypropyl)-2,2,2-trifluoroacetamide as an orange oil. Yield (2.6 g, 43%): $^1$H NMR (400 MHz, DMSO-$d_6$) δ 9.42 (bs, 1H), 7.67 (d, J=2.4 Hz, 1H), 7.45 (dd, J=8.8, 2.4 Hz, 1H), 7.33 (d, J=8.8 Hz, 1H), 5.64 (d, J=4.4 Hz, 1H), 3.33-3.29 (m, 2H), 1.96-1.80 (m, 1H), 1.68-1.59 (m, 1H).

Step 3: N-(3-(5-Bromo-2-chlorophenyl)-3-hydroxypropyl)-2,2,2-trifluoroacetamide was coupled with 4-ethynyl-heptan-4-ol to give N-(3-(2-chloro-5-(3-hydroxy-3-propyl-hex-1-ynyl)phenyl)-3-hydroxypropyl)-2,2,2-trifluoroacetamide as a pale yellow oil. Yield (1.03 g, 68%): $^1$H NMR (400 MHz, DMSO-$d_6$) δ 9.42 (t, J=5.6 Hz, 1H), 7.53 (d, J=2.0 Hz, 1H), 7.34 (d, J=8.0 Hz, 1H), 7.23 (dd, J=8.0 Hz, 2.0, 1H), 5.57 (d, J=4.0 Hz, 1H), 5.17 (s, 1H), 4.87-4.82 (m, 1H), 3.33-3.28 (m, 2H), 1.87-1.79 (m, 1H), 1.66-1.39 (m, 9H), 0.89 (t, J=7.2 Hz, 6H).

Step 4: N-(3-(2-Chloro-5-(3-hydroxy-3-propylhex-1-ynyl)phenyl)-3-hydroxypropyl)-2,2,2-trifluoroacetamide was deprotected to give 4-((3-(3-amino-1-hydroxypropyl)-4-chlorophenyl)ethynyl)heptan-4-ol as a pale yellow oil. Yield (0.77 g, 98%): ¹H NMR (400 MHz, DMSO-d₆) δ 7.53 (d, J=2.4 Hz, 1H), 7.34 (d, J=8.0 Hz, 1H), 7.23 (dd, J J=8.0, 2.4 Hz, 1H), 5.17 (bs, 1H), 4.93 (dd, J=8.8, 2.4 Hz, 1H), 2.72-2.63 (m, 2H), 1.70-1.62 (m, 1H), 1.59-1.39 (m, 9H), 0.89 (t, J=7.2 Hz, 6H).

Step 5: Hydrogenation of 44(343-amino-1-hydroxypropyl)-4-chlorophenyl)ethynyl)heptan-4-ol following the method used in Example 140 gave Example 147 as a pale yellow oil. Yield (0.11 g, 100%): ¹H NMR (400 MHz, DMSO-d₆) δ 7.37 (d, J=2.4 Hz, 1H), 7.21 (d, J=8.0 Hz, 1H), 7.03 (dd, J=8.0, 2.4 Hz, 1H), 4.94-4.91 (m, 1H), 3.99 (bs, 1H), 2.72 (t, J=7.0 Hz, 2H), 2.53-2.49 (m, 2H), 1.74-1.66 (m, 1H), 1.58-1.49 (m, 3H), 1.35-1.20 (m, 8H), 0.84 (t, J=6.8 Hz, 6H).

Example 148

Preparation of 4-(3-(3-Amino-1-Hydroxypropyl)-4-Methylphenethyl)Heptan-4-Ol

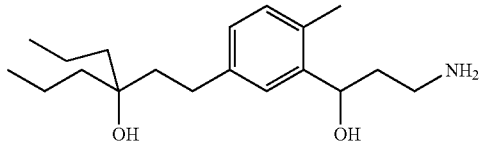 [SMILES: CCCC(O)(CCC)CCc1ccc(C)c(C(O)CCN)c1]

4-(3-(3-Amino-1-hydroxypropyl)-4-methylphenethyl)heptan-4-ol was prepared following the method used in Example 140:

Step 1: Addition of 5-bromo-2-methylbenzaldehyde to acetonitrile gave 345-bromo-2-methylphenyl)-3-hydroxypropanenitrile as a pale yellow oil. Yield (3.33 g, 86%): ¹H NMR (400 MHz, DMSO-d₆) δ 7.61 (d, J=2.0 Hz, 1H), 7.35 (dd, J=8.0, 2.0 Hz, 1H), 7.09 (d, J=8.0 Hz, 1H), 5.96 (d, J=4.4 Hz, 1H), 5.04-5.00 (m, 1H), 2.88 (ABd, J=16.8, 4.4 Hz, 1H), 2.77 (ABd, J=16.8, 6.4 Hz, 1H), 2.23 (s, 3H).

Step 2: Reduction of 3(3-bromo-2-methylphenyl)-3-hydroxypropanenitrile with BH₃-THF followed by protection of the amine gave N4343-bromo-2-methylphenyl)-3-hydroxypropyl)-2,2,2-trifluoroacetamide as a pale yellow oil. Yield (3.25 g, 69%): ¹H NMR (400 MHz, DMSO-d₆) δ 9.38 (bs, 1H), 7.53 (d, J=2.4 Hz, 1H), 7.28 (dd, J=8.0, 2.4 Hz, 1H), 7.05 (d, J=8.0 Hz, 1H), 4.73-4.70 (m, 1H), 3.36-3.26 (m, 2H), 2.17 (s, 3H), 1.79-1.71 (m, 1H), 1.68-1.59 (m, 1H).

Step 3: N-(3-(3-Bromo-2-methylphenyl)-3-hydroxypropyl)-2,2,2-trifluoroacetamide was coupled with 4-ethynylheptan-4-ol to give 2,2,2-trifluoro-N43-hydroxy-3-(5-(3-hydroxy-3-propylhex-1-ynyl)-2-methylphenyl)propyl) acetamide as a yellow oil. Yield (1.11 g, 62%): ¹H NMR (400 MHz, DMSO-d₆) δ 9.38 (t, J=5.2 Hz, 1H), 7.41 (d, J=1.6 Hz, 1H), 7.11 (dd, J=8.0, 1.6 Hz, 1H), 7.07 (d, J=8.0 Hz, 1H), 5.26 (d, J=4.4 Hz, 1H), 5.08 (s, 1H), 4.74-4.70 (m, 1H), 3.35-3.25 (m, 2H), 2.21 (s, 3H), 1.78-1.70 (m, 2H), 1.68-1.40 (m, 8H), 0.89 (t, J=7.2 Hz, 6H)

Step 4: 2,2,2-Trifluoro-N-(3-hydroxy-3-(5-(3-hydroxy-3-propylhex-1-ynyl)-2-methylphenyl)propyl)acetamide was deprotected to give 4-((3-(3-amino-1-hydroxypropyl)-4-methylphenyl)ethynyl)heptan-4-ol as a pale yellow oil. Yield (0.71 g, 85%): ¹H NMR (400 MHz, DMSO-d₆) δ 7.41 (d, J=1.6 Hz, 1H), 7.08 (dd, J=7.6, 1.4 Hz, 1H), 7.05 (d, J=7.6 Hz, 1H), 5.09 (bs, 1H), 4.83-4.80 (m, 1H), 2.72-2.61 (m, 2H), 2.23 (s, 3H), 1.61-1.41 (m, 10H), 0.89 (t, J=7.0 Hz, 6H).

Step 5: Hydrogenation of 4-((3-(3-amino-1-hydroxypropyl)-4-methylphenyl)ethynyl)heptan-4-ol following the method used in Example 140 gave Example 148 as a pale yellow oil. Yield (0.11 g, 100%): ¹H NMR (400 MHz, DMSO-d₆) δ 7.22 (d, J=1.6 Hz, 1H), 6.94 (d, J=7.6 Hz, 1H), 6.87 (dd, J=7.6, 1.6 Hz, 1H), 4.82-4.78 (m, 1H), 3.94 (bs, 1H), 2.74-2.64 (m, 2H), 2.47-2.43 (m, obs., 2H), 2.18 (s, 3H), 1.59-1.49 (m, 4H), 1.34-1.22 (m, 8H), 0.84 (t, J=7.0 Hz, 6H).

Example 149

Preparation of 1-(3-(3-Amino-2-Hydroxypropyl) Phenyl)-3-Ethylpentan-3-Ol

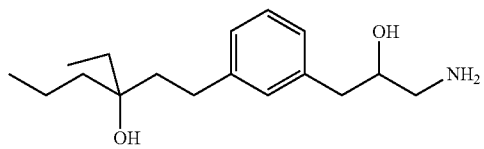 [SMILES: CCCC(O)(CC)CCc1cccc(CC(O)CN)c1]

1-(3-(3-Amino-2-hydroxypropyl)phenyl)-3-ethylpentan-3-ol was prepared following the method used in Example 143.

Step 1: Coupling of bromide 159 with 3-ethylpent-1-yn-3-ol gave N-(3-(3-(3-ethyl-3-hydroxypent-1-ynyl)phenyl)-2-hydroxypropyl)-2,2,2-trifluoroacetamide as a clear oil. Yield (0.472 g, 66%): ¹H NMR (400 MHz, DMSO-d₆) δ 9.32 (t, J=5.6 Hz, 1H), 7.26-7.22 (m, 2H), 7.20-7.16 (m, 2H), 5.11 (s, 1H), 4.96 (d, J=5.6 Hz, 1H), 3.80-3.74 (m, 1H), 3.21-3.07 (m, 2H), 2.68)dd, J=14.0, 4.8 Hz, 1H), 2.53 (dd, J=13.6, 7.6 Hz, 1H), 1.66-1.52 (m, 4H), 0.96 (t, J=7.2 Hz, 6H).

Step 2: Deprotection of N-(3-(3-(3-ethyl-3-hydroxypent-1-ynyl)phenyl)-2-hydroxypropyl)-2,2,2-trifluoroacetamide gave N-(3-(3-(3-ethyl-3-hydroxypent-1-ynyl)phenyl)-2-hydroxypropyl)-2,2,2-trifluoroacetamide as a pale yellow oil. Yield (0.232 g, 69%): ¹H NMR (400 MHz, DMSO-d₆) δ 7.24-7.20 (m, 2H), 7.17-7.15 (m, 2H), 5.11 (bs, 1H), 4.55 (bs, 1H), 3.51-3.45 (m, 1H), 2.67 (dd, J=13.6, 5.2 Hz, 1H), 2.51 (dd, J=13.6, 7.6 Hz, 1H), 2.45 (obs dm, J=4 4 Hz, 1H), 2.37 (dd, J=12.8, 6.8 Hz, 1H), 1.66-1.52 (m, 4H), 0.96 (t, J=7.2 Hz, 6H).

Step 3: Hydrogenation of N-(3-(3-(3-ethyl-3-hydroxypent-1-ynyl)phenyl)-2-hydroxypropyl)-2,2,2-trifluoroacetamide following the method used in Example 140 gave Example 149 as a pale yellow oil. Yield (0.83 g, 100%): ¹H NMR (400 MHz, DMSO-d₆) δ 7.12 (t, J=7.6 Hz, 1H), 6.99 (s, 1H), 6.97-6.95 (m, 2H), 3.91 (bs, 1H), 3.54-3.47 (m, 1H), 2.62 (dd, J=13.6, 5.6 Hz, 1H), 2.53 (dd, obs., 1H), 2.48-2.45 (m, obs., 3H), 2.37 (dd, J=12.8, 7.2 Hz, 1H), 1.54-1.50 (m, 2H), 1.37 (q, J=7.6 Hz, 4H), 0.79 (t, J=7.6 Hz, 6H).

Example 150

Preparation of 1-(3-(3-Amino-2-Hydroxypropyl) Phenethyl)Cyclopentanol

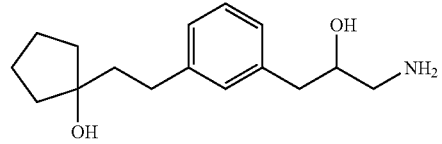 [SMILES: NCC(O)Cc1cccc(CCC2(O)CCCC2)c1]

1-(3-(3-Amino-2-hydroxypropyl)phenethyl)cyclopentanol was prepared following the method used in Example 149:

Step 1: Coupling of bromide 159 with 1-ethynylcyclopentanol gave 2,2,2-trifluoro-N-(2-hydroxy-3-(3-((1-hydroxycyclopentyl)ethynyl)phenyl)propyl)acetamide as a clear oil. Yield (0.441 g, 62%): $^1$H NMR (400 MHz, DMSO-d$_6$) δ 9.32 (t, J=5.6 Hz, 1H), 7.26-7.22 (m, 2H), 7.19-7.16 (0.441 g, 5.26 (bs, 1H), 4.97 (bs, 1H), 3.78 (bs, 1H), 3.20-3.06 (m, 2H), 2.67 (dd, J=14.0, 4.8 Hz, 1H), 2.53 (dd, J=13.6, 7.6 Hz, 1H), 1.91-1.79 (m, 4H), 1.76-1.60 (m, 4H).

Step 2: Deprotection of 2,2,2-trifluoro-N-(2-hydroxy-3-(3-((1-hydroxycyclopentyl)ethynyl)phenyl)propyl)acetamide gave 1-((3-(3-amino-2-hydroxypropyl)phenyl)ethynyl)cyclopentanol as a pale yellow solid. Yield (0.217 g, 69%): $^1$H NMR (400 MHz, DMSO-d$_6$) δ 7.24-7.20 (m, 2H), 7.17-7.15 (m, 2H), 5.26 (bs, 1H), 4.55 (bs, 1H), 3.51-3.45 (m, 1H), 2.66 (dd, J=13.6, 5.2 Hz, 1H), 2.51 (dd, J=13.6, 8.0 Hz, 1H), 2.45 (obs dm, J=4 4 Hz, 1H), 2.36 (dd, J=12.8, 6.8 Hz, 1H), 1.91-1.80 (m, 4H), 1.76-1.60 (m, 4H).

Step 3: Hydrogenation of 1-((3-(3-amino-2-hydroxypropyl)phenyl)ethynyl)cyclopentanol gave Example 150 as a pale yellow oil. Yield (0.11 g, 100%): $^1$H NMR (400 MHz, DMSO-d$_6$) δ 7.12 (t, J=7.4 Hz, 1H), 7.00 (s, 1H), 6.97-6.95 (m, 2H), 4.07 (bs, 1H), 3.57-3.45 (m, 1H), 2.62-2.58 (m, 3H), 2.52 (dd, J=13.2, 7.2 Hz, 1H), 2.49 (dd, obs., 1H), 2.36 (dd, J=12.8, 6.8 Hz, 1H), 1.72-1.67 (m, 4H), 1.57-1.40 (m, 6H).

Example 151

Preparation Of 1-(3-(3-Aminopropylphenyl)-2-Cyclohexylethanone

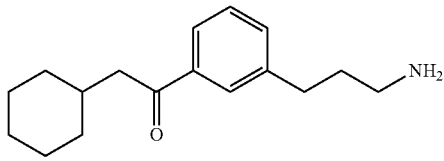 [SMILES: NCCCc1cccc(C(=O)CC2CCCCC2)c1]

1-(3-(3-Aminopropyl)phenyl)-2-cyclohexylethanone was prepared following the method shown in Scheme 32.

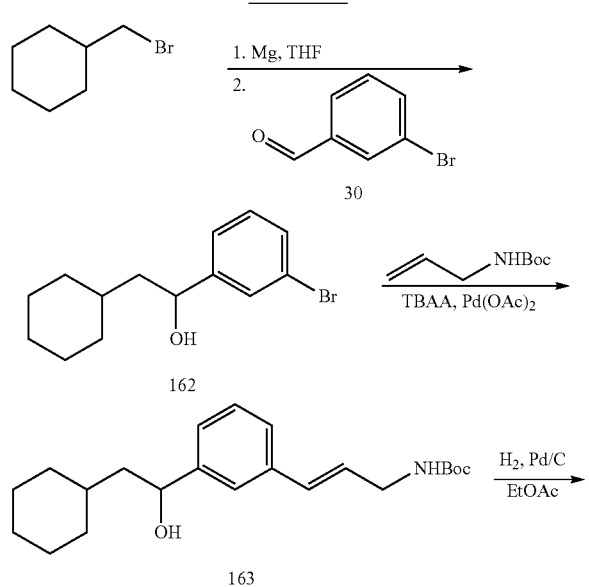

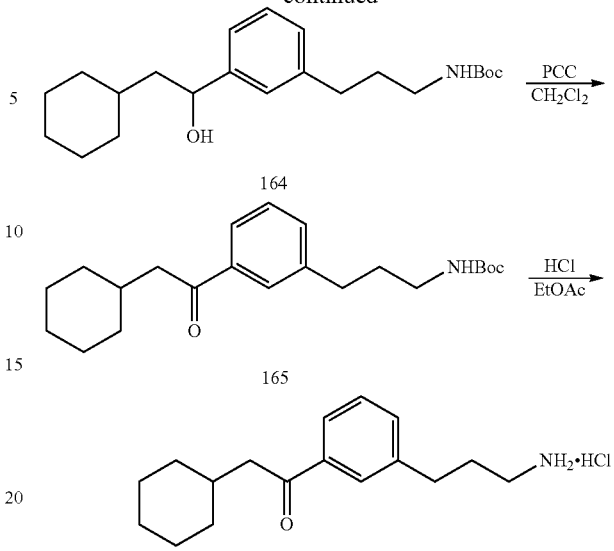

Step 1: Bromomethylcyclohexane (5.26 g, 29 7 mmoles) was added under argon to Mg turnings (0.72 g, 29.7 mmoles) in anhydrous THF containing a crystal of I$_2$. The mixture was refluxed under an argon atmosphere for 3 hrs, cooled to room temperature and added via syringe to a stirring solution of 3-bromobenzaldehyde (30) (5.0 g, 27.0 mmoles) in anhydrous THF cooled to 0° C. The reaction mixture was stirred at room temperature overnight and partitioned between sat. NH$_4$Cl and EtOAc. The organic layer was dried over anhydrous Na$_2$SO$_4$, and concentrated under reduced pressure. Purification by flash chromatography (10% EtOAc/hexanes) gave alcohol 162 as a clear oil. Yield (2.72 g, 36%): $^1$H NMR (400 MHz, DMSO-d$_6$) δ 7.47 (t, J=1.6 Hz, 1H), 7.37 (dt, J=7.2, 2.0 Hz, 1H), 7.28-7.21 (m, 2H), 5.17 (d, J=5.2 Hz, 1H), 4.59-4.54 (m, 1H), 1.76 (d, J=12.8 Hz, 1H), 1.64-1.56 (m, 4H), 1.49-1.27 (m, 3H), 1.21-1.06 (m, 3H), 0.93-0.80 (m, 2H).

Step 2: Heck coupling of bromide 162 and tent-butyl prop-2-ynylcarbamate following the method used in Example 154 gave (E)-alkene 163 as a clear oil. Yield (0.207 g, 48%): $^1$H NMR (400 MHz, DMSO-d$_6$) δ 7.29 (s, 1H), 7.24-7.19 (m, 2H), 7.14-7.12 (m, 1H), 7.14 (t, J=5.6 Hz, 1H), 6.41 (d, J=16.0 Hz, 1H), 6.16 (dt, J=16.0, 5.6 Hz, 1H), 5.01 (d, J=4.4 Hz, 1H), 4.57-4.53 (m, 1H), 3.69 (t, J=5.2 Hz, 2H), 1.74 (d, J=12.8 Hz, 1H), 1.66-1.42 (m, 5H), 1.40-1.28 (m, 11H), 1.21-1.04 (m, 3H), 0.92-0.84 (m, 2H).

Step 3: Hydrogenation of (E)-alkene 163 following the method used in Example 2 except that the reaction was carried out in EtOAc gave alkane 164 as a clear oil. Yield (0.197 g, 100%): $^1$H NMR (400 MHz, DMSO-d$_6$) δ 7.17 (t, =7.2 Hz, 1H), 7.11-7.06 (m, 2H), 6.99 (d, J=7.6 Hz, 1H), 6.82 (t, J=5.2 Hz, 1H), 4.96 (d, J=4.4 Hz, 1H), 4.55-4.51 (m, 1H), 2.90 (m, 2H), 2.52-2.46 (m, obs., 2H), 1.74 (d, J=12.4 Hz, 1H), 1.66-1.51 (m, 6H), 1.50-1.43 (m,1H), 1.40-1.27 (m, 11H), 1.21-1.06 (m, 3H), 0.91-0.82 (m, 2H).

Step 4: PCC oxidation of alcohol 164 following the method used in Example 70 gave ketone 165 as a clear oil. Yield (0.134 g, 74%): $^1$H NMR (400 MHz, DMSO-d$_6$) δ 7.75-7.72 (m, 2H), 7.43 (dt, J=8.0, 1.6 Hz, 1H), 7.39 (t, J=7.6 Hz, 1H), 6.84 (t, J=5.2 Hz, 1H), 2.93-2.88 (m, 2H), 2.84 (d, J=6.4 Hz, 2H), 2.60 (t, J=7.6 Hz, 2H), 1.86-1.77 (m, 1H), 1.70-1.56 (m, 7H), 1.35 (s, 9H), 1.24-1.07 (m, 3H), 1.00-0.91 (m, 2H).

Step 5: tert-Butyl 3-(3-(2-cyclohexylacetyl)phenyl)propylcarbamate (165) (0.124 g, mmole) was dissolved in EtOAc and cooled in an ice bath. HCl gas was bubbled into the solution for 2 min and allowed to stir at 0° C. for 2 hr. The white precipitate was collected by filtration, washed with EtOAc and dried in vacuo to give Example 153 hydrochloride as a white solid. Yield (0.7 g, 69%): $^1$H NMR (400 MHz, DMSO-$d_6$) δ 7.95 (br.s, 3H), 7.80-7.77 (m, 2H), 7.48-7.41 (m, 2H), 2.84 (d, J=6.8 Hz, 2H), 2.77-2.68 (m, 4H), 1.89-1.77 (m, 3H), 1.66-1.56 (m, 5H), 1.25-1.05 (m, 3H), 1.01-0.91 (m, 2H).

Example 152

Preparation of 1-(3-(3-Amino-2-Hydroxypropyl)Phenethyl)Cyclohexanol

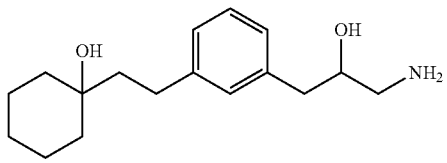 [SMILES: NCC(O)Cc1cccc(CCC2(O)CCCCC2)c1]

1-(3-(3-Amino-2-hydroxypropyl)phenethyl)cyclohexanol was prepared following the method used in Example 149.

Step 1: Coupling of bromide 159 with 1-ethynylcyclohexanol gave 2,2,2-trifluoro-N-(2-hydroxy-3-(3-(1-hydroxycyclohexyl)ethynyl)phenyl)propyl)acetamide as a clear oil. Yield (0.48 g, 65%): $^1$H NMR (400 MHz, DMSO-$d_6$) δ 9.32 (t, J=5.6 Hz, 1H), 7.26-7.22 (m, 2H), 7.20-7.16 (m, 2H), 5.37 (s, 1H), 4.97 (d, J=5.6 Hz, 1H), 3.82-3.75 (m, 1H), 3.21-3.07 (m, 2H), 2.66 (dd, J=14.0, 4.8 Hz, 1H), 2.55 (dd, J=13.6, 7.8 Hz, 1H), 1.83-1.79 (m, 2H), 1.63-1.60 (m, 2H), 1.54-1.44 (m, 5H), 1.23-1.18 (m, 1H).

Step 2: Deprotection of 2,2,2-trifluoro-N-(2-hydroxy-3-(3-((1-hydroxycyclohexyl)ethynyl)phenyl)propyl)acetamide gave 1-((3-(3-amino-2-hydroxypropyl)phenyl)ethynyl)cyclohexanol as a pale yellow solid. Yield (0.227 g, 65%): $^1$H NMR (400 MHz, DMSO-$d_6$) δ 7.25-7.21 (m, 2H), 7.18-7.15 (m, 2H), 5.37 (bs, 1H), 4.59 (bs, 1H), 3.53-3.47 (m, 1H), 2.67 (dd, J=13.6, 5.2 Hz, 1H), 2.51 (dd, J=13.6, 7.6 Hz, 1H), 2.48 (obs m, 1H), 2.38 (dd, JΔ12.8, 6.8 Hz, 1H), 1.83-1.77 (m, 2H), 1.63-1.60 (m, 2H), 1.54-1.45 (m, 5H), 1.23-1.18 (m, 1H).

Step 3: Hydrogenation of 1-((3-(3-amino-2-hydroxypropyl)phenyl)ethynyl)cyclohexanol gave Example 152 as a pale yellow oil. Yield (0.12 g, 100%): $^1$H NMR (400 MHz, DMSO-$d_6$) δ 7.12 (t, J=7.2 Hz, 1H), 6.99-6.94 (m, 3H), 3.96 (bs, 1H), 3.53-3.47 (m, 1H), 2.61 (dd, J=13.2, 5.6 Hz, 1H), 2.61-2.46 (m, obs., 4H), 2.37 (dd, J=12.8, 7.2 Hz, 1H), 1.59-1.51 (m, 4H), 1.48-1.40 (m, 3H), 1.37-1.27 (m, 4H), 1.23-1.15 (m, 1H).

Example 153

Preparation of 2-(3-(3-Aminopropylphenyl)-1-Cyclohexylethanone

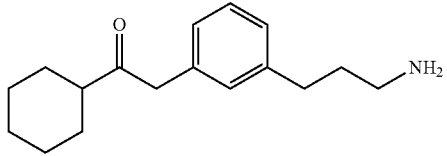 [SMILES: NCCCc1cccc(CC(=O)C2CCCCC2)c1]

2-(3-(3-Aminopropyl)phenyl)-1-cyclohexylethanone was prepared following the method used in Example 151.

Step 1: Grignard reaction between cyclohexanecarbaldehyde and 3-bromobenzyl magnesium bromide (0.25M in ether) gave 2-(3-bromophenyl)-1-cyclohexylethanol as a white solid. Yield (1.62 g, 23%): $^1$H NMR (400 MHz, DMSO-$d_6$) δ 7.39 (d, J=0.8 Hz, 1H), 7.34-7.31 (m, 1H), 7.20-7.17 (m, 2H), 4.37 (d, J=6.0 Hz, 1H), 3.38-3.32 (m, 1H), 2.69 (dd, J=13.6, 3.6 Hz, 1H), 2.51-2.45 (dd, obs., 1H), 1.78-1.60 (m, 5H), 1.24-0.94 (m, 6H).

Step 2: Heck coupling of 2-(3-bromophenyl)-1-cyclohexylethanol and tert-butyl prop-2-ynylcarbamate gave (E)-tent-butyl 3-(3-(2-cyclohexyl-2-hydroxyethyl)phenyl)allylcarbamate as a clear oil. Yield (0.362 g, 45%): $^1$H NMR (400 MHz, DMSO-$d_6$) δ 7.20 (s, 1H), 7.18-7.14 (m, 2H), 7.05-7.03 (m, 2H), 6.38 (d, J=16.0 Hz, 1H), 6.14 (dt, J=16.0, 5.8 Hz, 1H), 4.29 (d, J=6.0 Hz, 1H), 3.68 (t, J=6.2 Hz, 2H), 2.67 (dd, J=13.6, 4.4 Hz, 1H), 2.50 (dd, obs., 1H), 1.78-1.57 (m, 5H), 1.37 (s, 9H), 1.21-0.99 (m, 6H).

Step 3: Hydrogenation of (E)-tent-butyl 3-(3-(2-cyclohexyl-2-hydroxyethyl)phenyl)allylcarbamate gave tert-butyl 3-(3-(2-cyclohexyl-2-hydroxyethyl)phenyl)propylcarbamate as a clear oil. Yield (0.356 g, 100%): $^1$H NMR (400 MHz, DMSO-$d_6$) δ 7.12 (t, J=7.4, 1H), 6.99-6.94 (m, 3H), 6.82 (t, J=5.2 Hz, 1H), 4.26 (d, J=5.6 Hz, 1H), 3.40-3.34 (m, 1H), 2.89 (q, J=6.6 Hz, 2H), 2.64 (dd, J=13.6, 4.4 Hz, 1H), 2.50 (m, obs., 3H), 1.78-1.58 (m, 7H), 1.35 (s, 9H), 1.19-0.96 (m, 6H).

Step 4: PCC oxidation of tert-butyl 3-(3-(2-cyclohexyl-2-hydroxyethyl)phenyl)propylcarbamate gave tert-butyl 3-(3-(2-cyclohexyl-2-oxoethyl)phenyl)propylcarbamate as a clear oil. Yield (0.254 g, 73%): $^1$H NMR (400 MHz, DMSO-$d_6$) δ 7.17 (t, J=7.6 Hz, 1H), 7.02 (d, J=8.0 Hz, 1H), 6.93-6.93 (m, 2H), 6.82 (t, J=5.2 Hz, 1H), 3.73 (s, 2H), 2.89 (q, J=6.4 Hz, 2H), 2.51-2.42 (m, obs., 3H), 1.77-1.74 (m, 2H), 1.67-1.56 (m, 5H), 1.35 (s, 9H), 1.20-1.08 (m, 5H).

Step 5: Deprotection of tert-butyl 3-(3-(2-cyclohexyl-2-oxoethyl)phenyl)propylcarbamate gave Example 153 hydrochloride as an off-white solid. Yield (0.162 g, 80%): $^1$H NMR (400 MHz, DMSO-$d_6$) δ 8.04 (br.s, 3H), 7.20 (t, J=7.6 Hz, 1H), 7.05 (d, J=8.0 Hz, 1H), 6.98-6.96 (m, 2H), 3.75 (s, 2H), 2.76-2.69 (m, 2H), 2.59 (t, J=7.8 Hz, 2H), 2.49-2.43 (m, obs, 1H), 1.85-1.75 (m, 4H), 1.69-1.65 (m, 2H), 1.59-1.56 (m, 1H), 1.27-1.08 (m, 5H).

Example 154

Preparation of 1-(3-(3-Amino-1-Hydroxypropyl)-5-Fluorophenethyl)Cyclohexanol

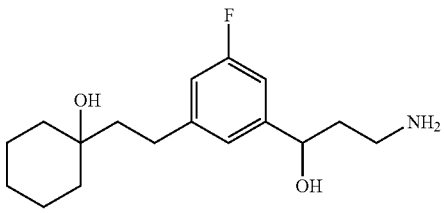 [SMILES: NCCC(O)c1cc(F)cc(CCC2(O)CCCCC2)c1]

1-(3-(3-Amino-1-hydroxypropyl)-5-fluorophenethyl)cyclohexanol was prepared following the method used in Examples 2, 16, 17, 19 and 118.

Step 1: Reaction of 3-bromo-5-fluorobenzaldehyde with acetonitrile following the method described in Example 16 gave 3-bromo-5-fluorobenzaldehyde as a pale yellow oil. Yield (2.5 g, 86%): $^1$H NMR (400 MHz, CDCl$_3$) δ 7.34 (t, J=1.6 Hz, 1H), 7.23 (dt, J=8.0, 1.6 Hz, 1H), 7.08-7.11 (m, 1H), 5.03 (t, J=6.4 Hz, 1H), 2.75 (d, J=6.0 Hz, 2H).

Step 2: Reduction of 3-bromo-5-fluorobenzaldehyde using borane-dimethylsulfide complex following the method described in Example 17, followed by protection with ethyl trifluoroacetate following the method described in Example 19 gave N-(3-(3-bromo-5-fluorophenyl)-3-hydroxypropyl)-2,2,2-trifluoroacetamide as a light yellow oil. Yield (1.0 g, 30%): $^1$H NMR (400 MHz, DMSO-d$_6$) δ 9.30 (t, J=5.6 Hz, 1H), 7.34-7.38 (m, 2H), 7.17 (dt, J=9.6, 1.6 Hz, 1H), 5.57 (d, J=4.4 Hz, 1H), 4.57-4.62 (m, 1H), 3.14-3.30 (m, 2H), 1.70-1.86 (m, 2H).

Step 3: A mixture of N-(3-(3-bromo-5-fluorophenyl)-3-hydroxypropyl)-2,2,2-trifluoroacetamide (0.58 g, 1.57 mmol), 1-vinylcyclohexanol (0.3 g, 2.38 mmol) and palladium acetate (0.03 g, 0.12 mmol) in tetrabutyl ammonium acetate (1.0 g) and DMF (1 ml) was heated at 90° C. for 1 h. After cooled to room temperature, the reaction mixture was partitioned between water (40 ml) and ethyl acetate (60 ml). Ethyl acetate portion was dried over Na$_2$SO$_4$. Purification by chromatography (40 to 60% EtOAc-hexanes gradient) gave (E)-2,2,2-trifluoro-N-(3-(3-fluoro-5-(2-(1-hydroxycyclohexyl)vinyl)phenyl)-3-hydroxypropyl)acetamide as a colorless oil. Yield (0.25 g, 54%): H NMR (400 MHz, DMSO-d$_6$) δ 9.32 (t, J=5.6 Hz, 1H), 6.94-7.18 (m, 3H), 6.41-6.53 (m, 2H), 5.42 (d, J=4.4 Hz, 1H), 4.54-4.60 (m, 1H), 3.18-3.26 (m, 2H), 1.72-1.86 (m, 2H), 1.38-1.66 (m, 10H).

Step 4: Deprotection of (E)-2,2,2-trifluoro-N-(3-(3-fluoro-5-(2-(1-hydroxycyclohexyl)vinyl)phenyl)-3-hydroxypropyl)acetamide following method described in Example 2 gave (E) -1-(3-(3-amino-1-hydroxypropyl)-5-fluorostyryl) cyclohexanol as a colorless oil. Yield (0.065 g, 43%): $^1$H NMR (400 MHz, MeOD) δ 7.19 (s, 1H), 7.00 (dt, J=9.6, 2.0 Hz, 1H), 6.94 (dt, J=9.6, 1.6 Hz, 1H), 6.58 (d, J=16.4 Hz, 1H), 6.39 (d, J=16.4 Hz, 1H), 4.72 (t, J=6.0 Hz, 1H), 2.70-2.80 (m, 2H), 1.50-1.88 (m, 10H).

Step 5: Hydrogenation of (E) -1-(3-(3-amino-1-hydroxypropyl)-5-fluorostyryl)cyclohexanol following method described in Example 2 gave Example 154 as a pale yellow oil which was dissolved in MeOH and treated with HO/EtOH. The mixture was concentrated under reduced pressure, the residue was resuspended in EtOAc and the solids were collected by filtration to give Example 154 hydrochloride as a white solid. Yield (0.05 g, 90%): $^1$H NMR (400 MHz, DMSO-d$_6$) δ 7.88 (bs, 3H), 6.98 (s, 1H), 6.86-6.93 (m, 2H), 5.60 (d, J=4.0 Hz, 1H), 4.66 (t, J=4.0 Hz, 1H), 2.74-2.84 (m, 2H), 2.58-2.62 (m, 2H), 1.72-1.90 (m, 2H), 1.10-1.58 (m, 13H).

Example 155

Preparation of 1-(3-(3-Amino-1-Hydroxypropyl)-2-Fluorophenethyl)Cyclohexanol

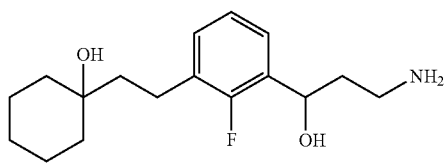 [SMILES: NCCC(O)c1cccc(CCC2(O)CCCCC2)c1F]

1-(3-(3-Amino-1-hydroxypropyl)-2-fluorophenethyl)cyclohexanol was prepared following the method used in Example 154.

Step 1: Reaction of 3-bromo-2-fluorobenzaldehyde with acetonitrile gave 3-(3-bromo-2-fluorophenyl)-3-hydroxypropanenitrile as a light yellow oil. $^1$H NMR (400 MHz, CDCl$_3$) δ 7.54 (t, J=7.2 Hz, 2H), 7.11 (td, J=7.6, 0.4 Hz, 1H), 5.37 (dd, J=6.8, 4.4 Hz, 1H), 2.73-2.91 (m, 2H).

Step 2: Reduction of 3-(3-bromo-2-fluorophenyl)-3-hydroxypropanenitrile using borane-dimethylsulfide complex gave N-(3-(3-bromo-2-fluorophenyl)-3-hydroxypropyl)-2,2,2-trifluoroacetamide as a light yellow oil. Yield (0.3 g, 44%): $^1$H NMR (400 MHz, DMSO-d$_6$) δ 7.54-7.58 (m, 1H), 7.45-7.49 (m, 1H), 7.12-7.17 (m, 1H), 4.86 (dd, J=6.8, 4.4 Hz, 1H), 3.27 (t, J=7.2 Hz, 2H), 1.73-1.86 (m, 2H).

Step 3: Coupling of N-(3-(3-bromo-2-fluorophenyl)-3-hydroxypropyl)-2,2,2-trifluoroacetamide and 1-vinylcyclohexanol gave (E)-2,2,2-trifluoro-N-(3-(2-fluoro-3-(2-(1-hydroxycyclohexyl)vinyl)phenyl)-3-hydroxypropyl)acetamide as a colorless oil. Yield (0.13 g, 54%): $^1$H NMR (400 MHz, CD$_3$OD) δ 7.42 (td, J=7.6, 1.2 Hz, 1H), 7.36 (td, J=7.2, 1.2 Hz, 1H), 7.11 (t, J=8.0 Hz, 1H), 6.76 (d, J=16 Hz, 1H), 6.42 (d, J=16 Hz, 1H), 5.02 (dd, J=6.8, 4.4 Hz, 1H), 3.41 (t, J=7.2 Hz, 2H), 1.73-2.00 (m, 2H), 1.50-1.78 (m, 9H), 1.30-1.40 (m, 1H).

Step 4: Deprotection of (E)-2,2,2-trifluoro-N-(3-(2-fluoro-3-(2-(1-hydroxycyclohexyl)vinyl)phenyl)-3-hydroxypropyl)acetamide gave (E)-1-(3-(3-amino-1-hydroxypropyl)-2-fluorostyryl)cyclohexanol as a colorless oil. Yield (0.05 g, 56% $^1$H NMR (400 MHz, DMSO-d$_6$) δ 7.39 (t, J=6.8 Hz, 1H), 7.29 (t, J=6.4 Hz, 1H), 7.09 (t, J=7.6 Hz, 1H), 6.62 (d, J=16 Hz, 1H), 6.42 (d, J=16 Hz, 1H), 4.88 (t, J=6.0 Hz, 1H), 2.57 (t, J=7.2 Hz, 2H), 1.10-1.68 (m, 12H).

Step 5: Hydrogenation of (E)-1-(3-(3-amino-1-hydroxypropyl)-2-fluorostyryl)cyclohexanol gave Example 155 hydrochloride as a while solid. Yield (0.045 g, 85%): $^1$H NMR (400 MHz, DMSO-d$_6$) δ 7.88 (br.s, 3H), 7.06-7.30 (m, 3H), 5.5 (br.s, 1H), 4.89-4.92 (m, 2H), 2.78-2.88 (m, 2H), 2.59-2.63 (m, 2H), 1.76-1.96 (m, 2H), 1.12-1.62 (m, 13H).

Example 156

Preparation of 3-(3-(Cyclohexylthiomethyl)Phenyl)Prop-2-Yn-1-Amine

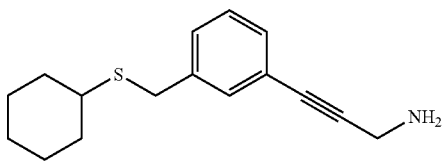 [SMILES: NCC#Cc1cccc(CSC2CCCCC2)c1]

3-(3-(Cyclohexylthiomethyl)phenyl)prop-2-yn-1-amine was prepared following the method below.

Step 1. A mixture of cyclohexylmercaptan (1.09 mL, 8.89 mmol), 3-bromobenzyl bromide (2.22 g, 8.882 mmol) and K$_2$CO$_3$ (2.54 g, 18.38 mmol) in acetone was stirred under argon at room temperature for 4 hrs then filtered. The filtrate was concentrated under reduced pressure. Purification by flash chromatography (0% to 20% EtOAc—hexanes gradient) gave (3-bromobenzyl)(cyclohexyl)sulfane as a colorless oil. Yield (2.02 g, 80%); $^1$H NMR (400 MHz, CDCl$_3$) δ 7.48 (t, J=1.8 Hz, 1H), 7.33-7.37 (m, 1H), 7.22-7.26 (m, 1H), 7.16 (t, J=7.8 Hz, 1H), 3.68 (s, 2H), tt, J=3.33, 10.0 Hz, 1H), 1.87-1.96 (m, 2H), 1.69-1.77 (m, 2H), 1.53-1.61 (m, 1H), 1.18-1.38 (m, 5H).

Step 2. Sonogashira coupling between (3-bromobenzyl)(cyclohexyl)sulfane and 2,2,2-trifluoro-N-(prop-2-ynyl)acetamide following the method used in Example 139 gave N-(3-(3-(cyclohexylthiomethyl)phenyl)prop-2-ynyl)-2,2,2-trifluoroacetamide as a yellow oil. Yield (0.70 g, 35%); $^1$H NMR (400 MHz, DMSO-$d_6$) δ 10.0 (br t, 1H), 7.24-7.37 (m, 4H), 4.25 (d, J=5.5 Hz, 2H), 3.72 (s, 2H), 2.48-2.53 (m, 1H), 1.79-1.87 (m, 2H), 1.58-1.65 (m, 2H), 1.45-1.52 (m, 1H), 1.12-1.27 (m, 5H).

Step 3. Deprotection of N-(3-(3-(cyclohexylthiomethyl)phenyl)prop-2-ynyl)-2,2,2-trifluoroacetamide following the method used in Example 138 followed by flash chromatography purification (50% to 100% of 10% 7N NH$_3$/MeOH/CH$_2$Cl$_2$—CH$_2$Cl$_2$ gradient) gave Example 156 as a light yellow oil. Yield (0.157 g, 85%); $^1$H NMR (400 MHz, CD$_3$OD) δ 7.35-7.37 (m, 1H), 7.20-7.29 (m, 3H), 3.70 (s, 2H), 3.58 (s, 2H), 2.46-2.54 (m, 1H), 1.86-1.92 (m, 2H), 1.67-1.75 (m, 2H), 1.53-1.60 (m, 1H), 1.20-1.34 (m, 5H); RP-HPLC (Method 2): 94.7% (AUC), $t_R$=7.08 min.

Example 157

Preparation of 3-(3-(Cyclohexylsulfonylmethyl)Phenyl)Prop-2-Yn-1-Amine

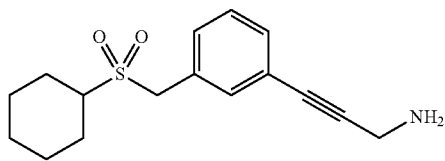 [SMILES: NCC#Cc1cccc(CS(=O)(=O)C2CCCCC2)c1]

3-(3-(Cyclohexylsulfonylmethyl)phenyl)prop-2-yn-1-amine was prepared following the method used in Example 135.

Step 1. Oxidation of N-(3-(3-(cyclohexylthiomethyl)phenyl)prop-2-ynyl)-2,2,2-trifluoroacetamide following the method used in Example 135 followed by flash chromatography purification (20% to 70% EtOAc—hexanes gradient) gave N-(3-(3-(cyclohexylsulfonylmethyl)phenyl)prop-2-ynyl)-2,2,2-trifluoroacetamide as a white solid. Yield (0.256 g, 86%); $^1$H NMR (400 MHz, DMSO-$d_6$) δ 10.06 (br. t, J=5.1 Hz, 1H), 7.35-7.45 (m, 4H), 4.42 (s, 2H), 4.26 (d, J=5.5 Hz, 2H), 2.94 (tt, J=3.3, 15.3 Hz, 1H), 2.02-2.08 (m, 2H), 1.74-1.82 (m, 2H), 1.56-1.63 (m, 1H), 1.30-1.42 (m, 2H), 1.07-1.30 (m, 3H).

Step 2. Deprotection of N-(3-(3-(cyclohexylsulfonylmethyl)phenyl)prop-2-ynyl)-2,2,2-trifluoroacetamide following the method used in Example 138 followed by flash chromatography purification (10% to 100% of 10% 7N NH$_3$/MeOH/CH$_2$Cl$_2$—CH$_2$Cl$_2$ gradient) gave Example 157 as a white solid. Yield (0.166 g, 91%); $^1$H NMR (400 MHz, CD$_3$OD) δ 7.45-7.48 (m, 1H), 7.40 (dt, J=1.8, 7.2 Hz, 1H), 7.37 (dt, J=1.8, 7.6 Hz, 1H), 7.33 (t, J=7.4 Hz, 1H), 4.33 (s, 2H), 3.59 (s, 2H), 2.93 (tt, J=3.3, 11.9 Hz, 1H), 2.10-2.20 (m, 2H), 1.85-1.93 (m, 2H), 1.66-1.73 (m, 1H), 1.45-1.57 (m, 2H), 1.16-1.37 (m, 3H); RP-HPLC (Method 2): 99.7% (AUC), $t_R$=5.56 min.

Example 158

Preparation of 3-(3-(Cyclohexylthiomethyl)Phenyl)Propan-1-Amine

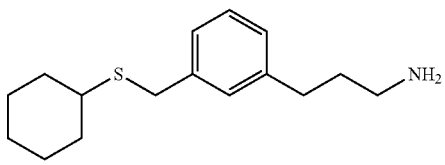 [SMILES: NCCCc1cccc(CSC2CCCCC2)c1]

3-(3-(Cyclohexylthiomethyl)phenyl)propan-1-amine was prepared following the method used in Example 135.

Step 1. Hydrogenation of Example 157 following the method used in Example 2 followed by flash chromatography purification (10% to 100% 10% 7N NH$_3$/MeOH/CH$_2$Cl$_2$—CH$_2$Cl$_2$ gradient) gave Example 158 as a colorless oil. Yield (0.0844 g, 91%); $^1$H NMR (400 MHz, CD$_3$OD) δ 7.14-7.20 (m, 2H), 7.09-7.13 (m, 1H), 7.01-7.07 (m, 1H), 3.70 (s, 2H), 2.58-2.66 (m, 4H), 2.45-2.57 (m, 1H), 1.86-1.94 (m, 2H), 1.67-1.80 (m, 4H), 1.54-1.60 (m, 1H), 1.20-1.33 (m, 5H); RP-HPLC (Method 2): 92.8% (AUC), $t_R$=7.09 min; LC-MS (ESI+) 264.221 [M+H]$^+$.

Example 159

Preparation of 3-(3-(Cyclohexylsulfonylmethyl)Phenyl)Propan-1-Amine

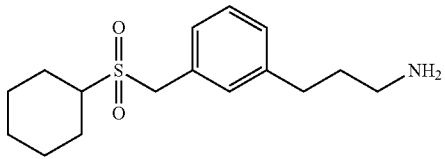 [SMILES: NCCCc1cccc(CS(=O)(=O)C2CCCCC2)c1]

3-(3-(Cyclohexylsulfonylmethyl)phenyl)propan-1-amine was prepared following the method below.

Step 1. Hydrogenation of N-(3-(3-(cyclohexylthiomethyl)phenyl)prop-2-ynyl)-2,2,2-trifluoroacetamide following the method used in Example 2 followed by flash chromatography purification (5% to 20% EtOAc—hexanes gradient) gave N-(3-(3-(cyclohexylthiomethyl)phenyl)propyl)-2,2,2-trifluoroacetamide as a colorless oil. Yield (0.121 g, 72%); $^1$H NMR (400 MHz, CDCl$_3$) δ 7.20-7.26 (m, 1H), 7.12-7.17 (m, 2H), 7.01-7.06 (m, 1H), 6.17 (br.s, 1H), 3.71 (s, 2H), 3.38 (q, J=6.9 Hz, 2H), 2.66 (t, J=7.4 Hz, 2H), 2.56 (tt, J=3.5, 10.4 Hz, 1H), 1.87-1.97 (m, 4H), 1.68-1.77 (m, 2H), 1.54-1.61 (m, 1H), 1.19-1.38 (m, 5H).

Step 2. Oxidation of N-(3-(3-(cyclohexylthiomethyl)phenyl)propyl)-2,2,2-trifluoroacetamide following the method used in Example 135 followed by flash chromatography purification (10% to 40% EtOAc—hexanes gradient) gave N-(3-(3-(cyclohexylsulfonylmethyl)phenyl)propyl)-2,2,2-trifluoroacetamide as a colorless oil, which solidified to white solid. Yield (0.112 g, 85%); $^1$H NMR (400 MHz, CDCl$_3$) δ 7.32 (t, J=7.4 Hz, 1H), 7.17-7.26 (m, 3H), 6.37 (br.s, 1H), 4.15 (s, 2H), 3.33 (q, J=6.7 Hz, 2H), 2.76 (tt, J=3.5, 12.1 Hz, 1H), 2.69 (t, J=7.6 Hz, 2H), 2.10-2.18 (m, 2H), 1.87-1.97 (m, 4H), 1.66-1.73 (m, 1H), 1.51-1.63 (m, 2H), 1.18-1.30 (m, 3H).

Deprotection of N-(3-(3-(cyclohexylsulfonylmethyl)phenyl)propyl)-2,2,2-trifluoroacetamide following the method used in Example 138 followed by flash chromatography purification (10% to 100% of 10% 7N NH₃/MeOH/CH₂Cl₂—CH₂Cl₂ gradient) gave Example 159 as a white solid. Yield (0.062 g, 73%); ¹H NMR (400 MHz, CD₃OD) δ 7.21-7.318 (m, 4H), 4.31 (s, 2H), 2.91 (tt, J=3.5, 11.9 Hz, 1H), 2.61-2.69 (m, 4H), 2.10-2.18 (m, 2H), 1.85-1.93 (m, 2H), 1.73-1.81 (m, 2H), 1.66-1.73 (m, 1H), 1.44-1.56 (m, 2H), 1.17-1.36 (m, 3H); ¹³C NMR (100 MHz, CD₃OD) δ 142.8, 131.1, 128.65, 128.54, 128.50, 128.08, 59.8, 55.5, 40.8, 34.3, 32.8, 25.2, 25.0, 24.9; RP-HPLC (Method 2): 96.8% (AUC), $t_R$=5.60 min; LC-MS (ESI+) 296.55 [M+H]⁺.

Example 160

Preparation of (E)-3-(3-(Cyclohexyloxymethyl)Phenyl)Prop-2-En-1-Amine

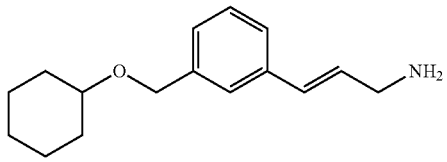 [SMILES: NC/C=C/c1cccc(COC2CCCCC2)c1]

(E)-3-(3-(Cyclohexyloxymethyl)phenyl)prop-2-en-1-amine was prepared following the method used in Examples 2, 9 and 118.

Step 1: Reaction of 1-bromo-3-(bromomethyl)benzene with cyclohexylamine following the method described in Example 9 except cesium carbonate was used as base and at 90° C. for 18h gave N-(3-bromobenzyl)cyclohexylamine as a white solid. Yield (0.70 g, 65%): ¹H NMR (400 MHz, CD₃OD) δ 7.53 (t, J=1.6 Hz, 1H), 7.38-7.41 (m, 1H), 7.29 (d, J=7.6 Hz, 1H), 7.23 (t, J=8.0 Hz, 1H), 3.73 (s, 2H), 2.38-2.46 (m, 1H), 1.92-1.95 (m, 2H), 1.70-1.78 (m, 2H), 1.58-1.66 (m, 1H), 1.06-1.30 (m, 5H).

Step 2: Heck coupling of N-(3-bromobenzyl)cyclohexanamine and N-allyl-2,2,2-trifluoroacetamide following the method described in Example 118 gave (E)-N-(3-(3-((cyclohexylamino)methyl)phenyl)allyl)-2,2,2-trifluoroacetamide as a colorless oil. Yield (0.20 g, 22%): ¹H NMR (400 MHz, CD₃OD) δ 7.55 (s, 1H), 7.48-7.50 (m, 1H), 7.42 (t, J=7.6 Hz, 1H), 7.35-7.37 (m, 1H), 6.61 (d, J=16.0 Hz, 1H), 6.32 (dt, J=16.0, 6.4 Hz, 1H), 4.19 (s, 2H), 4.05 (d, J=6.4 Hz, 2H), 3.07-3.16 (m, 1H), 2.14-2.22 (m, 2H), 1.66-1.82 (m, 2H), 1.68-1.76 (m, 1H), 1.16-1.50 (m, 5H).

Step 3: Deprotection of (E)-N-(3-(3-((cyclohexylamino)methyl)phenyl)allyl)-2,2,2-trifluoroacetamide following method described in Example 2 gave Example 160 as a white solid. Yield (0.04 g, 23%): ¹H NMR (400 MHz, CD₃OD) δ 7.69 (s, 1H), 7.53-7.56 (m, 1H), 7.42-7.48 (m, 2H), 6.84 (d, J=16.0 Hz, 1H), 6.40 (dt, J=16.0, 6.8 Hz, 1H), 4.23 (s, 2H), 4.73 (d, J=6.4 Hz, 2H), 3.08-3.16 (m, 1H), 2.16-2.24 (m, 2H), 1.86-1.94 (m, 2H), 1.68-1.76 (m, 1H), 1.30-1.50 (m, 5H).

Example 161

Preparation of 4-(3-(Aminomethyl)Phenethyl)Heptan-4-Ol

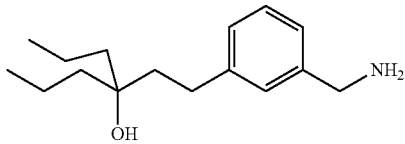 [SMILES: CCCC(O)(CCC)CCc1cccc(CN)c1]

4-(3-(Aminomethyl)phenethyl)heptan-4-ol was prepared following the method below.

Step 1: N-(3-Bromobenzyl)-2,2,2-trifluoroacetamide was coupled with 4-ethynylheptan-4-ol following the procedure described in Example 140 to give 2,2,2-trifluoro-N-(3-(3-hydroxy-3-propylhex-1-ynyl)benzyl)acetamide as a yellow oil. Yield (0.462 g, 38%): ¹H NMR (400 MHz, DMSO-d₆) δ 9.97 (t, J=5.6 Hz, 1H), 7.32 (t, J=7.8 Hz, 1H), 7.27-7.22 (m, 3H), 5.15 (bs, 1H), 4.35 (d, J=6.0 Hz, 2H), 1.60-1.41 (m, 8H), 0.89 (t, J=7.2 Hz, 6H).

Step 2: 2,2,2-Trifluoro-N-(3-(3-hydroxy-3-propylhex-1-ynyl)benzyl)acetamide was deprotected following the procedure in Example 140 to give 4-((3-(aminomethyl)phenyl)ethynyl)heptan-4-ol as a pale yellow oil. Yield (0.254 g, 78%): ¹H NMR (400 MHz, DMSO-d₆) δ 7.33 (s, 1H), 7.27-7.22 (m, 2H), 7.18-7.16 (m, 1H), 5.11 (bs, 1H), 3.66 (s, 2H), 1.97 (bs, 2H), 1.60-1.42 (m, 8H), 0.89 (t, J=7.0 Hz, 6H).

Step 3. Hydrogenation of 4-((3-(aminomethyl)phenyl)ethynyl)heptan-4-ol gave Example 161 as a pale yellow oil. Yield (0.10 g, 100%): ¹H NMR (400 MHz, DMSO-d₆) δ 7.15 (t, J=7.6 Hz, 1H), 7.11 (s, 1H), 7.07 (d, J=8.0 Hz, 1H), 6.97 (d, J=7.2 Hz, 1H), 3.94 (bs, 1H), 3.64 (s, 2H), 2.51-2.47 (m, obs., 2H), 1.92 (bs, 2H), 1.35-1.21 (m, 8H), 0.85 (t, J=7.0 Hz, 6H).

Example 162

Preparation of 4-(3-(2-Aminoethyl)Phenethyl)Heptan-4-Ol

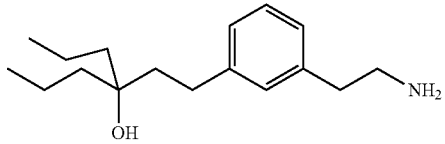 [SMILES: CCCC(O)(CCC)CCc1cccc(CCN)c1]

4-(3-(2-Aminoethyl)phenethyl)heptan-4-ol was prepared following the method used in Example 161.

Step 1. Coupling of N-(3-bromophenethyl)-2,2,2-trifluoroacetamide with 4-ethynylheptan-4-ol gave 2,2,2-trifluoro-N-(3-(3-hydroxy-3-propylhex-1-ynyl)phenethyl)acetamide as a yellow oil. Yield (0.902 g, 65%): ¹H NMR (400 MHz, DMSO-d₆) δ 9.43 (t, J=5.2 Hz, 1H), 7.25 (t, J=7.8 Hz, 1H), 7.20-7.15 (m, 3H), 5.11 (s, 1H), 3.41-3.36 (m, 2H), 2.76 (t, J=7.0 Hz, 2H), 1.61-1.40 (m, 8H), 0.89 (t, J=7.2 Hz, 6H).

Step 2. 2,2,2-Trifluoro-N-(3-(3-hydroxy-3-propylhex-1-ynyl)phenethyl)acetamide was deprotected to give 4-((3-(2-aminoethyl)phenyl)ethynyl)heptan-4-ol as a pale yellow oil. Yield (0.504 g, 78%): ¹H NMR (400 MHz, DMSO-d₆) δ 7.25-7.21 (m, 1H), 7.17-7.14 (m, 3H), 5.12 (bs, 1H), 2.74-

2.70 (m, 2H), 2.58 (t, J=7.2 Hz, 2H), 1.60-1.41 (m, 8H), 1.34 (bs, 2H), 0.89 (t, J=7.2 Hz, 6H).

Step 3. Hydrogenation of 4-((3-(2-aminoethyl)phenyl)ethynyl)heptan-4-ol gave Example 162 as a pale yellow oil. Yield (0.11 g, 100%): $^1$H NMR (400 MHz, DMSO-d$_6$) δ 7.13 (t, J=7.6 Hz, 1H), 6.96-6.94 (m, 3H), 3.93 (bs, 1H), 2.73-2.69 (m, 2H), 2.56 (t, J=7.4 Hz, 2H), 2.50-2.46 (m, obs., 2H), 1.55-1.51 (m, 2H), 1.34-1.20 (m, 8H), 0.84 (t, J=7.0 Hz, 6H).

Example 163

Preparation of 3-(3-Aminopropyl)-O-Cyclohexylbenzamide

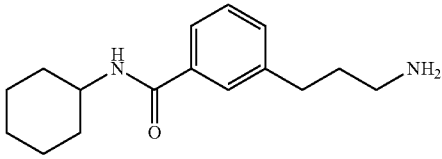 [SMILES: NCCCc1cccc(C(=O)NC2CCCCC2)c1]

3-(3-Aminopropyl)-o-cyclohexylbenzamide was prepared following the method used in Examples 2, 19 and 118.

Step 1: A solution of 3-bromobenzoyl chloride (2.0 g, 9 1 mmol) in CH$_2$Cl$_2$ was added solution triethylamine (1.9 ml, 13.7 mmol) and cyclohexylamine (1.15 ml, 10 0 mmol) in CH$_2$Cl$_2$ at room temperature with stirring. After 2 h, the mixture was washed with HCl (4N), brine, dried over Na$_2$SO$_4$ and concentrated under reduced pressure to give 3-bromo-N-cyclohexylbenzamide as a white solid. Yield (2.43 g, 95%): $^1$H NMR (400 MHz, CD$_3$OD) δ 8.29 (br s, 1H), 7.95 (t, J=2.0 Hz, 1H), 7.42-7.77 (m, 1H), 7.64-7.67 (m, 1H), 7.36 (t, J=8.0 Hz, 1H), 3.78-3.84 (m, 1H), 1.92-1.94 (m, 2H), 1.78-1.81 (m, 2H), 1.65-1.69 (m, 1H), 1.16-1.46 (m, 5H).

Step 2: Heck coupling of 3-bromo-N-cyclohexylbenzamide and N-allyl-2,2,2-trifluoroacetamide following the method described in Example 118 gave (E)-N-cyclohexyl-3-(3-(2,2,2-trifluoroacetamido)prop-1-enyl)benzamide as a light yellow solid. Yield (0.50 g, 71%): $^1$H NMR (400 MHz, CD$_3$OD) δ 8.18-8.26 (m, 1H), 7.83 (t, J=1.6 Hz, 1H), 7.65-7.68 (m, 1H), 7.54-7.56 (m, 1H), 7.39 (t, J=7.6 Hz, 1H), 6.62 (d, J=16.0 Hz, 1H), 6.32 (dt, J=16.0, 6.4 Hz, 1H), 4.06 (d, J=5.6 Hz, 2H), 3.80-3.90 (m, 1H), 1.93-1.95 (m, 2H), 1.79-1.82 (m, 2H), 1.66-1.70 (m, 1H), 1.18-1.48 (m, 5H).

Step 3: Hydrogenation of (E)-N-cyclohexyl-3-(3-(2,2,2-trifluoroacetamido)prop-1-enyl)benzamide following method described in Example 154 gave N-cyclohexyl-3-(3-(2,2,2-trifluoroacetamido)propyl)benzamide as a white solid. Yield (0.35 g, 87 $^1$H NMR (400 MHz, CD$_3$OD) δ 8.08-8.14 (m, 1H), 7.58-7.64 (m, 2H), 7.34-7.38 (m, 2H), 7.39 (t, J=7.6 Hz, 1H), 3.80-3.90 (m, 1H), 2.70 (t, J=8.0 Hz, 2H), 1.86-1.95 (m, 4H), 1.79-1.82 (m, 2H), 1.66-1.70 (m, 1H), 1.16-1.42 (m, 5H).

Step 4: Deprotection of N-cyclohexyl-3-(3-(2,2,2-trifluoroacetamido)propyl)benzamide following method described in Example 154 gave Example 163 hydrochloride as a white solid. Yield (0.07 g, 25%): $^1$H NMR (400 MHz, CD$_3$OD) δ 7.58-7.66 (m, 2H), 7.30-7.38 (m, 2H), 3.78-3.88 (m, 1H), 2.65-2.80 (m, 4H), 1.75-1.95 (m, 6H), 1.66-1.69 (m, 1H), 1.15-1.45 (m, 5H).

Example 164

Preparation of 3-(2-Aminoethoxy)-N-Cyclohexylbenzamide

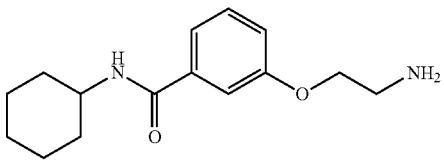 [SMILES: NCCOc1cccc(C(=O)NC2CCCCC2)c1]

3-(2-Aminoethoxy)-N-cyclohexylbenzamide was prepared following the method used in Examples 9 and 13.

Step 1: Coupling of methyl 3-hydroxybenzoate with 2-(tert-butoxycarbonylamino)ethyl methanesulfonate following the method used in Example 9 gave methyl 3-(2-(tert-butoxycarbonylamino)ethoxy)benzoate as a light yellow oil. Yield (0.65 g, 84%): $^1$H NMR (400 MHz, CD$_3$OD) δ 7.36 (t, J=8.0 Hz, 1H), 7.26 (t, J=8.0 Hz, 1H), 7.16 (ddd, J=8.4, 2.4, 0.8 Hz, 1H), 6.99 (ddd, J=8.0, 2.4, 0.8 Hz, 1H), 4.03 (t, J=5.6 Hz, 2H), 3.78 (s, 3H), 1.43 (s, 9H).

Step 2: Hydrolysis of methyl 3-(2-(tent-butoxycarbonylamino)ethoxy)benzoate following the method used in Example 9 except that LiOH and THF were used instead of K$_2$CO$_3$ and MeOH gave 3-(2-(tert-butoxycarbonylamino)ethoxy)benzoic acid that was used directly in next reaction without further purification.

Step 3: To a solution of 3-(2-(tert-butoxycarbonylamino)ethoxy)benzoic acid (0.73 g, 2.98 mmol), cyclohexylamine (0.34 ml, 2.98 mmol), EDCI (0.7 g, 3.58 mmol) and HOBT (0.49 g, 3.58 mmol) in DMF was added DIPEA (1.0 ml, 5.57 mmol). The resulting mixture was stirred at room temperature for 18 h, concentrated, and partitioned between ethyl acetate and water. The organic layer was dried over Na$_2$SO$_4$ and concentrated under reduced pressure. Purification by flash chromatography (30 to 65% EtOAc-hexanes gradient) gave tert-butyl 2-(3-(cyclohexylcarbamoyl)phenoxy)ethylcarbamate as an orange oil. Yield (0.20 g, 20%): $^1$H NMR (400 MHz, CD$_3$OD) δ 7.31-7.38 (m, 3H), 7.06-7.09 (m, 1H), 4.04 (t, J=5.6 Hz, 2H), 3.78-3.87 (m, 1H), 3.41-3.45 (m, 2H), 1.90-1.98 (m, 2H), 1.78-1.84 (m, 2H), 1.63-1.71 (m, 1H), 1.43 (s, 9H), 1.18-1.38 (m, 5H).

Step 4: Deprotection of tert-butyl 2-(3-(cyclohexylcarbamoyl)phenoxy)ethylcarbamate following method described in Example 151 gave Example 164 hydrochloride as a white solid. Yield (0.11 g, 60%): $^1$H NMR (400 MHz, CD$_3$OD) δ 7.36-7.44 (m, 3H), 7.14-7.17 (m, 1H), 4.27 (t, J=5.2 Hz, 2H), 3.80-3.90 (m, 1H), 3.37 (t, J=5.2 Hz, 2H), 1.92-1.98 (m, 2H), 1.78-1.86 (m, 2H), 1.65-1.72 (m, 1H), 1.15-1.48 (m, 5H).

Example 165

Preparation of 3-(3-Aminopropyl)-N-(Heptan-4-Yl)Benzamide

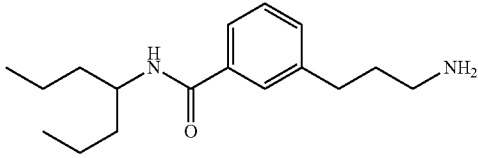 [SMILES: CCCC(CCC)NC(=O)c1cccc(CCCN)c1]

3-(3-Aminopropyl)-N-(heptan-4-yl)benzamide was prepared following the method used in Example 163:

Step 1: Reaction of 3-bromobenzoyl chloride with heptan-4-amine gave 3-bromo-N-(heptan-4-yl)benzamide as a white solid which was used in the next step without additional purification. Yield (2.43 g, 90%).

Step 2: Coupling of 3-bromo-N-(heptan-4-yl)benzamide and N-allyl-2,2,2-trifluoroacetamide gave (E)-N-(heptan-4-yl)-3-(3-(2,2,2-trifluoroacetamido)prop-1-enyl)benzamide as a light yellow solid. Yield (0.65 g, 80%): $^1$H NMR (400 MHz, CD$_3$OD) δ 8.09-8.11 (m, 1H), 7.81-7.84 (m, 1H), 7.65-7.68 (m, 1H), 7.54-7.56 (m, 1H), 7.40 (t, J=1.6 Hz, 1H), 6.63 (d, J=16.0 Hz, 1H), 6.33 (dt, J=16.0, 6.4 Hz, 1H), 4.06 (d, J=6.0 Hz, 2H), 1.50-1.56 (m, 4H), 1.32-1.46 (m, 5H), 0.93 (t, J=7.2 Hz, 6H).

Step 3: Hydrogenation of (E)-N-(heptan-4-yl)-3-(3-(2,2,2-trifluoroacetamido)prop-1-enyl)benzamide gave N-(heptan-4-yl)-3-(3-(2,2,2-trifluoroacetamido)propyl)benzamide as a white solid. Yield (0.30 g, 99%): $^1$H NMR (400 MHz, DMSO-d$_6$) δ 9.43 (t, J=5.6 Hz, 1H), 7.92 (d, J=8.80 Hz, 1H), 7.60-7.66 (m, 2H), 7.30-7.36 (m, 2H), 3.90-4.0 (m, 1H), 3.16-3.22 (m, 2H), 2.61 (t, J=8.4 Hz, 2H), 1.76-1.83 (m, 1H), 1.20-1.48 (m, 8H), 0.84 (t, J=7.2 Hz, 6H).

Step 4: Deprotection of N-(heptan-4-yl)-3-(3-(2,2,2-trifluoroacetamido)propyl)benzamide gave Example 165 hydrochloride as a white solid. Yield (0.18 g, 67%): $^1$H NMR (400 MHz, CD$_3$OD) δ 7.62-7.68 (m, 2H), 7.30-7.40 (m, 2H), 4.05-4.12 (m, 1H), 2.93 (t, J=8.0 Hz, 2H), 2.78 (t, J=7.6 Hz, 2H), 1.95-2.05 (m, 2H), 1.50-1.56 (m, 4H), 1.30-1.46 (m, 4H), 0.93 (t, J=7.6 Hz, 6H).

Example 166

Preparation of 3-(3-Aminopropyl)-N-(2,6-Deviethylphenyl)Benzamide

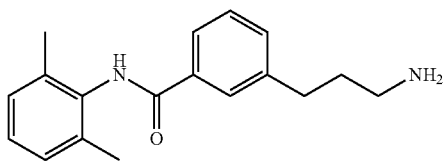 [SMILES: Cc1cccc(C)c1NC(=O)c1cccc(CCCN)c1]

3-(3-Aminopropyl)-N-(2,6-dimethylphenyl)benzamide was prepared following the method shown in Scheme 33.

SCHEME 33

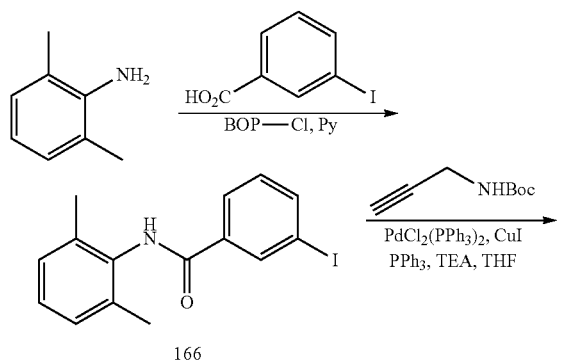

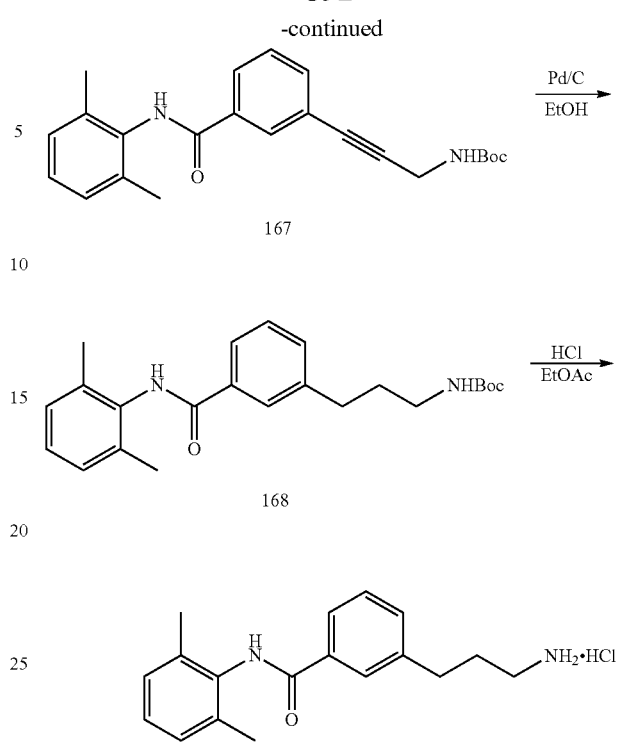

Step 1: To a solution of 2,6-dimethyl aniline (0.5 mL, 4.0 mmol) and 3-iodobenzoic acid (1.0 g, 4.0 mmol) in anhydrous pyridine was added BOP-Cl (2.05 g, 8 mmol). The reaction mixture was stirred at room temperature for two hrs, then extracted from 1N HCl with ethyl acetate. The combined organic layers were washed with HCl (1N), water, and brine, dried over Na$_2$SO$_4$, filtered, and concentrated under reduced vacuum. Purification by flash chromatography (10-20% ethyl acetate/hexanes gradient) gave amide 166 as a white solid. Yield (0.35 g, 25%): $^1$H NMR (400 MHz, DMSO-d6) δ 8.3 (s, 1H), 7.87-7.92 (m, 2H), 7.10-7.29 (m, 5H), 2.30 (s, 6H).

Step 2: Sonogashira coupling of iodide 166 with tent-butyl prop-2-ynylcarbamate following the method used in Example 2, except that triphenylphosphine was used instead of tri-tolyl-o-phosphine, followed by flash chromatography (15-40% ethyl acetate/hexanes gradient), gave the alkyne 167 as a light yellow solid. Yield (0.321 g, 83%): $^1$H NMR (400 MHz, DMSO-d$_6$) δ 7.96-7.99 (m, 1H), 7.88-7.92 (m, 1H), 7.60-7.65 (m, 1H), 7.48 (t, J=8.0 Hz, 1H), 7.33 (brs, 1H), 7.13-7.21 (m, 3H), 4.58 (brs, 1H), 4.10-4.30 (m, 2H), 2.31 (s, 6H), 1.50 (s, 9H).

Step 3: Hydrogenation of alkyne 167 following the method used in Example 2, followed by flash chromatography (10-35% EtOAc/hexanes gradient) gave alkane 168 as a colorless oil. Yield (0.083 g, 69%): $^1$H NMR (400 MHz, DMSO-d6) δ 8.01 (br.s, 1H), 7.78-7.86 (m, 2H), 7.37-7.47 (m, 2H), 7.10-7.28 (m, 3H), 4.65 (brs, 1H), 3.16-3.23 (m, 2H), 2.76 (t, J=8.0 Hz, 2H), 2.31 (s, 6H), 1.87 (quint, J=8.0 Hz, 2H), 1.38 (s, 9H).

Step 4: Deprotection of carbamate 168 following the method used in Example 34 gave Example 166 hydrochloride as a light tan solid. Yield (0.018 g, 43%): $^1$H NMR (400 MHz, DMSO-d6) δ 9.80 (s, 1H), 7.85-8.0 (m, 5H), 7.42-7.50 (m, 2H), 7.13 (s, 3H), 2.78-2.87 (m, 2H), 2.75 (t, J=8.0 Hz, 2H), 2.19 (s, 6H), 1.91 (quint, J=8.0 Hz, 2H). ESI MS m/z 283.3 [m+H]+

Example 167

Preparation of 4-(3-(1-Hydroxy-3-(Methylamino)Propyl)Phenethyl)Heptan-4-Ol

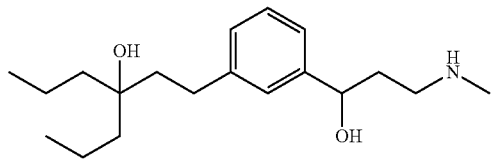 [SMILES: CCCC(O)(CCC)CCc1cccc(C(O)CCNC)c1]

4-(3-(1-Hydroxy-3-(methylamino)propyl)phenethyl)heptan-4-ol is prepared following the method used in Example 17 and in Scheme 34.

SCHEME 34

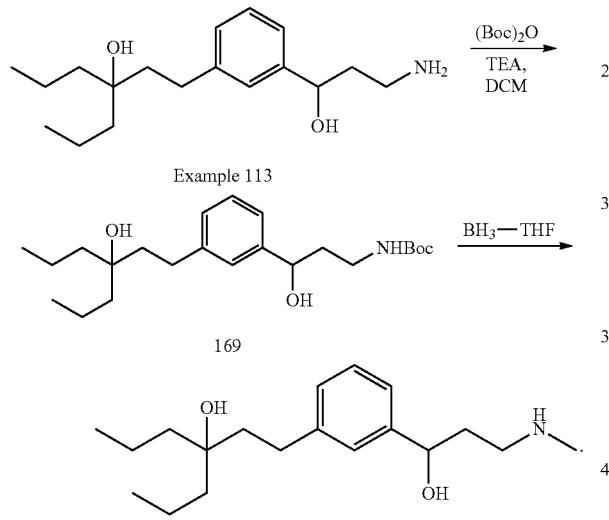

Step 1: Protection of 4-(3-(3-amino-1-hydroxypropyl)phenethyl)heptan-4-ol using (Boc)₂O following the method described in Example 17 gives tert-butyl 3-hydroxy-3-(3-(3-hydroxy-3-propylhexyl)phenyl)propylcarbamate.

Step 2: Reduction of tert-butyl 3-hydroxy-3-(3-(3-hydroxy-3-propylhexyl)phenyl)propylcarbamate using BH₃-THF gives Example 167.

Example 168

Preparation of 1-(3-(3-Hydroxy-3-Propylhexyl)Benzyl)Guanidine

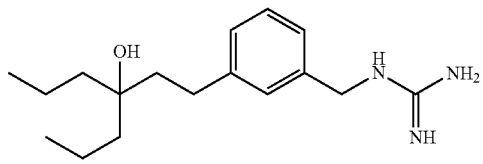 [SMILES: CCCC(O)(CCC)CCc1cccc(CNC(=N)N)c1]

1-(3-(3-Hydroxy-3-propylhexyl)benzyl)guanidine is prepared following the method described in Scheme 35.

SCHEME 35

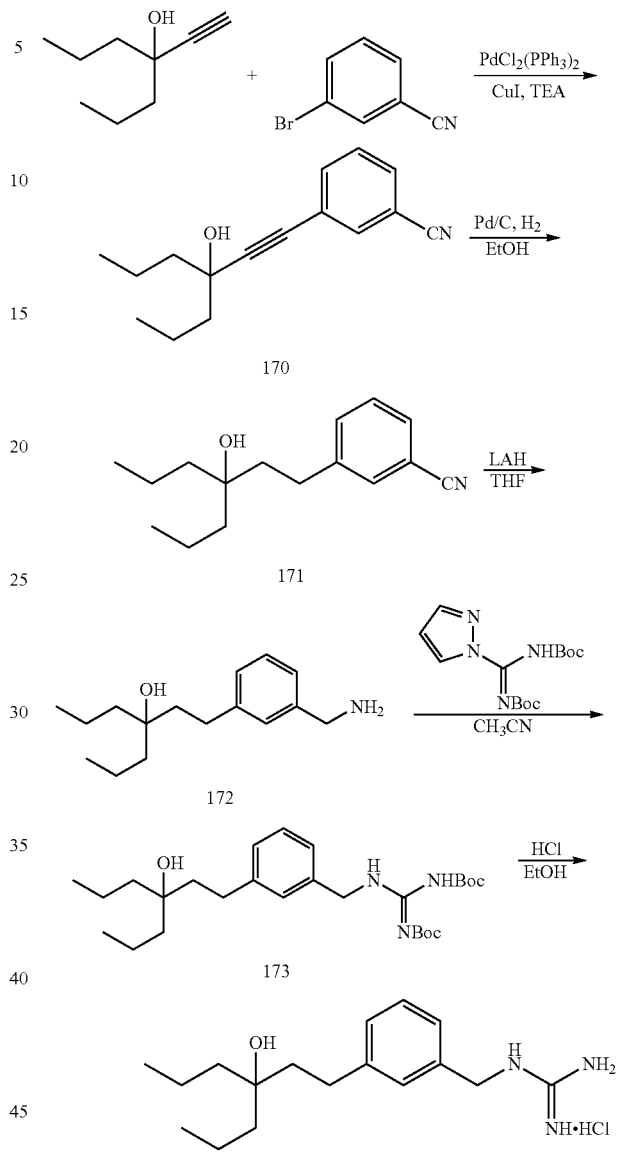

Step 1: Coupling of 4-ethynylheptan-4-ol with 3-bromobenzonitrile following the method described in Example 12 gives 3-(3-hydroxy-3-propylhex-1-ynyl)benzonitrile.

Step 2: Hydrogenation of 3-(3-hydroxy-3-propylhex-1-ynyl)benzonitrile following the method described in Example 12 gives 3-(3-hydroxy-3-propylhexyl)benzonitrile Step 3: Reduction of 3-(3-hydroxy-3-propylhexyl)benzonitrile following the method described in Example 15 gives 4-(3-(aminomethyl)phenethyl)heptan-4-ol.

Step 4: Reaction of 4-(3-(aminomethyl)phenethyl)heptan-4-ol with tert-butyl (1H-pyrazol-1-yl)methylenedicarbamate in CH₃CN gives tert-butyl(tert-butoxycarbonylamino)(3-(3-hydroxy-3-propylhexyl)benzylamino)methylenecarbamate.

Step 5: Deprotection of tert-butyl(tert-butoxycarbonylamino)(3-(3-hydroxy-3-propylhexyl)benzylamino)methylenecarbamate following the method used in Example 13 gives Example 168.

Example 169

Preparation of 1-(3-(3-(3-Hydroxy-3-Propylhexyl)Phenyl)Propyl)Guanidine

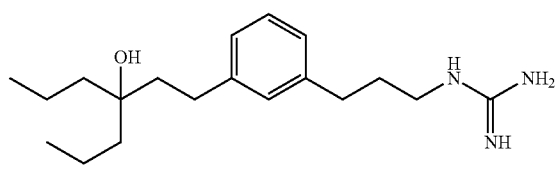 [SMILES: CCCC(O)(CCC)CCc1cccc(CCCNC(=N)N)c1]

1-(3-(3-(3-Hydroxy-3-propylhexyl)phenyl)propyl)guanidine is prepared following the method used in Examples 12, 118 and 168 in Scheme 35.

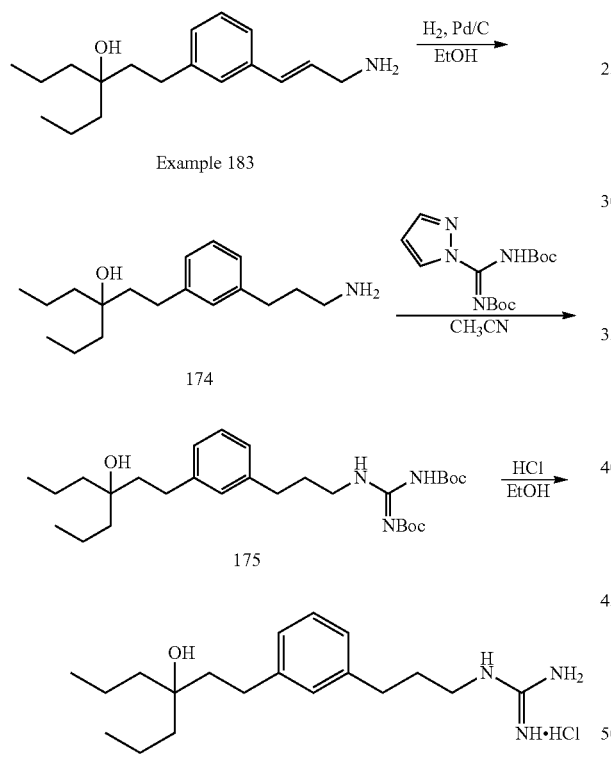

Step 1: Hydrogenation of (E)-4-(3-(3-aminoprop-1-enyl)phenethyl)heptan-4-ol following method described in Example 12 gives 4-(3-(3-aminopropyl)phenethyl)heptan-4-ol.

Step 2: Reaction of 4-(3-(3-aminopropyl)phenethyl)heptan-4-ol with tert-butyl (1H-pyrazol-1-yl)methylenedicarbamate following the method described in Example 168 gives tert-butyl(tert-butoxycarbonylamino)(3-(3-(3-hydroxy-3-propylhexyl)phenyl)propylamino)methylenecarbamate.

Step 3: Deprotection of tert-butyl(tert-butoxycarbonylamino)(3-(3-(3-hydroxy-3-propylhexyl)phenyl)propylamino)methylenecarbamate following the method used in Example 13 gives Example 169.

Example 170

Preparation of 3-Hydroxy-3-(3-(3-Hydroxy-3-Propylhexyl)Phenyl)Propanimidamide

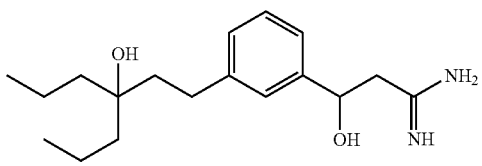 [SMILES: CCCC(O)(CCC)CCc1cccc(C(O)CC(=N)N)c1]

3-Hydroxy-3-(3-(3-hydroxy-3-propylhexyl)phenyl)propanimidamide is prepared following the method described in Scheme 36.

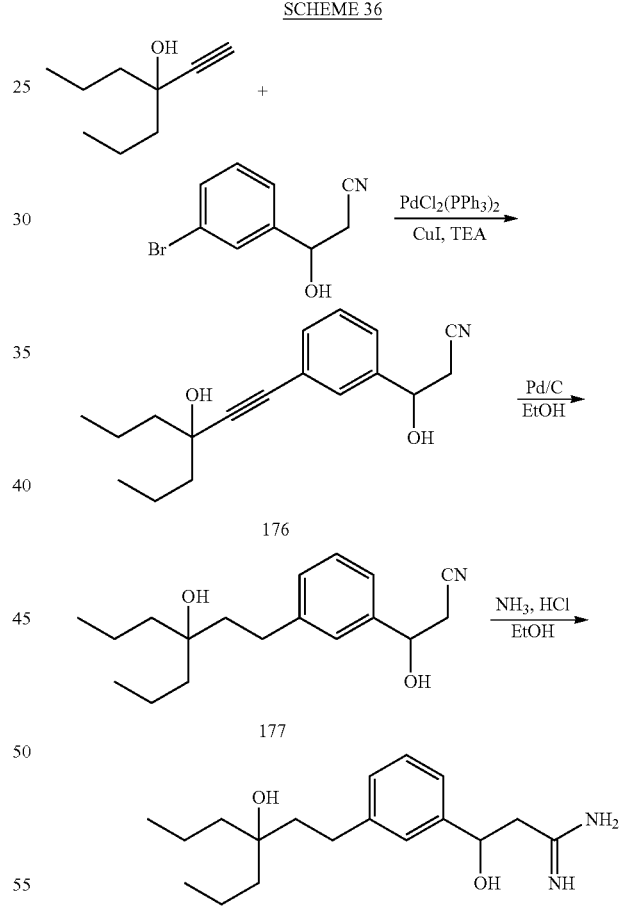

Step 1: Coupling of 4-ethynylheptan-4-ol with 3-(3-bromophenyl)-3-hydroxypropanenitrile following the method described in Example 12 gives 3-hydroxy-3-(3-(3-hydroxy-3-propylhex-1-ynyl)phenyl)propanenitrile as a light yellow oil.

Step 2: Hydrogenation of 3-hydroxy-3-(3-(3-hydroxy-3-propylhex-1-ynyl)phenyl)propanenitrile following the method described in Example 12 gives 3-hydroxy-3-(3-(3-hydroxy-3-propylhexyl)phenyl)propanenitrile.

Step 3: Into an ice cold solution of 3-hydroxy-3-(3-(3-hydroxy-3-propylhex-1-ynyl)phenyl) in absolute EtOH is bubbled HCl gas for 4 to 5 min This mixture is allowed to warm to room temperature and stirred. The solvent is removed under reduced pressure. To the residue is added absolute EtOH with cooling in an ice bath and NH₃ gas is bubbled into the solution for 2-3 min The mixture is allowed to warm to room temperature and stirred for 4 h. The mixture is concentrated under reduced pressure. To the residue is added absolute EtOH with cooling in an ice bath. HCl gas is bubbled into the solution for 1 min and the mixture is concentrated under reduced pressure. The residue is dissolved in H₂O and extracted with EtOAc. The aqueous layer is evaporated to dryness and dried under high vacuum overnight to give Example 170.

Example 171

Preparation of 1-Amino-3-(3-(3-Hydroxy-3-Propyl-hexyl)Phenyl)Propan-2-One

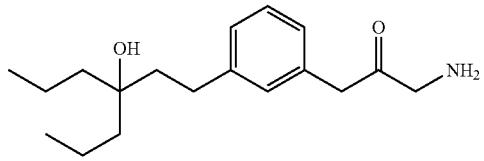 [SMILES: CCCC(O)(CCC)CCc1cccc(CC(=O)CN)c1]

1-Amino-3-(3-(3-hydroxy-3-propylhexyl)phenyl)propan-2-one is prepared following the method used in Example 19.

Step 1: Protection of 4-(3-(3-amino-2-hydroxypropyl)phenethyl)heptan-4-ol (Example 143) using (Boc)₂O following the method described in Example 17 gives tert-butyl 2-hydroxy-3-(3-(3-hydroxy-3-propylhexyl)phenyl)propylcarbamate.

Step 2: Oxidation of tert-butyl 2-hydroxy-3-(3-(3-hydroxy-3-propylhexyl)phenyl)propylcarbamate following the method used in Example 151 gives tert-butyl 3-(3-(3-hydroxy-3-propylhexyl)phenyl)-2-oxopropylcarbamate.

Step 3: Deprotection of tert-butyl 3-(3-(3-hydroxy-3-propylhexyl)phenyl)-2-oxopropylcarbamate following the method used in Example 13 gives Example 171 hydrochloride salt.

Example 172

Preparation of 4-(3-(3-Amino-2-Fluoropropyl)Phenethyl)Heptan-4-Ol

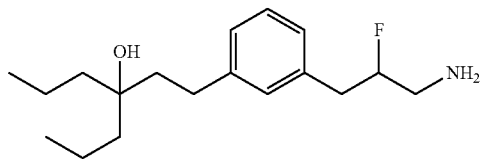 [SMILES: CCCC(O)(CCC)CCc1cccc(CC(F)CN)c1]

4-(3-(3-Amino-2-fluoropropyl)phenethyl)heptan-4-ol is prepared following the method used in Example 174 except Example 143 is used instead of alcohol 39.

Example 173

Preparation of 3-Amino-14343-Hydroxy-3-Propyl-hexylphenylpropan-1-One

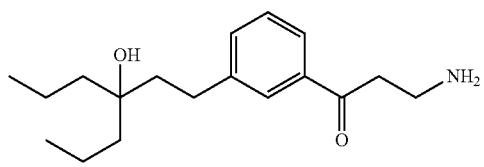 [SMILES: CCCC(O)(CCC)CCc1cccc(C(=O)CCN)c1]

3-Amino-1-(3-(3-hydroxy-3-propylhexyl)phenyl)propan-1-one is prepared following the method used in Example 19.

Step 1: Protection of 4-(3-(3-amino-1-hydroxypropyl)phenethyl)heptan-4-ol using (Boc)₂O following the method described in Example 17 gives tert-butyl 3-hydroxy-3-(3-(3-hydroxy-3-propylhexyl)phenyl)propylcarbamate.

Step 2: Oxidation of tert-butyl 3-hydroxy-3-(3-(3-hydroxy-3-propylhexyl)phenyl)propylcarbamate following the method used in Example 151 gives tert-butyl 3-hydroxy-3-(3-(3-hydroxy-3-propylhexyl)phenyl)propylcarbamate.

Step 3: Deprotection of tert-butyl 3-hydroxy-3-(3-(3-hydroxy-3-propylhexyl)phenyl)propylcarbamate following the method used in Example 13 gives Example 173 hydrochloride salt.

Example 174

Preparation of 443-(3-Amino-1-Fluoropropyl)Phenethyl)Heptan-4-Ol

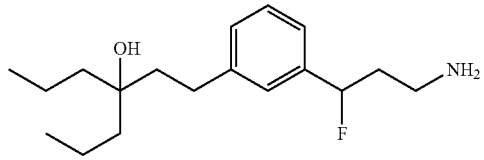

4-(3-(3-Amino-1-fluoropropyl)phenethyl)heptan-4-ol is prepared following the method below.

Step 1: Diethylaminosulphur trifluoride (DAST) is added under an inert atmosphere to a cold (−78° C.) solution of alcohol 39. The reaction mixture is stirred at −78° C. until no starting material is seen by TLC. The reaction mixture is partitioned between water and EtOAc, and aqueous layer is extracted with EtOAc. The combined organic layers are washed with brine and dried over anhydrous MgSO₄. Purification by flash chromatography gives tert-butyl 3(3-bromophenyl)-3-fluoropropylcarbamate.

Step 2: Sonogashira coupling of tert-butyl 3-(3-bromophenyl)-3-fluoropropylcarbamate and 4-ethynylheptan-4-ol following the method described in Example 12 gives tert-butyl 3-fluoro-3-(3-(3-hydroxy-3-propylhex-1-ynyl)phenyl)propylcarbamate.

Step 3: Hydrogenation of tert-butyl 3-fluoro-3-(3-(3-hydroxy-3-propylhex-1-ynyl)phenyl)propylcarbamate following the method used in Example 12 gives tert-butyl 3-fluoro-3-(3-(3-hydroxy-3-propylhexyl)phenyl)propylcarbamate.

Step 4. Deprotection of tert-butyl 3-fluoro-3-(3-(3-hydroxy-3-propylhexyl)phenyl)propylcarbamate following the method used in Example 13 gives Example 174.

Example 175

Preparation of 4-(3-(4-Aminobutan-2-Yl)Phenethyl)Heptan-4-Ol

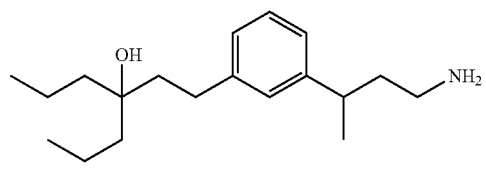

4-(3-(4-Aminobutan-2-yl)phenethyl)heptan-4-ol is prepared following the method used in Scheme 37.

SCHEME 37

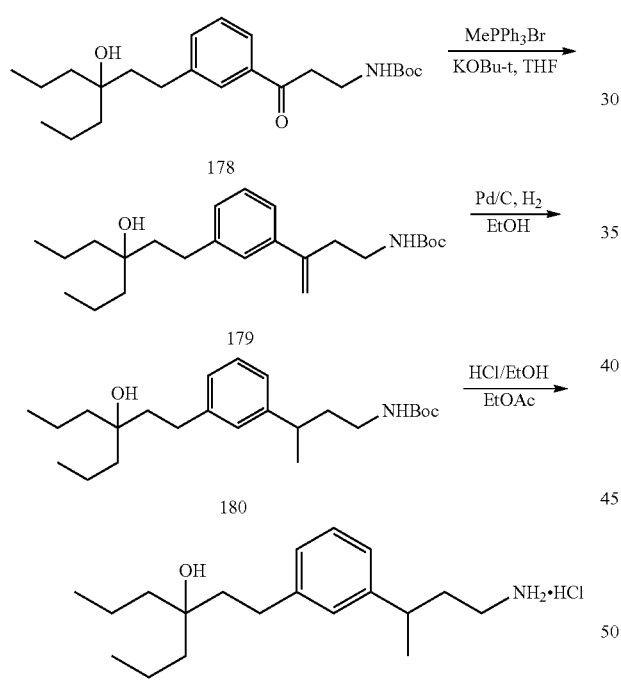

Step 1: To a suspension of methyltriphenylphosponium bromide in THF is added KOBu-t (1 M in THF, 6.1 mmol) at room temperature. After stirring for 30 mins, tert-butyl 3-(3-(3-hydroxy-3-propylhexyl)phenyl)-3-oxopropylcarbamate is added. The resulting mixture is stirred at room temperature for 18 h. The reaction is quenched by the addition of AcOH. The mixture is filtered and concentrated under reduced pressure. Purification by flash chromatography (15 to 50% EtOAc-hexanes gradient) gives tert-butyl 3-(3-(3-hydroxy-3-propylhexyl)phenyl)but-3-enylcarbamate.

Step 2: Hydrogenation of tert-butyl 3-(3-(3-hydroxy-3-propylhexyl)phenyl)but-3-enylcarbamate following the method described in Example 12 gives tert-butyl 3-(3-(3-hydroxy-3-propylhexyl)phenyl)butylcarbamate.

Step 3: Deprotection of tert-butyl 3-(3-(3-hydroxy-3-propylhexyl)phenyl)butylcarbamate following the method used in Example 13 gives Example 175 hydrochloride salt.

Example 176

Preparation of 4-(3-(3-Amino-1-Hydroxypropyl)-5-Chlorophenethyl)Heptan-4-Ol

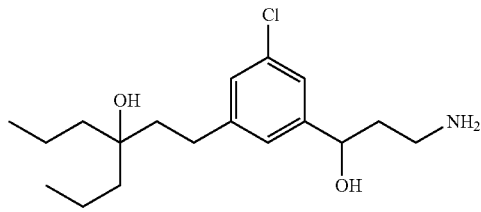 [SMILES: CCCC(O)(CCC)CCc1cc(Cl)cc(C(O)CCN)c1]

4-(3-(3-Amino-1-hydroxypropyl)-5-chlorophenethyl)heptan-4-ol is prepared following the methods used in Examples 16, 17 and 19 except 3-bromo-5-chlorobenzaldehyde is used instead of 3-bromobenzaldehyde.

Example 177

Preparation of (R)-3-(3-Amino-1-Hydroxypropyl)-N-(Heptan-4-Yl)Benzamide

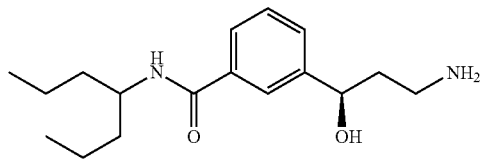 [SMILES: CCCC(CCC)NC(=O)c1cccc([C@H](O)CCN)c1]

(R)-3-(3-amino-1-hydroxypropyl)-N-(heptan-4-yl)benzamide is prepared following the methods used in Examples 71 and 163 using 3-formylbenzoic acid as starting material.

Example 178

Preparation of 4-(3-(3-Aminobutyl)Phenethyl)Heptan-4-Ol

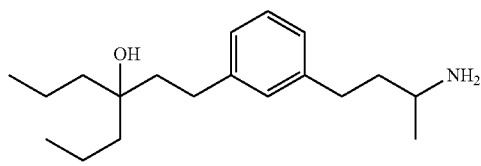 [SMILES: CCCC(O)(CCC)CCc1cccc(CCC(C)N)c1]

4-(3-(3-Aminobutyl)phenethyl)heptan-4-ol is prepared following the method used Examples 12 and 180 using vinyl methyl ketone in place of allyl trifluoroacetamide.

Example 179

Preparation of (R)-3-(3-Amino-1-Hydroxypropyl)-N-Cyclohexyl-N-Methylbenzamide

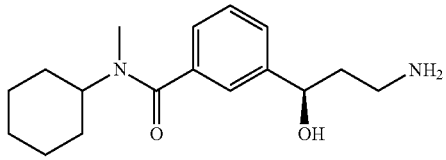 [SMILES: CN(C(=O)c1cccc([C@H](O)CCN)c1)C1CCCCC1]

(R)-3-(3-Amino-1-hydroxypropyl)-N-cyclohexyl-N-methylbenzamide is prepared following the method used in Example 177.

Example 180

Preparation of 1-(3-((1R,2R)-3-Amino-1-Hydroxy-2-Methylpropyl)Phenethyl)Cyclopentanol

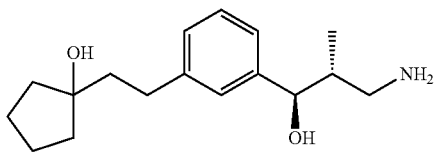 [SMILES: C[C@H](CN)[C@@H](O)c1cccc(CCC2(O)CCCC2)c1]

1-(3-((1R,2R)-3-Amino-1-hydroxy-2-methylpropyl)phenethyl)cyclopentanol is prepared following the method used in Scheme 38.

SCHEME 38

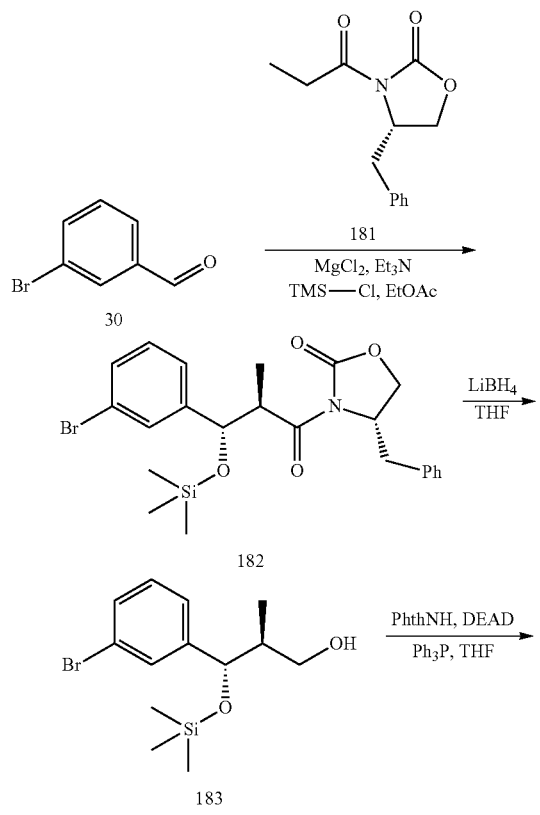

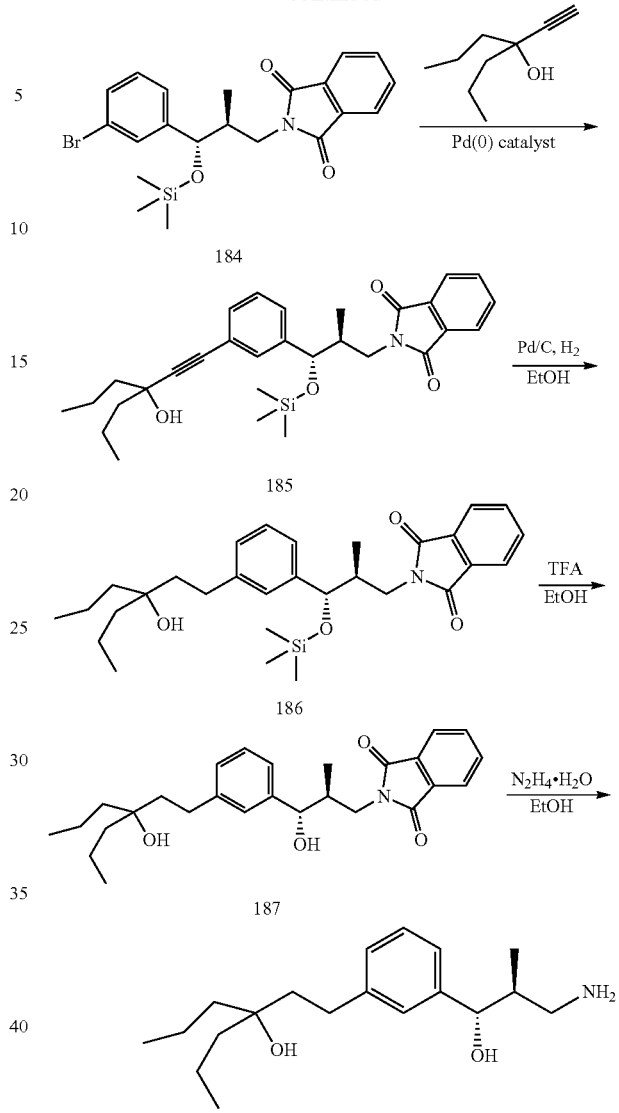

Step 1: To a mixture of (S)-4-benzyl-3-propionyloxazolidin-2-one, anhydrous MgCl$_2$ (0.104 g, 1.09 mmol) and 3-bromobenzaldehyde in EtOAc is added Et$_3$N followed by chlorotrimethylsilane. The reaction mixture is stirred under argon at room temperature for 24 h and then filtered through a layer of a silica gel, washing with EtOAc. The combined filtrates are concentrated under reduced pressure and the residue is purified by flash chromatography (1 to 30% EtOAc/hexane gradient) to give (S)-4-benzyl-3-((2R,3S)-3-(3-bromophenyl)-2-methyl-3-(trimethylsilyloxy)propanoyl)oxazolidin-2-one.

Step 2: To a solution of (S)-4-benzyl-3-((2R,3S)-3-(3-bromophenyl)-2-methyl-3-(trimethylsilyloxy)propanoyl)oxazolidin-2-one in anhydrous THF is added a solution of LiBH$_4$ in THF under argon. The reaction mixture is stirred for 18 h at room temperature and a saturated aqueous solution of NH$_4$Cl is slowly added followed by MTBE. The mixture is stirred for 15 mins, layers are separated, organic layer is washed with brine, dried over anhydrous MgSO$_4$, filtered and concentrated under reduced pressure. The residue is purified by flash chromatography (5 to 40% EtOAc/hexane gradient) to give (2S,3S)-3-(3-bromophenyl)-2-methyl-3-(trimethylsilyloxy)propan-1-ol.

Step 3: To a cold (0° C.) solution of (2S,3S)-3-(3-bromophenyl)-2-methyl-3-(trimethylsilyloxy)propan-1-ol, phthalimide and Ph₃P in anhydrous THF under argon is added solution of diethyl azodicarboxylate in anhydrous THF. The reaction mixture is stirred for 1 hour under argon while warming to room temperature and then the solvent is removed in vacuum, the residue is dissolved in dichloromethane/hexane and purified by flash chromatography (5 to 30% EtOAc/hexane gradient) to 2-((2S,3S)-3-(3-bromophenyl)-2-methyl-3-(trimethylsilyloxy)propyl)isoindoline-1,3- dione.

Step 4: Coupling of 2-((2S,3S)-3-(3-bromophenyl)-2-methyl-3-(trimethylsilyloxy)propyl)isoindoline-1,3-dione with 4-ethynylheptan-4-ol following the method in Example 12 gives 2-((2S,3S)-3-(3-(3-hydroxy-3-propylhex-1-ynyl)phenyl)-2-methyl-3-(trimethylsilyloxy)propyl)isoindoline-1,3-dione.

Step 5: Hydrogenation of 2-((2S,3S)-3-(3-(3-hydroxy-3-propylhex-1ynyl)phenyl)-2-methyl-3-(trimethylsilyloxy)propyl)isoindoline-1,3-dione following the method used in Example 12 gives 2-((2S,3S)-3-(3-(3-hydroxy-3-propylhexyl)phenyl)-2-methyl-3-(trimethylsilyloxy)propyl)isoindoline-1,3-dione.

Step 6: To a solution of 2-((2S,3S)-3-(3-(3-hydroxy-3-propylhexyl)phenyl)-2-methyl-3-(trimethylsilyloxy)propyl)isoindoline-1,3-dione in EtOH is added trifluoroacetic acid. The reaction mixture is stirred at room temperature then concentrated under reduced pressure, re-evaporated with EtOAc then with hexane to give 2-((2S,3S)-3-hydroxy-3-(3-(3-hydroxy-3-propylhexyl)phenyl)-2-methylpropyl)isoindoline-1,3-dione.

Step 7: Phthalimide cleavage of 2-((2S,3S)-3-hydroxy-3-(3-(3-hydroxy-3-propylhexyl)phenyl)-2-methylpropyl)isoindoline-1,3-dione is performed following the method described in Example 9 gives Example 180.

Example 181

Preparation of 1-(3-(3-Aminopropyl)-5-Methylphenethyl)Cyclohexanol

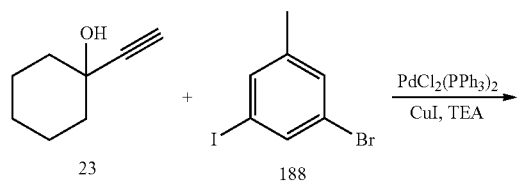

1-(3-(3-Aminopropyl)-5-methylphenethyl)cyclohexanol is prepared following the method shown in Scheme 39.

SCHEME 39

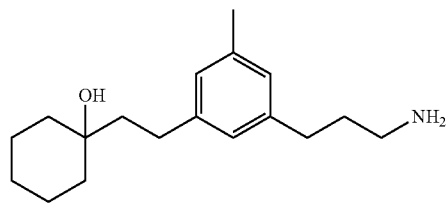

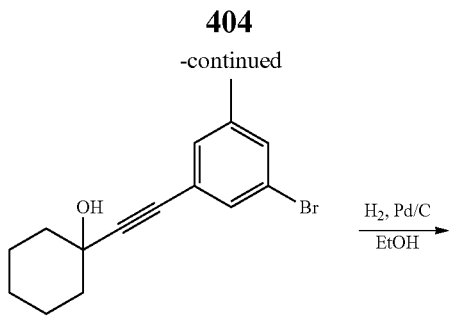

189

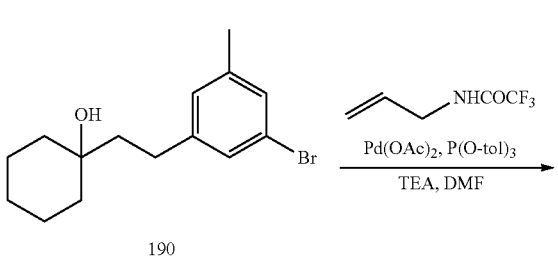

190

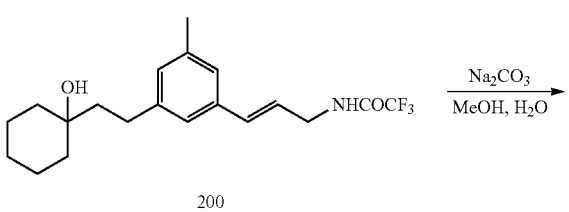

200

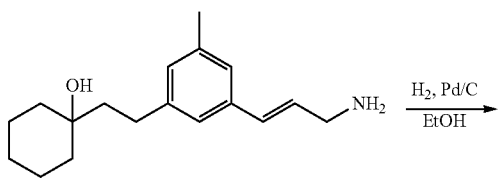

201

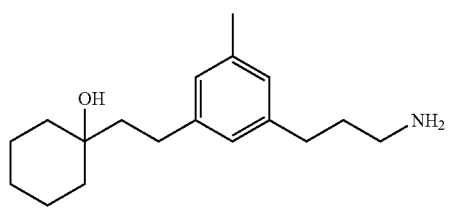 [SMILES: Cc1cc(CCCN)cc(CCC2(O)CCCCC2)c1]

Steps 1 to 4: The procedure for the synthesis of (E)-1-(3-(3-aminoprop-1-enyl)-5-methylphenethyl)cyclohexanol is the same as for the synthesis of Example 183 except 1-bromo-3-iodo-5-methylbenzene and 1-ethynylcyclohexanol are used instead of 1-bromo-3-iodobenzene and 4-ethynylheptan-4-ol.

Step 5: Hydrogenation of (E)-1-(3-(3-aminoprop-1-enyl)-5-methylphenethyl)cyclohexanol following the method described in Example 12 gives Example 181.

Example 182

Preparation of 1-(3-(3-Aminopropyl)-4-Fluorophenethyl)Cyclohexanol

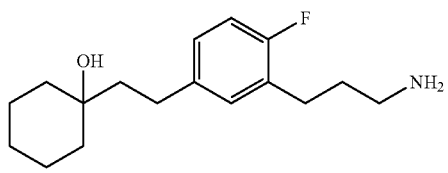 [SMILES: NCCCc1cc(CCC2(O)CCCCC2)ccc1F]

1-(3-(3-Aminopropyl)-4-fluorophenethyl)cyclohexanol is prepared following the method used in Example 181.

Steps 1 to 4: The procedure for the synthesis of (E)-1-(3-(3-aminoprop-1-enyl)-4-fluorophenethyl)cyclohexanol is the same as for the synthesis of Example 181 except 2-bromo-1-fluoro-4-iodobenzene is used instead of 1-bromo-3-iodobenzene.

Step 5: Hydrogenation of (E)-1-(3-(3-aminoprop-1-enyl)-4-fluorophenethyl)cyclohexanol following the method described in Example 12 gives Example 182.

Example 183

Preparation of (E)-1-(3-(3-Aminoprop-1-Enyl)Phenethyl)Cyclohexanol

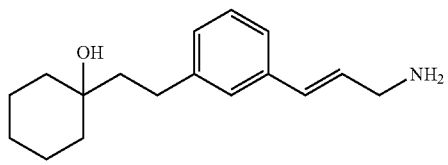 [SMILES: NC/C=C/c1cccc(CCC2(O)CCCCC2)c1]

(E)-1-(3-(3-Aminoprop-1-enyl)phenethyl)cyclohexanol is prepared following the method shown in Scheme 40.

SCHEME 40

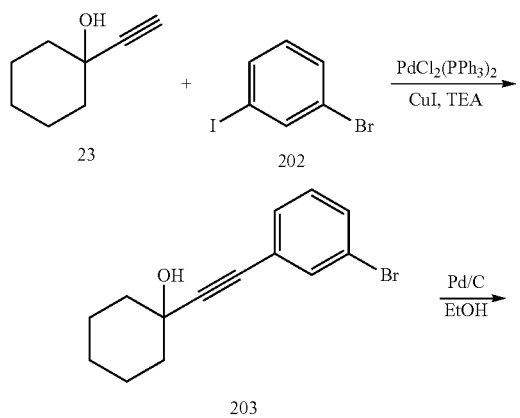

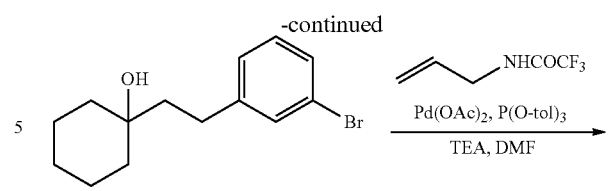

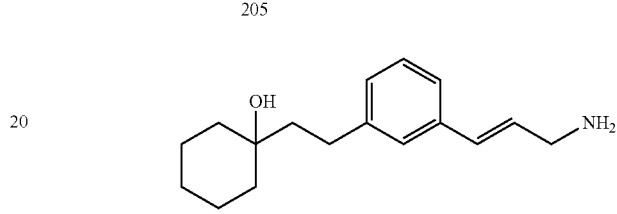

Step 1: Coupling of cyclohexylmethanol with 1-bromo-3-iodobenzene following the method described in Example 12 gives 1-((3-bromophenyl)ethynyl)cyclohexanol as a light yellow oil.

Step 2: Hydrogenation 1-((3-bromophenyl)ethynyl)cyclohexanol following the method described in Example 12 gives 1-(3-bromophenethyl)cyclohexanol.

Step 3: Coupling of 1-(3-bromophenethyl)cyclohexanol with N-allyl-2,2,2-trifluoroacetamide following the method described in Example 118 gives (E)-2,2,2-trifluoro-N-(3-(3-(2-(1-hydroxycyclohexyl)ethyl)phenyl)allyl)acetamide.

Step 4: Deprotection of (E)-2,2,2-trifluoro-N-(3-(3-(2-(1-hydroxycyclohexyl)ethyl)phenyl)allyl)acetamide following the method described in Example 2 gives Example 183.

Example 184

Preparation of 1-(3-(3-Aminoprop-1-Ynyl)Phenethyl)Cyclohexanol

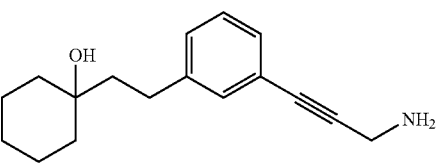 [SMILES: NCC#Cc1cccc(CCC2(O)CCCCC2)c1]

1-(3-(3-Aminoprop-1-ynyl)phenethyl)cyclohexanol is prepared following the method used in Example 12.

Step 1: Coupling of 1-(3-bromophenethyl)cyclohexanol with 2-(prop-2-ynyl)isoindoline-1,3-dione following the method described in Example 12 gives 2-(3-(3-(2-(1-hydroxycyclohexyl)ethyl)phenyl)prop-2-ynyl)isoindoline-1,3-dione.

Step 2: Deprotection of 2-(3-(3-(2-(1-hydroxycyclohexyl)ethyl)phenyl)prop-2-ynyl)isoindoline-1,3-dione following the method described in Example 12 gives Example 184.

Example 185

Preparation of 4-(3-(3-Aminopropdxy)Phenethyl)Heptan-4-Ol

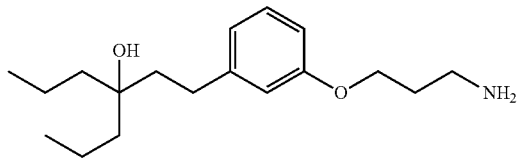 [SMILES: CCCC(O)(CCC)CCc1cccc(OCCCN)c1]

4-(3-(3-Aminopropoxy)phenethyl)heptan-4-ol is prepared following the method used Example 9.

Example 186

Preparation of 4-(3((2-Aminoethoxy)Methylphenethyl)Heptan-4-Ol

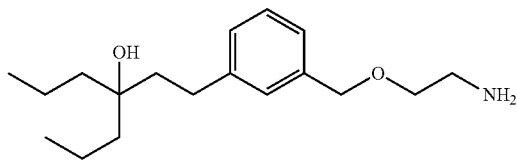 [SMILES: CCCC(O)(CCC)CCc1cccc(COCCN)c1]

4-(3-((2-Aminoethoxy)methyl)phenethyl)heptan-4-ol is prepared following the method shown in Scheme 41.

SCHEME 41

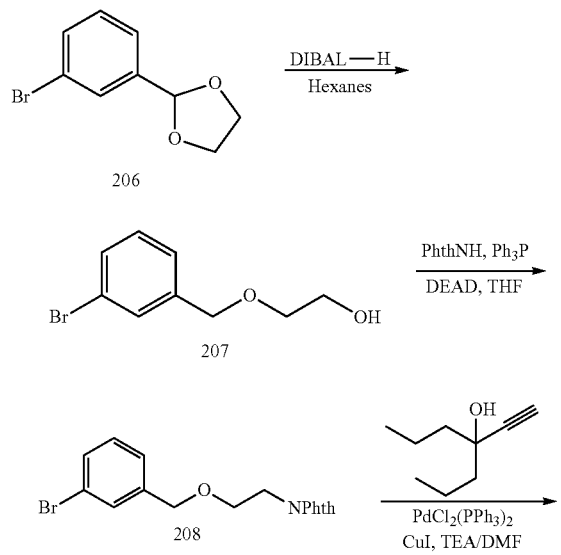

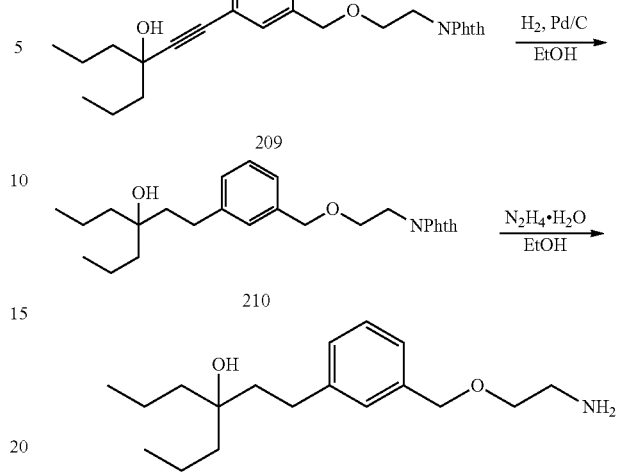

Step 1: A solution of DIBAL-H in heptane is added under an inert atmosphere to a cooled (−78° C.) solution of 2-(3-bromophenyl)-1,3-dioxolane in hexanes. The reaction mixture is stirred until no starting material is seen by TLC. Aqueous HCl (1N) is added to the reaction mixture while warming to room temperature. The product is extracted with EtOAc. Combined organic layers are dried over anhydrous MgSO$_4$, and concentrated under reduced pressure to give 2-(3-bromobenzyloxy)ethanol.

Step 2: Mitsunobu reaction of 2-(3-bromobenzyloxy)ethanol and phthalimide following the method used in Example 134 gives 2-(2-(3-bromobenzyloxy)ethyl)isoindoline-1,3-dione.

Step 3: Sonogashira coupling of 2-(2-(3-bromobenzyloxy)ethyl)isoindoline-1,3-dione and 4-ethynylheptan-4-ol following the method described in Example 12 gives 2-(2-(3-(3-hydroxy-3-propylhex-1-ynyl)benzyloxy)ethyl)isoindoline-1,3-dione.

Step 4: Hydrogenation of 2-(2-(3-(3-hydroxy-3-propylhex-1-ynyl)benzyloxy)ethyl)isoindoline-1,3-dione following the method used in Example 12 gives 2-(2-(3-(3-hydroxy-3-propylhexyl)benzyloxy)ethyl)isoindoline-1,3-dione. Step 5: Deprotection of 2-(2-(3-(3-hydroxy-3-propylhexyl)benzyloxy)ethyl)isoindoline-1,3-dione following the method used in Example 21 gives Example 186.

Example 187

Preparation of 2-(3-(3-Aminopropyl)Phenethyl)Cyclohexanol

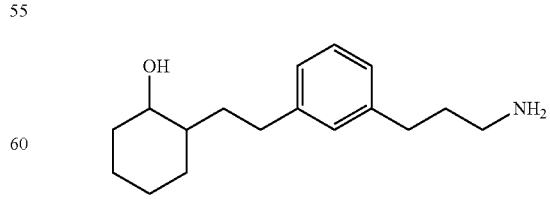

2-(3-(3-aminopropyl)phenethyl)cyclohexanol was prepared following the method used in Example 2:
Step 1: Sonogashira coupling of bromide (10) with 2-ethynylcyclohexanol, followed by flash chromatography (5-50%

EtOAc/hexanes gradient), gave 2,2,2-trifluoro-N-(3-(3-((2-hydroxycyclohexyl)ethynyl)phenyl)propyl)acetamide as a yellow oil. Yield (1.2 g, 43%): $^1$H NMR (400 MHz, CDCl$_3$) δ 7.18-7.28 (m, 3H), 7.06-7.11 (m, 1H), 6.33 (brs, 1H), 3.48-3.57 (m, 1H), 3.36 (ddd, J=6.8 Hz, 2H), 2.63 (t, J=7.2 Hz, 2H), 2.38-2.46 (m, 1H), 2.32 (brs, 1H), 2.02-2.10 (m, 2H), 1.91 (dddd, J=7.2 Hz, 2H), 1.74-1.82 (m, 1H), 1.66-1.74 (m, 1H), 1.40-1.52 (m, 1H), 1.16-1.40 (m, 3H).

Step 2: Deprotection of 2,2,2-trifluoro-N-(3-(3-((2-hydroxycyclohexyl)ethynyl)phenyl)propyl)acetamide followed by flash chromatography (10% (7N NH$_3$/MeOH)/dichloromethane) gave 2-((3-(3-aminopropyl)phenyl)ethynyl)cyclohexanol as an orange oil. Yield (0.606 g, 69%): $^1$H NMR (400 MHz, CDCl$_3$) δ 7.16-7.26 (m, 3H), 7.08-7.12 (m, 1H), 3.48-3.56 (m, 1H), 2.71 (t, J=7.2 Hz, 2H), 2.61 (t, J=7.2 Hz, 2H), 2.38-2.46 (m, 1H), 2.01-2.10 (m, 2H), 1.64-1.82 (m, 7H), 1.40-1.52 (m, 1H), 1.16-1.40 (m, 3H).

Step 3: Hydrogenation of 2-((3-(3-aminopropyl)phenyl)ethynyl)cyclohexanol followed by flash chromatography (10% (7N NH$_3$/MeOH)/dichloromethane) gave example 187 as a pale yellow solid. (0.265 g, 69%): $^1$H NMR (400 MHz, CDCl$_3$) δ 7.17 (tJ=7.6 Hz, 1H), 6.96-7.04 (m, 3H), 3.18 (m, 1H), 2.66-2.76 (m, 3H), 2.62 (t, J=7.8 Hz, 2H), 2.46-2.56 (m, 1H), 2.05-2.15 (m, 1H), 1.88-1.98 (m, 2H), 1.69-1.80 (m, 3H), 1.61-1.69 (m, 1H), 1.34-1.46 (m, 4H), 1.10-1.34 (m, 4H), 0.91-1.03 (m, 1H).

Example 188

In Vitro Isomerase Inhibition Assay

The capability of amine derivative compounds to inhibit the activity of a visual cycle isomerase was determined Isomerase inhibition reactions were performed essentially as described (Stecher et al., *J. Biol. Chem.* 274:8577-85 (1999); see also Golczak et al., *Proc. Natl. Acad. Sci. USA* 102:8162-67 (2005)). Bovine Retinal Pigment Epithelium (RPE) microsome membranes were the source of a visual cycle isomerase.

RPE Microsome Membrane Preparation

Bovine RPE microsome membrane extracts were prepared according to methods described (Golczak et al., *Proc. Natl. Acad. Sci. USA* 102:8162-67 (2005)) and stored at −80° C. Crude RPE microsome extracts were thawed in a 37° C. water bath, and then immediately placed on ice. 50 ml crude RPE microsomes were placed into a 50 ml Teflon-glass homogenizer (Fisher Scientific, catalog no. 0841416M) on ice, powered by a hand-held DeWalt drill, and homogenized ten times up and down on ice under maximum speed. This process was repeated until the crude RPE microsome solution was homogenized. The homogenate was then subjected to centrifugation (50.2 Ti rotor (Beckman, Fullerton, Calif.), 13,000 RPM; 15360 Rcf) for 15 minutes at 4° C. The supernatant was collected and subjected to centrifugation at 42,000 RPM (160,000 Rcf; 50.2 Ti rotor) for 1 hour at 4° C. The supernatant was removed, and the pellets were suspended in 12 ml (final volume) cold 10 mM MOPS buffer, pH 7.0. The resuspended RPE membranes in 5 ml aliquots were homogenized in a glass-to-glass homogenizer (Fisher Scientific, catalog no. K885500-0021) to high homogeneity. Protein concentration was quantified using the BCA protein assay according to the manufacturer's protocol (Pierce, Rockford, Ill.). The homogenized RPE preparations were stored at −80° C.

Isolation of Human Apo Cellular Retinaldehyde-Binding Protein (CRALBP)

Recombinant human apo cellular retinaldehyde-binding protein (CRALBP) was cloned and expressed according to standard methods in the molecular biology art (see Crabb et al., *Protein Science* 7:746-57 (1998); Crabb et al., *J. Biol. Chem.* 263:18688-92 (1988)). Briefly, total RNA was prepared from confluent ARPE19 cells (American Type Culture Collection, Manassas, Va.), cDNA was synthesized using an oligo(dT)$_{12-18}$ primer, and then DNA encoding CRALBP was amplified by two sequential polymerase chain reactions (see Crabb et al., *J. Biol. Chem.* 263:18688-92 (1988); Intres, et al., *J. Biol. Chem.* 269:25411-18 (1994); GenBank Accession No. L34219.1). The PCR product was sub-cloned into pTrcHis2-TOPO TA vector according to the manufacturer's protocol (Invitrogen Inc., Carlsbad, Calif.; catalog no. K4400-01), and then the sequence was confirmed according to standard nucleotide sequencing techniques. Recombinant 6× His-tagged human CRALBP was expressed in One Shot TOP 10 chemically competent *E. coli* cells (Invitrogen), and the recombinant polypeptide was isolated from *E. coli* cell lysates by nickel affinity chromatography using nickel (Ni) Sepharose XK16-20 columns for HPLC (Amersham Bioscience, Pittsburgh, Pa.; catalog no.17-5268-02). The purified 6× His-tagged human CRALBP was dialyzed against 10 mM bis-tris-Propane (BTP) and analyzed by SDS-PAGE. The molecular weight of the recombinant human CRALBP was approximately 39 kDal.

Isomerase Assay

Amine derivative compounds and control compounds were reconstituted in ethanol to 0.1 M. Ten-fold serial dilutions ($10^{-2}$, $10^{-3}$, $10^{-4}$, $10^{-5}$, $10^{-6}$ M) in ethanol of each compound were prepared for analysis in the isomerase assay.

The isomerase assay was performed in 10 mM bis-tris-propane (BTP) buffer, pH 7.5, 0.5% BSA (diluted in BTP buffer), 1 mM sodium pyrophosphate, 20 µM all-trans retinol (in ethanol), and 6 µM apo-CRALBP. The test compounds (2 µl) (final $\frac{1}{15}$ dilution of serial dilution stocks) were added to the above reaction mixture to which RPE microsomes were added. The same volume of ethanol was added to the control reaction (absence of test compound). Bovine RPE microsomes (9 µl) (see above) were then added, and the mixtures transferred to 37° C. to initiate the reaction (total volume=150 µl). The reaction were stopped after 30 minutes by adding methanol (300 µl). Heptane was added (300 µl) and mixed into the reaction mixture by pipetting. Retinoid was extracted by agitating the reaction mixtures, followed by centrifugation in a microcentrifuge. The upper organic phase was transferred to HPLC vials and then analyzed by HPLC using an Agilent 1100 HPLC system with normal phase column: SILICA (Agilent Technologies, dp 5µ, 4.6 mmX, 25 CM; running method had flow rate of 1.5 ml/min; injection volume 100 µl). The solvent components were 20% of 2% isopropanol in EtOAc and 80% of 100% hexane.

The area under the $A_{318}$ nm curve represents the 11-cis retinol peak, which is calculated by Agilent Chemstation software and recorded manually. The IC$_{50}$ values (concentration of compound that gives 50% inhibition of 11-cis retinol formation in vitro) are calculated using GraphPad Prism® 4 Software (Irvine, Calif.). All tests are performed in duplicate.

The concentration dependent effect of the compounds disclosed herein on the retinol isomerization reaction can also be evaluated with a recombinant human enzyme system. In particular, the in vitro isomerase assay was performed essentially as in Golczak et al. 2005, PNAS 102: 8162-8167, ref 3). A homogenate of HEK293 cell clone expressing recombinant human RPE65 and LRAT were the source of the visual enzymes, and exogenous all-trans-retinol (about 20 µM) was used as the substrate. Recombinant human CRALBP (about 80 ug/mL) was added to enhance the formation of 11 cis-retinal. The 200 µL Bis-Tris Phosphate buffer (10 mM, pH 7.2) based reaction mixture also contains 0.5% BSA, and 1 mM NaPPi. In this assay, the reaction was carried out at 37° C. in duplicates for one hour and was terminated by addition of 300 μL methanol. The amount of reaction product, 11-cis-retinol, was measured by HPLC analysis following Heptane extraction of the reaction mixture. The Peak Area Units (PAUs) corresponding to 11 cis-retinol in the HPLC chromatograms were recorded and concentration dependent curves analyzed by GraphPad Prism for $IC_{50}$ values. The ability of the numerous compounds disclosed herein to inhibit isomerization reaction is quantified and the respective $IC_{50}$ value is determined The tables below summarises the $IC_{50}$ values of various compounds of the present invention determined by either of the above two methods. $IC_{50}$s for human and bovine in vitro data are provided in Tables 6A and 6B.

TABLE 6A

Human In Vitro Inhibition Data

| $IC_{50}$ (μM) | Compound/Example Number |
|---|---|
| ≤0.01 μM | 9, 19, 20, 59, 71, 73, 90, 102, 100, 110 |
| >0.01 μM - ≤0.1 μM | 3, 7, 10, 11, 12, 14, 15, 16, 17, 18, 24, 25, 30, 33, 41, 42, 45, 46, 47, 48, 49, 50, 54, 58, 60, 61, 63, 64, 68, 70, 72, 77, 79, 80, 82, 84, 85, 89, 91, 92, 95, 97, 98, 99, 104, 105, 106, 109, 113, 114, 115, 116, 124, 133, 134, 137, 138, 140, 144, 145, 147, 150, 154, 155, 156, 157, 158, 162, 164, 187 |
| >0.1 μM - ≤1 μM | 22, 26, 27, 28, 31, 35, 36, 38, 39, 40, 51, 52, 53, 55, 57, 62, 65, 66, 67, 69, 74, 75, 76, 78, 79, 81, 86, 87, 88, 101, 103, 107, 108, 111, 112, 117, 118, 121, 122, 123, 127, 128, 130, 131, 132, 135, 136, 139, 142, 143, 146, 149, 151, 152, 153, 159, 160, 161, 165 |
| >1 μM - ≤10 μM | 37, 43, 56, 83, 93, 94, 96, 120, 125, 126, 129, 148, 163 |
| >10 μM | 44, 141 |
| No detectable activity | 119 |

TABLE 6B

Bovine In Vitro Inhibition data

| $IC_{50}$ (μM) | Compound/Example Number |
|---|---|
| ≤1 μM | 2, 3, 7, 9, 10, 11, 12, 13, 14, 15, 16, 17, 18, 19, 20, 24, 25, 26, 27, 28, 29, 30, 33, 35, 38 |
| >1 μM - ≤10 μM | 1, 4, 5, 8, 22, 31, 34, 36, 37 |
| >10 μM - ≤100 μM | 6, 21, 23, 32 |
| >100 μM - ≤1000 μM | 166 |

Example 189

In Vivo Murine Isomerase Assay

The capability of amine derivative compounds to inhibit isomerase was determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo. Delayed recovery, as represented by lower 11-cis-retinal oxime levels, indicates inhibition of isomerization reaction. Procedures were performed essentially as described by Golczak et al., *Proc. Natl. Acad. Sci. USA* 102:8162-67 (2005). See also Deigner et al., *Science*, 244: 968-71 (1989); Gollapalli et al., *Biochim Biophys Acta.* 1651: 93-101 (2003); Parish, et al., *Proc. Natl. Acad. Sci. USA*, 14609-13 (1998); Radu, et al., *Proc Natl Acad Sci USA* 101: 5928-33 (2004).

Six-week old dark-adapted CD-1 (albino) male mice were orally gavaged with compound (0.03-3 mg/kg) dissolved in 100 μl corn oil containing 10% ethanol (5-8 animals per group). Mice were orally gavaged with the several of the amine derivative compounds described herein. After 1-48 hours in the dark, the mice were exposed to photobleaching of 5,000 lux of white light for 10 minutes. The mice were allowed to recover 2 hours in the dark. The animals were then sacrificed by carbon dioxide inhalation. Retinoids were extracted from the eye and the regeneration of 11-cis-retinal was assessed at various time intervals.

Eye Retinoid Extraction

All steps were performed in darkness with minimal redlight illumination (low light darkroom lights and redfiltered flashlights for spot illumination as needed) (see, e.g., Maeda et al., *J. Neurochem* 85:944-956, 2003; Van Hooser et al., *J. Biol Chem* 277:19173-82, 2002). After the mice were sacrificed, the eyes were immediately removed and placed in liquid nitrogen for storage.

The eyes were placed in 500 μL of bis-tris propane buffer (10 mM, pH ~7.3) and 20 μL of 0.8M hydroxylamine (pH~7.3). The eyes were cut up into small pieces with small iris scissors and then thoroughly homogenized at 30000 rpm with a mechanical homogenizer (Polytron PT 1300 D) in the tube until no visible tissue remained. 500 μL of methanol and 500 μL of heptane were added to each tube. The tubes were attached to a vortexer so that the contents were mixed thoroughly for 15 minutes in room temperature. The organic phase was separated from the aqueous phase by centrifugation for 10 min at 13K rpm, 4° C. 240 μL of the solution from the top layer (organic phase) was removed and transferred to clean 300 μl glass inserts in HPLC vials using glass pipette and the vials were crimped shut tightly.

The samples were analyzed on an Agilent 1100 HPLC system with normal phase column: SILICA (Beckman Coutlier, dp 5 μm, 4.6 mM×250 mM). The running method has a flow rate of 1.5 ml/min; solvent components are 15% solvent 1 (1% isopropanol in ethyl acetate), and 85% solvent 2 (100% hexanes). Loading volume for each sample is 100 μl; detection wavelength is 360 nm. The area under the curve for 11-cis retinal oxime was calculated by Agilent Chemstation software and was recorded manually. Data processing was performed using Prizm software.

Positive control mice (no compound administered) were sacrificed fully dark-adapted and the eye retinoids analyzed. Light (bleached) control mice (no compound administered) were sacrificed and retinoids isolated and analyzed immediately after light treatment. As an example, the isomerase inhibitory activity of the compound of Example 3 (Compound 3) is presented in FIG. 1. The animals were orally gavaged with 1 mg/kg compound, then "photo-bleached" (5000 Lux white light for 10 minutes) at 4, 24 and 48 hours after dosing, and returned to darkness to allow recovery of the 11-cis-retinal content of the eyes. Mice were sacrificed 2 hours after bleaching, eyes were enucleated, and retinoid content was analyzed by HPLC. Results are presented in FIG. 1.

Figure 2A:
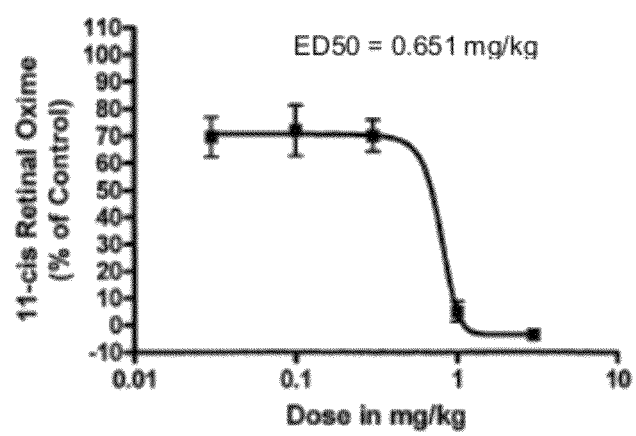
FIG. 2A shows concentration-dependent inhibition of 11-cis retinal (oxime) recovery.
Figure 2B:
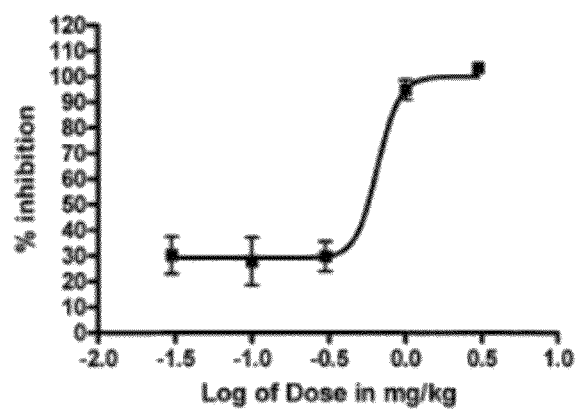
FIG. 2B shows the dose response (log dose, mg/ml) in which the data are normalized to percent inhibition of isomerase activity Inhibition of recovery was dose related, with the $ED_{50}$ (dose of compound that gives 50% inhibition of 11-cis retinal (oxime) recovery) estimated at 0.651 mg/kg. Five animals were included in each treatment group. The error bars correspond to standard error.

A dose response in vivo isomerase inhibition study was performed with several of the amine derivative compounds described herein. Six-week old dark-adapted CD-1 (albino) male mice were orally gavaged with 0.03, 0.1, 0.3, 1 and 3 mg/kg of compound in sterile water as solution, and photobleached 4 hours after dosing. The animals were allowed to recover 2 hours in the dark. The animals were then sacrificed by carbon dioxide inhalation. Retinoids were extracted from the eye and the regeneration of 11-cis-retinal was assessed at various time intervals. Retinoid analysis was performed as described above. Dark control mice were vehicle-only treated, sacrificed fully dark adapted without light treatment, and analyzed. As an example, the dose-dependent inhibition of the recovery of 11-cis retinal (oxime) at 4 hours post dosing of the compound of Example 19 (Compound 19) is presented in FIG. 2. FIG. 2A shows dose-dependent inhibition of isomerase activity and FIG. 2B shows the dose response (log dose, mg/kg) in which the data are normalized to percent inhibition of isomerase activity. Four animals were included in each treatment group. The error bars correspond to standard error Inhibition of recovery was dose related, with the $ED_{50}$ (dose of compound that gives 50% inhibition of 11-cis retinal (oxime) recovery) estimated at 0.651 mg/kg. The estimated $ED_{50}$ of compounds of Examples 3, 29, 15 and 19 (Compounds 3, 29, 15 and 19) are presented in Table 7A.

TABLE 7A

IN VIVO INHIBITION DATA

| Compound | $ED_{50}$ (mg/kg) |
|---|---|
| 3 | 2 |
| 29 | 4 |
| 15 | 2 |
| 19 | 0.65 |

A single dose study of several of the compounds disclosed herein was performed, at 1 mg/kg and in some cases also 5 mg/kg oral dosing, with photobleaching 4 and 24 hours post dosing. The experiments were also carried out in CD1 male mice. Results were analyzed by HPLC. % Inhibition results are presented in Table 7B.

TABLE 7B

IN VIVO INHIBITION DATA

| Example No. | % Inhibition 1 mg/kg | | % Inhibition 5 mg/kg | |
|---|---|---|---|---|
| | 4 h | 24 h | 4 h | 24 h |
| 3 | 36 | 13 | 95 | 0 |
| 7 | 23 | 12 | | |
| 9 | 12 | 6 | | |
| 10 | 9 | 1 | | |
| 11 | 0 | 0 | | |
| 12 | 27 | 12 | | |
| 16 | 6 | 0 | | |
| 17 | 84 | 0 | | |
| 20 | 0 | 2 | | |
| 27 | 6 | 29 | | |
| 29 | 0 | 0 | 62 | 0 |
| 35 | 0 | | | |
| 59 | 14 | | | |
| 71 | 67 | | | |
| 70 | 100 | | | |
| 85 | 70 | | | |
| 90 | 84 | | | |
| 99 | 22 | | | |
| 100 | 9 | | | |
| 109 | 79 | | | |
| 110 | 61 | | | |
| 113 | 87 | | | |
| 134 | 6 | | | |
| 140 | 87 | | | |
| 157 | 0 | | | |
| 164 | 0 | | | |
| 187 | 9 | | | |

Example 190

Preparation of Retinal Neuronal Cell Culture System

This example describes methods for preparing a long-term culture of retinal neuronal cells. All compounds and reagents can be obtained from Sigma Aldrich Chemical Corporation (St. Louis, Mo.) or other suitable vendors.

Retinal Neuronal Cell Culture

Porcine eyes are obtained from Kapowsin Meats, Inc. (Graham, Wash.). Eyes are enucleated, and muscle and tissue are cleaned away from the orbit. Eyes are cut in half along their equator and the neural retina is dissected from the anterior part of the eye in buffered saline solution, according to standard methods known in the art. Briefly, the retina, ciliary body, and vitreous are dissected away from the anterior half of the eye in one piece, and the retina is gently detached from the clear vitreous. Each retina is dissociated with papain (Worthington Biochemical Corporation, Lakewood, N.J.), followed by inactivation with fetal bovine serum (FBS) and addition of 134 Kunitz units/ml of DNaseI. The enzymatically dissociated cells are triturated and collected by centrifugation, resuspended in Dulbecco's modified Eagle's medium (DMEM)/F12 medium (Gibco BRL, Invitrogen Life Technologies, Carlsbad, Calif.) containing about 25 µg/ml of insulin, about 100 µg/ml of transferrin, about 60 µM putrescine, 30 nM selenium, about 20 nM progesterone, about 100 U/ml of penicillin, about 100 µg/ml of streptomycin, about 0.05 M Hepes, and about 10% FBS. Dissociated primary retinal cells are plated onto Poly-D-lysine- and Matrigel- (BD, Franklin Lakes, N.J.) coated glass coverslips that are placed in 24-well tissue culture plates (Falcon Tissue Culture Plates, Fisher Scientific, Pittsburgh, Pa.). Cells are maintained in culture for 5 days to one month in 0.5 ml of media (as above, except with only 1% FBS) at 37° C. and 5% $CO_2$.

Immunocytochemistry Analysis

The retinal neuronal cells are cultured for about 1, 3, 6, and 8 weeks, and the cells are analyzed by immunohistochemistry at each time point. Immunocytochemistry analysis is performed according to standard techniques known in the art. Rod photoreceptors are identified by labeling with a rhodopsin-specific antibody (mouse monoclonal, diluted about 1:500; Chemicon, Temecula, Calif.). An antibody to midweight neurofilament (NFM rabbit polyclonal, diluted about 1:10,000, Chemicon) is used to identify ganglion cells; an antibody to β3-tubulin (G7121 mouse monoclonal, diluted about 1:1000, Promega, Madison, Wis.) is used to generally identify interneurons and ganglion cells, and antibodies to calbindin (AB1778 rabbit polyclonal, diluted about 1:250, Chemicon) and calretinin (AB5054 rabbit polyclonal, diluted about 1:5000, Chemicon) are used to identify subpopulations of calbindin- and calretinin-expressing interneurons in the inner nuclear layer. Briefly, the retinal cell cultures are fixed with 4% paraformaldehyde (Polysciences, Inc, Warrington, Pa.) and/or ethanol, rinsed in Dulbecco's phosphate buffered saline (DPBS), and incubated with primary antibody for about 1 hour at 37° C. The cells are then rinsed with DPBS, incubated with a secondary antibody (Alexa 488- or Alexa 568-conjugated secondary antibodies (Molecular Probes, Eugene, Oreg.)), and rinsed with DPBS. Nuclei are stained with 4',6-diamidino-2-phenylindole (DAPI, Molecular Probes), and the cultures are rinsed with DPBS before removing the glass coverslips and mounting them with Fluoromount-G (Southern Biotech, Birmingham, Ala.) on glass slides for viewing and analysis.

Survival of mature retinal neurons after varying times in culture is indicated by the histochemical analyses. Photoreceptor cells are identified using a rhodopsin antibody; ganglion cells are identified using an NFM antibody; and amacrine and horizontal cells are identified by staining with an antibody specific for calretinin Cultures are analyzed by counting rhodopsin-labeled photoreceptors and NFM-labeled ganglion cells using an Olympus IX81 or CZX41 microscope (Olympus, Tokyo, Japan). About twenty fields of view are counted per coverslip with a 20× objective lens. At least five coverslips are analyzed by this method for each condition in each experiment. Cells that are not exposed to any stressor are counted, and cells exposed to a stressor are normalized to the number of cells in the control. It is expected that compounds presented in this disclosure promote dose-dependent and time-dependent survival of mature retinal neurons.

Example 191

Effect of Amine Derivative Compounds on Retinal Cell Survival

This Example describes the use of the mature retinal cell culture system that comprises a cell stressor for determining the effects of an amine derivative compound on the viability of the retinal cells.

Retinal cell cultures are prepared as described in Example 190. A2E is added as a retinal cell stressor. After culturing the cells for about 1 week, a chemical stress, A2E, is applied. A2E is diluted in ethanol and added to the retinal cell cultures at concentration of about 0, 10 μM, 20 μM, and 40 μM. Cultures are treated for about 24 and 48 hours. A2E is obtained from Dr. Koji Nakanishi (Columbia University, New York City, N.Y.) or is synthesized according to the method of Parish et al. (*Proc. Natl. Acad. Sci. USA* 95:14602-13 (1998)). An amine derivative compound is then added to the culture. To other retinal cell cultures, an amine derivative compound is added before application of the stressor or is added at the same time that A2E is added to the retinal cell culture. The cultures are maintained in tissue culture incubators for the duration of the stress at 37° C. and 5% $CO_2$. The cells are then analyzed by immunocytochemistry as described in Example 190.

Apoptosis Analysis

Retinal cell cultures are prepared as described in Example 190 and cultured for about 2 weeks and then exposed to white light stress at about 6000 lux for about 24 hours followed by about a 13-hour rest period. A device was built to uniformly deliver light of specified wavelengths to specified wells of the 24-well plates. The device contains a fluorescent cool white bulb (GE P/N FC12T9/CW) wired to an AC power supply. The bulb is mounted inside a standard tissue culture incubator. White light stress is applied by placing plates of cells directly underneath the fluorescent bulb. The $CO_2$ levels are maintained at about 5%, and the temperature at the cell plate is maintained at 37° C. The temperature is monitored by using thin thermocouples. The light intensities for all devices are measured and adjusted using a light meter from Extech Instruments Corporation (P/N 401025; Waltham, Mass.). Any amine derivative compound is added to wells of the culture plates prior to exposure of the cells to white light and is added to other wells of the cultures after exposure to white light. To assess apoptosis, TUNEL is performed as described herein.

Apoptosis analysis is also performed after exposing retinal cells to blue light. Retinal cell cultures are cultured as described in Example 190. After culturing the cells for about 1 week, a blue light stress is applied. Blue light is delivered by a custom-built light-source, which consists of two arrays of 24 (4×6) blue light-emitting diodes (Sunbrite LED P/N SSP-01TWB7UWB12), designed such that each LED is registered to a single well of a 24 well disposable plate. The first array is placed on top of a 24 well plate full of cells, while the second one is placed underneath the plate of cells, allowing both arrays to provide a light stress to the plate of cells simultaneously. The entire apparatus is placed inside a standard tissue culture incubator. The $CO_2$ levels are maintained at about 5%, and the temperature at the cell plate is maintained at about 37° C. The temperature is monitored with thin thermocouples. Current to each LED is controlled individually by a separate potentiometer, allowing a uniform light output for all LEDs. Cell plates are exposed to about 2000 lux of blue light stress for either about 2 hours or 48 hours, followed by a about 14-hour rest period. An amine derivative compound is added to wells of the culture plates prior to exposure of the cells to blue light and is added to other wells of the cultures after exposure to blue light. To assess apoptosis, TUNEL is performed as described herein.

To assess apoptosis, TUNEL is performed according to standard techniques practiced in the art and according to the manufacturer's instructions. Briefly, the retinal cell cultures are first fixed with 4% paraformaldehyde and then ethanol, and then rinsed in DPBS. The fixed cells are incubated with TdT enzyme (0.2 units/μl final concentration) in reaction buffer (Fermentas, Hanover, Md.) combined with Chroma-Tide Alexa568-5-dUTP (0.1 μM final concentration) (Molecular Probes) for about 1 hour at 37° C. Cultures are rinsed with DPBS and incubated with primary antibody either overnight at 4° C. or for about 1 hour at 37° C. The cells are then rinsed with DPBS, incubated with Alexa 488-conjugated secondary antibodies, and rinsed with DPBS. Nuclei are stained with DAPI, and the cultures are rinsed with DPBS before removing the glass coverslips and mounting them with Fluoromount-G on glass slides for viewing and analysis.

Cultures are analyzed by counting TUNEL-labeled nuclei using an Olympus IX81 or CZX41 microscope (Olympus, Tokyo, Japan). Twenty fields of view are counted per coverslip with a 20× objective lens. Six coverslips are analyzed by this method for each condition. Cells that are not exposed to an amine derivative compound are counted, and cells exposed to the antibody are normalized to the number of cells in the control. Data are analyzed using the unpaired Student's t-test. It is expected that amine derivative compounds reduce A2E-induced apoptosis and cell death in retinal cell cultures in a dose-dependent and time-dependent manner.

Example 192

In Vivo Light Mouse Model

This Example describes the effect of an amine derivative compound in an in vivo light damage mouse model.

Exposure of the eye to intense white light can cause photodamage to the retina. The extent of damage after light treatment can be evaluated by measuring cytoplasmic histone-associated-DNA-fragment (mono- and oligonucleosomes) content in the eye (see, e.g., Wenzel et al., *Prog. Retin. Eye Res.* 24:275-306 (2005)).

Dark adapted mice (for example, male Balb/c (albino, 10/group)) are gavaged with the amine derivative compounds of the present disclosure at various doses (about 0.01-25 mg/kg) or vehicle only is administered. About six hours after dosing, the animals are subjected to light treatment (about 8,000 lux of white light for about 1 hour). Mice are sacrificed after about 40 hours of recovery in dark, and retinas are dissected. A cell death detection ELISA assay is performed according to the manufacturer's instructions (such as ROCHE APPLIED SCIENCE, Cell Death Detection ELISA plus Kit). Contents of fragmented DNA in the retinas are measured to estimate the retinal-protective activity of the compounds. It is expected that compounds of the present disclosure mitigate or inhibit photo-damage to the retina.

Example 193

Electroretinographic (ERG) Study

This example describes determining the effect of an amine derivative compound that is a visual cycle modulator on the magnitude of the ERG response in the eyes of mice after oral dosing of the animals with the compound. The level of ERG response in the eyes is determined after administering the compound to the animals (for example at about 18 and 66 hours post administration).

Three groups of about nine-week old mice (about 19-25 grams), both genders (strain C5 7BL/6,Charles River Laboratories, Wilmington, Mass.) are housed at room temperature, 72±4° F., and relative humidity of approximately 25%. Animals are housed in a 12-hour light /dark cycle environment, have free access to feed and drinking water and are checked for general health and well-being prior to use and during the study. Body weights are determined for a representative sample of mice prior to initiation of dosing. The average weight determined from this sampling is used to establish the dose for all mice in the study.

Each test compound is dissolved in the control solvent (EtOH), and diluted about 1:10 (90 ml/900 ml) in the appropriate oil (for example corn oil (Crisco Pure Corn Oil, J.M. Smucker Company, Orrville, Ohio)) to the desired dose (mg/kg) in the desired volume (about 0.1 mL/animal) The control vehicle is ethanol: oil (about 1:10 (0.9 ml/9 ml)). An example of treatment designations and animal assignments are described in Table 8.

TABLE 8

| Group | Route | Treatment | Dose (mg/kg) | Animals |
|---|---|---|---|---|
| Test | oral | Amine derivative compound | (~0.01 - 25 mg/kg) | >4 |
| Control | oral | Vehicle | None | >4 |

Animals are dosed once orally by gavage, with the assigned vehicle control or test compounds during the light cycle (between about 30 min and about 3 hours 30 min after the beginning of the light cycle). The volume of the administered dose usually does not exceed about 10 mL/kg.

ERG recordings are made on dark-adapted and, subsequently (during the course of the same experiment), on light-adapted states. For the dark-adapted response, animals are housed in a dark-adapted environment for at least about 1 hour prior to the recording, commencing at least about 30 minutes after the start of the light cycle.

At about eighteen and about sixty six hours after dosing, the mice are anesthetized with a mixture of Ketamine and Xylazine (100 mg/kg and 20 mg/kg, respectively) and placed on a heating pad to maintain stable core body temperature during the course of the experiment. Pupils are dilated by placing about a 5 microliter drop of mydriatic solution (tropicamide 0.5%) in the recorded eye. A mouse corneal monopolar contact lens electrode (Mayo Corporation, Inazawa, Aichi, Japan) is placed on the cornea, and a subcutaneous reference low profile needle 12 mm electrode (Grass Telefactor, W Warwick, R.I.) is placed medial from the eye. A ground needle electrode is placed in the tail. Data collection is obtained using an Espion $E^2$ (Diagnosys LLC, Littleton, Mass.) ERG recording system with Color Dome Ganzfeld stimulator. Full dark-adapted intensity-response function is determined following a brief white flash stimuli of about 14 intensities ranging from about 0.0001 cd.s/m$^2$ to about 333 cd.s/m$^2$. Subsequently, full light-adapted intensity-response function is determined following a brief white flash stimuli of about 9 intensities ranging from about 0.33 cd.s/m$^2$ to about 333 cd.s/m$^2$. Analysis of the obtained responses is done off-line. Intensity-response function determination is done by fitting a sigmoid function to the data (Naka K I, Rushton W A, 1966; Naka K I, Rushton W A, 1967). It is expected that amine derivative compounds of the present disclosure will depress or suppress the dark-adapted ERG responses (measured at about 0.01 cd.s/m$^2$) while minimally affecting the photopic, light-adapted $V_{max}$ values when compared to control compounds.

Example 194

Effect of an Amine Derivative Compound on Reduction of Lipofuscin Fluorophores

This example describes testing the capability of an amine derivative compound to reduce the level of existing bis-retinoid, N-retinylidene-N-retinylethanolamine (A2E) and lipofuscin fluorophores in the retina of mice as well as prevention of the formation of A2E and lipofuscin fluorophores. A2E is the major fluorophore of toxic lipofuscin in ocular tissues.

The eyes of abca4-null (abca4−/−) mutant mice (see, e.g., Weng et al., Cell 98:13-23 (1999) have an increased accumulation of lipofuscin fluorophores, such as A2E (see, e.g., Karan et al., Proc. Natl. Acad. Sci. USA 102:4164-69 (2005)). Compounds (about 1 mg/kg) or vehicle are administered daily for about three months by oral gavage to abca4$^{-/-}$ mice that are about 2 months old. Mice are sacrificed after about three months of treatment. Retinas and RPE are extracted for A2E analysis.

A similar experiment is performed with aged balb/c mice (about 10 months old). The test mice are treated with about 1 mg/kg/day of compounds for about three months and the control mice are treated with vehicle.

Briefly, under dim red light, each pair of eye balls are harvested, homogenized in a mixture of PBS buffer and methanol and the A2E extracted into chloroform. The samples are dried down and reconstituted in a water/acetonitrile mix for HPLC analysis. The amount of A2E present is determined by comparison of the area under the curve (AUC) of the A2E peak in the sample with an A2E concentration/AUC curve for an A2E reference standard measuring at 440 nm.

It is expected that A2E levels are reduced upon treatment with one or more amine derivative compounds disclosed herein.

Example 195

Effect of an Amine Derivative Compound on Retinoid Nuclear Receptor Activity

Retinoid nuclear receptor activity is associated with transduction of the non-visual physiologic, pharmacologic, and toxicologic retinoid signals that affect tissue and organ growth, development, differentiation, and homeostasis.

The effect of one or more amine derivative compounds disclosed herein and the effect of a retinoic acid receptor (RAR) agonist (E-4-[2-(5,6,7,8-tetrahydro-5,5,8,8-tetramethyl-2-naphthylenyl)-1-propenyl] benzoic acid) (TTNPB), and of all-trans-retinoic acid (at-RA), which is an RAR and retinoid X receptor (RXR) agonist, were studied on RAR and RXR receptors essentially as described by Achkar et al. (*Proc. Natl. Acad. Sci. USA* 93:4879-84 (1996)). As expected several compounds of the present disclosure (Compounds of examples 7, 12, 20, and 16) tested did not show significant effects on retinoid nuclear receptors (RAR and RXR). By contrast, TTNPB and at-RA activated the $RXR_\alpha$, $RAR_\alpha$, $RAR_\beta$ and $RAR_\gamma$ receptors as expected (Table 9). Data represent calculated EC50 values (nM) ±95% Confidence Interval CI (in parentheses) from 7-point dose-response curves, as calculated by Graph Pad Prism Software. Each data point was determined in triplicate.

TABLE 9

| Compound | $RAR\alpha$ $EC_{50}$ (nM) | $RAR\beta$ $EC_{50}$ (nM) | $RAR\gamma$ $EC_{50}$ (nM) | $RXR\alpha$ $EC_{50}$ (nM) |
|---|---|---|---|---|
| TTNPB | 10 (.8-13) | 0.4 (.2-.7) | 0.1 (.05-.1) | ND |
| at-RA | NA | NA | NA | 316 +/− 57 |
| 9-cis RA | NA | NA | NA | 1.4 (.45-4.2) |
| Compound 7 | NA | NA | NA | NA |
| Compound 12 | NA | NA | NA | NA |
| Compound 20 | NA | NA | NA | NA |
| Compound 16 | NA | NA | NA | NA |

NA = Not active

When ranges are used herein for physical properties, such as molecular weight, or chemical properties, such as chemical formulae, all combinations and subcombinations of ranges and specific embodiments therein are intended to be included.

The various embodiments described herein can be combined to provide further embodiments. All U.S. patents, U.S. patent application publications, U.S. patent applications, foreign patents, foreign patent applications, and non-patent publications referred to in this specification and/or listed in the Application Data Sheet, are incorporated herein by reference in their entireties.

From the foregoing it will be appreciated that, although specific embodiments have been described herein for purposes of illustration, various modifications may be made. Those skilled in the art will recognize, or be able to ascertain, using no more than routine experimentation, many equivalents to the specific embodiments described herein. Such equivalents are intended to be encompassed by the following claims. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A compound of Formula (A) or stereoisomer, or a pharmaceutically acceptable salt, or N-oxide thereof:

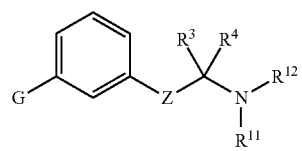

Formula (A)

wherein,
Z is —X—C($R^{31}$)($R^{32}$);
X is —O—;
G is —C($R^{41}$)$_2$—C($R^{41}$)$_2$—$R^{40}$;
$R^{40}$ is selected from —C ($R^{16}$)($R^{17}$)($R^{18}$), aryl, pyridinyl, or thiophenyl;
$R^{41}$ is hydrogen;
$R^{31}$ and $R^{32}$ are each independently selected from hydrogen, $C_1$-$C_5$ alkyl, or fluoroalkyl;
$R^3$ and $R^4$ are hydrogen;
$R^{11}$ and $R^{12}$ are hydrogen;
$R^{16}$ and $R^{17}$ are each independently selected from hydrogen, $C_1$-$C_5$ alkyl, benzyl or aryl; or $R^{16}$ and $R^{17}$, together with the carbon to which they are attached form a carbocyclyl or heterocycle;
$R^{18}$ is selected from hydrogen, alkoxy, or hydroxy; and
with the provision that G is not an unsubstituted normal alkyl.

2. The compound of claim 1 having the structure of Formula (E):

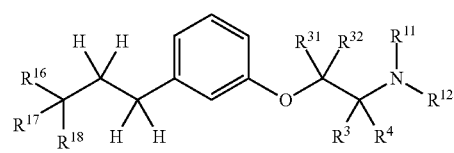

Formula (E)

wherein,
$R^{16}$ and $R^{17}$ are each independently selected from hydrogen, or $C_1$-$C_5$ alkyl; or $R^{16}$ and $R^{17}$, together with the carbon atom to which they are attached, form a carbocyclyl or heterocycle; and
$R^{18}$ is selected from a hydrogen, alkoxy, or hydroxy.

3. The compound of claim 2 wherein,
$R^{31}$ and $R^{32}$ are each independently hydrogen, or $C_1$-$C_5$ alkyl;
$R^{16}$ and $R^{17}$, together with the carbon atom to which they are attached, form a carbocyclyl; and
$R^{18}$ is hydrogen, hydroxy, or alkoxy.

4. The compound of claim 3 wherein $R^{16}$ and $R^{17}$, together with the carbon atom to which they are attached form a cyclopropyl, cyclobutyl, cyclopentyl, cyclohexyl, cycloheptyl or cyclooctyl and $R^{18}$ is hydrogen or hydroxy.

5. The compound of claim 2 wherein, $R^{31}$ and $R^{32}$ are each independently selected from hydrogen, or $C_1$-$C_5$ alkyl; and $R^{18}$ is hydrogen, hydroxy or alkoxy.

6. The compound of claim 2, wherein
$R^{31}$ and $R^{32}$ are each independently hydrogen, or $C_1$-$C_5$ alkyl;
$R^6$ and $R^{19}$ are each independently hydrogen or alkyl;

$R^{16}$ and $R^{17}$ is independently selected from $C_1$-$C_5$ alkyl; and $R^{18}$ is hydrogen, hydroxy or alkoxy.

7. A compound having a structure of Formula (I):

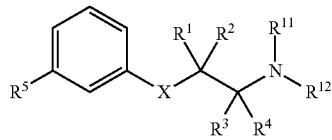

Formula (I)

as a pharmaceutically acceptable salt, or N-oxide thereof, wherein:

$R^1$ and $R^2$ are each the same or different and independently hydrogen, $C_1$-$C_5$ alkyl, or fluoroalkyl;

$R^3$ and $R^4$ are hydrogen;

$R^5$ is $C_5$-$C_{15}$ alkyl, $C_7$-$C_{10}$ aralkyl, or $C_5$-$C_{10}$ carbocyclylalkyl;

X is —O—; and $R^{11}$ and $R^{12}$ are hydrogen.

8. The compound of claim 7 wherein each of $R^1$, $R^2$, $R^3$ and $R^4$ is hydrogen, and $R^5$ is $C_5$-$C_9$ alkyl, or $C_5$-$C_{10}$ carbocyclylalkyl.

9. The compound of claim 1 selected from the group consisting of:

4-(3-(2-aminoethoxy)phenethyl)heptan-4-ol;
1-(3(2-aminoethoxy)phenethyl)cyclohexanol;
1-(3-(2-aminoethoxy)phenethyl)cycloheptanol;
4-(3-(2-aminoethoxy)phenethyl)tetrahydro-2H-thiopyran-4-ol;
6-(3-(2-aminoethoxy)phenyl)hexan-1-ol;
2-(3-(3-cyclopentylpropyl)phenoxy)ethanamine;
2-(3-(2-(pyridin-3-yl)ethyl)phenoxy)ethanamine;
2-(3-(2-(pyridin-2-yl)ethyl)phenoxy)ethanamine; and
2-(3-(2-(thiophen-2-yl)ethyl)phenoxy)ethanamine.

10. The compound of claim 1 selected from the group consisting of:

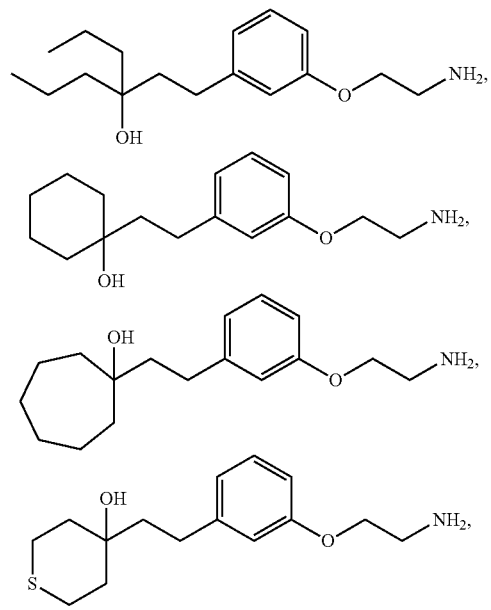

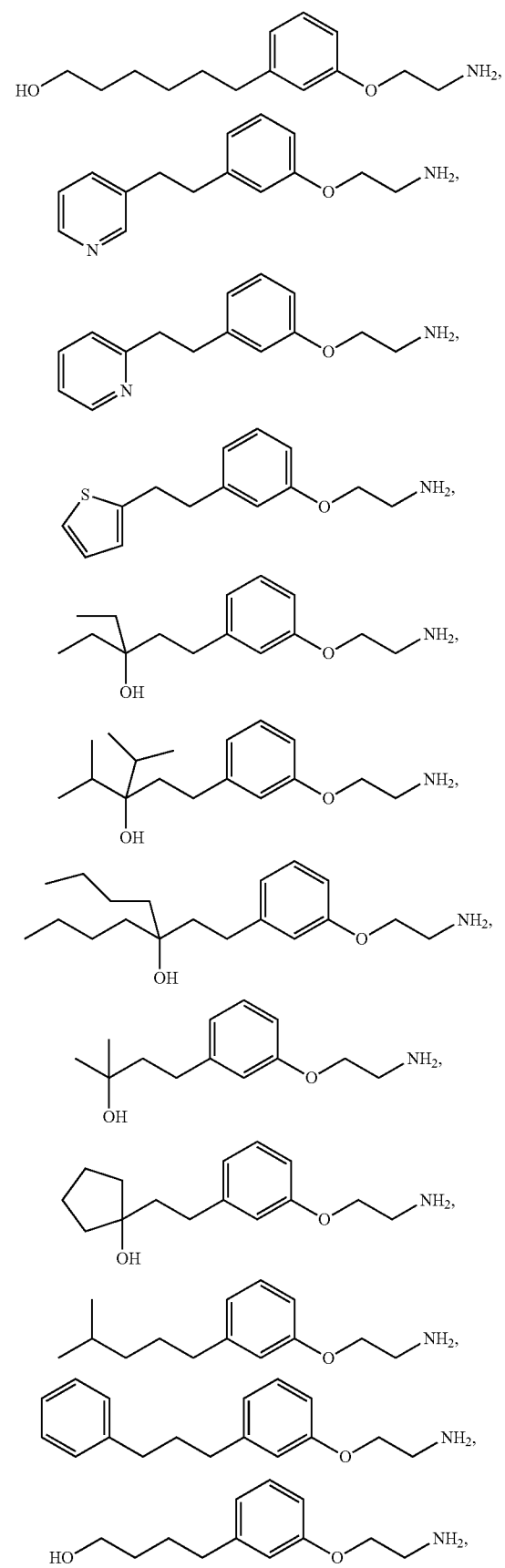

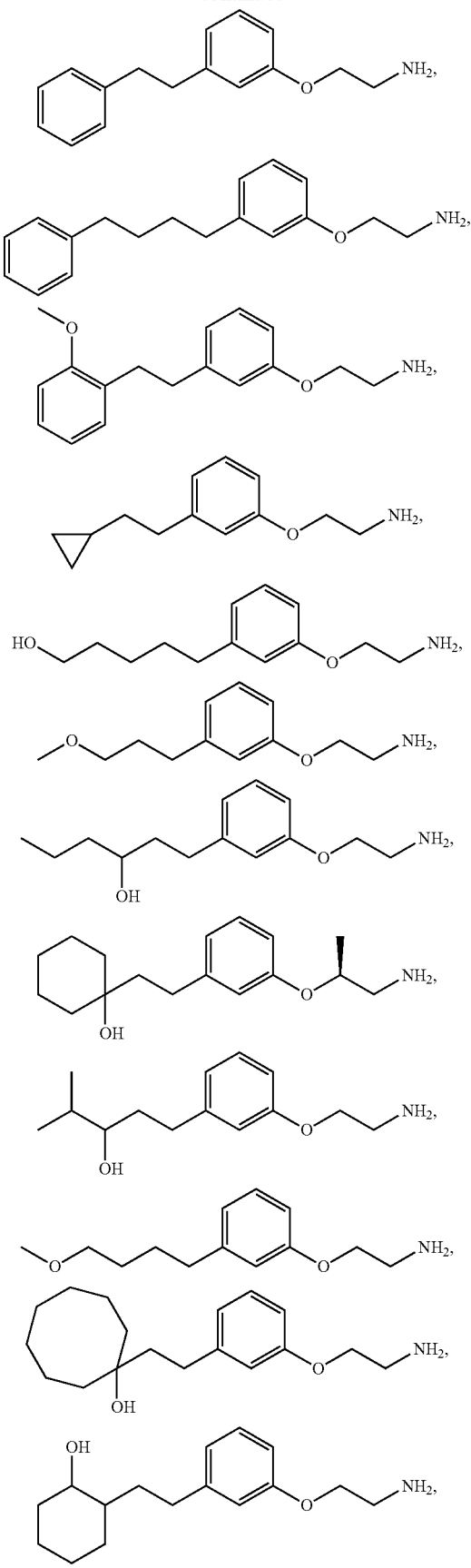
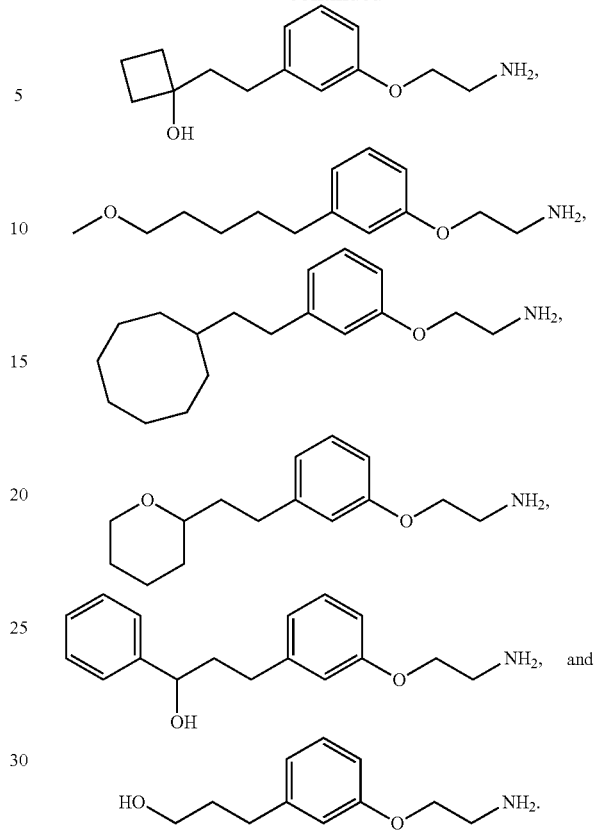

11. A compound of Formula (A) or stereoisomer, or a pharmaceutically acceptable salt, or N-oxide thereof:

Formula (A)

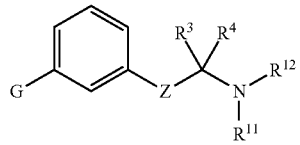

wherein,
one, more than one, or all of the non-exchangeable $^1$H atoms have been substituted with $^2$H atoms;
Z is —X—C(R$^{31}$)(R$^{32}$);
X is —O—;
G is —C(R$^{41}$)$_2$-C(R$^{41}$)$_2$-R$^{40}$;
R$^{40}$ is selected from —C(R$^{16}$)(R$^{17}$)(R$^{18}$), aryl, pyridinyl, or thiophenyl;
R$^{41}$ is hydrogen;
R$^{31}$ and R$^{32}$ are each independently selected from hydrogen, C$_1$-C$_5$ alkyl, or fluoroalkyl;
R$^3$ and R$^4$ are hydrogen;
R$^{11}$ and R$^{12}$ are hydrogen;
R$^{16}$ and R$^{17}$ are each independently selected from hydrogen, C$_1$-C$_5$ alkyl, benzyl or aryl; or R$^{16}$ and R$^{17}$, together with the carbon to which they are attached form a carbocyclyl or heterocycle;
R$^{18}$ is selected from hydrogen, alkoxy, or hydroxy;
and with the provision that G is not an unsubstituted normal alkyl.

12. A pharmaceutical composition comprising a pharmaceutically acceptable carrier, and a compound as described in any one of claim 1, 7, or 10, or a stereoisomer, N-oxide, or pharmaceutically acceptable salt thereof.

* * * * *